United States Patent
Duffy et al.

(10) Patent No.: US 8,742,110 B2
(45) Date of Patent: Jun. 3, 2014

(54) SPIROXAZOLIDINONE COMPOUNDS

(75) Inventors: Joseph L. Duffy, Cranford, NJ (US);
Jianming Bao, Princeton, NJ (US);
Debra L. Ondeyka, Fanwood, NJ (US);
Sriram Tyagarajan, Edison, NJ (US);
Patrick Shao, Fanwood, NJ (US); Feng Ye, Scotch Plains, NJ (US); Revathi Katipally, Monmouth Junction, NJ (US);
Aaron Zwicker, New Haven, CT (US);
Edward C. Sherer, Manville, NJ (US);
Michael A. Plotkin, Frenchtown, NJ (US); Remond Moningka, Rahway, NJ (US); Zahid Hussain, Dayton, NJ (US);
Harold B. Wood, Westfield, NJ (US);
Feroze Ujjainwalla, Scotch Plains, NJ (US); F. Anthony Romero, Redwood City, CA (US); Paul E. Finke, Milltown, NJ (US); Yi Zang, Princeton, NJ (US);
Weiguo Liu, Princeton, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 13/810,946

(22) PCT Filed: Aug. 12, 2011

(86) PCT No.: PCT/US2011/047590
§ 371 (c)(1),
(2), (4) Date: Jan. 18, 2013

(87) PCT Pub. No.: WO2012/024183
PCT Pub. Date: Feb. 23, 2012

(65) Prior Publication Data
US 2013/0131042 A1    May 23, 2013

Related U.S. Application Data

(60) Provisional application No. 61/374,773, filed on Aug. 18, 2010.

(51) Int. Cl.
*C07D 215/00* (2006.01)
*C07D 229/00* (2006.01)
*A61K 31/44* (2006.01)
*A61K 31/397* (2006.01)

(52) U.S. Cl.
USPC ......... 546/18; 548/950; 514/210.16; 514/278

(58) Field of Classification Search
None
See application file for complete search history.

(56) References Cited

U.S. PATENT DOCUMENTS 5,939,418 A   8/1999   Quan et al.
6,214,834 B1  4/2001   Jadhav et al.

2007/0179167 A1   8/2007   Cottrell et al.
2008/0045550 A1   2/2008   Christ et al.
2008/0064697 A1   3/2008   Christ et al.
2008/0269271 A1   10/2008  Frank et al.
2008/0293756 A1   11/2008  Christ et al.
2011/0207737 A1   8/2011   He et al.
2012/0041012 A1   2/2012   Aster et al.

FOREIGN PATENT DOCUMENTS

| WO | 2006/094682 A1 | 9/2006 |
| WO | 2006/128803 A1 | 12/2006 |
| WO | 2007/025897 A2 | 3/2007 |
| WO | 2007/025897 A3 | 3/2007 |
| WO | 2007/110340 A2 | 10/2007 |
| WO | 2007/110340 A3 | 10/2007 |
| WO | 2008/000692 A2 | 1/2008 |
| WO | 2008/000692 A3 | 1/2008 |
| WO | 2008/019967 A2 | 2/2008 |
| WO | 2008/109967 A3 | 2/2008 |
| WO | WO 2009037542 A2 * | 3/2009 |
| WO | 2011/146324 A1 | 11/2011 |
| WO | 2012/024183 A1 | 2/2012 |

OTHER PUBLICATIONS

Guba, W. et al., "From Astemizole to a Novel Hit Series of Small-Molecule Somatostatin 5 Receptor Antagonists via GPCR Affinity Profiling", J. Med. Chem, 2007, p. 6295-6298, vol. 50.
Hay, B. A. et al., "Small Molecule Somatostatin Receptor Subtype-2 Antagonists", Bioorganic & Medicinal Chemistry Letters, 2011, p. 2731-2734, vol. 11.
Kaupmann, K. et al., "Two amino acids, located in transmembrane domains VI and VII, determine the selectivity of the peptide agonist SMS 201-995 for the SSTR2 somatostatin receptor", The EMBO Journal, 1995, p. 727-735, vol. 14, No. 4.

* cited by examiner

*Primary Examiner* — Heidi Reese
(74) *Attorney, Agent, or Firm* — Janet E. Fair; Catherine D. Fitch

(57) ABSTRACT

Substituted spirocyclic amines of structural formula (I) are selective antagonists of the somatostatin subtype receptor 5 (SSTR5) and are useful for the treatment, control or prevention of disorders responsive to antagonism of SSTR5, such as Type 2 diabetes, insulin resistance, lipid disorders, obesity, atherosclerosis, Metabolic Syndrome, depression, and anxiety.

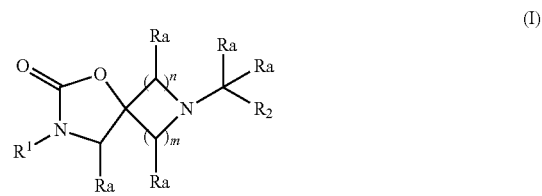

(I)

15 Claims, No Drawings

SPIROXAZOLIDINONE COMPOUNDS

CROSS-REFERENCE TO RELATED APPLICATIONS

This application is a U.S. National Phase application under 35 U.S.C. §371 of PCT Application No. PCT/US2011/047590, filed Aug. 12, 2011, which published as WO 2012/024183 A1 on Feb. 23, 2012, and claims priority under 35 U.S.C. §365(b) from U.S. patent application No. 61/374,773 filed Aug. 18, 2010.

FIELD OF THE INVENTION

The instant invention is concerned with substituted spiroxazolidinone compounds, which are selective antagonists of the somatostatin subtype receptor 5 (SSTR5) and are useful for the treatment, control or prevention of disorders responsive to antagonism of SSTR5, such as Type 2 diabetes mellitus, insulin resistance, obesity, lipid disorders, atherosclerosis, Metabolic Syndrome, depression, and anxiety.

BACKGROUND

Diabetes is a disease derived from multiple causative factors and characterized by elevated levels of plasma glucose (hyperglycemia) in the fasting state or after administration of glucose during an oral glucose tolerance test. There are two generally recognized forms of diabetes. In Type 1 diabetes, or insulin-dependent diabetes mellitus (IDDM), patients produce little or no insulin, the hormone which regulates glucose utilization. In Type 2 diabetes, or noninsulin-dependent diabetes mellitus (NIDDM), insulin is still produced by islet cells in the pancreas. Patients having Type 2 diabetes have a resistance to the effects of insulin. These patients often have normal levels of insulin, and may have hyperinsulinemia (elevated plasma insulin levels), as they compensate for the reduced effectiveness of insulin by secreting increased amounts of insulin (Polonsky, Int. J. Obes, Relat. Metab. Disord. 24 Suppl 2:S29-31, 2000). The beta cells within the pancreatic islets initially compensate for insulin resistance by increasing insulin output. Insulin resistance is not primarily caused by a diminished number of insulin receptors but rather by a post-insulin receptor binding defect that is not yet completely understood. This lack of responsiveness to insulin results in insufficient insulin-mediated activation of uptake, oxidation and storage of glucose in muscle, and inadequate insulin-mediated repression of lipolysis in adipose tissue and of glucose production and secretion in the liver. Eventually, a patient may be become diabetic due to the inability to properly compensate for insulin resistance. In humans, the onset of Type 2 diabetes due to insufficient increases (or actual declines) in beta cell mass is apparently due to increased beta cell apoptosis relative to non-diabetic insulin resistant individuals (Butler et al., Diabetes 52:102-110, 2003).

Persistent or uncontrolled hyperglycemia that occurs with diabetes is associated with increased and premature morbidity and mortality. Often abnormal glucose homeostasis is associated both directly and indirectly with obesity, hypertension, and alterations of the lipid, lipoprotein and apolipoprotein metabolism, as well as other metabolic and hemodynamic disease. Patients with Type 2 diabetes mellitus have a significantly increased risk of macrovascular and microvascular complications, including atherosclerosis, corollary heart disease, stroke, peripheral vascular disease, hypertension, nephropathy, neuropathy, and retinopathy. Therefore, effective therapeutic control of glucose homeostasis, lipid metabolism, obesity, and hypertension are critically important in the clinical management and treatment of diabetes mellitus.

Patients who have insulin resistance often exhibit several symptoms that together are referred to as Syndrome X or Metabolic Syndrome. According to one widely used definition, a patient having Metabolic Syndrome is characterized as having three or more symptoms selected from the following group of five symptoms: (1) abdominal obesity, (2) hypertriglyceridemia, (3) low levels of high-density lipoprotein cholesterol (HDL), (4) high blood pressure, and (5) elevated fasting glucose, which may be in the range characteristic of Type 2 diabetes if the patient is also diabetic. Each of these symptoms is defined clinically in the Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670. Patients with Metabolic Syndrome, whether they have or develop overt diabetes mellitus, have an increased risk of developing the macrovascular and microvascular complications that occur with Type 2 diabetes, such as atherosclerosis and coronary heart disease.

There are several available treatments for Type 2 diabetes, each of which has its own limitations and potential risks. Physical exercise and a reduction in dietary intake of calories often dramatically improves the diabetic condition and are the usual recommended first-line treatment of Type 2 diabetes and of pre-diabetic conditions associated with insulin resistance. Compliance with this treatment is generally very poor because of well-entrenched sedentary lifestyles and excess food consumption, especially of foods containing high amounts of fat and carbohydrates. Pharmacologic treatments have largely focused on three areas of pathophysiology: (1) hepatic glucose production (biguanides such as phenformin and metformin), (2) insulin resistance (PPAR agonists such as rosiglitazone and pioglitazone), (3) insulin secretagogues (sulfonylureas such as tolbutamide, glipizide, and glimepiride); (4) incretin hormone mimetics (GLP-1 derivatives and analogs, such as exenatide and luraglitide); and (5) inhibitors of incretin hormone degradation (DPP-4 inhibitors, such as sitagliptin, vildagliptin, saxagliptin, and alogliptin).

Recent research has focused on pancreatic islet-based insulin secretion that is controlled by glucose-dependent insulin secretion. This approach has the potential for stabilization and restoration of β-cell function. In this regard, research has been done on the affects of antagonizing one or more of the somatostatin receptors. Somatostatin (SST) is a cyclic tetradecapeptide hormone that is widely distributed throughout the body and exhibits multiple biological functions that are mostly inhibitory in function, such as the release of growth hormone, pancreatic insulin, glucagon, and gastrin.

SST hormone activity is mediated through SST-14 and SST-28 isoforms that differentially bind to the five different SST receptor subtypes (SSTR1-5). In humans SSTR1 and SSTR2 are found in the pituitary, small intestine, heart and spleen with SSTR2 predominately in the pancreas, pituitary and the stomach. SSTR3 and SSTR4 are found in the pituitary, heart, liver, spleen stomach, small intestine and kidney. SSTR5 is found in high concentration in the pituitary, as well as the pancreas. It has been shown that S-28 and S-14 bind with similar affinity to SSTR1, SSTR2, SSTR3, and SSTR4. The receptor SSTR5 can be characterized by its preferential affinity for S-28 (Chisholm et al., Am. J. Physiol Endocrinol Metab. 283:E311-E317 (2002)).

SSTR5 is expressed by human islet β cells that are responsible for producing insulin and amylin. Therefore, binding to the SSTR5 could affect insulin secretion. For example, by using in vitro isolated perfused pancreas preparations from 3-month-old mice, it was demonstrated that SSTR5 global knockout mice pancreata have low basal insulin production, but a near normal response to glucose stimulation. It was theorized that, since along with SSTR5, SSTR1 is also expressed in islet β cells up-regulated SSTR1 compensates for the loss of SSTR5 in young knockout mice. As the mice aged, however, SSTR1 expression decreased in both the knockout mice and the aged-control wild-type mice. With lower SSTR1 expression in vivo, SSTR5 knockout mice had increased basal and glucose stimulated insulin secretion due to near complete lack of SSTRs on the knockout mice islet β cells with subsequent loss of the inhibitory SST response (Wang et al., Journal of Surgical Research, 129, 64-72 (2005)).

The proximity of D cells producing S-28 and L-cells containing GLP-1 in the ileum suggest that S-28 acting through SSTR5 may additionally participate in the direct regulation of GLP-1 secretion. To determine if S-28 acting through SSTR5 participates in the direct regulation of GLP-1 secretion, fetal rat intestinal cell cultures were treated with somatostatin analogs with relatively high specificity for SSTR2-5. GLP-1 secretion was inhibited by an SSTR5-selective analog more potently that S-14 and nearly as effectively as S-28 (Chisholm et al., Am. J. Physiol Endocrinol Metab. 283:E311-E317, 2002). A selective antagonist of SSTR5 is anticipated to block the suppression of GLP-1 secretion by endogenous somatostatin peptides, thereby elevating circulating GLP-1 levels. Elevated endogenous GLP-1 levels are associated with beneficial effects in the treatment of Type 2 diabetes (Arulmozhi et al., European Journal of Pharmaceutical Sciences, 28, 96-108 (2006)).

US 2008/0293756 discloses 4,4 disubstituted piperidine derivatives as SST Receptor Subtype 5 antagonists useful to treat diabetes.

Small molecule SSTR antagonists are also disclosed in US 20080249101; WO 2008031735; WO 2008019967; WO 2006094682; WO 2006128803; WO 2007025897; WO 20070110340 and WO 2008000692.

Other small molecule and peptide SSTR antagonists known in the art are disclosed in Wilkinson et al., British Journal of Pharmacology 118, 445-447 (1996); Hocart et al., J. Med. Chem. 41, 1146-1154 (1998); Hay et al., Bioorg. Med. Chem. Lett. 11, 2731-2734 (2001), Martin et al., J. Med. Chem. 50, 6291-6295 (2007) and Guba et al., J. Med. Chem. 50, 6295-6298 (2007), Martin et al., Bioorg. Med. Chem. Lett. 19, 6106-6113 (2009), and Sprecher et al., Regulatory Peptides 159, 19-27 (2010).

Described herein are selective, directly acting SSTR5 antagonists, which are useful as therapeutically active agents for the treatment and/or prevention of diseases that are associated with the modulation of SSTR5. Diseases that can be treated or prevented with SSTR5 antagonists include diabetes mellitus, impaired glucose tolerance and elevated fasting glucose.

SUMMARY

The present invention is directed to compounds of structural formula I, and pharmaceutically acceptable salts thereof:

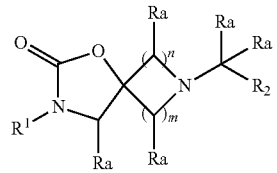

I

These substituted spiroxazolidinones are effective as antagonists of SSTR5, and are useful for the treatment, control or prevention of disorders responsive to antagonism of SSTR5, such as Type 2 diabetes, insulin resistance, lipid disorders, obesity, atherosclerosis, Metabolic Syndrome, depression, and anxiety.

The present invention also relates to pharmaceutical compositions comprising the compounds of the present invention and a pharmaceutically acceptable carrier.

The present invention also relates to methods for the treatment, control, or prevention of disorders, diseases, or conditions responsive to antagonism of SSTR5 in a subject in need thereof by administering the compounds and pharmaceutical compositions of the present invention.

The present invention also relates to methods for the treatment, control, or prevention of Type 2 diabetes, hyperglycemia, insulin resistance, obesity, lipid disorders, atherosclerosis, and Metabolic Syndrome by administering the compounds and pharmaceutical compositions of the present invention to a subject in need thereof.

The present invention also relates to methods for the treatment, control, or prevention of depression and anxiety by administering the compounds and pharmaceutical compositions of the present invention in a subject in need thereof.

The present invention also relates to methods of enhancing GLP-1 secretion by administering the compounds and pharmaceutical compositions of the present invention to a subject in need thereof.

The present invention also relates to methods for the treatment, control, or prevention of obesity by administering the compounds of the present invention in combination with a therapeutically effective amount of another agent known to be useful to treat obesity.

The present invention also relates to methods for the treatment, control, or prevention of Type 2 diabetes by administering the compounds of the present invention in combination with a therapeutically effective amount of another agent known to be useful to treat Type 2 diabetes.

The present invention also relates to methods for the treatment, control, or prevention of atherosclerosis by administering the compounds of the present invention in combination with a therapeutically effective amount of another agent known to be useful to treat atherosclerosis.

The present invention also relates to methods for the treatment, control, or prevention of lipid disorders by administering the compounds of the present invention in combination with a therapeutically effective amount of another agent known to be useful to treat lipid disorders.

The present invention also relates to methods for treating Metabolic Syndrome by administering the compounds of the present invention in combination with a therapeutically effective amount of another agent known to be useful to treat Metabolic Syndrome.

The present invention also relates to methods for the treatment, control, or prevention of depression and anxiety by administering the compounds of the present invention in combination with a therapeutically effective amount of another agent known to be useful to treat depression or anxiety.

The present invention also relates to the use of the compounds of the present invention in the manufacture of a medicament for the treatment, control or prevention of disorders, diseases, or conditions responsive to antagonism of SSTR5.

The present invention also relates to the use of the compounds of the present invention in the manufacture of a medicament for the treatment, control or prevention of Type 2 diabetes, hyperglycemia, insulin resistance, obesity, lipid disorders, atherosclerosis, and Metabolic Syndrome.

The present invention also relates to the use of the compounds of the present invention in the manufacture of a medicament for the treatment, control or prevention of depression, and anxiety.

The present invention also relates to the use of the compounds of the present invention in the manufacture of a medicament for the suppression of GLP-1 secretion in a subject in need thereof.

The present invention also relates to the use of the compounds of the present invention in the manufacture of a medicament that also includes a therapeutically effective amount of another agent for the treatment of diabetes.

DETAILED DESCRIPTION

The present invention is concerned with substituted spiroxazolidinones useful as antagonists of SSTR5. Compounds of the present invention are described by structural formula I and pharmaceutically acceptable salts thereof:

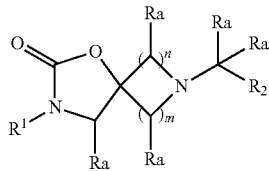

I wherein each occurrence of Ra is independently selected from the group consisting of hydrogen, halogen, —$C_1$-$C_{10}$alkyl and halogen-substituted $C_1$-$C_{10}$alkyl;

$R^1$ is selected from the group consisting of hydrogen, phenyl and heterocycle, wherein the phenyl or heterocycle is substituted with at least one substituent selected from α;

$R^2$ is selected from the group consisting of aryl and heterocycle, wherein the aryl or heterocycle is substituted with 1-5 substituents independently selected from α;

α is selected from the group consisting of:
halogen,
—$C_1$-$C_{10}$alkyl,
—$C_3$-$C_{10}$cycloalkyl,
heterocycle,
aryl,
—OH,
—O—$C_1$-$C_{10}$alkyl,
—O—$C_3$-$C_{10}$cycloalkyl,
—O-aryl,
—O-heterocycle,
—NRbS(O)$_2$Rc,
—NRbRc,
—CN,
—NRbC(O)Rc,
—S(O)$_2$Rb,
—S(O)$_2$NRbRc,
—C(O)NRbRc,
—C(O)NRb($C_1$-$C_{10}$alkyl-NH—$C_1$-$C_{10}$alkyl),
—NRbC(O)ORc,
—NRbC(O)NRcRd,
—NRbC(O)NH$_2$,
—NRbS(O)$_2$Rc,
—NO$_2$,
—C(O)Rd,
—COORd, and
—OC(O)Rd,
wherein, Rb, Rc and Rd are independently selected from the group consisting of hydrogen, —$C_1$-$C_{10}$alkyl, —$C_3$-$C_{10}$cycloalkyl, aryl, and heterocycle; and wherein any —$C_3$-$C_{10}$cycloalkyl, aryl, or heterocycle is independently unsubstituted or substituted with 1-4 substituents selected from the group consisting of halogen, NH$_2$, N(CH$_2$)$_2$, —$C_3$-$C_{10}$cycloalkyl, heterocycle, —COORd, —OH, —O—$C_1$-$C_{10}$alkyl and —$C_1$-$C_{10}$alkyl; and wherein any —$C_1$-$C_{10}$alkyl or —O$C_1$-$C_{10}$alkyl is independently unsubstituted or substituted with 1-4 substituents selected from the group consisting of halogen, OH, —COORd, —$C_3$-$C_{10}$cycloalkyl and aryl; and wherein n and m are independently selected from the group consisting of 1, 2 and 3.

In certain embodiments of the compounds described herein, Ra is halogen. Suitable halogens include, but are not limited to, chlorine and fluorine. In other embodiments, Ra is —$C_1$-$C_{10}$alkyl. Suitable alkyls include methyl, ethyl, butyl, isobutyl and t-butyl. In still other embodiments, Ra is halogen-substituted $C_1$-$C_{10}$alkyl. Suitable halogen-substituted alkyls include, but are not limited to trifluoromethyl. In yet other embodiments, Ra is hydrogen. In certain embodiments, every occurrence of Ra is hydrogen.

Compounds described herein also include compounds of formula II:

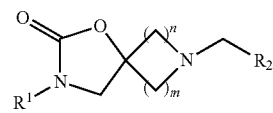

II

In any of the above formulas, n and m are independently selected from the group consisting of 1, 2 and 3. In certain embodiments, n is 1. In other embodiments n is 2. In still other embodiments, n is 3. In certain embodiments, m is 1. In other embodiments m is 2. In still other embodiments, m is 3.

Compounds described herein also include compounds of formulas Ia-Id:

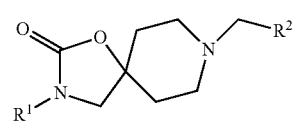

Ia

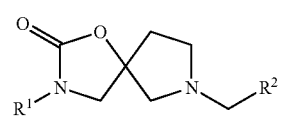

Ib

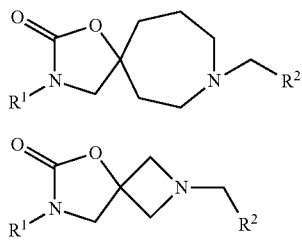

In any of the compounds described above, $R^1$ is selected from the group consisting of hydrogen, phenyl and heterocycle, wherein the phenyl or heterocycle is substituted with at least one substituent selected from α. In certain embodiments, $R^1$ is hydrogen. In other embodiments, $R^1$ is phenyl. In other embodiments, $R^1$ is heterocycle. Suitable examples of heterocycle, include but are not limited to, pyridine.

With regard to the compounds described herein, $R^1$ is substituted with at least one substituent selected from α. In certain embodiments, $R^1$ is substituted with one substituent selected from α. In another embodiment, $R^1$ is substituted with two substituents selected from α.

With regard to the compounds described herein, α is selected from the group consisting of: halogen, —$C_1$-$C_{10}$alkyl, —$C_3$-$C_{10}$cycloalkyl, heterocycle, aryl, —OH, —O—$C_1$-$C_{10}$alkyl, —O—$C_3$-$C_{10}$cycloalkyl, —O-aryl, —O-heterocycle, —NRbS(O)$_2$Rc, —NRbRc, —CN, —NRbC(O)Rc, —S(O)$_2$Rb, —S(O)$_2$NRbRc, —C(O)NRbRc, —C(O)NRb($C_1$-$C_{10}$alkyl-NH—$C_1$-$C_{10}$alkyl), —NRbC(O)ORc, —NRbC(O)NRcRd, —NRbC(O)NH$_2$, —NRbS(O)$_2$Rc, —NO$_2$, —C(O)Rd, —COORd, and —OC(O)Rd, wherein, Rb, Rc and Rd are independently selected from the group consisting of hydrogen, —$C_1$-$C_{10}$alkyl, —$C_3$-$C_{10}$cycloalkyl, aryl, and heterocycle; and wherein any —$C_3$-$C_{10}$cycloalkyl, aryl, or heterocycle is independently unsubstituted or substituted with 1-4 substituents selected from the group consisting of halogen, —COORd, —OH, —O—$C_1$-$C_{10}$alkyl and —$C_1$-$C_{10}$alkyl; and wherein any —$C_1$-$C_{10}$alkyl is independently unsubstituted or substituted with 1-4 substituents selected from the group consisting of halogen, —OH, —COORd, —$C_3$-$C_{10}$cycloalkyl and aryl.

In certain embodiments, Rb is hydrogen. In other embodiments, Rb is —$C_1$-$C_{10}$alkyl, such as methyl. In still other embodiments, Rb is —$C_3$-$C_{10}$cycloalkyl, such as cyclopropyl. In yet other embodiments, Rb is aryl, such as phenyl. In still other embodiments, Rb is heterocycle.

In certain embodiments, Rc is hydrogen. In other embodiments, Rc is —$C_1$-$C_{10}$alkyl, such as methyl. In still other embodiments, Rc is —$C_3$-$C_{10}$cycloalkyl, such as cyclopropyl. In yet other embodiments, Rc is aryl, such as phenyl. In still other embodiments, Rc is heterocycle.

In certain embodiments, Rd is hydrogen. In other embodiments, Rd is —$C_1$-$C_{10}$alkyl, such as methyl. In still other embodiments, Rd is —$C_3$-$C_{10}$cycloalkyl, such as cyclopropyl. In yet other embodiments, Rd is aryl, such as phenyl. In still other embodiments, Rd is heterocycle.

With regard to the compounds describes herein, any —$C_3$-$C_{10}$cycloalkyl, aryl, or heterocycle can be independently unsubstituted or substituted with 1-4 substituents selected from the group consisting of halogen, —COORd, —OH, —O—$C_1$-$C_{10}$alkyl and —$C_1$-$C_{10}$alkyl. In certain embodiments, the —$C_3$-$C_{10}$cycloalkyl, aryl, or heterocycle is unsubstituted. In other examples, the —$C_3$-$C_{10}$cycloalkyl, aryl, or heterocycle is substituted. For example when R1, R2, α, Rb, Rc or Rd is —$C_3$-$C_{10}$cycloalkyl, aryl, or heterocycle, the —$C_3$-$C_{10}$cycloalkyl, aryl, or heterocycle can be independently unsubstituted or substituted with 1, 2, 3 or 4 substituents selected from the group consisting of halogen, such as chlorine or fluorine; —COORd, such as COOH; —OH; —O—$C_1$-$C_{10}$alkyl, such as methoxy and —$C_1$-$C_{10}$alkyl, such as methyl or t-butyl.

Additionally, with regard to the compounds described herein, and wherein any —$C_1$-$C_{10}$alkyl can be unsubstituted or substituted with 1-4 substituents selected from the group consisting of halogen, —OH, —COORd, —$C_3$-$C_{10}$cycloalkyl and aryl. In certain embodiments, the —$C_1$-$C_{10}$alkyl is unsubstituted. In other embodiments, the —$C_1$-$C_{10}$alkyl is substituted. For example when R1, R2, α, Rb, Rc or Rd is —$C_1$-$C_{10}$alkyl, the —$C_1$-$C_{10}$alkyl can be unsubstituted or substituted with 1-4 substituents selected from the group consisting of halogen, —OH; —COORd, such as COOH, —$C_3$-$C_{10}$cycloalkyl, such as cyclopropyl and aryl, such as phenyl.

In certain embodiments of the compounds described herein, $R^1$ is substituted with —OH, —$C_1$-$C_{10}$alkyl, COOH, —COO—$C_1$-$C_{10}$alkyl, —O—$C_1$-$C_{10}$alkyl, —$C_3$-$C_{10}$cycloalkyl, —SO$_2$$C_1$-$C_{10}$alkyl, —CONC$_1$-$C_{10}$alkyl)$_2$ NH$_2$($C_1$-$C_{10}$alkyl) or heterocycle, wherein the —$C_1$-$C_{10}$alkyl, —$C_3$-$C_{10}$cycloalkyl or —OC$_1$-$C_{10}$alkyl is unsubstituted or substituted with 1-4 substituents selected from the group consisting of halogen and —COOH. In other embodiments of the compounds described herein, $R^1$ is substituted with —OH, COOH, halogen-substituted $C_1$-$C_{10}$alkyl, —O—$C_1$-$C_{10}$alkyl, —$C_3$-$C_{10}$cycloalkyl, halogen or heterocycle, wherein the —$C_1$-$C_{10}$alkyl, —$C_3$-$C_{10}$cycloalkyl or —OC$_1$-$C_{10}$alkyl is unsubstituted or substituted with —COOH.

In still other embodiments, when $R^1$ is phenyl, the phenyl is substituted with one or two substituents selected from the group consisting of cyclopropyl, tetrazol, trifluoromethyl, methyl, chloro, fluoro, methoxy, —COOH and t-butyl, wherein the t-butyl and the cyclopropyl is substituted with —COOH. In yet other embodiments, when $R^1$ is phenyl, the phenyl is substituted with —COOH.

In other embodiments, when $R^1$ is pyridine, the pyridine is substituted with one or two substituents selected from the group consisting of —OH and —COOH.

In any of the compounds described above, $R^2$ is selected from the group consisting of aryl and heterocycle, wherein the aryl or heterocycle is substituted with 1-4 substituents independently selected from α. In certain embodiments, $R^2$ is aryl. Suitable aryl includes, but is not limited to, phenyl. In other embodiments, $R^2$ is heterocycle wherein the heterocycle is imidazole, naphthalene, phenyl, pyridine, benzimidazole, indole, oxazole, thiazole, benzofuran, benzocyclopentane, benzotetrahydropyran or pyrazole. In certain embodiments, $R^2$ is pyridine. In yet other embodiments, $R^2$ is imidazole.

With regard to the compounds described herein, $R^2$ is substituted with 1-5 substituents independently selected from α. In certain embodiments, $R^2$ is substituted with one substituent independently selected from α. In other embodiments, $R^2$ is substituted with two substituents independently selected from α. In still other embodiments, $R^2$ is substituted with three substituents independently selected from α. In still other embodiments, $R^2$ is substituted with four substituents independently selected from α. In still other embodiments, $R^2$ is substituted with five substituents independently selected from α.

With regard to the compounds described herein, $R^2$ is substituted with 1-5 substituents independently selected from α, wherein α is selected from the group consisting of: halogen, —C₁-C₁₀alkyl, —C₃-C₁₀cycloalkyl, heterocycle, aryl, —OH, —O—C₁-C₁₀alkyl, —O—C₃-C₁₀cycloalkyl, —O-aryl, —O-heterocycle, —NRbS(O)₂Rc, —NRbRc, —CN, —NRbC(O)Rc, —S(O)₂Rb, —S(O)₂NRbRc, —C(O)NRbRc, —C(O)NRb(C₁-C₁₀alkyl-NH—C₁-C₁₀alkyl), —NRbC(O)ORc, —NRbC(O)NRcRd, —NRbC(O)NH₂, —NRbS(O)₂Rc, —NO₂, —C(O)Rd, —COORd, and —OC(O)Rd, wherein, Rb, Rc and Rd are independently selected from the group consisting of hydrogen, —C₁-C₁₀alkyl, —C₃-C₁₀cycloalkyl, aryl, and heterocycle; and wherein any —C₃-C₁₀cycloalkyl, aryl, or heterocycle is independently unsubstituted or substituted with 1-4 substituents selected from the group consisting of halogen, NH₂, N(CH₂)₂, —C₃-C₁₀cycloalkyl, heterocycle, —COORd, —OH, —O—C₁-C₁₀alkyl and —C₁-C₁₀alkyl; and wherein any —C₁-C₁₀alkyl or —OC₁-C₁₀alkyl is independently unsubstituted or substituted with 1-4 substituents selected from the group consisting of halogen, —OH, —COORd, —C₃-C₁₀cycloalkyl and aryl.

In certain embodiments, R² is substituted with substituents selected from the group consisting of halogen, —C₁-C₁₀alkyl, —O—C₁-C₁₀alkyl, aryl, heterocycle and —C₃-C₁₀cycloalkyl wherein the aryl, —C₁-C₁₀alkyl, heterocycle, —O—C₁-C₁₀alkyl or —C₃-C₁₀cycloalkyl is unsubstituted or substituted with 1-4 substituents selected from the group consisting of halogen, —C₁-C₁₀alkyl and —O—C₁-C₁₀alkyl. Suitable —C₁-C₁₀alkyls include, but are not limited to, methyl, butyl and hexane. Suitable —O—C₁-C₁₀alkyls include, but are not limited to, methoxy, ethoxy and propoxy. Suitable aryls include, but are not limited to, phenyl and naphthalene. Suitable heterocycles include, but are not limited to, pyridine, benzodioxane, thiazole and pyrazole. Suitable cycloalkyls include, but are not limited to, cyclopropyl, cyclohexane and dimethylbicycloheptane. In other embodiments, R² is substituted with 1-3 substituents selected from the group consisting of —O—C₁-C₁₀alkyl, —O-halogen-substituted C₁-C₁₀alkyl and halogen-substituted phenyl.

The aryl, —C₁-C₁₀alkyl, heterocycle, —O—C₁-C₁₀alkyl or —C₃-C₁₀cycloalkyl is unsubstituted or substituted with 1-4 substituents selected from the group consisting of halogen, —C₁-C₁₀alkyl and —O—C₁-C₁₀alkyl. In certain embodiments, the aryl, —C₁-C₁₀alkyl, heterocycle, —O—C₁-C₁₀alkyl or —C₃-C₁₀cycloalkyl is unsubstituted. In other embodiments, the aryl, —C₁-C₁₀alkyl, heterocycle, —O—C₁-C₁₀alkyl or —C₃-C₁₀cycloalkyl is substituted with 1 substituent. In still other embodiments, the aryl, —C₁-C₁₀alkyl, heterocycle, —O—C₁-C₁₀alkyl or —C₃-C₁₀cycloalkyl is substituted with 2 substituents. In still other embodiments, the aryl, —C₁-C₁₀alkyl, heterocycle, —O—C₁-C₁₀alkyl or —C₃-C₁₀cycloalkyl is substituted with 3 substituents. In still other embodiments, the aryl, —C₁-C₁₀alkyl, heterocycle, —O—C₁-C₁₀alkyl or —C₃-C₁₀cycloalkyl is substituted with 4 substituents. Suitable —C₁-C₁₀alkyls and —O—C₁-C₁₀alkyls are discussed above. Suitable halogens include chlorine, fluorine and bromine.

In certain embodiments, R² is substituted with substituents selected from the group consisting of t-butyl, trifluorophenyl, difluorophenyl, fluorophenyl, methoxy, ethoxy, cyclohexane, chloro-fluorophenyl, phenyl, methoxyphenyl, cyclopropyl, trifluoromethylphenyl, bimethylphenyl, cloro-di-florophenyl, methyl, trifluomethyl, butyl, propoxy, benxodioxane, trifluoromethoxyphenyl, trifluoromethoxy, trifluoromethylpyridine, dimethylbicycloheptane, chlorine, bromine, naphthalene, methylpyridine, fluoropyridine, fluoromethoxyphenyl, pyrazole, thiazole, hexane and trifluorohexane.

In certain embodiments, R² is phenyl, wherein the phenyl is substituted with substituents consisting of ethoxy and phenyl, wherein the phenyl is substituted with 1-3 halogens such as fluorine and chlorine.

Also described herein are compounds of structural formula Ib and Ic:

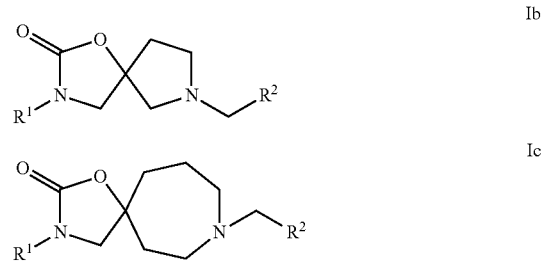

or a pharmaceutically acceptable salt thereof, wherein R¹ is phenyl, wherein the phenyl is substituted with at least one substituent selected from α. In certain embodiments, R¹ is substituted with —COOH. R² is phenyl or heterocycle, wherein the phenyl or heterocycle is substituted with 1-4 substituents independently selected from α; wherein α is discussed above. In certain embodiments, R² is imidazole or phenyl. In other embodiments, R² is imidazole, indole or phenyl. In other embodiments, R² is substituted with 1-4 substituents selected from the group consisting of —C₁-C₁₀alkyl, —O—C₁-C₁₀alkyl, heterocycle and aryl, wherein the aryl, heterocycle —C₁-C₁₀alkyl or —O—C₁-C₁₀alkyl is unsubstituted or substituted with 1-4 substituents selected from the group consisting of halogen, -halogen-substituted C₁-C₁₀alkyl and —O—C₁-C₁₀alkyl.

Examples of the compounds described herein include, but are not limited to:

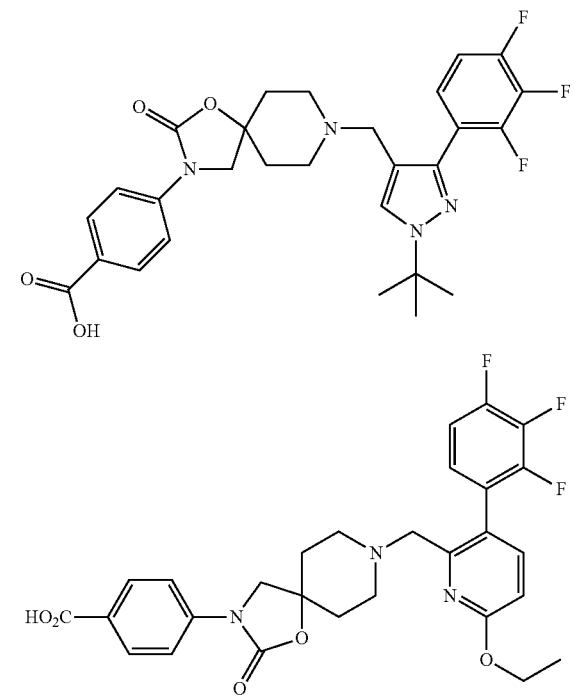

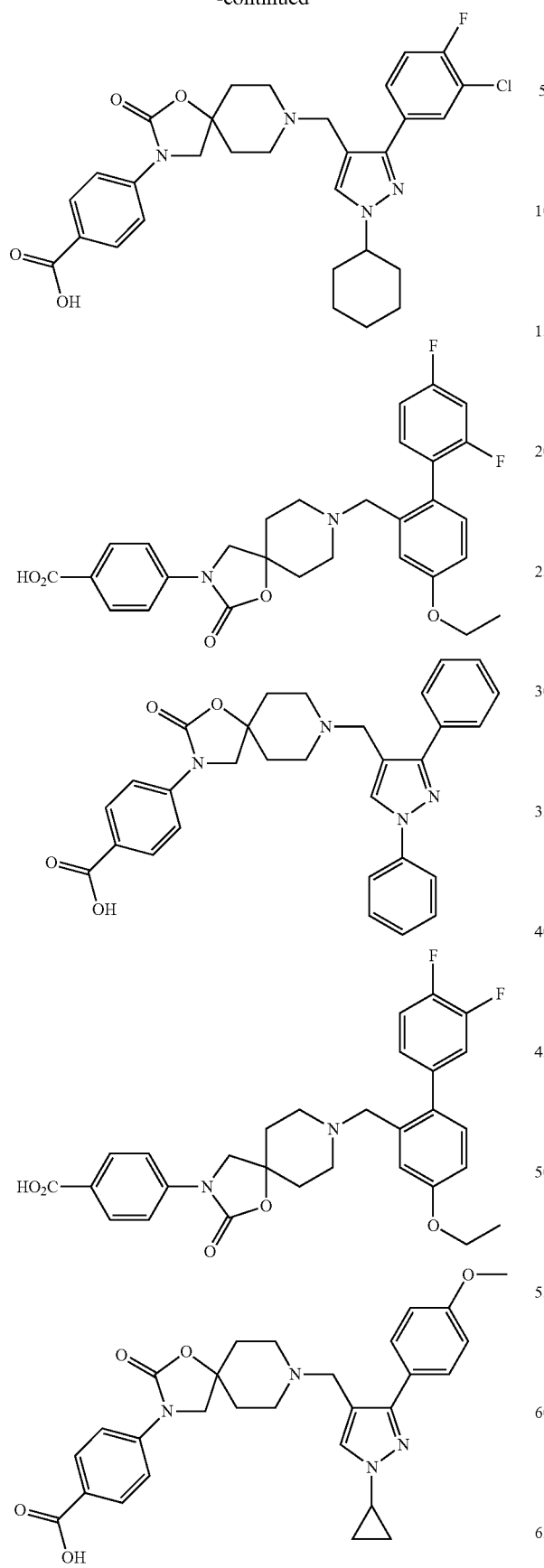
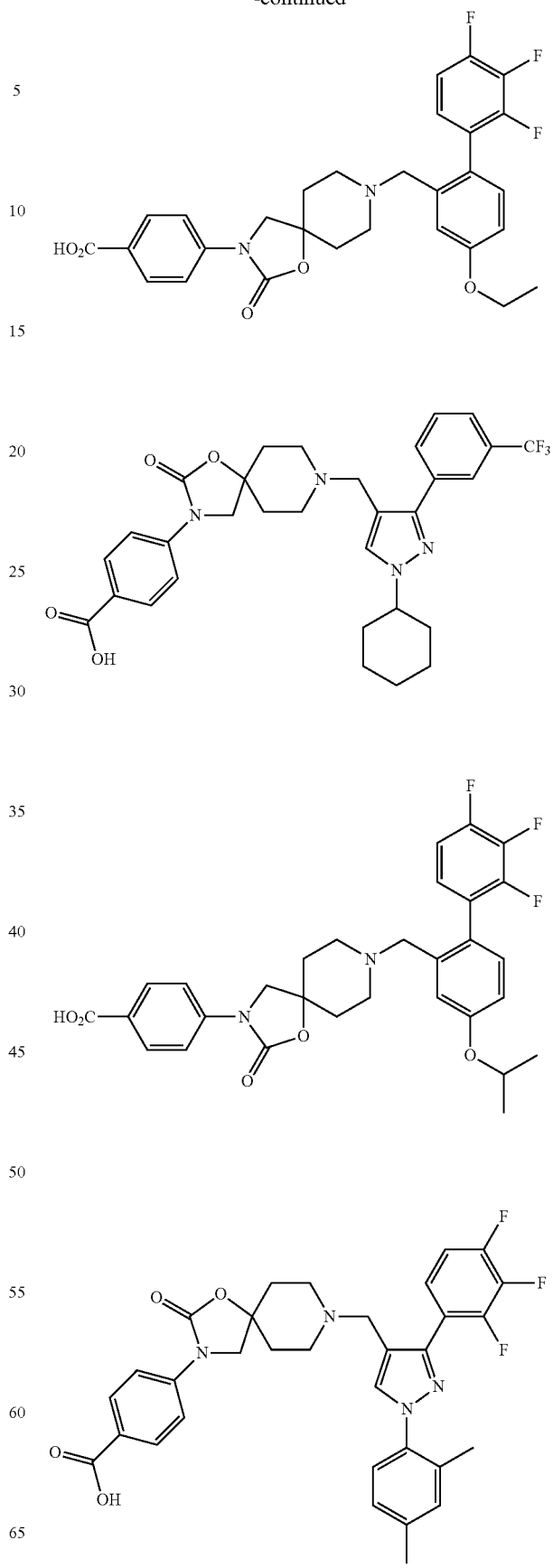

-continued
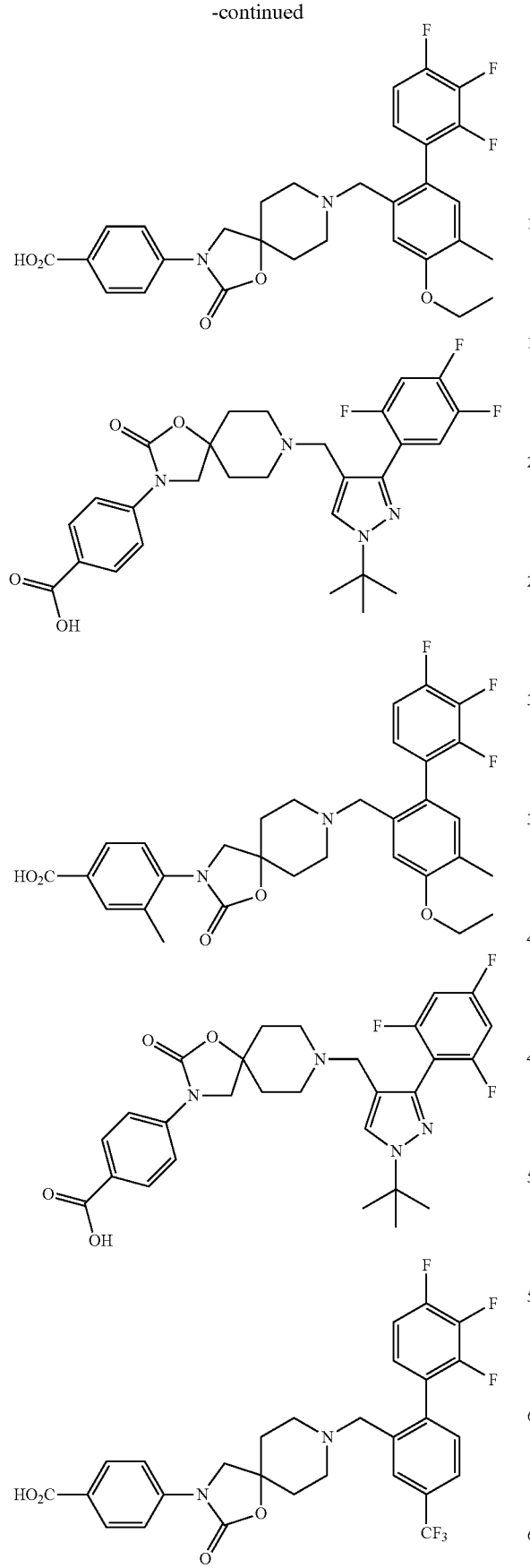
-continued
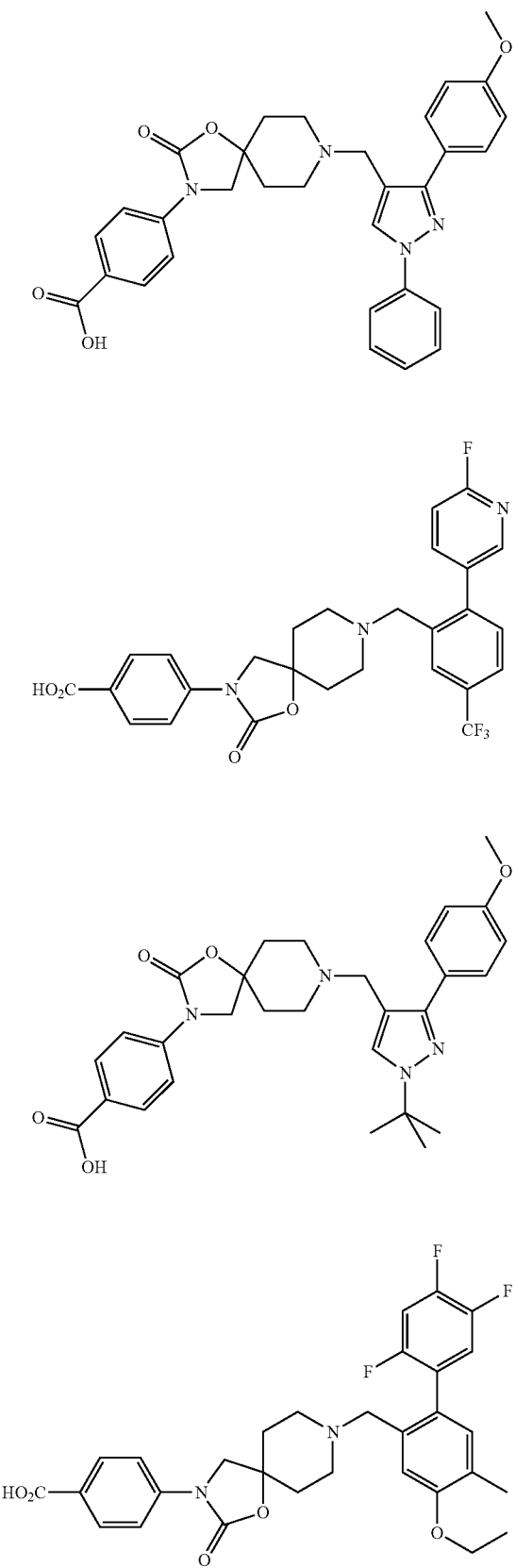

15
-continued
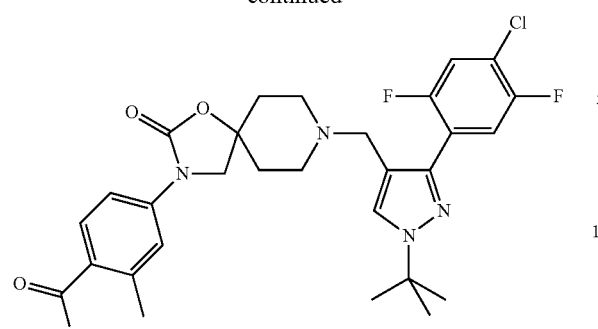
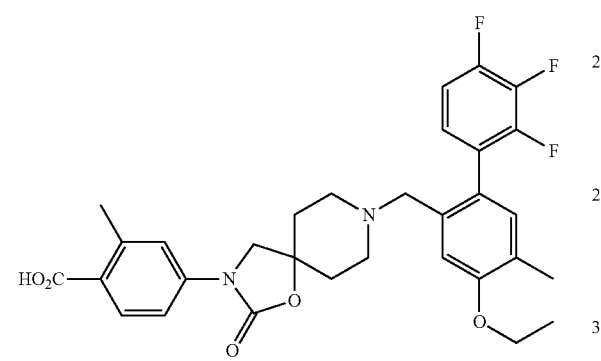
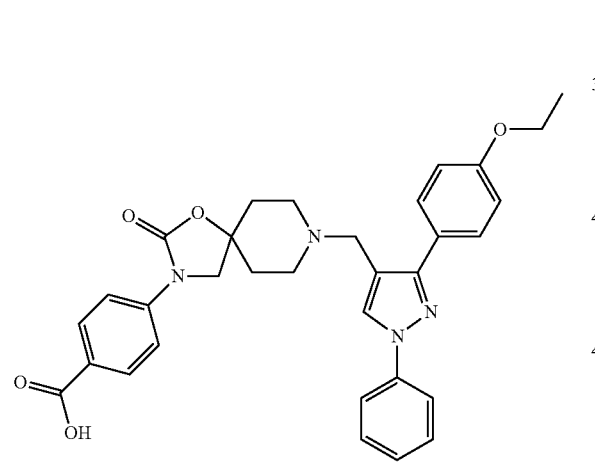
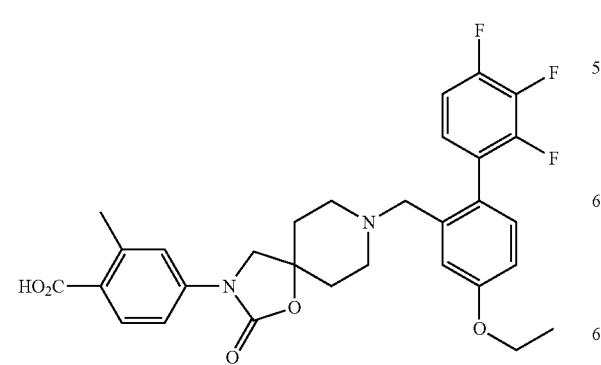
16
-continued
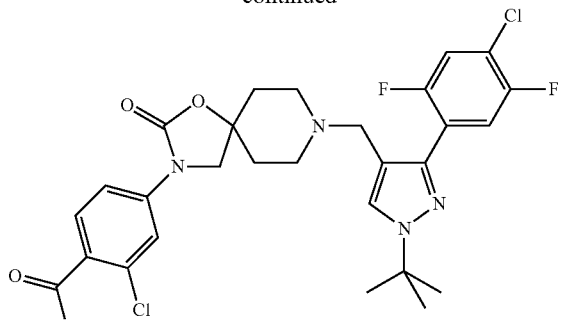
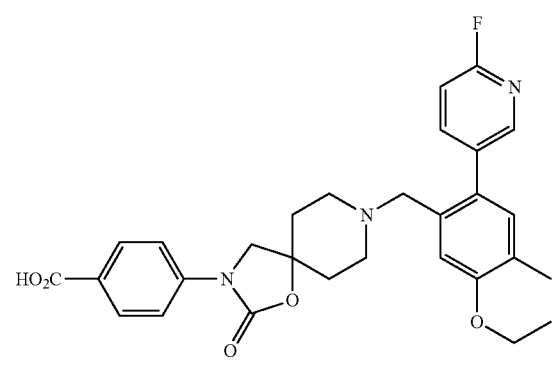
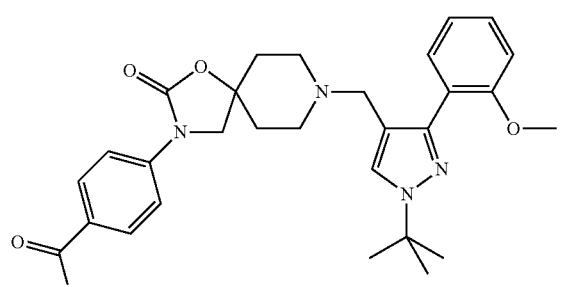
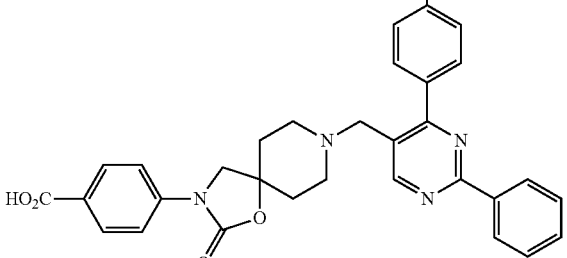
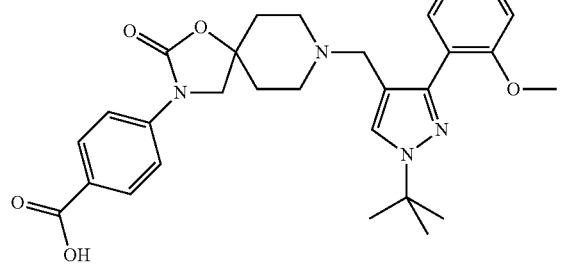

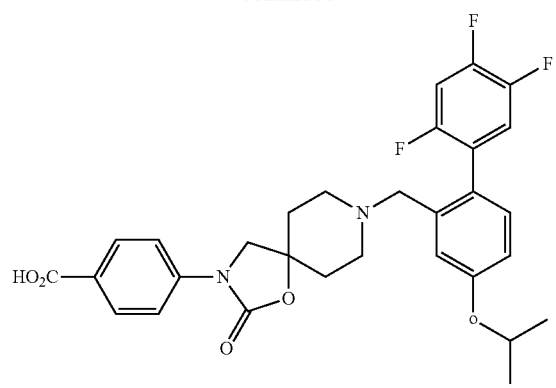
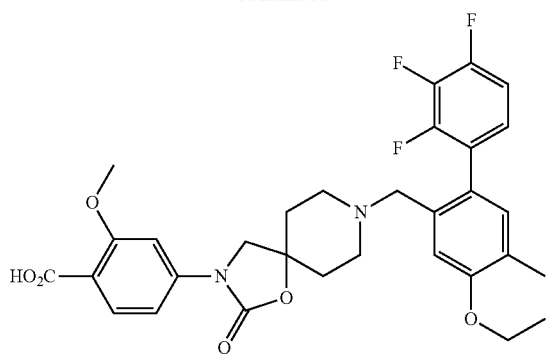
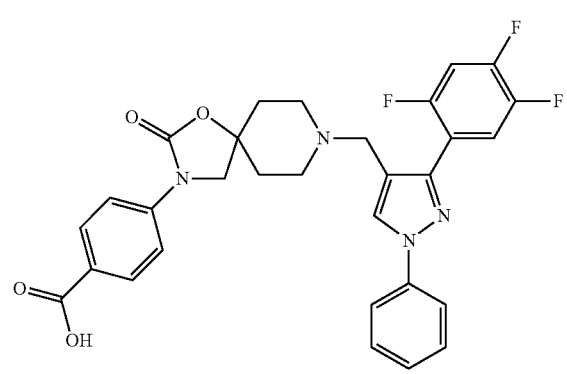
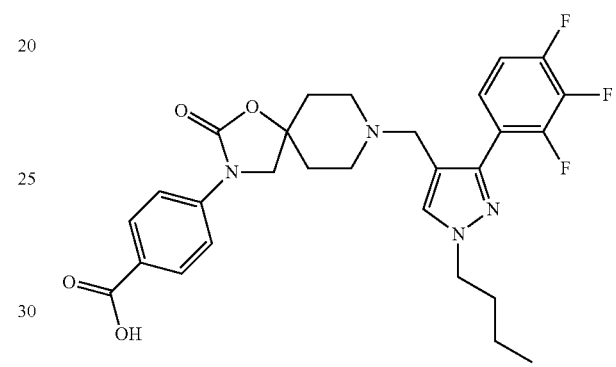
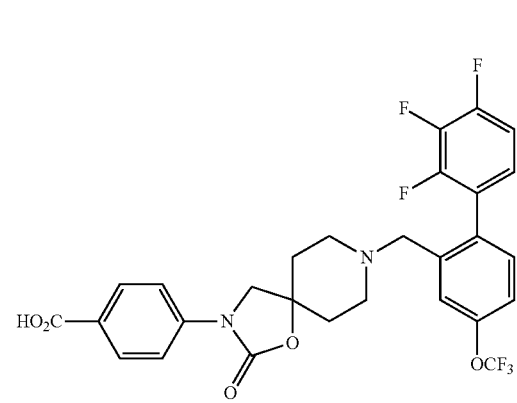
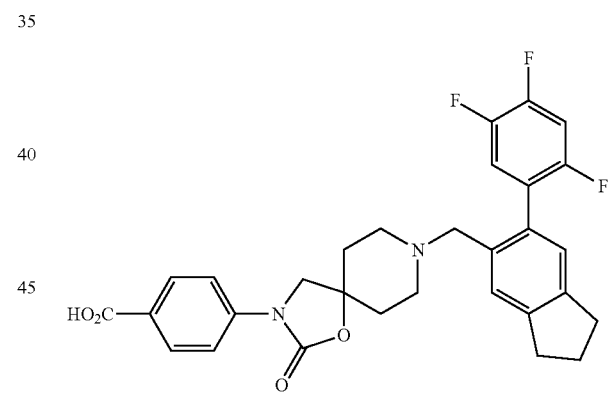
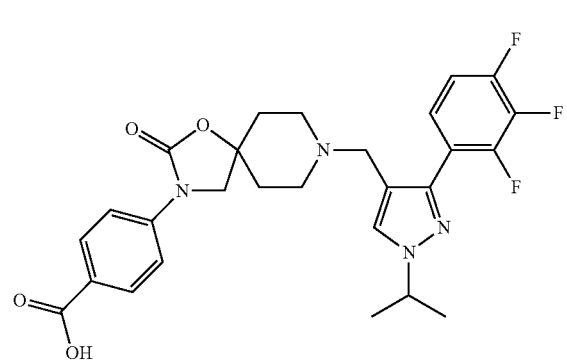
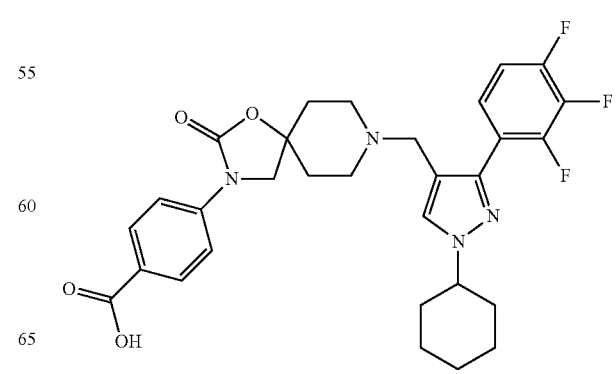

-continued
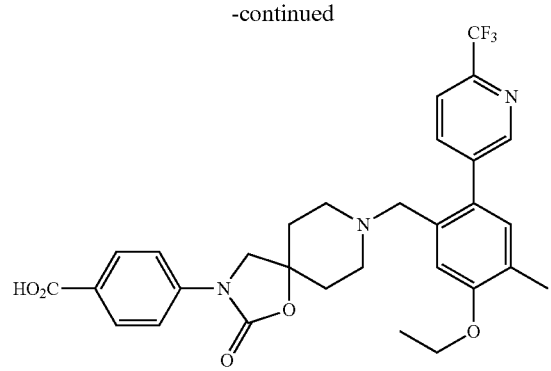
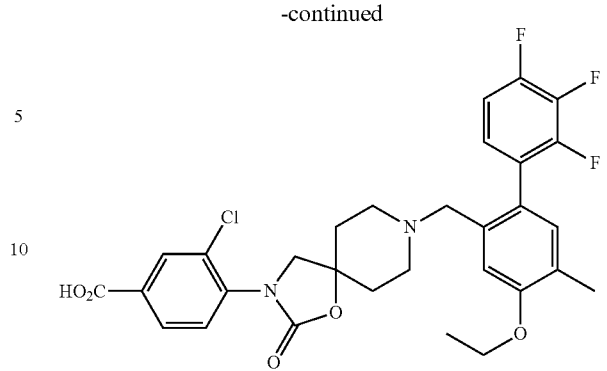
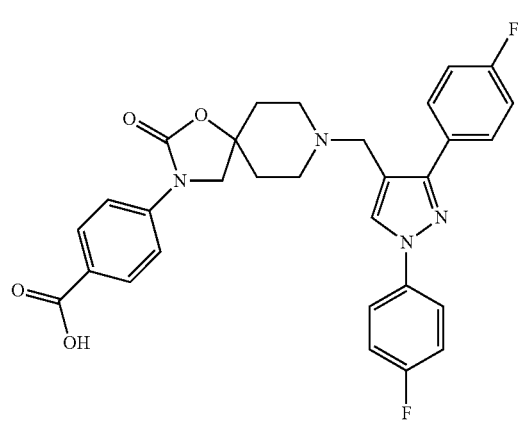
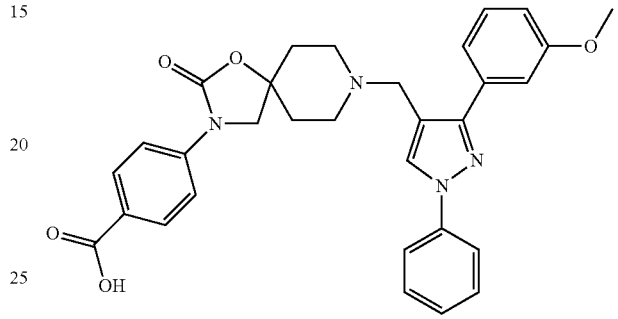
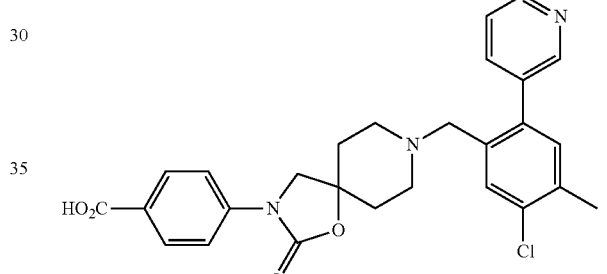
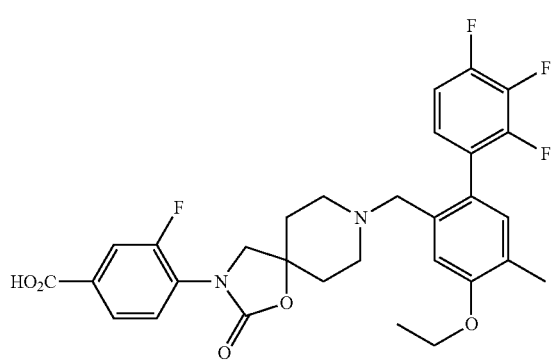
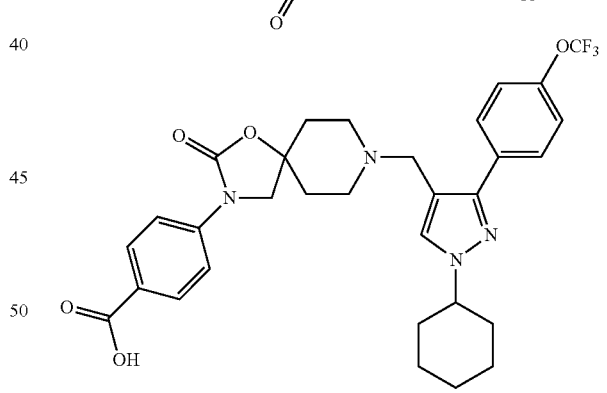
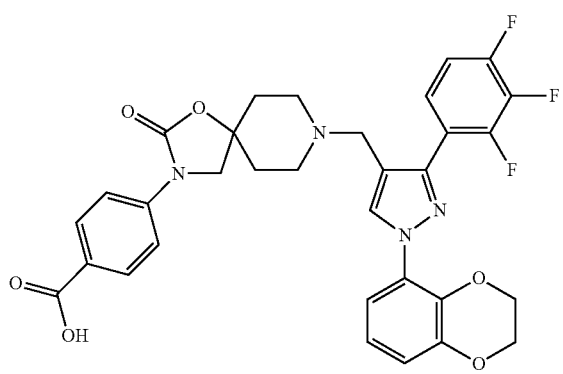
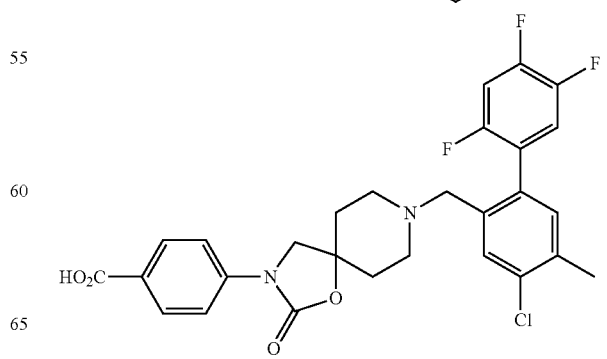

21
-continued
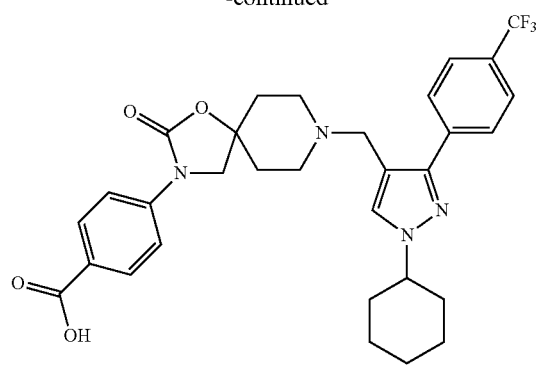
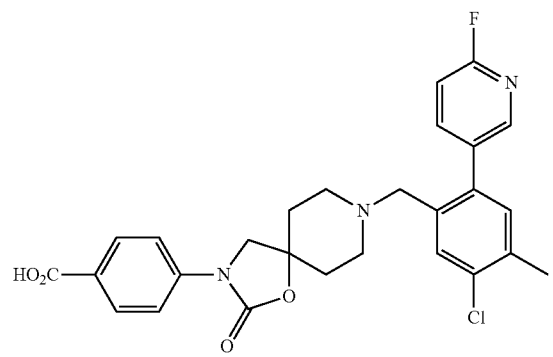
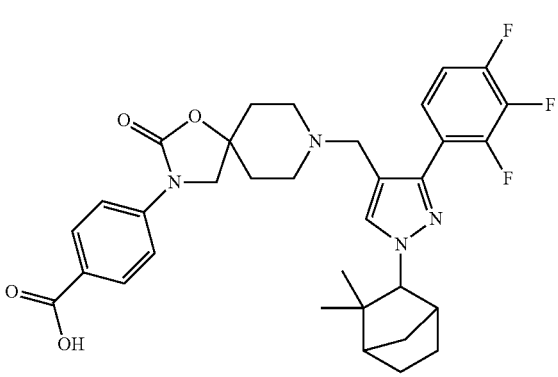
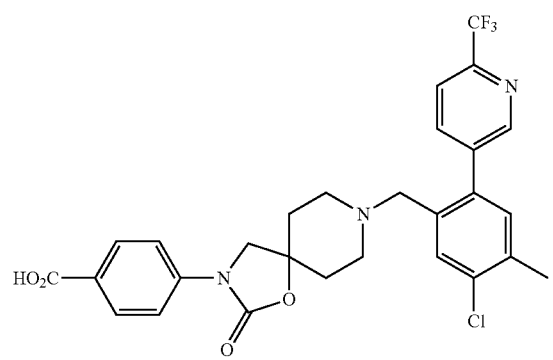
22
-continued
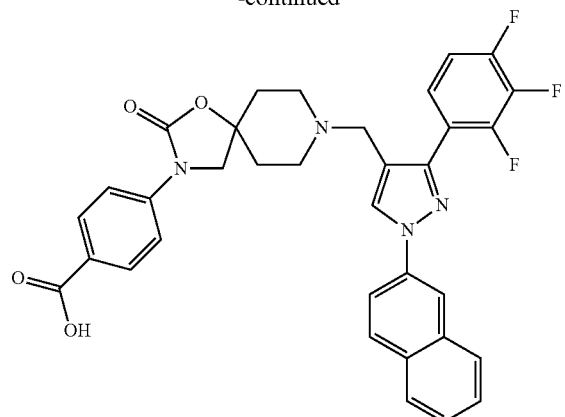
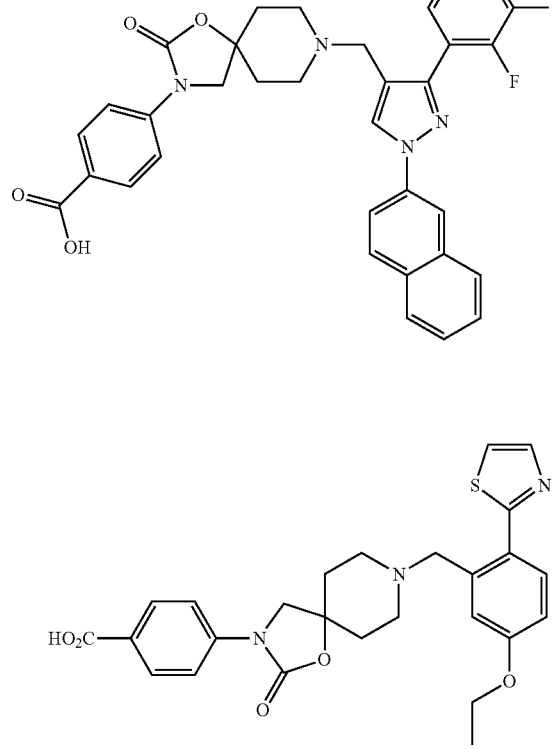
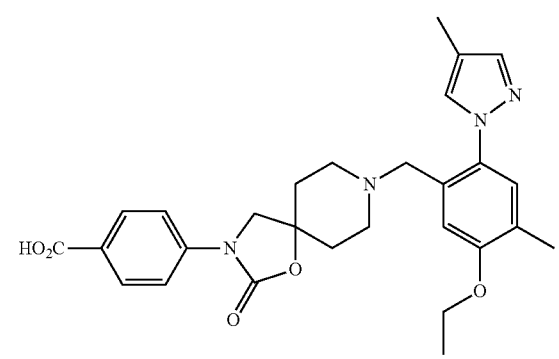

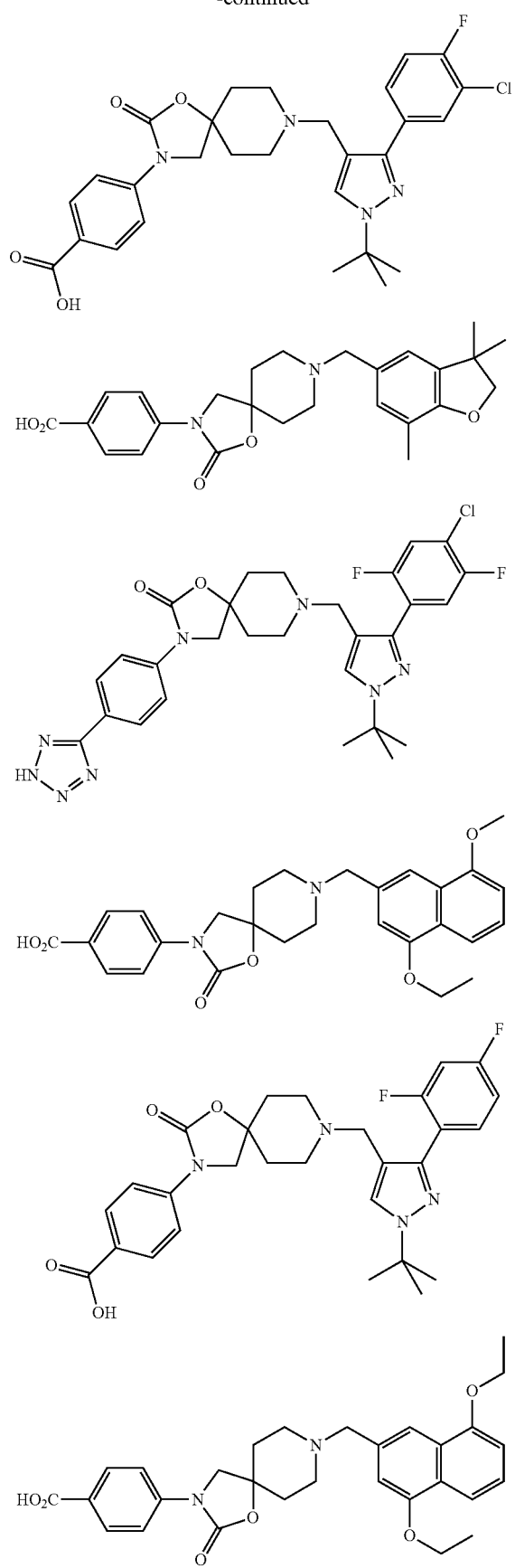
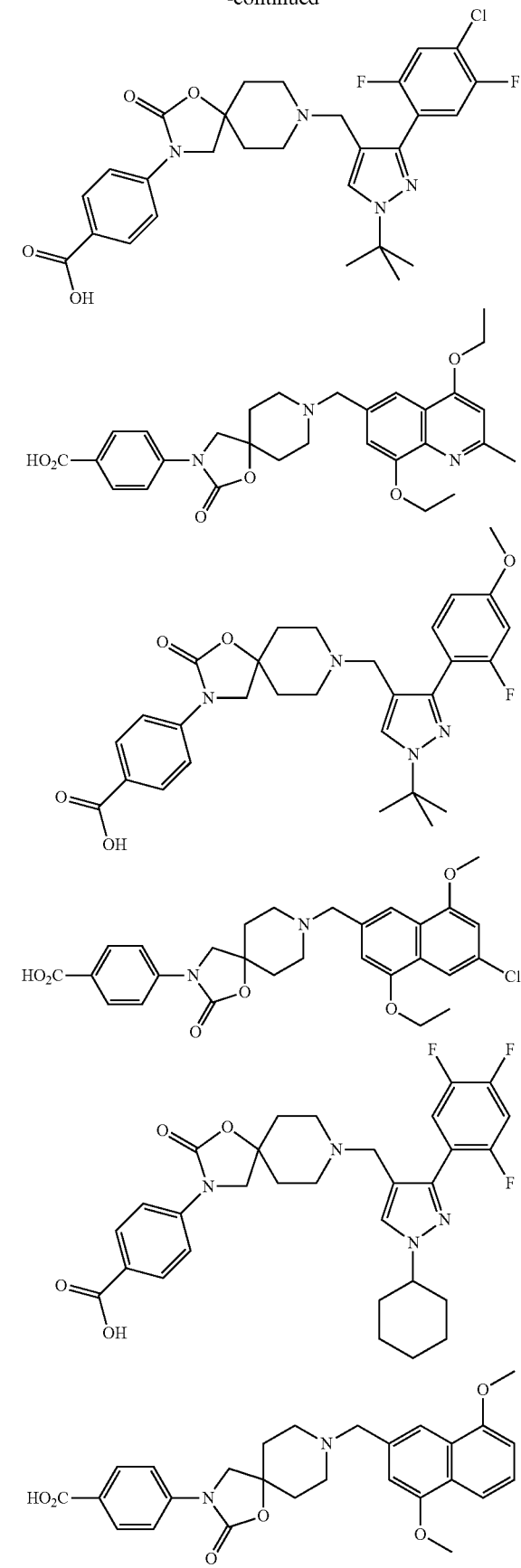

25
-continued
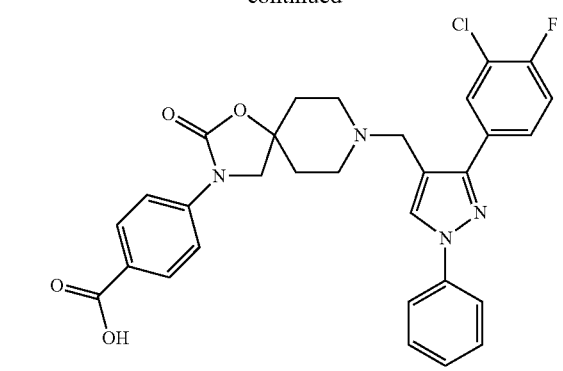
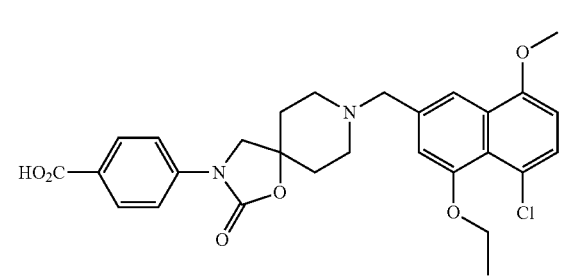
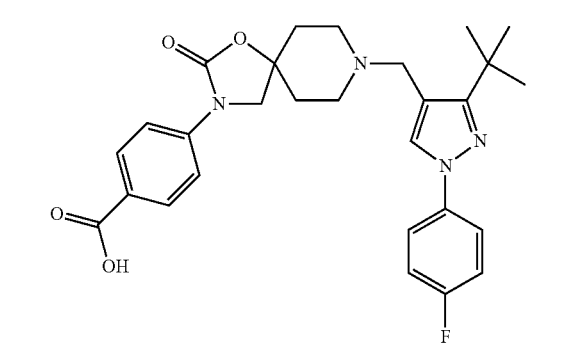
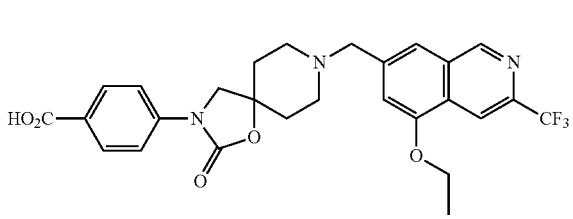
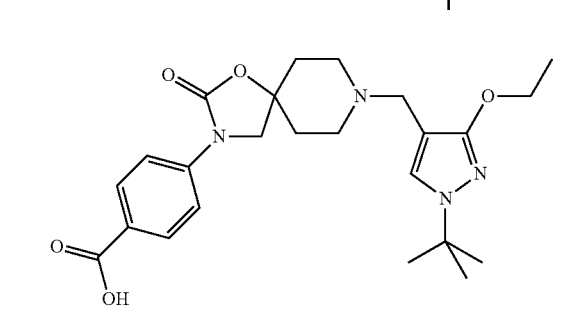
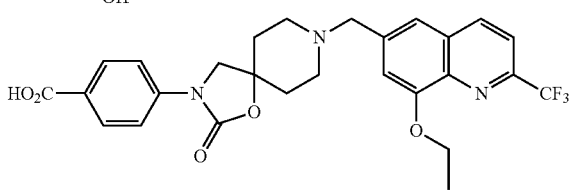
26
-continued
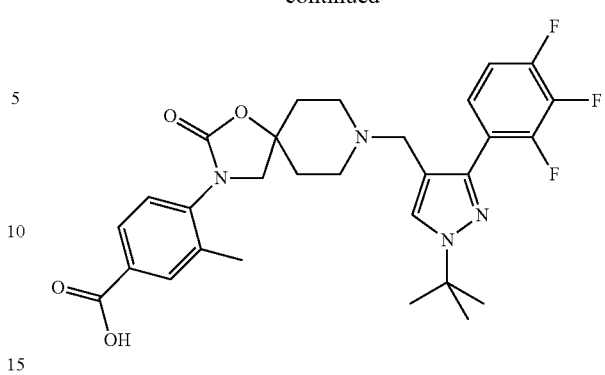
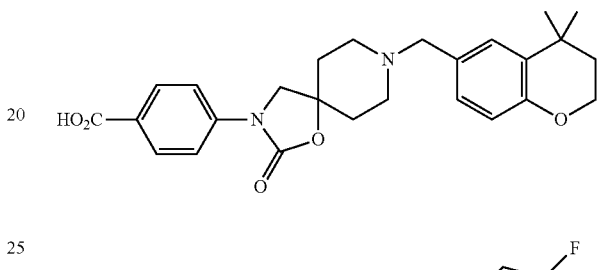
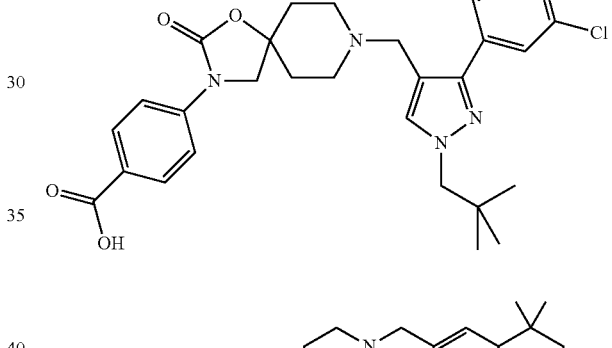
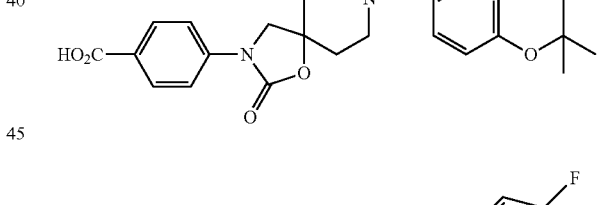
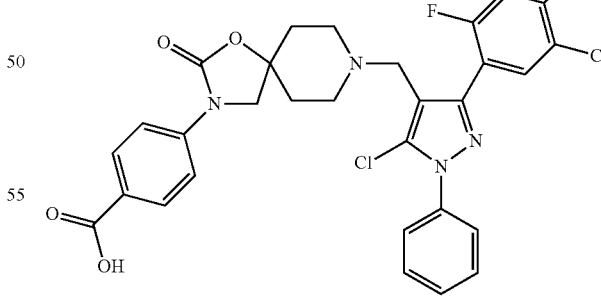
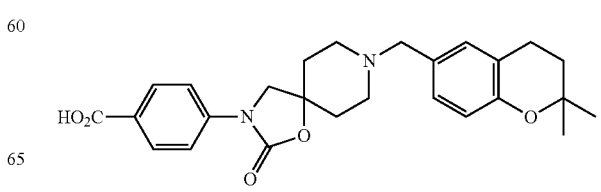

27
-continued
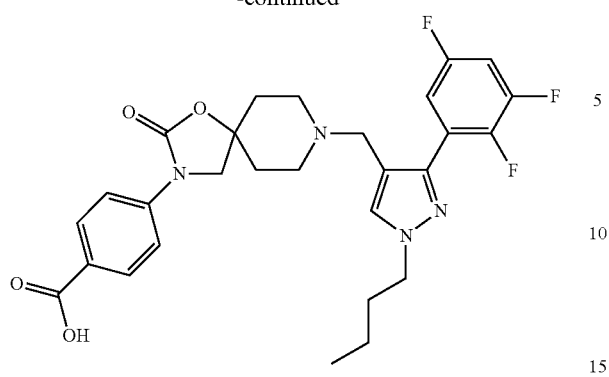
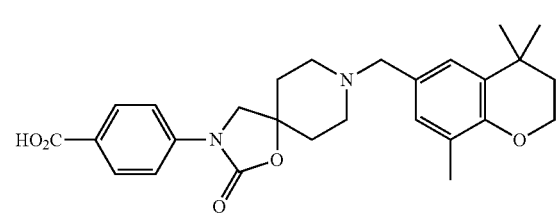
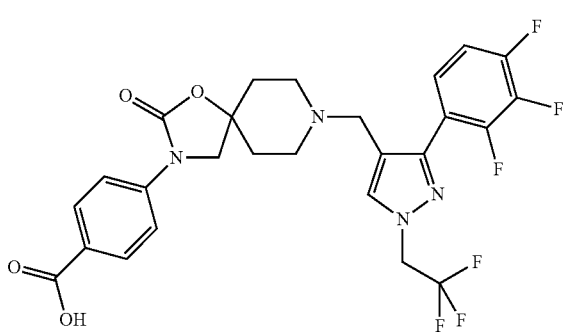
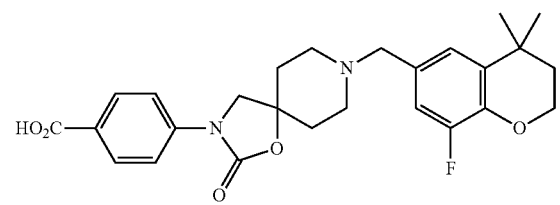
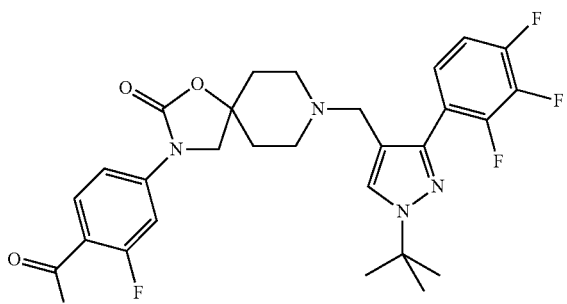
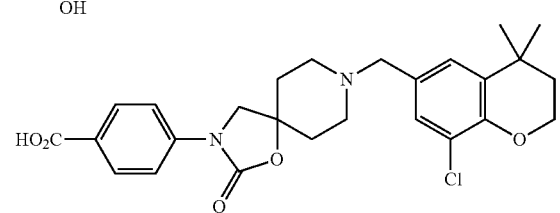
28
-continued
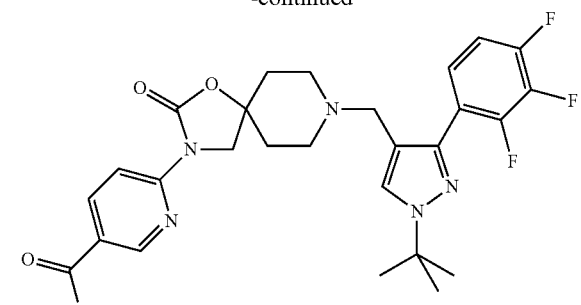
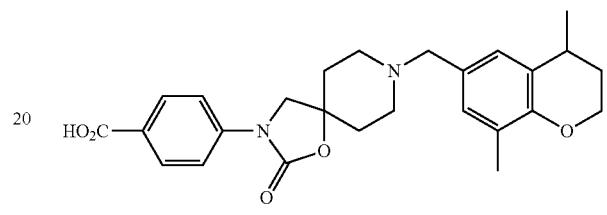
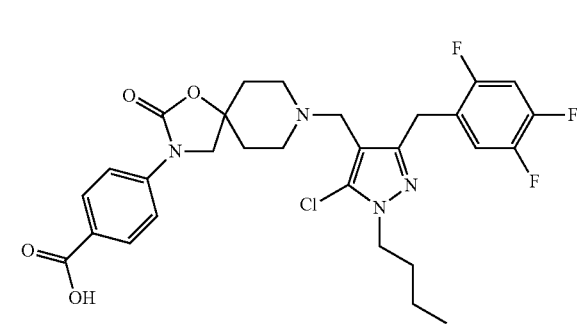
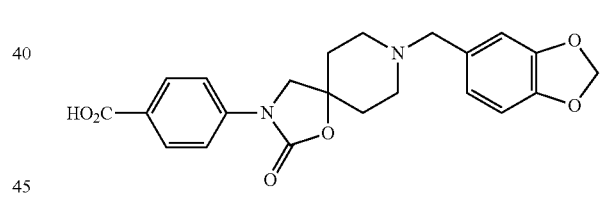
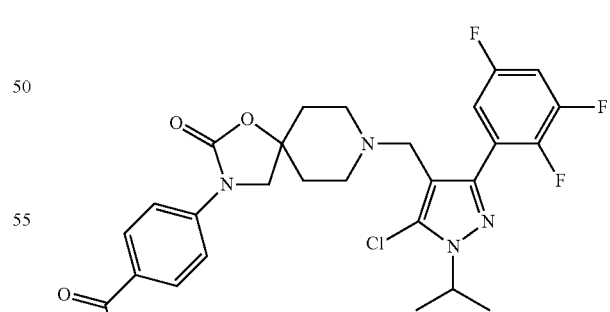
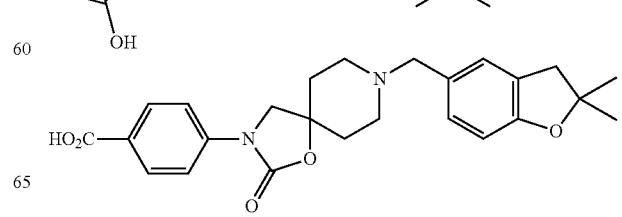

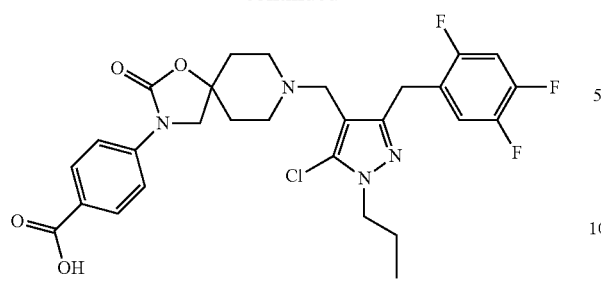
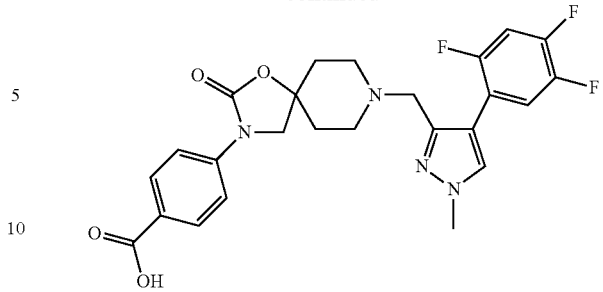
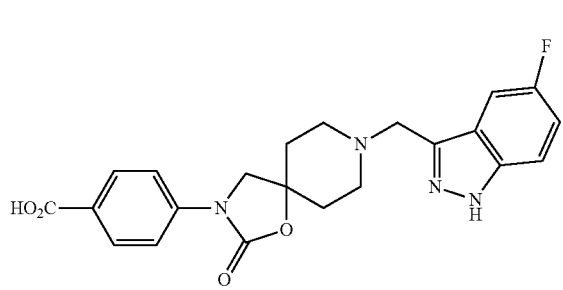
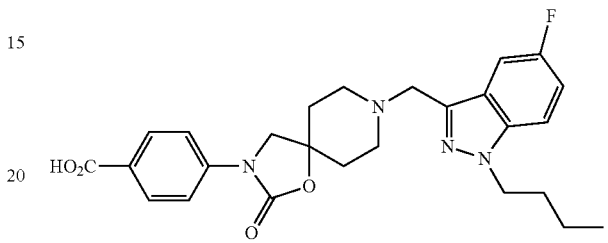
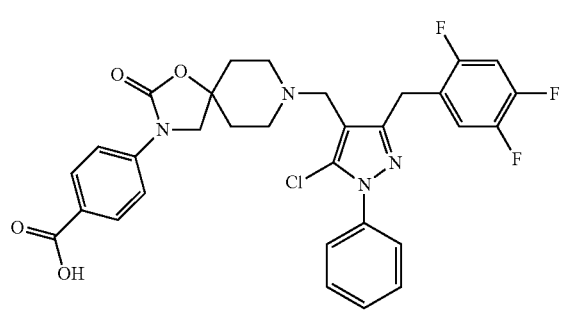
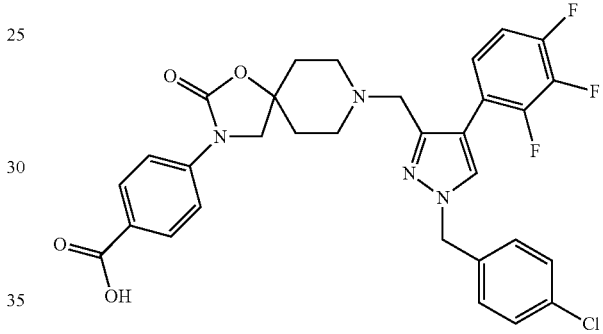
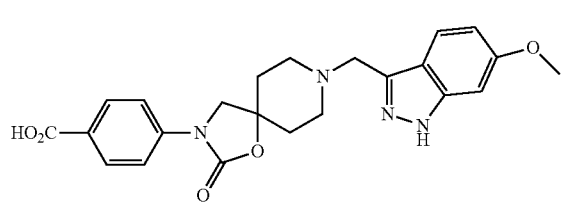
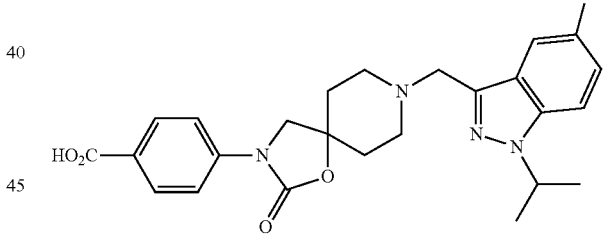
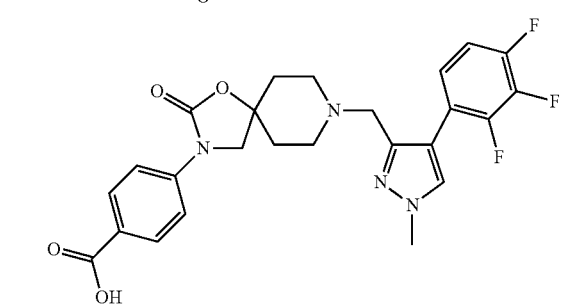
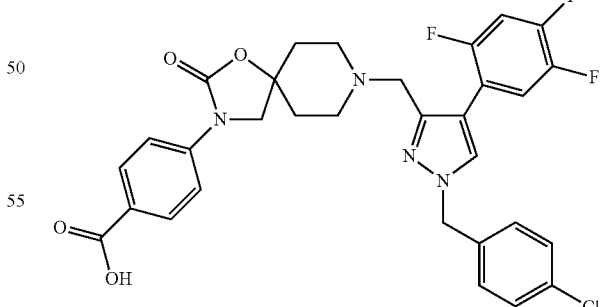
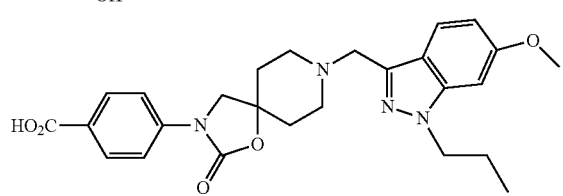
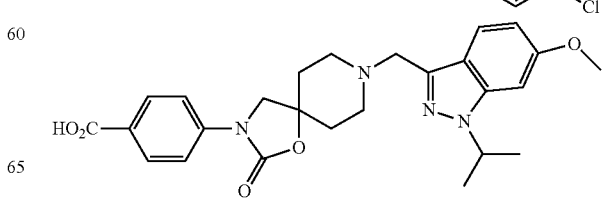

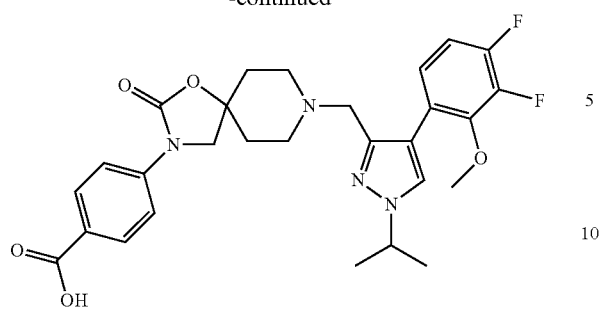
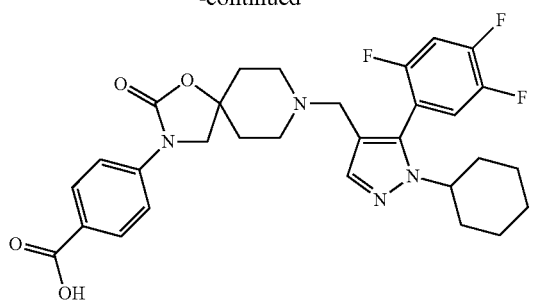
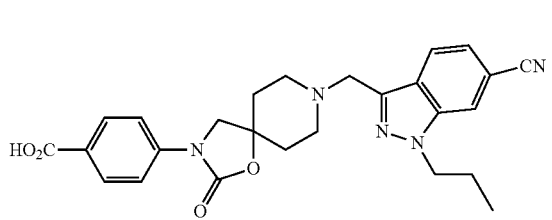
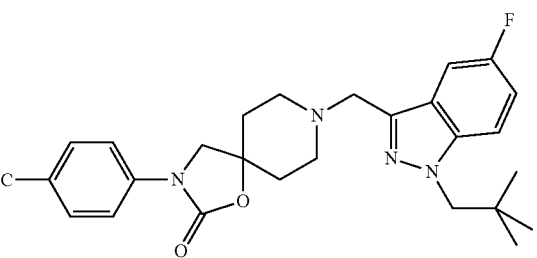
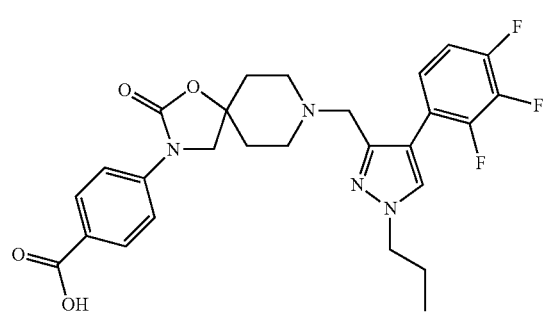
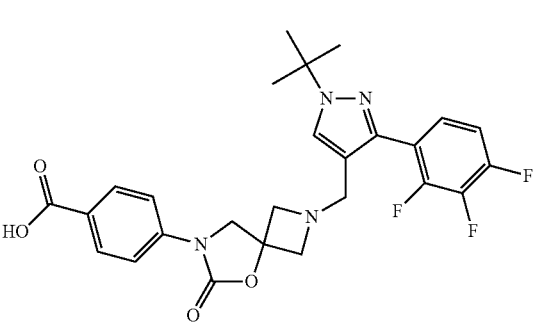
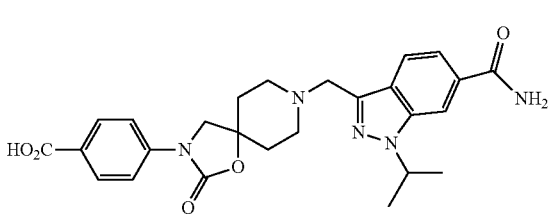
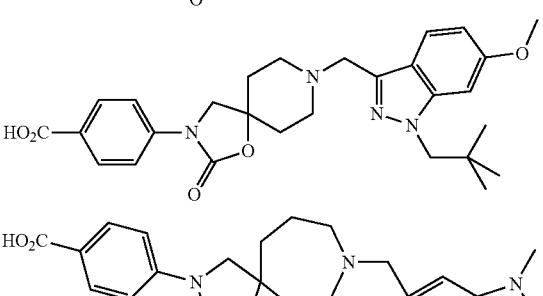
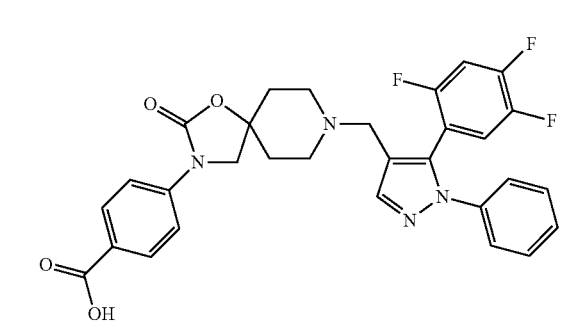
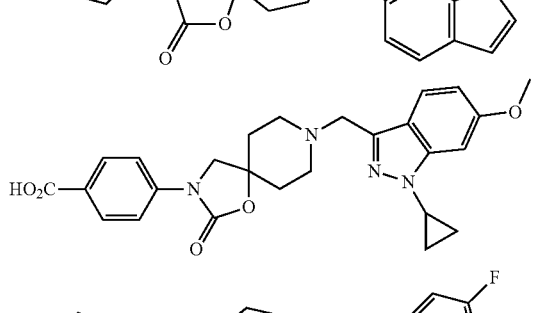
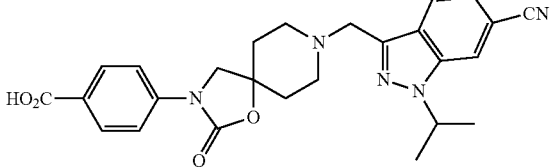
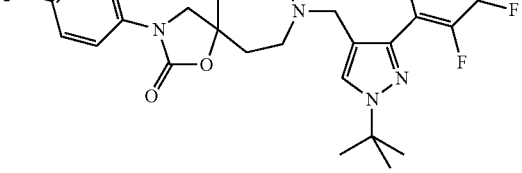

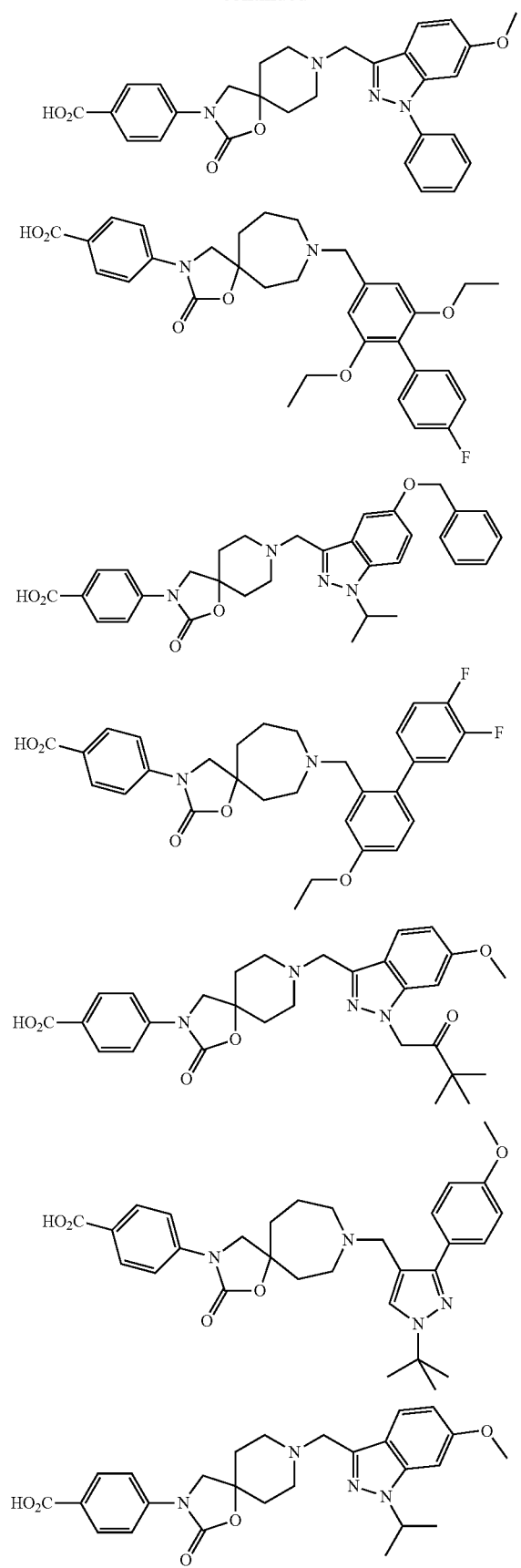
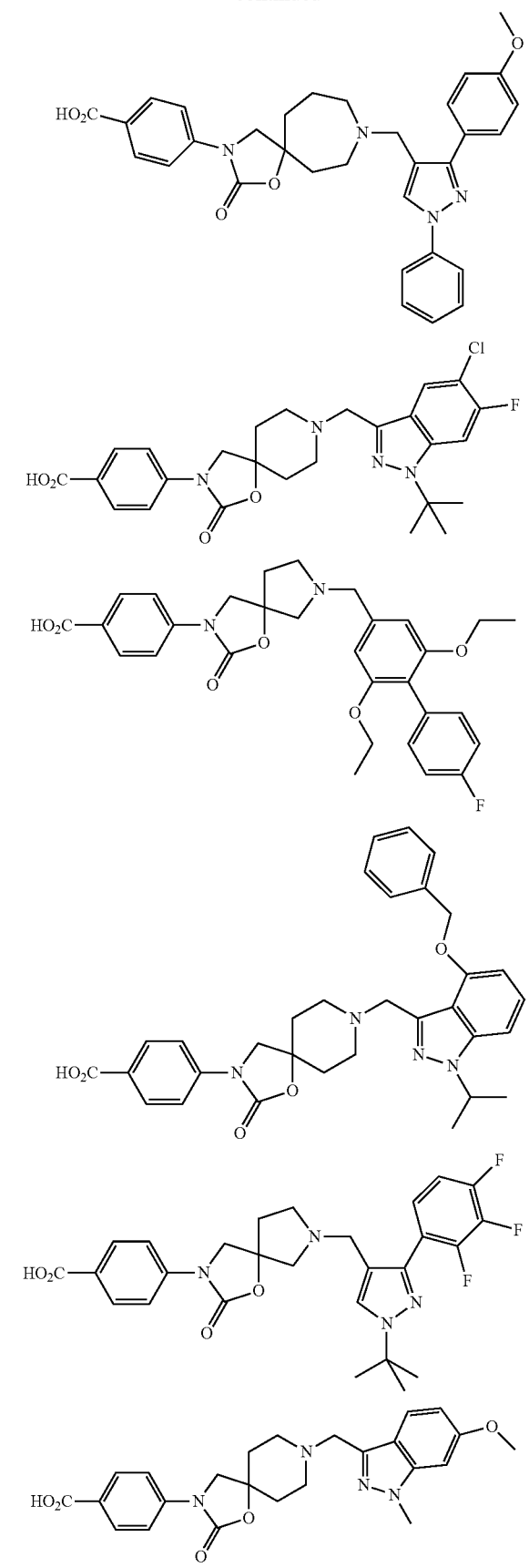

35
-continued
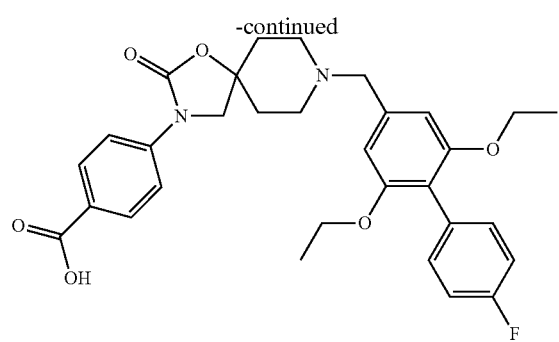
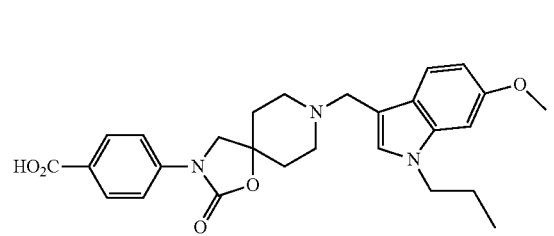
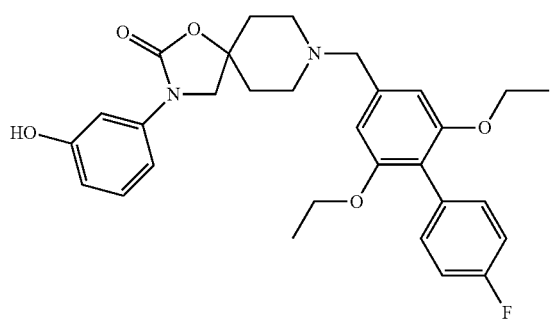
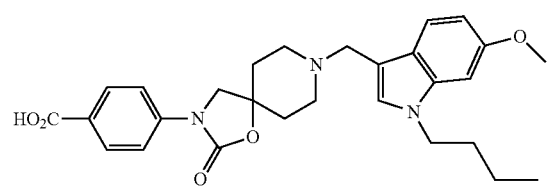
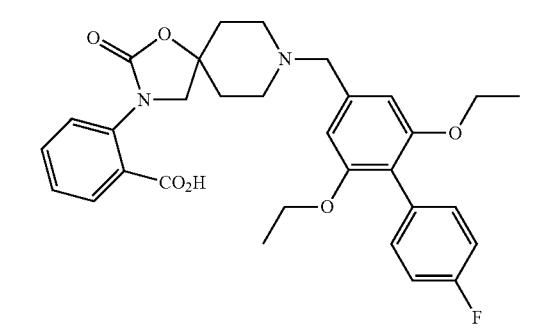
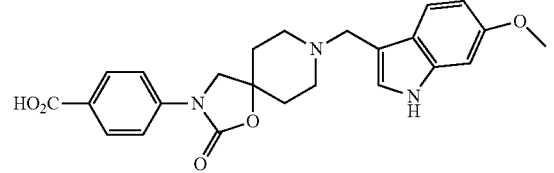
36
-continued
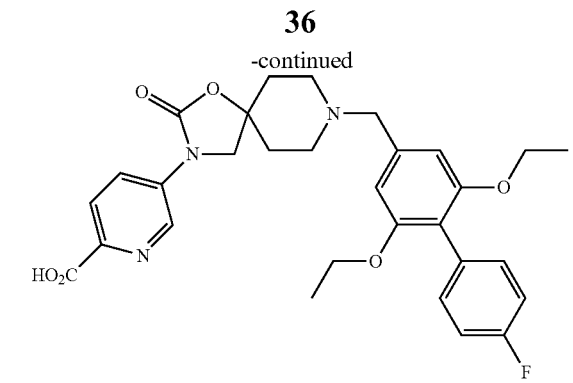
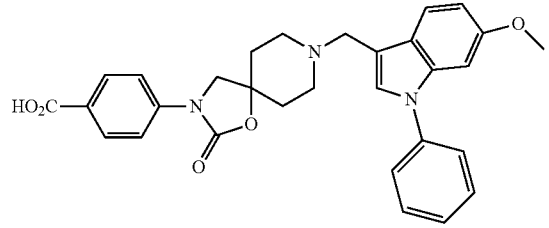
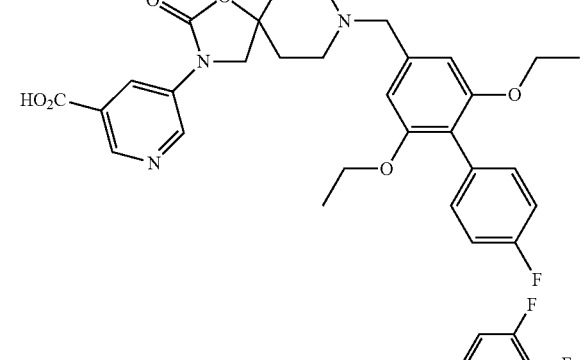
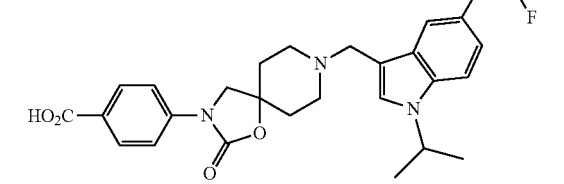
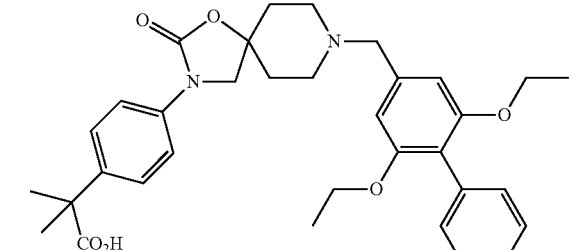
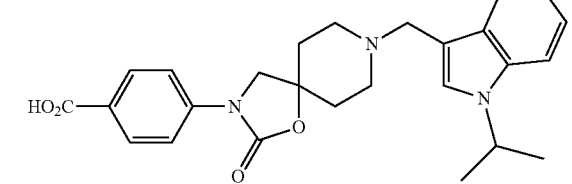

-continued
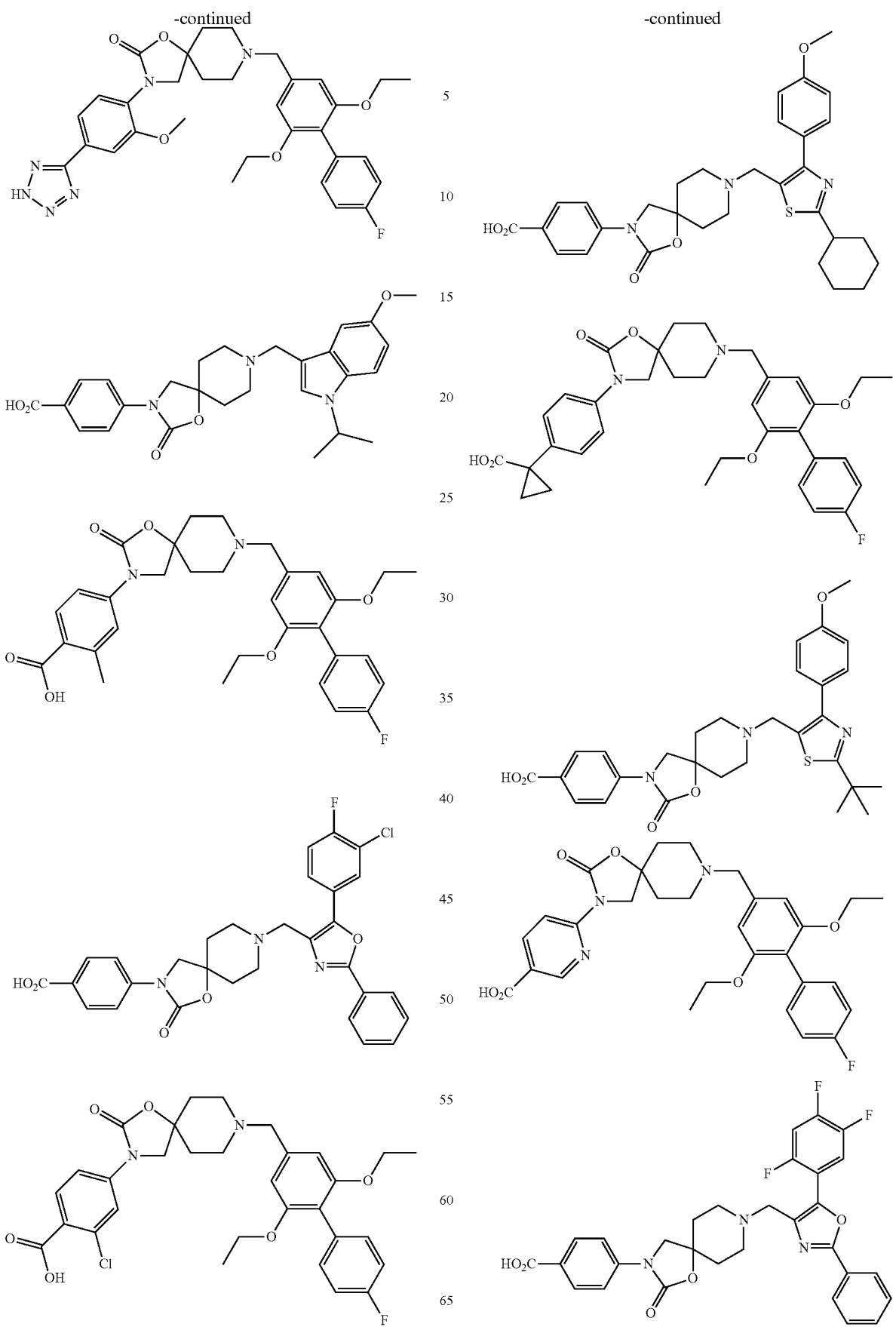

39
-continued
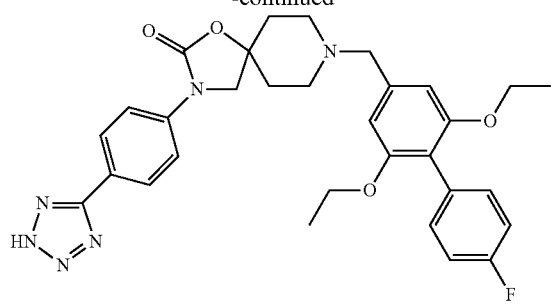
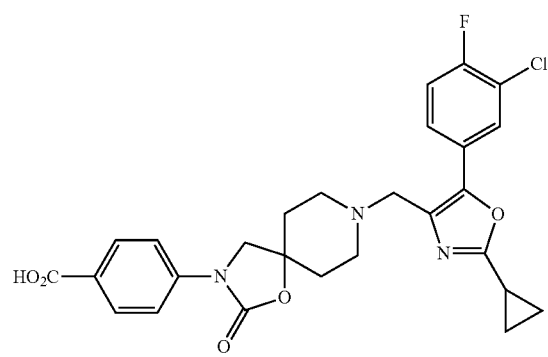
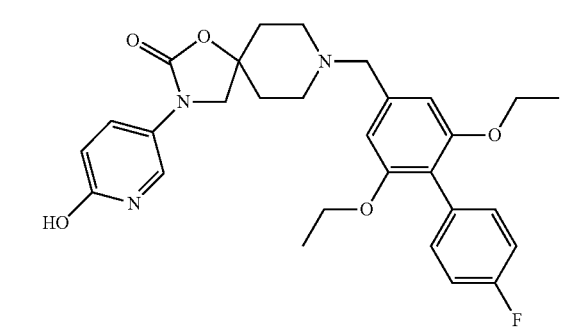
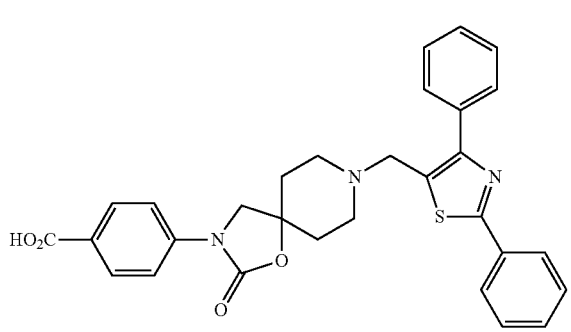
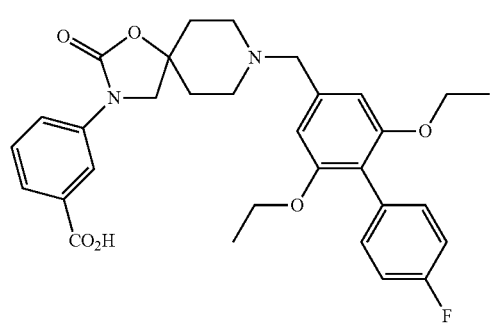
40
-continued
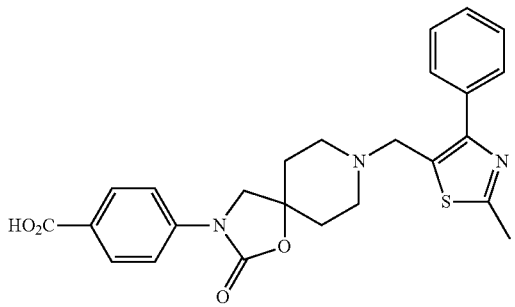
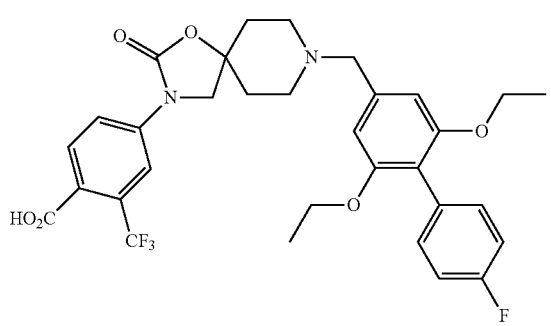
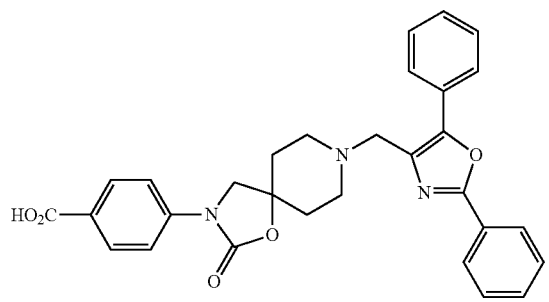
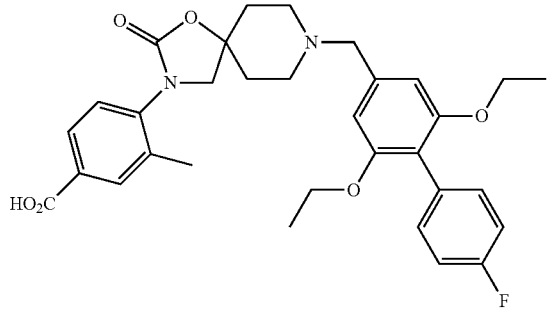
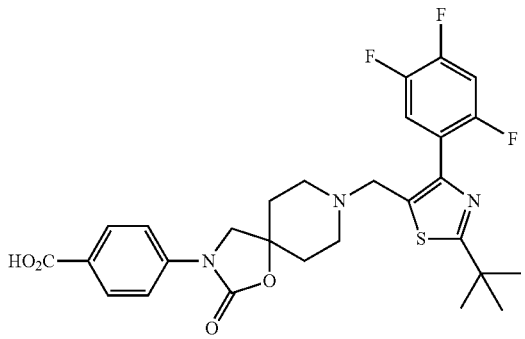

41
-continued
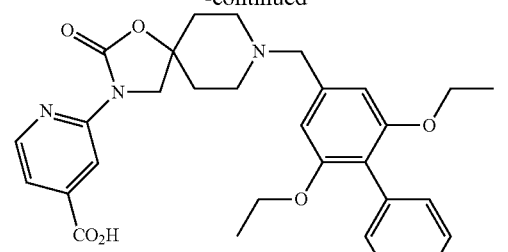
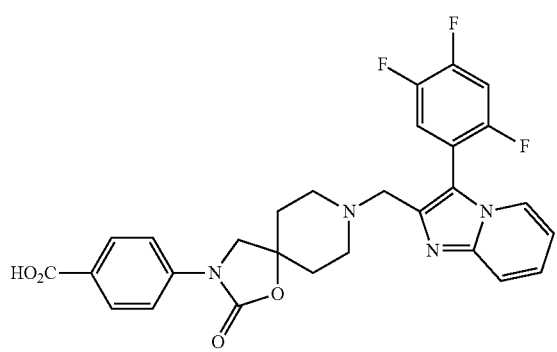
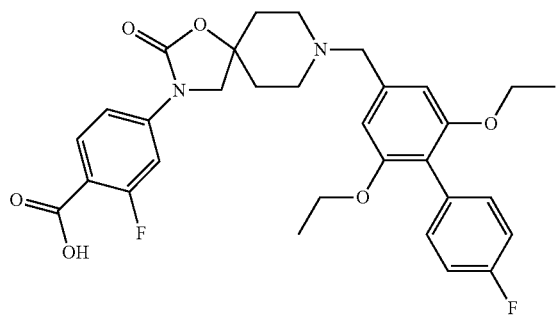
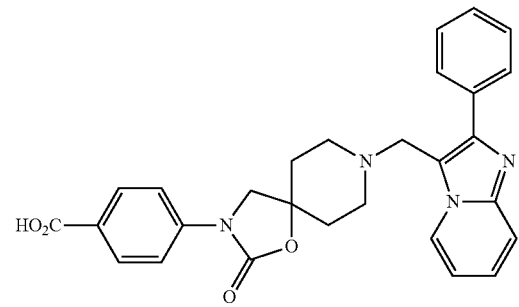
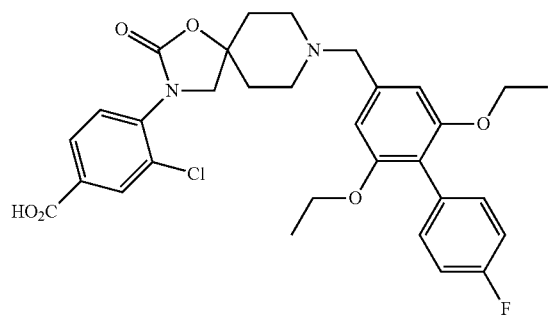
42
-continued
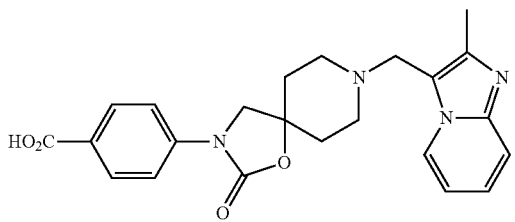
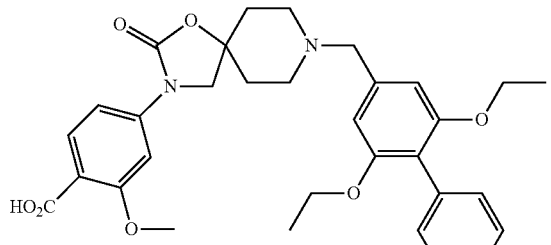
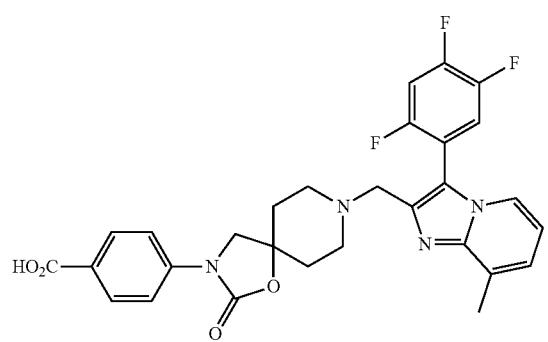
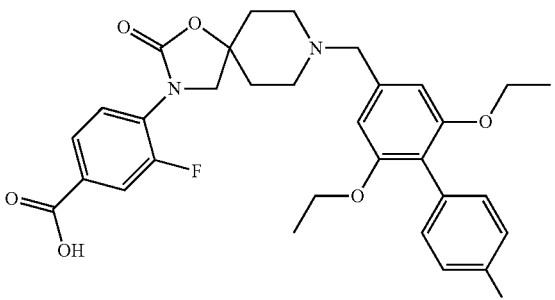
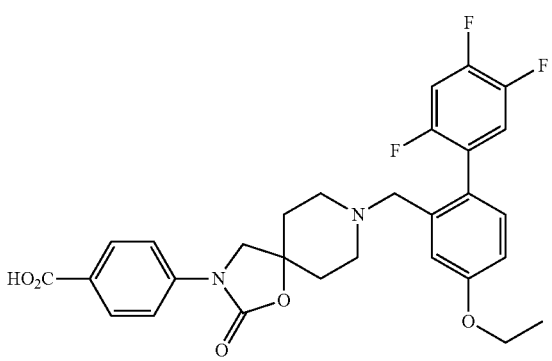

43
-continued
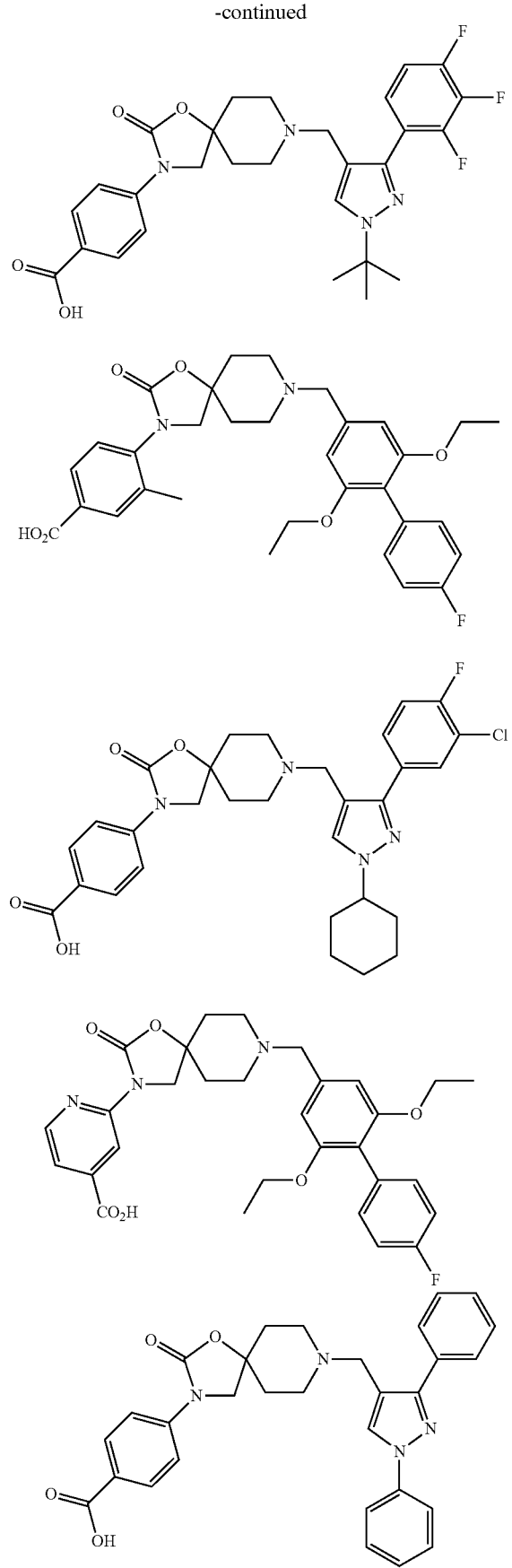
44
-continued
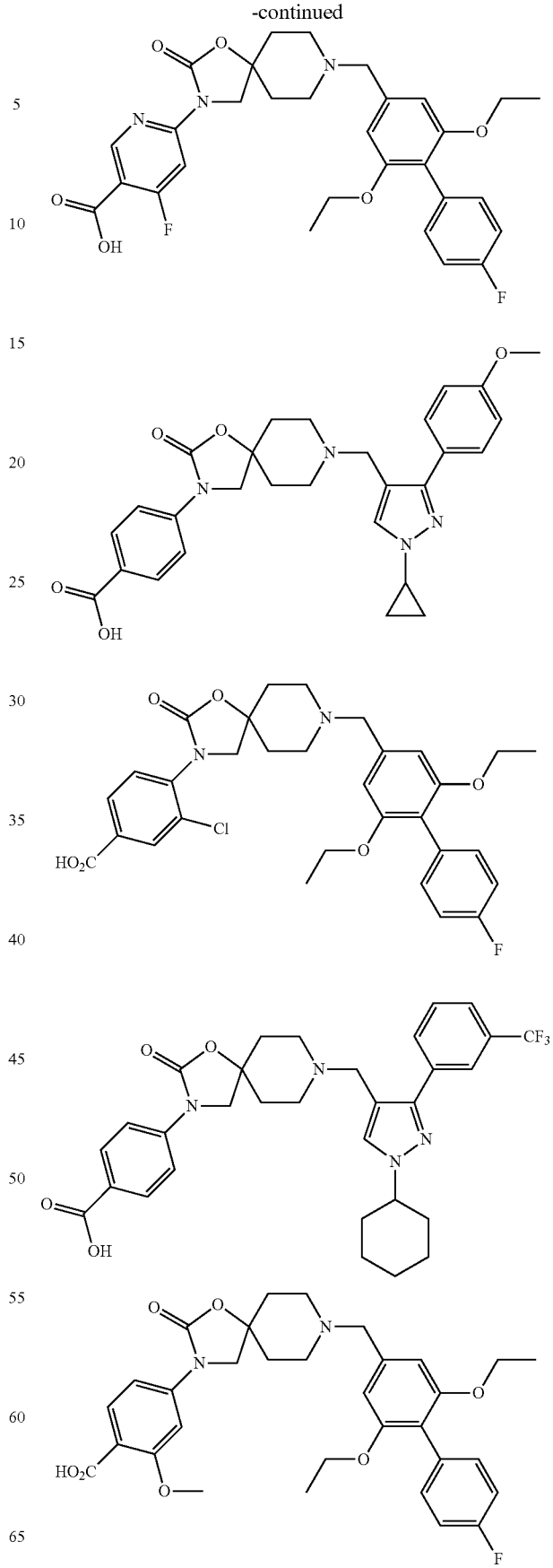

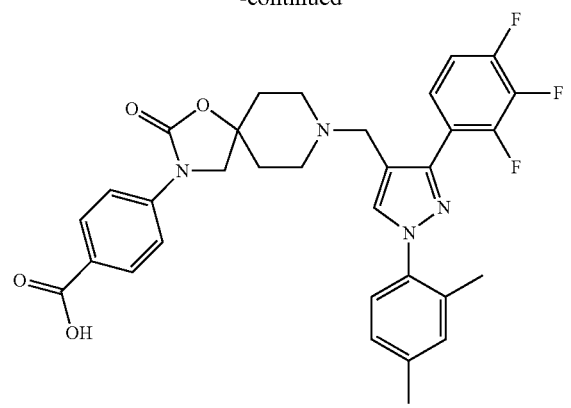
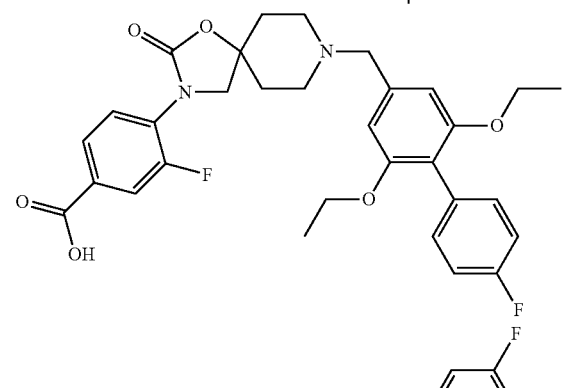
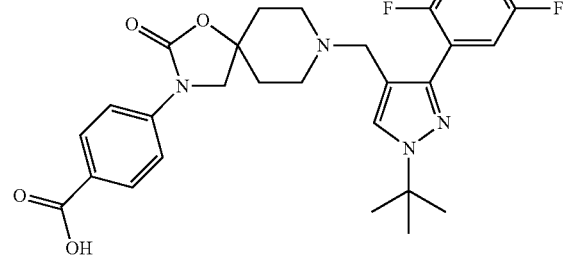
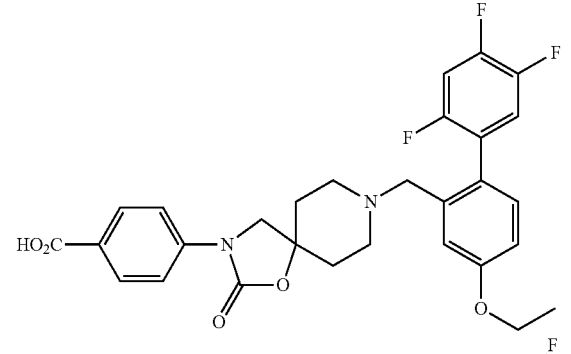
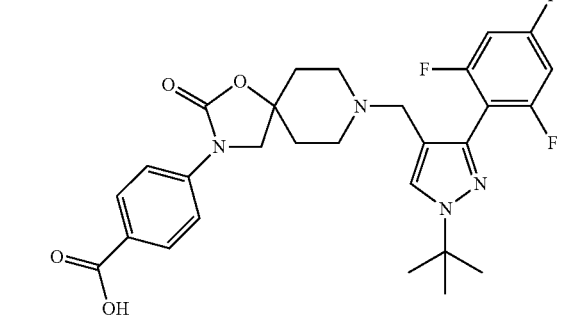
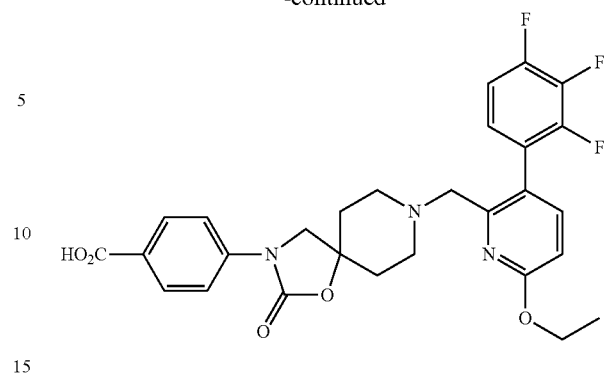
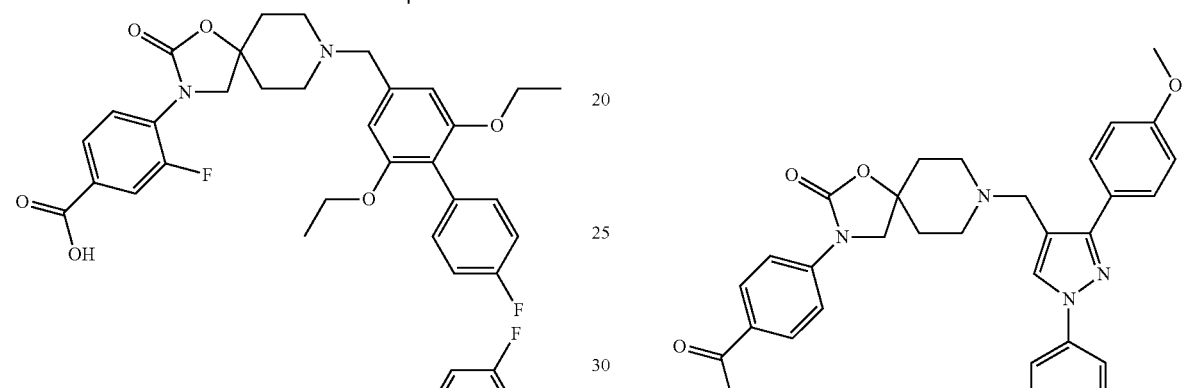
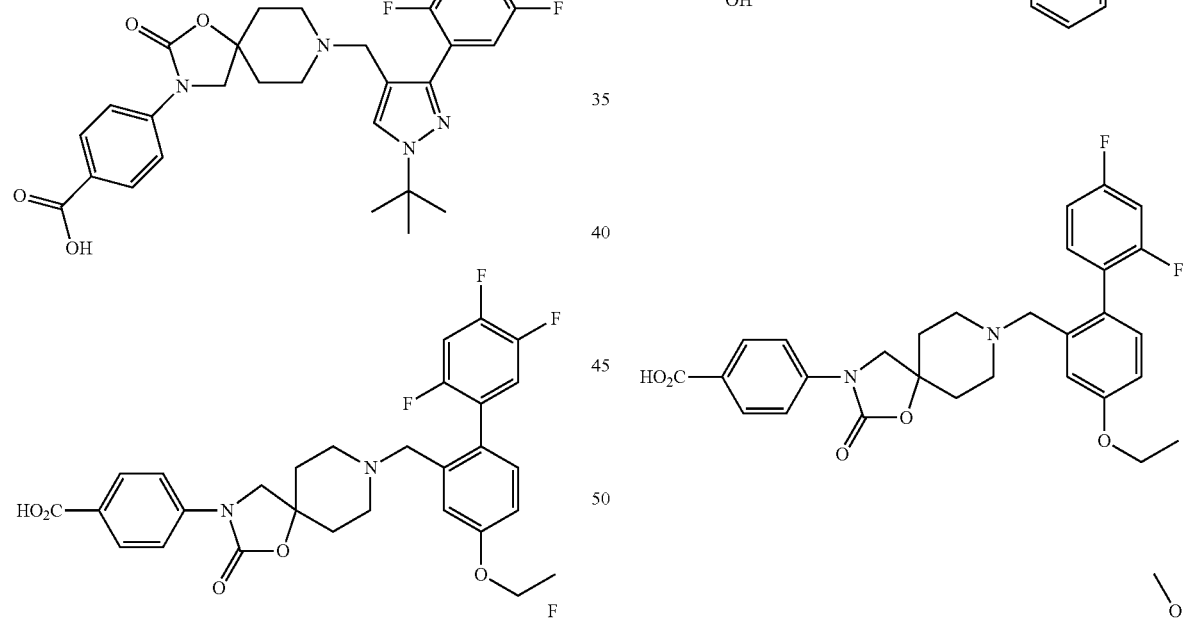

-continued
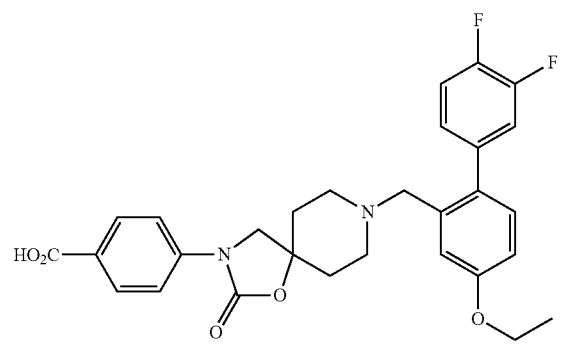
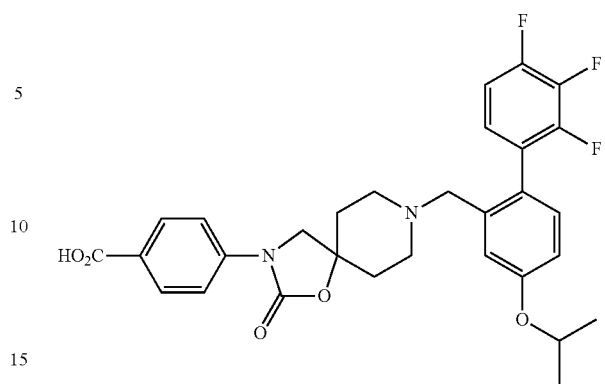
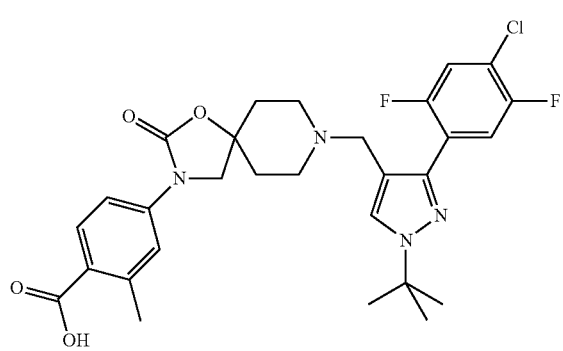
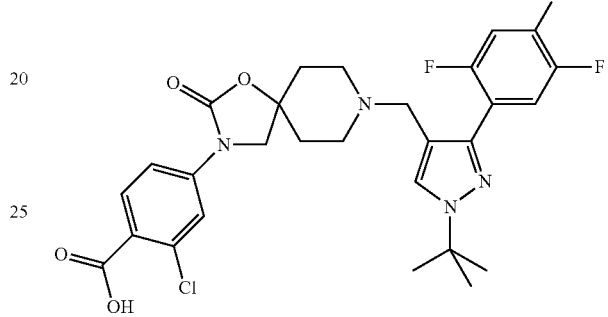
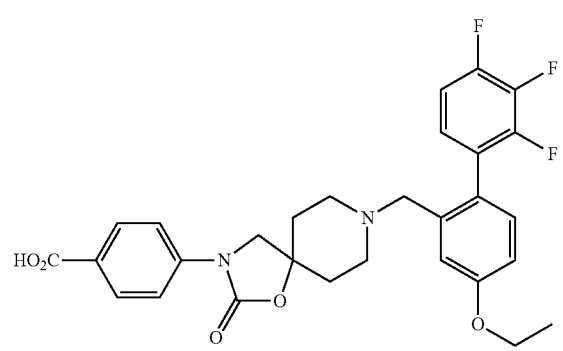
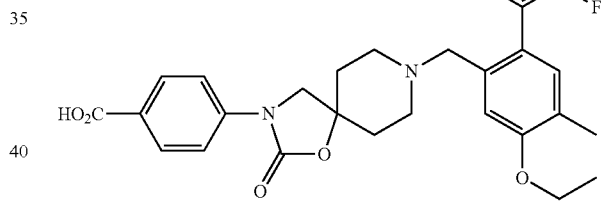
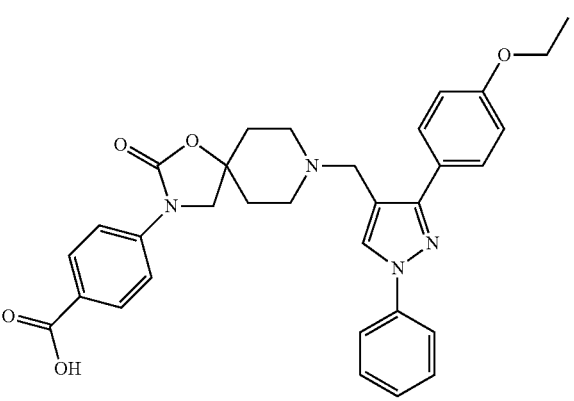
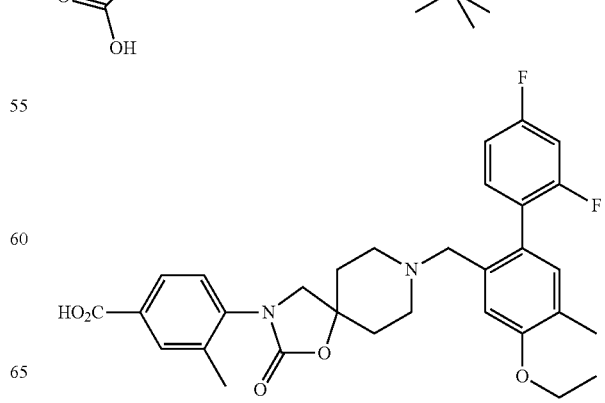

49
-continued
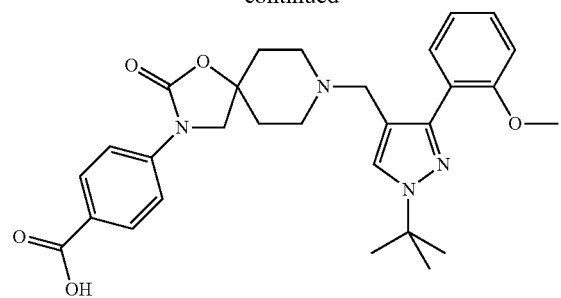
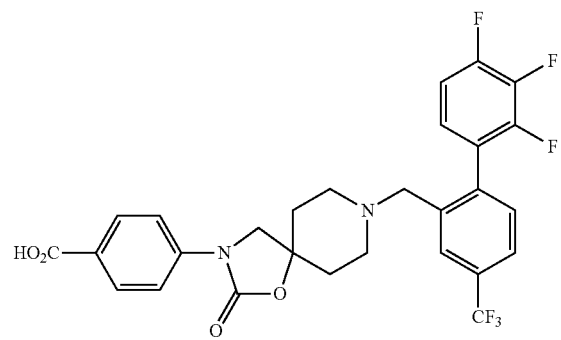
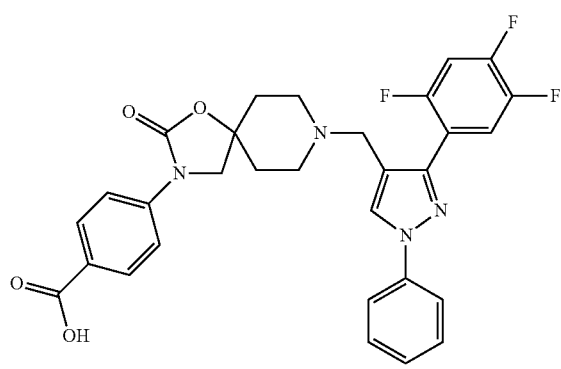
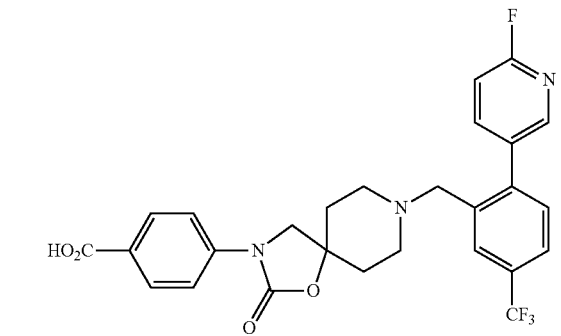
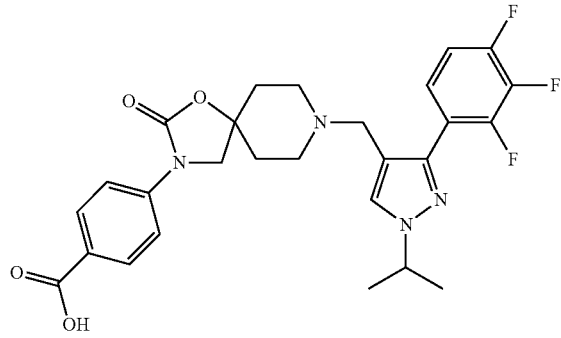
50
-continued
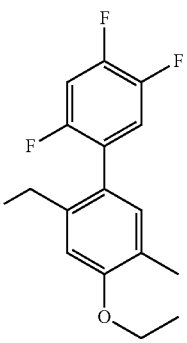
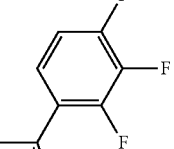

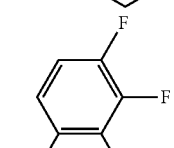
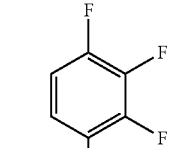

51
-continued
52
-continued
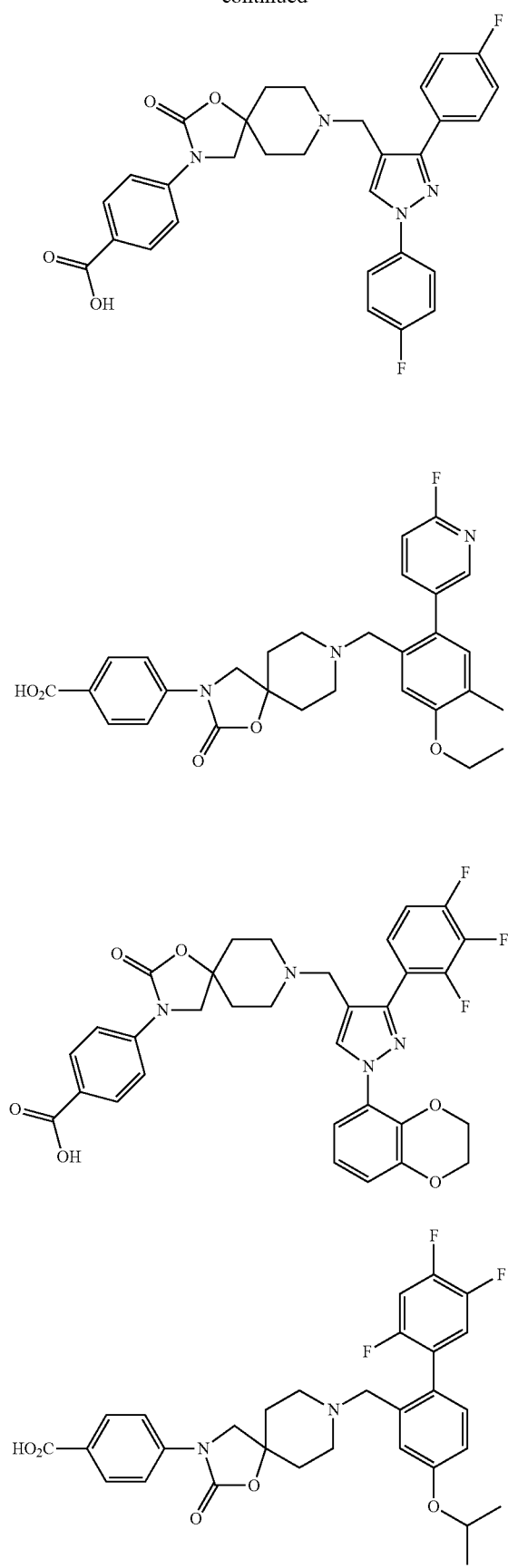
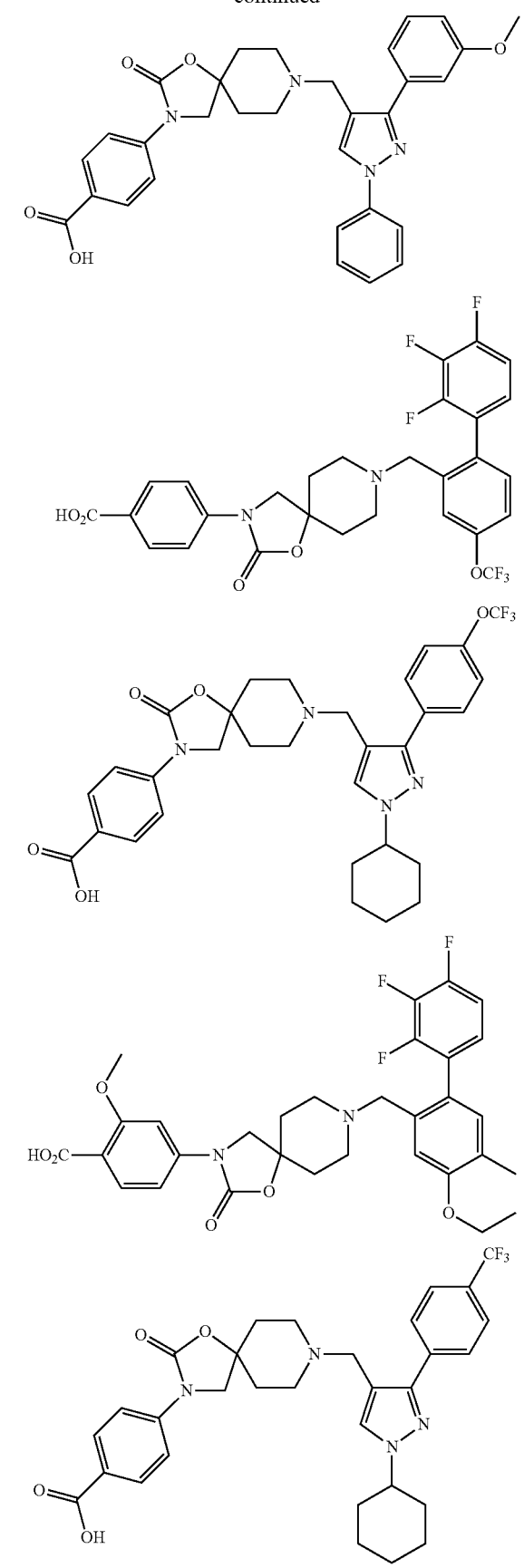

53
-continued
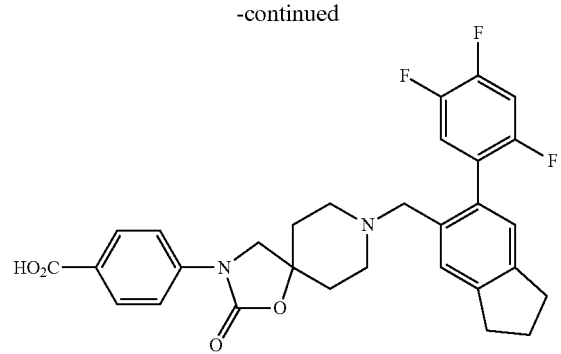
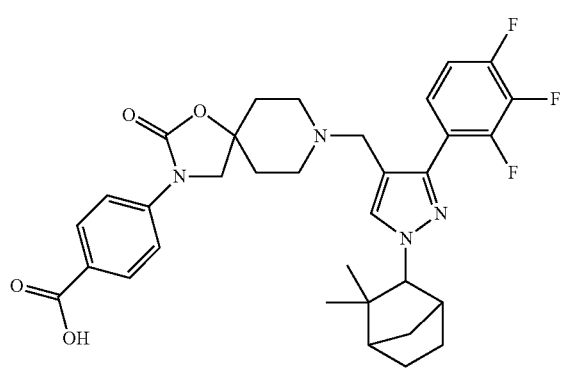
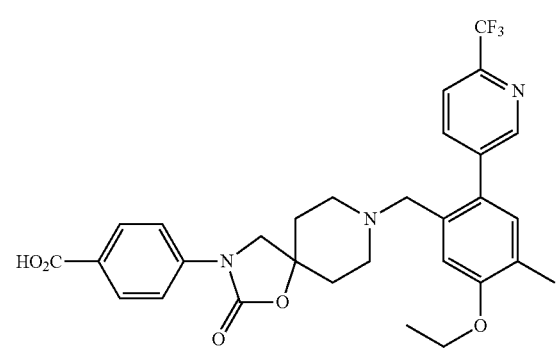
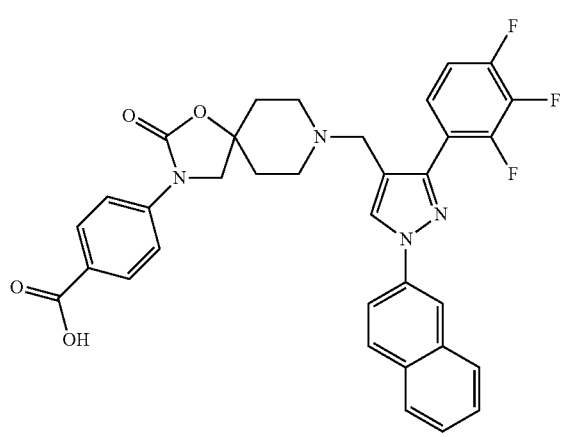
54
-continued
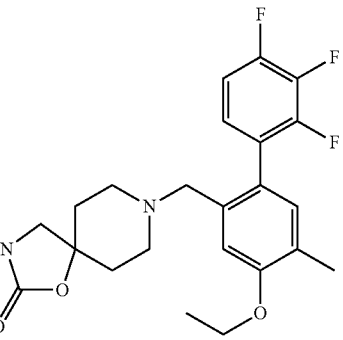
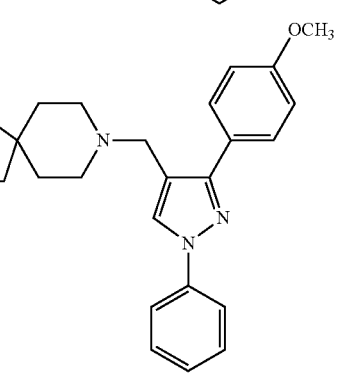
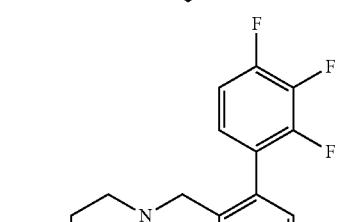
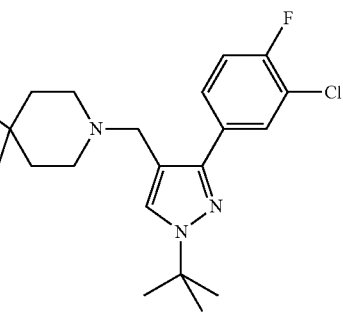
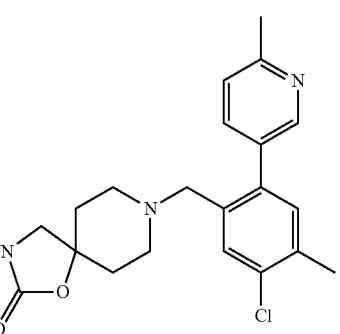

55
-continued
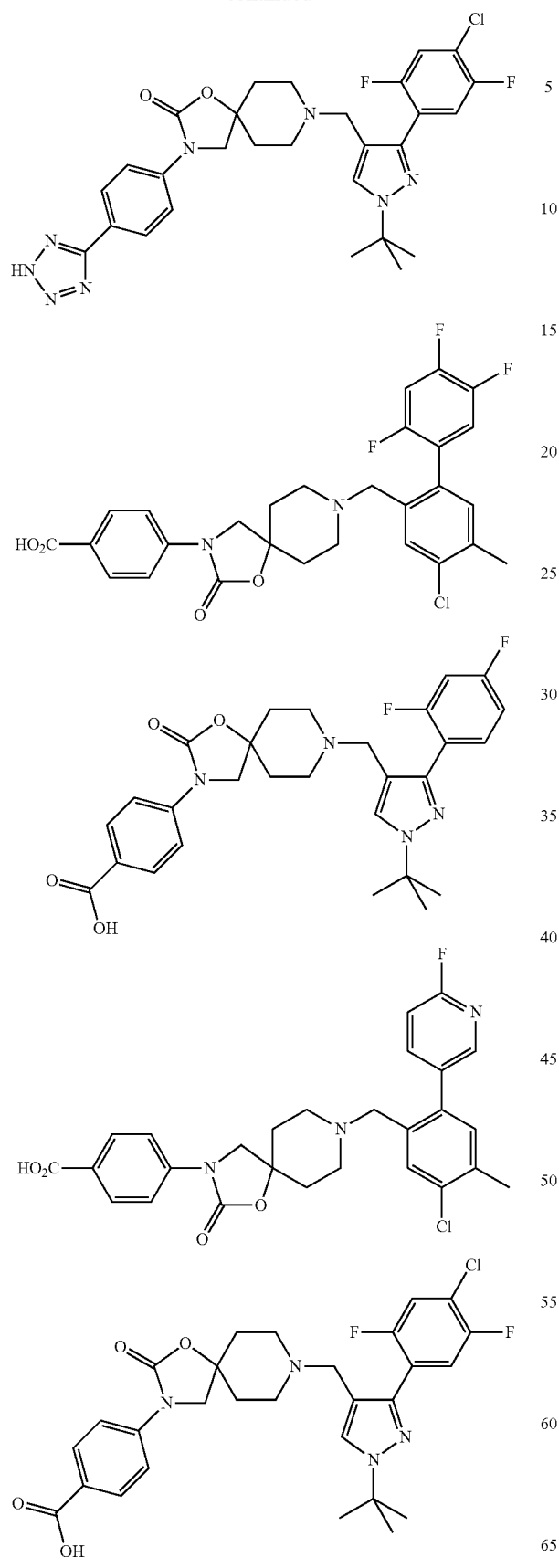
56
-continued
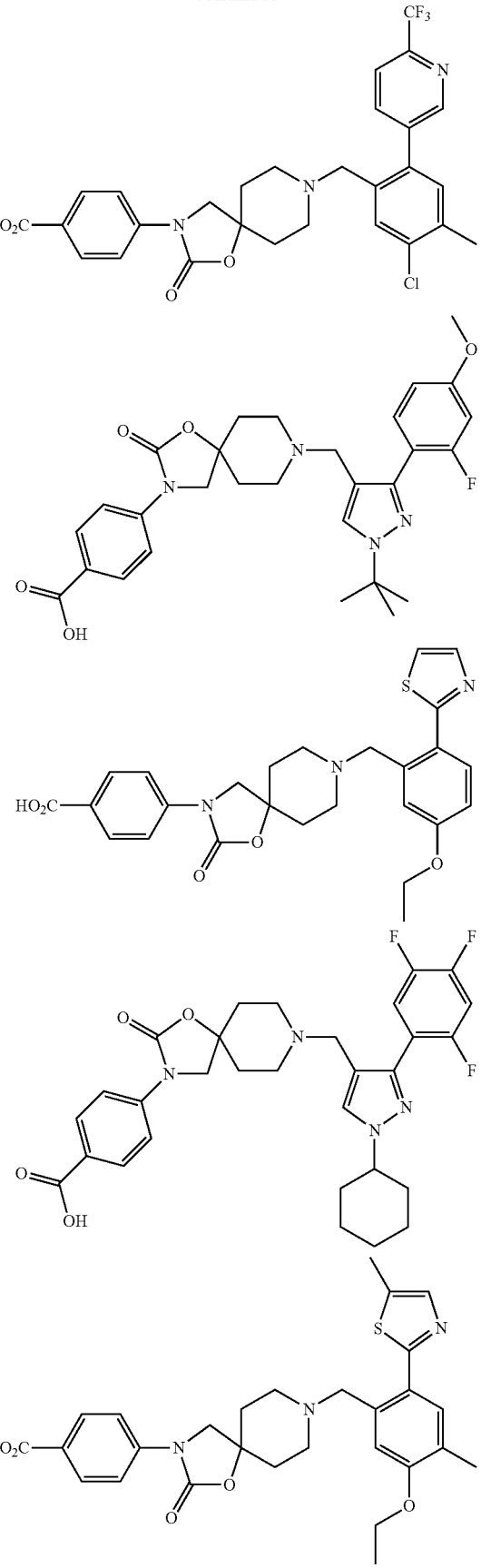

57
-continued
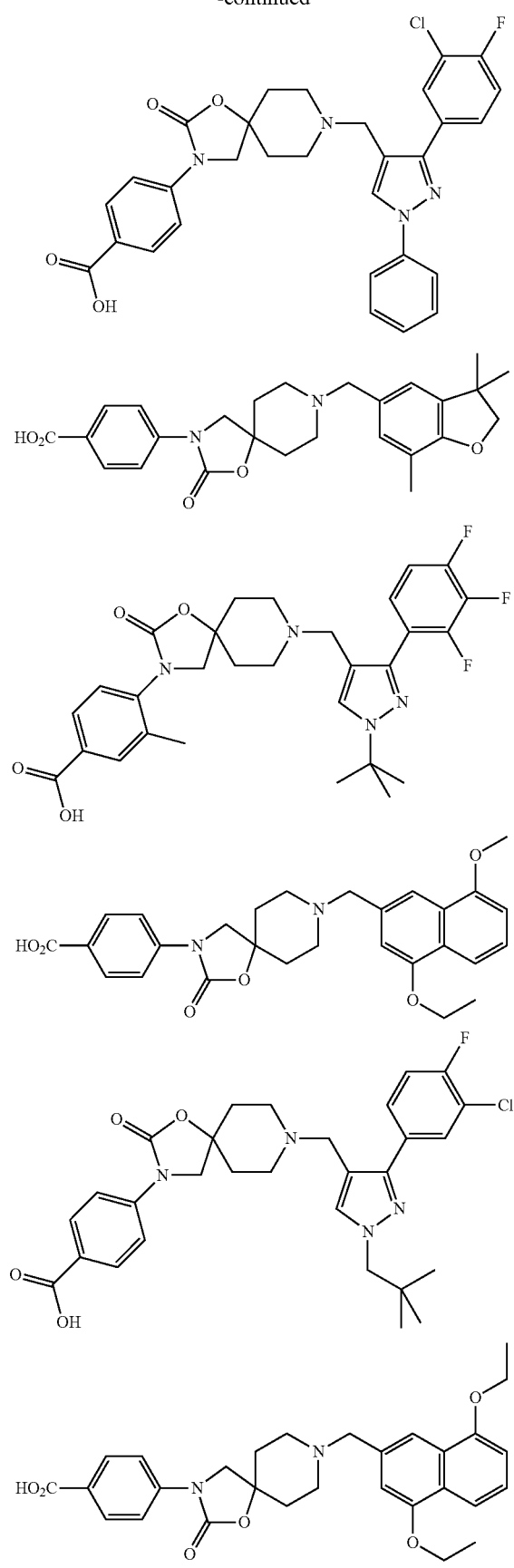
58
-continued
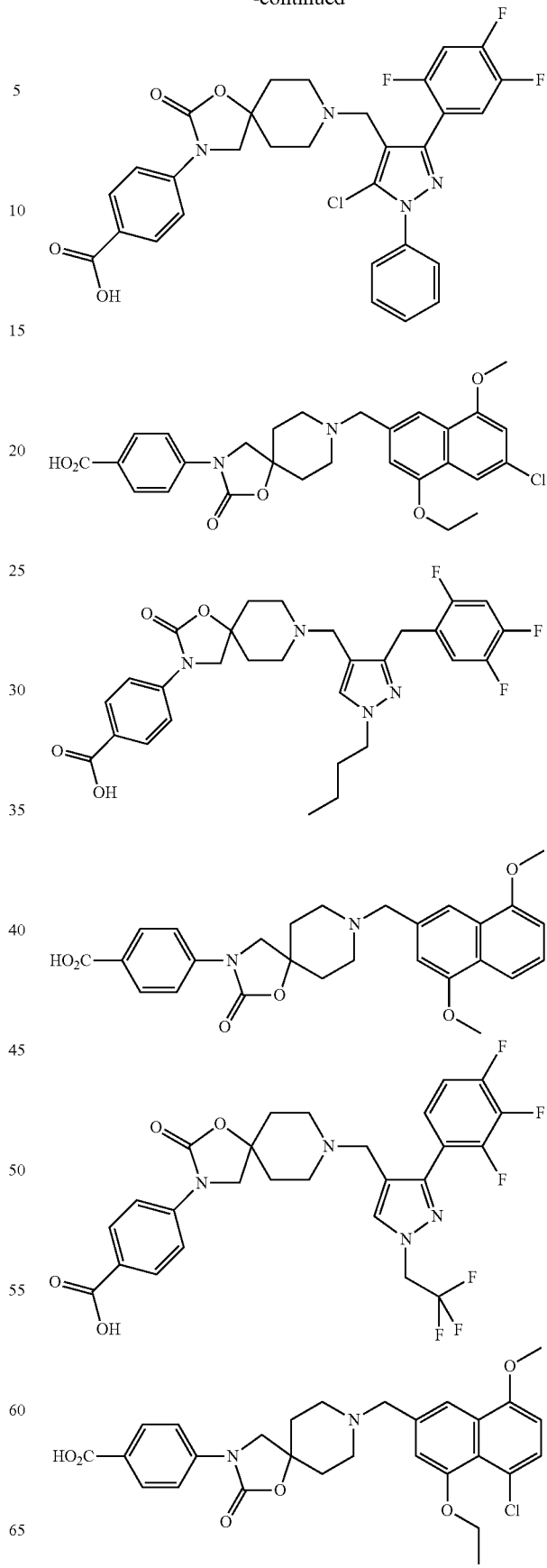

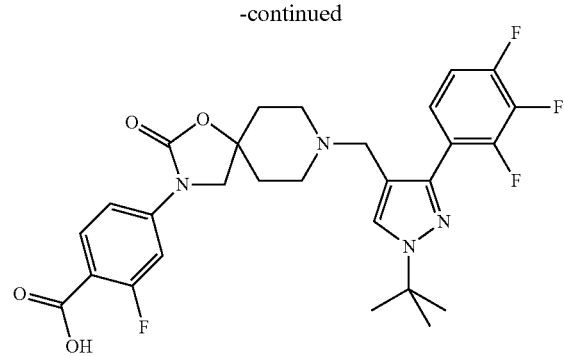
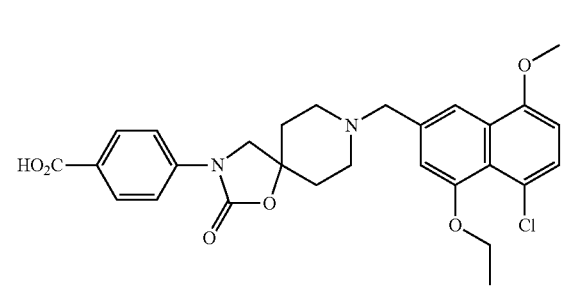
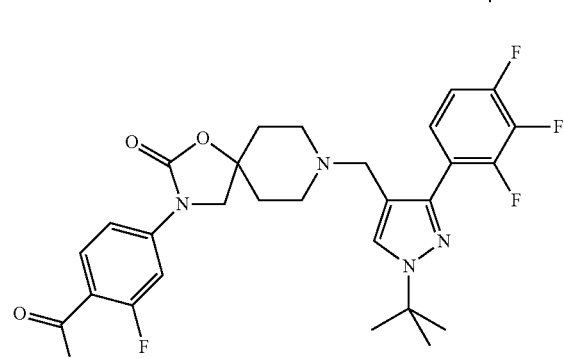
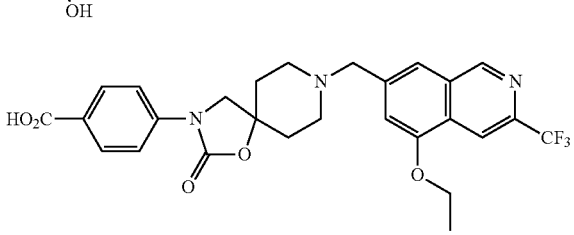
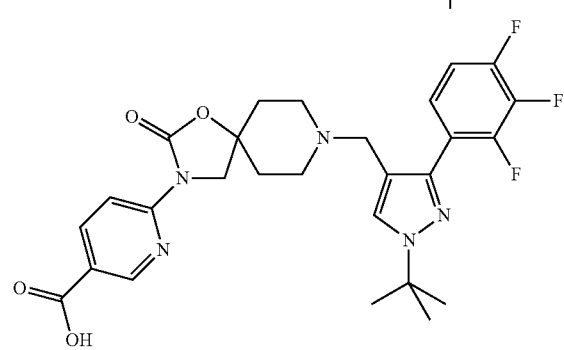
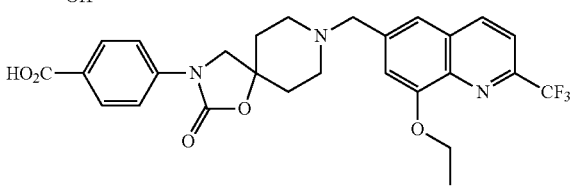
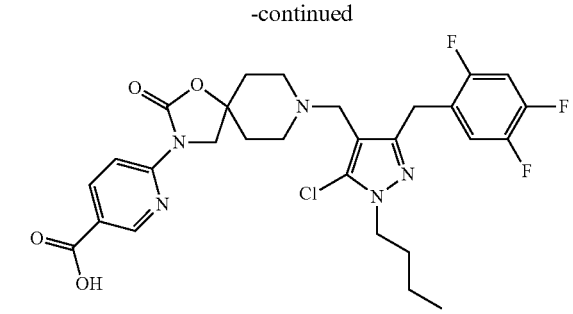
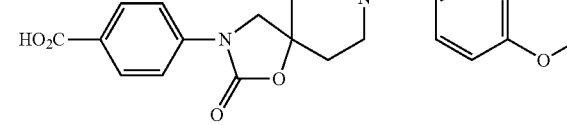
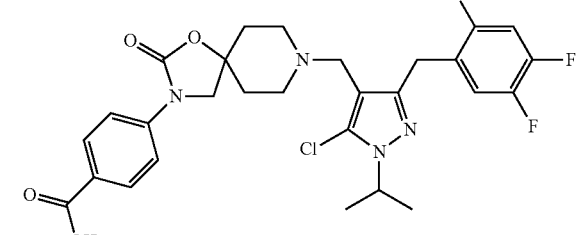
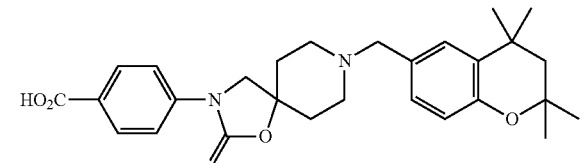
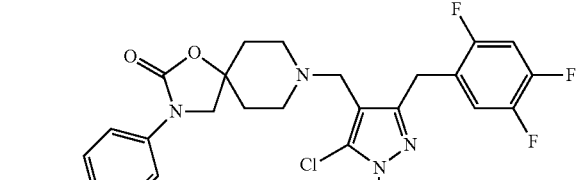
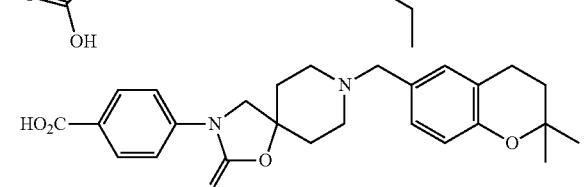
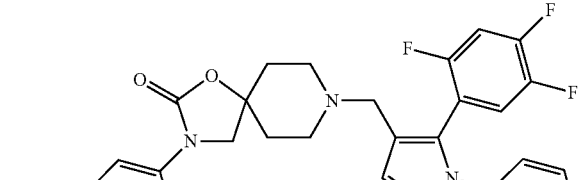

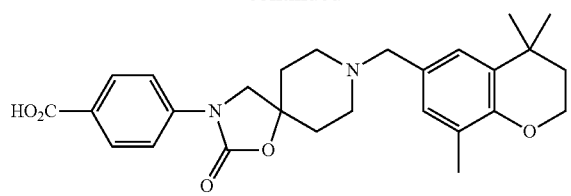
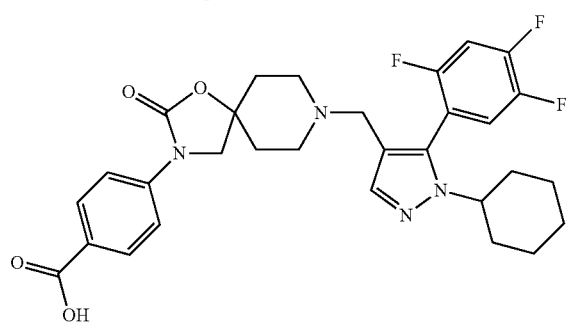
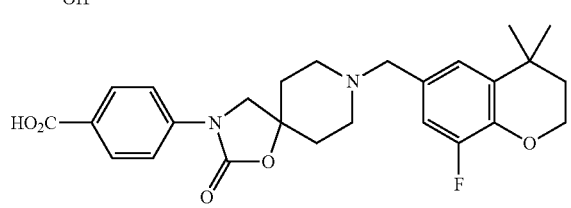
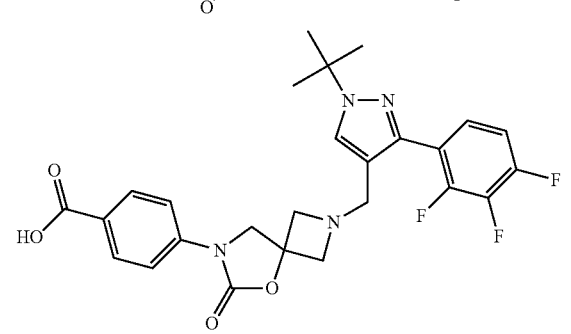
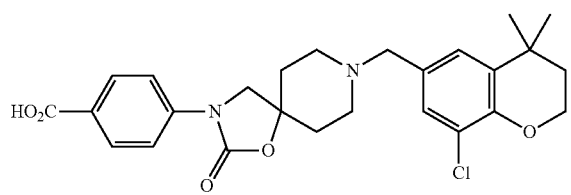
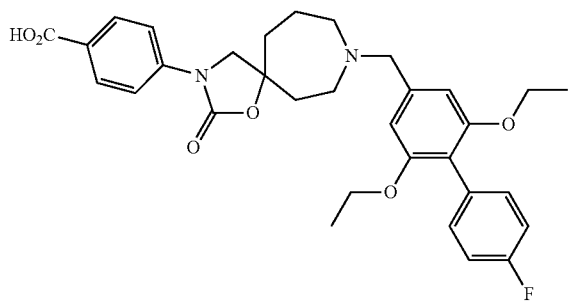
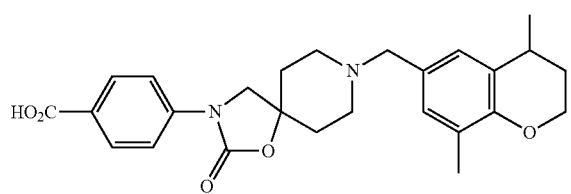
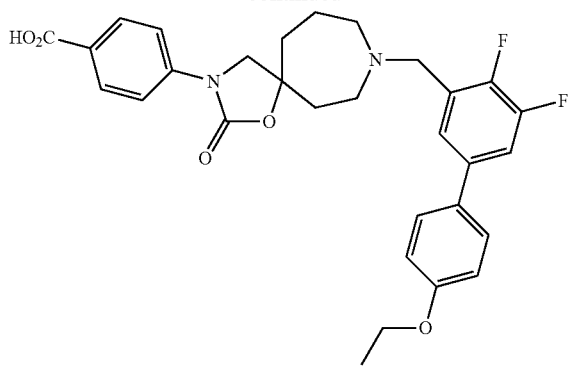
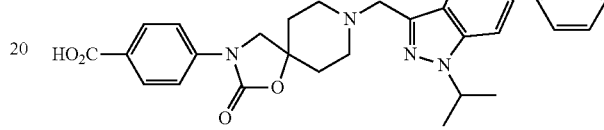
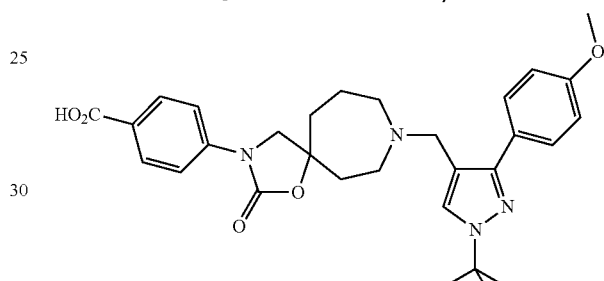
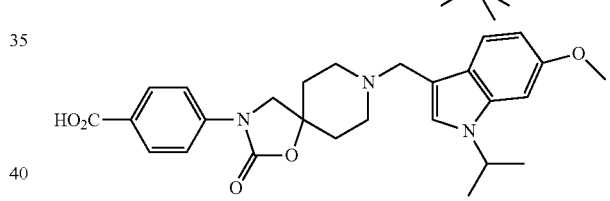
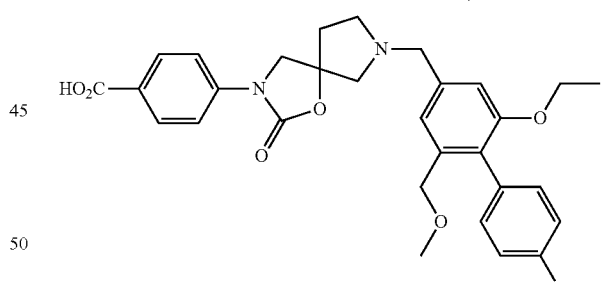
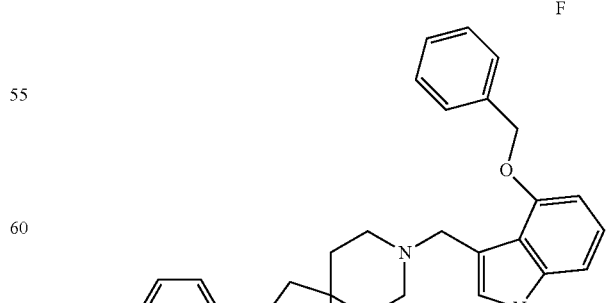
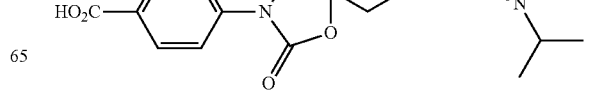

63
-continued
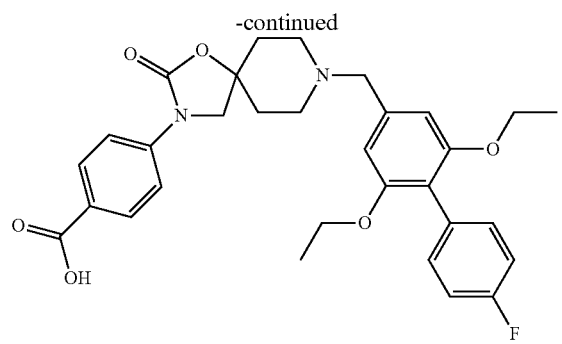
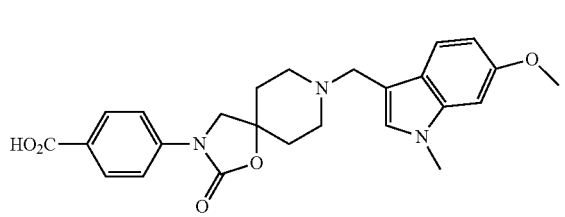
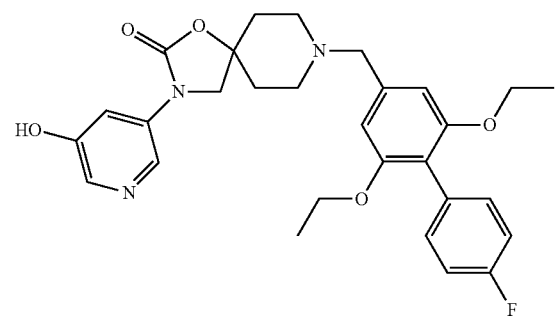
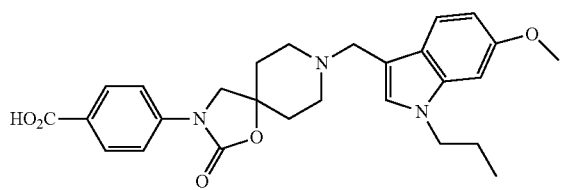
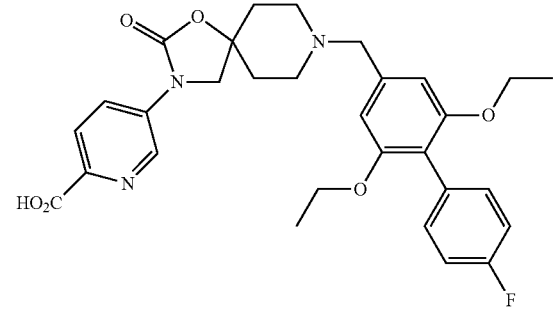
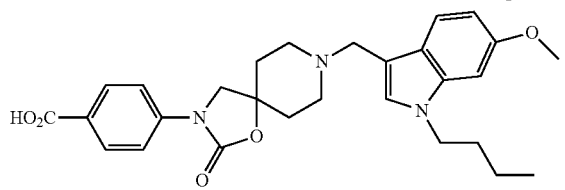
64
-continued
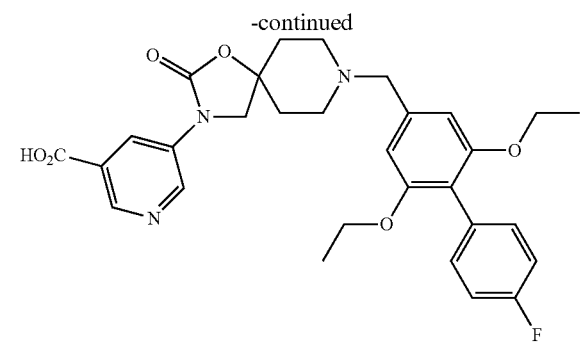
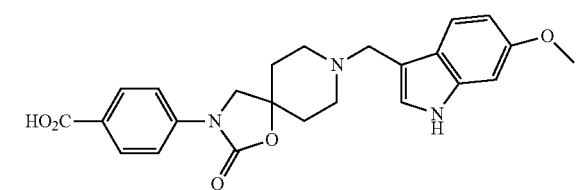
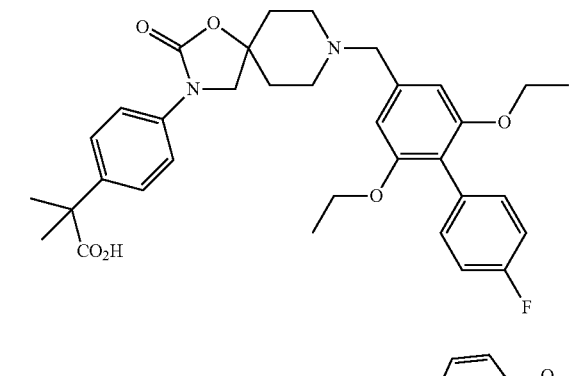
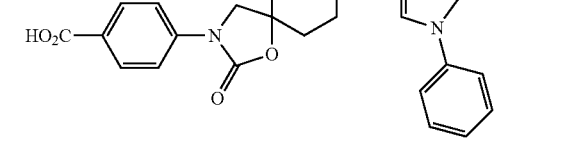
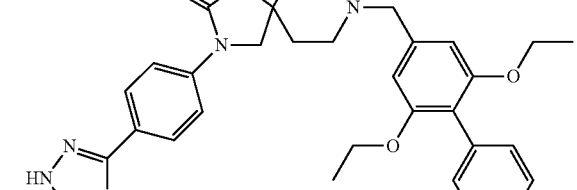
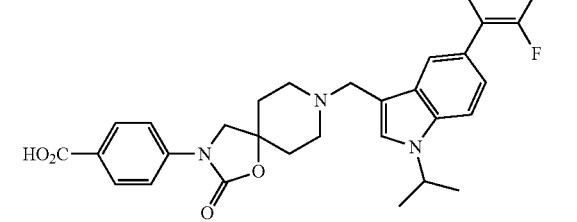

65
-continued
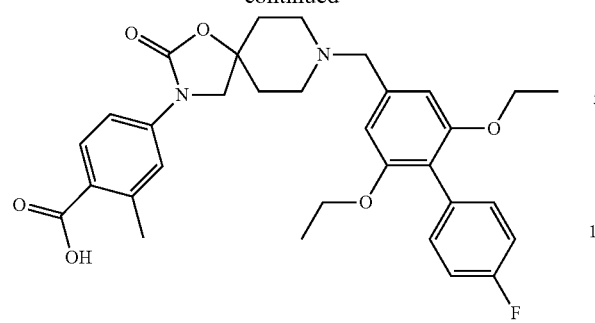
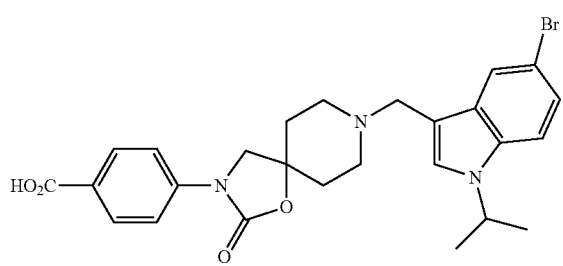
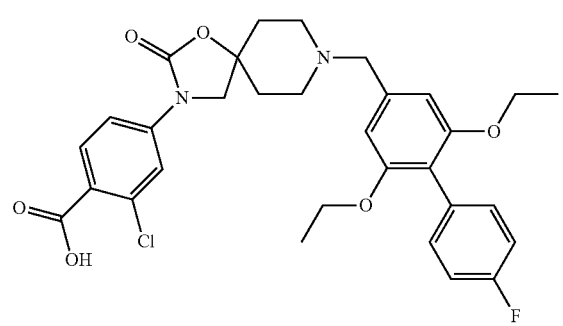
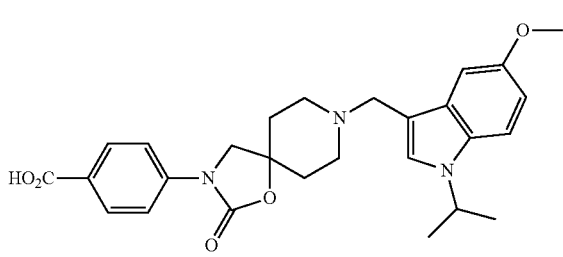
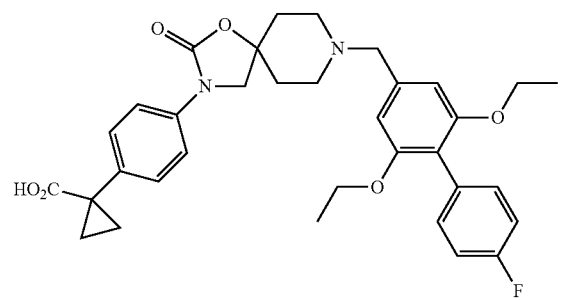
66
-continued
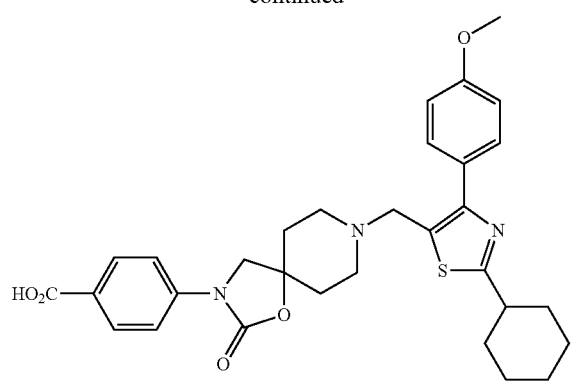
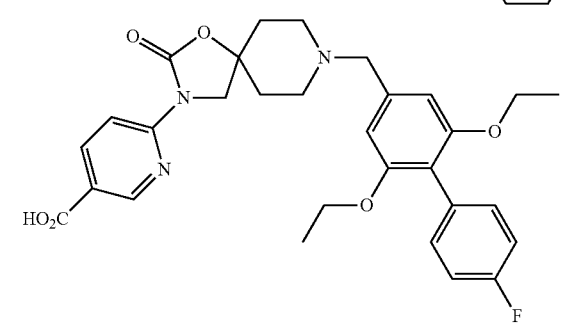
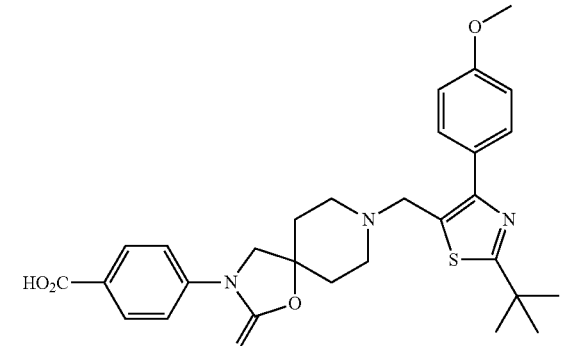
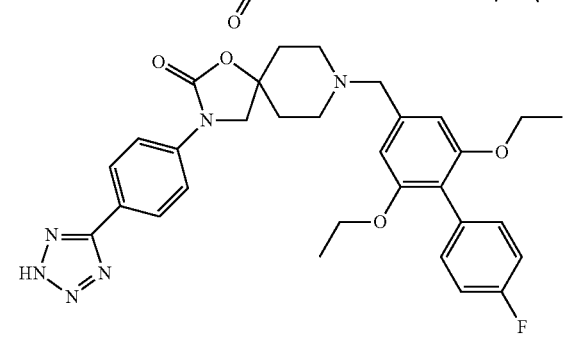
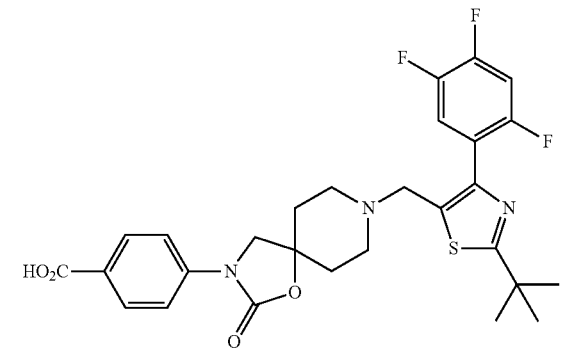

67
-continued
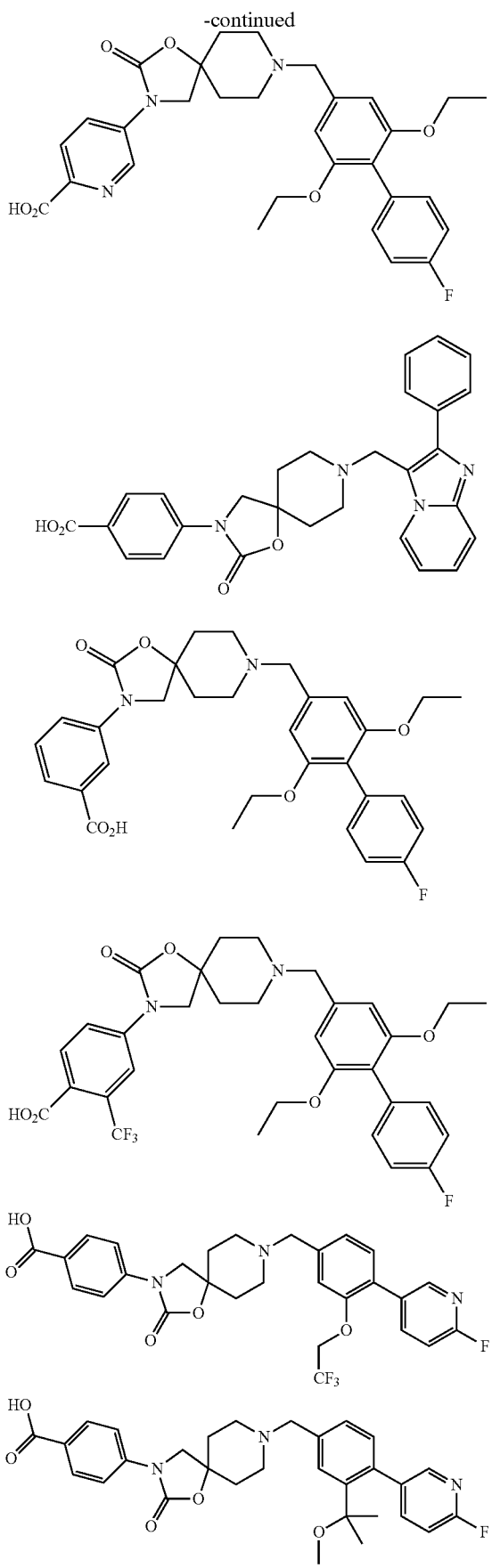
68
-continued
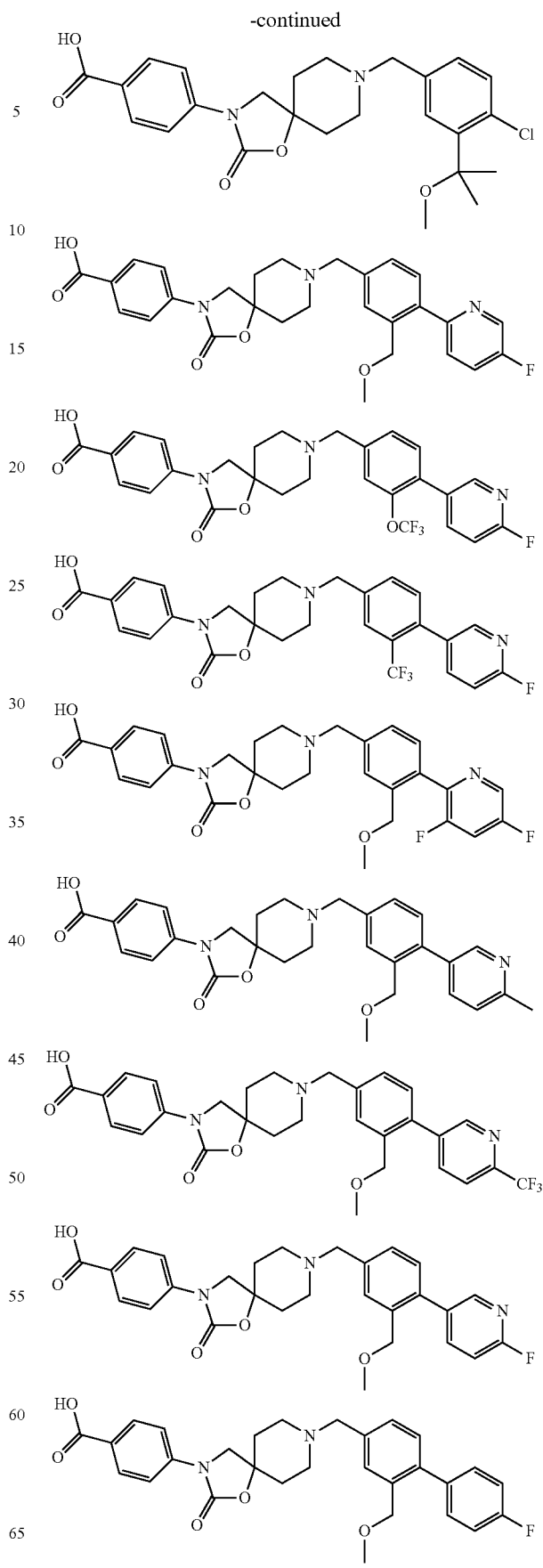

-continued

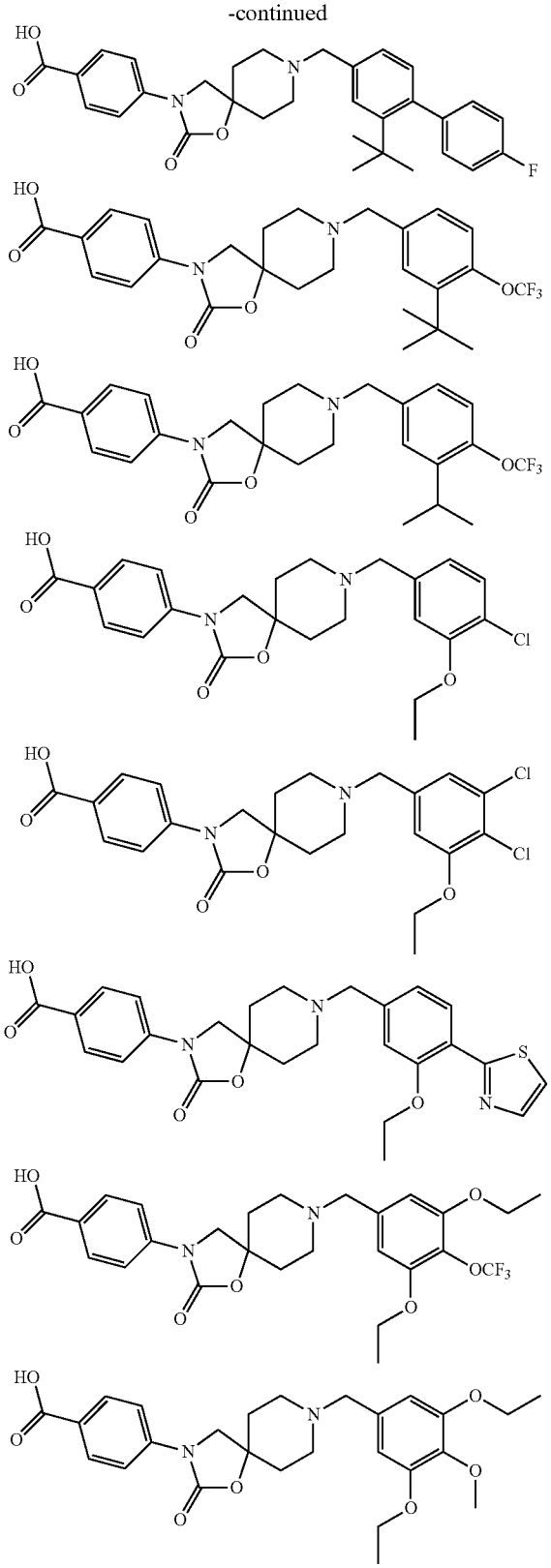

DEFINITIONS

Examples of "halogen" include a fluorine atom, a chlorine atom, a bromine atom, and an iodine atom.

"$C_3$-$C_{10}$cycloalkyl" encompasses cycloalkyl having 3 to 10 carbons, forming one or more carboxylic rings that are fused. "Cycloalkyl" also includes monocyclic rings fused to an aryl group in which the point of attachment is on the non-aromatic portion. Examples of cycloalkyl include cyclopropyl, cyclobutyl, cyclopentyl, cyclohexyl, cycloheptyl, tetrahydronaphthyl, decahydronaphthyl, indanyl and the like.

"—O—$C_1$-$C_{10}$alkyl" refers to an alkyl group having 1 to 10 carbons linked to oxygen, also known as an alkoxy group. Examples include methoxy, ethoxy, butoxy, isopropoxy and propoxy. "—O—$C_1$-$C_{10}$halogen-substituted alkyl" refers to an alkoxy group, wherein one or more hydrogens is replaced with a halogen. Examples include trifluoromethoxy.

The term "$C_1$-$C_{10}$alkyl" encompasses straight alkyl having a carbon number of 1 to 10 and branched alkyl having a carbon number of 3 to 10. Specific examples thereof include methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl, 1-ethyl-1-methylpropyl, and the like.

The term "halogen-substituted $C_1$-$C_{10}$alkyl" encompasses $C_1$-$C_{10}$alkyl with the hydrogen atoms thereof being partially or completely substituted with halogen, examples thereof including fluoromethyl, difluoromethyl, trifluoromethyl, 2-fluoroethyl, 1,2-difluoroethyl, 2,2-difluoroethyl and the like.

"Heterocycle" unless otherwise specified, means an aromatic, partially aromatic or non-aromatic monocyclic or polycyclic (including bicyclic) ring having at least one ring heteroatom selected from O, S and N. Examples of heterocyclic groups include pyrrolyl, isoxazolyl, isothiazolyl, pyrazolyl, pyridinyl, 2-oxo-(1H)-pyridinyl (2-hydroxy-pyridinyl), oxazolyl, 1,2,4-oxadiazolyl, 1,3,4-oxadiazolyl, thiadiazolyl, thiazolyl, imidazolyl, triazolyl, tetrazolyl, furyl, triazinyl, thienyl, pyrimidinyl, pyrazinyl, benzisoxazolyl, benzoxazolyl, benzothiazolyl, benzothiadiazolyl, dihydrobenzofuranyl, indolinyl, pyridazinyl, indazolyl, isoindolyl, dihydrobenzothienyl, indolizinyl, cinnolinyl, phthalazinyl, quinazolinyl, naphthyridinyl, carbazolyl, benzodioxolyl, quinoxalinyl, purinyl, furazanyl, isobenzylfuranyl, benzimidazolyl, benzofuranyl, benzothienyl, quinolyl, indolyl, isoquinolyl, dibenzofuranyl, imidazo[1,2-a]pyridinyl, [1,2,4-triazolo][4,3-a]pyridinyl, pyrazolo[1,5-a]pyridinyl, [1,2,4-triazolo][1,5-a]pyridinyl, 2-oxo-1,3-benzoxazolyl, 4-oxo-3H-quinazolinyl, 3-oxo-[1,2,4]-triazolo[4,3-a]-2H-pyridinyl, 5-oxo-[1,2,4]-4H-oxadiazolyl, 2-oxo-[1,3,4]-3H-oxadiazolyl, 2-oxo-1,3-dihydro-2H-imidazolyl, 3-oxo-2,4-dihydro-3H-1,2,4-triazolyl, and the like. Examples of "heterocycle" also include tetrahydropyranyl, tetrahydrofuranyl, pyrrolidinyl, piperidinyl, piperazinyl, dioxanyl, imidazolidinyl, 2,3-dihydrofuro(2,3-b)pyridyl, benzoxazinyl, benzoxazolinyl, 2-H-phthalazinyl, isoindolinyl, benzoxazepinyl, 5,6-dihydroimidazo[2,1-b]thiazolyl, tetrahydroquinolinyl, morpholinyl, tetrahydroisoquinolinyl, dihydroindolyl, 2- or 4-pyridones attached through the nitrogen or N-substituted-(1H, 3H)-pyrimidine-2,4-diones (N-substituted uracils). The term also includes bridged rings such as 5-azabicyclo[2.2.1]heptyl, 2,5-diazabicyclo[2.2.1]heptyl, 2-azabicyclo[2.2.1]heptyl, 7-azabicyclo[2.2.1]heptyl, 2,5-diazabicyclo[2.2.2]octyl, 2-azabicyclo[2.2.2]octyl, and 3-azabicyclo[3.2.2]nonyl, and azabicyclo[2.2.1]heptanyl.

"Halogen-substituted heterocycle" means an aromatic, partially aromatic or non-aromatic monocyclic or polycyclic (including bicyclic) ring having at least one ring heteroatom selected from O, S and N, wherein one or more of the hydrogens is replaced with a halogen. Examples include fluoropryidine.

"Aryl" means mono- or bicyclic aromatic rings containing only carbon atoms. The term also includes aryl group fused to a monocyclic cycloalkyl or monocyclic cycloheteroalkyl group in which the point of attachment is on the aromatic portion. Examples of aryl include phenyl, naphthyl, indanyl, indenyl, tetrahydronaphthyl, and the like.

"Halogen-substituted aryl" means mono- or bicyclic aromatic rings containing only carbon atoms wherein one or more of the hydrogens is replaced with one or more halogen atoms. Examples include fluorophenyl, difluorophenyl, trifluorophenyl and chlorophenyl.

"Oxo" means the functional group "═O", such as, for example, (1) "C═(O)", that is a carbonyl group; (2) "S═(O)", that is, a sulfoxide group; and (3) "N═(O)", that is, an N-oxide group, such as pyridyl-N-oxide.

The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, benzenesulfonate, benzoate, bicarbonate, bisulfate, bitartrate, borate, bromide, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

The compounds of the present invention contain one or more asymmetric centers and can thus occur as racemates, racemic mixtures, single enantiomers, diastereomeric mixtures, and individual diastereomers. The present invention is meant to comprehend all such isomeric forms of these compounds.

Some of the compounds described herein contain olefinic double bonds, and unless specified otherwise, are meant to include both E and Z geometric isomers.

The independent syntheses of these diastereomers or their chromatographic separations may be achieved as known in the art by appropriate modification of the methodology disclosed herein. Their absolute stereochemistry may be determined by the X-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

It will be understood that, as used herein, references to the compounds of the structural formulas described herein are meant to also include the pharmaceutically acceptable salts, and also salts that are not pharmaceutically acceptable when they are used as precursors to the free compounds or their pharmaceutically acceptable salts or in other synthetic manipulations.

It will be also understood that these alcohol compounds can be converted to the esters of phosphate, amino acid, acetic acid, etc, which can be used as pro-drugs to improve pharmacokinetic or pharmaceutical properties.

Solvates, and in particular, the hydrates of the compounds of structural formula I are included in the present invention as well.

Some of the compounds described herein may exist as tautomers, which have different points of attachment of hydrogen accompanied by one or more double bond shifts. For example, a ketone and its enol form are keto-enol tautomers. The individual tautomers as well as mixtures thereof are encompassed with compounds of the present invention.

In the compounds described herein, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds described herein. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic formula can be prepared without undue experimentation by conventional techniques well known to those skilled in the art or by processes analogous to those described in the Schemes and Examples herein using appropriate isotopically-enriched reagents and/or intermediates.

When any variable (e.g., $R^1$, α, etc.) occurs more than one time in any constituent or in any of the formulas described herein, its definition on each occurrence is independent of its definition at every other occurrence. Also, combinations of substituents and/or variables are permissible only if such combinations result in stable compounds.

In choosing compounds of the present invention, one of ordinary skill in the art will recognize that the various substituents, i.e. $R^1$, $R^2$, etc., are to be chosen in conformity with well-known principles of chemical structure connectivity and stability.

The term "substituted" shall be deemed to include multiple degrees of substitution by a named substituent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

Methods of Use

The present invention relates to methods for the treatment, control, or prevention of diseases that are responsive to antagonism of SSTR5. The compounds described herein are potent and selective antagonists of the SSTR5. The compounds are efficacious in the treatment of diseases that are modulated by SSTR5 ligands, which are generally antagonists. One or more of the following diseases may be treated by the administration of a therapeutically effective amount of a compound of the formulas described herein, or a pharmaceutically acceptable salt thereof, to a subject in need thereof: (1) Type 2 diabetes (also known as non-insulin dependent diabetes mellitus, or NIDDM), (2) hyperglycemia, (3) impaired glucose tolerance, (4) insulin resistance, (5) obesity, (6) lipid disorders, (7) dyslipidemia, (8) hyperlipidemia, (9) hypertriglyceridemia, (10) hypercholesterolemia, (11) low HDL levels, (12) high. LDL levels, (13) atherosclerosis and its sequelae, (14) vascular restenosis, (15) abdominal obesity, (16) retinopathy, (17) Metabolic Syndrome, (18) high blood pressure (hypertension), (19) mixed or diabetic dyslipidemia, and (20) hyperapolipoproteinemia.

The present invention also relates to methods for the treatment, control, or prevention of diseases, including but not limited to, diabetes, hyperglycemia, insulin resistance, obesity, lipid disorders, atherosclerosis, and Metabolic Syndrome by administering, to a subject, the compounds and pharmaceutical compositions described herein. Also, the compounds of the formulas described herein may be used for the manufacture of a medicament for treating one or more of these diseases.

One embodiment of the uses of the compounds is directed to the treatment of one or more of the following diseases by administering a therapeutically effective amount to a subject in need of treatment: Type 2 diabetes; insulin resistance; hyperglycemia; lipid disorders; Metabolic Syndrome; obesity; and atherosclerosis.

The compounds may be used for manufacturing a medicament for use in the treatment of one or more of these diseases.

The compounds are expected to be effective in lowering glucose and lipids in diabetic patients and in non-diabetic patients who have impaired glucose tolerance and/or are in a pre-diabetic condition. The compounds may ameliorate hyperinsulinemia, which often occurs in diabetic or pre-diabetic patients, by modulating the swings in the level of serum glucose that often occurs in these patients. The compounds may also be effective in treating or reducing insulin resistance. The compounds may be effective in treating or preventing gestational diabetes.

The compounds, compositions, and medicaments as described herein may also be effective in reducing the risks of adverse sequelae associated with Metabolic Syndrome, and in reducing the risk of developing atherosclerosis, delaying the onset of atherosclerosis, and/or reducing the risk of sequelae of atherosclerosis. Sequelae of atherosclerosis include angina, claudication, heart attack, stroke, and others.

By keeping hyperglycemia under control, the compounds may also be effective in delaying or preventing vascular restenosis and diabetic retinopathy.

The compounds of this invention may also have utility in improving or restoring β-cell function, so that they may be useful in treating Type 1 diabetes or in delaying or preventing a patient with Type 2 diabetes from needing insulin therapy.

One aspect of the invention provides a method for the treatment and control of mixed or diabetic dyslipidemia, hypercholesterolemia, atherosclerosis, low HDL levels, high LDL levels, hyperlipidemia, and/or hypertriglyceridemia, which comprises administering to a patient in need of such treatment a therapeutically effective amount of a compound of the formulas described herein. The compound may be used alone or advantageously may be administered with a cholesterol biosynthesis inhibitor, particularly an HMG-CoA reductase inhibitor such as lovastatin, simvastatin, rosuvastatin, pravastatin, fluvastatin, atorvastatin, rivastatin, itavastatin, or ZD-4522. The compound may also be used advantageously in combination with other lipid lowering drugs such as cholesterol absorption inhibitors (for example stanol esters, sterol glycosides such as tiqueside, and azetidinones such as ezetimibe), ACAT inhibitors (such as avasimibe), CETP inhibitors (for example anacetrapib and dalcetrapil), niacin and niacin receptor agonists, bile acid sequestrants, microsomal triglyceride transport inhibitors, and bile acid reuptake inhibitors. These combination treatments may be effective for the treatment or control of one or more related conditions selected from the group consisting of hypercholesterolemia, atherosclerosis, hyperlipidemia, hypertriglyceridemia, dyslipidemia, high LDL, and low HDL.

The term "diabetes" as used herein includes both insulin-dependent diabetes (that is, also known as IDDM, Type-1 diabetes), and insulin-independent diabetes (that is, also known as NIDDM, Type-2 diabetes).

Diabetes is characterized by a fasting plasma glucose level of greater than or equal to 126 mg/dl. A diabetic subject has a fasting plasma glucose level of greater than or equal to 126 mg/dl. Prediabetes is characterized by an impaired fasting plasma glucose (FPG) level of greater than or equal to 110 mg/dl and less than 126 mg/dl; or impaired glucose tolerance; or insulin resistance. A prediabetic subject is a subject with impaired fasting glucose (a fasting plasma glucose (FPG) level of greater than or equal to 110 mg/dl and less than 126 mg/dl); or impaired glucose tolerance (a 2 hour plasma glucose level of >140 mg/dl and <200 mg/dl); or insulin resistance, resulting in an increased risk of developing diabetes.

The compounds and compositions described herein are useful for treatment of both Type 1 diabetes and Type 2 diabetes. The compounds and compositions are especially useful for treatment of Type 2 diabetes. The compounds and compositions described herein are especially useful for treatment and/or prevention of pre-diabetes. Also, the compounds and compositions described herein are especially useful for treatment and/or prevention of gestational diabetes mellitus.

Treatment of diabetes mellitus refers to the administration of a compound or combination described herein to treat a diabetic subject. One outcome of the treatment of diabetes is to reduce an increased plasma glucose concentration. Another outcome of the treatment of diabetes is to reduce an increased insulin concentration. Still another outcome of the treatment of diabetes is to reduce an increased blood triglyceride concentration. Still another outcome of the treatment of diabetes is to increase insulin sensitivity. Still another outcome of the treatment of diabetes may be enhancing glucose tolerance in a subject with glucose intolerance. Still another outcome of the treatment of diabetes is to reduce insulin resistance. Another outcome of the treatment of diabetes is to lower plasma insulin levels. Still another outcome of treatment of diabetes is an improvement in glycemic control, particularly in Type 2 diabetic subjects. Yet another outcome of treatment is to increase hepatic insulin sensitivity.

Prevention of diabetes mellitus, in particular diabetes associated with obesity, refers to the administration of a compound or combination described herein to prevent or treat the onset of diabetes in a subject in need thereof. A subject in need of preventing diabetes is a prediabetic subject. In certain embodiments the compounds described herein can be useful in the treatment, control or prevention of Type 2 diabetes and in the treatment, control and prevention of the numerous conditions that often accompany Type 2 diabetes, including Metabolic Syndrome X, reactive hypoglycemia, and diabetic dyslipidemia. Obesity, discussed below, is another condition that is often found with Type 2 diabetes that may respond to treatment with the compounds described herein.

The following diseases, disorders and conditions are related to Type 2 diabetes, and therefore may be treated, controlled or in some cases prevented, by treatment with the compounds described herein: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) irritable bowel syndrome, (15) inflammatory bowel disease, including Crohn's disease and ulcerative colitis, (16) other inflammatory conditions, (17) pancreatitis, (18) abdominal obesity, (19) neurodegenerative disease, (20) retinopathy, (21) nephropathy, (22) neuropathy, (23) Syndrome X, (24) ovarian hyperandrogenism (polycystic ovarian syndrome), and other disorders where insulin resistance is a component.

Dyslipidemias or disorders of lipid metabolism, include various conditions characterized by abnormal concentrations of one or more lipids (i.e. cholesterol and triglycerides), and/or apolipoproteins (i.e., apolipoproteins A, B, C and E), and/or lipoproteins (i.e., the macromolecular complexes formed by the lipid and the apolipoprotein that allow lipids to circulate in blood, such as LDL, VLDL and HDL). Dyslipidemia includes atherogenic dyslipidemia. Hyperlipidemia is associated with abnormally high levels of lipids, LDL and VLDL cholesterol, and/or triglycerides. An outcome of the treatment of dyslipidemia, including hyperlipemia, is to reduce an increased LDL cholesterol concentration. Another outcome of the treatment is to increase a low-concentration of HDL cholesterol. Another outcome of treatment is to decrease very low density lipoproteins (VLDL) and/or small density LDL.

The term "Metabolic Syndrome", also known as Syndrome X, is defined in the Third Report of the National Cholesterol Education Program Expert Panel on Detection, Evaluation and Treatment of High Blood Cholesterol in Adults (ATP-III). E. S. Ford et al., JAMA, vol. 287 (3), Jan. 16, 2002, pp 356-359. Briefly, a person is defined as having Metabolic Syndrome if the person has three or more of the following symptoms: abdominal obesity, hypertriglyceridemia, low HDL cholesterol, high blood pressure, and high fasting plasma glucose. The criteria for these are defined in ATP-III.

The term "obesity" as used herein is a condition in which there is an excess of body fat, and includes visceral obesity. The operational definition of obesity is based on the Body Mass Index (BMI), which is calculated as body weight per height in meters squared (kg/m2). "Obesity" refers to a condition whereby an otherwise healthy subject has a Body Mass Index (BMI) greater than or equal to 30 kg/m2, or a condition whereby a subject with at least one co-morbidity has a BMI greater than or equal to 27 kg/m2. An "obese subject" is an otherwise healthy subject with a Body Mass Index (BMI) greater than or equal to 30 kg/m2 or a subject with at least one co-morbidity with a BMI greater than or equal to 27 kg/m2. A "subject at risk of obesity" is an otherwise healthy subject with a BMI of 25 kg/m2 to less than 30 kg/m2 or a subject with at least one co-morbidity with a BMI of 25 kg/m2 to less than 27 kg/m2. The increased risks associated with obesity occur at a lower Body Mass Index (BMI) in Asians than that in Europeans and Americans. In Asian countries, including Japan, "obesity" refers to a condition whereby a subject with at least one obesity-induced or obesity-related co-morbidity, that requires weight reduction or that would be improved by weight reduction, has a BMI greater than or equal to 25 kg/m2. In Asia-Pacific, a "subject at risk of obesity" is a subject with a BMI of greater than 23 kg/m2 to less than 25 kg/m2.

As used herein, the term "obesity" is meant to encompass all of the above definitions of obesity.

Obesity-induced or obesity-related co-morbidities include, but are not limited to, diabetes, impaired glucose tolerance, insulin resistance syndrome, dyslipidemia, hypertension, hyperuricacidemia, gout, coronary artery disease, myocardial infarction, angina pectoris, sleep apnea syndrome, Pickwickian syndrome, fatty liver; cerebral infarction, cerebral thrombosis, transient ischemic attack, orthopedic disorders, arthritis deformans, lumbodynia, emmeniopathy, and infertility. In particular, co-morbidities include: hypertension, hyperlipidemia, dyslipidemia, glucose intolerance, cardiovascular disease, sleep apnea, diabetes mellitus, and other obesity-related conditions.

Treatment of obesity and obesity-related disorders refers to the administration of the compounds or combinations described herein to reduce or maintain the body weight of an obese subject. One outcome of treatment may be reducing the body weight of an obese subject relative to that subject's body weight immediately before the administration of the compounds or combinations described herein. Another outcome of treatment may be decreasing body fat, including visceral body fat. Another outcome of treatment may be preventing body weight gain. Another outcome of treatment may be preventing body weight regain of body weight previously lost as a result of diet, exercise, or pharmacotherapy. Another outcome of treatment may be decreasing the occurrence of and/or the severity of obesity-related diseases. The treatment may suitably result in a reduction in food or calorie intake by the subject, including a reduction in total food intake, or a reduction of intake of specific components of the diet such as carbohydrates or fats; and/or the inhibition of nutrient absorption; and/or the inhibition of the reduction of metabolic rate. The treatment may also result in an alteration of metabolic rate, such as an increase in metabolic rate, rather than or in addition to an inhibition of the reduction of metabolic rate; and/or in minimization of the metabolic resistance that normally results from weight loss.

Prevention of obesity and obesity-related disorders refers to the administration of the compounds or combinations described herein to reduce or maintain the body weight of a subject at risk of obesity. One outcome of prevention may be reducing the body weight of a subject at risk of obesity relative to that subject's body weight immediately before the administration of the compounds or combinations described herein. Another outcome of prevention may be preventing body weight regain of body weight previously lost as a result of diet, exercise, or pharmacotherapy. Another outcome of prevention may be preventing obesity from occurring if the treatment is administered prior to the onset of obesity in a subject at risk of obesity. Another outcome of prevention may be decreasing the occurrence and/or severity of obesity-related disorders if the treatment is administered prior to the onset of obesity in a subject at risk of obesity. Moreover, if treatment is commenced in already obese subjects, such treatment may prevent the occurrence, progression or severity of obesity-related disorders, such as, but not limited to, arteriosclerosis, Type 2 diabetes, polycystic ovary disease, cardiovascular diseases, osteoarthritis, dermatological disorders, hypertension, insulin resistance, hypercholesterolemia, hypertriglyceridemia, and cholelithiasis.

The term "subject" is a mammal, including but not limited to a human, cat and dog.

In certain embodiments, the pharmaceutical formulations described herein are useful for the treatment, control, or prevention of obesity and the conditions associated with obesity. Obesity may be due to any cause, whether genetic or environmental. Other conditions associated with obesity include gestational diabetes mellitus and prediabetic conditions such as, elevated plasma insulin concentrations, impaired glucose tolerance, impaired fasting glucose and insulin resistance syndrome. Prediabetes is characterized by an impaired fasting plasma glucose (FPG) level of greater than or equal to 110 mg/dl and less than 126 mg/dl; or impaired glucose tolerance; or insulin resistance. A prediabetic subject is a subject with impaired fasting glucose (a fasting plasma glucose (FPG) level of greater than or equal to 110 mg/dl and less than 126 mg/dl); or impaired glucose tolerance (a 2 hour plasma glucose level of >140 mg/dl and <200 mg/dl); or insulin resistance, resulting in an increased risk of developing diabetes.

Also described herein, are methods of enhancing GLP-1 secretion in a subject by administering, to a subject, the compounds and pharmaceutical compositions described herein. The incretin hormone GLP-1 is believed to have several beneficial effects for the treatment of diabetes mellitus and obesity. GLP-1 stimulates glucose-dependent biosynthesis and secretion of insulin, suppresses glucaon secretion, and slows gastric emptying. Glucagon serves as the major regulatory hormone attenuating the effect of insulin in its inhibition of liver gluconeogenesis and is normally secreted by alpha cells in pancreatic islets in response to falling blood glucose levels. The hormone binds to specific receptors in liver cells that trigger glycogenolysis and an increase in gluconeogenesis through cAMP-mediated events. These responses generate glucose (e.g. hepatic glucose production) to help maintain euglycemia by preventing blood glucose levels from falling significantly. In addition to elevated levels of circulating insulin, Type 2 diabetics have elevated levels of plasma glucagon and increased rates of hepatic glucose production. Compounds that can enhance GLP-1 secretion are useful in improving insulin responsiveness in the liver, decreasing the rate of gluconeogenesis and glycogenolysis, and lowering the rate of hepatic glucose output resulting in a decrease in the levels of plasma glucose.

Administration and Dose Ranges

Any suitable route of administration may be employed for providing a subject, especially a human, with an effective dose of a compound described herein. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds described herein are administered orally.

The effective dosage of active ingredient employed may vary depending on the particular compound employed, the mode of administration, the condition being treated and the severity of the condition being treated. Such dosage may be ascertained readily by a person skilled in the art.

When treating or controlling diabetes mellitus and/or hyperglycemia or hypertriglyceridemia or other diseases for which compounds described herein are indicated, generally satisfactory results are obtained when the compounds described herein are administered at a daily dosage of from about 0.1 milligram to about 100 milligram per kilogram of animal body weight, preferably given as a single daily dose or in divided doses two to six times a day, or in sustained release form. For most large subjects, the total daily dosage is from about 1.0 milligrams to about 1000 milligrams. In the case of a 70 kg adult human, the total daily dose will generally be from about 1 milligram to about 500 milligrams. For a particularly potent compound, the dosage for an adult human may be as low as 0.1 mg. In some cases, the daily dose may be as high as 1 gram. The dosage regimen may be adjusted within this range or even outside of this range to provide the optimal therapeutic response.

Oral administration will usually be carried out using tablets or capsules. Examples of doses in tablets and capsules are 0.1 mg, 0.25 mg, 0.5 mg, 1 mg, 2 mg, 5 mg, 10 mg, 15 mg, 20 mg, 25 mg, 30 mg, 40 mg, 50 mg, 100 mg, 200 mg, 250 mg, 300 mg, 400 mg, 500 mg, and 750 mg. Other oral forms may also have the same or similar dosages.

Pharmaceutical Compositions

Another aspect of the present invention provides pharmaceutical compositions which comprise a compound of the formulas described herein and a pharmaceutically acceptable carrier. The pharmaceutical compositions of the present invention comprise a compound of the formulas described herein or a pharmaceutically acceptable salt as an active ingredient, as well as a pharmaceutically acceptable carrier and unsubstituted or other therapeutic ingredients. The term "pharmaceutically acceptable salts" refers to salts prepared from pharmaceutically acceptable non-toxic bases or acids including inorganic bases or acids and organic bases or acids. A pharmaceutical composition may also comprise a prodrug, or a pharmaceutically acceptable salt thereof, if a prodrug is administered.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of the formulas described herein can be combined as the active ingredient in an intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions as oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

In some instances, depending on the solubility of the compound or salt being administered, it may be advantageous to formulate the compound or salt as a solution in an oil such as a triglyceride of one or more medium chain fatty acids, a lipophilic solvent such as triacetin, a hydrophilic solvent (e.g. propylene glycol), or a mixture of two or more of these, also unsubstituted or including one or more ionic or nonionic surfactants, such as sodium lauryl sulfate, polysorbate 80, polyethoxylated triglycerides, and mono and/or diglycerides of one or more medium chain fatty acids. Solutions containing surfactants (especially 2 or more surfactants) will form emulsions or microemulsions on contact with water. The compound may also be formulated in a water soluble polymer in which it has been dispersed as an amorphous phase by such methods as hot melt extrusion and spray drying, such polymers including hydroxylpropylmethylcellulose acetate (HP-MCAS), hydroxylpropylmethyl cellulose (HPMCS), and polyvinylpyrrolidinones, including the homopolymer and copolymers.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of the formulas described herein may also be administered parenterally. Solutions or suspensions of these active compounds can be prepared in water suitably mixed with a surfactant or mixture of surfactants such as hydroxypropylcellulose, polysorbate 80, and mono and diglycerides of medium and long chain fatty acids. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Combination Therapy

The compounds of the present invention are further useful in methods for the prevention or treatment of the aforementioned diseases, disorders and conditions in combination with other therapeutic agents.

The compounds of the present invention may be used in combination with one or more other drugs in the treatment, prevention, suppression or amelioration of diseases or conditions for which compounds of the formulas described herein or the other drugs may have utility, where the combination of the drugs together are safer or more effective than either drug alone. Such other drug(s) may be administered, by a route and in an amount commonly used therefore, contemporaneously or sequentially with a compound of the formulas described herein. When a compound of the formulas described herein is used contemporaneously with one or more other drugs, a pharmaceutical composition in unit dosage form containing such other drugs and the compound of the formulas described here is preferred. However, the combination therapy may also include therapies in which the compound of the formulas described herein and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of the formulas described herein.

Examples of other active ingredients that may be administered in combination with a compound of the formulas described herein, and either administered separately or in the same pharmaceutical composition, include, but are not limited to:

(1) dipeptidyl peptidase-IV (DPP-4) inhibitors;
(2) insulin sensitizers, including (i) PPARγ agonists, such as the glitazones (e.g. pioglitazone, rosiglitazone, netoglitazone, rivoglitazone, and balaglitazone) and other PPAR ligands, including (1) PPARα/γ dual agonists, such as muraglitazar, aleglitazar, sodelglitazar, and naveglitazar, (2) PPARα agonists, such as fenofibric acid derivatives (gemfibrozil, clofibrate, ciprofibrate, fenofibrate and bezafibrate), (3) selective PPARγ modulators (SPPARγM's), such as those disclosed in WO 02/060388 WO 02/08188, WO 2004/019869, WO 2004/020409, WO 2004/020408, and WO 2004/066963, and (4) PPARγ partial agonists; (ii) biguanides, such as metformin and its pharmaceutically acceptable salts, in particular, metformin hydrochloride, and extended-release formulations thereof, such as Glumetza®, Fortamet®, and GlucophageXR®; (iii) protein tyrosine phosphatase-1B (PTP-1B) inhibitors;

(3) insulin or insulin analogs, such as insulin lispro, insulin detemir, insulin glargine, insulin glulisine, and inhalable formulations of each thereof;

(4) leptin and leptin derivatives and agonists;

(5) amylin and amylin analogs, such as pramlintide;

(6) sulfonylurea and non-sulfonylurea insulin secretagogues, such as tolbutamide, glyburide, glipizide, glimepiride, mitiglinide, and meglitinides, such as nateglinide and repaglinide;

(7) α-glucosidase inhibitors (such as acarbose, voglibose and miglitol);

(8) glucagon receptor antagonists, such as those disclosed in WO 98/04528, WO 99/01423, WO 00/39088, and WO 00/69810;

(9) incretin mimetics, such as GLP-1, GLP-1 analogs, derivatives, and mimetics; and GLP-1 receptor agonists, such as exenatide, liraglutide, taspoglutide, AVE0010, CJC-1131, and BIM-51077, including intranasal, transdermal, and once-weekly formulations thereof;

(10) LDL cholesterol lowering agents such as (i) HMG-CoA reductase inhibitors (lovastatin, simvastatin, pravastatin, cerivastatin, fluvastatin, atorvastatin, pitavastatin, and rosuvastatin), (ii) bile acid sequestering agents (such as cholestyramine, colestimide, colesevelam hydrochloride, colestipol, and dialkylaminoalkyl derivatives of a cross-linked dextran, (iii) inhibitors of cholesterol absorption, such as ezetimibe, and (iv) acyl CoA:cholesterol acyltransferase inhibitors, such as avasimibe;

(11) HDL-raising drugs, such as niacin or a salt thereof and extended-release versions thereof; MK-524A, which is a combination of niacin extended-release and the DP-1 antagonist MK-524; and nicotinic acid receptor agonists;

(12) antiobesity compounds;

(13) agents intended for use in inflammatory conditions, such as aspirin, non-steroidal anti-inflammatory drugs (NSAIDs), glucocorticoids, and selective cyclooxygenase-2 (COX-2) inhibitors;

(14) antihypertensive agents, such as ACE inhibitors (such as enalapril, lisinopril, ramipril, captopril, quinapril, and tandolapril), A-II receptor blockers (such as losartan, candesartan, irbesartan, olmesartan medoxomil, valsartan, telmisartan, and eprosartan), renin inhibitors (such as aliskiren), beta blockers (such as and calcium channel blockers (such as;

(15) glucokinase activators (GKAs), such as LY2599506;

(16) inhibitors of 11β-hydroxysteroid dehydrogenase type 1, such as those disclosed in U.S. Pat. No. 6,730,690; WO 03/104207; and WO 04/058741;

(17) inhibitors of cholesteryl ester transfer protein (CETP), such as anacetrapib and dalcetrapib;

(18) inhibitors of fructose 1,6-bisphosphatase, such as those disclosed in U.S. Pat. Nos. 6,054,587; 6,110,903; 6,284,748; 6,399,782; and 6,489,476;

(19) inhibitors of acetyl CoA carboxylase-1 or 2 (ACC1 or ACC2);

(20) AMP-activated Protein Kinase (AMPK) activators;

(21) agonists of the G-protein-coupled receptors: GPR-109, GPR-119, and GPR-40;

(22) SSTR3 antagonists, such as those disclosed in WO 2009/011836;

(23) neuromedin U receptor agonists, such as those disclosed in WO2009/042053, including, but not limited to, neuromedin S (NMS);

(24) inhibitors of stearoyl-coenzyme A delta-9 desaturase (SCD);

(25) GPR-105 antagonists, such as those disclosed in WO 2009/000087;

(26) inhibitors of glucose uptake, such as sodium-glucose transporter (SGLT) inhibitors and its various isoforms, such as SGLT-1; SGLT-2, such as dapagliflozin and remogliflozin; and SGLT-3;

(27) inhibitors of acyl coenzyme A:diacylglycerol acyltransferase 1 and 2 (DGAT-1 and DGAT-2);

(28) inhibitors of fatty acid synthase;

(29) inhibitors of acetyl-CoA carboxylase-1 and 2 (ACC-1 and ACC-2);

(30) inhibitors of acyl coenzyme A:monoacylglycerol acyltransferase 1 and 2 (MGAT-1 and MGAT-2);

(31) agonists of the TGR5 receptor (also known as GPBAR1, BG37, GPCR19, GPR131, and M BAR); and

(32) bromocriptine mesylate and rapid-release formulations thereof.

Dipeptidyl peptidase-IV (DPP-4) inhibitors that can be used in combination with compounds of the formulas described herein include, but are not limited to, sitagliptin (disclosed in U.S. Pat. No. 6,699,871), vildagliptin, saxagliptin, alogliptin, denagliptin, carmegliptin, dutogliptin, melogliptin, linagliptin, and pharmaceutically acceptable salts thereof, and fixed-dose combinations of these compounds with metformin hydrochloride, pioglitazone, rosiglitazone, simvastatin, atorvastatin, or a sulfonylurea.

Other dipeptidyl peptidase-IV (DPP-4) inhibitors that can be used in combination with compounds of the formulas described herein include, but are not limited to:

(2R,3S,5R)-5-(1-methyl-4,6-dihydropyrrolo[3,4-c]pyrazol-5(1H)-yl)-2-(2,4,5-trifluorophenyl)tetrahydro-2H-pyran-3-amine;

(2R,3S,5R)-5-(1-methyl-4,6-dihydropyrrolo[3,4-c]pyrazol-5(1H)-yl)-2-(2,4,5-trifluorophenyl)tetrahydro-2H-pyran-3-amine;

(2R,3S,5R)-2-(2,5-difluorophenyl)tetrahydro-5-(4,6-dihydropyrrolo[3,4-c]pyrazol-5(1H)-yl)tetrahydro-2H-pyran-3-amine;

(3R)-4-[(3R)-3-amino-4-(2,4,5-trifluorophenyl)butanoyl]-hexahydro-3-methyl-2H-1,4-diazepin-2-one;

4-[(3R)-3-amino-4-(2,5-difluorophenyl)butanoyl]hexahydro-1-methyl-2H-1,4-diazepin-2-one hydrochloride; and (3R)-4-[(3R)-3-amino-4-(2,4,5-trifluorophenyl)butanoyl]-hexahydro-3-(2,2,2-trifluoroethyl)-2H-1,4-diazepin-2-one; and pharmaceutically acceptable salts thereof.

Antiobesity compounds that can be combined with compounds of the formulas described herein include topiramate; zonisamide; naltrexone; phenteimine; bupropion; the combination of bupropion an naltrexone; the combination of bupropion and zonisamide; the combination of topiramate and phentermine; fenfluramine; dexfenfluramine; sibutramine; lipase inhibitors, such as orlistat and cetilistat; melanocortin receptor agonists, in particular, melanocortin-4 receptor agonists; CCK-1 agonists; melanin-concentrating hormone (MCH) receptor antagonists; neuropeptide $Y_1$ or $Y_5$ antagonists (such as MK-0557); CB1 receptor inverse agonists and antagonists (such as rimonabant and taranabant); $β_3$ adrenergic receptor agonists; ghrelin antagonists; bombesin receptor agonists (such as bombesin receptor subtype-3 agonists); and 5-hydroxytryptamine-2c (5-HT2c) agonists, such as lorcaserin. For a review of anti-obesity compounds that can be combined with compounds of the present invention, see S. Chaki et al., "Recent advances in feeding suppressing agents: potential therapeutic strategy for the treatment of obesity," *Expert Opin. Ther. Patents,* 11: 1677-1692 (2001); D. Spanswick and K. Lee, "Emerging antiobesity drugs," *Expert Opin. Emerging Drugs,* 8: 217-237 (2003); J. A. Fernandez-Lopez, et al., "Pharmacological Approaches for the Treatment of Obesity," *Drugs*, 62: 915-944 (2002); and K. M. Gadde, et al., "Combination pharmaceutical therapies for obesity," *Exp. Opin. Pharmacother.*, 10: 921-925 (2009).

Glucagon receptor antagonists that can be used in combination with the compounds of the formulas described herein include, but are not limited to:
N-[4-((1S)-1-{3-(3,5-dichlorophenyl)-5-[6-(trifluoromethoxy)-2-naphthyl]-1H-pyrazol-1-yl}ethyl)benzoyl]-β-alanine;
N-[4-((1R)-1-{3-(3,5-dichlorophenyl)-5-[6-(trifluoromethoxy)-2-naphthyl]-1H-pyrazol-1-yl}ethyl)benzoyl]-β-alanine;
N-(4-{1-[3-(2,5-dichlorophenyl)-5-(6-methoxy-2-naphthyl)-1H-pyrazol-1-yl]ethyl}benzoyl)-β-alanine;
N-(4-{(1S)-1-[3-(3,5-dichlorophenyl)-5-(6-methoxy-2-naphthyl)-1H-pyrazol-1-yl]ethyl}benzoyl)-β-alanine;
N-(4-{(1S)-1-[(R)-(4-chlorophenyl)(7-fluoro-5-methyl-1H-indol-3-yl)methyl]butyl}benzoyl)-β-alanine; and
N-(4-{(1S)-1-[(4-chlorophenyl)(6-chloro-8-methylquinolin-4-yl)methyl]butyl}benzoyl)-β-alanine; and
pharmaceutically acceptable salts thereof.

Inhibitors of stearoyl-coenzyme A delta-9 desaturase (SCD) that can be used in combination with the compounds of the formulas described herein include, but are not limited to:
[5-(5-{4-[2-(trifluoromethyl)phenoxy]piperidin-1-yl}-1,3,4-thiadiazol-2-yl)-2H-tetrazol-2-yl]acetic acid;
(2'-{4-[2-(trifluoromethyl)phenoxy]piperidin-1-yl}-2,5'-bi-1,3-thiazol-4-yl)acetic acid;
(5-{3-[4-(2-bromo-5-fluorophenoxy)piperidin-1-yl]isoxazol-5-yl}-2H-tetrazol-2-yl)acetic acid;
(3-{3-[4-(2-bromo-5-fluorophenoxy)piperidin-1-yl]-1,2,4-oxadiazol-5-yl}-1H-pyrrol-1-yl)acetic acid;
(5-{5-[4-(2-bromo-5-fluorophenoxy)piperidin-1-yl]pyrazin-2-yl}-2H-tetrazol-2-yl)acetic acid; and
(5-{2-[4-(5-bromo-2-chlorophenoxy)piperidin-1-yl]pyrimidin-5-yl}-2H-tetrazol-2-yl)acetic acid;
and pharmaceutically acceptable salts thereof.

Glucokinase activators that can be used in combination with the compounds of the formulas described herein include, but are not limited to:
3-(6-ethanesulfonylpyridin-3-yloxy)-5-(2-hydroxy-1-methyl-ethoxy)-N-(1-methyl-1H-pyrazol-3-yl)benzamide;
5-(2-hydroxy-1-methyl-ethoxy)-3-(6-methanesulfonylpyridin-3-yloxy)-N-(1-methyl-1H-pyrazol-3-yl)benzamide;
5-(1-hydroxymethyl-propoxy)-3-(6-methanesulfonylpyridin-3-yloxy)-N-(1-methyl-1H-pyrazol-3-yl)benzamide;
3-(6-methanesulfon ylpyridin-3-yloxy)-5-(1-methoxymethyl-propoxy)-N-(1-methyl-1H-pyrazol-3-yl)benzamide;
5-isopropoxy-3 (6-methanesulfonylpyridin-3-yloxy)-N-(1-methyl-1H-pyrazol-3-yl)benzamide;
5-(2-fluoro-1-fluoromethyl-ethoxy)-3-(6-methanesulfonylpyridin-3-yloxy)-N-(1-methyl-1H-pyrazol-3-yl)benzamide;
3-({4-[2-(dimethylamino)ethoxy]phenyl}thio)-N-(3-methyl-1,2,4-thiadiazol-5-yl)-6-[(4-methyl-4H-1,2,4-triazol-3-yl)thio]pyridine-2-carboxamide;
3-({4-[(1-methylazetidin-3-yl)oxy]phenyl}thio)-N-(3-methyl-1,2,4-thiadiazol-5-yl)-6-[(4-methyl-4H-1,2,4-triazol-3-yl)thio]pyridine-2-carboxamide;
N-(3-methyl-1,2,4-thiadiazol-5-yl)-6-[(4-methyl-4H-1,2,4-triazol-3-yl)thio]-3-{[4-(2-pyrrolidin-1-ylethoxy)phenyl]thio}pyridine-2-carboxamide; and
3-[(4-{2-[(2R)-2-methylpyrrolidin-1-yl]ethoxy}phenyl)thio-N-(3-methyl-1,2,4-thiadiazol-5-yl)-6-[(4-methyl-4H-1,2,4-triazol-3-yl)thio]pyridine-2-carboxamide; and pharmaceutically acceptable salts thereof.

Agonists of the GPR-119 receptor that can be used in combination with the compounds of the formulas described herein include, but are not limited to:
rac-cis 5-chloro-2-{4-[2-(2-{[5-(methylsulfonyl)pyridin-2-yl]oxy}ethyl)cyclopropyl]piperidin-1-yl}pyrimidine;
5-chloro-2-{4-[(1R,2S)-2-(2-{[5-(methylsulfonyl)pyridin-2-yl]oxy}ethyl)cyclopropyl]piperidin-1-yl}pyrimidine;
rac cis-5-chloro-2-[4-(2-{2-[4-(methylsulfonyl)phenoxy]ethyl}cyclopropyl)piperidin-1-yl]pyrimidine;
5-chloro-2-[4-((1S,2R)-2-{2-[4-(methylsulfonyl)phenoxy]ethyl}cyclopropyl)piperidin-1-yl]pyrimidine;
5-chloro-2-[4-((1R,2S)-2-{2-[4-(methylsulfonyl)phenoxy]ethyl}cyclopropyl)piperidin-1-yl]pyrimidine;
rac cis-5-chloro-2-[4-(2-{2-[3-(methylsulfonyl)phenoxy]ethyl}cyclopropyl)piperidin-1-yl]pyrimidine; and
rac cis-5-chloro-2-[4-(2-{2-[3-(5-methyl-1,3,4-oxadiazol-2-yl)phenoxy]ethyl}cyclopropyl)piperidin-1-yl]pyrimidine;
and pharmaceutically acceptable salts thereof.

Selective PPARγ modulators (SPPARγM's) that can be used in combination with the compound of the formulas described herein include, but are not limited to:
(2S)-2-({6-chloro-3-[6-(4-chlorophenoxy)-2-propylpyridin-3-yl]-1,2-benzisoxazol-5-yl}oxy)propanoic acid;
(2S)-2-({6-chloro-3-[6-(4-fluorophenoxy)-2-propylpyridin-3-yl]-1,2-benzisoxazol-5-yl}oxy)propanoic acid;
(2S)-2-{[6-chloro-3-(6-phenoxy-2-propylpyridin-3-yl)-1,2-benzisoxazol-5-yl]oxy}propanoic acid;
(2R)-2-({6-chloro-3-[6-(4-chlorophenoxy)-2-propylpyridin-3-yl]-1,2-benzisoxazol-5-yl}oxy)propanoic acid;
(2R)-2-{3-[3-(4-methoxy)benzoyl-2-methyl-6-(trifluoromethoxy)-1H-indol-1-yl]phenoxy}butanoic acid;
(2S)-2-{3-[3-(4-methoxy)benzoyl-2-methyl-6-(trifluoromethoxy)-1H-indol-1-yl]phenoxy}butanoic acid;
2-{3-[3-(4-methoxy)benzoyl-2-methyl-6-(trifluoromethoxy)-1H-indol-1-yl]phenoxy}-2-methylpropanoic acid; and
(2R)-2-{3-[3-(4-chloro)benzoyl-2-methyl-6-(trifluoromethoxy)-1H-indol-1-yl]phenoxy}propanoic acid; and
pharmaceutically acceptable salts thereof.

Inhibitors of 11β-hydroxysteroid dehydrogenase type 1 that can be used in combination with the compounds of the formulas described herein include, but are not limited to:
3-[1-(4-chlorophenyl)-trans-3-fluorocyclobutyl]-4,5-dicyclopropyl-r-4H-1,2,4-triazole;
3-[1-(4-chlorophenyl)-trans-3-fluorocyclobutyl]-4-cyclopropyl-5-(1-methylcyclopropyl)-r-4H-1,2,4-triazole;
3-[1-(4-chlorophenyl)-trans-3-fluorocyclobutyl]-4-methyl-5-[2-(trifluoromethoxy)phenyl]-r-4H-1,2,4-triazole;
3-[1-(4-chlorophenyl)cyclobutyl]-4-methyl-5-[2-(trifluoromethyl)phenyl]-4H-1,2,4-triazole;
3-{4-[3-(ethylsulfonyl)propyl]bicyclo[2.2.2]oct-1-yl}-4-methyl-5-[2-(trifluoromethyl)phenyl]-4H-1,2,4-triazole;
4-methyl-3-{4-[4-(methylsulfonyl)phenyl]bicyclo[2.2.2]oct-1-yl}-5-[2-(trifluoromethyl)phenyl]-4H-1,2,4-triazole;
3-(4-{4-methyl-5-[2-(trifluoromethyl)phenyl]-4H-1,2,4-triazol-3-yl}bicyclo[2.2.2]oct-1-yl)-5-(3,3,3-trifluoropropyl)-1,2,4-oxadiazole;
3-(4-{4-methyl-5-[2-(trifluoromethyl)phenyl]-4H-1,2,4-triazol-3-yl}bicyclo[2.2.2]oct-1-yl)-5-(3,3,3-trifluoroethyl)-1,2,4-oxadiazole;
5-(3,3-difluorocyclobutyl)-3-(4-{4-methyl-5-[2-(trifluoromethyl)phenyl]-4H-1,2,4-triazol-3-yl}bicyclo[2.2.2]oct-1-yl)-1,2,4-oxadiazole;
5-(1-fluoro-1-methyl ethyl)-3-(4-{4-methyl-5-[2-(trifluoromethyl)phenyl]-4H-1,2,4-triazol-3-yl}bicyclo[2.2.2]oct-1-yl)-1,2,4-oxadiazole;

2-(1,1-difluoroethyl)-5-(4-{4-methyl-5-[2-(trifluoromethyl)phenyl]-4H-1,2,4-triazol-3-yl}bicyclo[2.2.2]oct-1-yl)-1,3,4-oxadiazole;
2-(3,3-difluorocyclobutyl)-5-(4-{4-methyl-5-[2-(trifluoromethyl)phenyl]-4H-1,2,4-triazol-3-yl}bicyclo[2.2.2]oct-1-yl)-1,3,4-oxadiazole; and
5-(1,1-difluoroethyl)-3-(4-{4-methyl-5-[2-(trifluoromethyl)phenyl]-4H-1,2,4-triazol-3-yl}bicyclo[2.2.2]oct-1-yl)-1,2,4-oxadiazole; and pharmaceutically acceptable salts thereof.

Somatostatin subtype receptor 3 (SSTR3) antagonists that can be used in combination with the compounds of the formulas described herein include, but are not limited to:

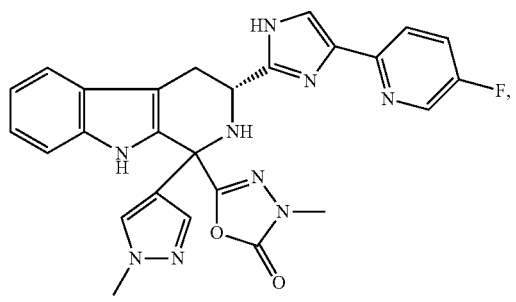

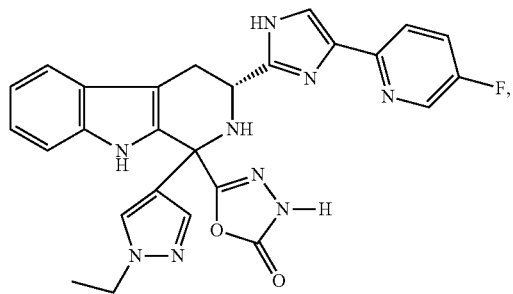

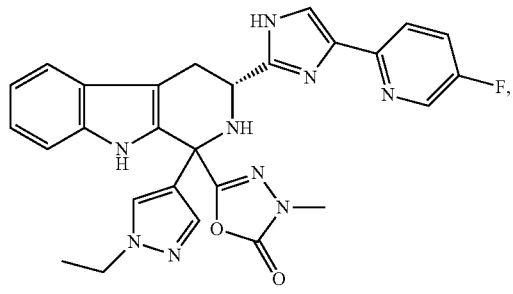

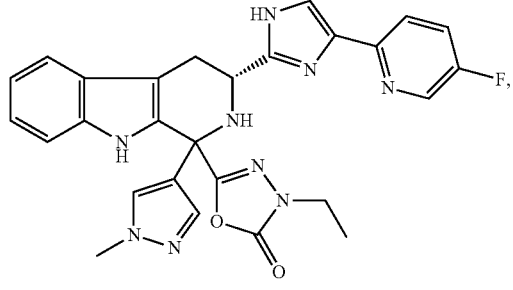

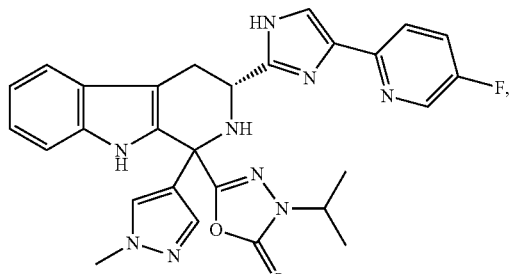

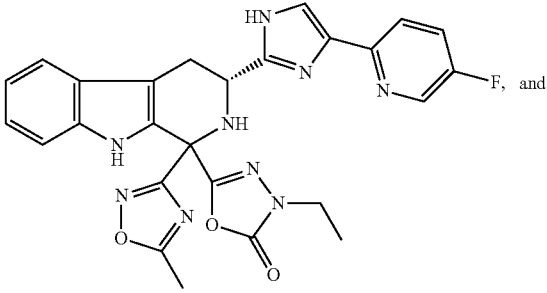

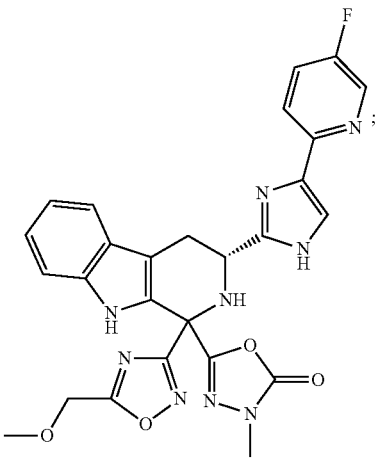 [SMILES: COCc1nc(C2(c3nn(C)c(=O)o3)N[C@@H](c3nc(-c4ccc(F)cn4)c[nH]3)Cc3c2[nH]c2ccccc32)no1]

and pharmaceutically acceptable salts thereof.

AMP-activated Protein Kinase (AMPK) activators that can be used in combination with the compounds of the formulas described herein include, but are not limited to:

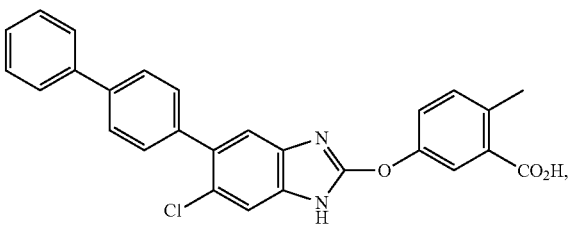

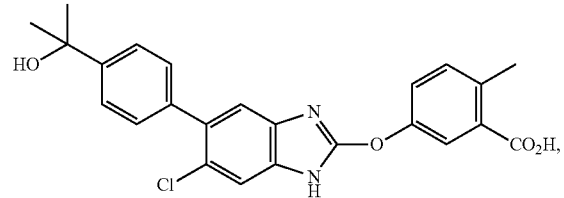

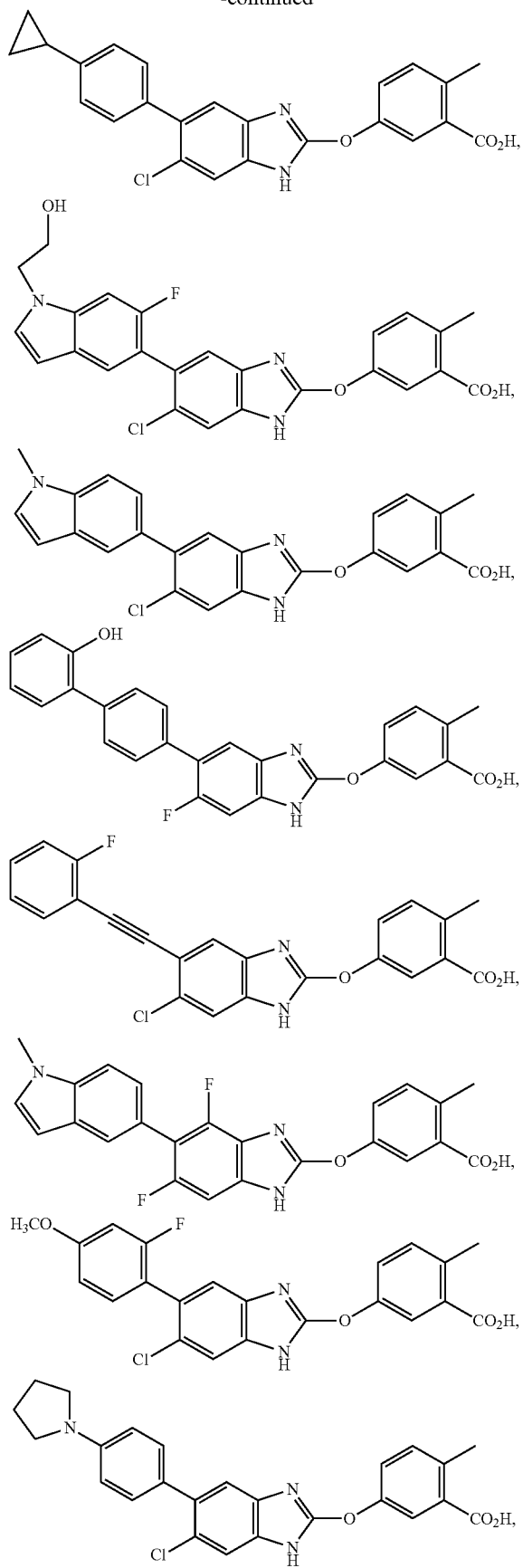
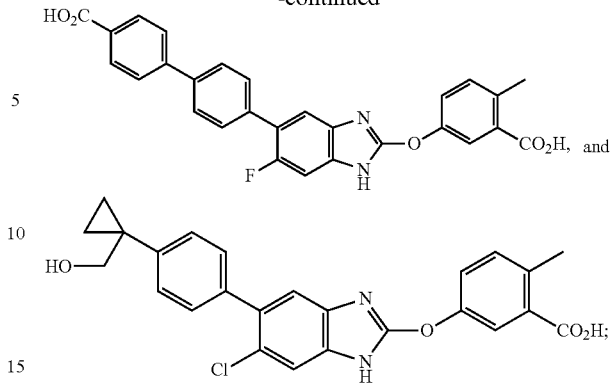

and pharmaceutically acceptable salts thereof.

Inhibitors of acetyl-CoA carboxylase-1 and 2 (ACC-1 and ACC-2) that can be used in combination with the compounds of the formulas described herein include, but are not limited to:

3-{1'-[(1-cyclopropyl-4-methoxy-1H-indol-6-yl)carbonyl]-4-oxospiro[chroman-2,4'-piperidin]-6-yl}benzoic acid;

5-{1'-[(1-cyclopropyl-4-methoxy-1H-indol-6-yl)carbonyl]-4-oxospiro[chroman-2,4'-piperidin]-6-yl}nicotinic acid;

1'-[(1-cyclopropyl-4-methoxy-1H-indol-6-yl)carbonyl]-6-(1H-tetrazol-5-yl)spiro[chroman-2,4'-piperidin]-4-one;

1'-[(1-cyclopropyl-4-ethoxy-3-methyl-1H-indol-6-yl)carbonyl]-6-(1H-tetrazol-5-yl)spiro[chroman-2,4'-piperidin]-4-one; and 5-{1'-[(1-cyclopropyl-4-methoxy-3-methyl-1H-indol-6-yl)carbonyl]-4-oxo-spiro[chroman-2,4'-piperidin]-6-yl}nicotinic acid; and pharmaceutically acceptable salts thereof.

In another aspect of the invention, a pharmaceutical composition is disclosed which comprises one or more of the following agents:

(a) a compound of structural formula I, formula Ia, formula Ib or formula Ic;

(b) one or more compounds selected from the group consisting of:

(1) dipeptidyl peptidase-IV (DPP-4) inhibitors;

(2) insulin sensitizers, including (i) PPARγ agonists, such as the glitazones (e.g. pioglitazone, rosiglitazone, netoglitazone, rivoglitazone, and balaglitazone) and other PPAR ligands, including (1) PPARα/γ dual agonists, such as muraglitazar, aleglitazar, sodelglitazar, and naveglitazar, (2) PPARα agonists, such as fenofibric acid derivatives (gemfibrozil, clofibrate, ciprofibrate, fenofibrate and bezafibrate), (3) selective PPARγ modulators (SPPARγM's), and (4) PPARγ partial agonists; (ii) biguanides, such as metformin and its pharmaceutically acceptable salts, in particular, metformin hydrochloride, and extended-release formulations thereof, such as Glumetza®, Fortamd®, and GlucophageXR®; (iii) protein tyrosine phosphatase-1B (PTP-1B) inhibitors;

(3) sulfonylurea and non-sulfonylurea insulin secretagogues, such as tolbutamide, glyburide, glipizide, glimepiride, mitiglinide, and meglitinides, such as nateglinide and repaglinide;

(4) α-glucosidase inhibitors (such as acarbose, voglibose and miglitol);

(5) glucagon receptor antagonists;

(6) LDL cholesterol lowering agents such as (i) HMG-CoA reductase inhibitors (lovastatin, simvastatin, pravastatin, cerivastatin, fluvastatin, atorvastatin, pitavastatin, and rosuvastatin (ii) bile acid sequestering agents (such as cholestyramine, colestimide, colesevelam hydrochloride, colestipol, and dialkylaminoalkyl derivatives of a cross-linked dextran, (iii) inhibitors of cholesterol absorption, such as ezetimibe, and (iv) acyl CoA:cholesterol acyltransferase inhibitors, such as avasimibe;
(7) HDL-raising drugs, such as niacin or a salt thereof and extended-release versions thereof; MK-524A, which is a combination of niacin extended-release and the DP-1 antagonist MK-52 and nicotinic acid receptor agonists;
(8) antiobesity compounds;
(9) agents intended for use in inflammatory conditions, such as aspirin, non-steroidal anti-inflammatory drugs (NSAIDs), glucocorticoids, and selective cyclooxygenase-2 (COX-2) inhibitors;
(10) antihypertensive agents, such as ACE inhibitors (such as enalapril, lisinopril, ramipril, captopril, quinapril, and tandolapril), A-II receptor blockers (such as losartan, candesartan, irbesartan, olmesartan medoxomil, valsartan, telmisartan, and eprosartan), renin inhibitors (such as aliskiren), beta blockers (such as and calcium channel blockers;
(11) glucokinase activators (GKAs), such as LY2599506;
(12) inhibitors of 11β-hydroxysteroid dehydrogenase type 1;
(13) inhibitors of cholesteryl ester transfer protein (CETP), such as anacetrapib and dalcetrapib;
(14) inhibitors of fructose 1,6-bisphosphatase;
(15) inhibitors of acetyl CoA carboxylase-1 or 2 (ACC1 or ACC2);
(16) AMP-activated Protein Kinase (AMPK) activators;
(17) agonists of the G-protein-coupled receptors: GPR-109, GPR-119, and GPR-40;
(18) SSTR3 antagonists;
(19) neuromedin U receptor agonists, including, but not limited to, neuromedin S (NMS
(20) inhibitors of stearoyl-coenzyme A delta-9 desaturase (SCD);
(21) GPR-105 antagonists;
(22) inhibitors of glucose uptake, such as sodium-glucose transporter (SGLT) inhibitors and its various isoforms, such as SGLT-1; SGLT-2, such as dapagliflozin and remogliflozin; and SGLT-3;
(23) inhibitors of acyl coenzyme A:diacylglycerol acyltransferase 1 and 2 (DGAT-1 and DGAT-2);
(24) inhibitors of fatty acid synthase;
(25) inhibitors of acetyl-CoA carboxylase-1 and 2 (ACC-1 and ACC-2);
(26) inhibitors of acyl coenzyme A:monoacylglycerol acyltransferase 1 and 2 (MGAT-1 and MGAT-2);
(27) agonists of the TGR5 receptor (also known as GPBAR1, BG37, GPCR19, GPR131 and M-BAR); and
(28) bromocriptine mesylate and rapid-release formulations thereof; and
(c) a pharmaceutically acceptable carrier.

When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

EXAMPLES

The compounds of the present invention can be prepared according to the procedures of the following Schemes, Intermediates and Examples, using appropriate materials and are further exemplified by the following specific examples. Moreover, by utilizing the procedures described in the disclosure contained herein, one of ordinary skill in the art can readily prepare additional compounds of the present invention claimed herein. The compounds illustrated in the examples are not, however, to be construed as forming the only genus that is considered as the invention. The Examples further illustrate details for the preparation of the compounds of the present invention. Those skilled in the art will readily understand that known variations of the conditions and processes of the following preparative procedures can be used to prepare these compounds. The instant compounds are generally isolated in the form of their pharmaceutically acceptable salts, such as those previously described herein. The use of protecting groups for the amine and carboxylic acid functionalities to facilitate the desired reaction and minimize undesired reactions is well documented. Conditions required to remove protecting groups are found in standard textbooks such as Greene, T, and Wuts, P. G. M., Protective Groups in Organic Synthesis, John Wiley & Sons, Inc., New York, N.Y., 1991. CBZ and BOC are commonly used protecting groups in organic synthesis, and their removal conditions are known to those skilled in the art.

Reactions sensitive to moisture or air were performed under nitrogen or argon using anhydrous solvents and reagents. The progress of reactions was determined by either analytical thin layer chromatography (TLC) or liquid chromatography-mass spectrum (LC-MS). Concentration of solutions was carried out on a rotary evaporator under reduced pressure. 1H NMR spectra were acquired on a 500 MHz Varian Unity INOVA NMR spectrometer in CDCl$_3$ solutions unless otherwise noted. Chemical shifts were reported in parts per million (ppm). Tetramethylsilane (TMS) was used as internal reference in CD$_3$Cl solutions, and residual CH$_3$OH peak or TMS was used as internal reference in CD$_3$OD solutions. Coupling constants (J) were reported in hertz (Hz). All temperatures are degrees Celsius unless otherwise noted. Mass spectra (MS) were measured by electron-spray ion-mass spectroscopy.

Abbreviations Used in the Following Schemes and Examples:

aq.: aqueous; API-ES: atmospheric pressure ionization-electrospray (mass spectrum term); Ac: acetate; AcCN: acetonitrile; Bop reagent: (benzotriazol-1-yloxy)tris(dimethylamino)phosonium hexafluorophosphate; Boc: tert-butyloxycarbonyl; B(OTMS)$_3$: tris(trimethylsilyl)borate; Celite™: diatomaceous earth; CDI: carbonyl diimidazole; d: day(s); d is doublet (NMR); DCM: dichloromethane; Dess-Martin reagent: 1,1,1-triacetoxy-1,1-dihydro-1,2-benziodoxol-3(1H)-one; DIBAL: diisobutylaluminum hydride; DIEA and DIPEA: N,N-diisopropyl-ethylamine (Hunig's base); DMAP: 4-dimethylaminopyridine; DMF: N,N-dimethylformamide; DMSO: dimethylsulfoxide; DTBPF is 1,1'-bis(di-tert-butylphosphino)-ferrocene; eq: equivalent(s); Et is ethyl; OEt is ethoxy; EtOAc: ethyl acetate; EtOH: ethanol; g: gram(s); h or hr: hour(s); Hunig's base: N,N-diisopropylethylamine; HPLC: high pressure liquid chromatography; HPLC/MS: high pressure liquid chromatography/mass spectrum; in vacuo: rotary evaporation under diminished pressure; iPrOH or IPA: isopropyl alcohol; IPAC or IPAc: isopropyl acetate; [Ir(COD)Cl]$_2$: chloro-1,5-cyclooctadiene iridium (I) dimmer; L: liter; LC: Liquid chromatography; LC-MS or LCMS: liquid chromatography-mass spectrum; m is multiplet (NMR); M: molar; M+1: molecular ion plus H+ ion; m/e: ion mass divided by ionic charge; Me: methyl; MeCN: methylcyanide; MeI: methyl iodide; MeOH: methanol; Ms: methanesulfonyl; MsCl: methanesulfonyl chloride; MHz: megahertz; mg: milligram; min: minute(s); ml or mL: milliliter; mmol: millimole; MPLC: medium-pressure liquid chromatography; MS or ms: mass spectrum; N: normal; nM: nanomole(s); NMR: nuclear magnetic resonance; NMM: N-methylmorpholine; Pd$_2$(dba)$_3$: tris(dibenzyldeneacetone)dipalladium(0); q is quadruplet (NMR); Rt: retention time; room temperature or RT: room temperature; s is singlet (NMR); satd.: saturated; SRIF is somatotropin release-inhibiting factor or somatostatin; t is triplet (NMR); TBAF is tetrabutyl ammonium fluoride; TBS is tert-butyldimethylsilyl; TBSCl is tert-butyldimethylsily chloride; TEA: triethylamine; TFA: trifluoroacetic acid; THF: tetrahydrofuran; TLC or tlc: thin layer chromatography; Tf is trifluoromethane sulfonyl; and Ts is toluene sulfonyl.

The present compounds can be prepared using essentially the general Schemes provided below as well as the procedures provided in the Examples. The following Schemes and Examples further describe, but do not limit, the scope.

Example 1-1

4-(8-{[1-tert-Butyl-3-(2,3,4-trifluorophenyl)-1H-pyrazol-4-yl]methyl}-2-oxo-1-oxa-3,8-diazaspiro[4.5]dec-3-yl)benzoic acid, TFA salt

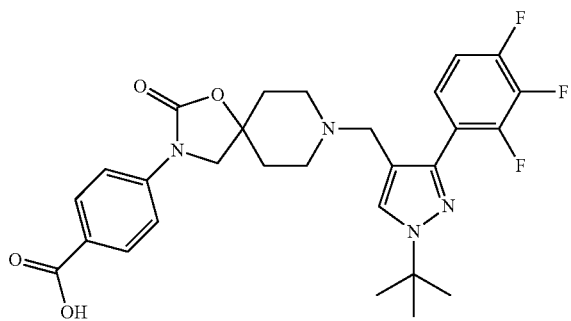 [SMILES: CC(C)(C)n1cc(CN2CCC3(CC2)CN(c2ccc(C(=O)O)cc2)C(=O)O3)c(-c2ccc(F)c(F)c2F)n1]

Step 1. Synthesis of tert-butyl 3-[4-(methoxycarbonyl)phenyl]-2-oxo-1-oxa-3,8-diazaspiro[4.5]decane-8-carboxylate

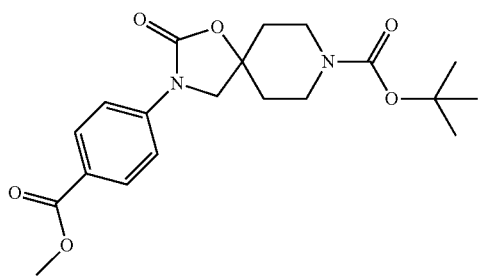 [SMILES: COC(=O)c1ccc(N2CC3(CCN(C(=O)OC(C)(C)C)CC3)OC2=O)cc1]

A mixture of cesium carbonate (4.27 g, 13.11 mmol), copper (I) iodide (0.832 g, 4.37 mmol), tert-butyl 2-oxo-1-oxa-3,8-diazaspiro[4.5]decane-8-carboxylate (1.12 g, 4.37 mmol), N,N'-dimethylethane-1,2-diamine (0.385 g, 437 mmol) and methyl 4-bromobenzoate (1.128 g, 5.24 mmol) was heated under nitrogen for 18 hours. The crude mixture was filtered through celite. Upon removal of the volatiles, the crude was purified by flash chromatography (EtOAc/hexanes 20 to 100%) to afford the title intermediate as a white solid.

$^1$H-NMR (CDCl$_3$): δ 8.08 (d, J=8.9 Hz, 2H), 7.65 (d, J=8.9 Hz, 2H), 3.95 (m, 2H), 3.94 (s, 3H), 3.82 (s, 2H), 3.37 (m, 2H), 2.02 (m, 2H), 1.82 (m, 2H), 1.51 (s, 9H).

LCMS (m/e): 391 (M+1).

Step 2. Synthesis of methyl 4-(2-oxo-1-oxa-3,8-diazaspiro[4.5]dec-3-yl)benzoate, hydrochloride salt

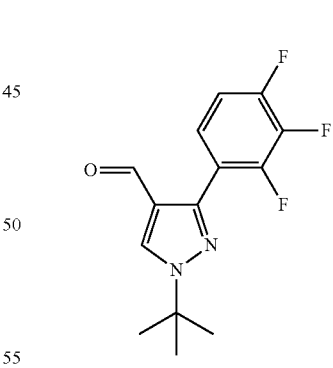

A solution of tert-butyl 3-[4-(methoxycarbonyl)phenyl]-2-oxo-1-oxa-3,8-diazaspiro[4.5]decane-8-carboxylate (1.68 g, 4.3 mmol) in 4 N HCl in dioxane (20 mL) was stirred at room temperature for 1 hour to give a white suspension. Upon removal of the volatiles, the title compound was collected as its HCl salt as a white solid.

LCMS (m/e): 291 (M+1).

Step 3. Synthesis of 1-tert-butyl-3-(2,3,4-trifluorophenyl)-1H-pyrazole-4-carbaldehyde

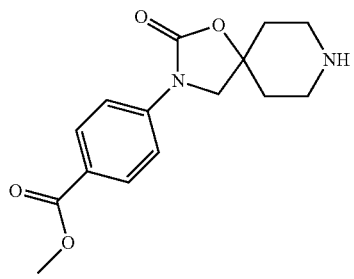 [SMILES: COC(=O)c1ccc(N2CC3(CCNCC3)OC2=O)cc1]

A solution of NaOAc (0.7 g, 8.53 mmol), t-butylhydrazine HCl salt (1.063 g, 8.53 mmol) and 2,3,4-trifluoroacetophenone (1.486 g, 8.53 mmol) in EtOH (5 mL) was heated at 85° C. for 2.5 hours. Most of the EtOH was removed under vacuum to afford the crude hydrazone intermediate which was used directly in the next reaction.

In a separate vessel, to POCl$_3$ (3.92 g, 25.6 mmol) in an ice bath was added slowly DMF (1.98 mL, 25.6 mmol) and the mixture was stirred in the ice bath for 10 minutes to afford a white solid. The hydrazone intermediate in DMF (15 mL) was then added to this white suspension. The resulting mixture was heated at 82° C. for 18 hours. The crude reaction mixture was slowly quenched with aq. $K_2CO_3$ solution and was diluted with EtOAc. The organic layer was washed with brine, dried with $Na_2SO_4$, filtered and concentrated. The crude residue was purified by flash chromatography to afford the title intermediate as an oil.

$^1$H-NMR (CDCl$_3$): δ: 9.82 (s, 1H), 8.18 (s, 1H), 7.38 (m, 1H), 7.11 (m, 1H), 1.67 (s, 9H).

LCMS (m/e): 283 (M+1).

Step 4. Synthesis of methyl 4-(8-{[1-tert-butyl-3-(2,3,4-trifluorophenyl)-1H-pyrazol-4-yl]methyl}-2-oxo-1-oxa-3,8-diazaspiro[4.5]dec-3-yl)benzoate, TFA salt

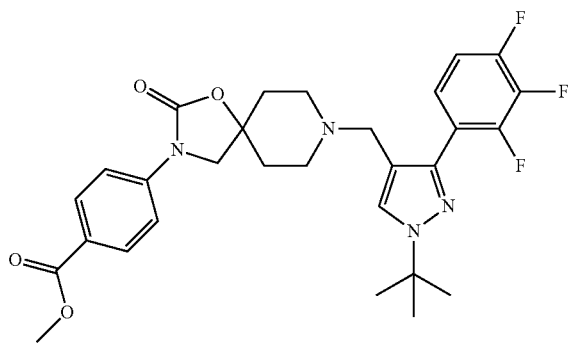 [SMILES: COC(=O)c1ccc(N2CC3(CCN(Cc4cn(C(C)(C)C)nc4-c4ccc(F)c(F)c4F)CC3)OC2=O)cc1]

A solution of 1-tert-butyl-3-(2,3,4-trifluorophenyl)-1H-pyrazole-4-carbaldehyde (43.7 mg, 0.155 mmol), methyl 4-(2-oxo-1-oxa-3,8-diazaspiro[4.5]dec-3-yl)benzoate HCl salt (50.6 mg, 0.155 mmol), NaB(OAc)$_3$H (65.6 mg, 0.310 mmol) in CH$_2$Cl$_2$ (3 mL) was added Hunig's base (0.054 mL, 0.310 mmol) and mixture was stirred at room temperature for 16 hours. Upon removal of the volatiles under vacuum, the crude residue was purified by reverse phase HPLC (gradient of acetonitrile/water with 0.1% TFA) to give the title compound which was isolated as a TFA salt.

LCMS (m/e): 557 (M+1).

Step 5. Synthesis of 4-(8-{[1-tert-butyl-3-(2,3,4-trifluorophenyl)-1H-pyrazol-4-yl]methyl}-2-oxo-1-oxa-3,8-diazaspiro[4.5]dec-3-yl)benzoic acid, TFA salt

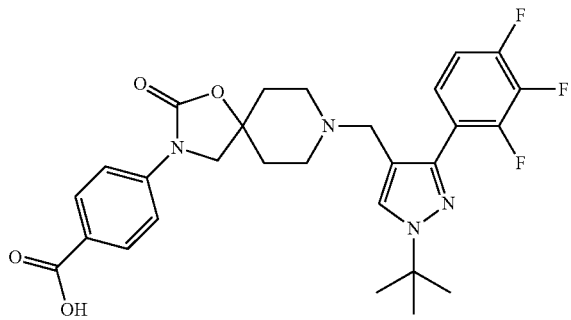 [SMILES: CC(C)(C)n1cc(CN2CCC3(CC2)CN(c2ccc(C(=O)O)cc2)C(=O)O3)c(-c2ccc(F)c(F)c2F)n1]

To a solution of methyl 4-(8-{[1-tert-butyl-3-(2,3,4-trifluorophenyl)-1H-pyrazol-4-yl]methyl}-2-oxo-1-oxa-3,8-diazaspiro[4.5]dec-3-yl)benzoate, TFA salt (38 mg, 0.068 mmol) in THF (2 mL) and MeOH (1 mL) was added 2N NaOH (0.341 mL, 0.68 mmol) and water (1 mL). The solution was stirred at room temperature for 16 hours. Upon removal of the volatiles under vacuum, the crude residue was purified by reverse phase HPLC to afford the title compound as its TFA salt.

LCMS (m/e): 543 (M+1).

Example 1-2

4-(8-{[3-(3-Chloro-4-fluorophenyl)-1-cyclohexyl-1H-pyrazol-4-yl]methyl}-2-oxo-1-oxa-3,8-diazaspiro[4.5]dec-3-yl)benzoic acid, TFA salt

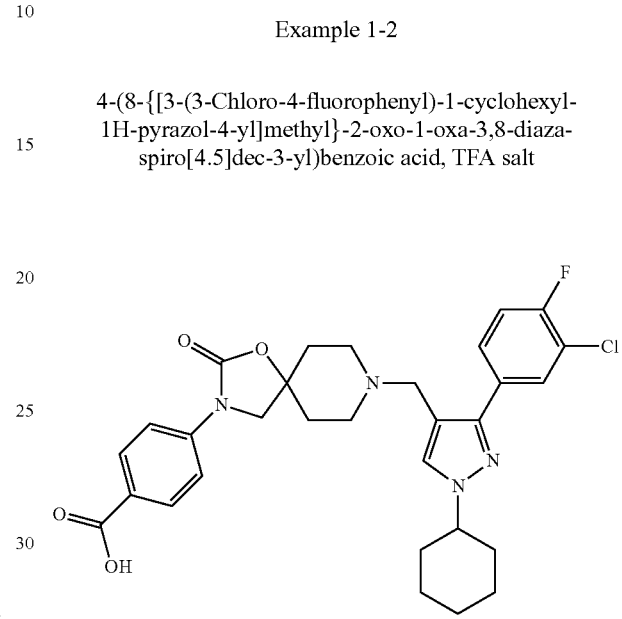

The title compound was prepared and purified using essentially the same experimental procedures as Example 1-1 and was isolated as a TFA salt.

LCMS (m/e): 567 (M+1).

Example 1-3

4-{8-[(1,3-Diphenyl-1H-pyrazol-4-yl)methyl]-2-oxo-1-oxa-3,8-diazaspiro[4.5]dec-3-yl}benzoic acid, TFA salt

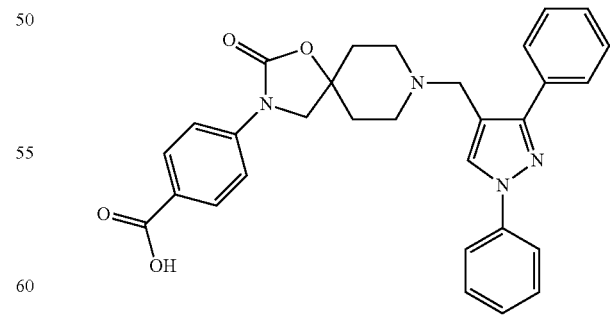

The title compound was prepared and purified using essentially the same experimental procedures as Example 1-1 and was isolated and was isolated as a TFA salt.

LCMS (m/e): 509 (M+1).

Example 1-4

4-(8-{[1-Cyclopropyl-3-(4-methoxyphenyl)-1,1-pyrazol-4-yl]methyl}-2-oxo-1-oxa-3,8-diazaspiro[4.5]dec-3-yl)benzoic acid, TFA salt

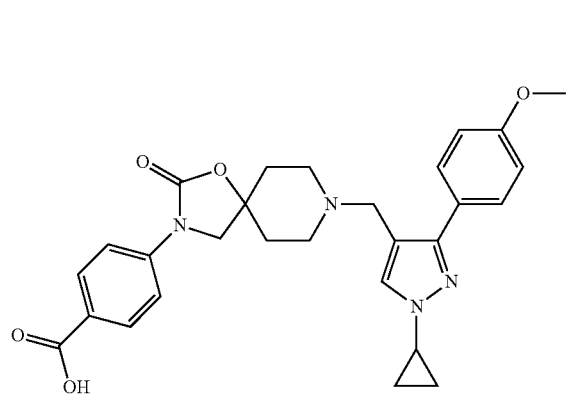 [SMILES: COc1ccc(-c2nn(C3CC3)cc2CN2CCC3(CC2)CN(c2ccc(C(=O)O)cc2)C(=O)O3)cc1]

The title compound was prepared and purified using essentially the same experimental procedures as Example 1-1 and was isolated as a TFA salt.

LCMS (m/e): 503 (M+1).

Example 1-5

4-[8-({1-Cyclohexyl-3-[3-(trifluoromethyl)phenyl]-1H-pyrazol-4-yl}methyl)-2-oxo-1-oxa-3,8-diazaspiro[4.5]dec-3-yl]benzoic acid, TFA salt

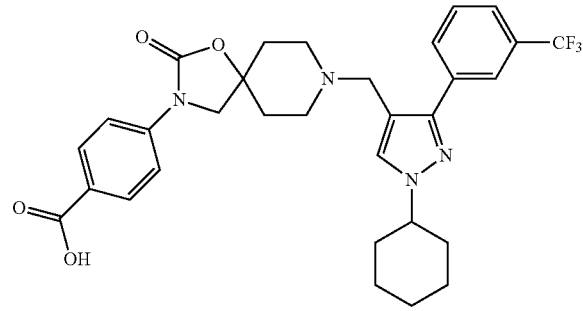 [SMILES: O=C(O)c1ccc(N2CC3(CCN(Cc4cn(C5CCCCC5)nc4-c4cccc(C(F)(F)F)c4)CC3)OC2=O)cc1]

The title compound was prepared and purified using essentially the same experimental procedures as Example 1-1 and was isolated as a TFA salt.

LCMS (m/e): 583 (M+1).

Example 1-6

4-(8-{[1-(2,4-Dimethylphenyl)-3-(2,3,4-trifluorophenyl)-1H-pyrazol-4-yl]methyl}-2-oxo-1-oxa-3,8-diazaspiro[4.5]dec-3-yl)benzoic acid, TFA salt

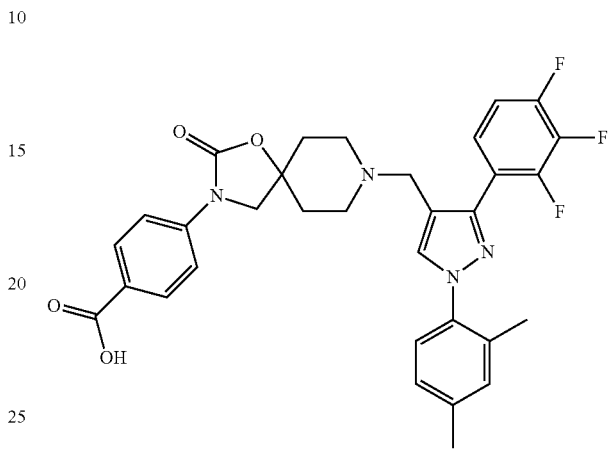

The title compound was prepared and purified using essentially the same experimental procedures as Example 1-1 and was isolated as a TFA salt.

LCMS (m/e): 591 (M+1).

Example 1-7

4-(8-{[1-tert-Butyl-3-(2,4,5-trifluorophenyl)-1H-pyrazol-4-yl]methyl}-2-oxo-1-oxa-3,8-diazaspiro[4.5]dec-3-yl)benzoic acid, TFA salt

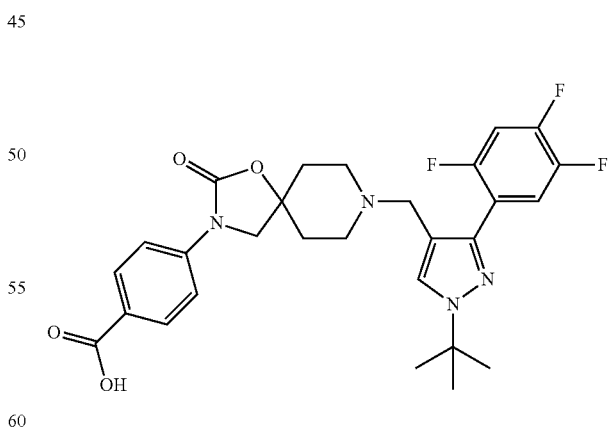

The title compound was prepared and purified using essentially the same experimental procedures as Example 1-1 and was isolated as a TFA salt.

LCMS (m/e): 543 (M+1).

Example 1-8

4-(8-{[1-tert-Butyl-3-(2,4,6-trifluorophenyl)-1H-pyrazol-4-yl]methyl}-2-oxo-1-oxa-3,8-diazaspiro[4.5]dec-3-yl)benzoic acid, TFA salt

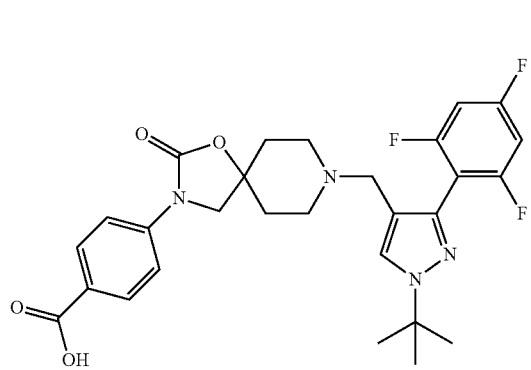 [SMILES: CC(C)(C)n1cc(CN2CCC3(CC2)CN(c2ccc(C(=O)O)cc2)C(=O)O3)c(-c2c(F)cc(F)cc2F)n1]

The title compound was prepared and purified using essentially the same experimental procedures as Example 1-1 and was isolated as a TFA salt.

LCMS (m/e): 543 (M+1).

Example 1-9

4-(8-{[3-(4-Methoxyphenyl)-1-phenyl-1H-pyrazol-4-yl]methyl}-2-oxo-1-oxa-3,8-diazaspiro[4.5]dec-3-yl)benzoic acid, TFA salt

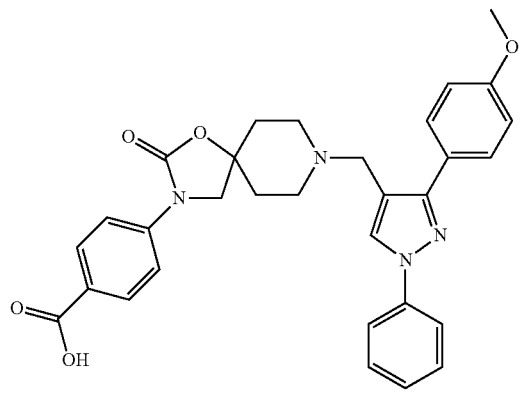 [SMILES: COc1ccc(-c2nn(-c3ccccc3)cc2CN2CCC3(CC2)CN(c2ccc(C(=O)O)cc2)C(=O)O3)cc1]

The title compound was prepared and purified using essentially the same experimental procedures as Example 1-1 and was isolated as a TFA salt.

LCMS (m/e): 539 (M+1).

Example 1-10

4-(8-{[1-tert-Butyl-3-(4-methoxyphenyl)-1H-pyrazol-4-yl]methyl}-2-oxo-1-oxa-3,8-diazaspiro[4.5]dec-3-yl)benzoic acid, TFA salt

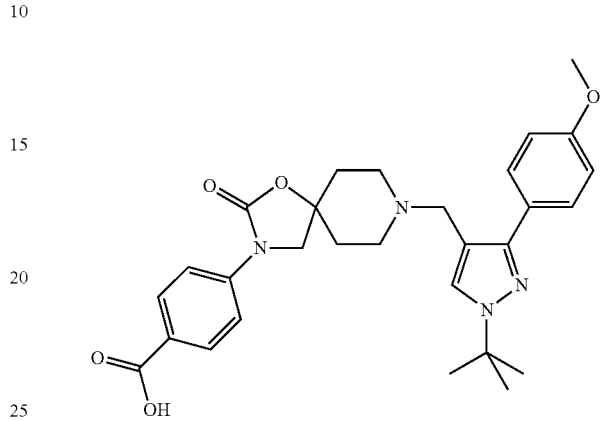

The title compound was prepared and purified using essentially the same experimental procedures as Example 1-1 and was isolated as a TFA salt.

LCMS (m/e): 519 (M+1).

Example 1-11

4-(8-{[1-tert-Butyl-3-(4-chloro-2,5-difluorophenyl)-1H-pyrazol-4-yl]methyl}-2-oxo-1-oxa-3,8-diazaspiro[4.5]dec-3-yl)-2-methylbenzoic acid, TFA salt

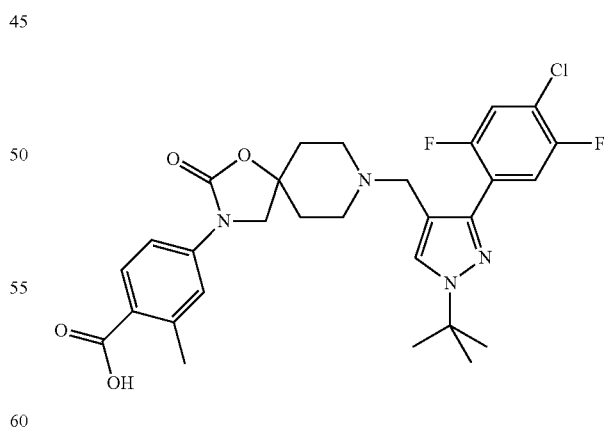

The title compound was prepared and purified using essentially the same experimental procedures as Example 1-1 and was isolated as a TFA salt.

LCMS (m/e): 573 (M+1).

Example 1-12

4-(8-{[3-(4-Ethoxyphenyl)-1-phenyl-1H-pyrazol-4-yl]methyl}-2-oxo-1-oxa-3,8-diazaspiro[4.5]dec-3-yl)benzoic acid, TFA salt

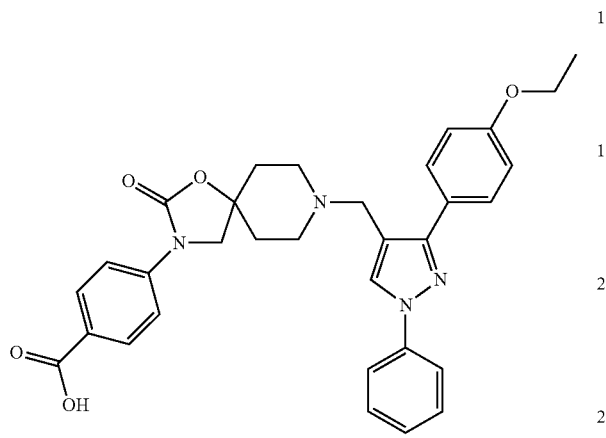

The title compound was prepared and purified using essentially the same experimental procedures as Example 1-1 and was isolated as a TFA salt.

LCMS (m/e): 553 (M+1).

Example 1-13

4-(8-{[1-tert-Butyl-3-(4-chloro-2,5-difluorophenyl)-1H-pyrazol-4-yl]methyl}-2-oxo-1-oxa-3,8-diazaspiro[4.5]dec-3-yl)-2-chlorobenzoic acid, TFA salt

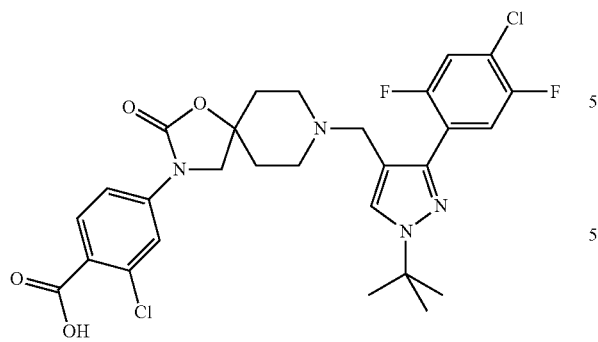

The title compound was prepared and purified using essentially the same experimental procedures as Example 1-1 and was isolated as a TFA salt.

LCMS (m/e): 593 (M+1).

Example 1-14

4-(8-{[1-tert-butyl-3-(2-Methoxyphenyl)-1H-pyrazol-4-yl]methyl}-2-oxo-1-oxa-3,8-diazaspiro[4.5]dec-3-yl)benzoic acid, TFA salt

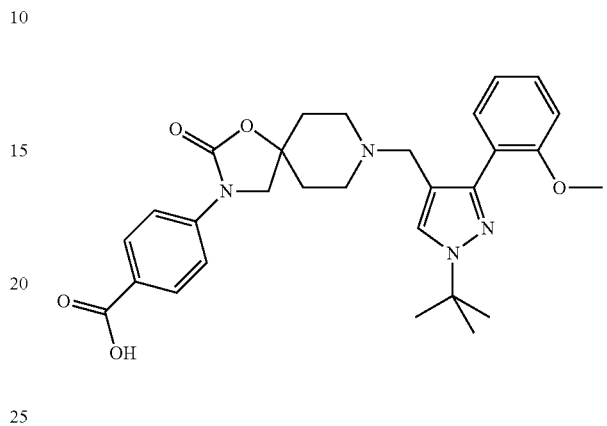

The title compound was prepared and purified using essentially the same experimental procedures as Example 1-1 and was isolated as a TFA salt.

LCMS (m/e): 519 (M+1).

Example 1-15

4-(2-Oxo-8-{[1-phenyl-3-(2,3,4-trifluorophenyl)-1H-pyrazol-4-yl]methyl}-1-oxa-3,8-diazaspiro[4.5]dec-3-yl)benzoic acid, TFA salt

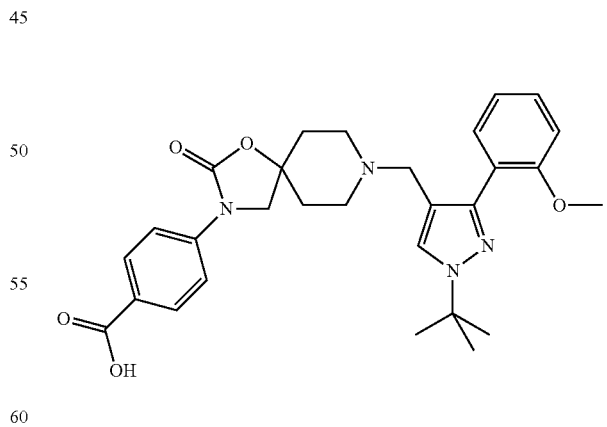

The title compound was prepared and purified using essentially the same experimental procedures as Example 1-1 and was isolated as a TFA salt.

LCMS (m/e): 563 (M+1).

Example 1-16

4-(2-Oxo-8-{[1-phenyl-3-(2,3,5-trifluorophenyl)-1H-pyrazol-4-yl]methyl}-1-oxa-3,8-diazaspiro[4.5]dec-3-yl)benzoic acid, TFA salt

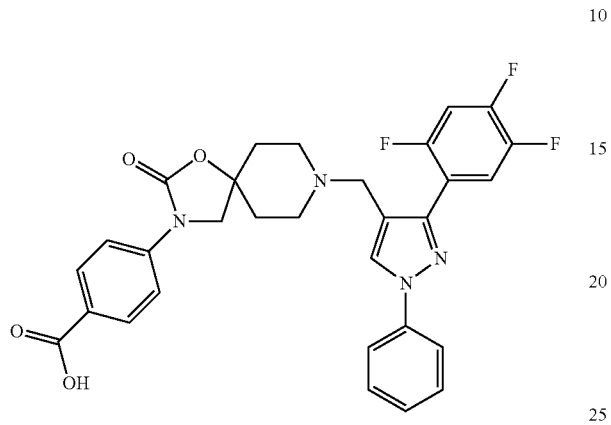

The title compound was prepared and purified using essentially the same experimental procedures as Example 1-1 and was isolated as a TFA salt.

LCMS (m/e): 563 (M+1).

Example 1-17

4-(2-Oxo-8-{[1-(propan-2-yl)-3-(2,3,4-trifluorophenyl)-1H-pyrazol-4-yl]methyl}-1-oxa-3,8-diazaspiro[4.5]dec-3-yl)benzoic acid, TFA salt

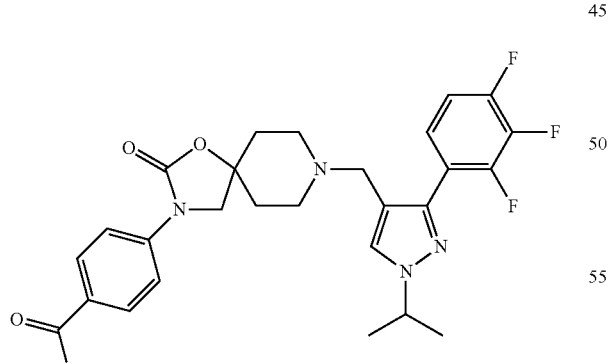

The title compound was prepared and purified using essentially the same experimental procedures as Example 1-1 and was isolated as a TFA salt.

LCMS (m/e): 529 (M+1).

Example 1-18

4-(8-{[1-Butyl-3-(2,3,4-trifluorophenyl)-1H-pyrazol-4-yl]methyl}-2-oxo-1-oxa-3,8-diazaspiro[4.5]dec-3-yl)benzoic acid, TFA salt

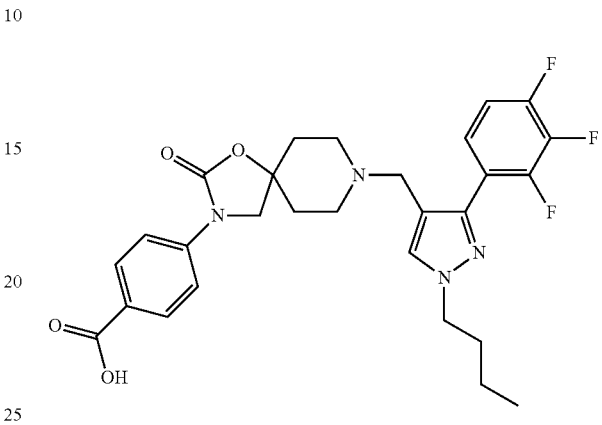

The title compound was prepared and purified using essentially the same experimental procedures as Example 1-1 and was isolated as a TFA salt.

LCMS (m/e): 543 (M+1).

Example 1-19

4-(8-{[1-Cyclohexyl-3-(2,3,4-trifluorophenyl)-1H-pyrazol-4-yl]methyl}-2-oxo-1-oxa-3,8-diazaspiro[4.5]dec-3-yl)benzoic acid, TFA salt

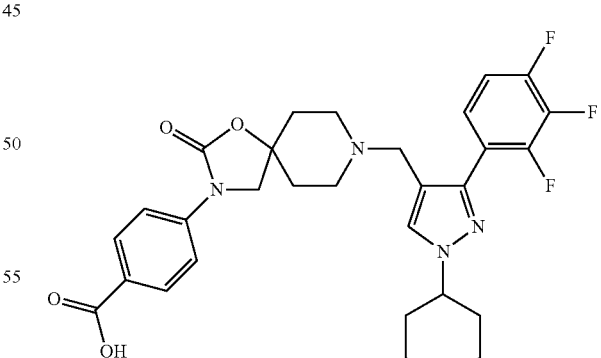

The title compound was prepared and purified using essentially the same experimental procedures as Example 1-1 and was isolated as a TFA salt.

LCMS (m/e): 569 (M+1).

Example 1-20

4-(8-{[1,3-Bis(4-fluorophenyl)-1H-pyrazol-4-yl]methyl}-2-oxo-1-oxa-3,8-diazaspiro[4.5]dec-3-yl)benzoic acid, TFA salt

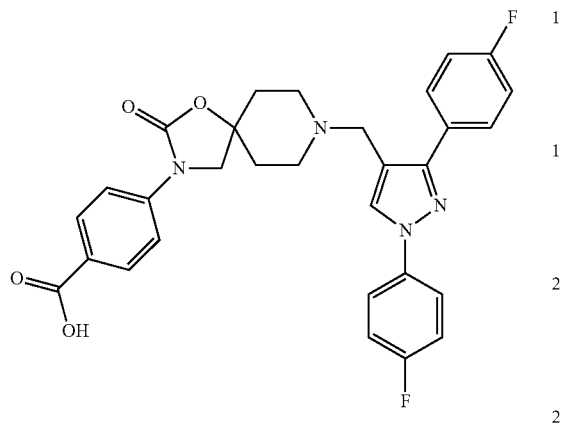

The title compound was prepared and purified using essentially the same experimental procedures as Example 1-1 and was isolated as a TFA salt.

LCMS (m/e): 547 (M+1).

Example 1-21

4-(8-{[1-(2,3-Dihydro-1,4-benzodioxin-5-yl)-3-(2,3,4-trifluorophenyl)-1H-pyrazol-4-yl]methyl}-2-oxo-1-oxa-3,8-diazaspiro[4.5]dec-3-yl)benzoic acid, TFA salt

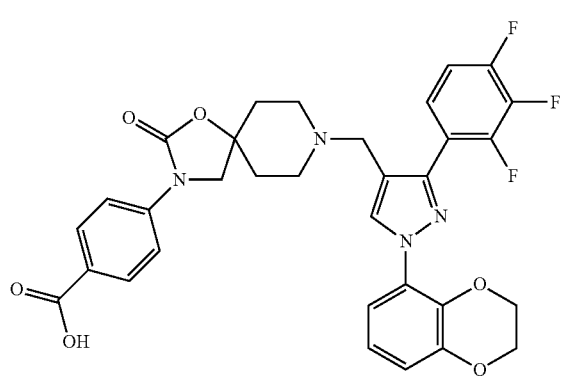 [SMILES: O=C(O)c1ccc(N2CC3(CCN(Cc4cn(-c5cccc6c5OCCO6)nc4-c4ccc(F)c(F)c4F)CC3)OC2=O)cc1]

The title compound was prepared and purified using essentially the same experimental procedures as Example 1-1 and was isolated as a TFA salt.

LCMS (m/e): 621 (M+1).

Example 1-22

4-(8-{[3-(3-Methoxyphenyl)-1-phenyl-1H-pyrazol-4-yl]methyl}-2-oxo-1-oxa-3,8-diazaspiro[4.5]dec-3-yl)benzoic acid, TFA salt

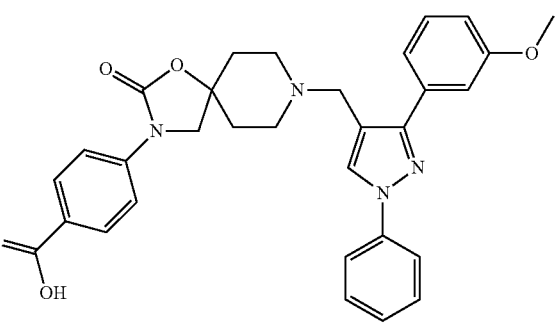

The title compound was prepared and purified using essentially the same experimental procedures as Example 1-1 and was isolated as a TFA salt.

LCMS (m/e): 539 (M+1).

Example 1-23

4-[8-({1-Cyclohexyl-3-[4-(trifluoromethoxy)phenyl]-1H-pyrazol-4-yl}methyl)-2-oxo-1-oxa-3,8-diazaspiro[4.5]dec-3-yl]benzoic acid, TFA salt

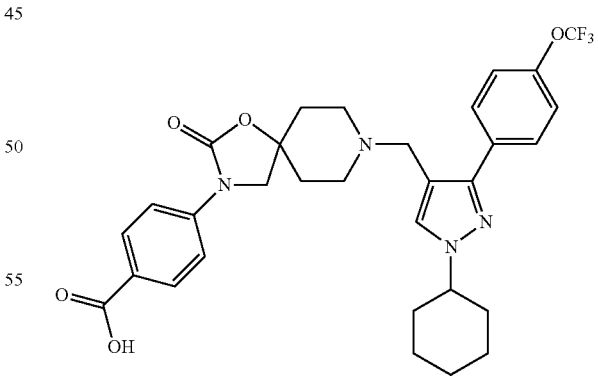

The title compound was prepared and purified using essentially the same experimental procedures as Example 1-1 and was isolated as a TFA salt.

LCMS (m/e): 599 (M+1).

Example 1-24

4-[8-({1-Cyclohexyl-3-[4-(trifluoromethyl)phenyl]-1H-pyrazol-4-yl}methyl)-2-oxo-1-oxa-3,8-diazaspiro[4.5]dec-3-yl]benzoic acid, TFA salt

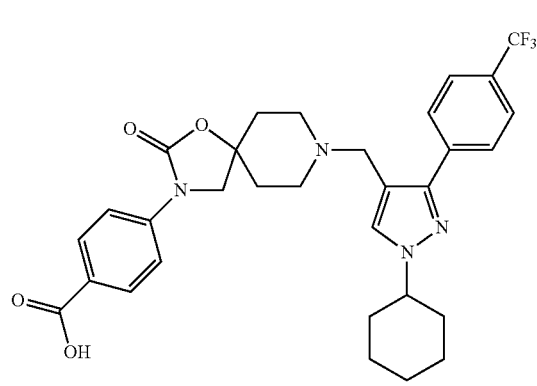 [SMILES: O=C(O)c1ccc(N2CC3(CCN(Cc4cn(C5CCCCC5)nc4-c4ccc(C(F)(F)F)cc4)CC3)OC2=O)cc1]

The title compound was prepared and purified using essentially the same experimental procedures as Example 1-1 and was isolated as a TFA salt.

LCMS (m/e): 583 (M+1).

Example 1-25

4-(8-{[1-(3,3-Dimethylbicyclo[2.2.1]hept-2-yl)-3-(2,3,4-trifluorophenyl)-1H-pyrazol-4-yl]methyl}-2-oxo-1-oxa-3,8-diazaspiro[4.5]dec-3-yl)benzoic acid, TFA salt

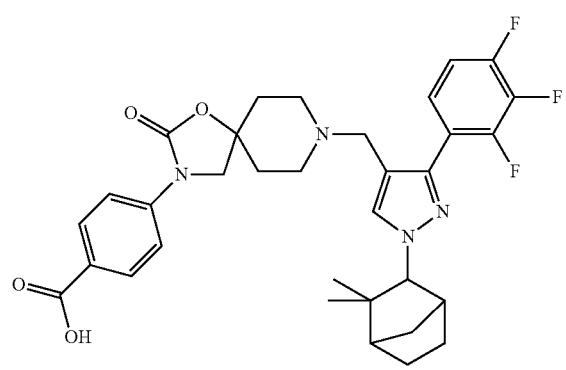 [SMILES: CC1(C)C2CCC(C2)C1n1cc(CN2CCC3(CC2)CN(c2ccc(C(=O)O)cc2)C(=O)O3)c(-c2ccc(F)c(F)c2F)n1]

The title compound was prepared and purified using essentially the same experimental procedures as Example 1-1 and was isolated as a TFA salt.

LCMS (m/e): 609 (M+1).

Example 1-26

4-(8-{[1-(Naphthalen-2-yl)-3-(2,3,4-trifluorophenyl)-1H-pyrazol-4-yl]methyl}-2-oxo-1-oxa-3,8-diazaspiro[4.5]dec-3-yl)benzoic acid, TFA salt

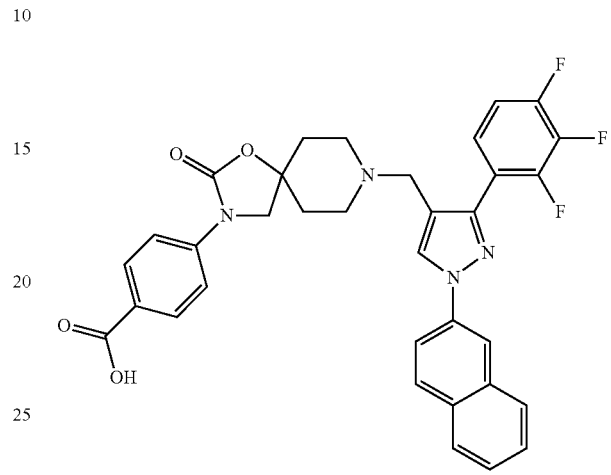

The title compound was prepared and purified using essentially the same experimental procedures as Example 1-1 and was isolated as a TFA salt.

LCMS (m/e): 615 (M+1).

Example 1-27

4-[2-Oxo-8-({1-phenyl-3-[4-(trifluoromethoxy)phenyl]-1H-pyrazol-4-yl}methyl)-1-oxa-3,8-diazaspiro[4.5]dec-3-yl]benzoic acid, TFA salt

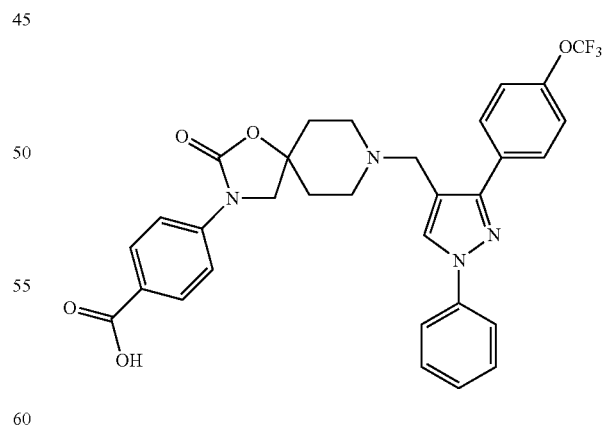

The title compound was prepared and purified using essentially the same experimental procedures as Example 1-1 and was isolated as a TFA salt.

LCMS (m/e): 593 (M+1).

Example 1-28

4-(8-{[1-tert-Butyl-3-(3-chloro-4-fluorophenyl)-1H-pyrazol-4-yl]methyl}-2-oxo-1-oxa-3,8-diazaspiro[4.5]dec-3-yl)benzoic acid, TFA salt

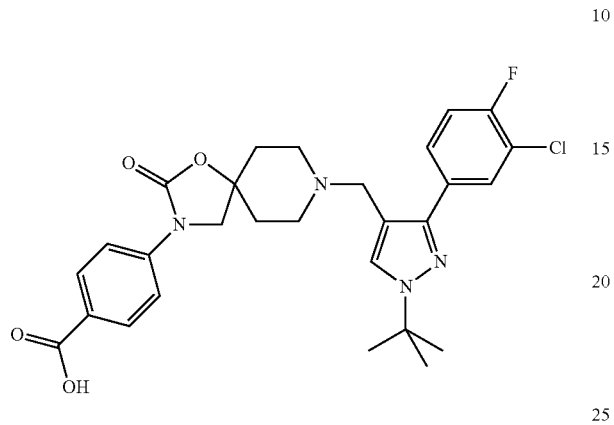

The title compound was prepared and purified using essentially the same experimental procedures as Example 1-1 and was isolated as a TFA salt.

LCMS (m/e): 541 (M+1).

Example 1-29

8-{[1-tert-Butyl-3-(4-chloro-2,5-difluorophenyl)-1H-pyrazol-4-yl]methyl}-3-[4-(2H-tetrazol-5-yl)phenyl]-1-oxa-3,8-diazaspiro[4.5]decan-2-one, TFA salt

Example 1-30

4-(8-{[1-tert-Butyl-3-(2,4-difluorophenyl)-1H-pyrazol-4-yl]methyl}-2-oxo-1-oxa-3,8-diazaspiro[4.5]dec-3-yl)benzoic acid, TFA salt The title compound was prepared and purified using essentially the same experimental procedures as Example 1-1 and was isolated as a TFA salt.

LCMS (m/e): 526 (M+1).

Example 1-31

4-(8-{[1-tert-Butyl-3-(4-chloro-2,5-difluorophenyl)-1H-pyrazol-4-yl]methyl}-2-oxo-1-oxa-3,8-diazaspiro[4.5]dec-3-yl)benzoic acid, TFA salt

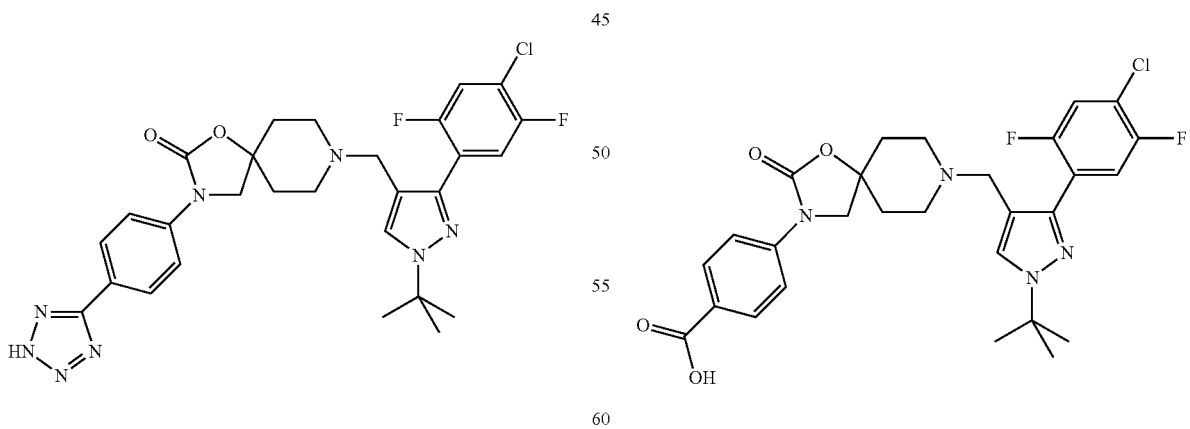

The title compound was prepared and purified using essentially the same experimental procedures as Example 1-1 and was isolated as a TFA salt.

LCMS (m/e): 583 (M+1).

The title compound was prepared and purified using essentially the same experimental procedures as Example 1-1 and was isolated as a TFA salt.

LCMS (m/e): 559 (M+1).

Example 1-32

4-(8-{[1-tert-Butyl-3-(2-fluoro-4-methoxyphenyl)-1H-pyrazol-4-yl]methyl}-2-oxo-1-oxa-3,8-diazaspiro[4.5]dec-3-yl)benzoic acid, TFA salt

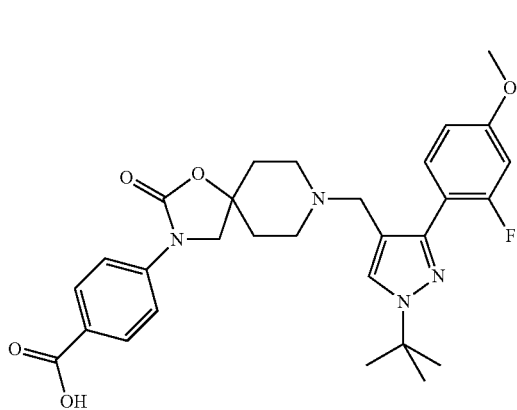 [SMILES: COc1ccc(-c2nn(C(C)(C)C)cc2CN2CCC3(CC2)CN(c2ccc(C(=O)O)cc2)C(=O)O3)c(F)c1]

The title compound was prepared and purified using essentially the same experimental procedures as Example 1 and was isolated as a TFA salt.

LCMS (m/e): 537 (M+1).

Example 1-33

4-(8-{[1-Cyclohexyl-3-(2,4,5-trifluorophenyl)-1H-pyrazol-4-yl]methyl}-2-oxo-1-oxa-3,8-diazaspiro[4.5]dec-3-yl)benzoic acid, TFA salt

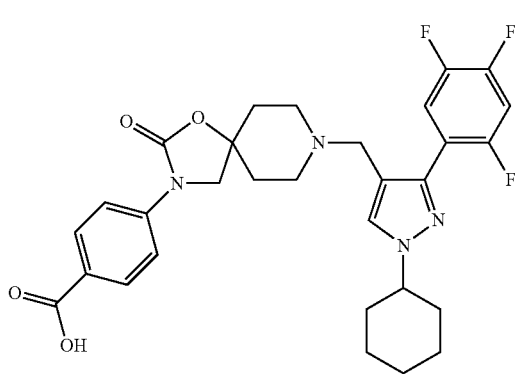 [SMILES: O=C(O)c1ccc(N2CC3(CCN(Cc4cn(C5CCCCC5)nc4-c4cc(F)c(F)cc4F)CC3)OC2=O)cc1]

The title compound was prepared and purified using essentially the same experimental procedures as Example 1-1 and was isolated as a TFA salt.

LCMS (m/e): 569 (M+1).

Example 1-34

4-(8-{[3-(3-Chloro-4-fluorophenyl)-1-phenyl-1H-pyrazol-4-yl]methyl}-2-oxo-1-oxa-3,8-diazaspiro[4.5]dec-3-yl)benzoic acid, TFA salt

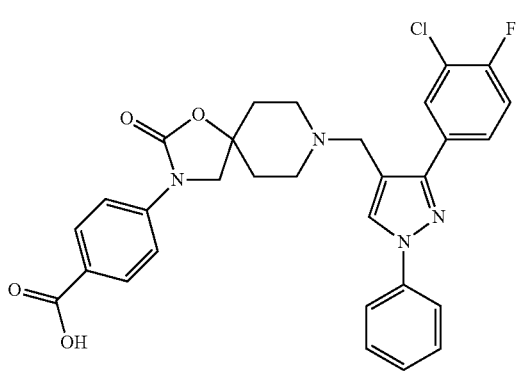 [SMILES: O=C(O)c1ccc(N2CC3(CCN(Cc4cn(-c5ccccc5)nc4-c4ccc(F)c(Cl)c4)CC3)OC2=O)cc1]

The title compound was prepared and purified using essentially the same experimental procedures as Example 1-1 and was isolated as a TFA salt.

LCMS (m/e): 561 (M+1).

Example 1-35

4-(8-{[3-tert-Butyl-1-(4-fluorophenyl)-1H-pyrazol-4-yl]methyl}-2-oxo-1-oxa-3,8-diazaspiro[4.5]dec-3-yl)benzoic acid, TFA salt

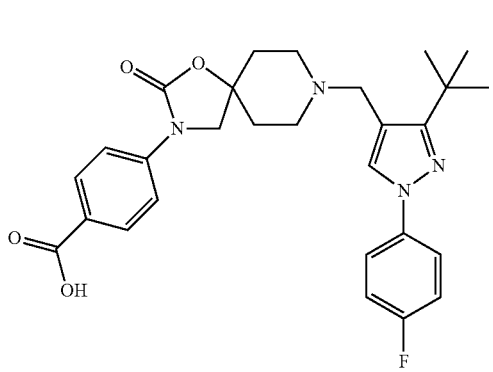 [SMILES: CC(C)(C)c1nn(-c2ccc(F)cc2)cc1CN1CCC2(CC1)CN(c1ccc(C(=O)O)cc1)C(=O)O2]

The title compound was prepared and purified using essentially the same experimental procedures as Example 1-1 and was isolated as a TFA salt.

LCMS (m/e): 507 (M+1).

Example 1-36

4-{8-[(1-tert-Butyl-3-ethoxy-1H-pyrazol-4-yl)methyl]-2-oxo-1-oxa-3,8-diazaspiro[4.5]dec-3-yl}benzoic acid, TFA salt

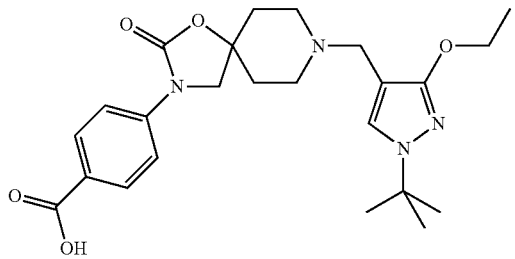 [SMILES: CCOc1nn(C(C)(C)C)cc1CN1CCC2(CC1)CN(c1ccc(C(=O)O)cc1)C(=O)O2]

The title compound was prepared and purified using essentially the same experimental procedures as Example 1-1 and was isolated as a TFA salt.

LCMS (m/e): 457 (M+1).

Example 1-37

4-(8-{[1-tert-Butyl-3-(2,3,4-trifluorophenyl)-1H-pyrazol-4-yl]methyl}-2-oxo-1-oxa-3,8-diazaspiro[4.5]dec-3-yl)-3-methylbenzoic acid, TFA salt

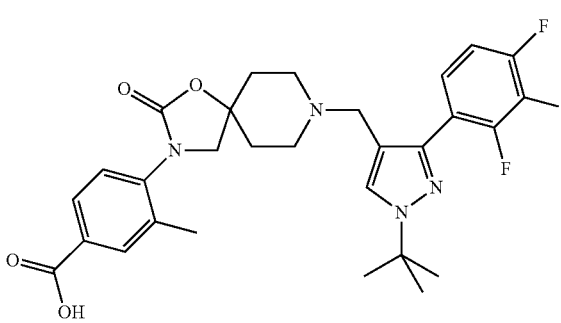

The title compound was prepared and purified using essentially the same experimental procedures as Example 1-1 and was isolated as a TFA salt.

LCMS (m/e): 557 (M+1).

Example 1-38

4-(8-{[3-(3-Chloro-4-fluorophenyl)-1-(2,2-dimethylpropyl)-1H-pyrazol-4-yl]methyl}-2-oxo-1-oxa-3,8-diazaspiro[4.5]dec-3-yl)benzoic acid, TFA salt

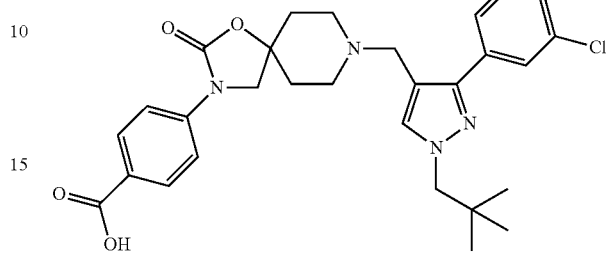

The title compound was prepared and purified using essentially the same experimental procedures as Example 1-1 and was isolated as a TFA salt.

LCMS (m/e): 555 (M+1).

Example 1-39

4-(8-{[5-Chloro-1-phenyl-3-(2,4,5-trifluorophenyl)-1H-pyrazol-4-yl]methyl}-2-oxo-1-oxa-3,8-diazaspiro[4.5]dec-3-yl)benzoic acid, TFA salt

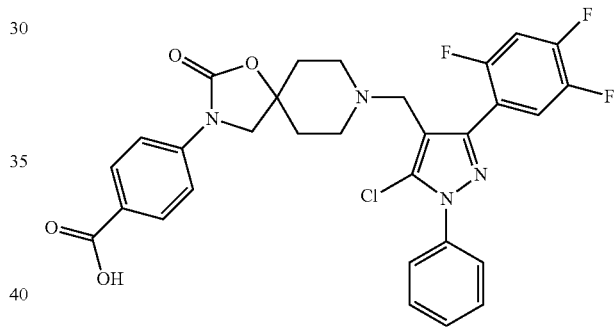

Step 1. Synthesis of 2-phenyl-5-(2,4,5-trifluorophenyl)-2,4-dihydro-3H-pyrazol-3-one

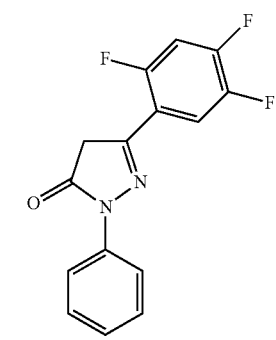 [SMILES: O=C1CC(c2cc(F)c(F)cc2F)=NN1c1ccccc1]

Potassium carbonate (153 mg, 1.10 mmol) was added to a stirred mixture of phenyl hydrazine HCl salt (160 mg, 1.10 mmol) and ethyl 3-oxo-3-(2,4,5-trifluorophenyl)propanoate (272 mg, 1.10 mmol) in EtOH (6 mL) and the mixture was heated at 70° C. for 1 hour. The solution was cooled to room temperature and was concentrated to give the title compound, which was taken on to the next step.

LCMS (m/e): 291 (M+1).

Step 2. Synthesis of 5-chloro-1-phenyl-3-(2,4,5-trifluorophenyl)-1H-pyrazole-4-carbaldehyde

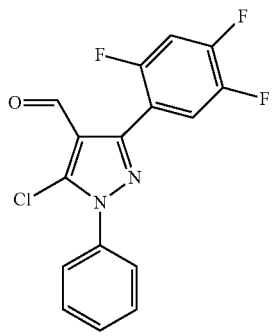 [SMILES: O=Cc1c(-c2cc(F)c(F)cc2F)nn(-c2ccccc2)c1Cl]

DMF (0.257 mL, 3.32 mmol) was added to a stirred mixture of POCl$_3$ (0.722 mL, 7.74 mmol) at 0° C. and the reaction mixture was stirred at room temperature for 5 minutes. Then 2-phenyl-5-(2,4,5-trifluorophenyl)-2,4-dihydro-3H-pyrazol-3-one (321 mg, 1.106 mmol) in DMF (1 mL) was added slowly to the reaction mixture at 0° C. and the reaction mixture was heated at 70° C. for 16 hours. It was then poured into a cooled saturated solution of potassium carbonate and the mixture was extracted with ethyl acetate. The organic layer was washed with water and brine, dried over sodium sulfate, filtered and concentrated. The residue was purified by column chromatography on silica gel (Biotage 12M) eluting with EtOAc/hexanes to give the product as a colorless solid.

Step 3. Synthesis of 4-(8-{[5-chloro-1-phenyl-3-(2,4,5-trifluorophenyl)-1H-pyrazol-4-yl]methyl}-2-oxo-1-oxa-3,8-diazaspiro[4.5]dec-3-yl)benzoic acid, TFA salt

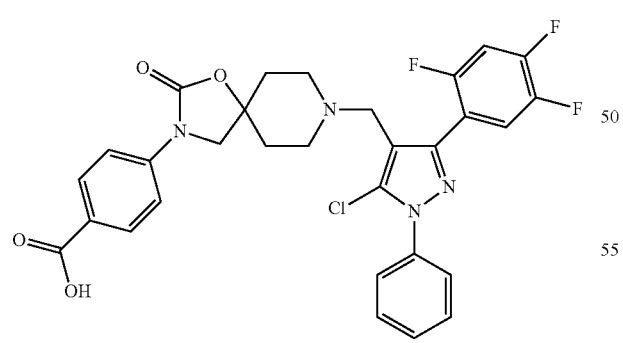

The title compound was prepared and purified using essentially the same experimental procedures as Example 1-1 and was isolated as a TFA salt.

LCMS (m/e): 597 (M+1).

Example 1-40

4-(8-{[1-Butyl-3-(2,4,5-trifluorobenzyl)-1H-pyrazol-4-yl]methyl}-2-oxo-1-oxa-3,8-diazaspiro[4.5]dec-3-yl)benzoic acid, TFA salt

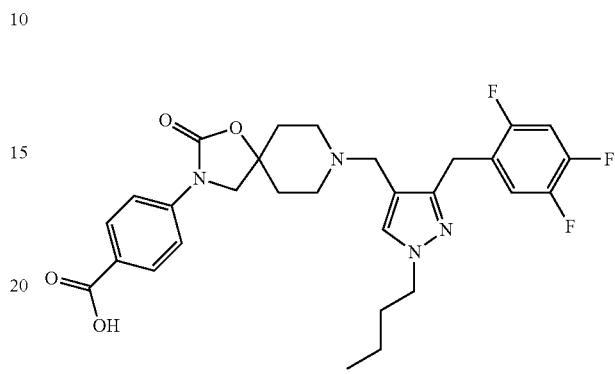

The title compound was prepared and purified using essentially the same experimental procedures as Example 1-1 and was isolated as a TFA salt.

LCMS (m/e): 557 (M+1).

Example 1-41

4-(2-Oxo-8-{[1-(2,2,2-trifluoroethyl)-3-(2,3,4-trifluorophenyl)-1H-pyrazol-4-yl]methyl}-1-oxa-3,8-diazaspiro[4.5]dec-3-yl)benzoic acid, TFA salt

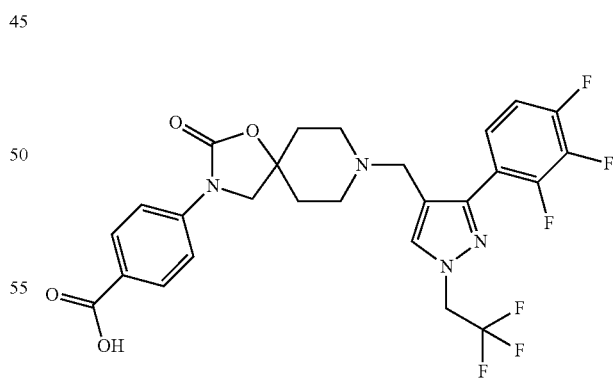

The title compound was prepared and purified using essentially the same experimental procedures as Example 1-1 and was isolated as a TFA salt.

LCMS (m/e): 569 (M+1).

Example 1-42

4-(8-{[1-tert-Butyl-3-(2,3,4-trifluorophenyl)-1H-pyrazol-4-yl]methyl}-2-oxo-1-oxa-3,8-diazaspiro[4.5]dec-3-yl)-2-fluorobenzoic acid, TFA salt

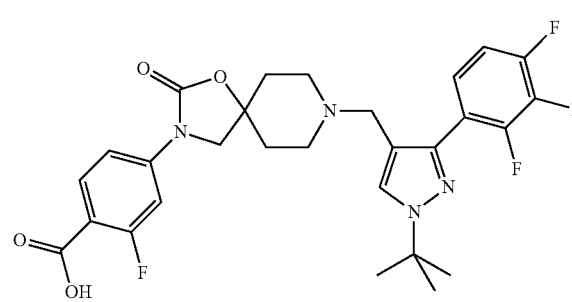

The title compound was prepared and purified using essentially the same experimental procedures as Example 1-1 and was isolated as a TFA salt.

LCMS (m/e): 561 (M+1).

Example 1-43

6-(8-{[1-tert-Butyl-3-(2,3,4-trifluorophenyl)-1H-pyrazol-4-yl]methyl}-2-oxo-1-oxa-3,8-diazaspiro[4.5]dec-3-yl)pyridine-3-carboxylic acid, TFA salt

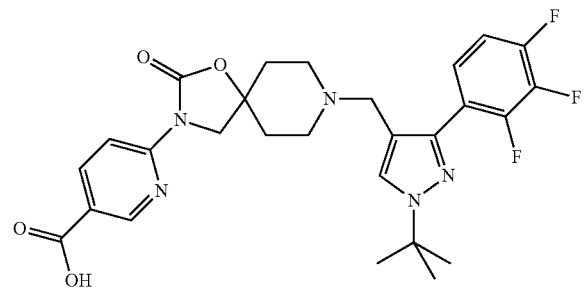 [SMILES: CC(C)(C)n1cc(CN2CCC3(CC2)CN(c2ccc(C(=O)O)cn2)C(=O)O3)c(-c2ccc(F)c(F)c2F)n1]

The title compound was prepared and purified using essentially the same experimental procedures as Example 1-1 and was isolated as a TFA salt.

LCMS (m/e): 544 (M+1).

Example 1-44

4-(8-{[5-Chloro-1-butyl-3-(2,4,5-trifluorobenzyl)-1H-pyrazol-4-yl]methyl}-2-oxo-1-oxa-3,8-diazaspiro[4.5]dec-3-yl)benzoic acid, TFA salt

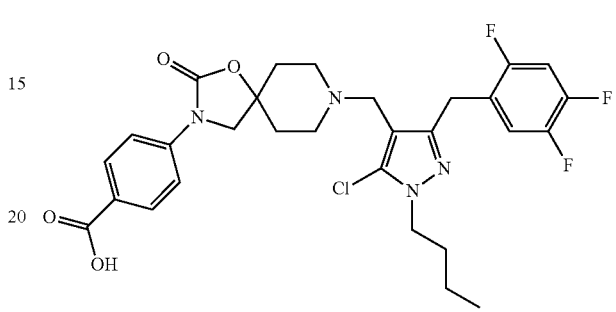

The title compound was prepared and purified using essentially the same experimental procedures as Example 1-39 and was isolated as a TFA salt.

LCMS (m/e): 590 (M+1).

Example 1-45

4-(8-{[5-Chloro-1-(propan-2-yl)-3-(2,4,5-trifluorobenzyl)-1H-pyrazol-4-yl]methyl}-2-oxo-1-oxa-3,8-diazaspiro[4.5]dec-3-yl)benzoic acid, TFA salt The title compound was prepared and purified using essentially the same experimental procedures as Example 1-39 and was isolated as a TFA salt.

LCMS (m/e): 576 (M+1).

Example 1-46

4-(8-{[5-Chloro-1-propyl-3-(2,4,5-trifluorobenzyl)-1H-pyrazol-4-yl]methyl}-2-oxo-1-oxa-3,8-diazaspiro[4.5]dec-3-yl)benzoic acid, TFA salt

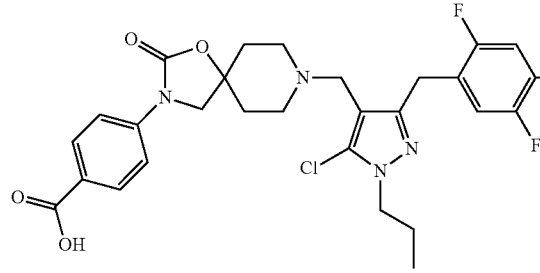

The title compound was prepared and purified using essentially the same experimental procedures as Example 1-39 and was isolated as a TFA salt.

LCMS (m/e): 576 (M+1).

Example 1-47

4-(8-{[5-Chloro-1-phenyl-3-(2,4,5-trifluorobenzyl)-1H-pyrazol-4-yl]methyl}-2-oxo-1-oxa-3,8-diazaspiro[4.5]dec-3-yl)benzoic acid, TFA salt

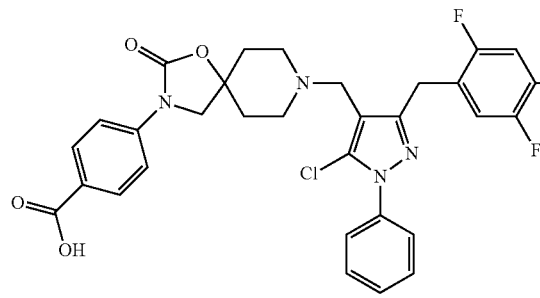

The title compound was prepared and purified using essentially the same experimental procedures as Example 1-39 and was isolated as a TFA salt.

LCMS (m/e): 611 (M+1).

Example 2-1

4-(8-{[1-Methyl-4-(2,3,4-trifluorophenyl)-1H-pyrazol-3-yl]methyl}-2-oxo-1-oxa-3,8-diazaspiro[4.5]dec-3-yl)benzoic acid, TFA salt

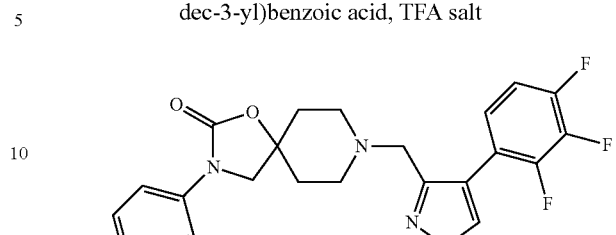

Step 1. Synthesis of 1-methyl-4-(2,3,4-trifluorophenyl)-1H-pyrazole-3-carbaldehyde

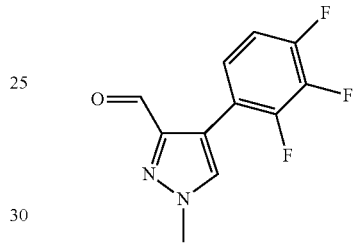

Potassium carbonate (0.418 mL, 0.836 mmol), Pd(OAc)$_2$ (2.82 mg, 0.013 mmol) was added to a stirred, room temperature mixture of 4-bromo-1-methyl-1H-pyrazole-3-carbaldehyde (79 mg, 0.418 mmol) and (2,3,4-trifluorophenyl)boronic acid (96 mg, 0.543 mmol) in EtOH (0.7 mL) and the mixture was stirred at 90° C. for 24 hours. The mixture was cooled, aqueous sodium hydrogen carbonate (saturated, 10 mL) was added and the mixture was extracted with ethyl acetate (2×15 mL). The combined organic fractions were washed with water, dried (MgSO$_4$) and filtered. The solvent was evaporated under reduced pressure to give the crude intermediate which was used in the next step.

Step 2. Synthesis of 4-(8-{[1-methyl-4-(2,3,4-trifluorophenyl)-1H-pyrazol-3-yl]methyl}-2-oxo-1-oxa-3,8-diazaspiro[4.5]dec-3-yl)benzoic acid, TFA salt

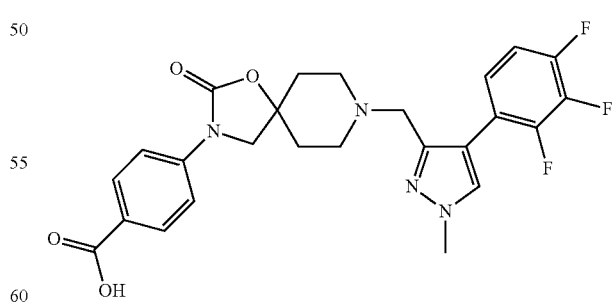

The title compound was prepared and purified using essentially the same experimental procedures as Example 1-1, Steps 4-5, but using 1-methyl-4-(2,3,4-trifluorophenyl)-1H-pyrazole-3-carbaldehyde in Step 4 and was isolated as a TFA salt.

LCMS (m/e): 501 (M+1).

Example 2-2

4-(8-{[1-Methyl-4-(2,4,5-trifluorophenyl)-1H-pyrazol-3-yl]methyl}-2-oxo-1-oxa-3,8-diazaspiro[4.5]dec-3-yl)benzoic acid, TFA salt

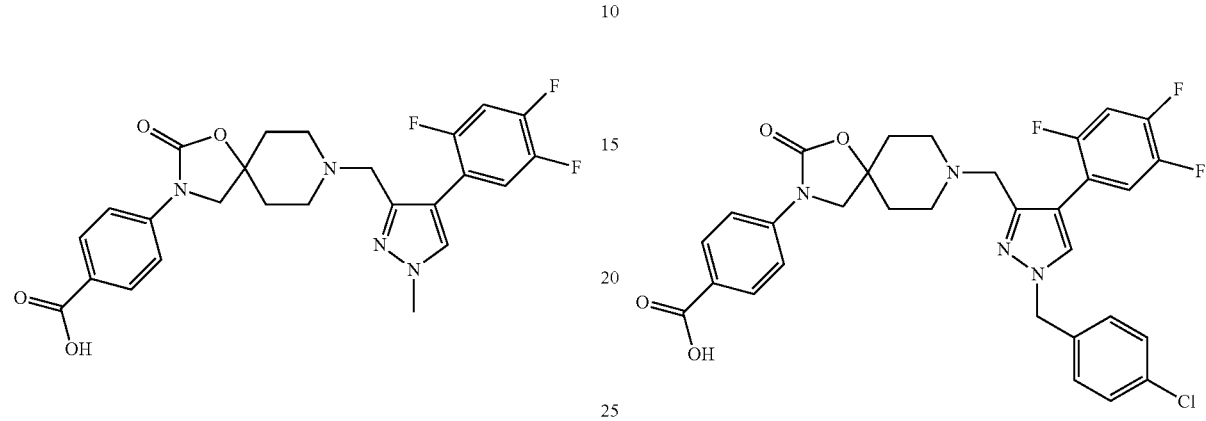

The title compound was prepared and purified using essentially the same experimental procedures as Example 2-1 and was isolated as a TFA salt.

LCMS (m/e): 501 (M+1).

Example 2-3

4-(8-{[1-(4-Chlorobenzyl)-4-(2,3,4-trifluorophenyl)-1H-pyrazol-3-yl]methyl}-2-oxo-1-oxa-3,8-diazaspiro[4.5]dec-3-yl)benzoic acid, TFA salt

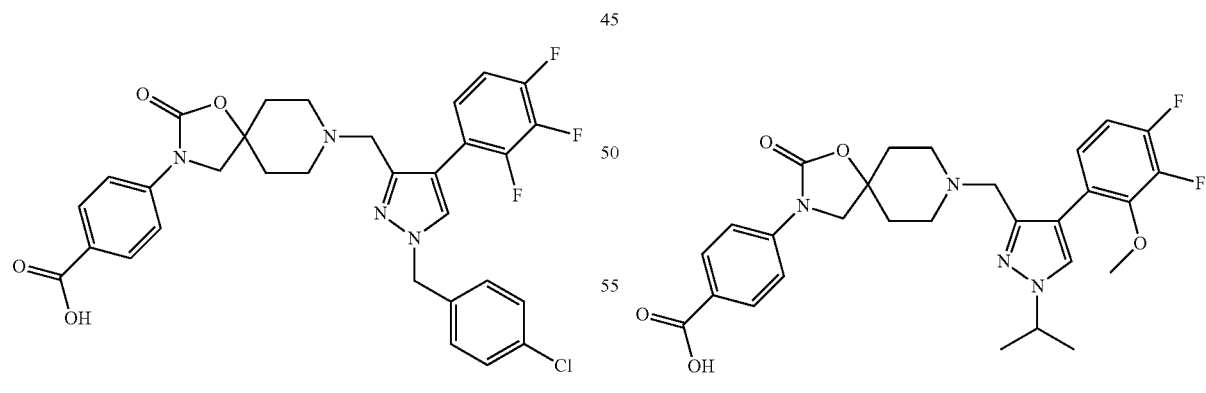

The title compound was prepared and purified using essentially the same experimental procedures as Example 2-1 and was isolated as a TFA salt.

LCMS (m/e): 611 (M+1).

Example 2-4

4-(8-{[1-(4-Chlorobenzyl)-4-(2,4,5-trifluorophenyl)-1H-pyrazol-3-yl]methyl}-2-oxo-1-oxa-3,8-diazaspiro[4.5]dec-3-yl)benzoic acid, TFA salt The title compound was prepared and purified using essentially the same experimental procedures as Example 2-1 and was isolated as a TFA salt.

LCMS (m/e): 611 (M+1).

Example 2-5

4-(8-{[4-(3,4-Difluoro-2-methoxyphenyl)-1-(propan-2-yl)-1H-pyrazol-3-yl]methyl}-2-oxo-1-oxa-3,8-diazaspiro[4.5]dec-3-yl)benzoic acid, TFA salt

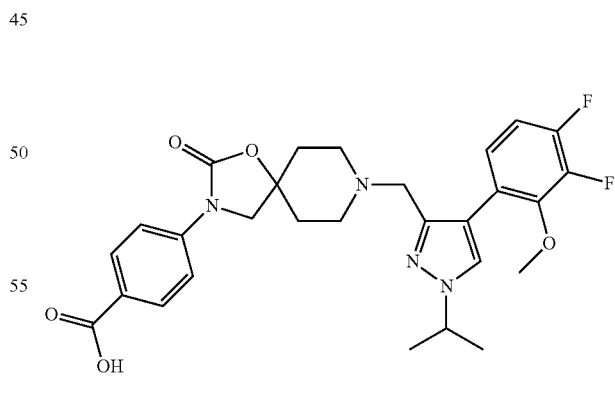

The title compound was prepared and purified using essentially the same experimental procedures as Example 2-1 and was isolated as a TFA salt.

LCMS (m/e): 541 (M+1).

Example 2-6

4-(2-Oxo-8-{[1-propyl-4-(2,3,4-trifluorophenyl)-1H-pyrazol-3-yl]methyl}-1-oxa-3,8-diazaspiro[4.5]dec-3-yl)benzoic acid, TFA salt

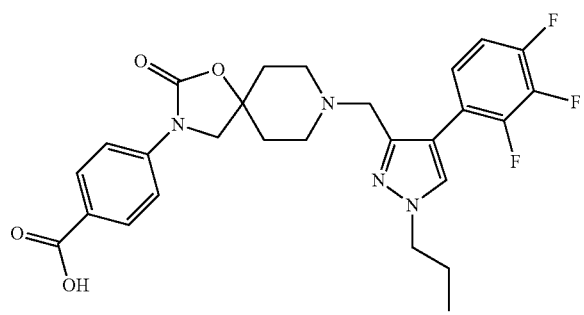 [SMILES: CCCn1cc(-c2ccc(F)c(F)c2F)c(CN2CCC3(CC2)CN(c2ccc(C(=O)O)cc2)C(=O)O3)n1]

The title compound was prepared and purified using essentially the same experimental procedures as Example 2-1 and was isolated as a TFA salt.

LCMS (m/e): 541 (M+1).

Example 2-7

4-(2-Oxo-8-{[1-phenyl-5-(2,4,5-trifluorophenyl)-1H-pyrazol-4-yl]methyl}-1-oxa-3,8-diazaspiro[4.5]dec-3-yl)benzoic acid, TFA salt

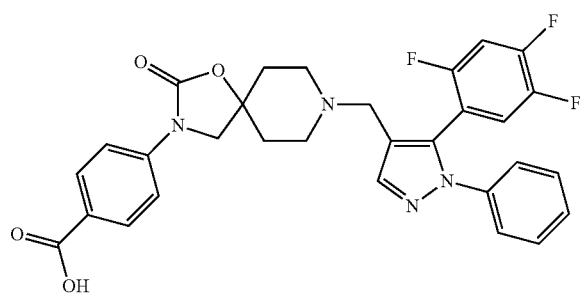 [SMILES: O=C(O)c1ccc(N2CC3(CCN(Cc4cnn(-c5ccccc5)c4-c4cc(F)c(F)cc4F)CC3)OC2=O)cc1]

Step 1. Synthesis of ethyl 1-phenyl-5-(2,4,5-trifluorophenyl)-1H-pyrazole-4-carboxylate

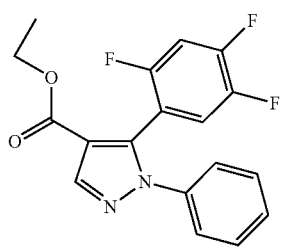 [SMILES: CCOC(=O)c1cnn(-c2ccccc2)c1-c1cc(F)c(F)cc1F]

A solution of ethyl 3-oxo-3-(2,4,5-trifluorophenyl)propanoate (0.326 g, 1.32 mmol) and N,N-dimethyformamide dimethyl acetal in ethanol (5 mL) was heated in a 90° C. oil bath for 3 hours. Upon removal of the volatiles, the residue was dissolved in EtOH (3 mL) and phenylhydrazine hydrochloride salt (191 mg, 1.324 mmol) was added. The mixture was then heated at reflux for 6 hours. The reaction was cooled and diluted with EtOAc and the organic layer was washed with NaHCO$_3$ and brine. The organic phase was dried with Na$_2$SO$_4$, filtered and concentrated to afford the title compound as oil.

LCMS (m/e): 347 (M+1).

Step 2. Synthesis of 1-phenyl-5-(2,4,5-trifluorophenyl)-1H-pyrazole-4-carbaldehyde

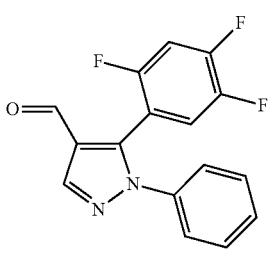 [SMILES: O=Cc1cnn(-c2ccccc2)c1-c1cc(F)c(F)cc1F]

To a solution of ethyl 1-phenyl-5-(2,4,5-trifluorophenyl)-1H-pyrazole-4-carboxylate (459 mg, 1.325 mmol) in THF (5 mL) was added LAH (1.988 mL, 1.988 mmol as a 1 M THF solution) at room temperature and the reaction was then heated at 50° C. for 2 hours. The reaction was quenched with addition of 0.2 mL of water, 0.2 mL of 0.5 N NaOH and then 0.2 mL of water. The suspension was diluted with ether and was filtered through celite. Upon removal of the volatiles, the crude residue was purified by flash chromatography to afford an oil. The oil was then dissolved in 5 mL of CH$_2$Cl$_2$ and Dess-Martin periodinane (233.8 mg, 0.768 mmol) was added. The suspension was stirred at room temperature for 16 hours. The mixture was poured into EtOAc and was washed with brine. The organic phase was dried with Na$_2$SO$_4$, filtered and concentrated. The crude residue was purified by flash chromatography using a gradient of ethyl acetate/hexanes to afford the title intermediate as white solid.

$^1$H-NMR (CDCl$_3$): δ: 9.83 (s, 1H), 8.28 (s, 1H), 7.41 (m, 3H), 7.29 (m, 2H), 7.17 (m, 1H), 7.04 (m, 1H).

LCMS (m/e): 303 (M+1).

Step 3. Synthesis of 4-(2-oxo-8-{[1-phenyl-5-(2,4,5-trifluorophenyl)-1H-pyrazol-4-yl]methyl}-1-oxa-3,8-diazaspiro[4.5]dec-3-yl)benzoic acid, TFA salt

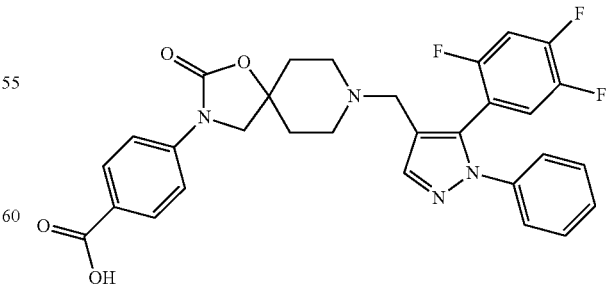

The title compound was prepared and purified using essentially the same experimental procedures as Example 2-1 and was isolated as a TFA salt.

LCMS (m/e): 563 (M+1).

Example 2-8

4-(8-{[1-Cyclohexyl-5-(2,4,5-trifluorophenyl)-1H-pyrazol-4-yl]methyl}-2-oxo-1-oxa-3,8-diazaspiro[4.5]dec-3-yl)benzoic acid, TFA salt

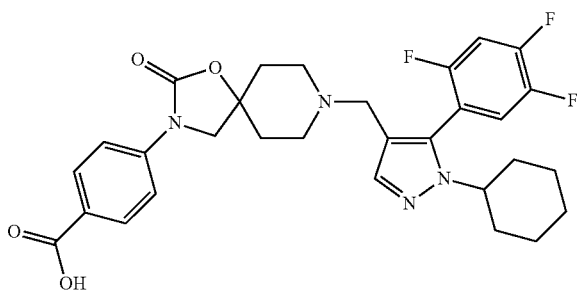 [SMILES: O=C(O)c1ccc(N2CC3(CCN(Cc4cnn(C5CCCCC5)c4-c4cc(F)c(F)cc4F)CC3)OC2=O)cc1]

The title compound was prepared and purified using essentially the same experimental procedures as Example 2-7 and was isolated as a TFA salt.

LCMS (m/e): 569 (M+1).

Example 2-9

4-(2-{[1-tert-Butyl-3-(2,3,4-trifluorophenyl)-1H-pyrazol-4-yl]methyl}-6-oxo-5-oxa-2,7-diazaspiro[3.4]oct-7-yl)benzoic acid, TFA salt

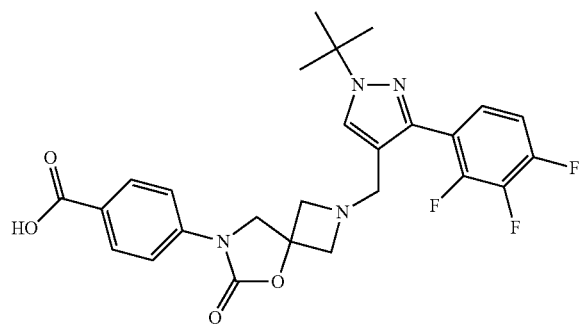 [SMILES: CC(C)(C)n1cc(CN2CC3(C2)CN(c2ccc(C(=O)O)cc2)C(=O)O3)c(-c2ccc(F)c(F)c2F)n1]

Step 1. Synthesis of [1-(tert-butoxycarbonyl)-3-hydroxyazetidin-3-yl]acetic acid

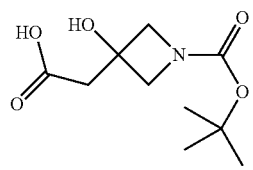 [SMILES: CC(C)(C)OC(=O)N1CC(O)(CC(=O)O)C1]

LHMDS (6.43 mL of 1N solution in THF) was cooled to −78° C. Ethyl acetate (0.63 mL, 6.43 mmol) was added and the reaction mixture was stirred for 10 minutes. tert-Butyl 3-oxoazetidine-1-carboxylate (1 g, 5.84 mmol) was added to the mixture and the reaction was stirred for 15 minutes. The reaction mixture was warmed to 0° C. and was then quenched with water (25 mL). The reaction mixture was extracted with ether. The organic phase was dried over anhydrous magnesium sulfate, filtered and concentrated. The remaining oil was dissolved in MeOH (25 mL) and 1N NaOH (15 mL) was added and the mixture was stirred at room temperature overnight. This was concentrated in vacuo to remove MeOH and then to the remaining aqueous solution was added 1N HCl (100 mL). This mixture was extracted with $CH_2Cl_2$ (100 mL). The organic phase was dried over anhydrous magnesium sulfate, filtered and concentrated to afford the title intermediate (215 mg) as an oil.

$^1$H-NMR (CDCl$_3$): δ 3.91 (d, J=8 Hz, 2H), 3.82 (d, J=8 Hz, 2H), 2.78 (s, 2H), 1.42 (s, 9H).

Step 2. Synthesis of tert-butyl 7-[4-(methoxycarbonyl)phenyl]-6-oxo-5-oxa-2,7-diazaspiro[3.4]octane-2-carboxylate

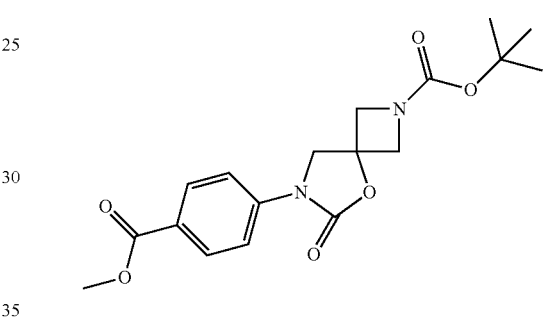

To a 50 mL round bottom flask was added [1-(tert-butoxycarbonyl)-3-hydroxyazetidin-3-yl]acetic acid (215 mg, 0.930 mmol) dissolved in toluene (9.3 mL) were added triethylamine (0.143 mL, 1.023 mmol) and diphenylphosphoryl azide (0.221 mL, 1.023 mmol). The mixture was heated to 120° C. for 16 hours. The reaction mixture was cooled to room temperature and the toluene was removed under vacuum. The crude mixture was diluted with EtOAc (100 mL) and washed with brine. The organic phase was dried over anhydrous magnesium sulfate, filtered and concentrated to give a light brown solid. Ether (2 mL) was added and the solid was filtered to afford of an off white solid (85 mg). This white solid was added to a 5 mL microwave vial containing copper (1) iodide (70.9 mg, 0.372 mmol), methyl 4-iodobenzoate (117 mg, 0.447 mmol), cesium carbonate (364 mg, 1.117 mmol) and N,N'-dimethylethane-1,2-diamine (40.1 µL, 0.372 mmol). The vial was sealed and 2.48 mL dioxane was added by syringe. This was heated in a microwave reactor at 100° C. for 20 minutes. The reaction mixture was filtered through celite, the cake was washed with $CH_2Cl_2$ and the combined filtrate was concentrated. The mixture was dissolved in acetonitrile and purified on a Gilson HPLC eluting with a gradient of acetonitrile/water with 0.1% TFA. The desired fractions were concentrated to give the title product (11.4 mg) as a white solid.

$^1$H-NMR (CDCl$_3$): δ 8.09 (d, J=8 Hz, 2H), 7.62 (d, J=8 Hz, 2H), 4.42 (d, J=10 Hz, 2H), 4.28 (s, 2H), 4.15 (d, J=10 Hz, 2H), 3.94 (s, 3H), 1.49 (s, 9H).

Step 3. Synthesis of methyl 4-(2-{[1-tert-butyl-3-(2,3,4-trifluorophenyl)-1H-pyrazol-4-yl]methyl}-6-oxo-5-oxa-2,7-diazaspiro[3.4]oct-7-yl)benzoate

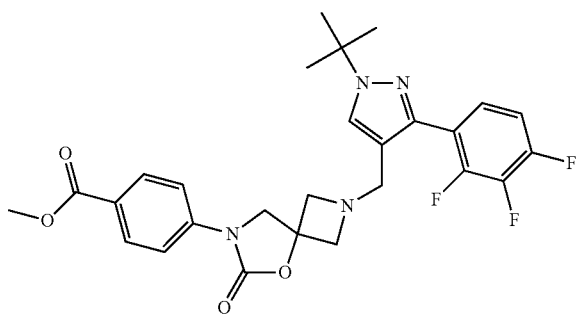 [SMILES: COC(=O)c1ccc(N2CC3(CN(Cc4cn(C(C)(C)C)nc4-c4ccc(F)c(F)c4F)C3)OC2=O)cc1]

To tert-butyl 7-[4-(methoxycarbonyl)phenyl]-6-oxo-5-oxa-2,7-diazaspiro[3.4]octane-2-carboxylate (11.4 mg, 0.043 mmol) was added trifluoroacetic acid (2 mL). The mixture was stirred for 10 minutes and then the trifluoroacetic acid was removed under a nitrogen stream to afford a clear oil (10.4 mg). This was dissolved in MeOH (1 mL) and 1-tert-butyl-3-(2,3,4-trifluorophenyl)-1H-pyrazole-4-carbaldehyde (34.1 mg, 0.121 mmol), acetic acid (17 μL), triethylamine (17 μL) and sodium triacetoxyborohydride (25 mg, 0.119 mmol) were added. The reaction mixture was stirred at room temperature for two hours. The reaction mixture was dissolved in $CH_2Cl_2$ and extracted with saturated sodium bicarbonate solution. The organic phase was dried with anhydrous magnesium sulfate, filtered and concentrated. The crude mixture was dissolved in acetonitrile and purified by Gilson HPLC eluting with a gradient of acetonitrile/water with 0.1% TFA. The desired fractions were concentrated to give the desired intermediate (25.5 mg) as a white solid.

LCMS (m/e): 529 (M+1).

Step 4. Synthesis of 4-(2-{[1-tert-butyl-3-(2,3,4-trifluorophenyl)-1H-pyrazol-4-yl]methyl}-6-oxo-5-oxa-2,7-diazaspiro[3.4]oct-7-yl)benzoic acid, TFA salt

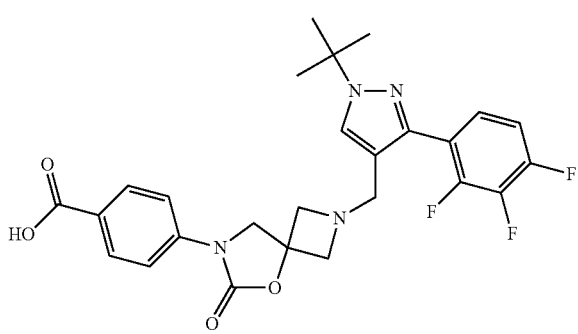 [SMILES: CC(C)(C)n1cc(CN2CC3(C2)CN(c2ccc(C(=O)O)cc2)C(=O)O3)c(-c2ccc(F)c(F)c2F)n1]

To methyl 4-(2-{[1-tert-butyl-3-(2,3,4-trifluorophenyl)-1H-pyrazol-4-yl]methyl}-6-oxo-5-oxa-2,7-diazaspiro[3.4]oct-7-yl)benzoate (10.1 mg, 0.016 mmol) dissolved in MeOH (0.5 mL) was added lithium hydroxide monohydrate (2 mg, 0.047 mmol). The mixture was heated to 60° C. for 16 hours. The MeOH was removed under vacuum and the crude residue was dissolved in 0.5 mL acetonitrile and purified by Gilson HPLC eluting with a gradient of acetonitrile/water with 0.1% TFA. The desired fractions were concentrated to afford the title compound (3 mg) as a white solid.

$^1$H-NMR (DMSO): δ 8.13 (s, 1H), 7.98 (d, J=10 Hz, 2H), 7.58 (d, J=10 Hz, 2H), 7.42 (m, 1H), 7.38 (m, 1H), 4.30 (m, 8H), 1.56 (s, 9H).

LCMS (m/e): 515 (M+1).

Example 2-10

4-{8-[(1-Methyl-1H-indol-7-yl)methyl]-2-oxo-1-oxa-3,8-diazaspiro[4.6]undec-3-yl}benzoic acid, TFA salt

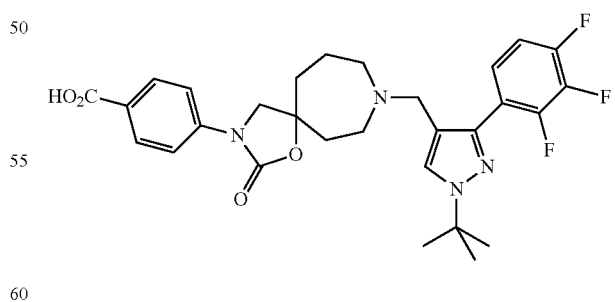

The title compound was prepared and purified using essentially the same experimental procedures as Example 2-9 and was isolated as a TFA salt.

LCMS (m/e): 434 (M+1).

Example 2-11

4-(8-{[1-tert-Butyl-3-(2,3,4-trifluorophenyl)-1H-pyrazol-4-yl]methyl}-2-oxo-1-oxa-3,8-diazaspiro[4.6]undec-3-yl)benzoic acid, TFA salt The title compound was prepared and purified using essentially the same experimental procedures as Example 2-9 and was isolated as a TFA salt.

LCMS (m/e): 557 (M+1).

Example 2-12

4-{8-[(2,6-Diethoxy-4'-fluorobiphenyl-4-yl)methyl]-2-oxo-1-oxa-3,8-diazaspiro[4.6]undec-3-yl}benzoic acid, TFA salt

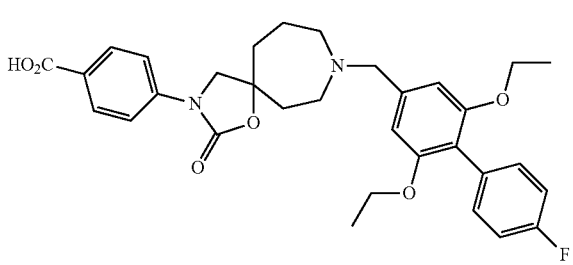 [SMILES: CCOc1cc(CN2CCCC3(CC2)CN(c2ccc(C(=O)O)cc2)C(=O)O3)cc(OCC)c1-c1ccc(F)cc1]

The title compound was prepared and purified using essentially the same experimental procedures as Example 2-9 and was isolated as a TFA salt.

LCMS (m/e): 563 (M+1).

Example 2-13

4-{8-[(4-Ethoxy-3',4'-difluorobiphenyl-2-yl)methyl]-2-oxo-1-oxa-3,8-diazaspiro[4.6]undec-3-yl}benzoic acid, TFA salt

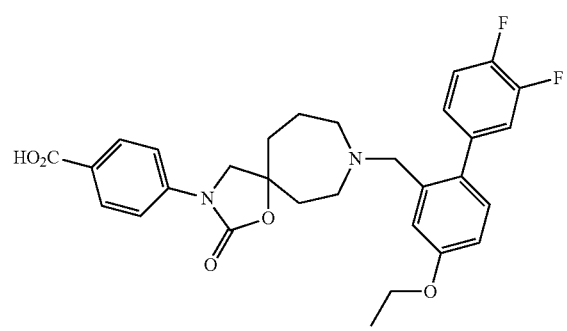 [SMILES: CCOc1ccc(-c2ccc(F)c(F)c2)c(CN2CCCC3(CC2)CN(c2ccc(C(=O)O)cc2)C(=O)O3)c1]

The title compound was prepared and purified using essentially the same experimental procedures as Example 2-9 and was isolated as a TFA salt.

LCMS (m/e): 537 (M+1).

Example 2-14

4-(8-{[1-tert-Butyl-3-(4-methoxyphenyl)-1H-pyrazol-4-yl]methyl}-2-oxo-1-oxa-3,8-diazaspiro[4.6]undec-3-yl)benzoic acid, TFA salt

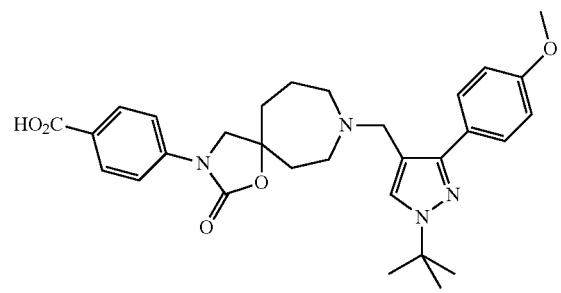 [SMILES: COc1ccc(-c2nn(C(C)(C)C)cc2CN2CCCC3(CC2)CN(c2ccc(C(=O)O)cc2)C(=O)O3)cc1]

The title compound was prepared and purified using essentially the same experimental procedures as Example 2-9 and was isolated as a TFA salt.

LCMS (m/e): 533 (M+1).

Example 2-15

4-(8-{[3-(4-Methoxyphenyl)-1-phenyl-1H-pyrazol-4-yl]methyl}-2-oxo-1-oxa-3,8-diazaspiro[4.6]undec-3-yl)benzoic acid, TFA salt

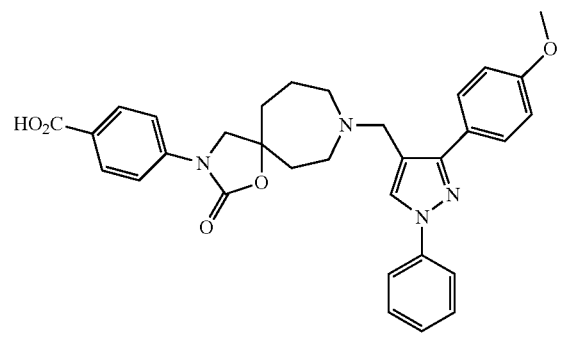 [SMILES: COc1ccc(-c2nn(-c3ccccc3)cc2CN2CCCC3(CC2)CN(c2ccc(C(=O)O)cc2)C(=O)O3)cc1]

The title compound was prepared and purified using essentially the same experimental procedures as Example 2-9 and was isolated as a TFA salt.

LCMS (m/e): 553 (M+1).

Example 2-16

4-{7-[(2,6-Diethoxy-4'-fluorobiphenyl-4-yl)methyl]-2-oxo-1-oxa-3,7-diazaspiro[4.4]non-3-yl}benzoic acid, TFA salt

Example 3-1

4-{8-[(2,6-Diethoxy-4'-fluorobiphenyl-4-yl)methyl]-2-oxo-1-oxa-3,8-diazaspiro[4.5]dec-3-yl}benzoic acid, TFA salt

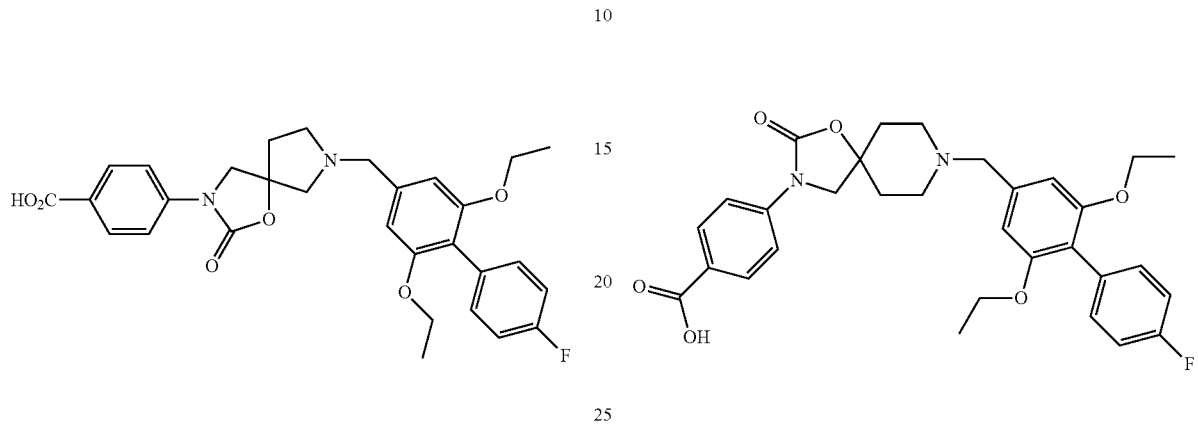

The title compound was prepared and purified using essentially the same experimental procedures as Example 2-9 and was isolated as a TFA salt.

LCMS (m/e): 535 (M+1).

Step 1. Synthesis methyl 4-{8-[(2,6-diethoxy-4'-fluorobiphenyl-4-yl)methyl]-2-oxo-1-oxa-3,8-diazaspiro[4.5]dec-3-yl}benzoate

Example 2-17

4-(7-{[1-tert-Butyl-3-(2,3,4-trifluorophenyl)-1H-pyrazol-4-yl]methyl}-2-oxo-1-oxa-3,7-diazaspiro[4.4]non-3-yl)benzoic acid, TFA salt

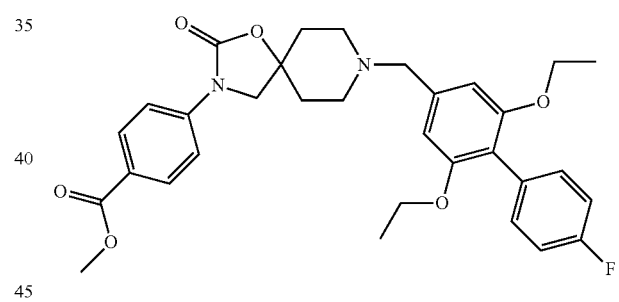

To a mixture of methyl 4-(2-oxo-1-oxa-3,8-diazaspiro[4.5]dec-3-yl)benzoate HCl salt (53 mg, 0.162 mmol) and 4-(chloromethyl)-2,6-diethoxy-4'-fluorobiphenyl (55.1 mg, 0.178 mmol) in DMF (5 mL) was added Hunig's base (62.9 mg, 0.487 mmol) and the reaction was heated at 70° C. for 5 hours. After removal of the volatiles, the residue was purified by reverse phase HPLC to afford the title compound as its TFA salt.

LCMS (m/e): 563 (M+1).

Step B. Synthesis of 4-{8-[(2,6-diethoxy-4'-fluorobiphenyl-4-yl)methyl]-2-oxo-1-oxa-3,8-diazaspiro[4.5]dec-3-yl}benzoic acid, TFA salt The title compound was prepared and purified using essentially the same experimental procedures as Example 2-9 and was isolated as a TFA salt.

LCMS (m/e): 529 (M+1).

The title compound was prepared and purified using essentially the same experimental procedure as in Example 1-1, Step 5, and was isolated and was isolated as a TFA salt.

LCMS (m/e): 549 (M+1).

Example 3-2

8-[(2,6-Diethoxy-4'-fluorobiphenyl-4-yl)methyl]-3-(5-hydroxypyridin-3-yl)-1-oxa-3,8-diazaspiro[4.5]decan-2-one, TFA salt

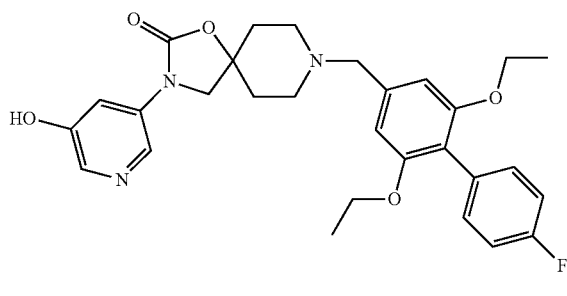 [SMILES: CCOc1cc(CN2CCC3(CC2)CN(c2cncc(O)c2)C(=O)O3)cc(OCC)c1-c1ccc(F)cc1]

The title compound was prepared and purified using essentially the same experimental procedures in Example 3-1 and was isolated as a TFA salt.

LCMS (m/e): 522 (M+1).

Example 3-3

2-{8-[(2,6-Diethoxy-4'-fluorobiphenyl-4-yl)methyl]-2-oxo-1-oxa-3,8-diazaspiro[4.5]dec-3-yl}benzoic acid, TFA salt

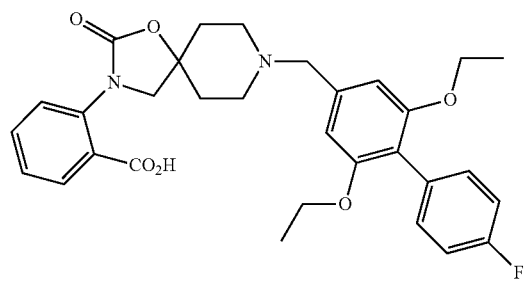 [SMILES: CCOc1cc(CN2CCC3(CC2)CN(c2ccccc2C(=O)O)C(=O)O3)cc(OCC)c1-c1ccc(F)cc1]

The title compound was prepared and purified using essentially the same experimental procedures in Example 3-1 and was isolated as a TFA salt.

LCMS (m/e): 549 (M+1).

Example 3-4

5-{8-[(2,6-Diethoxy-4'-fluorobiphenyl-4-yl)methyl]-2-oxo-1-oxa-3,8-diazaspiro[4.5]dec-3-yl}pyridine-2-carboxylic acid, TFA salt

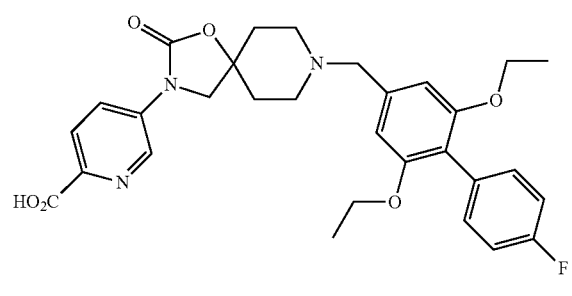 [SMILES: CCOc1cc(CN2CCC3(CC2)CN(c2ccc(C(=O)O)nc2)C(=O)O3)cc(OCC)c1-c1ccc(F)cc1]

The title compound was prepared and purified using essentially the same experimental procedures as example 3-1 and was isolated as a TFA salt.

LCMS (m/e): 550 (M+1).

Example 3-5

5-{8-[(2,6-Diethoxy-4'-fluorobiphenyl-4-yl)methyl]-2-oxo-1-oxa-3,8-diazaspiro[4.5]dec-3-yl}pyridine-3-carboxylic acid, TFA salt

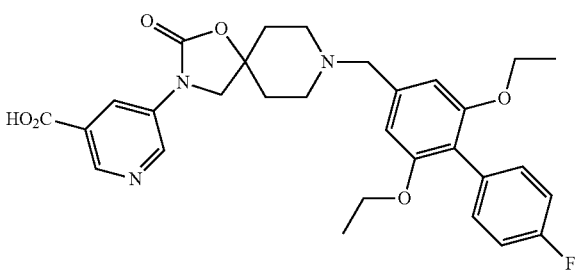 [SMILES: CCOc1cc(CN2CCC3(CC2)CN(c2cncc(C(=O)O)c2)C(=O)O3)cc(OCC)c1-c1ccc(F)cc1]

The title compound was prepared and purified using essentially the same experimental procedures as example 3-1 and was isolated as a TFA salt.

LCMS (m/e): 550 (M+1).

Example 3-6

2-(4-{8-[(2,6-Diethoxy-4'-fluorobiphenyl-4-yl)methyl]-2-oxo-1-oxa-3,8-diazaspiro[4.5]dec-3-yl}phenyl)-2-methylpropanoic acid, TFA salt

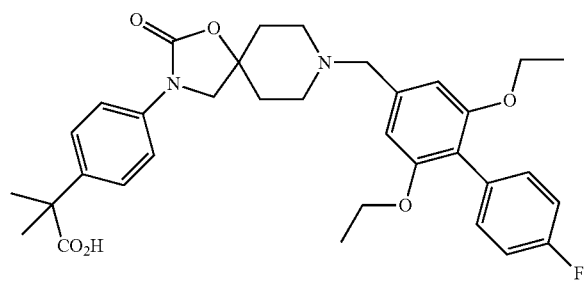 [SMILES: CCOc1cc(CN2CCC3(CC2)CN(c2ccc(C(C)(C)C(=O)O)cc2)C(=O)O3)cc(OCC)c1-c1ccc(F)cc1]

The title compound was prepared and purified using essentially the same experimental procedures in Example 3-1 and was isolated as a TFA salt.

LCMS (m/e): 591 (M+1).

Example 3-7

8-[(2,6-Diethoxy-4'-fluorobiphenyl-4-yl)methyl]-3-[2-methoxy-4-(2H-tetrazol-5-yl)phenyl]-1-oxa-3,8-diazaspiro[4.5]decan-2-one, TFA salt

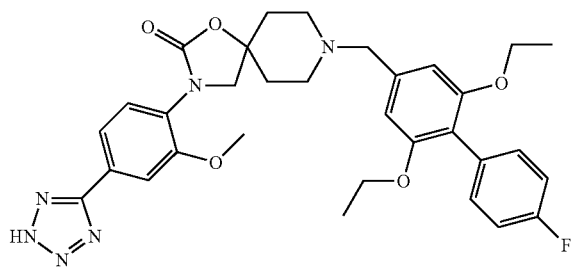 [SMILES: CCOc1cc(CN2CCC3(CC2)CN(c2ccc(-c4nn[nH]n4)cc2OC)C(=O)O3)cc(OCC)c1-c1ccc(F)cc1]

The title compound was prepared and purified using essentially the same experimental procedures in Example 3-1 and was isolated as a TFA salt.

LCMS (m/e): 603 (M+1).

Example 3-8

4-{8-[(2,6-Diethoxy-4'-fluorobiphenyl-4-yl)methyl]-2-oxo-1-oxa-3,8-diazaspiro[4.5]dec-3-yl}-2-methylbenzoic acid, TFA salt

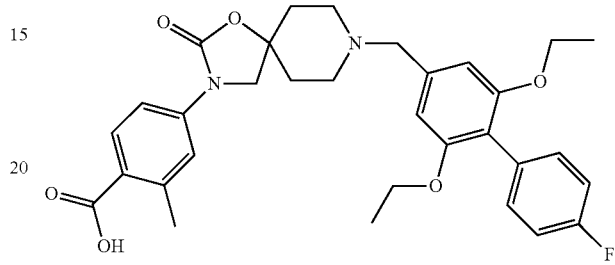

The title compound was prepared and purified using essentially the same experimental procedures in Example 3-1 and was isolated as a TFA salt.

LCMS (m/e): 563 (M+1).

Example 3-9

2-Chloro-4-{8-[(2,6-diethoxy-4'-fluorobiphenyl-4-yl)methyl]-2-oxo-1-oxa-3,8-diazaspiro[4.5]dec-3-yl}benzoic acid, TFA salt

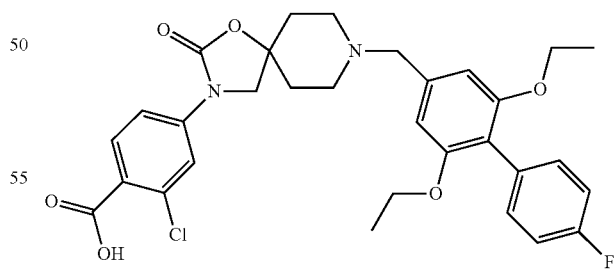

The title compound was prepared and purified using essentially the same experimental procedures in Example 3-1 and was isolated as a TFA salt.

LCMS (m/e): 583 (M+1).

Example 3-10

1-(4-{8-[(2,6-Diethoxy-4'-fluorobiphenyl-4-yl)methyl]-2-oxo-1-oxa-3,8-diazaspiro[4.5]dec-3-yl}phenyl)cyclopropanecarboxylic acid, TFA salt

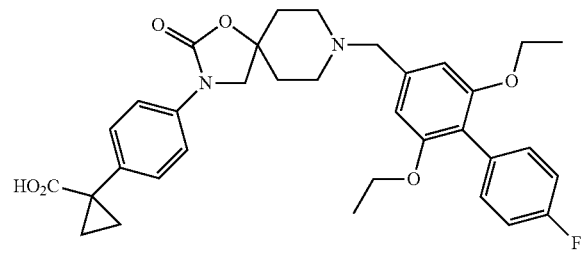 [SMILES: CCOc1cc(CN2CCC3(CC2)CN(c2ccc(C4(C(=O)O)CC4)cc2)C(=O)O3)cc(OCC)c1-c1ccc(F)cc1]

The title compound was prepared and purified using essentially the same experimental procedures in Example 3-1 and was isolated as a TFA salt.

LCMS (m/e): 589 (M+1).

Example 3-11

6-{8-[(2,6-Diethoxy-4'-fluorobiphenyl-4-yl)methyl]-2-oxo-1-oxa-3,8-diazaspiro[4.5]dec-3-yl}pyridine-3-carboxylic acid, TFA salt

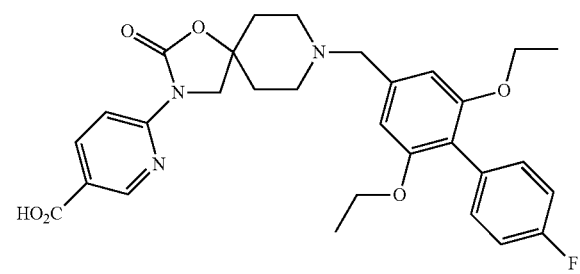 [SMILES: CCOc1cc(CN2CCC3(CC2)CN(c2ccc(C(=O)O)cn2)C(=O)O3)cc(OCC)c1-c1ccc(F)cc1]

The title compound was prepared and purified using essentially the same experimental procedures in Example 3-1 and was isolated as a TFA salt.

LCMS (m/e): 550 (M+1).

Example 3-12

8-[(2,6-Diethoxy-4'-fluorobiphenyl-4-yl)methyl]-3-[4-(2H-tetrazol-5-yl)phenyl]-1-oxa-3,8-diazaspiro[4.5]decan-2-one, TFA salt

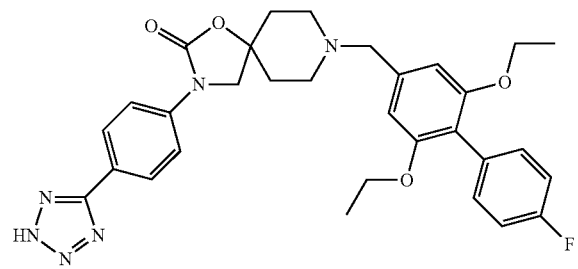 [SMILES: CCOc1cc(CN2CCC3(CC2)CN(c2ccc(-c4nn[nH]n4)cc2)C(=O)O3)cc(OCC)c1-c1ccc(F)cc1]

The title compound was prepared and purified using essentially the same experimental procedures in Example 3-1 and was isolated as a TFA salt.

LCMS (m/e), 573 (M+1).

Example 3-13

8-[(2,6-Diethoxy-4-fluorobiphenyl-4-yl)methyl]-3-(6-hydroxypyridin-3-yl)-1-oxa-3,8-diazaspiro[4.5]decan-2-one, TFA salt

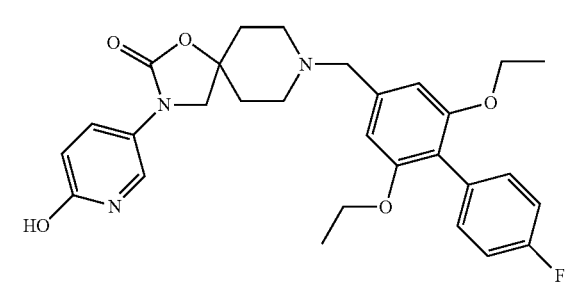 [SMILES: CCOc1cc(CN2CCC3(CC2)CN(c2ccc(O)nc2)C(=O)O3)cc(OCC)c1-c1ccc(F)cc1]

The title compound was prepared and purified using essentially the same experimental procedures in Example 3-1 and was isolated as a TFA salt.

LCMS (m/e): 522 (M+1).

Example 3-14

3-{8-[(2,6-Diethoxy-4'-fluorobiphenyl-4-yl)methyl]-2-oxo-1-oxa-3,8-diazaspiro[4.5]dec-3-yl}benzoic acid, TFA salt

The title compound was prepared and purified using essentially the same experimental procedures in Example 3-1 and was isolated as a TFA salt LCMS (m/e): 548 (M+1).

Example 3-15

4-{8-[(2,6-Diethoxy-4'-fluorobiphenyl-4-yl)methyl]-2-oxo-1-oxa-3,8-diazaspiro[4.5]dec-3-yl}-2-(trifluoromethyl)benzoic acid, TFA salt

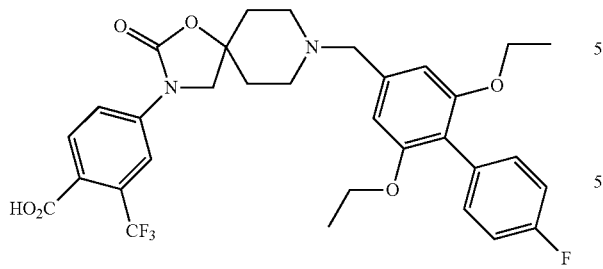

The title compound was prepared and purified using essentially the same experimental procedures in Example 3-1 and was isolated as a TFA salt.

LCMS (m/e): 617 (M+1).

Example 3-16

4-{8-[(2,6-Diethoxy-4'-fluorobiphenyl-4-yl)methyl]-2-oxo-1-oxa-3,8-diazaspiro[4.5]dec-3-yl}-3-methylbenzoic acid, TFA salt

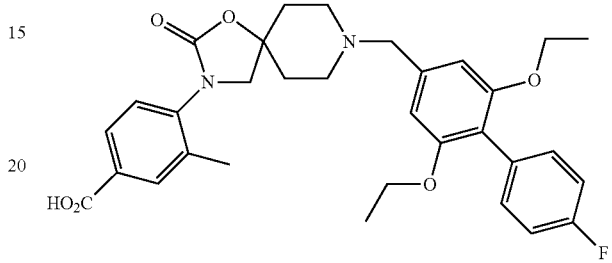

The title compound was prepared and purified using essentially the same experimental procedures as in Example 3-1 and was isolated as a TFA salt.

LCMS (m/e): 563 (M+1).

Example 3-17

2-{8-[(2,6-Diethoxy-4'-fluorobiphenyl-4-yl)methyl]-2-oxo-1-oxa-3,8-diazaspiro[4.5]dec-3-yl}pyridine-4-carboxylic acid, TFA salt

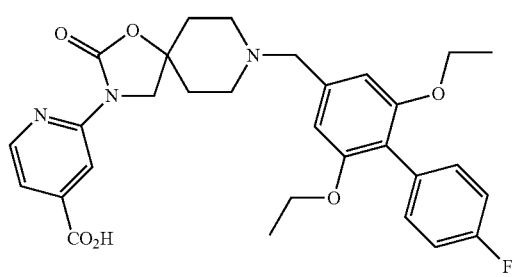 [SMILES: CCOc1cc(CN2CCC3(CC2)CN(c2cc(C(=O)O)ccn2)C(=O)O3)cc(OCC)c1-c1ccc(F)cc1]

The title compound was prepared and purified using essentially the same experimental procedures in Example 3-1 and was isolated as a TFA salt.

LCMS (m/e): 550 (M+1).

Example 3-18

4-{8-[(2,6-Diethoxy-4'-fluorobiphenyl-4-yl)methyl]-2-oxo-1-oxa-3,8-diazaspiro[4.5]dec-3-yl}-2-fluorobenzoic acid, TFA salt

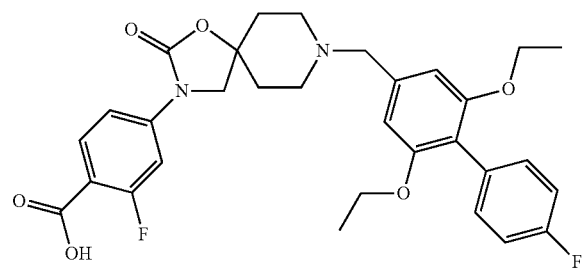 [SMILES: CCOc1cc(CN2CCC3(CC2)CN(c2ccc(C(=O)O)c(F)c2)C(=O)O3)cc(OCC)c1-c1ccc(F)cc1]

The title compound was prepared and purified using essentially the same experimental procedures in Example 3-1 and was isolated as a TFA salt.

LCMS (m/e): 567 (M+1).

Example 3-19

3-Chloro-4-{8-[(2,6-diethoxy-4'-fluorobiphenyl-4-yl)methyl]-2-oxo-1-oxa-3,8-diazaspiro[4.5]dec-3-yl}benzoic acid, TFA salt

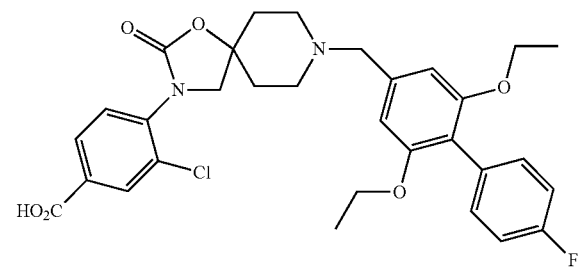 [SMILES: CCOc1cc(CN2CCC3(CC2)CN(c2ccc(C(=O)O)cc2Cl)C(=O)O3)cc(OCC)c1-c1ccc(F)cc1]

The title compound was prepared and purified using essentially the same experimental procedures in Example 3-1 and was isolated as a TFA salt.

LCMS (m/e): 583 (M+1).

Example 3-20

4-{8-[(2,6-Diethoxy-4'-fluorobiphenyl-4-yl)methyl]-2-oxo-1-oxa-3,8-diazaspiro[4.5]dec-3-yl}-2-methoxybenzoic acid, TFA salt

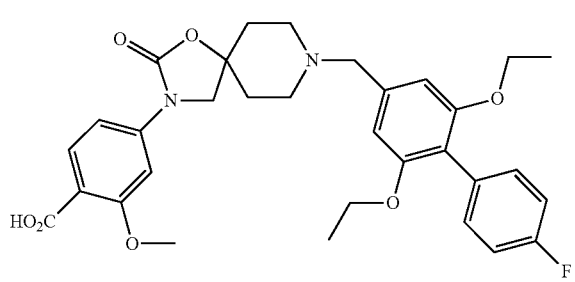

The title compound was prepared and purified using essentially the same experimental procedures in Example 3-1 and was isolated as a TFA salt.

LCMS (m/e): 579 (M+1).

Example 3-21

4-{8-[(2,6-Diethoxy-4'-fluorobiphenyl-4-yl)methyl]-2-oxo-1-oxa-3,8-diazaspiro[4.5]dec-3-yl}-3-fluorobenzoic acid, TFA salt

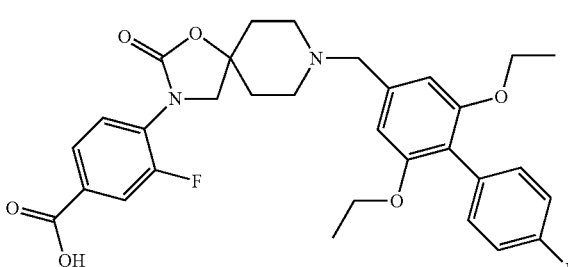

The title compound was prepared and purified using essentially the same experimental procedures in Example 3-1 and was isolated as a TFA salt.

LCMS (m/e): 567 (M+1).

Example 4-1

4-{8-[(4-Ethoxy-2',4',5'-trifluorobiphenyl-2-yl)methyl]-2-oxo-1-oxa-3,8-diazaspiro[4.5]dec-3-yl}benzoic acid, TFA salt

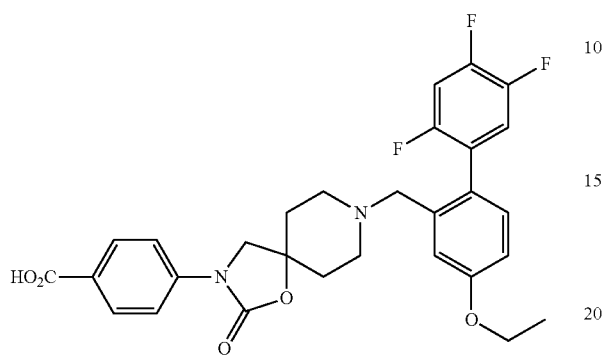

Step 1. Synthesis of 2-bromo-5-ethoxybenzaldehyde (CAS. 43192-34-1)

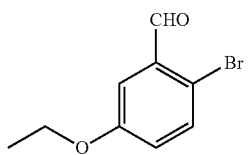

To a solution of 2-bromo-5-hydroxybenzaldehyde (5 g, 24.87 mmol) in DMF (20 mL) was added iodoethane (5.82 g, 37.3 mmol) and $K_2CO_3$ (6.88 g, 49.7 mmol) portion wise. The resulting reaction mixture was stirred at 50° C. overnight. After cooling, the mixture was diluted with EtOAc/hexanes (1:1) and water. Layers were separated and the organic layer was washed with brine, dried over sodium sulfate, filtered and concentrated to give the title intermediate (4.6 g) as white solid.

$^1$H-NMR (CDCl$_3$): δ 10.3 (s, 1H), 7.51 (d, J=9.0 Hz, 1H), 7.39 (d, J=3.0 Hz, 1H) 7.02 (dd, J=3.5 Hz, J=8.5 Hz, 1H), 4.06 (q, 16.5 Hz, 2H), 1.42 (t, J=6.5 Hz, 3H).

Step 2. Synthesis of 4-Ethoxy-2',3',4'-trifluorobiphenyl-2-carbaldehyde

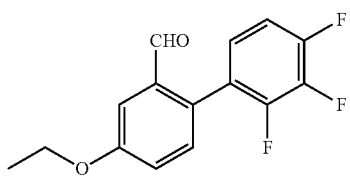 [SMILES: CCOc1ccc(-c2ccc(F)c(F)c2F)c(C=O)c1]

To a degassed solution of 2-bromo-5-ethoxybenzaldehye (300 mg, 1.31 mmol), 2-dicyclohexylphosphino-2',6'-dimethoxy-1,1'-biphenyl (53.8 mg, 0.131 mmol; S-Phos ligand), palladium (II) acetate (14.7 mg, 0.065 mmol) in THF (8 mL) were added $K_3PO_4$ (834 mg, 3.93 mmol) and (2,3,4-trifluorophenyl)boronic acid (276, 1.57 mmol). Reaction mixture was stirred at 70° C. under a N$_2$ atmosphere for 16 hours, cooled to room temperature and then filtered. The filtrate was concentrated by evaporation under reduced pressure. The residue was purified on a silica gel column eluting with 5 to 10% EtOAc in hexanes to provide the title intermediate (255 mg) as white solid.

$^1$H-NMR (CDCl$_3$): δ 9.88 (s, 1H), 7.53 (s, 1H), 7.30 (m, 1H), 7.24 (dd, J=3.0 Hz, J=8.5 Hz, 1H), 7.08 (m, 1H), 4.17 (q, J=7.0 Hz, 2H), 1.49 (t, J=7.0 Hz, 3H).

Step 3. Synthesis of 4-{8-[(4-ethoxy-2',4',5'-trifluorobiphenyl-2-yl)methyl]-2-oxo-1-oxa-3,8-diazaspiro[4.5]dec-3-yl}benzoic acid, TFA salt

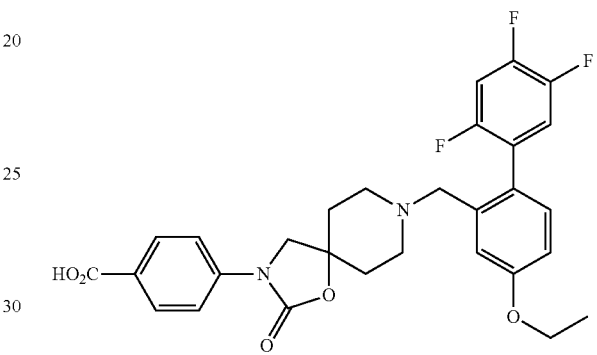

The title compound was prepared and purified using essentially the same experimental procedures in Example 1-1, Steps 4-5, and was isolated as a TFA salt.

LCMS (m/e): 541 (M+1).

Example 4-2

4-(8-{[6-Ethoxy-3-(2,3,4-trifluorophenyl)pyridin-2-yl]methyl}-2-oxo-1-oxa-3,8-diazaspiro[4.5]dec-3-yl)benzoic acid, TFA salt

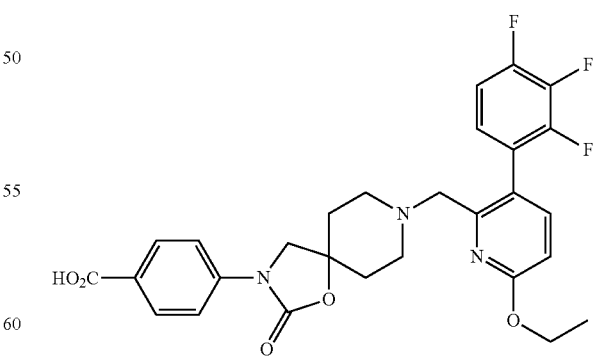

The title compound was prepared and purified using essentially the same experimental procedures in Example 4-1 and was isolated as a TFA salt.

LCMS (m/e): 542 (M+1).

Example 4-3

4-{8-[(4-Ethoxy-2',4'-difluorobiphenyl-2-yl)methyl]-2-oxo-1-oxa-3,8-diazaspiro[4.5]dec-3-yl}benzoic acid, TFA salt

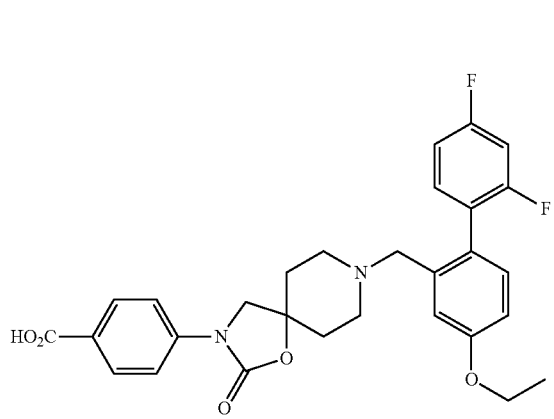 [SMILES: CCOc1ccc(-c2ccc(F)cc2F)c(CN2CCC3(CC2)CN(c2ccc(C(=O)O)cc2)C(=O)O3)c1]

The title compound was prepared and purified using essentially the same experimental procedures in Example 4-1 and was isolated as a TFA salt.

LCMS (m/e): 523 (M+1).

Example 4-4

4-{8-[(4-Ethoxy-3',4'-difluorobiphenyl-2-yl)methyl]-2-oxo-1-oxa-3,8-diazaspiro[4.5]dec-3-yl}benzoic acid, TFA salt

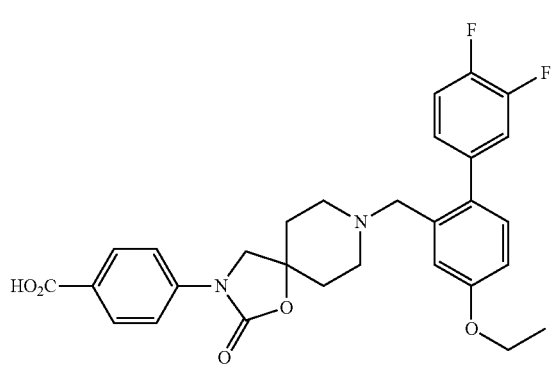 [SMILES: CCOc1ccc(-c2ccc(F)c(F)c2)c(CN2CCC3(CC2)CN(c2ccc(C(=O)O)cc2)C(=O)O3)c1]

The title compound was prepared and purified using essentially the same experimental procedures in Example 4-1 and was isolated as a TFA salt.

LCMS (m/e): 523 (M+1).

Example 4-5

4-{8-[(4-Ethoxy-2',3',4'-trifluorobiphenyl-2-yl)methyl]-2-oxo-1-oxa-3,8-diazaspiro[4.5]dec-3-yl}benzoic acid, TFA salt

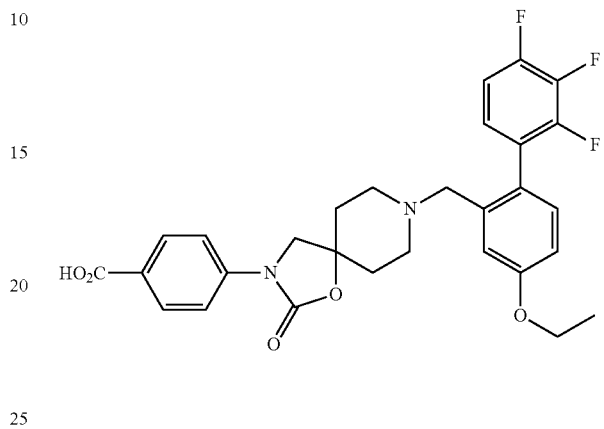

The title compound was prepared and purified using essentially the same experimental procedures in Example 4-1 and was isolated as a TFA salt.

LCMS (m/e): 541 (M+1).

Example 4-6

4-{8-[(4-(Prop-2-yloxy)-2',3',4'-trifluorobiphenyl-2-yl)methyl]-2-oxo-1-oxa-3,8-diazaspiro[4.5]dec-3-yl}benzoic acid, TFA salt

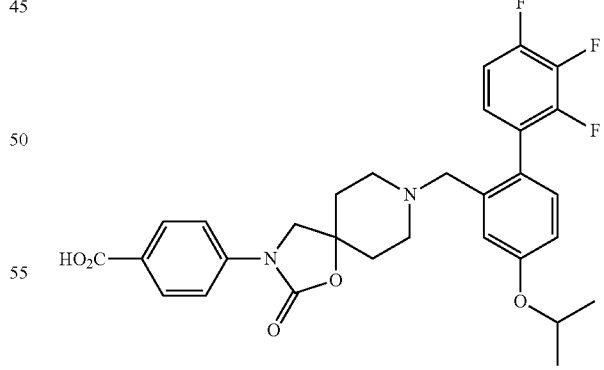

The title compound was prepared and purified using essentially the same experimental procedures in Example 4-1 and was isolated as a TFA salt.

LCMS (m/e): 555 (M+1).

Example 4-7

4-{8-[(4-Ethoxy-2',3',4'-trifluoro-5-methylbiphenyl-2-yl)methyl]-2-oxo-1-oxa-3,8-diazaspiro[4.5]dec-3-yl}benzoic acid, TFA salt

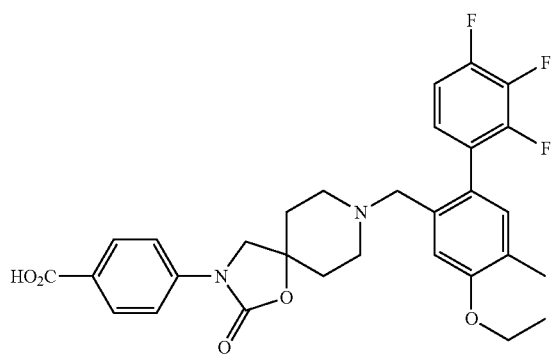 [SMILES: CCOc1cc(CN2CCC3(CC2)CN(c2ccc(C(=O)O)cc2)C(=O)O3)c(-c2ccc(F)c(F)c2F)cc1C]

Step 1. Synthesis of ethyl 2-bromo-5-ethoxy-4-methylbenzoate

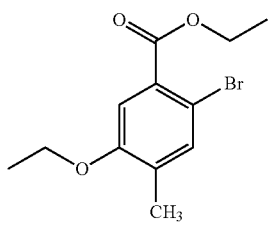 [SMILES: CCOC(=O)c1cc(OCC)c(C)cc1Br]

To a solution of ethyl 5-ethoxy-4-methylbenzoate (500 mg, 2.40 mmol) in acetic acid (10 mL) and water (10 mL) at room temperature was added bromine (385 mg, 2.40 mmol). The resulting reaction mixture was stirred at 60° C. for 1 hour. After cooling to room temperature, the reaction mixture was diluted with hexanes/ether (80/20). Layers were separated and the organic layer was washed with saturated $Na_2CO_3$, brine, dried over $Na_2SO_4$, filtered and concentrated. The residue was purified on a silica gel column eluting with 5 to 10% EtOAc in hexanes to yield the title intermediate (660 mg, 2.23 mmol) as light yellow solid.

$^1$H-NMR (CDCl$_3$): δ 7.54 (d, J=7.0 Hz, 1H), 7.47 (s, 1H), 7.17 (d, J=7.5 Hz, 1H), 4.36 (q, 2H), 4.09 (q, 2H), 2.26 (s, 3H), 1.44 (t, J=7.0 Hz, 3H), 1.38 (t, J=7.5 Hz, 3H).

Step 2. Synthesis of (2-bromo-5-ethoxy-4-methylphenyl)methanol

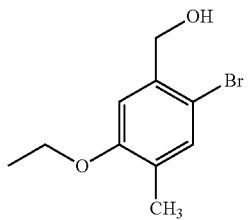

To a solution of 2-bromo-5-ethoxy-4-methylbenzoate (660 mg, 2.23 mmol) in ether (20 mL) at 0° C. was added DIBAL (5.75 mL, 5.75 mmol, 1 M in toluene). The reaction was stirred at 0° C. for 10 minutes. EtOAc (20 mL) and wet silica gel (~50 g silica gel and 3 mL of water) were added portion wise at 0° C. The resulting slurry was stirred for ~15 minutes and was filtered, washed with EtOAc (20 mL). The organic phase was dried over sodium sulfate, filtered and concentrated. The residue was purified on a silica gel column eluting with EtOAc/hexanes (20/80) to give the title intermediate (550 mg) as colorless liquid.

$^1$H-NMR (CDCl$_3$). δ. 7.28 (s, 1H), 6.93 (s, 1H), 4.68 (d, J=6.5 Hz, 2H), 4.021 (q, 2H), 2.18 (s, 3H), 1.99 (t, J=6.5 Hz, 3H).

Step 3. Synthesis of 2-bromo-5-ethoxy-4-methylbenzaldehyde

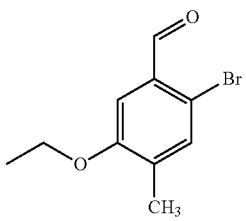

To a solution of (2-bromo-5-ethoxy-4-methylphenyl)methanol (2.30 g, 9.38 mmol) in DCM (40 mL) was added Dess-Martin periodinane (5.97 g, 14.08 mmol). The resulting mixture was stirred at room temperature for 1 hour. The reaction mixture was diluted with ether and was then concentrated. The residue was taken up in ether and was washed with of a mixture of 10% aqueous $Na_2S_2O_3$ and saturated aqueous $NaHCO_3$ (1/1), water and brine. The aqueous washings were back-extracted with ether and the organic layer was washed with water and brine. The combined organic layers were dried over $Na_2SO_4$ and concentrated. The residue was purified on a silica gel column eluting with 5 to 10% EtOAc in hexanes to afford the title intermediate as a white solid $^1$H-NMR (CDCl$_3$): δ 10.2 (s, 1H), 7.39 (s, 1H), 7.32 (s, 1H), 4.08 (q, 2H), 2.26 (s, 3H), 1.43 (t, J=7.0 Hz, 3H).

Step 4. Synthesis of 4-ethoxy-2',3',4'-trifluoro-5-methylbiphenyl-2-carbaldehyde

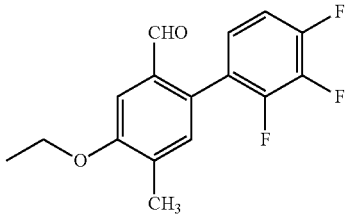 [SMILES: CCOc1cc(C=O)c(-c2ccc(F)c(F)c2F)cc1C]

To a degassed solution of 2-bromo-5-ethoxy-4-methylbenzaldehyde (300 mg, 1.31 mmol), 2-dicyclohexylphosphino-2',6'-dimethoxy-1,1'-biphenyl (53.8 mg, 0.131 mmol; S-Phos ligand) palladium (II) acetate (14.7 mg, 0.065 mmol) in THF (8 mL) were added $K_3PO_4$ (834 mg, 3.93 mmol) and (2,3,4-trifluorophenyl)boronic acid (276, 1.57 mmol). The reaction mixture was stirred at 70° C. under a $N_2$ atmosphere for 16 hours, cooled to room temperature and filtered and the filtrate was concentrated by evaporation under reduced pressure. The residue was purified on a silica gel column eluting with 5 to 10% EtOAc in hexanes to provide the title intermediate (255 mg) as white solid.

¹H-NMR (CDCl₃): δ 9.79 (s, 1H), 7.43 (s, 1H), 7.13 (s, 1H), 7.04 (m, 2H), 4.16 (q, 2H), 2.32 (s, 3H), 1.46 (t, J=7.0 Hz, 3H).

Step 5. Synthesis of 4-{8-[(4-ethoxy-2',3',4'-trifluoro-5-methylbiphenyl-2-yl)methyl]-2-oxo-1-oxa-3,8-diazaspiro[4.5]dec-3-yl}benzoic acid, TFA salt

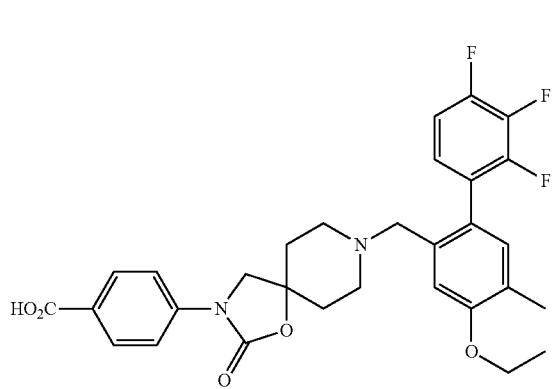 [SMILES: CCOc1cc(CN2CCC3(CC2)CN(c2ccc(C(=O)O)cc2)C(=O)O3)c(-c2ccc(F)c(F)c2F)cc1C]

The title compound was prepared and purified using essentially the same experimental procedures in Example 4-1 and was isolated as a TFA salt.

LCMS (m/e): 555 (M+1).

Example 4-8

4-{8-[(4-Ethoxy-2',3',4'-trifluoro-5-methylbiphenyl-2-yl)methyl]-2-oxo-1-oxa-3,8-diazaspiro[4.5]dec-3-yl}-3-methylbenzoic acid, TFA salt

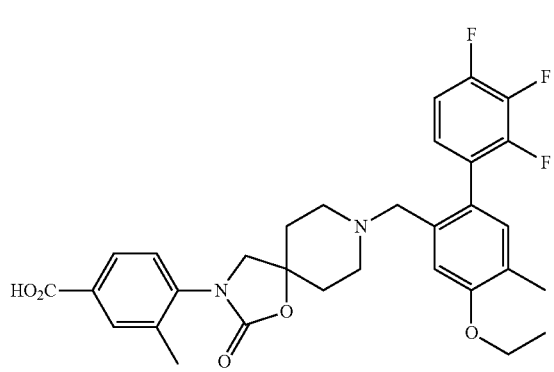 [SMILES: CCOc1cc(CN2CCC3(CC2)CN(c2ccc(C(=O)O)cc2C)C(=O)O3)c(-c2ccc(F)c(F)c2F)cc1C]

The title compound was prepared and purified using essentially the same experimental procedures in Example 4-1 and was isolated as a TFA salt.

LCMS (m/e): 569 (M+1).

Example 4-9

4-(2-Oxo-8-{[2',3',4'-trifluoro-4-(trifluoromethyl)biphenyl-2-yl]methyl}-1-oxa-3,8-diazaspiro[4.5]dec-3-yl)benzoic acid, TFA salt

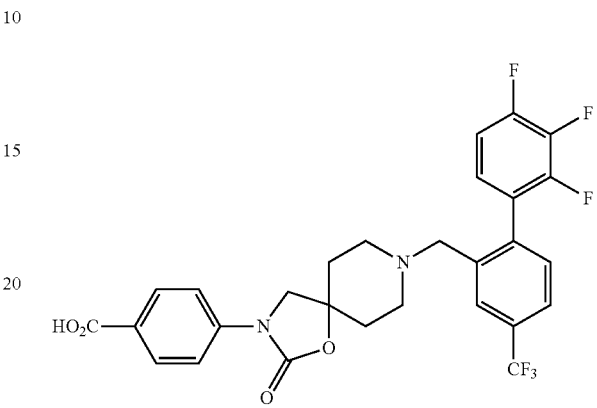

The title compound was prepared and purified using essentially the same experimental procedures in Example 4-1 and was isolated as a TFA salt.

LCMS (m/e): 565 (M+1).

Example 4-10

4-{8-[2-(6-Fluoropyridin-3-yl)-5-(trifluoromethyl)benzyl]-2-oxo-1-oxa-3,8-diazaspiro[4.5]dec-3-yl}benzoic acid, TFA salt

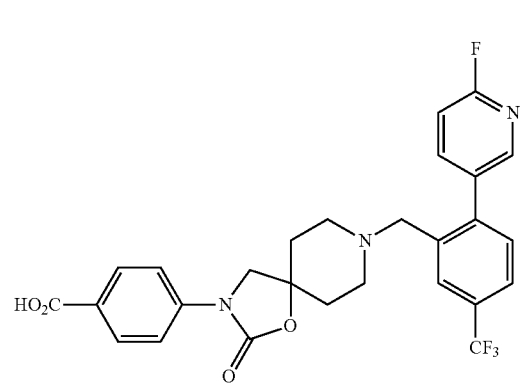 [SMILES: O=C(O)c1ccc(N2CC3(CCN(Cc4cc(C(F)(F)F)ccc4-c4ccc(F)nc4)CC3)OC2=O)cc1]

The title compound was prepared and purified using essentially the same experimental procedures in Example 4-1 and was isolated as a TFA salt.

LCMS (m/e): 530 (M+1).

Example 4-11

4-{8-[(4-Ethoxy-2',4',5'-trifluoro-5-methylbiphenyl-2-yl)methyl]-2-oxo-1-oxa-3,8-diazaspiro[4.5]dec-3-yl}benzoic acid, TFA salt

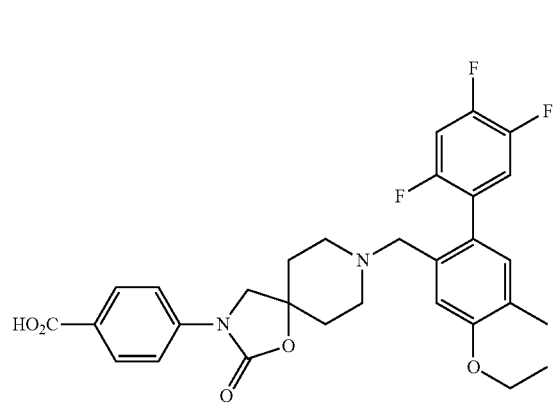 [SMILES: CCOc1cc(CN2CCC3(CC2)CN(c2ccc(C(=O)O)cc2)C(=O)O3)c(-c2cc(F)c(F)cc2F)cc1C]

The title compound was prepared and purified using essentially the same experimental procedures in Example 4-1 and was isolated as a TFA salt.

LCMS (m/e): 555 (M+1).

Example 4-12

4-{8-[(4-Ethoxy-2',3',4'-trifluoro-5-methylbiphenyl-2-yl)methyl]-2-oxo-1-oxa-3,8-diazaspiro[4.5]dec-3-yl}-2-methylbenzoic acid, TFA salt

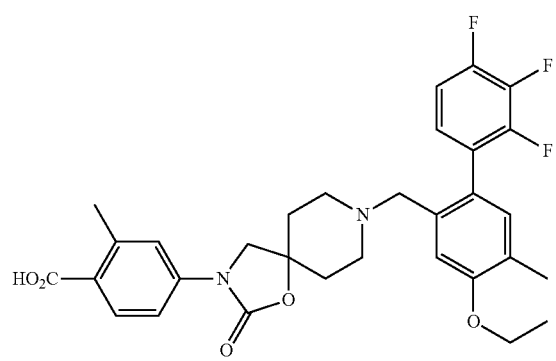 [SMILES: CCOc1cc(CN2CCC3(CC2)CN(c2ccc(C(=O)O)c(C)c2)C(=O)O3)c(-c2ccc(F)c(F)c2F)cc1C]

The title compound was prepared and purified using essentially the same experimental procedures in Example 4-1 and was isolated as a TFA salt.

LCMS (m/e): 569 (M+1).

Example 4-13

4-{8-[(4-Ethoxy-2',3',4'-trifluorobiphenyl-2-yl)methyl]-2-oxo-1-oxa-3,8-diazaspiro[4.5]dec-3-yl}-2-methylbenzoic acid, TFA salt

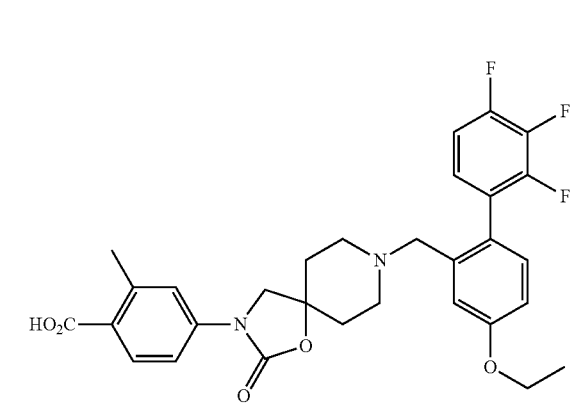 [SMILES: CCOc1ccc(-c2ccc(F)c(F)c2F)c(CN2CCC3(CC2)CN(c2ccc(C(=O)O)c(C)c2)C(=O)O3)c1]

The title compound was prepared and purified using essentially the same experimental procedures in Example 4-1 and was isolated as a TFA salt.

LCMS (m/e): 555 (M+1).

Example 4-14

4-{8-[5-Ethoxy-2-(6-fluoropyridin-3-yl)-4-methylbenzyl]-2-oxo-1-oxa-3,8-diazaspiro[4.5]dec-3-yl}benzoic acid, TFA salt

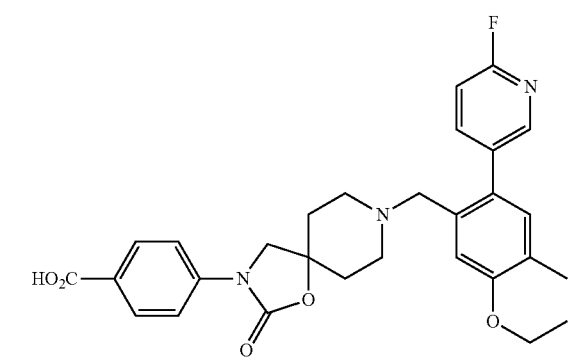 [SMILES: CCOc1cc(CN2CCC3(CC2)CN(c2ccc(C(=O)O)cc2)C(=O)O3)c(-c2ccc(F)nc2)cc1C]

The title compound was prepared and purified using essentially the same experimental procedures in Example 4-1 and was isolated as a TFA salt.

LCMS (m/e): 520 (M+1).

Example 4-15

4-(8-{[4-(4-Fluorophenyl)-2-phenylpyrimidin-5-yl]methyl}-2-oxo-1-oxa-3,8-diazaspiro[4.5]dec-3-yl)benzoic acid, TFA salt

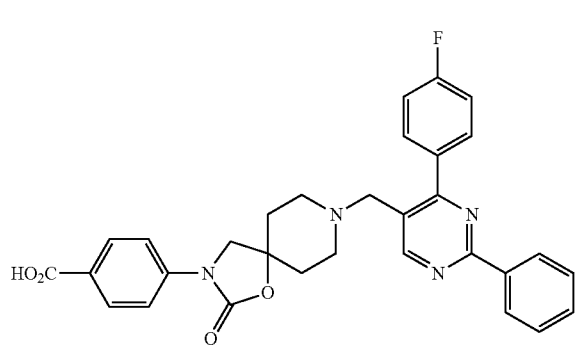 [SMILES: O=C(O)c1ccc(N2CC3(CCN(Cc4cnc(-c5ccccc5)nc4-c4ccc(F)cc4)CC3)OC2=O)cc1]

The title compound was prepared and purified using essentially the same experimental procedures in Example 4-1 and was isolated as a TFA salt.

LCMS (m/e): 539 (M+1).

Example 4-16

4-(2-Oxo-8-{[2',4',5'-trifluoro-4-(propan-2-yloxy)biphenyl-2-yl]methyl}-1-oxa-3,8-diazaspiro[4.5]dec-3-yl)benzoic acid, TFA salt

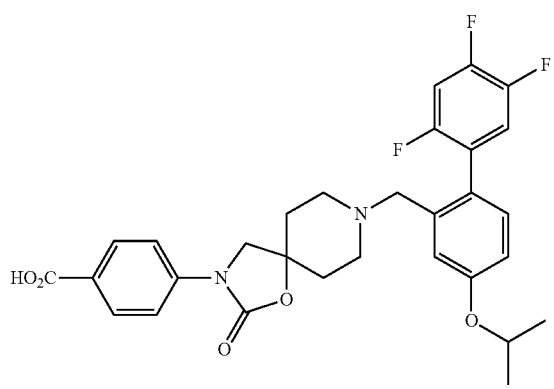 [SMILES: CC(C)Oc1ccc(-c2cc(F)c(F)cc2F)c(CN2CCC3(CC2)CN(c2ccc(C(=O)O)cc2)C(=O)O3)c1]

The title compound was prepared and purified using essentially the same experimental procedures in Example 4-1 and was isolated as a TFA salt.

LCMS (m/e): 555 (M+1).

Example 4-17

4-(2-Oxo-8-{[2',3',4'-trifluoro-4-(trifluoromethoxy)biphenyl-2-yl]methyl}-1-oxa-3,8-diazaspiro[4.5]dec-3-yl)benzoic acid, TFA salt

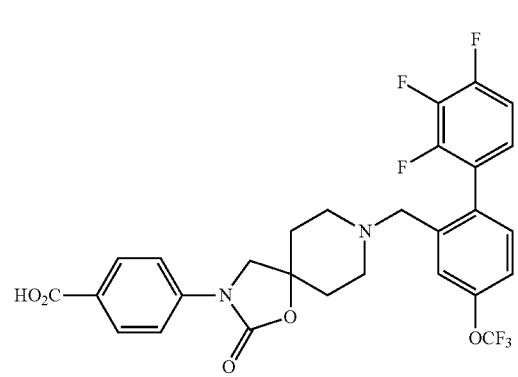 [SMILES: O=C(O)c1ccc(N2CC3(CCN(Cc4cc(OC(F)(F)F)ccc4-c4ccc(F)c(F)c4F)CC3)OC2=O)cc1]

The title compound was prepared and purified using essentially the same experimental procedures in Example 4-1 and was isolated as a TFA salt.

LCMS (m/e): 581 (M+1).

Example 4-18

4-{8-[(4-Ethoxy-2',3',4'-trifluoro-5-methylbiphenyl-2-yl)methyl]-2-oxo-1-oxa-3,8-diazaspiro[4.5]dec-3-yl}-2-methoxybenzoic acid, TFA salt

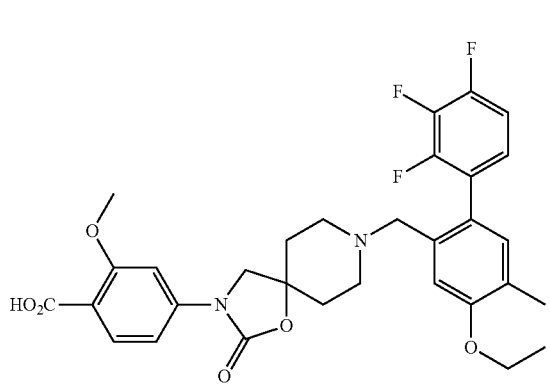 [SMILES: CCOc1cc(CN2CCC3(CC2)CN(c2ccc(C(=O)O)c(OC)c2)C(=O)O3)c(-c2ccc(F)c(F)c2F)cc1C]

The title compound was prepared and purified using essentially the same experimental procedures in Example 4-1 and was isolated as a TFA salt.

LCMS (m/e): 585 (M+1).

Example 4-19

4-(2-Oxo-8-{[6-(2,4,5-trifluorophenyl)-2,3-dihydro-1H-inden-5-yl]methyl}-1-oxa-3,8-diazaspiro[4.5]dec-3-yl)benzoic acid, TFA salt

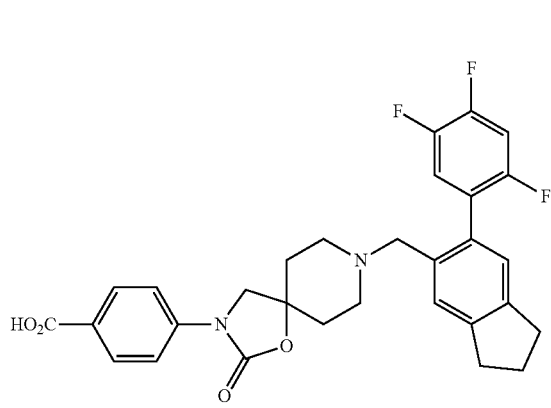 [SMILES: O=C(O)c1ccc(N2CC3(CCN(Cc4cc5c(cc4-c4cc(F)c(F)cc4F)CCC5)CC3)OC2=O)cc1]

The title compound was prepared and purified using essentially the same experimental procedures in Example 4-1 and was isolated as a TFA salt.

LCMS (m/e): 537 (M+1).

Example 4-20

4-(8-{5-Ethoxy-4-methyl-2-[6-(trifluoromethyl)pyridin-3-yl]benzyl}-2-oxo-1-oxa-3,8-diazaspiro[4.5]dec-3-yl)benzoic acid, TFA salt

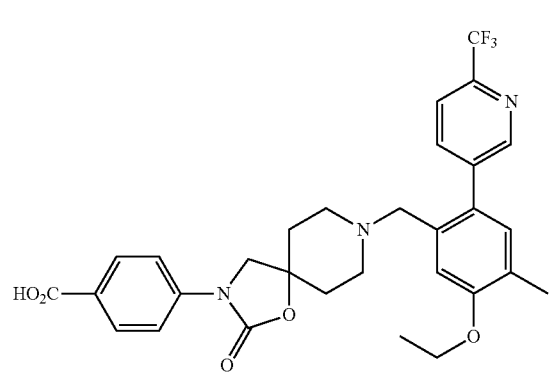 [SMILES: CCOc1cc(CN2CCC3(CC2)CN(c2ccc(C(=O)O)cc2)C(=O)O3)c(-c2ccc(C(F)(F)F)nc2)cc1C]

The title compound was prepared and purified using essentially the same experimental procedures in Example 4-1 and was isolated as a TFA salt.

LCMS (m/e): 570 (M+1).

Example 4-21

4-{8-[(4-Ethoxy-2',3',4'-trifluoro-5-methylbiphenyl-2-yl)methyl]-2-oxo-1-oxa-3,8-diazaspiro[4.5]dec-3-yl}-3-fluorobenzoic acid, TFA salt

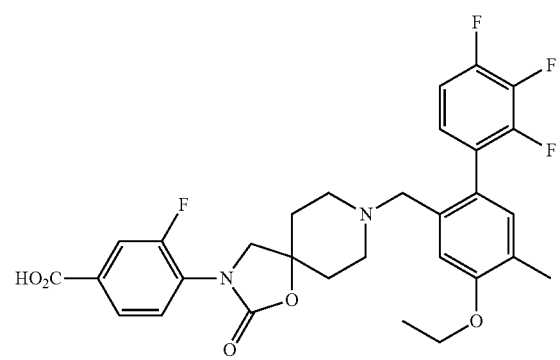 [SMILES: CCOc1cc(CN2CCC3(CC2)CN(c2ccc(C(=O)O)cc2F)C(=O)O3)c(-c2ccc(F)c(F)c2F)cc1C]

The title compound was prepared and purified using essentially the same experimental procedures in Example 4-1 and was isolated as a TFA salt.

LCMS (m/e): 573 (M+1).

Example 4-22

3-Chloro-4-{8-[(4-ethoxy-2',3',4'-trifluoro-5-methyl-biphenyl-2-yl)methyl]-2-oxo-1-oxa-3,8-diaza spiro[4.5]dec-3-yl}benzoic acid, TFA salt

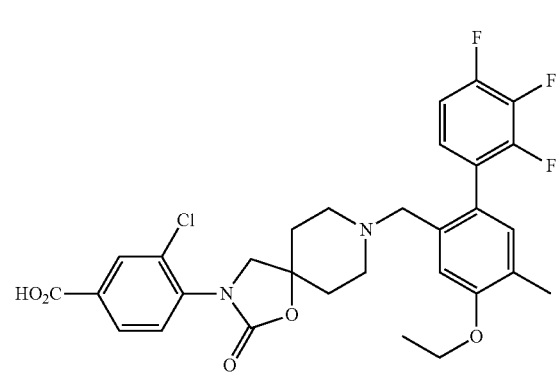 [SMILES: CCOc1cc(CN2CCC3(CC2)CN(c2ccc(C(=O)O)cc2Cl)C(=O)O3)c(-c2ccc(F)c(F)c2F)cc1C]

The title compound was prepared and purified using essentially the same experimental procedures in Example 4-1 and was isolated as a TFA salt.

LCMS (m/e): 589 (M+1).

Example 4-23

4-{8-[5-Chloro-4-methyl-2-(6-methylpyridin-3-yl)benzyl]-2-oxo-1-oxa-3,8-diazaspiro[4.5]dec-3-yl}benzoic acid, TFA salt

Example 4-25

4-{8-[5-Chloro-2-(6-fluoropyridin-3-yl)-4-methylbenzyl]-2-oxo-1-oxa-3,8-diazaspiro[4.5]dec-3-yl}benzoic acid, TFA salt

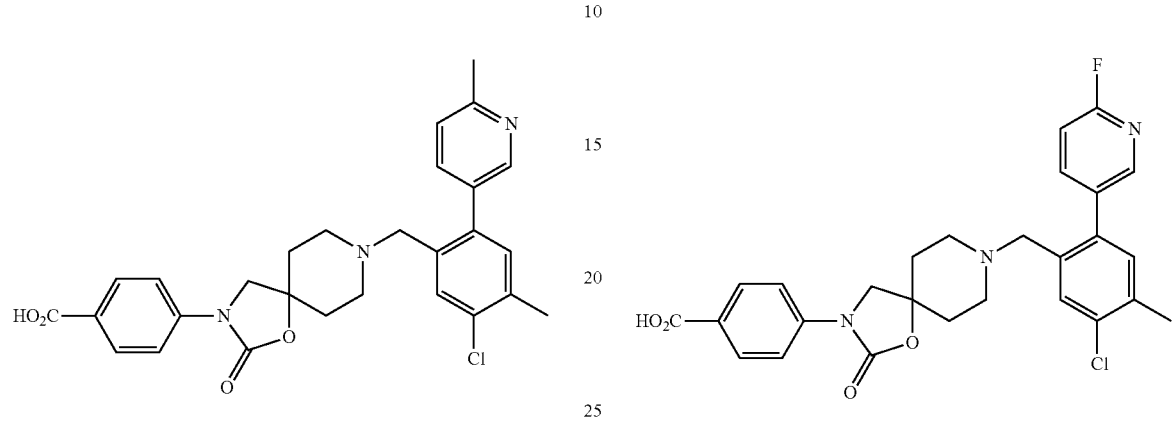

The title compound was prepared and purified using essentially the same experimental procedures in Example 4-1 and was isolated as a TFA salt.

LCMS (m/e): 506 (M+1).

The title compound was prepared and purified using essentially the same experimental procedures in Example 4-1 and was isolated as a TFA salt.

LCMS (m/e): 510 (M+1).

Example 4-24

4-{8-[(4-Chloro-2',4',5'-trifluoro-5-methylbiphenyl-2-yl)methyl]-2-oxo-1-oxa-3,8-diazaspiro[4.5]dec-3-yl}benzoic acid, TFA salt

Example 4-26

4-(8-{5-Chloro-4-methyl-2-[6-(trifluoromethyl)pyridin-3-yl]benzyl}-2-oxo-1-oxa-3,8-diazaspiro[4.5]dec-3-yl)benzoic acid, TFA salt

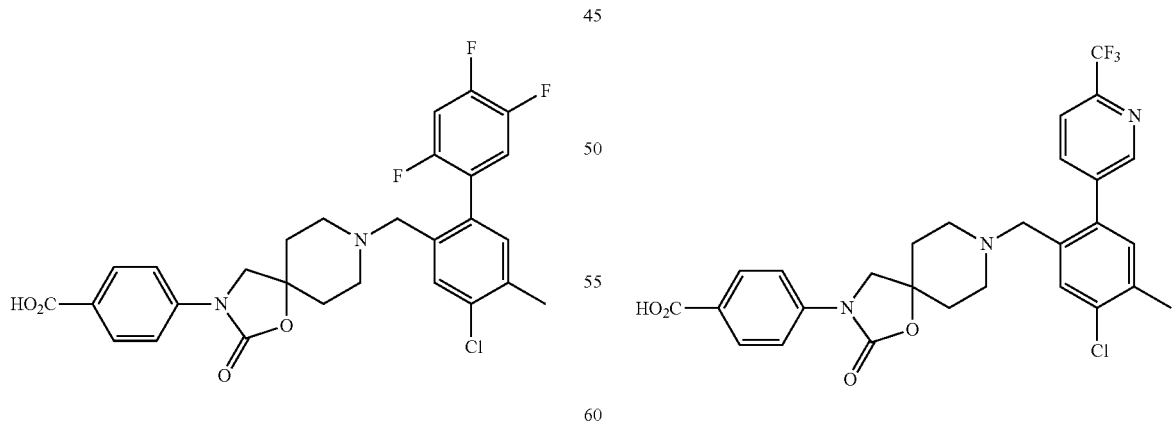

The title compound was prepared and purified using essentially the same experimental procedures in Example 4-1 and was isolated as a TFA salt.

LCMS (m/e): 545 (M+1).

The title compound was prepared and purified using essentially the same experimental procedures in Example 4-1 and was isolated as a TFA salt.

LCMS (m/e): 560 (M+1).

Example 4-27

4-{8-[5-Ethoxy-2-(1,3-thiazol-2-yl)benzyl]-2-oxo-1-oxa-3,8-diazaspiro[4.5]dec-3-yl}benzoic acid, TFA salt

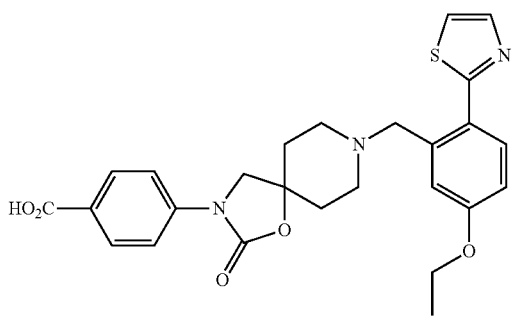 [SMILES: CCOc1ccc(-c2nccs2)c(CN2CCC3(CC2)CN(c2ccc(C(=O)O)cc2)C(=O)O3)c1]

The title compound was prepared and purified using essentially the same experimental procedures in Example 4-1 and was isolated as a TFA salt.
LCMS (m/e): 494 (M+1).

Example 4-28

4-{8-[5-Ethoxy-4-methyl-2-(4-methyl-1H-pyrazol-1-yl)benzyl]-2-oxo-1-oxa-3,8-diazaspiro[4.5]dec-3-yl}benzoic acid, TFA salt

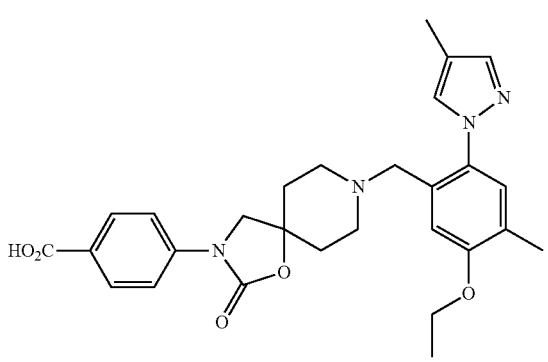 [SMILES: CCOc1cc(CN2CCC3(CC2)CN(c2ccc(C(=O)O)cc2)C(=O)O3)c(-n2cc(C)cn2)cc1C]

Step 1. Synthesis of 5-ethoxy-4-methyl-2-(4-methyl-1H-pyrazol-1-yl)benzaldehyde

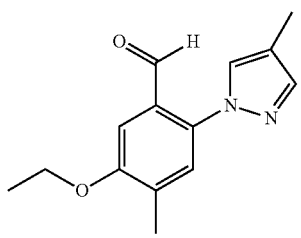 [SMILES: CCOc1cc(C=O)c(-n2cc(C)cn2)cc1C]

A solution of 2-bromo-5-ethoxy-4-methylbenzaldehyde (100 mg, 0.41 mmol), 4-methyl-1H-pyrazole (40.5 mg, 0.49 mmol), $K_2CO_3$ (114 mg, 0.82 mmol), CuI (78 mg, 0.41 mmol) in DMF (2 mL) was stirred at 110° C. for 3 hours. The reaction mixture then was filtered concentrated and the residue was purified on a silica gel column eluting with 30% EtOAc in hexanes and then with 5% MeOH in DCM to provide the title intermediate (20 mg).
$^1$H-NMR (CDCl$_3$): δ 9.89 (s, 1H), 7.57 (s, 1H), 7.51 (s, 1H), 7.39 (s, 1H), 7.25 (s, 1H), 4.15 (q, 2H), 2.32 (s, 3H), 2.19 (s, 3H), 1.46 (t, J=7.0 Hz, 3H).

Step 2. Synthesis of 4-{8-[5-ethoxy-4-methyl-2-(4-methyl-1H-pyrazol-1-yl)benzyl]-2-oxo-1-oxa-3,8-diazaspiro[4.5]dec-3-yl}benzoic acid, TFA salt The title compound was prepared and purified using essentially the same experimental procedures in Example 4-1 and was isolated as a TFA salt.
LCMS (m/e): 505 (M+1).

Example 4-29

4-(8-{[1-(Prop-2-yl)-7-chloro-1H-indol-4-yl]methyl}-2-oxo-1-oxa-3,8-diazaspiro[4.5]dec-3-yl)benzoic acid, TFA salt

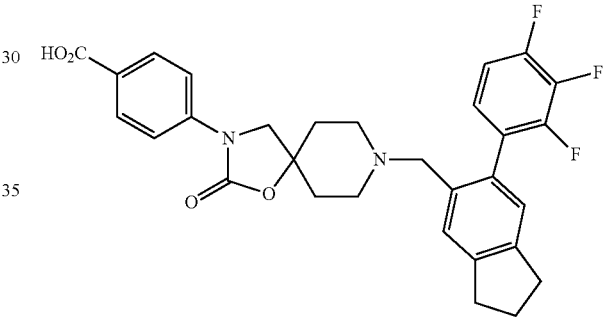

The title compound was prepared and purified according to same experimental procedures in Example 4-1 as a TFA salt.
LCMS (m/e): 537 (M+1).

Example 4-30

4-(8-{[1-(Prop-2-yl)-7-chloro-1H-indol-4-yl]methyl}-2-oxo-1-oxa-3,8-diazaspiro[4.5]dec-3-yl)benzoic acid, TFA salt

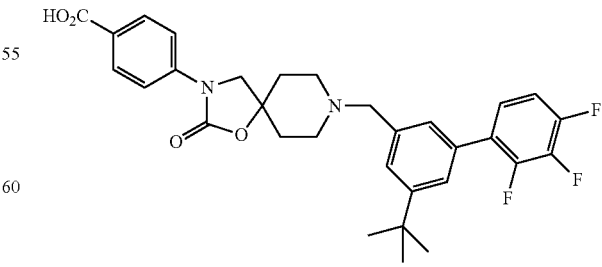

The title compound was prepared and purified according to same experimental procedures in Example 4-1 as a TFA salt.
LCMS (m/e): 553 (M+1).

Example 4-31

4-{8-[(5-Methyl-4-trifluoromethyl-2',3',4'-trifluorobiphen-2-yl)methyl]-2-oxo-1-oxa-3,8-diazaspiro[4.5]dec-3-yl}benzoic acid

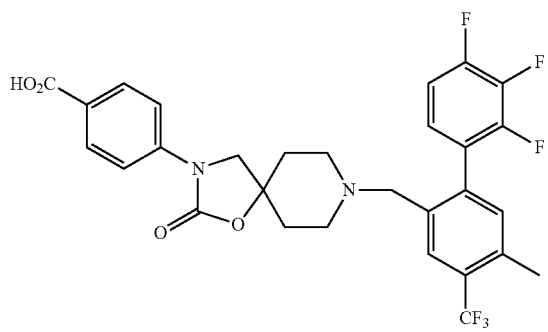 [SMILES: Cc1cc(-c2ccc(F)c(F)c2F)c(CN2CCC3(CC2)CN(c2ccc(C(=O)O)cc2)C(=O)O3)cc1C(F)(F)F]

Step 1. Synthesis of 2-bromo-4-methyl-5-trifluoromethylbenzaldehyde

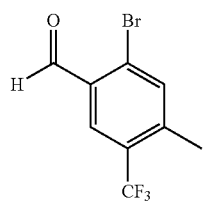

A 100 mL 3-neck flask was fitted with a Teflon temperature sensor and charged under nitrogen with anhydrous THF (10 mL) and n-BuLi (1.6 M, 5.75 mL, 9.2 mmol). The solution was cooled in a dry ice/acetone bath to −78° C. Tetramethylpiperidine (1.56 mL, 9.20 mmol) was added while keeping the temperature below −75° C. and was followed by dropwise addition of 4-bromo-2-methyltrifluoromethylbenzene (0.575 mL, 4.18 mmol) while keeping the temperature below −75° C. Once the addition was complete, the dark brown solution was stirred at −75° C. for 45 minutes, then DMF (0.349 mL, 4.18 mmol) was added and the reaction was stirred at −75° C. for 2 hours. The reaction was warmed to room temperature and then partitioned between water and ether. The mixture was extracted three times with ether and the organic layers were each washed with 4.0 M HCl and twice with brine. The combined organic layers were dried over sodium sulfate and the solvent was evaporated. The residue was purified on a silica gel column (COMBI FLASH 12 gm column) eluted with a gradient of 10-20% ethyl acetate/hexanes to afford the title intermediate (430 mg) as a yellow solid. NMR indicated about a >10:1 ratio of desired product and isomers.

$^1$H-NMR (CDCl$_3$, 500 MHz); δ 10.35 (s, 1H), 8.16 (s, 1), 7.61 (s, 1H, 2.54 (s, 3H).

$^{19}$F-NMR (CDCl$_3$, 500 MHz), major: δ −62.8; minor: δ −62.1

Step 2. Synthesis of methyl 4-{8-[(4-methyl-5-trifluoromethyl-2-bromophenyl)methyl]-2-oxo-1-oxa-3,8-diazaspiro[4.5]dec-3-yl}benzoate

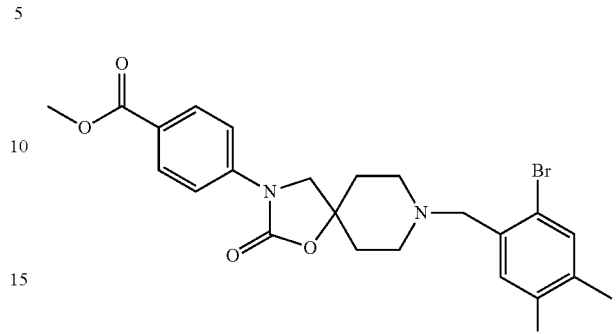

To a solution of 2-bromo-4-methyl-5-trifluoromethylbenzaldehyde (100 mg, 0.374 mmol) in DMF (3 mL) was added methyl 4-(2-oxo-1-oxa-3,8-diazaspiro[4.5]dec-3-yl)benzoate (122 mg, 0.374 mmol) (from Example 1-1, Step 2) and DIPEA (0.326 mL, 1.87 mmol). The mixture was stirred at room temperature for 15 minutes and then acetic acid (0.107 mL, 1.87 mmol) and sodium triacetoxyborohydride (120 mg, 0.562 mmol) were added. The reaction was stirred at room temperature and was followed by LC/MS until complete. Water was added and the mixture was extracted twice with ethyl acetate. The organic layers were combined and dried over sodium sulfate and evaporated. The residue was purified on silica gel (CombiFlash 4 gm pre-packed column) eluting with a 10-30% ethyl acetate/hexanes gradient to afford the title intermediate (130 mg) as a white solid.

LCMS (m/e): 542 (M+1).

Step 3. Synthesis of 4-{8-[(5-methyl-4-trifluoromethyl-2',3',4'-trifluorobiphen-2-yl)methyl]-2-oxo-1-oxa-3,8-diazaspiro[4.5]dec-3-yl}benzoic acid

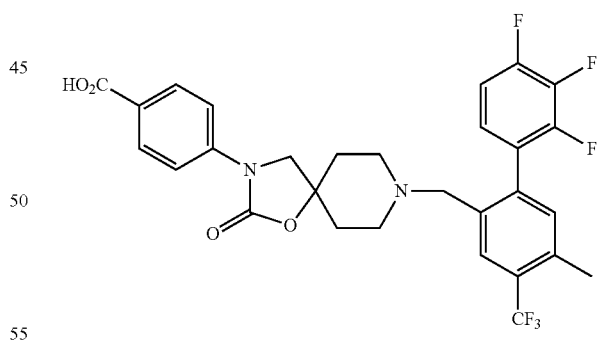

To a solution of methyl 4-{8-[(4-methyl-5-trifluoromethyl-2-bromophenyl)methyl]-2-oxo-1-oxa-3,8-diazaspiro[4.5]dec-3-yl}benzoate (30 mg, 0.055 mmol) in dioxane (1.5 mL) and water (0.5 mL) in a 5 mL microwave reaction vial were added 2,3,4-trifluorophenylboronic acid (20 mg, 0.111 mmol), 1,1'-bis(diphenylphosphino)ferrocene palladium (II) dichloride dichloromethane complex (9 mg, 0.011 mmol) and lithium hydroxide mono-hydrate (5 mg, 0.111 mmol). The reaction was heated in a microwave at 120° C. for 15-30 minutes. The crude reaction was diluted with acetonitrile and water, filtered and purified by reverse phase chromatography using a gradient of acetonitrile and water with 0.1% ammonium hydroxide. Lypholization of the desired fractions afforded the title compound (13.4 mg) as a white solid.

LCMS (m/e): 579 (M+1).

$^1$H-NMR (CDCl$_3$, 500 MHz); δ 8.10 (d, J=8.4 Hz, 2H), 7.83 (s, 1), 7.62 (d, J=8.4 Hz, 2H), 7.17 (s, 1H), 7.08 (m, 1H), 6.97 (m, 1H), 3.78 (s, 2H), 3.42 (s, 2H), 2.52 (s, 3H), 2.48 (m, 4H), 1.96 (m, 2H), 1.83 (m, 2H).

Example 4-32

4-{8-[(5-Methyl-4-trifluoromethyl-2'-chlorobiphen-2-yl)methyl]-2-oxo-t-oxa-3,8-diazaspiro[4.5]dec-3-yl}benzoic acid

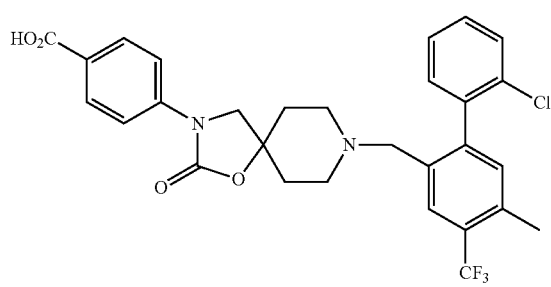 [SMILES: Cc1cc(-c2ccccc2Cl)c(CN2CCC3(CC2)CN(c2ccc(C(=O)O)cc2)C(=O)O3)cc1C(F)(F)F]

Using essentially the same procedure as Example 4-31, Step 3, but using 2-chlorophenylboronic acid, the title compound was obtained after reverse phase (C18) chromatography (acetonitrile/water with 0.1% ammonium hydroxide) and evaporation of the product fractions.

LCMS (m/e): 559/561 (M+1).

Example 4-33

4-{8-[(4-Methyl-5-trifluoromethyl-2-(pyridin-4-yl)phenyl)methyl]-2-oxo-1-oxa-3,8-diazaspiro[4.5]dec-3-yl}benzoic acid

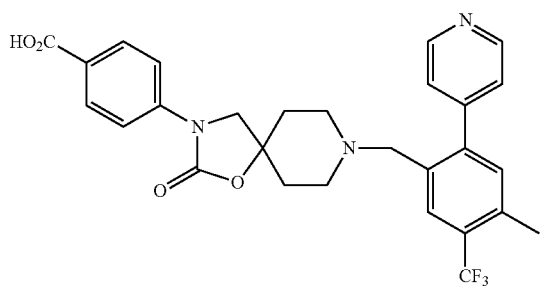 [SMILES: Cc1cc(-c2ccncc2)c(CN2CCC3(CC2)CN(c2ccc(C(=O)O)cc2)C(=O)O3)cc1C(F)(F)F]

Using essentially the same procedure as Example 4-31, Step 3, but using pyridin-4-ylboronic acid, the title compound was obtained after reverse phase (C18) chromatography (acetonitrile/water with 0.1% ammonium hydroxide) and evaporation of the product fractions.

LCMS (m/e): 526 (M+1).

Example 4-34

4-{8-[(5-Methyl-4-trifluoromethyl-2',4'-dichlorobiphen-2-yl)methyl]-2-oxo-1-oxa-3,8-diazaspiro[4.5]dec-3-yl}benzoic acid

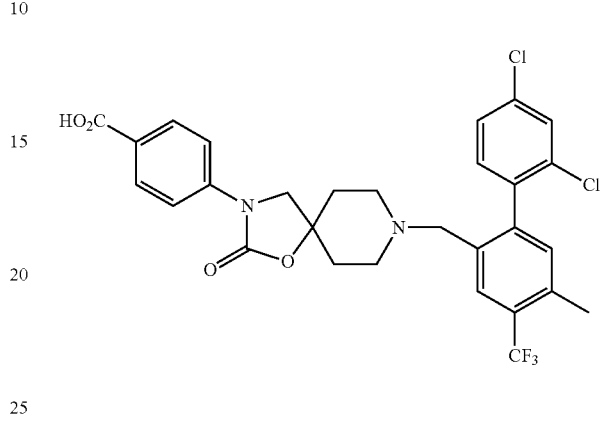

Using essentially the same procedure as Example 4-31, Step 3, but using 2,4-dichlorophenylboronic acid, the title compound was obtained after reverse phase (C18) chromatography (acetonitrile/water with 0.1% ammonium hydroxide) and evaporation of the product fractions.

LCMS (m/e): 593/595 (M+1).

Example 4-35

4-{8-[(4-Methyl-5-trifluoromethyl-2-(2-fluoropyridin-4-yl)phenyl)methyl]-2-oxo-1-oxa-3,8-diazaspiro[4.5]dec-3-yl}benzoic acid

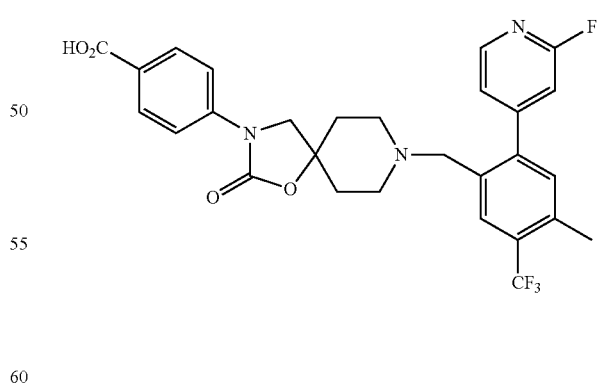

Using essentially the same procedure as Example 4-31, Step 3, but using 2-fluoropyridin-4-ylboronic acid, the title compound was obtained after reverse phase (C18) chromatography (acetonitrile/water with 0.1% ammonium hydroxide) and evaporation of the product fractions.

LCMS (m/e): 544 (M+1).

Example 4-36

4-{8-[(4-Methyl-5-trifluoromethyl-2-(3-fluoropyridin-4-yl)phenyl)methyl]-2-oxo-1-oxa-3,8-diazaspiro[4.5]dec-3-yl}benzoic acid

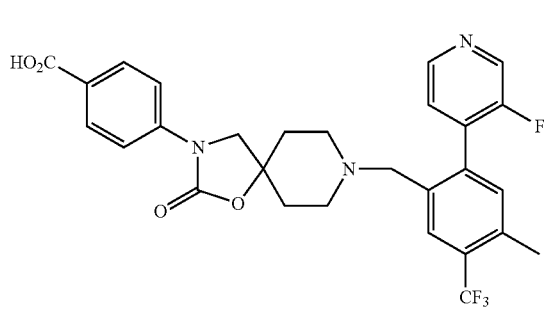 [SMILES: Cc1cc(-c2ccncc2F)c(CN2CCC3(CC2)CN(c2ccc(C(=O)O)cc2)C(=O)O3)cc1C(F)(F)F]

Using essentially the same procedure as Example 4-31, Step 3, but using 3-fluoropyridin-4-ylboronic acid, the title compound was obtained after reverse phase (C18) chromatography (acetonitrile/water with 0.1% ammonium hydroxide) and evaporation of the product fractions.

LCMS (m/e): 544 (M+1).

Example 4-37

4-{8-[(4-Methyl-5-trifluoromethyl-2-(pyridin-3-yl)phenyl)methyl]-2-oxo-1-oxa-3,8-diazaspiro[4.5]dec-3-yl}benzoic acid

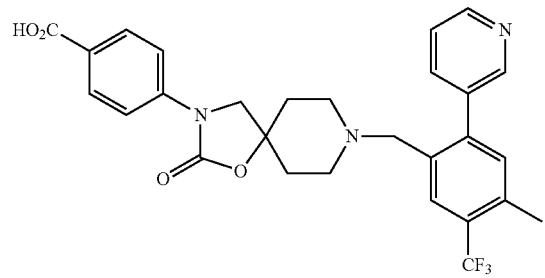 [SMILES: Cc1cc(-c2cccnc2)c(CN2CCC3(CC2)CN(c2ccc(C(=O)O)cc2)C(=O)O3)cc1C(F)(F)F]

Using essentially the same procedure as Example 4-31, Step 3, but using pyridin-3-ylboronic acid, the title compound was obtained after reverse phase (C18) chromatography (acetonitrile/water with 0.1% ammonium hydroxide) and evaporation of the product fractions.

LCMS (m/e): 526 (M+1).

Example 4-38

4-{8-[(4-Methyl-5-trifluoromethyl-2-(2-chloropyridin-5-yl)phenyl)methyl]-2-oxo-1-oxa-3,8-diazaspiro[4.5]dec-3-yl}benzoic acid

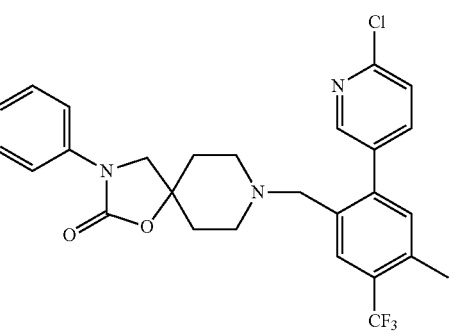

Using essentially the same procedure as Example 4-31, Step 3, but using 2-chloropyridin-5-ylboronic acid, the title compound was obtained after reverse phase (C18) chromatography (acetonitrile/water with 0.1% ammonium hydroxide) and evaporation of the product fractions.

LCMS (m/e): 560/562 (M+1).

Example 4-39

4-{8-[(4-Methyl-5-trifluoromethyl-2-cyclopropylphenyl)methyl]-2-oxo-1-oxa-3,8-diazaspiro[4.5]dec-3-yl}benzoic acid

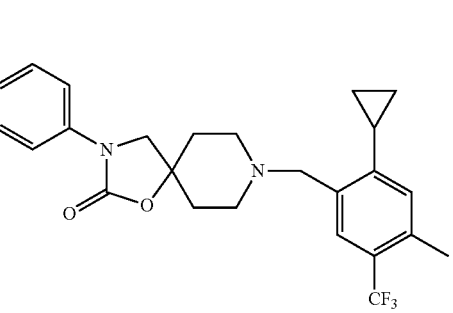

Using essentially the same procedure as Example 4-31, Step 3, but using cyclopropylboronic acid pinacol ester, the title compound was obtained after reverse phase (C18) chromatography (acetonitrile/water with 0.1% ammonium hydroxide) and evaporation of the product fractions.

LCMS (m/e): 489 (M+1).

Example 4-40

4-{8-[(4-Methyl-5-trifluoromethyl-2-(thien-2-yl)phenyl)methyl]-2-oxo-1-oxa-3,8-diazaspiro[4.5]dec-3-yl}benzoic acid

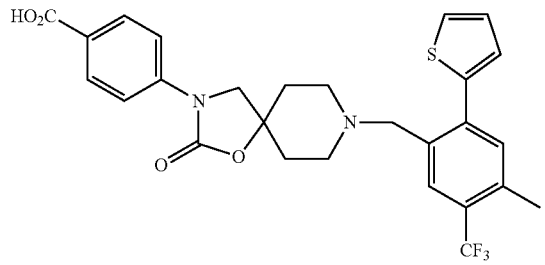 [SMILES: Cc1cc(-c2cccs2)c(CN2CCC3(CC2)CN(c2ccc(C(=O)O)cc2)C(=O)O3)cc1C(F)(F)F]

Using essentially the same procedure as Example 4-31, Step 3, but using (thien-2-yl)boronic acid, the title compound was obtained after reverse phase (C18) chromatography (acetonitrile/water with 0.1% ammonium hydroxide) and evaporation of the product fractions.

LCMS (m/e): 531 (M+1).

Example 4-41

4-{8-[(5-Methyl-4-trifluoromethyl-2'-chloro-4'-fluorobiphen-2-yl)methyl]-2-oxo-1-oxa-3,8-diazaspiro[4.5]dec-3-yl}benzoic acid

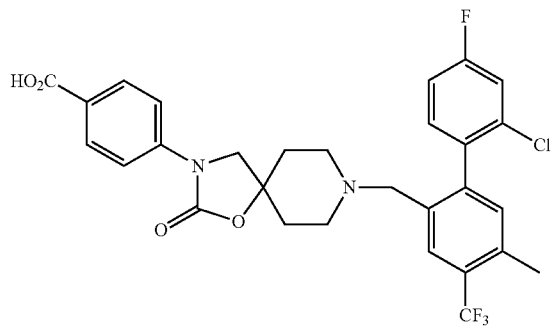

Using essentially the same procedure as Example 4-31, Step 3, but using 2-chloro-4-fluorophenylboronic acid, the title compound was obtained after reverse phase (C18) chromatography (acetonitrile/water with 0.1% ammonium hydroxide) and evaporation of the product fractions.

LCMS (m/e): 577/579 (M+1).

Example 4-42

4-{8-[(4-Methyl-5-trifluoromethyl-2-cyclobutylphenyl)methyl]-2-oxo-1-oxa-3,8-diazaspiro[4.5]dec-3-yl}benzoic acid

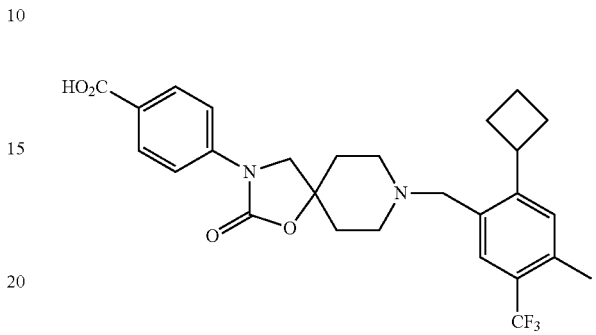

Using essentially the same procedure as Example 4-31, Step 3, but using cyclobutylboronic acid pinacol ester, the title compound was obtained after reverse phase (C18) chromatography (acetonitrile/water with 0.1% ammonium hydroxide) and evaporation of the product fractions.

LCMS (m/e): 503 (M+1).

Example 4-43

4-{8-[(4-Methyl-5-trifluoromethyl-2-(2-aminopyridin-5-yl)phenyl)methyl]-2-oxo-1-oxa-3,8-diazaspiro[4.5]dec-3-yl}benzoic acid

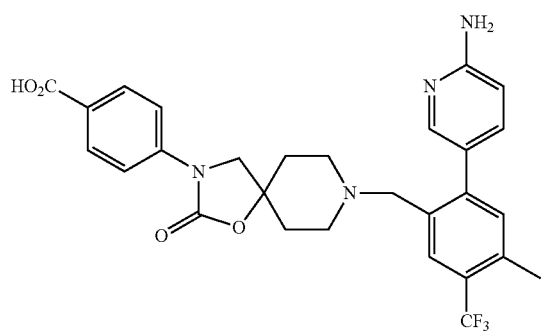 [SMILES: Cc1cc(-c2ccc(N)nc2)c(CN2CCC3(CC2)CN(c2ccc(C(=O)O)cc2)C(=O)O3)cc1C(F)(F)F]

Using essentially the same procedure as Example 4-31, Step 3, but using (2-aminopyridin-5-yl)boronic acid pinacol ester, the title compound was obtained after reverse phase (C18) chromatography (acetonitrile/water with 0.1% ammonium hydroxide) and evaporation of the product fractions.

LCMS (m/e): 541 (M+1).

Example 4-44

4-{8-[(4-Methyl-5-trifluoromethyl-2-(2-cyclopropylpyridin-5-yl)phenyl)methyl]-2-oxo-1-oxa-3,8-diazaspiro[4.5]dec-3-yl}benzoic acid

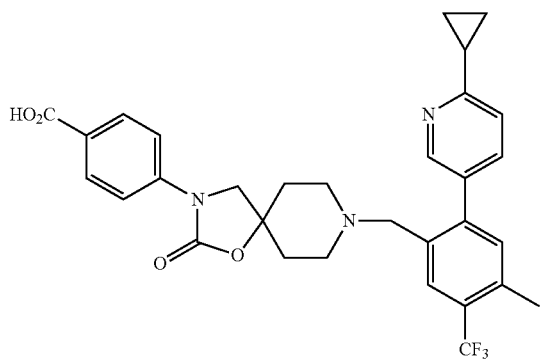 [SMILES: Cc1cc(-c2ccc(C3CC3)nc2)c(CN2CCC3(CC2)CN(c2ccc(C(=O)O)cc2)C(=O)O3)cc1C(F)(F)F]

Using essentially the same procedure as Example 4-31, Step 3, but using (2-cyclopropylpyridin-5-yl)boronic acid pinacol ester, the title compound was obtained after reverse phase (C18) chromatography (acetonitrile/water with 0.1% ammonium hydroxide) and evaporation of the product fractions.

LCMS (m/e): 566 (M+1).

Example 4-45

4-{8-[(4-Methyl-5-trifluoromethyl-2-(2-(pyrrolidin-1-yl)pyridin-5-yl)phehyl)methyl]-2-oxo-1-oxa-3,8-diazaspiro[4.5]dec-3-yl}benzoic acid

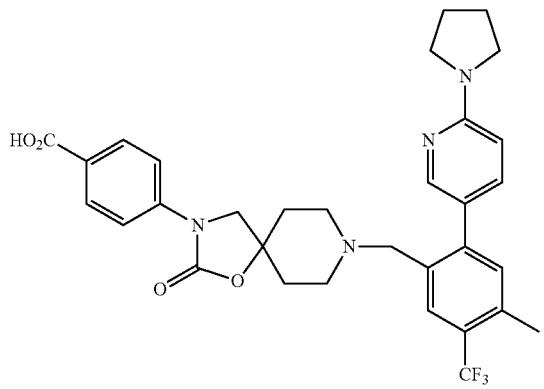 [SMILES: Cc1cc(-c2ccc(N3CCCC3)nc2)c(CN2CCC3(CC2)CN(c2ccc(C(=O)O)cc2)C(=O)O3)cc1C(F)(F)F]

Using essentially the same procedure as Example 4-31, Step 3, but using [2-(pyrrolidine-1-yl)pyridin-5-yl]boronic acid pinacol ester, the title compound was obtained after reverse phase (C18) chromatography (acetonitrile/water with 0.1% ammonium hydroxide) and evaporation of the product fractions.

LCMS (m/e): 595 (M+1).

Example 4-46

4-{8-[(2'-Chloro-4-trifluoromethylbiphen-2-yl)methyl]-2-oxo-1-oxa-3,8-diazaspiro[4.5]dec-3-yl}benzoic acid

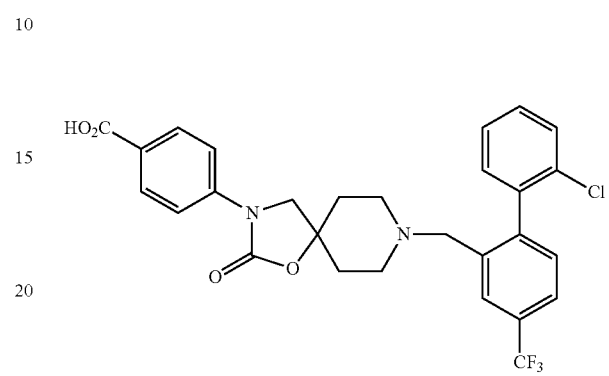

Using essentially the same procedures as Example 4-31, Steps 2-3, but using 2-bromo-5-trifluoromethylbenzaldehyde in Step 2 and 2-chlorophenylboronic acid in Step 3, the title compound was obtained after reverse phase (C18) chromatography (acetonitrile/water with 0.1% ammonium hydroxide) and evaporation of the product fractions.

LCMS (m/e): 545/547 (M+1).

Example 4-47

4-{8-[(2-(Pyridin-4-yl)-5-trifluoromethylphenyl)methyl]-2-oxo-1-oxa-3,8-diazaspiro[4.5]dec-3-yl}benzoic acid

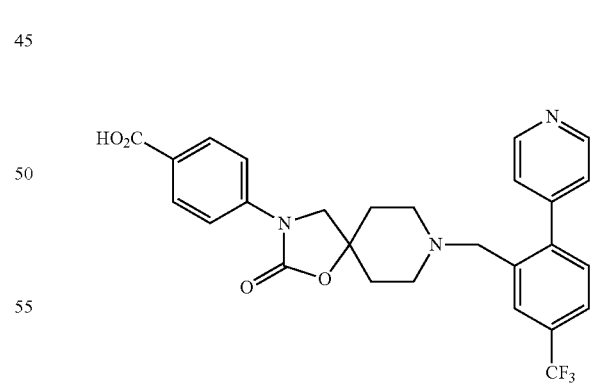

Using essentially the same procedures as Example 4-31, Steps 2-3, but using 2-bromo-5-trifluoromethylbenzaldehyde in Step 2 and pryidin-4-ylboronic acid in Step 3, the title compound was obtained after reverse phase (C18) chromatography (acetonitrile/water with 0.1% ammonium hydroxide) and evaporation of the product fractions.

LCMS (m/e): 512 (M+1).

Example 4-48

4-{8-[(2-(2-Chloropyridin-5-yl)-5-trifluoromethylphenyl)methyl]-2-oxo-1-oxa-3,8-diazaspiro[4.5]dec-3-yl}benzoic acid

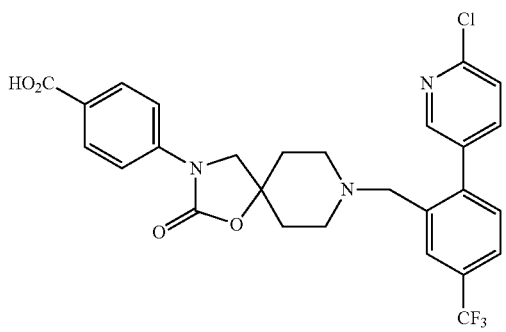 [SMILES: O=C(O)c1ccc(N2CC3(CCN(Cc4cc(C(F)(F)F)ccc4-c4ccc(Cl)nc4)CC3)OC2=O)cc1]

Using essentially the same procedures as Example 4-31, Steps 2-3, but using 2-bromo-5-trifluoromethylbenzaldehyde in Step 2 and 2-chloropyridin-5-ylboronic acid in Step 3, the title compound was obtained after reverse phase (C18) chromatography (acetonitrile/water with 0.1% ammonium hydroxide) and evaporation of the product fractions.

LCMS (m/e): 546/548 (M+1).

Example 4-49

4-{8-[(2-(Pyridin-3-yl)-5-trifluoromethylphenyl)methyl]-2-oxo-1-oxa-3,8-diazaspiro[4.5]dec-3-yl}benzoic acid

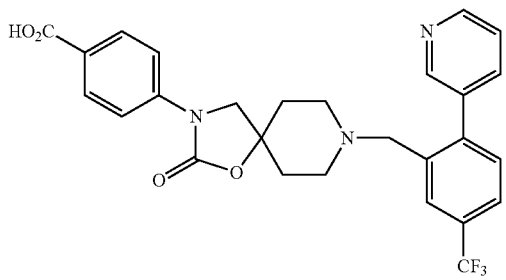 [SMILES: O=C(O)c1ccc(N2CC3(CCN(Cc4cc(C(F)(F)F)ccc4-c4cccnc4)CC3)OC2=O)cc1]

Using essentially the same procedures as Example 4-31, Steps 2-3, but using 2-bromo-5-trifluoromethylbenzaldehyde in Step 2 and pyridin-3-ylboronic acid in Step 3, the title compound was obtained after reverse phase (C18) chromatography (acetonitrile/water with 0.1% ammonium hydroxide) and evaporation of the product fractions.

LCMS (m/e): 512 (M+1).

Example 4-50

4-{8-[(2-(Cyclopropyl)-5-trifluoromethylphenyl)methyl]-2-oxo-1-oxa-3,8-diazaspiro[4.5]dec-3-yl}benzoic acid

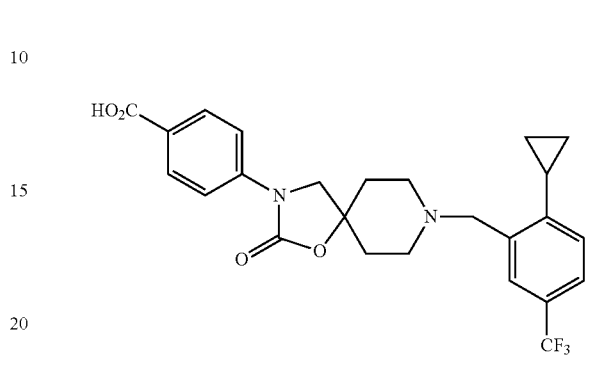

Using essentially the same procedures as Example 4-31, Steps 2-3, but using 2-bromo-5-trifluoromethylbenzaldehyde in Step 2 and cyclopropylboronic acid in Step 3, the title compound was obtained after reverse phase (C18) chromatography (acetonitrile/water with 0.1% ammonium hydroxide) and evaporation of the product fractions.

$^1$H-NMR (CD$_3$OD-d$_4$, 600 MHz): δ 8.15 (d, J=8.4 Hz, 2H), 7.9 (s, J=8.4 Hz, 1H), 7.67 (d, J=1.2 Hz, 1H), 7.55 (d, J=7.8 Hz, 1H), 7.33 (dd, J=1.2 Hz, 7.8 Hz, 1H), 4.75 (s, 2H), 4.05 (s, 2H), 3.6 (dd, J=2.4 Hz, 4H), 2.36-2.34 (m, 5H), 1.22 (m, 2H), 0.8 (m, 2H).

LCMS (m/e): 475 (M+1).

Example 4-51

4-{8-[(2-(Cyclobutyl)-5-trifluoromethylphenyl)methyl]-2-oxo-1-oxa-3,8-diazaspiro[4.5]dec-3-yl}benzoic acid

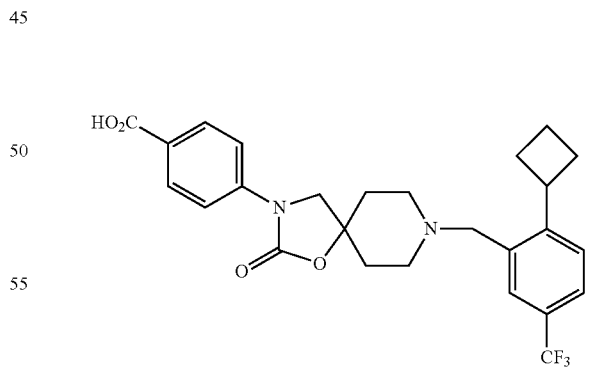

Using essentially the same procedures as Example 4-31, Steps 2-3, but using 2-bromo-5-trifluoromethylbenzaldehyde in Step 2 and cyclobutylboronic acid in Step 3, the title compound was obtained after reverse phase (C18) chromatography (acetonitrile/water with 0.1% ammonium hydroxide) and evaporation of the product fractions.

LCMS (m/e): 489 (M+1).

Example 4-52

4-{8-[(2-(2-(Pyrrolidin-1-yl)pyridin-5-yl)-5-trifluoromethylphenyl)methyl]-2-oxo-1-oxa-3,8-diazaspiro[4.5]dec-3-yl}benzoic acid

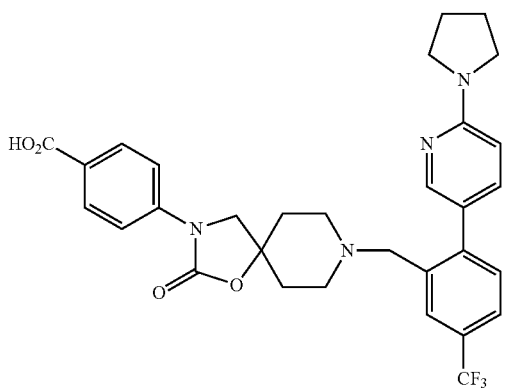 [SMILES: O=C(O)c1ccc(N2CC3(CCN(Cc4cc(C(F)(F)F)ccc4-c4ccc(N5CCCC5)nc4)CC3)OC2=O)cc1]

Using essentially the same procedures as Example 4-31, Steps 2-3, but using 2-bromo-5-trifluoromethylbenzaldehyde in Step 2 and 2-(pyrrolidin-1-yl)pyridin-5-ylboronic acid in Step 3, the title compound was obtained after reverse phase (C18) chromatography (acetonitrile/water with 0.1% ammonium hydroxide) and evaporation of the product fractions.
LCMS (m/e): 581 (M+1).

Example 4-53

4-{8-[(3,2'-Dichloro-4-trifluoromethylbiphen-2-yl)methyl]-2-oxo-1-oxa-3,8-diazaspiro[4.5]dec-3-yl}benzoic acid

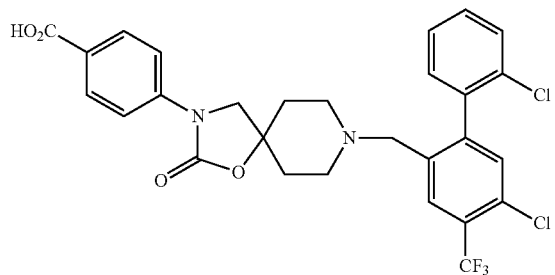

Step 1. Synthesis of 2-bromo-4-chloro-5-trifluoromethylbenzaldehyde and 6-bromo-2-chloro-3-trifluoromethylbenzaldehyde

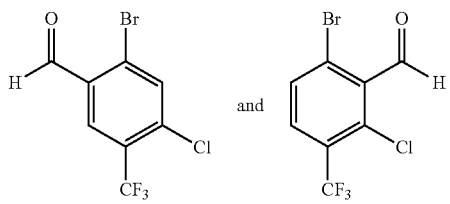

Using essentially the same procedure as Example 4-31, Step 1, but using 4-bromo-2-chlorotrifluoromethylbenzene in Step 1, the title intermediates were obtained in a 1 to 3 ratio of desired 2-bromo-4-chloro-5-trifluoromethylbenzaldehyde to the major isomeric 6-bromo-2-chloro-3-trifluoromethylbenzaldehyde.

$^1$H-NMR (CDCl$_3$, 500 MHz), minor desired: δ 10.32 (s, 1H), 8.35 (s, 1), 7.89 (s, 1H); major isomer: δ 10.38 (s, 1H), 7.75 and 7.71 (ABq, 2H).

Step 2. Synthesis of methyl 4-{8-[(2-bromo-4-chloro-5-trifluoromethylphenyl)methyl]-2-oxo-1-oxa-3,8-diazaspiro[4.5]dec-3-yl}benzoate and methyl 4-{8-[(6-bromo-2-chloro-3-trifluoromethylphenyl)methyl]-2-oxo-1-oxa-3,8-diazaspiro[4.5]dec-3-yl}benzoate

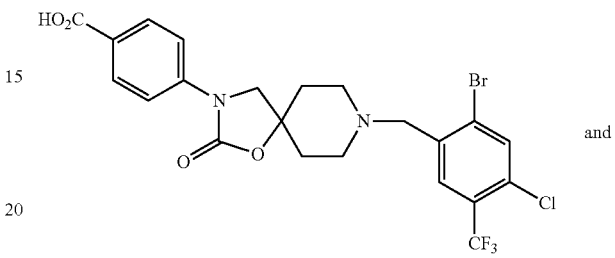

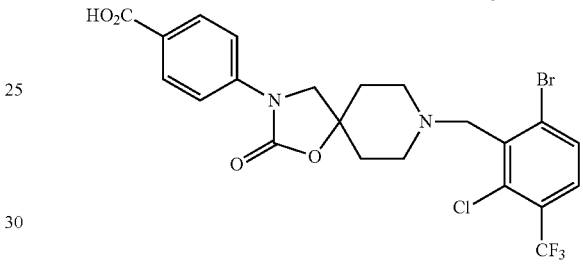

Using essentially the same procedure as Example 4-31, Step 2, but using a 1:3 mixture of 2-bromo-4-chloro-5-trifluoromethylbenzaldehyde and 6-bromo-2-chloro-3-trifluoromethylbenzaldehyde from Step 1, the title intermediates were separated to afford a 1 to 2 ratio of methyl 4-{8-[(2-bromo-4-chloro-5-trifluoromethylphenyl)methyl]-2-oxo-1-oxa-3,8-diazaspiro[4.5]dec-3-yl}benzoate and methyl 4-{8-[(6-bromo-2-chloro-3-trifluoromethylphenyl)methyl]-2-oxo-1-oxa-3,8-diazaspiro[4.5]dec-3-yl}benzoate LCMS (m/e): slower (R$_f$=1.26 minutes) minor, 561/563 (M+1); faster (R$_f$=1.21 minutes) major, 561/563 (M+1).

Step 3. Synthesis of 4-{8-[(3,2'-dichloro-4-trifluoromethylbiphen-2-yl)methyl]-2-oxo-1-oxa-3,8-diazaspiro[4.5]dec-3-yl}benzoic acid

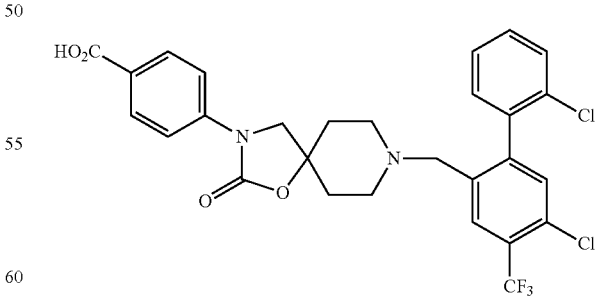

Using essentially the same procedure as Example 4-31, Step 3, but using methyl 4-{8-[(2-bromo-4-chloro-5-trifluoromethylphenyl)methyl]-2-oxo-1-oxa-3,8-diazaspiro[4.5]dec-3-yl}benzoate (minor isomer from Step 2) and 2-chlorophenylboronic acid, the title compound was obtained after reverse phase (C18) chromatography (acetonitrile/water with 0.1% ammonium hydroxide) and evaporation of the product fractions.

LCMS (m/e): 579/581 (M+1).

Example 4-54

4-{8-[(4-Chloro-2-(2-fluoropyridin-3-yl)-5-trifluoromethylphenyl)methyl]-2-oxo-1-oxa-3,8-diazaspiro[4.5]dec-3-yl}benzoic acid

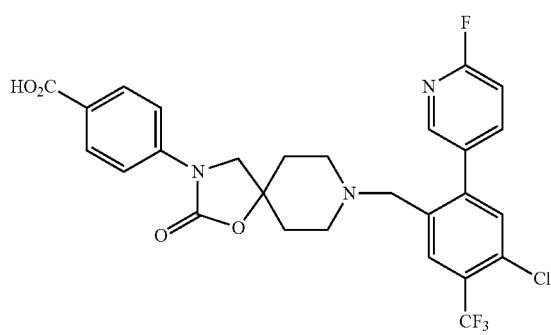 [SMILES: O=C(O)c1ccc(N2CC3(CCN(Cc4cc(C(F)(F)F)c(Cl)cc4-c4ccc(F)nc4)CC3)OC2=O)cc1]

Using essentially the same procedure as Example 4-53, Step 3, but using 2-fluoropyridin-3-ylboronic acid, the title compound was obtained after reverse phase (C18) chromatography (acetonitrile/water with 0.1% ammonium hydroxide) and evaporation of the product fractions.

LCMS (m/e): 564/566 (M+1).

Example 4-55

4-{8-[(5-Chloro-4-trifluoromethyl-2',3',4'-trifluorobiphen-2-yl)methyl]-2-oxo-1-oxa-3,8-diazaspiro[4.5]dec-3-yl}benzoic acid

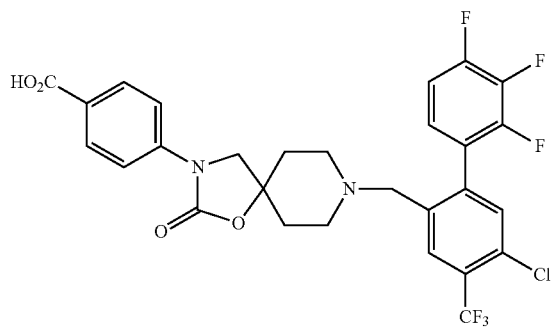 [SMILES: O=C(O)c1ccc(N2CC3(CCN(Cc4cc(C(F)(F)F)c(Cl)cc4-c4ccc(F)c(F)c4F)CC3)OC2=O)cc1]

Using essentially the same procedure as Example 4-53, Step 3, but using 2,3,4-trifluorophenylboronic acid, the title compound was obtained after reverse phase (C18) chromatography (acetonitrile/water with 0.1% ammonium hydroxide) and evaporation of the product fractions.

LCMS (m/e): 599/601 (M+1).

Example 4-56

4-{8-[(4-Chloro-2-cyclopropyl-5-trifluoromethylphenyl)methyl]-2-oxo-1-oxa-3,8-diazaspiro[4.5]dec-3-yl}benzoic acid

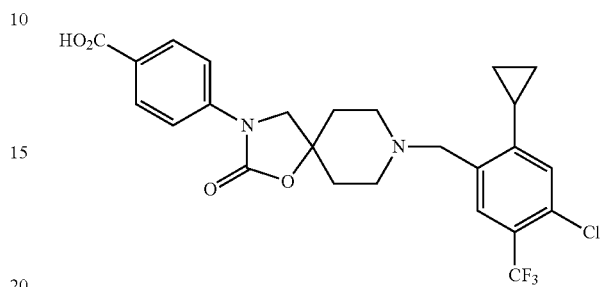

Using essentially the same procedure as Example 4-53, Step 3, but using cyclopropylboronic acid pinacol ester, the title compound was obtained after reverse phase (C18) chromatography (acetonitrile/water with 0.1% ammonium hydroxide) and evaporation of the product fractions.

$^1$H-NMR (CD$_3$OD-d$_4$, 600 MHz): δ 8.15 (d, J=8.4 Hz, 2H), 8.05 (s, 1H), 7.7 (d, J=8.4 Hz, 2H), 7.3 (s, 1H), 4.7 (s, 2H), 4.05 (s, 2H), 3.6 (m, 4H), 2.3 (m, 5H), 1.25 (m, 2H), 0.8 (m, 2H).

LCMS (m/e): 509/511 (M+1).

Example 4-57

4-{8-[(2-Cyclopropyl-3,5-bis-trifluoromethylphenyl)methyl]-2-oxo-1-oxa-3,8-diazaspiro[4.5]dec-3-yl}benzoic acid

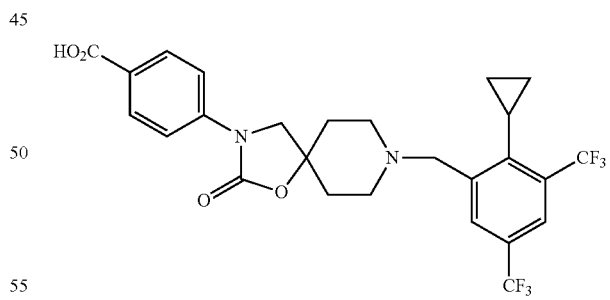

Using essentially the same procedure as Example 4-31, Steps 2-3, but using 2-bromo-3,5-bis-trifluoromethylbenzaldehyde in Step 2 and cyclopropylboronic acid pinacol ester in Step 3, the title compound was obtained after reverse phase (C18) chromatography (acetonitrile/water with 0.1% ammonium hydroxide) and evaporation of the product fractions.

LCMS (m/e): 543 (M+1).

Example 4-58

4-{8-[(3,5-Bis-trifluoromethyl-2-(2-pyrrolidin-1-yl)pyridin-5-yl)phenyl)methyl]-2-oxo-1-oxa-3,8-diazaspiro[4.5]dec-3-yl}benzoic acid

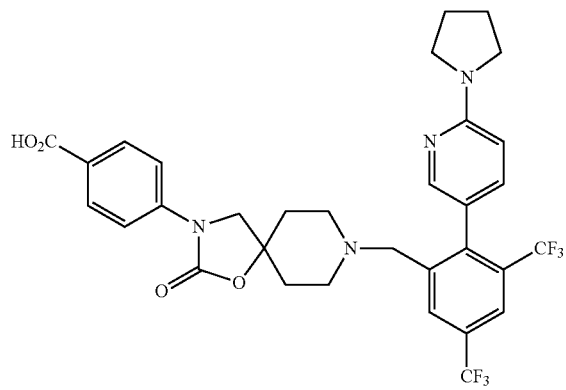 [SMILES: O=C(O)c1ccc(N2CC3(CCN(Cc4cc(C(F)(F)F)cc(C(F)(F)F)c4-c4ccc(N5CCCC5)nc4)CC3)OC2=O)cc1]

Using essentially the same procedure as Example 4-31, Steps 2-3, but using 2-bromo-3,5-bis-trifluoromethylbenzaldehyde in Step 2 and 2-(pyrrolidin-1-yl)pyridine-5-ylboronic acid pinacol ester in Step 3, the title compound was obtained after reverse phase (C18) chromatography (acetonitrile/water with 0.1% ammonium hydroxide) and evaporation of the product fractions.

LCMS (m/e): 649 (M+1).

Example 4-59

4-{8-[(5-Cyclopropyl-2-methoxypyridin-3-yl)methyl]-2-oxo-1-oxa-3,8-diazaspiro[4.5]dec-3-yl}benzoic acid

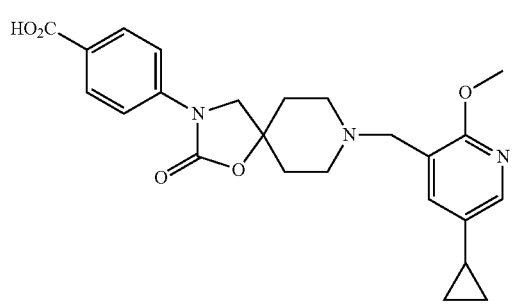 [SMILES: COc1ncc(C2CC2)cc1CN1CCC2(CC1)CN(c1ccc(C(=O)O)cc1)C(=O)O2]

Using essentially the same procedure as Example 4-31, Steps 2-3, but using 5-bromo-2-methoxypyridine-3-carboxaldehyde in Step 2 and cyclopropylboronic acid pinacol ester in Step 3, the title compound was obtained after reverse phase (C18) chromatography (acetonitrile/water with 0.1% ammonium hydroxide) and evaporation of the product fractions.

LCMS (m/e): 438 (M+1).

Example 4-60

4-{8-[(2,4-Dicyclopropyl-5-trifluoromethylphenyl)methyl]-2-oxo-1-oxa-3,8-diazaspiro[4.5]dec-3-yl}benzoic acid

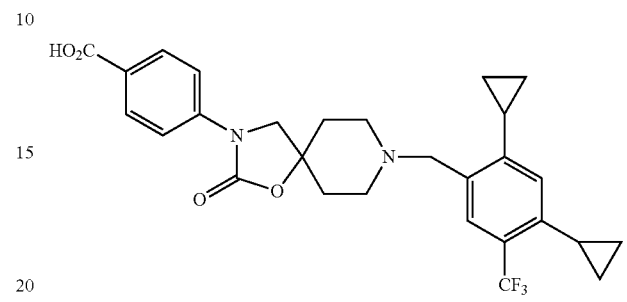

Using essentially the same procedure as Example 4-31, Steps 1-3, but starting with 2,4-dibromo-trifluoromethylbenzene in Step 1 and using cyclopropylboronic acid pinacol ester in Step 3, the title compound was obtained after reverse phase (C18) chromatography (acetonitrile/water with 0.1% ammonium hydroxide) and evaporation of the product fractions.

LCMS (m/e): 515 (M+1).

Example 4-61

4-{8-[(2-(Pyrazol-4-yl)-5-trifluoromethylphenyl)methyl]-2-oxo-1-oxa-3,8-diazaspiro[4.5]dec-3-yl}benzoic acid, formic acid salt

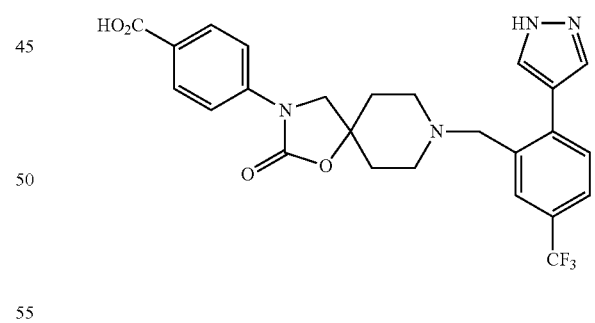

Using essentially the same procedure as Example 4-31, Step 3, but using (pyrazol-4-yl)boronic acid and methyl 4-{8-[(4-methyl-5-trifluoromethyl-2-bromophenyl)methyl]-2-oxo-1-oxa-3,8-diazaspiro[4.5]dec-3-yl}benzoate (prepared in Example 4-46, Step 2), the title compound was obtained after reverse phase (C18) chromatography (acetonitrile/water with 0.1% formic acid) and evaporation of the product fractions.

LCMS (m/e): 501 (M+1).

Example 4-62

4-{8-[(2-(4,5,6,7-Tetrahydropyrazolo[1,5-a]pyridin-3-yl)-5-trifluoromethylphenyl)methyl]-2-oxo-1-oxa-3,8-diazaspiro[4.5]dec-3-yl}benzoic acid, formic acid salt

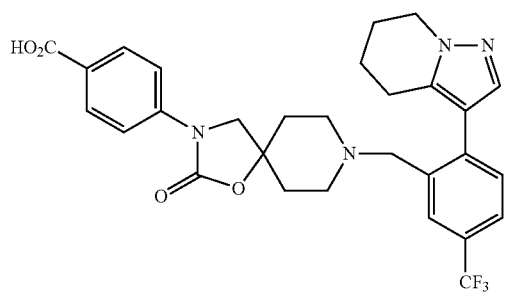 [SMILES: O=C(O)c1ccc(N2CC3(CCN(Cc4cc(C(F)(F)F)ccc4-c4cnn5c4CCCC5)CC3)OC2=O)cc1]

Using essentially the same procedure as Example 4-31, Step 3, but using (4,5,6,7-tetrahydropyrazolo[1,5-a]pyridin-3-yl)boronic acid and methyl 4-{8-[(4-methyl-5-trifluoromethyl-2-bromophenyl)methyl]-2-oxo-1-oxa-3,8-diazaspiro[4.5]dec-3-yl}benzoate (prepared in Example 4-46, Step 2), the title compound was obtained after reverse phase (C18) chromatography (acetonitrile/water with 0.1% formic acid) and evaporation of the product fractions.

LCMS (m/e): 555 (M+1).

Example 4-63

4-{8-[(2-(5,6-Dihydro-4H-pyrrolo[1,2-b]pyrazol-3-yl)-5-trifluoromethylphenyl)methyl]-2-oxo-1-oxa-3,8-diazaspiro[4.5]dec-3-yl}benzoic acid, formic acid salt

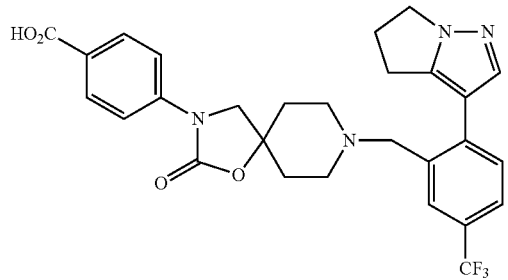 [SMILES: O=C(O)c1ccc(N2CC3(CCN(Cc4cc(C(F)(F)F)ccc4-c4cnn5c4CCC5)CC3)OC2=O)cc1]

Using essentially the same procedure as Example 4-31, Step 3, but using (5,6-dihydro-4H-pyrrolo[1,2-b]pyrazol-3-yl)boronic acid and methyl 4-{8-[(4-methyl-5-trifluoromethyl-2-bromophenyl)methyl]-2-oxo-1-oxa-3,8-diazaspiro[4.5]dec-3-yl}benzoate (prepared in Example 4-46, Step 2), the title compound was obtained after reverse phase (C18) chromatography (acetonitrile/water with 0.1% formic acid) and evaporation of the product fractions.

LCMS (m/e): 541 (M+1).

Example 4-64

4-{8-[(2-(1-(2-Methylpropyl)-1H-pyrazol-4-yl)-5-trifluoromethylphenyl)methyl]-2-oxo-1-oxa-3,8-diazaspiro[4.5]dec-3-yl}benzoic acid, formic acid salt

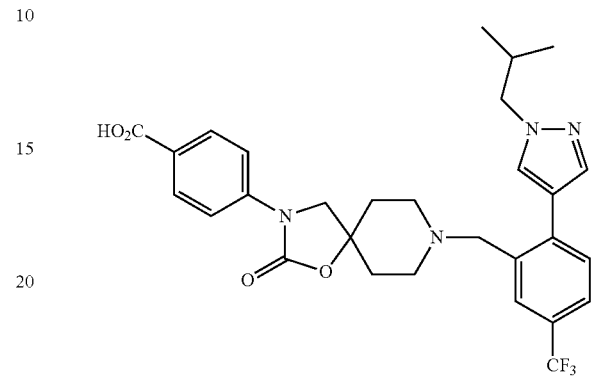

Using essentially the same procedure as Example 4-31, Step 3, but using [1-(2-methylpropyl)-1H-pyrazol-4-yl]boronic acid and methyl 4-{8-[(4-methyl-5-trifluoromethyl-2-bromophenyl)methyl]-2-oxo-1-oxa-3,8-diazaspiro[4.5]dec-3-yl}benzoate (prepared in Example 4-46, Step 2), the title compound was obtained after reverse phase (C18) chromatography (acetonitrile/water with 0.1% formic acid) and evaporation of the product fractions.

LCMS (m/e): 557 (M+1).

Example 4-65

4-{8-[(2-(1H-Indazol-4-yl)-5-trifluoromethylphenyl)methyl]-2-oxo-1-oxa-3,8-diazaspiro[4.5]dec-3-yl}benzoic acid, formic acid salt

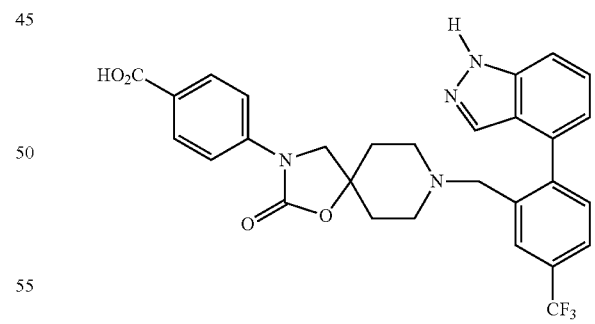

Using essentially the same procedure as Example 4-31, Step 3, but using (1H-indazol-4-yl)boronic acid and methyl 4-{8-[(4-methyl-5-trifluoromethyl-2-bromophenyl)methyl]-2-oxo-1-oxa-3,8-diazaspiro[4.5]dec-3-yl}benzoate (prepared in Example 4-46, Step 2), the title compound was obtained after reverse phase (C18) chromatography (acetonitrile/water with 0.1% formic acid) and evaporation of the product fractions.

LCMS (m/e): 551 (M+1).

Example 4-66

4-{8-[(2-(1H-Indazol-5-yl)-5-trifluoromethylphenyl)methyl]-2-oxo-1-oxa-3,8-diazaspiro[4.5]dec-3-yl}benzoic acid, formic acid salt

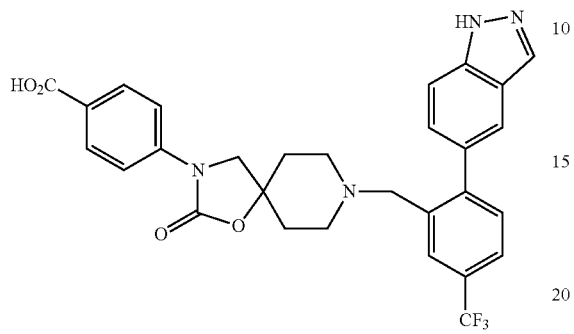

Using essentially the same procedure as Example 4-31, Step 3, but using (1H-indazol-5-yl)boronic acid and methyl 4-{8-[(4-methyl-5-trifluoromethyl-2-bromophenyl)methyl]-2-oxo-1-oxa-3,8-diazaspiro[4.5]dec-3-yl}benzoate (prepared in Example 4-46, Step 2), the title compound was obtained after reverse phase (C18) chromatography (acetonitrile/water with 0.1% formic acid) and evaporation of the product fractions.

LCMS (m/e): 551 (M+1).

Example 4-67

4-{8-[(2-(1-Propyl-1H-pyrazol-4-yl)-5-trifluoromethylphenyl)methyl]-2-oxo-1-oxa-3,8-diazaspiro[4.5]dec-3-yl}benzoic acid, formic acid salt

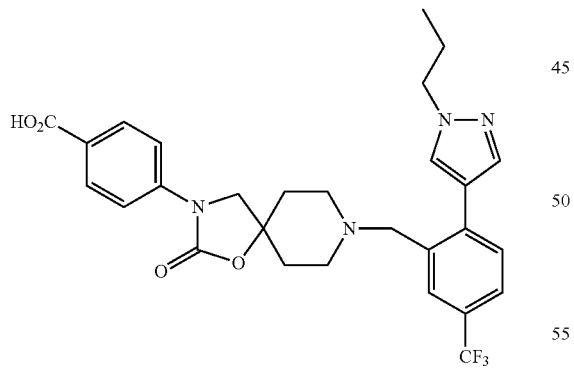

Using essentially the same procedure as Example 4-31, Step 3, but using (1-propyl-1H-pyrazol-4-yl)boronic acid and methyl 4-{8-[(4-methyl-5-trifluoromethyl-2-bromophenyl)methyl]-2-oxo-1-oxa-3,8-diazaspiro[4.5]dec-3-yl}benzoate (prepared in Example 4-46, Step 2), the title compound was obtained after reverse phase (C18) chromatography (acetonitrile/water with 0.1% formic acid) and evaporation of the product fractions.

LCMS (m/e): 543 (M+1).

Example 4-68

4-{8-[(2-(Thien-3-yl)-5-trifluoromethylphenyl)methyl]-2-oxo-1-oxa-3,8-diazaspiro[4.5]dec-3-yl}benzoic acid, formic acid salt

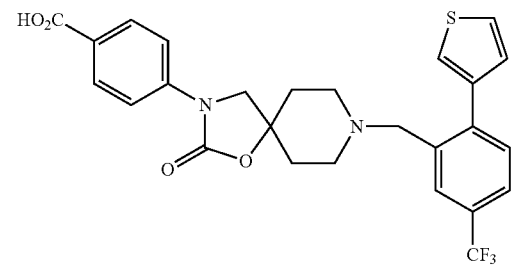

Using essentially the same procedure as Example 4-31, Step 3, but using (thien-3-yl)boronic acid and methyl 4-{8-[(4-methyl-5-trifluoromethyl-2-bromophenyl)methyl]-2-oxo-1-oxa-3,8-diazaspiro[4.5]dec-3-yl}benzoate (prepared in Example 4-46, Step 2), the title compound was obtained after reverse phase (C18) chromatography (acetonitrile/water with 0.1% formic acid) and evaporation of the product fractions.

LCMS (m/e): 517 (M+1).

Example 4-69

4-{8-[(2-(2-Dimethylaminopyridin-5-yl)-5-trifluoromethylphenyl)methyl]-2-oxo-1-oxa-3,8-diazaspiro[4.5]dec-3-yl}benzoic acid, formic acid salt

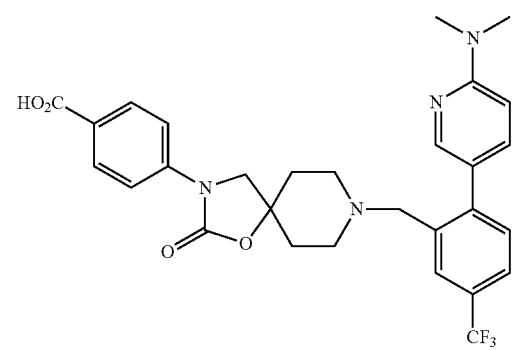 [SMILES: CN(C)c1ccc(-c2ccc(C(F)(F)F)cc2CN2CCC3(CC2)CN(c2ccc(C(=O)O)cc2)C(=O)O3)cn1]

Using essentially the same procedure as Example 4-31, Step 3, but using (2-dimethylaminopyridin-5-yl)boronic acid and methyl 4-{8-[(4-methyl-5-trifluoromethyl-2-bromophenyl)methyl]-2-oxo-1-oxa-3,8-diazaspiro[4.5]dec-3-yl}benzoate (prepared in Example 4-46, Step 2), the title compound was obtained after reverse phase (C18) chromatography (acetonitrile/water with 0.1% formic acid) and evaporation of the product fractions.

LCMS (m/e): 555 (M+1).

Example 4-70

4-{8-[(2-(2-Methoxypyridin-5-yl)-5-trifluoromethylphenyl)methyl]-2-oxo-1-oxa-3,8-diazaspiro[4.5]dec-3-yl}benzoic acid, formic acid salt

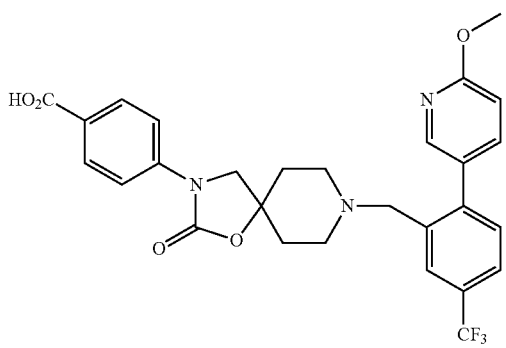 [SMILES: COc1ccc(-c2ccc(C(F)(F)F)cc2CN2CCC3(CC2)CN(c2ccc(C(=O)O)cc2)C(=O)O3)cn1]

Using essentially the same procedure as Example 4-31, Step 3, but using (2-methoxypyridin-5-yl)boronic acid and methyl 4-{8-[(4-methyl-5-trifluoromethyl-2-bromophenyl)methyl]-2-oxo-1-oxa-3,8-diazaspiro[4.5]dec-3-yl}benzoate (prepared in Example 4-46, Step 2), the title compound was obtained after reverse phase (C18) chromatography (acetonitrile/water with 0.1% formic acid) and evaporation of the product fractions.

LCMS (m/e): 542 (M+1).

Example 5-1

4-{2-Oxo-8-[(3,3,7-trimethyl-2,3-dihydro-1-benzofuran-5-yl)methyl]-1-oxa-3,8-diazaspiro[4.5]dec-3-yl}benzoic acid, TFA salt

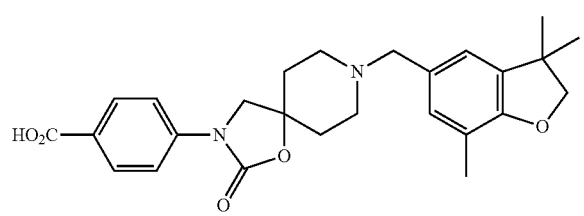 [SMILES: Cc1cc(CN2CCC3(CC2)CN(c2ccc(C(=O)O)cc2)C(=O)O3)cc2c1OCC2(C)C]

Step 1. Synthesis of 2,4-dibromo-6-methylphenyl 2-methylprop-2-en-1-yl ether

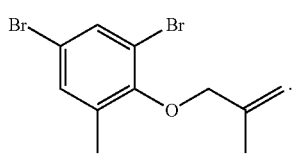

A solution of 2,4-dibromo-6-methylphenol (2.0 g, 7.5 mmol), 3-bromo-2-methylprop-1-ene (1.5 g, 11.3 mmol), $K_2CO_3$ (3.12 g, 22.6 mmol) in DMF (15 mL) was heated at 70° C. 2 hours. The reaction was then cooled to room temperature and was diluted with water and hexanes. The layers were separated and the organic layer was dried over sodium sulfate, filtered and concentrated. The residue was purified on a silica gel column eluting with a gradient of 0-10% EtOAc/hexanes to give the title intermediate (1.05 g) as colorless liquid.

$^1$H-NMR (CDCl$_3$): δ 7.55 (d, J=1.7 Hz, 1H), 7.28 (d, 1H), 5.18 (s, 1H), 5.03 (s, 1H), 4.30 (s, 2H), 2.32 (s, 3H), 1.94 (s, 3H).

Step 2. Synthesis of 5-bromo-3,3,7-trimethyl-2,3-dihydro-1-benzofuran

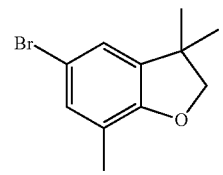

To a nitrogen flushed 100 mL round bottom flask were added 2,4-dibromo-6-methylphenyl 2-methylprop-2-en-1-yl ether (710 mg, 2.22 mmol), Pd(dppf)Cl$_2$ (36 mg, 0.044 mmol), Et$_4$NCl (490 mg, 2.66 mmol), KOAc (544 mg, 5.55 mmol), HCO$_2$Na (181 mg, 2.66 mmol), DMF (20 mL) and water (1 mL). The reaction mixture was heated at 75° C. overnight. After cooling to room temperature, it was diluted with water and extracted with EtOAc/hexanes (1:3). The organic layer was dried over sodium sulfate, filtered and concentrated. The residue was purified on a silica gel column eluting with a gradient of 100% hexanes to 10% EtOAc/hexanes to give the title intermediate (110 mg, 70% purity) as light yellow liquid.

$^1$H-NMR (CDCl$_3$): δ 7.08 (s, 1H), 7.04 (s, 1H), 4.25 (s, 2H), 2.20 (s, 3H), 1.34 (s, 6H).

Step 3. Synthesis of 3,3,7-trimethyl-2,3-dihydro-1-benzofuran-5-carbaldehyde

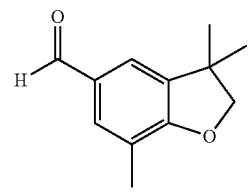

To a nitrogen flushed 50 mL round bottom flask were added 5-bromo-3,3,7-trimethyl-2,3-dihydro-1-benzofuran (0.11 g, 0.46 mmol) and THF (3 mL). A solution of n-BuLi (0.20 mL, 2.5 M solution in hexanes) was added via a syringe at −78° C. The reaction mixture was stirred at −78° C. for 10 minutes, then DMF (0.053 mL, 0.68 mmol) was added. The reaction mixture was allowed to warm to room temperature. EtOAc (20 mL) and wet silica gel (5 g silica gel/0.5 mL of water) were added. The resulting mixture was stirred at room temperature for 10 minutes and then filtered. The resulting solid was rinsed with EtOAc. The filtrate was concentrated. The residue was purified on a silica gel column eluting with a gradient of 100% hexanes to 10% EtOAc/hexanes to give the title intermediate (40 mg) as colorless solid.

¹H-NMR (CDCl₃): δ 9.84 (s, 1H), 7.54 (s, 1H), 7.53 (s, 1H), 4.38 (s, 2H), 2.29 (s, 3H), 1.39 (s, 6H).

Step 4. Synthesis of 4-(2-oxo-1-oxa-3,8-diazaspiro[4.5]dec-3-yl)benzoic acid, HCl salt

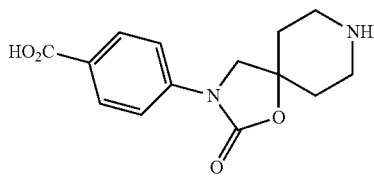 [SMILES: O=C(O)c1ccc(N2CC3(CCNCC3)OC2=O)cc1]

To a 500 mL round bottom flask were added methyl 4-(2-oxo-1-oxa-3,8-diazaspiro[4.5]dec-3-yl)benzoate hydrochloride (20.5 g, 62.7 mmol), LiOH.H₂O (6.6 g, 157 mmol), water (15 mL) and methanol (150 mL). The reaction mixture was heated at 55° C. and the progress was carefully monitored by LC-MS. After heating at 55° C. for 4 hours, LC-MS indicated complete conversion. After cooling to ambient temperature, the pH of the mixture was carefully adjusted to ~5 with addition of 1N HCl. This caused heavy precipitation. The resulting suspension was cooled in an ice bath and filtered. The solid was washed with water and MeOH, air dried and then under high vacuum over the weekend to give the title intermediate (17.2 g) as white solid.

¹H-NMR (CD₃OD): δ 8.05 (d, J=8.7 Hz, 2H), 7.70 (d, J=8.8 Hz, 2H), 4.04 (s, 2H), 3.4 (m, 4H), 2.3 (m, 2H), 2.2 (s, 2H).

LCMS (m/e): (m/e), 277 (M+1).

Step 5. Synthesis of 4-{8-[(3,3,7-trimethyl-2,3-dihydro-1-benzofuran-5-yl)methyl]-1-oxa-2-oxo-3,8-diazaspiro[4.5]dec-3-yl}benzoic acid, TFA salt

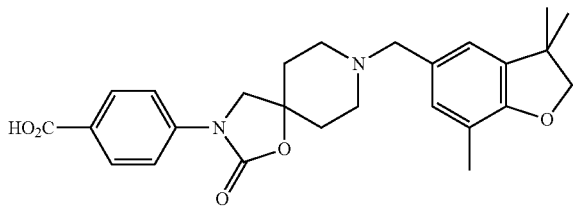 [SMILES: Cc1cc(CN2CCC3(CC2)CN(c2ccc(C(=O)O)cc2)C(=O)O3)cc2c1OCC2(C)C]

To a vial was added 4-(2-oxo-1-oxa-3,8-diazaspiro[4.5]dec-3-yl)benzoic acid (70 mg, 0.25 mmol), 3,3,7-trimethyl-2,3-dihydro-1-benzofuran-5-carbaldehyde (40 mg, 0.21 mmol), sodium triacetoxyborohydride (178 mg, 0.84 mmol), AcOH (0.072 mL, 1.26 mmol) and DMSO (2 mL). The reaction mixture was stirred at 50° C. overnight. It was diluted with DMSO and water, acidified with TFA and purified by HPLC eluted with an acetonitrile/water (0.1% TFA) gradient. The desired fractions were concentrated to give the title compound as white solid.

¹H-NMR (CD₃OD): δ 8.04 (d, J=8.9 Hz, 2H), 7.69 (d, J=8.9 Hz, 2H), 7.12 (s, 1H), 7.10 (s, 1H), 4.29 (s, 2H), 4.23 (s, 2H), 4.02 (s, 2H), 3.4 (m, 4H), 2.3 (m, 2H), 2.21 (s, 3H), 2.2 (m, 2H), 1.35 (s, 6H).

LCMS (m/e): 451 (M+1).

Example 5-2

4-{8-[(4-Ethoxy-8-methoxynaphthalen-2-yl)methyl]-2-oxo-1-oxa-3,8-diazaspiro[4.5]dec-3-yl}benzoic acid, TFA salt

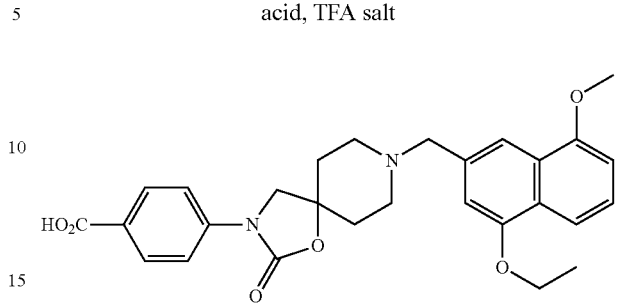

Step 1. Synthesis of ethyl 8-methoxy-4-hydroxynaphthalene-2-carboxylate

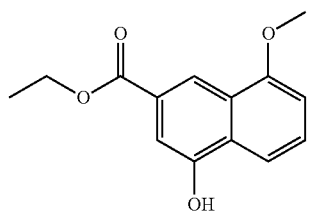 [SMILES: CCOC(=O)c1cc(O)c2cccc(OC)c2c1]

To a 250 mL round bottom flask were added 2-methoxybenzaldehyde (2.0 g, 14.7 mmol), diethyl butanedioate (6.4 g, 36.7 mmol) and t-BuOH (35 mL). KO-t-Bu (3.3 g, 29.4 mmol) was added in portions. The reaction mixture was stirred at room temperature for 2 hours and then diluted with 0.5 N HCl (120 mL) and extracted with EtOAc. The organic layer was back extracted with 5% KOH (60 mL). Aqueous layer was acidified with 1N HCl and extracted with EtOAc. Organic layer was washed with brine, dried over sodium sulfate, filtered and concentrated. The crude product was treated with Ac₂O (9.7 mL, 103 mmol) and NaOAc (2.05 g, 25 mmol) at 120° C. under nitrogen overnight. The reaction mixture was cooled with an ice bath and diluted with 150 mL of water. The aqueous solution was carefully removed by slow decantation. The remaining residue was dissolved in EtOAc (30 mL), dried over sodium sulfate, filtered and concentrated. The crude product was purified on a silica gel column eluting with a gradient of 100% hexanes to 25% EtOAc/hexanes to give the title intermediate (0.52 g) as a light yellow solid.

¹H-NMR (CDCl₃): δ 8.96 (s, 1H), 7.87 (d, J=0.6 Hz, 1H), 7.56 (t, J=8.1 Hz, 1H), 7.46 (d, J=8.5 Hz, 1H), 6.93 (d, J=8.7 Hz, 1H), 4.47 (q, J=7.1 Hz, 2H), 4.06 (s, 3H), 1.47 (t, J=7.1 Hz, 3H).

Step 2. Synthesis of ethyl 4-ethoxy-8-methoxynaphthalene-2-carboxylate

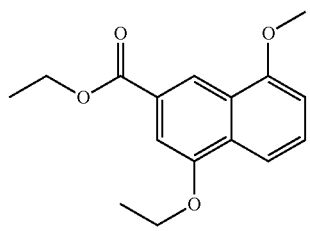 [SMILES: CCOC(=O)c1cc(OCC)c2cccc(OC)c2c1]

To a 25 mL round bottom flask were added ethyl 8-methoxy-4-hydroxynaphthalene-2-carboxylate (0.25 g, 1.02 mmol), Cs$_2$CO$_3$ (0.33 g, 1.02 mmol), iodoethane (0.79 g, 5.1 mmol) and DMF (4 mL). The resulting reaction mixture was stirred at 70° C. overnight. After cooling to room temperature, the reaction was diluted with EtOAc (30 mL), washed with water and brine. The organic layer was dried over Na$_2$SO$_4$, filtered and concentrated. The crude product was purified on a silica gel column eluting with a gradient of 10-20% EtOAc/hexanes to give the title intermediate (0.19 g) as a light yellow solid.

$^1$H-NMR (CDCl$_3$): δ 8.63 (s, 1H), 7.90 (d, J=8.6 Hz, 1H), 7.51 (t, J=8.1 Hz, 1H), 7.45 (d, J=1 Hz, 1H), 6.92 (d, J=7.6 Hz, 1H), 4.47 (q, J=7.1 Hz, 2H), 4.30 (q, J=7.0 Hz, 2H), 4.05 (s, 3H), 1.59 (t, J=7.0 Hz, 3H), 1.48 (t, J=7.1 Hz, 3H).

Step 3. Synthesis of (4-ethoxy-8-methoxynaphthalen-2-yl)methanol

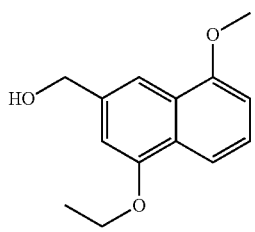 [SMILES: CCOc1cc(CO)cc2c(OC)cccc12]

To a nitrogen flushed 100 mL round bottom flask were added ethyl 4-ethoxy-8-methoxynaphthalene-2-carboxylate (0.19 g, 0.69 mmol) and dry ether (10 mL). DIBAL (1.7 mL, 1 M in toluene) was added. The reaction mixture was stirred at room temperature for 5 minutes and was then diluted with EtOAc (20 mL). Wet silica gel (10 g silica gel/0.5 mL water) was added. The resulting mixture was stirred for 10 minutes and then filtered and the filtrate was concentrated. The crude product was purified on a silica gel column eluting with a gradient of 100% hexanes to 40% EtOAc/hexanes to give the title intermediate (136 mg) as a white solid.

$^1$H-NMR (CDCl$_3$): δ 7.88 (d, J=8.4 Hz, 1H), 7.79 (s, 1H), 7.39 (t, J=8.0 Hz, 1H), 6.89 (s, 1H), 6.88 (d, J=7.8 Hz, 1H), 4.82 (s, 2H), 4.23 (q, J=7.0 Hz, 2H), 4.01 (s, 3H), 1.57 (t, J=7.0 Hz, 3H).

Step 4. Synthesis of 3-(chloromethyl)-1-ethoxy-5-methoxynaphthalene

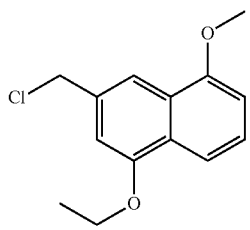 [SMILES: CCOc1cc(CCl)cc2c(OC)cccc12]

To a solution of ethyl (4-ethoxy-8-methoxynaphthalen-2-yl)methanol (0.136 g, 0.59 mmol) and TEA (0.25 mL, 1.76 mmol) in dry CH$_2$Cl$_2$ (6 mL) was added MsCl (0.068 mL, 0.88 mmol). The resulting reaction mixture was stirred at room temperature overnight and was then diluted with CH$_2$Cl$_2$ (25 mL) and washed with brine. The organic layer was dried over Na$_2$SO$_4$, filtered and concentrated. The residue was purified on a silica gel column eluting with a gradient of 100% hexanes to 10% EtOAc/hexanes to give the title intermediate (23 mg) as a white solid.

$^1$H-NMR (CDCl$_3$): δ 7.86 (d, J=8.5 Hz, 1H), 7.83 (s, 1H), 7.40 (t, J=8.1 Hz, 1H), 6.89 (m, 2H), 4.76 (s, 2H), 4.25 (q, J=7.0 Hz, 2H), 4.01 (s, 3H), 1.57 (t, J=7.0 Hz, 3H).

Step 5. Synthesis of 4-{8-[(4-ethoxy-8-methoxynaphthalen-2-yl)methyl]-2-oxo-1-oxa-3,8-diazaspiro[4.5]dec-3-yl}benzoic acid, TFA salt

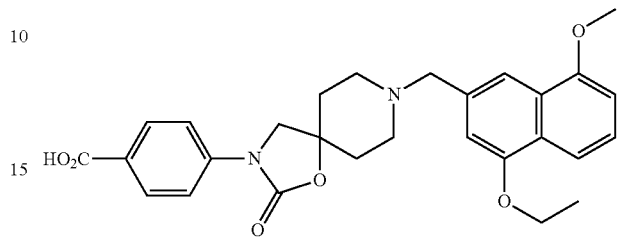

The title compound was prepared and purified using essentially the same experimental procedure as in Example 2-9, and was isolated and was isolated as a TFA salt.

LCMS (m/e): 491 (M+1).

Example 5-3

4-{8-[(4,8-Diethoxynaphthalen-2-yl)methyl]-2-oxo-1-oxa-3,8-diazaspiro[4.5]dec-3-yl}benzoic acid, TFA salt

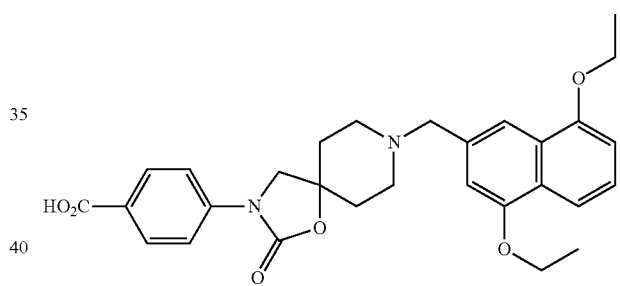

The title compound was prepared and purified using essentially the same experimental procedures in Example 5-1 and was isolated as a TFA salt.

LCMS (m/e): 505 (M+1).

Example 5-4

4-{8-[(4,8-Diethoxy-2-methylquinolin-6-yl)methyl]-2-oxo-1-oxa-3,8-diazaspiro[4.5]dec-3-yl}benzoic acid, TFA salt

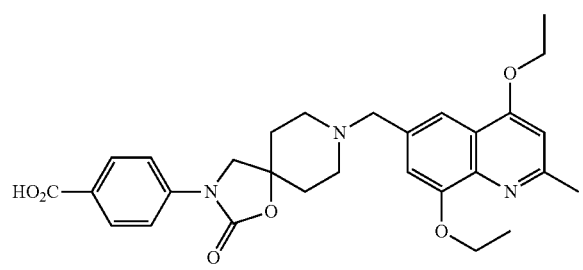 [SMILES: CCOc1cc(C)nc2c(OCC)cc(CN3CCC4(CC3)CN(c3ccc(C(=O)O)cc3)C(=O)O4)cc12]

Step 1. Synthesis of ethyl 4-(acetylamino)-3-ethoxybenzoate

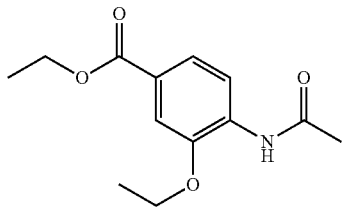 [SMILES: CCOC(=O)c1ccc(NC(C)=O)c(OCC)c1]

To a 100 mL round bottom flask were added ethyl 4-amino-3-ethoxybenzoate (1.3 g, 6.2 mmol), TEA (2.6 mL, 18.6 mmol), N,N-dimethylpyridin-4-amine (catalytic), acetic anhydride (0.88 mL, 9.3 mmol) and EtOAc (20 mL). The reaction mixture was stirred at ambient temperature for 3 hours and was then diluted with EtOAc (20 mL) and washed with 5% KOH (50 mL). The organic layer was dried over $Na_2SO_4$, filtered and concentrated. The crude product was purified on a silica gel column eluting with a gradient of EtOAc/hexanes to give the title intermediate (1.1 g) as a pale yellow solid.

$^1$H-NMR (CDCl$_3$): δ 8.49 (d, J=8.2 Hz, 1H), 7.95 (b, 1H), 7.70 (dd, J=8.6 Hz, 1.6 Hz, 1H), 7.56 (d, J=1.7 Hz), 4.39 (q, J=7.1 Hz, 2H), 4.22 (q, J=7.0 Hz, 2H), 2.27 (s, 3H), 1.52 (t, J=7.0 Hz, 3H), 1.42 (t, J=7.1 Hz, 3H).

Step 2. Synthesis of ethyl 4,8-diethoxy-2-methylquinoline-6-carboxylate

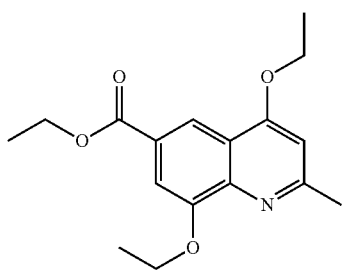 [SMILES: CCOC(=O)c1cc(OCC)c2nc(C)cc(OCC)c2c1]

To a nitrogen flushed vial were added ethyl 4-(acetylamino)-3-ethoxybenzoate (100 mg, 0.40 mmol), 2-chloropyridine (90 mg, 0.80 mmol) and $CH_2Cl_2$ (2 mL). Triflic anhydride (0.40 mmol) was added via a syringe at −78° C. The reaction mixture was stirred at −78° C. for 5 minutes. Ethyl ethynyl ether (0.174 mL, 40% in hexanes, 0.80 mmol) was added. The resulting reaction mixture was allowed to warm to room temperature and was stirred at room temperature for 1 hour. The reaction was quenched by addition of $Na_2CO_3$ (5 mL, sat'd.), water (20 mL) and EtOAc (20 mL). The layers were separated and the organic layer was dried over $Na_2SO_4$, filtered and concentrated. The crude product was purified on a silica gel column eluting with a gradient of 10-20% EtOAc/hexanes to give the title intermediate (10 mg) as a light brown sticky material.

$^1$H-NMR (CDCl$_3$): δ 8.52 (s, 1H), 7.87 (s, 1H), 6.93 (s, 1H), 4.5 (m, 6H), 3.26 (s, 3H), 1.7 (m, 6H), 1.49 (t, J=7.1 Hz, 3H).

Step 3. Synthesis of 4,8-diethoxy-2-methylquinoline-6-carbaldehyde

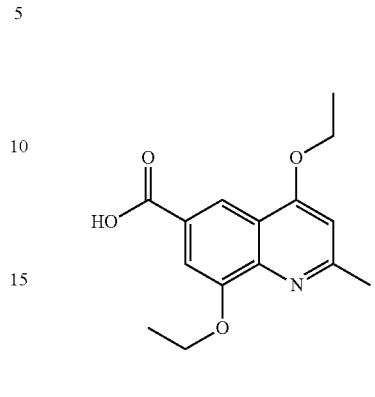

To a solution of ethyl 4,8-diethoxy-2-methylquinoline-6-carboxylate (60 mg, 0.20 mmol) in THF (2 mL) was added DIBAL (0.79 mL, 1M in toluene) at −78° C. The reaction mixture was allowed to warm up to room temperature and was stirred for 10 additional minutes before it was diluted with EtOAc (20 mL) and 5% KOH (20 mL). The layers were separated and the organic layer was washed with brine, dried over $Na_2SO_4$, filtered and concentrated. The residue was redissolved in DCM (3 mL) and Dess-Martin periodinane (110 mg, 0.26 mmol) was added. The reaction mixture was stirred at room temperature for 30 minutes and was then diluted with EtOAc and washed with 10% KOH. The organic layer was dried over $Na_2SO_4$, filtered and concentrated. The crude product was purified on a silica gel column eluting with a gradient of 20-35% EtOAc/hexanes (with 1% TEA) to give the title intermediate (20 mg).

$^1$H-NMR (CDCl$_3$): δ 10.1 (s, 1H), 8.28 (d, J=1.6 Hz, 1H), 7.51 (d, J=1.4 Hz, 1H), 6.77 (s, 1H), 4.41 (q, J=7.0 Hz, 2H), 4.33 (q, J=7.1 Hz, 2H), 2.83 (s, 3H), 1.6 (m, 6H).

Step 4. Synthesis of 4-{8-[(4,8-diethoxy-2-methylquinolin-6-yl)methyl]-2-oxo-1-oxa-3,8-diazaspiro[4.5]dec-3-yl}benzoic acid, TFA salt

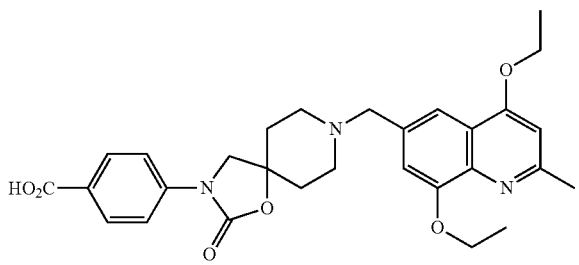 [SMILES: CCOc1cc(C)nc2c(OCC)cc(CN3CCC4(CC3)CN(c3ccc(C(=O)O)cc3)C(=O)O4)cc12]

The title compound was prepared and purified using essentially the same experimental procedures in Example 5-1 and was isolated as a TFA salt.

LCMS (m/e): 520 (M+1).

Example 5-5

4-{8-[(6-Chloro-4-ethoxy-8-methoxynaphthalen-2-yl)methyl]-2-oxo-1-oxa-3,8-diazaspiro[4.5]dec-3-yl}benzoic acid, TFA salt

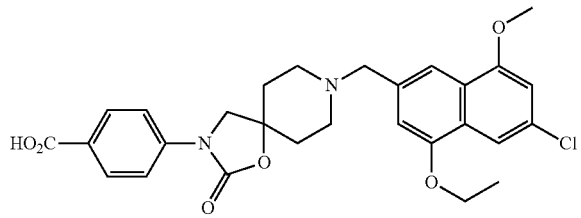 [SMILES: CCOc1cc(CN2CCC3(CC2)CN(c2ccc(C(=O)O)cc2)C(=O)O3)cc2c(OC)cc(Cl)cc12]

The title compound was prepared and purified using essentially the same experimental procedures in Example 5-1 and was isolated as a TFA salt.

LCMS (m/e): 525 (M+1).

Example 5-6

4-{8-[(4,8-Dimethoxynaphthalen-2-yl)methyl]-2-oxo-1-oxa-3,8-diazaspiro[4.5]dec-3-yl}benzoic acid, TFA salt

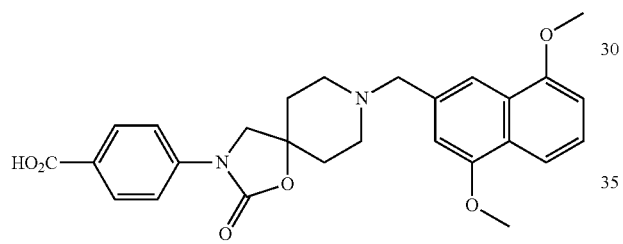

The title compound was prepared and purified using essentially the same experimental procedures in Example 5-1 and was isolated as a TFA salt.

LCMS (m/e): 477 (M+1).

Example 5-7

4-{8-[(5-Chloro-4-ethoxy-8-methoxynaphthalen-2-yl)methyl]-2-oxo-1-oxa-3,8-diazaspiro[4.5]dec-3-yl}benzoic acid, TFA salt

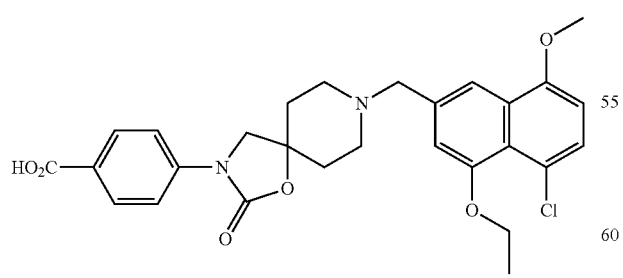

The title compound was prepared and purified using essentially the same experimental procedures in Example 5-1 and was isolated as a TFA salt.

LCMS (m/e): 525 (M+1).

Example 5-8

4-(8-{[5-Ethoxy-3-(trifluoromethyl)isoquinolin-7-yl]methyl}-2-oxo-1-oxa-3,8-diazaspiro[4.5]dec-3-yl)benzoic acid, TFA salt

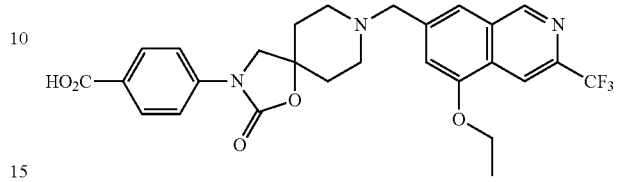

The title compound was prepared and purified using essentially the same experimental procedures in Example 5-1 and was isolated as a TFA salt.

LCMS (m/e): 530 (M+1).

Example 5-9

4-(8-{[8-Ethoxy-2-(trifluoromethyl)quinolin-6-yl]methyl}-2-oxo-1-oxa-3,8-diazaspiro[4.5]dec-3-yl)benzoic acid, TFA salt

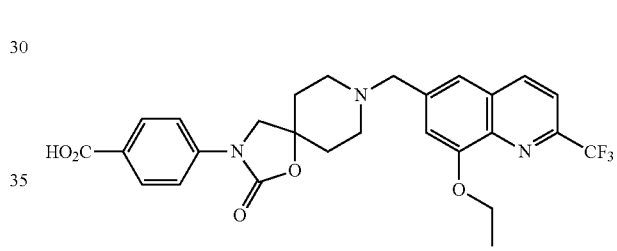

The title compound was prepared and purified using essentially the same experimental procedures in Example 5-1 and was isolated as a TFA salt.

LCMS (m/e): 530 (M+1).

Example 5-10

4-{8-[(4,4-Dimethyl-3,4-dihydro-2H-chromen-6-yl)methyl]-2-oxo-1-oxa-3,8-diazaspiro[4.5]dec-3-yl}benzoic acid, TFA salt

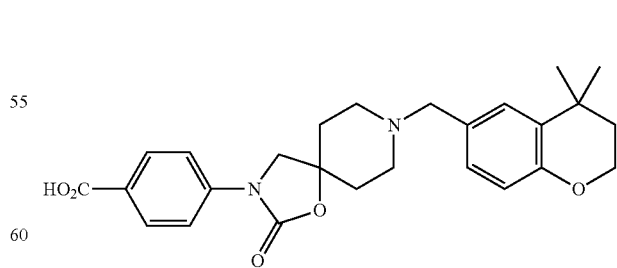

The title compound was prepared and purified using essentially the same experimental procedures in Example 5-1 and was isolated as a TFA salt.

LCMS (m/e): 451 (M+1).

Example 5-11

4-{2-Oxo-8-[(2,2,4,4-tetramethyl-3,4-dihydro-2H-chromen-6-yl)methyl]-1-oxa-3,8-diazaspiro[4.5]dec-3-yl}benzoic acid, TFA salt

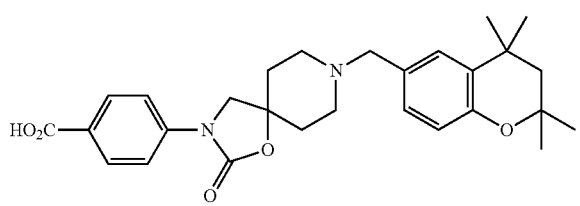 [SMILES: CC1(C)CC(C)(C)c2cc(CN3CCC4(CC3)CN(c3ccc(C(=O)O)cc3)C(=O)O4)ccc2O1]

The title compound was prepared and purified using essentially the same experimental procedures in Example 5-1 and was isolated as a TFA salt.

LCMS (m/e): 479 (M+1).

Example 5-12

4-{2-Oxo-8-[(2,2-dimethyl-3,4-dihydro-2H-chromen-6-yl)methyl]-1-oxa-3,8-diazaspiro[4.5]dec-3-yl}benzoic acid, TFA salt

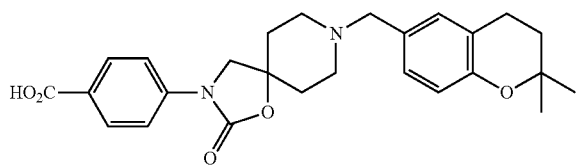 [SMILES: CC1(C)CCc2cc(CN3CCC4(CC3)CN(c3ccc(C(=O)O)cc3)C(=O)O4)ccc2O1]

Step 1. Synthesis of 6-bromo-2,2-dimethyl-3,4-dihydro-2H-chromene

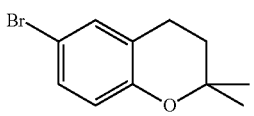

To a 100 mL round bottom flask were added 4-bromophenyl 3-methylbut-2-en-1-yl ether (1.0 g, 4.15 mmol) and $CH_2Cl_2$ (15 mL). The solution was cooled to −78° C. and TfOH (0.37 mL, 4.15 mmol) was added. The reaction mixture was allowed to warm to room temperature and was stirred for 10 minutes when it was diluted with $CH_2Cl_2$ (30 mL) and washed with 5% KOH (40 mL). The organic layer was dried over sodium sulfate, filtered and concentrated. The crude product was purified on a silica gel column eluting with a gradient of 100% hexanes to 10% EtOAc/hexanes to give the title intermediate (0.65 g).

$^1$H-NMR (CDCl$_3$): δ 7.21 (s, 1H), 7.19 (m, 1H), 6.69 (d, J=8.5 Hz, 1H), 2.78 (t, J=6.7 Hz, 2H), 1.81 (t, J=6.8 Hz, 2H), 1.35 (s, 6H).

Step 2. Synthesis of 2,2-dimethyl-3,4-dihydro-2H-chromene-6-carbaldehyde

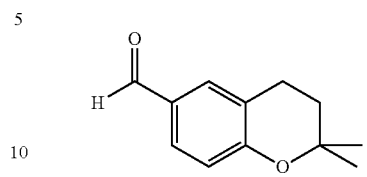

To a nitrogen flushed 100 mL round bottom flask were added 6-bromo-2,2-dimethyl-3,4-dihydro-2H-chromene (0.41 g, 1.7 mmol) and THF (6 mL). A solution of n-BuLi in hexanes (0.69 mL, 2.6 M, 1.79 mmol) was added at −78° C. The resulting reaction mixture was stirred at −78° C. for 10 minutes when DMF (0.20 mL, 2.55 mmol) was added. The reaction mixture was allowed to warm to room temperature and was diluted with EtOAc (25 mL). It was stirred over wet silica gel (10 g silica gel/0.5 mL water) for 10 minutes and was filtered. The solid was rinsed with EtOAc and the filtrate was concentrated. The residue was purified on a silica gel column eluting with a gradient of 100% hexanes to 20% EtOAc/hexanes to give the title intermediate (0.25 g) as a light yellow oil.

$^1$H-NMR (CDCl$_3$): δ 9.85 (s, 1H), 7.65 (s, 1H), 7.64 (d, 1H), 6.90 (d, J=8.9 Hz, 1H), 2.87 (t, 6.7 Hz, 2H), 1.87 (t, J=6.7 Hz, 2H), 1.39 (s, 614).

Step 3. Synthesis of 4-{2-oxo-8-[(2,2-dimethyl-3,4-dihydro-2H-chromen-6-yl)methyl]-1-oxa-3,8-diazaspiro[4.5]dec-3-yl}benzoic acid, TFA salt

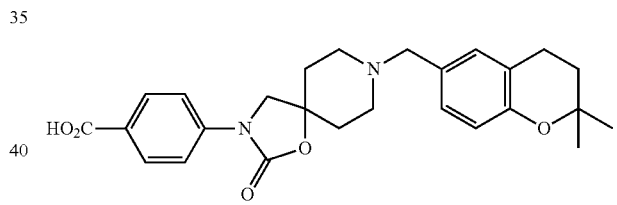

The title compound was prepared and purified using essentially the same experimental procedures in Example 5-1 and was isolated as a TFA salt.

LCMS (m/e): 451 (M+1).

Example 5-13

4-{2-Oxo-8-[(4,4,8-trimethyl-3,4-dihydro-2H-chromen-6-yl)methyl]-1-oxa-3,8-diazaspiro[4.5]dec-3-yl}benzoic acid, TFA salt

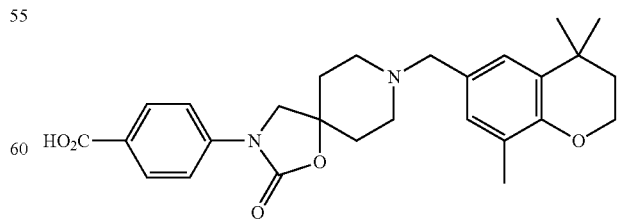

The title compound was prepared and purified using essentially the same experimental procedures in Example 5-1 and was isolated as a TFA salt.

LCMS (m/e): 465 (M+1).

Example 5-14

4-{8-[(8-Fluoro-4,4-dimethyl-3,4-dihydro-2H-chromen-6-yl)methyl]-2-oxo-1-oxa-3,8-diazaspiro[4.5]dec-3-yl}benzoic acid, TFA salt

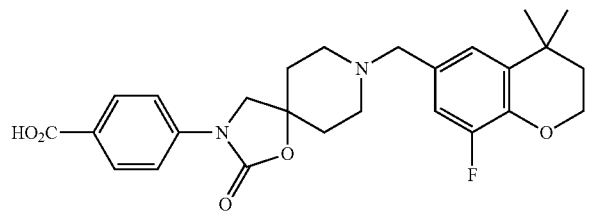

The title compound was prepared and purified using essentially the same experimental procedures in Example 5-1 and was isolated as a TFA salt.
LCMS (m/e): 469 (M+1).

Example 5-15

4-{8-[(8-Chloro-4,4-dimethyl-3,4-dihydro-2H-chromen-6-yl)methyl]-2-oxo-1-oxa-3,8-diazaspiro[4.5]dec-3-yl}benzoic acid, TFA salt

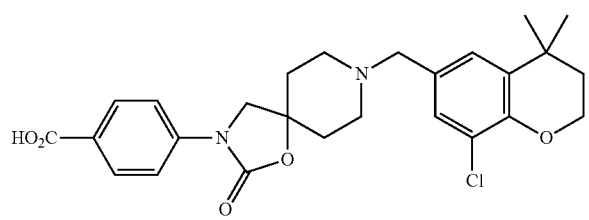 [SMILES: CC1(C)CCOc2c(Cl)cc(CN3CCC4(CC3)CN(c3ccc(C(=O)O)cc3)C(=O)O4)cc21]

The title compound was prepared and purified using essentially the same experimental procedures in Example 5-1 and was isolated as a TFA salt.
LCMS (m/e): 485 (M+1).

Example 5-16

4-{8-[(4,8-Dimethyl-3,4-dihydro-2H-chromen-6-yl)methyl]-2-oxo-1-oxa-3,8-diazaspiro[4.5]dec-3-yl}benzoic acid, TFA salt

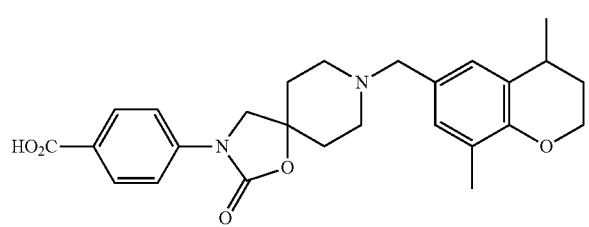 [SMILES: Cc1cc(CN2CCC3(CC2)CN(c2ccc(C(=O)O)cc2)C(=O)O3)cc2c1OCCC2C]

The title compound was prepared and purified using essentially the same experimental procedures in Example 5-1 and was isolated as a TFA salt.
LCMS (m/e): 451 (M+1).

Example 5-17

4-{8-[(1,3-Benzodioxol-5-yl)methyl]-2-oxo-1-oxa-3,8-diazaspiro[4.5]dec-3-yl}benzoic acid, TFA salt

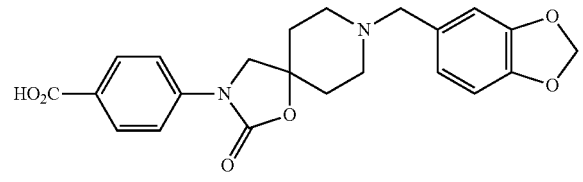 [SMILES: O=C(O)c1ccc(N2CC3(CCN(Cc4ccc5c(c4)OCO5)CC3)OC2=O)cc1]

The title compound was prepared and purified using essentially the same experimental procedures in Example 5-1 and was isolated as a TFA salt.
LCMS (m/e): 411 (M+1).

Example 5-18

4-{8-[(2,2-Dimethyl-2,3-dihydro-1-benzofuran-5-yl)methyl]-2-oxo-1-oxa-3,8-diazaspiro[4.5]dec-3-yl}benzoic acid, TFA salt

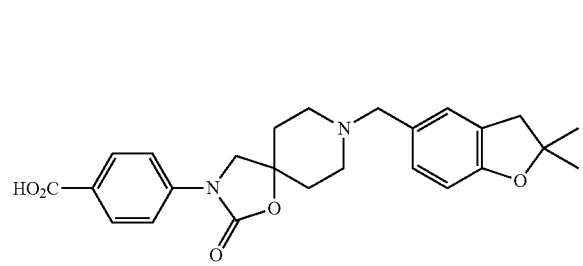 [SMILES: CC1(C)Cc2cc(CN3CCC4(CC3)CN(c3ccc(C(=O)O)cc3)C(=O)O4)ccc2O1]

The title compound was prepared and purified using essentially the same experimental procedures in Example 5-1 and was isolated as a TFA salt.
LCMS (m/e): 437 (M+1).

Example 5-19

4-(8-{[4,4-Dimethyl-8-(propan-2-yl)-3,4-dihydro-2H-chromen-6-yl]methyl}-2-oxo-1-oxa-3,8-diazaspiro[4.5]dec-3-yl)benzoic acid, TFA salt

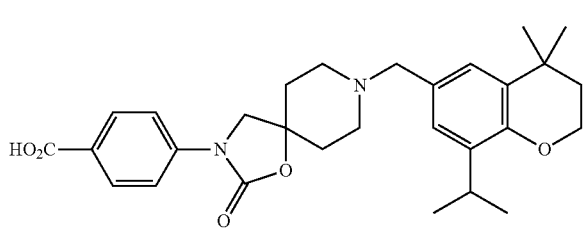 [SMILES: CC(C)c1cc(CN2CCC3(CC2)CN(c2ccc(C(=O)O)cc2)C(=O)O3)cc2c1OCCC2(C)C]

Step 1. Synthesis of 4-bromo-1-[(3-methylbut-3-en-1-yl)oxy]-2-(propan-2-yl)benzene

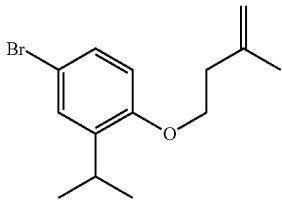 [SMILES: C=C(C)CCOc1ccc(Br)cc1C(C)C]

4-Bromo-2-isopropylphenol (897 mg, 4.17 mmol) was dissolved in DMF (4.17 mL) and 4-bromo-2-methylbut-1-ene (1.24 g, 8.34 mmol) was added followed by $K_2CO_3$ (1.15 g, 8.34 mmol). The reaction mixture was heated to 60° C. overnight, cooled to room temperature, and diluted with Hexanes: EtOAc (1:1). Water was added and the organic layer was separated, dried over $Na_2SO_4$, filtered, and concentrated under vacuum. The crude residue was purified by silica gel chromatography, eluting with 0-15% EtOAc/Hexanes to give the title compound as a colorless oil.

$^1$H-NMR (CDCl$_3$, 500 MHz): δ 7.30 (d, J=2.0 Hz, 1H), 7.25 (dd, J=9.0 Hz, 2.5 Hz, 1H), 6.73 (d, J=8.5 Hz, 1H), 4.87 (s, 1H), 4.83 (s, 1H), 4.07 (t, J=7.0 Hz, 2H), 3.30 (septet, J=7.0 Hz, 1H), 2.54 (t, J=7.0 Hz, 2H), 1.83 (s, 3H), 1.21 (d, J=7.0 Hz, 6H).

Step 2. Synthesis of 6-bromo-4,4-dimethyl-8-(propan-2-yl)-3,4-dihydro-2H-chromene

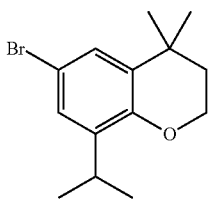 [SMILES: CC(C)c1cc(Br)cc2c1OCCC2(C)C]

4-Bromo-1-[(3-methylbut-3-en-1-yl)oxy]-2-(propan-2-yl)benzene (293 mg, 1.03 mmol) dissolved in dichloromethane (3.10 mL) was cooled to 0° C. and aluminum chloride (138 mg, 1.03 mmol) in dichloromethane (3.0 mL) was added via a syringe. The reaction mixture was stirred at 0° C. for 30 minutes. It was then poured into an Erlenmeyer flask containing a 10% aqueous NaOH solution and ice. The mixture was extracted with dichloromethane (2×), and the combined organic layers were dried over $Na_2SO_4$, filtered, and concentrated under vacuum. The crude residue was purified by silica gel chromatography, eluting with 0-10% EtOAc/Hexanes to give the title compound as a colorless oil.

$^1$H-NMR (CDCl$_3$, 500 MHz): δ 7.23 (d, J=2.5 Hz, 1H), 7.12 (d, J=2.4 Hz, 1H), 4.20 (t, J=5.3 Hz, 2H), 3.25 (septet, J=7.0 Hz, 1H), 1.83 (t, J=5.4 Hz, 2H), 1.34 (s, 6H), 1.20 (d, J=6.9 Hz, 6H).

Step 3. Synthesis of 4,4-dimethyl-8-(propan-2-yl)-3,4-dihydro-2H-chromene-6-carbaldehyde 6-Bromo-4,4-dimethyl-8-(propan-2-yl)-3,4-dihydro-2H-chromene (154 mg, 0.54 mmol) in tetrahydrofuran (5.44 mL) was cooled to −78° C. and n-BuLi (261 μL, 0.65 mmol) was added dropwise via a syringe. The reaction mixture was stirred at −78° C. for 30 minutes, and then DMF (168 μL, 2.17 mmol) was added dropwise. The resulting mixture was allowed to warm to room temperature, and stirred for 30 minutes before water was added. It was then extracted with EtOAc (2×) and the combined organic layers were dried over $Na_2SO_4$, filtered, and concentrated under vacuum. The crude residue was purified by silica gel chromatography eluting with 0-10% EtOAc/Hexanes to obtain the desired product as a colorless oil.

$^1$H-NMR (CDCl$_3$, 400 MHz): δ 9.81 (s, 1H), 7.66 (d, J=1.9 Hz, 1H), 7.54 (d, J=1.8 Hz, 1H), 4.28 (t, J=5.4 Hz, 2H), 3.25 (septet, J=6.9 Hz, 1H), 1.84 (t, J=5.5 Hz, 2H), 1.36 (s, 6H), 1.20 (d, J=6.9 Hz, 6H).

Step 4. Synthesis of 4-(8-{[4,4-dimethyl-8-(propan-2-yl)-3,4-dihydro-2H-chromen-6-yl]methyl}-2-oxo-1-oxa-3,8-diazaspiro[4.5]dec-3-yl)benzoic acid, TFA salt

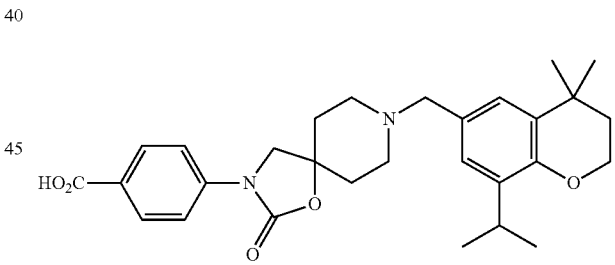

4-(2-Oxo-1-oxa-3,8-diazaspiro[4.5]dec-3-yl)benzoic acid hydrochloride (10.0 mg, 0.03 mmol, Example 5-1, Step 4) and 4,4-dimethyl-8-(propan-2-yl)-3,4-dihydro-2H-chromene-6-carbaldehyde (8.91 mg, 0.04 mmol) were dissolved in DCE (160 μL): methanol (160 μL) and MP-cyanoborohydride (55.4 mg, 0.13 mmol) was added followed by acetic acid (5.50 μl, 0.10 mmol). The reaction mixture was stirred at 55° C. overnight, allowed to cool to room temperature, filtered, and concentrated under vacuum. The crude mixture was purified by reverse-phase Gilson HPLC (Sunfire prep C18 30 mm×100 mm), eluting with acetonitrile/water+ 0.1% TFA to give the title compound as a colorless oil.

$^1$H-NMR (CD$_3$OD, 400 MHz): δ 8.00 (d, J=8.7 Hz, 2H), 7.65 (d, J=8.7 Hz, 2H), 7.28 (d, J=1.7 Hz, 1H), 7.11 (d, J=1.7 Hz, 1H), 4.26 (s, 1H), 4.21 (t, J=5.3 Hz, 2H), 3.97 (s, 1H), 3.43-3.52 (m, 1H), 3.19-3.37 (m, 6H), 2.26-2.39 (m, 2H), 2.03-2.16 (m, 2H), 1.82 (t, J=5.2 Hz, 2H), 1.33 (s, 6H), 1.17 (d, J=6.9 Hz, 6H). LCMS (m/e): 493.

Example 5-20

4-{8-[(8-Cyclopropyl-4,4-dimethyl-3,4-dihydro-2H-chromen-6-yl)methyl]-2-oxo-1-oxa-3,8-diazaspiro[4.5]dec-3-yl}benzoic acid, TFA salt

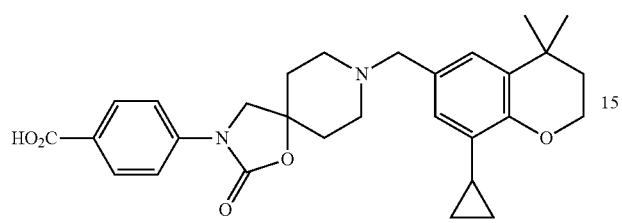

Step 1. Synthesis of 4-bromo-2-chloro-1-[(3-methyl-but-3-en-1-yl)oxy]benzene

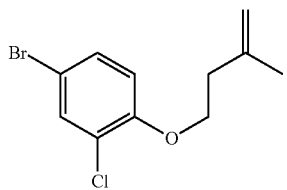

To a mixture of 4-bromo-2-chlorophenol (0.98 g, 4.71 mmol), and Cs$_2$CO$_3$ (2.05 g, 6.28 mmol) in DMF (4.49 mL) at room temperature was added 3-methylbut-3-en-1-yl diphenyl phosphate (1.00 g, 3.14 mmol, synthesized according to a procedure in U.S. Pat. No. 5,006,550, 9 Apr. 1991) dropwise via a syringe. The reaction mixture was heated to 85° C. for 1 hour. It was then allowed to cool to room temperature and was diluted with water (20.0 mL). The resulting mixture was extracted with hexane (75.0 mL, 2×) and the combined organic layers were dried over Na$_2$SO$_4$, filtered, and concentrated under vacuum. The crude mixture was purified by silica gel chromatography eluting with 0-5% EtOAc/hexanes to give the title compound as a colorless oil.
$^1$H-NMR (CDCl$_3$, 500 MHz): δ 7.52 (d, J=3.0 Hz, 1H), 7.33 (dd, J=8.6 Hz, 2.4 Hz, 1H), 6.82 (d, J=8.7 Hz, 1H), 4.89 (s, 1H), 4.84 (s, 1H), 4.13 (t, J=6.8 Hz, 2H), 2.58 (t, J=6.9 Hz, 2H), 1.85 (s, 3H).

Step 2. Synthesis of 6-bromo-8-chloro-4,4-dimethyl-3,4-dihydro-2H-chromene

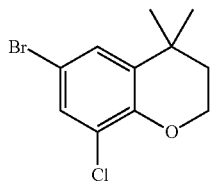

To a mixture of aluminum chloride (403 mg, 3.03 mmol) and dichloromethane (10.0 mL) cooled to −78° C. was added 4-bromo-2-chloro-1-[(3-methylbut-3-en-1-yl)oxy]benzene (758 mg, 2.75 mmol) in dichloromethane (6.00 mL) via a cannula to give a light yellow solution. The reaction mixture was allowed to warm to room temperature, stirred for 5 minutes, and then poured into an Erlenmeyer flask containing a cold 10% NaOH solution (75.0 mL). The mixture was extracted with hexane (40.0 mL, 3×) and the combined organic layers were dried over Na$_2$SO$_4$, filtered, and concentrated under vacuum. The crude mixture was purified by silica gel chromatography eluting with 0-5% EtOAc/hexanes to afford the desired product as a colorless oil.
$^1$H-NMR (CDCl$_3$, 500 MHz) δ 7.33 (d, J=2.3 Hz, 1H), 7.29 (d, J=2.3 Hz, 1H), 4.32 (t, J=5.5 Hz, 2H), 1.87 (t, J=5.4 Hz, 2H), 1.36 (s, 6H).

Step 3. Synthesis of 8-chloro-4,4-dimethyl-3,4-dihydro-2H-chromene-6-carbaldehyde

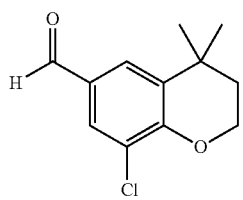

6-Bromo-8-chloro-4,4-dimethyl-3,4-dihydro-2H-chromene (483 mg, 1.75 mmol) in THF (12.0 mL) under N$_2$ atmosphere was cooled to −78° C., and n-BuLi (841 μL, 2.10 mmol) was added dropwise via a syringe. The reaction mixture was stirred at −78° C. for 10 minutes and then DMF (543 μL, 7.01 mmol) was added dropwise via a syringe. The resulting mixture was allowed to warm to room temperature and wet silica gel (5.0 g/0.5 mL of water) was added. The mixture was allowed to stir at room temperature for 10 minutes before it was filtered. The silica gel was rinsed with EtOAc, and the filtrate was concentrated under vacuum. The crude residue was purified by silica gel chromatography eluting with 0-20% EtOAc/hexanes to obtain the title compound as a white solid.
$^1$H-NMR (CDCl$_3$, 500 MHz): δ 9.84 (s, 1H), 7.77 (d, J=1.9 Hz, 1H), 7.74 (d, J=2.0 Hz, 1H), 4.43 (t, J=5.5 Hz, 2H), 1.93 (t, J=5.5 Hz, 2H), 1.42 (s, 6H).

Step 4. Synthesis of 8-cyclopropyl-4,4-dimethyl-3,4-dihydro-2H-chromene-6-carbaldehyde

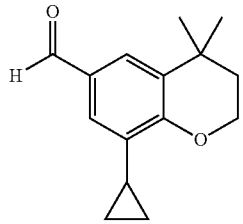

A vial was charged with Pd(OAc)$_2$ (2.40 mg, 10.7 μmol), XPhos (10.2 mg, 0.02 mmol), potassium carbonate (148 mg, 1.07 mmol), potassium cyclopropyltrifluoroborate (58.0 mg, 0.39 mmol) and 8-chloro-4,4-dimethyl-3,4-dihydro-2H-chromene-6-carbaldehyde (80.0 mg, 0.36 mmol). The mixture was dissolved in cyclopropylmethyl ether (2.00 mL) and water (0.20 mL) and purged with Ar. The reaction mixture was then stirred at 100° C. overnight, cooled to room temperature, and filtered through a pad of celite. The filtrate was concentrated under vacuum, and the crude residue was purified by silica gel chromatography eluting with 0-15% EtOAc/hexanes to afford the desired product as a yellow oil.

$^1$H-NMR (CDCl$_3$, 500 MHz): δ 9.87 (s, 1H), 7.66 (d, J=1.9 Hz, 1H), 7.21 (d, J=1.9 Hz, 1H), 4.38 (t, J=5.3 Hz, 2H), 2.13-2.19 (m, 1H), 1.91 (t, J=5.5 Hz, 2H), 1.41 (s, 6H), 0.98 (ddd, J=10.8 Hz, 6.5 Hz, 4.6 Hz, 2H), 0.71 (ddd, J=9.7 Hz, 6.1 Hz, 4.5 Hz, 2H).

Step 5. Synthesis of 4-{8-[(8-cyclopropyl-4,4-dimethyl-3,4-dihydro-2H-chromen-6-yl)methyl]-2-oxo-1-oxa-3,8-diazaspiro[4.5]dec-3-yl}benzoic acid, TFA salt

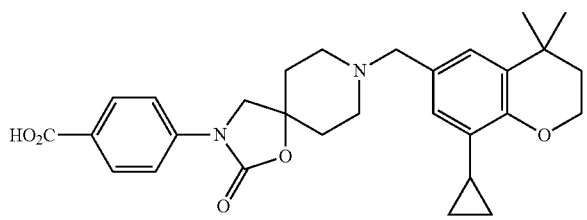

The title compound was prepared and purified according to the same experimental procedure as in Example 5-19, Step 4. LCMS (m/e): 491.

Example 5-21

4-{2-Oxo-8-[(2,2,8-trimethyl-3,4-dihydro-2H-chromen-6-yl)methyl]-1-oxa-3,8-diazaspiro[4.5]dec-3-yl}benzoic acid, TFA salt

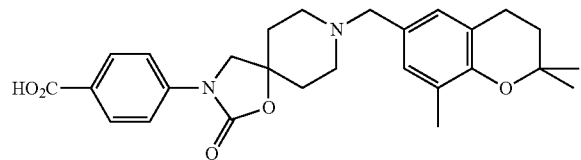 [SMILES: Cc1cc(CN2CCC3(CC2)CN(c2ccc(C(=O)O)cc2)C(=O)O3)cc2c1OC(C)(C)CC2]

Step 1. Synthesis of 4-bromo-2-methyl-1-[(3-methylbut-2-en-1-yl)oxy]benzene

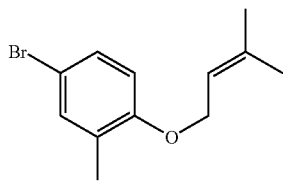

Using essentially the same procedure as Example 5-20, Step 1, 4-bromo-2-methylphenol (1.00 g, 5.35 mmol), cesium carbonate (3.48 g, 10.7 mmol) and 4-bromo-2-methyl-2-butene (0.75 mL, 6.42 mmol) afforded the desired product as a pale-yellow oil.

$^1$H-NMR (CDCl$_3$, 400 MHz): δ 7.19-7.24 (m, 2H), 6.67 (d, J=8.3 Hz, 1H), 5.42-5.46 (m, 1H), 4.47 (d, J=6.4 Hz, 2H), 2.17 (s, 3H), 1.77 (s, 3H), 1.71 (s, 3H).

Step 2. Synthesis of 6-bromo-2,2,8-trimethyl-3,4-dihydro-2H-chromene

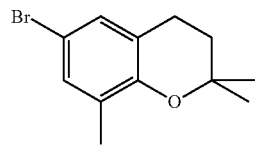

To aluminum chloride (0.76 g, 5.69 mmol) in dichloromethane (15.0 mL) at −78° C. was added 4-bromo-2-methyl-1-[(3-methylbut-2-en-1-yl)oxy]benzene (1.32 g, 5.17 mmol) dissolved in CH$_2$Cl$_2$ (4.00 mL) via a syringe. The reaction mixture was allowed to warm to room temperature and stirred for another 5 minutes. A cold 10% aqueous NaOH solution (20.0 mL) was then added, and the mixture was extracted with dichloromethane (50.0 mL, 2×). The combined organic layers were washed with brine, dried over Na$_2$SO$_4$, filtered and concentrated under vacuum. The crude residue was purified by silica gel chromatography eluting with 0-5% EtOAc/hexanes to give the desired product as a colorless oil.

$^1$H-NMR (CDCl$_3$, 400 MHz): δ 6.97-7.09 (m, 2H), 2.71 (t, J=6.8 Hz, 2H), 2.10 (s, 3H), 1.75 (t, J=6.7 Hz, 2H), 1.29 (s, 6H).

Step 3. Synthesis of 2,2,8-trimethyl-3,4-dihydro-2H-chromene-6-carbaldehyde

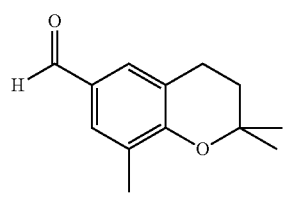

Using essentially the same procedure as Example 5-20, Step 3, 6-bromo-2,2,8-trimethyl-3,4-dihydro-2H-chromene (684 mg, 2.68 mmol), n-BuLi (1.30 mL, 3.22 mmol) and DMF (830 µL, 10.7 mmol) afforded the desired product as a pale-yellow oil.

$^1$H-NMR (CDCl$_3$, 500 MHz): δ 9.82 (s, 1H), 7.53 (s, 1H), 7.50 (s, 1H), 2.86 (t, J=6.7 Hz, 2H), 2.23 (s, 3H), 1.86 (t, J=6.7 Hz, 2H), 1.39 (s, 6H).

Step 4. Synthesis of 4-{2-oxo-8-[(2,2,8-trimethyl-3,4-dihydro-2H-chromen-6-yl)methyl]-1-oxa-3,8-diazaspiro[4.5]dec-3-yl}benzoic acid, TFA salt

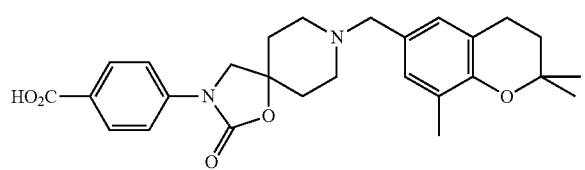 [SMILES: Cc1cc(CN2CCC3(CC2)CN(c2ccc(C(=O)O)cc2)C(=O)O3)cc2c1OC(C)(C)CC2]

The title compound was prepared and purified according to the same experimental procedure as in Example 5-19, Step 4. LCMS (m/e): 465.

Example 5-22

4-{8-[(8-Cyclopropyl-2,2-dimethyl-3,4-dihydro-2H-chromen-6-yl)methyl]-2-oxo-1-oxa-3,8-diazaspiro[4.5]dec-3-yl}benzoic acid, TFA salt

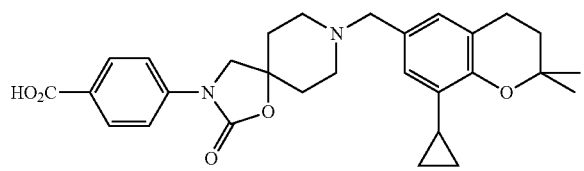 [SMILES: CC1(C)CCc2cc(CN3CCC4(CC3)CN(c3ccc(C(=O)O)cc3)C(=O)O4)cc(C3CC3)c2O1]

Step 1. Synthesis of 4-bromo-2-chloro-1-[(3-methylbut-2-en-1-yl)oxy]benzene

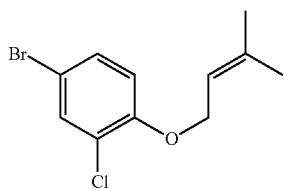

To a mixture of 4-bromo-2-chlorophenol (1.00 g, 4.82 mmol) and cesium carbonate (3.14 g, 9.64 mmol) in DMF (6.89 mL) at room temperature was added 4-bromo-2-methyl-2-butene (0.68 mL, 5.78 mmol) dropwise via a syringe. The reaction mixture was stirred at 85° C. for 1 hour before it was allowed to cool to room temperature. Water (30.0 mL) was then added and the mixture was extracted with hexane (75.0 mL, 2×). The combined organic layers were dried over Na$_2$SO$_4$, filtered and concentrated under vacuum. The crude mixture was purified by silica gel chromatography eluting with 0-5% EtOAc/hexanes to afford the product as a colorless oil.

$^1$H-NMR (CDCl$_3$, 400 MHz): δ 7.47 (d, J=2.4 Hz, 1H), 7.27 (dd, J=8.8 Hz, 2.3 Hz, 1H), 6.78 (d, J=8.8 Hz, 1H), 5.43-5.47 (m, 1H), 4.55 (d, J=6.5 Hz, 2H), 1.77 (s, 3H), 1.72 (s, 3H).

Step 2. Synthesis of 6-bromo-8-chloro-2,2-dimethyl-3,4-dihydro-2H-chromene

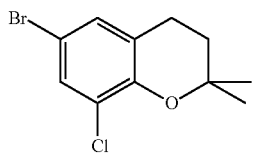

To aluminum chloride (0.71 g, 5.35 mmol) in dichloromethane (15.0 mL) was added 4-bromo-2-chloro-1-[(3-methylbut-2-en-1-yl)oxy]benzene (1.34 g, 4.86 mmol) dissolved in dichloromethane (5.00 mL) at −78° C. via a cannula. The reaction mixture was stirred at −78° C. for 10 minutes before addition of a 10% KOH (2.00 mL) solution at the same temperature. The mixture was then allowed to warm to room temperature and extracted with dichloromethane (50.0 mL, 2×). The combined organic layers were washed with brine, dried over Na$_2$SO$_4$, filtered and concentrated under vacuum. The crude residue was purified silica gel chromatography eluting with 0-5% EtOAc/hexanes to give the desired product as a colorless oil.

$^1$H-NMR (CDCl$_3$, 400 MHz): δ 7.29 (d, J=2.2 Hz, 1H), 7.08 (s, 1H), 2.75 (t, J=6.7 Hz, 2H), 1.79 (t, J=6.8 Hz, 2H), 1.35 (s, 6H).

Step 3. Synthesis of 8-chloro-2,2-dimethyl-3,4-dihydro-2H-chromene-6-carbaldehyde

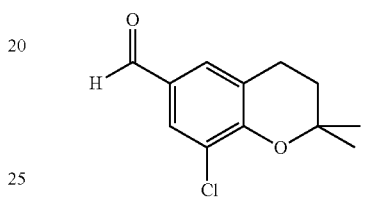

6-Bromo-8-chloro-2,2-dimethyl-3,4-dihydro-2H-chromene (483 mg, 1.75 mmol) in THF (8.76 mL) was cooled to −78° C. and n-BuLi (841 μL, 2.10 mmol) was added dropwise via a syringe. The reaction mixture was stirred at −78° C. for 10 minutes and then DMF (543 μL, 7.01 mmol) was added dropwise via a syringe. The resulting mixture was allowed to warm to room temperature, and wet silica gel (5.0 g/0.5 mL of water) was added. The mixture was allowed to stir at room temperature for 10 minutes before it was filtered. The silica gel was rinsed with EtOAc, and the filtrate was concentrated under vacuum. The crude mixture was purified by silica gel chromatography eluting with 0-15% EtOAc/hexanes to obtain the desired product as a pale-yellow oil.

$^1$H-NMR (CD$_3$OD, 500 MHz): δ 7.20 (d, J=1.8 Hz, 1H), 7.06 (d, J=0.9 Hz, 1H), 2.82 (t, J=6.9 Hz, 2H), 1.84 (t, J=6.7 Hz, 2H), 1.36 (s, 6H).

Step 4. 8-Cyclopropyl-2,2-dimethyl-3,4-dihydro-2H-chromene-6-carbaldehyde

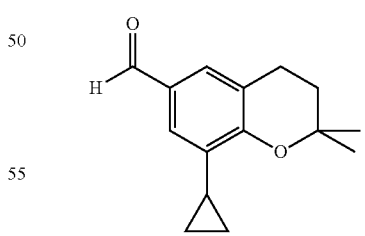

A vial was charged with Pd(OAc)$_2$ (7.99 mg, 0.04 mmol), XPhos (25.5 mg, 0.05 mmol), potassium carbonate (148 mg, 1.07 mmol), potassium cyclopropyltrifluoroborate (58.0 mg, 0.39 mmol) and 8-chloro-2,2-dimethyl-3,4-dihydro-2H-chromene-6-carbaldehyde (80 mg, 0.36 mmol). The mixture was dissolved in cyclopropylmethyl ether (1.62 mL) and water (0.16 mL) and purged with Ar. The reaction mixture was then stirred at 100° C. overnight, cooled to room temperature and filtered through a pad of celite. The filtrate was concentrated under vacuum, and the crude residue was purified by silica gel chromatography eluting with 0-20% EtOAc/hexanes to afford the desired product as a pale-yellow oil.

¹H-NMR (CDCl₃, 400 MHz): δ 9.75 (s, 1H), 7.39-7.41 (m, 1H), 7.18 (d, J=1.7 Hz, 1H), 2.83 (t, J=6.8 Hz, 2H), 2.09-2.16 (m, 1H), 1.84 (t, J=6.8 Hz, 2H), 1.37 (s, 6H), 0.92 (ddd, J=10.7 Hz, 6.4 Hz, 4.5 Hz, 2H), 0.66 (ddd, J=9.6 Hz, 6.1 Hz, 4.3 Hz, 2H).

Step 5. Synthesis of 4-{8-[(8-cyclopropyl-2,2-dimethyl-3,4-dihydro-2H-chromen-6-yl)methyl]-2-oxo-1-oxa-3,8-diazaspiro[4.5]dec-3-yl}benzoic acid, TPA salt

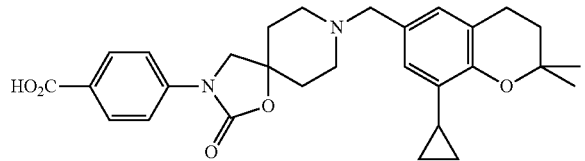 [SMILES: CC1(C)CCc2cc(CN3CCC4(CC3)CN(c3ccc(C(=O)O)cc3)C(=O)O4)cc(C3CC3)c2O1]

The title compound was prepared and purified according to the same experimental procedure as in Example 5-19, Step 4. LCMS (m/e): 491.

Example 5-23

4-{8-[(2,2-Dimethyl-2,3-dihydrospiro[chromene-4,1'-cyclopropan]-6-yl)methyl]-2-oxo-1-oxa-3,8-diazaspiro[4.5]dec-3-yl}benzoic acid, TFA salt

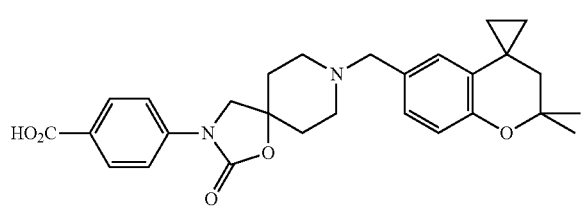 [SMILES: CC1(C)CC2(CC2)c2cc(CN3CCC4(CC3)CN(c3ccc(C(=O)O)cc3)C(=O)O4)ccc2O1]

Step 1. Synthesis of methyl 2,2-dimethyl-4-oxo-3,4-dihydro-2H-chromene-6-carboxylate

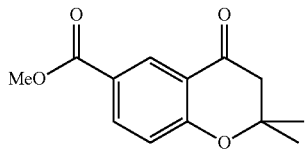 [SMILES: COC(=O)c1ccc2c(c1)C(=O)CC(C)(C)O2]

Methyl 3-acetyl-4-hydroxybenzoate (200 mg, 1.03 mmol), acetone (151 μL, 2.06 mmol) and pyrrolidine (25.6 μL, 0.31 mmol) were mixed in toluene (515 μL) and stirred at room temperature for 1 hour. It was then heated to 100° C. for 5 hours, allowed to cool to room temperature, diluted with EtOAc (50.0 mL) and poured into ice. The two layers were separated. The organic layer was washed with 2 N aqueous HCl (10.0 mL), 2 N aqueous NaOH (10.0 mL), water (10.0 mL), dried over Na₂SO₄, filtered and concentrated under vacuum. The crude mixture was purified by silica gel chromatography eluting with 0-30% EtOAc/hexanes to give the desired product as a pale-yellow oil.

¹H-NMR (CDCl₃, 400 MHz): δ: 8.54 (d, J=2.2 Hz, 1H), 8.11 (dd, J=8.8 Hz, 2.2 Hz, 1H), 6.95 (d, J=8.8 Hz, 1H), 3.88 (s, 3H), 2.74 (s, 2H), 1.46 (s, 6H).

Step 2. Synthesis of methyl 2,2-dimethyl-4-methylidene-3,4-dihydro-2H-chromene-6-carboxylate

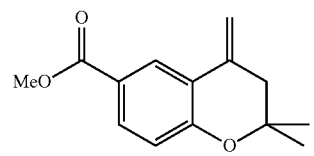

Potassium tert-butoxide (96.0 mg, 0.85 mmol) was added to a suspension of triphenylmethylphosphonium bromide (305 mg, 0.85 mmol) in toluene (3.00 mL) while stirring at −30° C. under N₂ atmosphere. After stirring for 1 hour at −30° C., a solution of methyl 2,2-dimethyl-4-oxo-3,4-dihydro-2H-chromene-6-carboxylate (100 mg, 0.43 mmol) in toluene (2.00 mL) was added slowly via a syringe. The suspension was stirred for a further 30 minutes at −30° C. and then heated to reflux overnight. The mixture was allowed to cool to room temperature, diluted with EtOAc (50.0 mL) and washed with water (10.0 mL). The organic layer was dried over Na₂SO₄, filtered and concentrated under vacuum. The crude residue was purified by silica gel chromatography eluting with 0-25% EtOAc/hexanes to give the desired product as a pale-yellow oil.

¹H-NMR (CDCl₃, 500 MHz): δ 8.30 (d, J=2.2 Hz, 1H), 7.87 (dd, =8.5 Hz, 2.0 Hz, 1H), 6.85 (d, J=8.6 Hz, 1H), 5.69 (s, 1H), 5.00 (s, 1H), 3.92 (s, 3H), 2.52 (s, 2H), 1.37 (s, 6H).

Step 3. Synthesis of methyl 2,2-dimethyl-2,3-dihydrospiro[chromene-4,1'-cyclopropane]-6-carboxylate

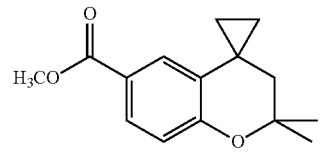 [SMILES: COC(=O)c1ccc2c(c1)C1(CC1)CC(C)(C)O2]

To a mixture of methyl 2,2-dimethyl-4-methylidene-3,4-dihydro-2H-chromene-6-carboxylate (34.0 mg, 0.15 mmol) and diethylzinc (1.17 mL, 1.17 mmol) in toluene (2.90 mL) under N₂ atmosphere was added diiodomethane (189 μL, 2.34 mmol) dropwise via a syringe at room temperature. The mixture was stirred at room temperature overnight and then partitioned between diethyl ether (10.0 mL) and 5% aqueous HCl (10.0 mL). The aqueous layer was extracted with diethyl ether (20.0 mL, 2×). The combined organic layers were dried over Na₂SO₄, filtered and concentrated under vacuum. The crude residue was purified by silica gel chromatography eluting with 0-15% EtOAc/hexanes to afford the desired product as a pale-yellow solid.

LCMS (m/e): 247.

Step 4. Synthesis of 2,2-dimethyl-2,3-dihydrospiro[chromene-4,1'-cyclopropane]-6-carbaldehyde

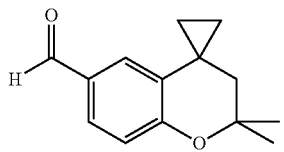

Methyl 2,2-dimethyl-2,3-dihydrospiro[chromene-4,1'-cyclopropane]-6-carboxylate (33.0 mg, 0.13 mmol) was dissolved in dry toluene (1.34 mL), and cooled to −78° C. DIBAL-H (536 μL, 0.54 mmol) was added dropwise via a syringe. The reaction mixture was stirred for 2 hours at −78° C. It was then quenched with methanol (500 μL) at the same temperature, and diluted with EtOAc (15.0 mL). The organic layer was washed with water (10.0 mL), dried over $Na_2SO_4$, filtered and concentrated under vacuum to afford the crude alcohol, which was used directly to the next step. The crude alcohol was dissolved in dichloromethane (4.00 mL) and Dess-Martin periodinane (114 mg, 0.27 mmol) was added in one portion at room temperature. The resulting mixture was stirred at room temperature for 1 hour and concentrated under vacuum on silica gel. It was then purified by silica gel chromatography eluting with 0-15% EtOAc/hexanes to give the desired product as a colorless oil.

$^1$H-NMR (CDCl$_3$, 500 MHz): δ 9.83 (s, 1H), 7.59 (dd, J=8.3 Hz, 1.9 Hz, 1H), 7.25 (d, J=2.0 Hz, 1H), 6.91 (d, J=8.3 Hz, 1H), 1.83 (s, 2H), 1.45 (s, 6H), 1.16 (dd, J=6.9 Hz, 5.0 Hz, 2H), 0.96 (dd, J=6.5 Hz, 4.7 Hz, 2H).

Step 5. Synthesis of 4-{8-[(2,2-dimethyl-2,3-dihydrospiro[chromene-4,1'-cyclopropan]-6-yl)methyl]-2-oxo-1-oxa-3,8-diazaspiro[4.5]dec-3-yl}benzoic acid, TFA salt

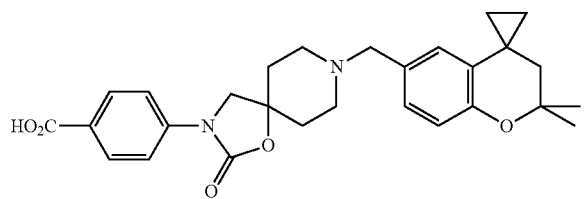 [SMILES: CC1(C)CC2(CC2)c2cc(CN3CCC4(CC3)CN(c3ccc(C(=O)O)cc3)C(=O)O4)ccc2O1]

The title compound was prepared and purified according to the same experimental procedure as in Example 5-19, Step 4.
LCMS (m/e): 477.

Example 5-24

4-{8-[(4-Cyclopropyl-2H-chromen-6-yl)methyl]-2-oxo-1-oxa-3,8-diazaspiro[4.5]dec-3-yl}benzoic acid, TFA salt

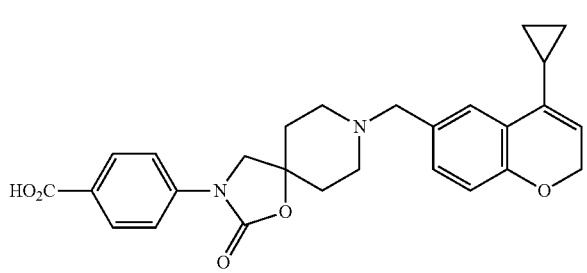 [SMILES: O=C(O)c1ccc(N2CC3(CCN(Cc4ccc5c(c4)C(C4CC4)=CCO5)CC3)OC2=O)cc1]

Step 1. Synthesis of methyl 4-oxo-3,4-dihydro-2H-chromene-6-carboxylate

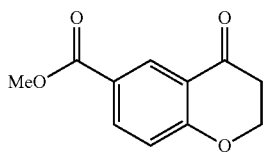 [SMILES: COC(=O)c1ccc2c(c1)C(=O)CCO2]

Methyl 3,4-dihydro-2H-chromene-6-carboxylate (790 mg, 4.11 mmol) was added to a solution of iron (III) chloride hexahydrate (22.2 mg, 0.08 mmol) in pyridine (4.11 mL). After the addition of tell-butyl hydroperoxide (1.80 mL, 12.33 mmol, 70 wt. % in water), the reaction mixture was heated at 82° C. for 21 hours. The mixture was then allowed to cool to room temperature and poured into a 1 N solution of aqueous HCl in order to remove pyridine. The organic phase was extracted with EtOAc (2×), dried over Na2SO4, filtered and concentrated under vacuum. The crude residue was purified by silica gel chromatography eluting with 0-35% EtOAc/hexanes to give the desired product as a pale-orange oil.

$^1$H-NMR (CDCl$_3$, 400 MHz): δ 8.57 (d, J=2.1 Hz, 1H), 8.12 (dd, j=8.7 Hz, 2.3 Hz, 1H), 7.00 (d, J=8.7 Hz, 1H), 4.58 (t, J=6.4 Hz, 2H), 3.89 (s, 3H), 2.83 (t, J=6.7 Hz, 2H).

Step 2. Synthesis of methyl 4-{[(trifluoromethyl)sulfonyl]oxy}-2H-chromene-6-carboxylate

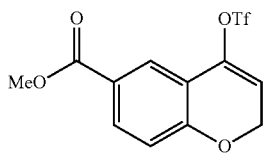 [SMILES: COC(=O)c1ccc2c(c1)C(OS(=O)(=O)C(F)(F)F)=CCO2]

Methyl 4-oxo-3,4-dihydro-2H-chromene-6-carboxylate (60.0 mg, 0.29 mmol) was dissolved in THF (2.91 mL), and cooled to −78° C. LiHMDS (73.0 mg, 0.44 mmol) was then added to the reaction and was stirred at −78° C. for 1 hour before Commin's reagent (229 mg, 0.58 mmol) in THF (600 μl) was added at the same temperature and stirred for another 1.5 hour. The reaction mixture was then warmed to room temperature and quenched with water. It was then extracted with EtOAc (2×), and the combined organic layers were dried over Na$_2$SO$_4$, filtered and concentrated under vacuum. The crude residue was purified by silica gel chromatography to afford the desired product as a brown oil.
LCMS (m/e): 339.

Step 3. Synthesis of methyl 4-cyclopropyl-2H-chromene-6-carboxylate

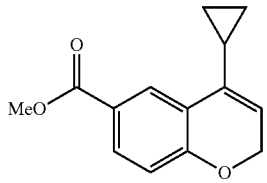 [SMILES: COC(=O)c1ccc2c(c1)C(C1CC1)=CCO2]

Methyl 4-{[(trifluoromethyl)sulfonyl]oxy}-2H-chromene-6-carboxylate (596 mg, 1.76 mmol), cyclopropylboronic acid pinacol ester (803 μL, 4.40 mmol), lithium hydroxide monohydrate (185 mg, 4.40 mmol), and [1,1'-bis(diphenylphosphino)ferrocene]dichloropalladium(II) (387 mg, 0.53 mmol) were mixed in a microwave vial and dioxane (4.40 mL) and water (1.50 mL) were added. The reaction mixture was heated to 120° C. for 30 minutes under microwave irradiation before concentrating under vacuum. The crude residue was purified by silica gel chromatography to afford the desired product as a pale-yellow oil.

$^1$H-NMR (CDCl$_3$, 500 MHz): δ 8.19 (d, J=2.1 Hz, 1H), 7.86 (dd, J=8.4 Hz, 2.2 Hz, 1H), 6.82 (d, J=8.4 Hz, 1H), 5.50-5.54 (m, 1H), 4.87 (d, J=1.9 Hz, 1H), 4.86 (d, J=1.8 Hz, 1H), 3.92 (s, 3H), 0.89 (ddd, J=10.4 Hz, 6.2 Hz, 4.5 Hz, 2H), 0.54 (ddd, J=9.8 Hz, 5.8 Hz, 4.4 Hz, 2H).

Step 4. Synthesis of 4-cyclopropyl-2H-chromene-6-carbaldehyde

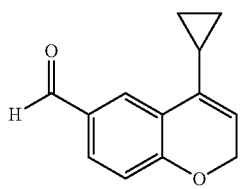 [SMILES: O=Cc1ccc2c(c1)C(C1CC1)=CCO2]

Methyl 4-cyclopropyl-2H-chromene-6-carboxylate (101 mg, 0.44 mmol) was dissolved in dichloromethane (4.40 mL), and cooled to −78° C. DIBAL-H (877 µL, 0.88 mmol) was added dropwise. The reaction mixture was stirred for 2 hours at −78° C. and warmed to room temperature. It was then quenched with methanol at room temperature and diluted with dichloromethane. The organic layer was washed with water, dried over Na$_2$SO$_4$, filtered and concentrated under vacuum. The crude residue was used directly in the next step. The crude alcohol was dissolved in dichloromethane (4.00 mL) and Dess-Martin periodinane (372 mg, 0.88 mmol) was added in one portion at room temperature. The mixture was stirred at room temperature for 1 hour and concentrated under vacuum on silica gel. The crude residue was purified by silica gel chromatography eluting with 0-20% EtOAc/Hexanes to afford the desired product as a colorless oil.

LCMS (m/e): 201.

Step 5. Synthesis of 4-{8-[(4-cyclopropyl-2H-chromen-6-yl)methyl]-2-oxo-1-oxa-3,8-diazaspiro[4.5]dec-3-yl}benzoic acid, TFA salt

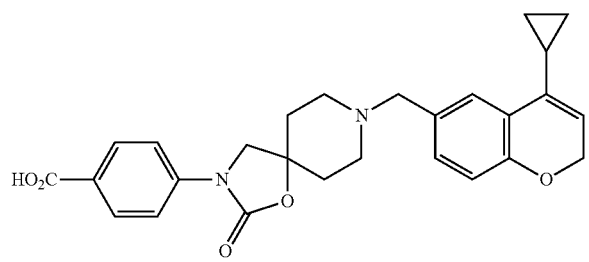 [SMILES: O=C(O)c1ccc(N2CC3(CCN(Cc4ccc5c(c4)C(C4CC4)=CCO5)CC3)OC2=O)cc1]

The title compound was prepared and purified according to the same experimental procedure as in Example 5-19, Step 4.
LCMS (m/e): 461.

Example 5-25

4-{8-[(2,2-Dimethyl-3,4-dihydro-2H-chromen-8-yl)methyl]-2-oxo-1-oxa-3,8-diazaspiro[4.5]dec-3-yl}benzoic acid, TFA salt

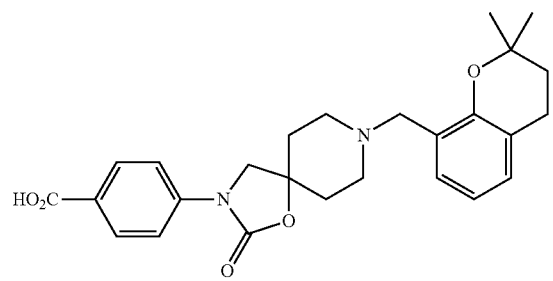 [SMILES: CC1(C)CCc2cccc(CN3CCC4(CC3)CN(c3ccc(C(=O)O)cc3)C(=O)O4)c2O1]

Step 1. Synthesis of 2,2-dimethyl-3,4-dihydro-2H-chromene-8-carbaldehyde

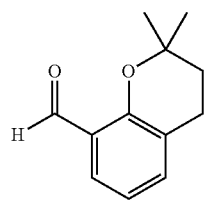

2,2-Dimethyl-3,4-dihydro-2H-chromene-8-carboxylic acid (300 mg, 1.45 mmol) dissolved in THF (3.60 mL) was cooled to 0° C. and BH$_3$-THF (5.82 mL, 5.82 mmol) was added dropwise via a syringe. The resulting solution was stirred at 65° C. for 1 hour, and then allowed to cool to room temperature before addition of 6 N HCl (2.50 mL). The mixture was again heated at 65° C. for 30 minutes. The solution was cooled to room temperature, made basic with 1N NaOH and extracted with EtOAc (40.0 mL, 3×). The combined organic layers were dried over Na$_2$SO$_4$, filtered and concentrated under vacuum to obtain the crude alcohol as a colorless oil, which was directly used to the next step. The crude alcohol was dissolved in dichloromethane (5.00 mL), and Dess-Martin periodinane (1.23 g, 2.91 mmol) was added in one portion at room temperature. The reaction mixture was stirred for 1 hour at room temperature and concentrated under vacuum on silica gel. The crude residue was purified by silica gel chromatography eluting with 0-15% EtOAc/hexanes to give the desired product as a colorless oil.

$^1$H-NMR (CDCl$_3$, 400 MHz): δ 10.4 (s, 1H), 7.63 (d, J=7.7 Hz, 1H), 7.25 (d, J=7.7 Hz, 1H), 6.85 (t, J=7.5 Hz, 1H), 2.80 (t, J=6.7 Hz, 2H), 1.85 (t, J=6.9 Hz, 2H), 1.38 (s, 6H).

Step 2. Synthesis of 4-{8-[(2,2-dimethyl-3,4-dihydro-2H-chromen-8-yl)methyl]-2-oxo-1-oxa-3,8-diazaspiro[4.5]dec-3-yl}benzoic acid, TFA salt

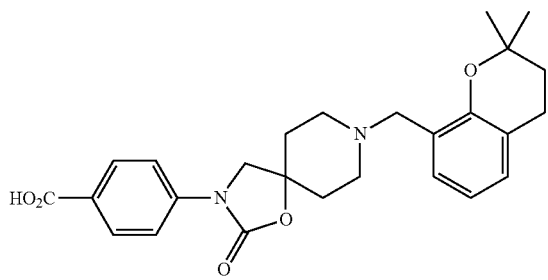 [SMILES: CC1(C)CCc2cccc(CN3CCC4(CC3)CN(c3ccc(C(=O)O)cc3)C(=O)O4)c2O1]

The title compound was prepared and purified according to the same experimental procedure as in Example 5-19, Step 4. LCMS (m/e): 451.

Example 5-26

4-{8-[(6-Chloro-2,2-dimethyl-3,4-dihydro-2H-chromen-8-yl)methyl]-2-oxo-1-oxa-3,8-diazaspiro[4.5]dec-3-yl}benzoic acid, TFA salt

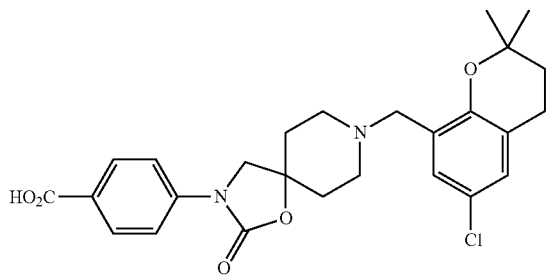 [SMILES: CC1(C)CCc2cc(Cl)cc(CN3CCC4(CC3)CN(c3ccc(C(=O)O)cc3)C(=O)O4)c2O1]

Step 1. Synthesis of methyl 2,2-dimethyl-3,4-dihydro-2H-chromene-8-carboxylate

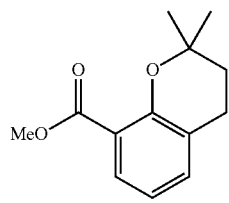 [SMILES: COC(=O)c1cccc2c1OC(C)(C)CC2]

To a solution of 2,2-dimethyl-3,4-dihydro-2H-chromene-8-carboxylic acid (300 mg, 1.45 mmol) in methanol (2.10 mL) and toluene (5.20 mL) cooled to 0° C. was added TMS-diazomethane (1.82 mL, 3.64 mmol) dropwise via a syringe. The reaction mixture was warmed to room temperature and stirred for 45 minutes. It was then cooled to 0° C., and acetic acid (2.00 mL) was added carefully. The solvent was evaporated under vacuum and the residue was re-dissolved in EtOAc (80.0 mL), washed with a saturated NaHCO$_3$ solution (20.0 mL, dried over Na$_2$SO$_4$, filtered and concentrated under vacuum. The crude product was used directly to the next step without further purification.
$^1$H-NMR (CDCl$_3$, 400 MHz) δ: 7.57 (d, J=7.7 Hz, 1H), 7.16 (d, J=7.4 Hz, 1H), 6.79 (t, J=7.7 Hz, 1H), 3.84 (s, 3H), 2.79 (t, J=6.7 Hz, 2H), 1.82 (t, J=6.7 Hz, 2H), 1.35 (s, 6H).

Step 2. Synthesis of methyl 6-chloro-2,2-dimethyl-3,4-dihydro-2H-chromene-8-carboxylate

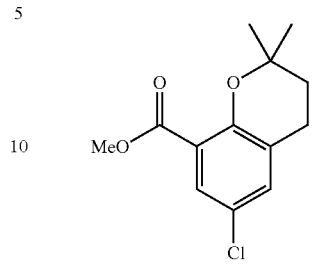

To a solution of methyl 2,2-dimethyl-3,4-dihydro-2H-chromene-8-carboxylate (330 mg, 1.50 mmol) in dichloromethane (3.74 mL) and methanol (3.74 mL) was added concentrated HCl (61.5 μL, 0.75 mmol) at 10° C. NCS (206 mg, 1.54 mmol) as added portion-wise. The solution was stirred for 1 hour at 8-12° C. The solution was then poured into a mixture of water (5.00 mL), saturated aqueous sodium thiosulfate (5.00 mL), 1 N aqueous NaOH (5.00 mL) and dichloromethane (30.0 mL). The mixture was stirred for 15 minutes at room temperature and the two phases were separated. The organic phase was acidified to pH<2 with 1 N aqueous HCl. The mixture was then extracted with dichloromethane (10.0 mL, 2×). The combined organic layers were dried over Na$_2$SO$_4$, filtered and concentrated under vacuum. The crude residue was purified by silica gel chromatography eluting with 0-15% EtOAc/hexanes to give the desired product as a colorless oil.
$^1$H-NMR (CDCl$_3$, 400 MHz): δ 7.54 (d, J=2.7 Hz, 1H), 7.14 (app d, J=2.6 Hz, 1H), 3.84 (s, 3H), 2.77 (t, J=6.8 Hz, 2H), 1.81 (t, J=6.8 Hz, 2H), 1.34 (s, 6H).

Step 3. Synthesis of 6-chloro-2,2-dimethyl-3,4-dihydro-2H-chromene-8-carbaldehyde

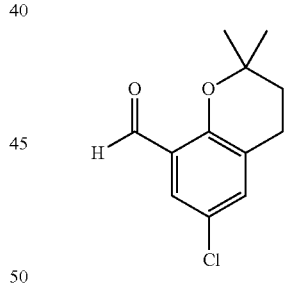

6-Chloro-2,2-dimethyl-3,4-dihydro-2H-chromene-8-carboxylate (350 mg, 1.37 mmol) was dissolved in dichloromethane (6.87 mL) and cooled to −78° C. DIBAL-H (4.12 mL, 4.12 mmol) was added dropwise. The reaction mixture was warmed to room temperature and stirred for 1 hour. It was then cooled to 0° C., diluted with dichloromethane (10.0 mL) and water (2.00 mL) was added slowly, followed by a 15% aqueous NaOH solution (5.00 mL). The mixture was warmed to room temperature and stirred for 15 minutes. The organic layer was separated, dried over Na$_2$SO$_4$, filtered, and concentrated under vacuum. The crude alcohol was used directly in the next step without further purification. The crude alcohol was dissolved in dichloromethane (7.00 mL), and Dess-Martin periodinane (1.20 g, 2.75 mmol) was added in one portion at room temperature. The reaction mixture was stirred at room temperature for 30 minutes and then concentrated under vacuum on silica gel. It was then purified by silica gel chromatography eluting with 0-15% EtOAc/hexanes to give the desired product as a white solid.

¹H-NMR (DMSO-d6, 400 MHz): δ 10.2 (s, 1H), 7.44 (app d, J=2.7 Hz, 1H), 7.36 (d, J=2.6 Hz, 1H), 2.76 (t, J=6.8 Hz, 2H), 1.79 (t, J=6.7 Hz, 2H), 1.30 (s, 6H).

Step 4. Synthesis of 4-{8-[(6-chloro-2,2-dimethyl-3,4-dihydro-2H-chromen-8-yl)methyl]-2-oxo-1-oxa-3,8-diazaspiro[4.5]dec-3-yl}benzoic acid, TFA salt

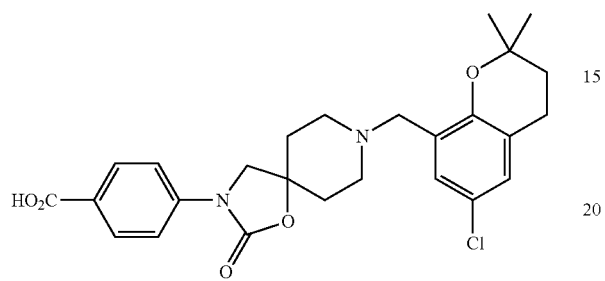

The title compound was prepared and purified according to the same experimental procedure as in Example 5-19, Step 4. LCMS (m/e): 485.

Example 5-27

4-{8-[(6-Cyclopropyl-2,2-dimethyl-3,4-dihydro-2H-chromen-8-yl)methyl]-2-oxo-1-oxa-3,8-diazaspiro[4.5]dec-3-yl}benzoic acid, TFA salt

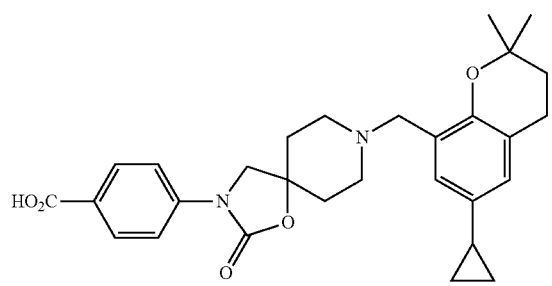 [SMILES: CC1(C)CCc2cc(C3CC3)cc(CN3CCC4(CC3)CN(c3ccc(C(=O)O)cc3)C(=O)O4)c2O1]

Step 1. Synthesis of 6-cyclopropyl-2,2-dimethyl-3,4-dihydro-2H-chromene-8-carbaldehyde

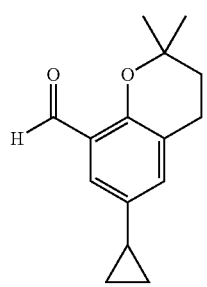 [SMILES: CC1(C)CCc2cc(C3CC3)cc(C=O)c2O1]

Using essentially the same procedure as Example 5-22, Step 4, Pd(OAc)₂ (7.04 mg, 0.03 mmol), X-Phos (29.9 mg, 0.06 mmol), potassium carbonate (434 mg, 3.14 mmol), potassium cyclopropyltrifluoroborate (170 mg, 1.15 mmol) and 6-chloro-2,2-dimethyl-3,4-dihydro-2H-chromene-8-carbaldehyde (235 mg, 1.05 mmol, Example 5-26, Step 3) afforded the desired product as a pale-yellow oil.

¹H-NMR (DMSO-d₆, 400 MHz): δ 10.2 (s, 1H), 7.14 (d, J=2.2 Hz, 1H), 7.08 (d, J=2.0 Hz, 1H), 2.70 (t, J=6.7 Hz, 2H), 1.76-185 (m, 1H), 1.76 (t, J=6.7 Hz, 2H), 1.28 (s, 6H), 0.82 (ddd, J=10.5 Hz, 6.3 Hz, 4.3 Hz, 2H), 0.53 (ddd, J=9.3 Hz, 6.2 Hz, 4.3 Hz, 21-1).

Step 2. Synthesis of 4-{8-[(6-cyclopropyl-2,2-dimethyl-3,4-dihydro-2H-chromen-8-yl)methyl]-2-oxo-1-oxa-3,8-diazaspiro[4.5]dec-3-yl}benzoic acid, TFA salt

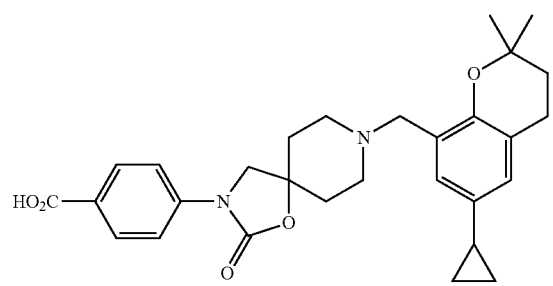 [SMILES: CC1(C)CCc2cc(C3CC3)cc(CN3CCC4(CC3)CN(c3ccc(C(=O)O)cc3)C(=O)O4)c2O1]

The title compound was prepared and purified according to the same experimental procedure as in Example 5-19, Step 4. LCMS (m/e): 491.

Example 5-28

4-{8-[(4,4-Dimethyl-3,4-dihydro-2H-thiochromen-6-yl)methyl]-2-oxo-1-oxa-3,8-diazaspiro[4.5]dec-3-yl}benzoic acid, TFA salt

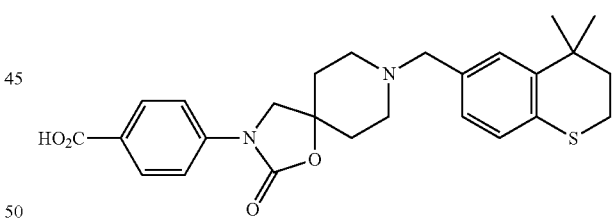

Step 1. Synthesis of 1-bromo-4-[(3-methylbut-3-en-1-yl)sulfanyl]benzene

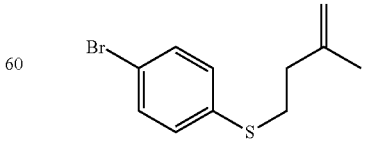

Using essentially the same procedure as Example 5-20, Step 1, 4-bromobenzenethiol (1.34 g, 7.07 mmol), 3-methylbut-3-en-1-yl diphenyl phosphate (1.50 g, 4.71 mmol, synthesized according to a procedure in U.S. Pat. No. 5,006,550, 9 Apr. 1991), Cs₂CO₃ (4.61 g, 14.1 mmol) afforded the desired product as a colorless oil.

¹H-NMR (CDCl₃, 400 MHz): δ 7.35-7.41 (m, 2H), 7.15-7.20 (m, 2H), 4.79 (s, 1H), 4.72 (s, 1H), 2.99 (t, J=7.6 Hz, 2H), 2.31 (t, J=7.8 Hz, 2H), 1.73 (s, 3H).

Step 2. Synthesis of 4,4-dimethyl-3,4-dihydro-2H-thiochromene-6-carbaldehyde

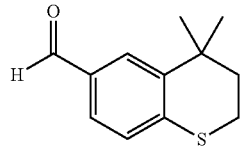

1-Bromo-4-[(3-methylbut-3-en-1-yl)sulfanyl]benzene (1.05 g, 4.08 mmol) dissolved in dichloromethane (24.0 mL) was cooled to 0° C., and aluminum chloride (0.60 g, 4.49 mmol) was added portionwise. The reaction mixture was stirred at 0° C. for 1 hour and warmed to room temperature for another hour. It was then poured into an Erlenmeyer flask containing a 10% aqueous NaOH solution and ice. The mixture was extracted with dichloromethane (2×, 40.0 mL), and the combined organic layers were dried over Na₂SO₄, filtered, and concentrated under vacuum. The crude residue was purified by silica gel chromatography eluting with 0-10% EtOAc/Hexanes to give 6-bromo-4,4-dimethyl-3,4-dihydro-2H-thiochromene as a pale-yellow oil. 6-Bromo-4,4-dimethyl-3,4-dihydro-2H-thiochromene (798 mg, 3.10 mmol) in THF (21.0 mL) was cooled to −78° C. and n-BuLi (1.50 mL, 3.72 mmol) was added dropwise. The reaction mixture was stirred at −78° C. for 10 minutes and then DMF (961 μl, 12.4 mmol) was added dropwise via a syringe. The resulting mixture was allowed to warm to room temperature and wet silica gel (5.0 g/0.5 mL of water) was added. The mixture was allowed to stir at room temperature for 10 minutes before it was filtered. The silica gel was rinsed with EtOAc and the filtrate was concentrated under vacuum. The crude residue was purified by silica gel chromatography eluting with 0-20% EtOAc/hexanes to obtain the desired product as a pale-yellow oil.

¹H-NMR (CD₃OD, 500 MHz): δ 9.83 (s, 1H), 7.94 (d, J=1.7 Hz, 1H), 7.53 (dd, J=8.1 Hz, 1.7 Hz, 1H), 7.22 (d, J=8.1 Hz, 1H), 3.09-3.14 (m, 2H), 1.97-2.01 (m, 2H), 1.38 (s, 6H).

Step 3. Synthesis of 4-{8-[(4,4-dimethyl-3,4-dihydro-2H-thiochromen-6-yl)methyl]-2-oxo-1-oxa-3,8-diazaspiro[4.5]dec-3-yl}benzoic acid, TFA salt

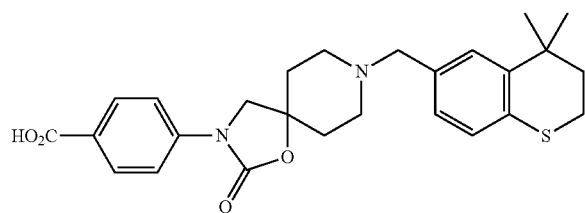 [SMILES: CC1(C)CCSc2ccc(CN3CCC4(CC3)CN(c3ccc(C(=O)O)cc3)C(=O)O4)cc21]

The title compound was prepared and purified according to the same experimental procedure as in Example 5-19, Step 4.
LCMS (m/e): 467.

Example 5-29

4-{8-[(8-Chloro-4,4-dimethyl-3,4-dihydro-2H-thiochromen-6-yl)methyl]-2-oxo-1-oxa-3,8-diazaspiro[4.5]dec-3-yl}benzoic acid, TFA salt

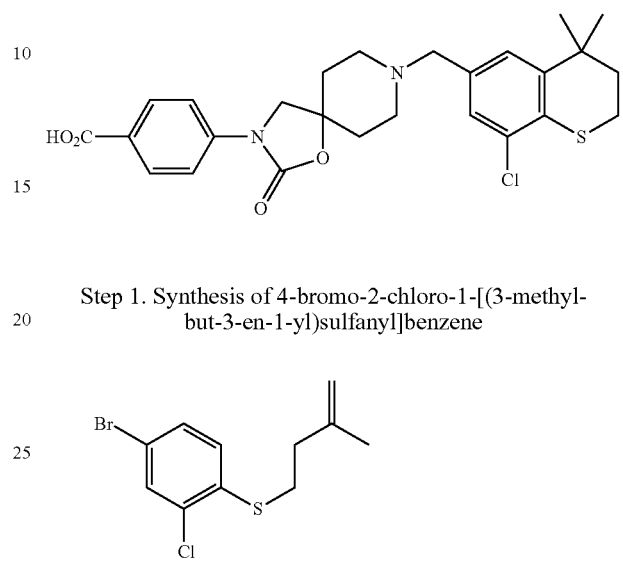

Step 1. Synthesis of 4-bromo-2-chloro-1-[(3-methylbut-3-en-1-yl)sulfanyl]benzene

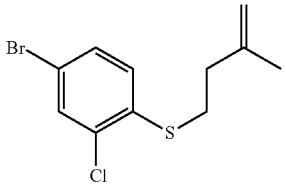

To a mixture of 4-bromo-2-chlorobenzenethiol (1.68 g, 7.54 mmol) and Cs₂CO₃ (4.09 g, 12.6 mmol) in DMF (8.98 mL) at room temperature was added 3-methylbut-3-en-1-yl diphenyl phosphate (2.00 g, 6.28 mmol, synthesized according to a procedure in U.S. Pat. No. 5,006,550, 9 Apr. 1991) dropwise via a syringe. The reaction mixture was heated to 85° C. for 1 hour. It was then allowed to cool to room temperature and diluted with water (20.0 mL). The resulting mixture was extracted with EtOAc:hexanes mixture (1:1, 75.0 mL, 2×) and the combined organic layers were dried over Na₂SO₄, filtered and concentrated under vacuum. The crude mixture was purified by silica gel chromatography eluting with 0-10% EtOAc/hexanes to give the desired product as a colorless oil.

¹H-NMR (CDCl₃, 500 MHz): δ 7.55 (d, J=2.0 Hz, 1H), 7.37 (dd, J=8.4 Hz, 2.0 Hz, 1H), 7.16 (d, J=8.4 Hz, 1H), 4.86 (s, 1H), 4.81 (s, 1H), 3.05 (t, J=7.6 Hz, 2H), 2.40 (t, J=7.7 Hz, 2H), 1.80 (s, 3H).

Step 2: Synthesis of 6-bromo-8-chloro-4,4-dimethyl-3,4-dihydro-2H-thiochromene

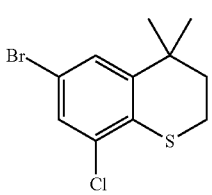

To a mixture of aluminum chloride (0.58 g, 4.34 mmol) and dichloromethane (23.2 mL) cooled to −78° C. was added 4-bromo-2-chloro-1-[(3-methylbut-3-en-1-yl)sulfanyl]benzene (1.15 g, 3.94 mmol) in dichloromethane (6.00 mL) via a cannula to give a light yellow solution. The reaction mixture was allowed to warm to room temperature, stirred for 5 minutes, and then poured into an Erlenmeyer flask containing a cold 10% aqueous NaOH solution (75.0 mL). The mixture was extracted with dichloromethane (2×, 40.0 mL) and the combined organic layers were dried over Na₂SO₄, filtered and concentrated under vacuum. The crude residue was purified by silica gel chromatography eluting with 0-20% EtOAc/hexanes to afford the desired product as a pale-yellow oil.

¹H-NMR (CDCl₃, 500 MHz): δ 7.42 (d, J=2.0 Hz, 1H), 7.35 (d, J=2.1 Hz, 1H), 3.04-3.07 (m, 2H), 1.94-1.97 (m, 2H), 1.35 (s, 6H).

Step 3. Synthesis of 8-chloro-4,4-dimethyl-3,4-dihydro-2H-thiochromene-6-carbaldehyde

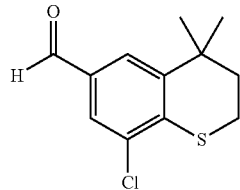

Using essentially the same procedure as Example 5-20, Step 3, 6-bromo-8-chloro-4,4-dimethyl-3,4-dihydro-2H-thiochromene (954 mg, 3.27 mmol), n-BuLi (1.57 mL, 3.93 mmol) and DMF (1.01 mL, 13.1 mmol) afforded the desired product as a pale-yellow oil.

¹H-NMR (CDCl₃, 500 MHz): δ 9.88 (s, 1H), 7.82 (d, J=1.8 Hz, 1H), 7.68 (d, J=1.6 Hz, 1H), 3.11-3.15 (m, 2H), 1.98-2.02 (m, 2H), 1.41 (s, 6H).

Step 4. Synthesis of 4-{8-[(8-chloro-4,4-dimethyl-3,4-dihydro-2H-thiochromen-6-yl)methyl]-2-oxo-1-oxa-3,8-diazaspiro[4.5]dec-3-yl}benzoic acid, TFA salt

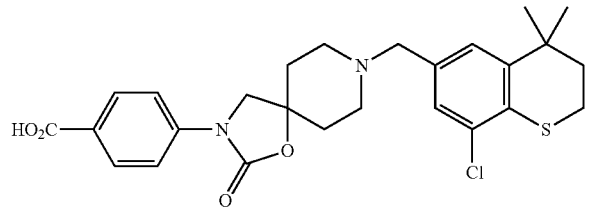

The title compound was prepared and purified according to the same experimental procedure as in Example 5-19, Step 4. LCMS (m/e): 501.

Example 5-30

4-{8-[(8-Cyclopropyl-4,4-dimethyl-3,4-dihydro-2H-thiochromen-6-yl)methyl]-2-oxo-1-oxa-3,8-diazaspiro[4.5]dec-3-yl}benzoic acid, TFA salt

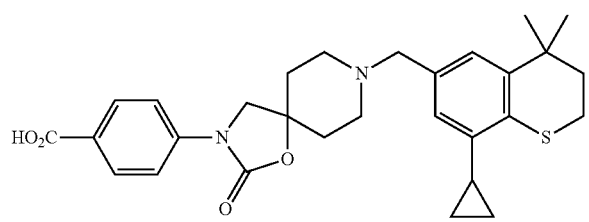 [SMILES: CC1(C)CCSc2c(C3CC3)cc(CN3CCC4(CC3)CN(c3ccc(C(=O)O)cc3)C(=O)O4)cc21]

Step 1. Synthesis of 8-cyclopropyl-4,4-dimethyl-3,4-dihydro-2H-thiochromene-6-carbaldehyde

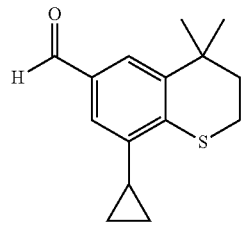 [SMILES: CC1(C)CCSc2c(C3CC3)cc(C=O)cc21]

Using essentially the same procedure as Example 5-22, Step 4, Pd(OAc)₂ (5.18 mg, 0.02 mmol), X-Phos (22.0 mg, 0.05 mmol), potassium carbonate (319 mg, 2.30 mmol), potassium cyclopropyltrifluoroborate (125 mg, 0.84 mmol), and 8-chloro-4,4-dimethyl-3,4-dihydro-2H-thiochromene-6-carbaldehyde (185 mg, 0.77 mmol, Example 5-29, Step 3) afforded the desired product as a yellow oil.

¹H-NMR (CDCl₃, 500 MHz): δ 9.88 (s, 1H), 7.77 (d, J=1.7 Hz, 1H), 7.39 (d, J=1.0 Hz, 1H), 3.10-3.13 (m, 2H), 1.98-2.02 (m, 2H), 1.84-1.91 (m, 1H), 1.41 (s, 6H), 1.02 (ddd, J=10.8 Hz, 6.3 Hz, 4.6 Hz, 2H), 0.72 (ddd, J=9.9 Hz, 5.9 Hz, 4.4 Hz, 2H).

Step 2. Synthesis of 4-{8-[(8-cyclopropyl-4,4-dimethyl-3,4-dihydro-2H-thiochromen-6-yl)methyl]-2-oxo-1-oxa-3,8-diazaspiro[4.5]dec-3-yl}benzoic acid, TFA salt

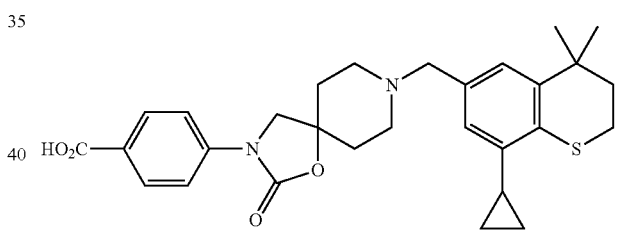

The title compound was prepared and purified according to the same experimental procedure as in Example 5-19, Step 4. LCMS (m/e): 507.

Example 5-31

4-{8-[(4,4-Dimethyl-1,1-dioxido-3,4-dihydro-2H-thiochromen-6-yl)methyl]-2-oxo-1-oxa-3,8-diazaspiro[4.5]dec-3-yl}benzoic acid, TFA salt

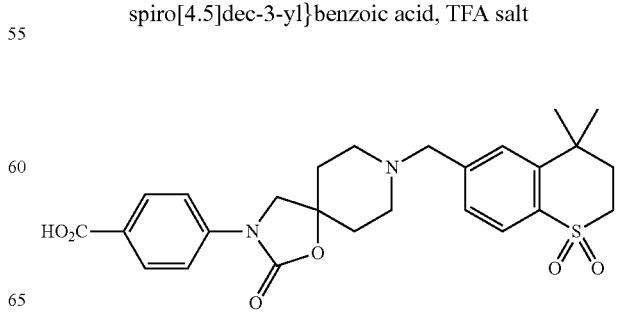

Step 1. Synthesis of 4,4-dimethyl-3,4-dihydro-2H-thiochromene-6-carbaldehyde 1-oxide

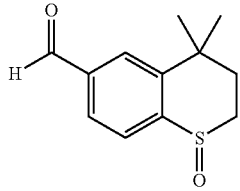

4,4-Dimethyl-3,4-dihydro-2H-thiochromene-6-carbaldehyde (449 mg, 2.18 mmol, Example 5-28, Step 2) was dissolved in dichloromethane (22.0 mL) and mCPBA (751 mg, 4.35 mmol) was added in one portion. The reaction mixture was stirred at room temperature for 30 minutes. The mixture was then diluted with dichloromethane, washed with saturated aqueous NaHCO3, saturated aqueous NaCl, dried over Na2SO4, filtered and concentrated under vacuum. The crude mixture was purified by silica gel chromatography eluting with 0-5% MeOH/dichloromethane to afford the desired product as a colorless oil.

$^1$H-NMR (CDCl$_3$, 500 MHz): δ 8.00 (d, J=7.8 Hz, 1H), 7.98 (d, J=1.3 Hz, 1H), 7.87 (dd, J=8.0 Hz, 1.5 Hz, 1H), 3.33 (ddd, J=12.4 Hz, 9.6 Hz, 2.4 Hz, 1H), 3.16 (ddd, J=12.5 Hz, 9.9 Hz, 2.4 Hz, 1H), 2.41 (ddd, J=15.2 Hz, 9.6 Hz, 2.3 Hz, 1H), 1.99 (ddd, J=15.1 Hz, 9.8 Hz, 2.3 Hz, 1H), 1.52 (s, 3H), 1.40 (s, 3H).

LCMS (m/e): 223.

Step 2. Synthesis of 4,4-dimethyl-3,4-dihydro-2H-thiochromene-6-carbaldehyde 1,1-dioxide

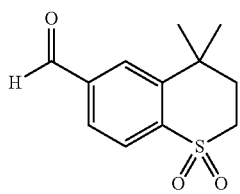 [SMILES: CC1(C)CCS(=O)(=O)c2ccc(C=O)cc21]

A solution of 4,4-dimethyl-3,4-dihydro-2H-thiochromene-6-carbaldehyde 1-oxide (148 mg, 0.67 mmol) in ethanol (5.94 mL): THF (2.40 mL) and hydrogen peroxide (2.33 mL, 26.6 mmol, 35 wt. % in water) was treated with ammonium molybdate (26.1 mg, 0.13 mmol) at room temperature. The mixture was stirred at room temperature for 80 minutes before being diluted with dichloromethane (30.0 mL) and saturated aqueous NH$_4$Cl (5.00 mL). The organic layer was separated, and the aqueous layer was extracted with dichloromethane (2×, 30.0 mL). The combined organic layers were dried over Na$_2$SO$_4$, filtered and concentrated under vacuum. The crude mixture was purified by silica gel chromatography eluting with 0-5% MeOH/dichloromethane to give the desired product as a white solid.

$^1$H-NMR (CDCl$_3$, 500 MHz): δ 8.12 (d, J=8.1 Hz, 1H), 7.98 (d, J=1.2 Hz, 1H), 7.91 (dd, J=8.1 Hz, 1.4 Hz, 1H), 3.45-3.50 (m, 2H), 2.45-2.50 (m, 2H), 1.50 (s, 6H).

LCMS (m/e): 239.

Step 3. Synthesis of 4-{8-[(4,4-dimethyl-1,1-dioxido-3,4-dihydro-2H-thiochromen-6-yl)methyl]-2-oxo-1-oxa-3,8-diazaspiro[4.5]dec-3-yl}benzoic acid, TFA salt

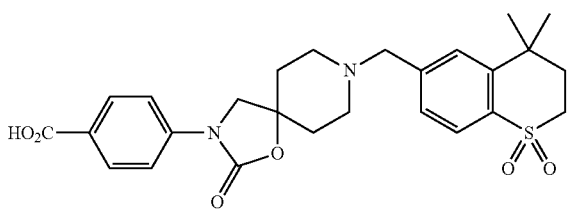 [SMILES: CC1(C)CCS(=O)(=O)c2ccc(CN3CCC4(CC3)CN(c3ccc(C(=O)O)cc3)C(=O)O4)cc21]

The title compound was prepared and purified according to the same experimental procedure as in Example 5-19, Step 4.

LCMS (m/e): 499.

Example 6-1

4-{8-[(5-Fluoro-1H-indazol-3-yl)methyl]-2-oxo-1-oxa-3,8-diazaspiro[4.5]dec-3-yl}benzoic acid, TFA salt

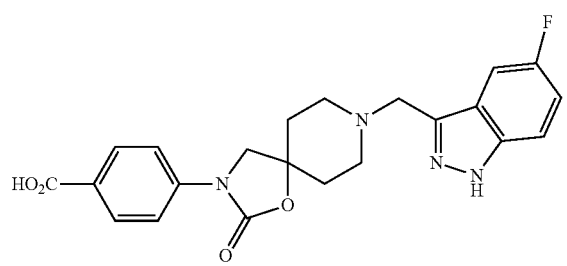 [SMILES: O=C(O)c1ccc(N2CC3(CCN(Cc4n[nH]c5ccc(F)cc45)CC3)OC2=O)cc1]

Triethylamine (9.29 mg, 0.02 mmol) was added to a stirred room temperature mixture of methyl 4-(2-oxo-1-oxa-3,8-diazaspiro[4.5]dec-3-yl)benzoate hydrochloride (30 mg, 0.09 mmol) in methanol (3.0 mL) and the mixture was stirred at room temperature for 5 minutes. Tert-butyl 5-fluoro-3-formyl-1H-indazole-1-carboxylate (24.2 mg, 0.09 mmol) was added to the reaction mixture followed by decaborane (3.3 mg, 0.03 mmol) and the reaction mixture was stirred for 16 hours at room temperature. The solution was concentrated and the residue partitioned between ethyl acetate (2×15 mL) and saturated sodium bicarbonate (10 mL), washed with brine (10 mL), dried over sodium sulfate, filtered and concentrated under reduced pressure. The residue was dissolved in methanol (1.0 mL) and potassium hydroxide (0.149 mL, 2N, 0.298 mmol) was added. The reaction mixture was heated at 65° C. for 4 hours. It was cooled to room temperature and concentrated. Water (1 mL) followed by trifluoroacetic acid (0.3 mL) was added to the residue followed by acetonitrile (2 mL). The solution was purified by HPLC reverse phase (C-18), eluting with acetonitrile/water+0.1% TFA, to give the title compound (25 mg) as a colorless solid after lypholization (acetonitrile/water).

$^1$H NMR (CD$_3$OD): δ 8.03 (d, J=8.5 Hz, 2H), 7.68 (d, J=8.5 Hz, 2H), 7.65-7.60 (m, 1H), 7.52-7.48 (m, 1H), 7.32-7.28 (m, 1H), 4.79 (s, 2H), 4.02 (s, 2H), 3.72-3.62 (m, 2H), 3.54-3.42 (m, 2H), 2.45-2.32 (m, 2H), 2.30-2.15 (m, 2H).

LCMS (m/e): 425 (M+1).

Example 6-2

4-{8-[(6-Methoxy-1H-indazol-3-yl)methyl]-2-oxo-1-oxa-3,8-diazaspiro[4.5]dec-3-yl}benzoic acid, TFA salt

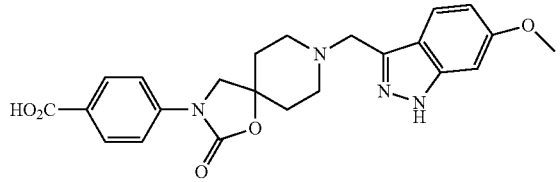 [SMILES: COc1ccc2c(CN3CCC4(CC3)CN(c3ccc(C(=O)O)cc3)C(=O)O4)n[nH]c2c1]

Triethyl amine (9.29 mg, 0.02 mmol) was added to a stirred room temperature mixture of methyl 4-(2-oxo-1-oxa-3,8-diazaspiro[4.5]dec-3-yl)benzoate hydrochloride (30 mg, 0.09 mmol) in methanol (3.0 mL) and the mixture was stirred at room temperature for 5 minutes. Tert-butyl 6-methoxy-3-formyl-1H-indazole-1-carboxylate (24.2 mg, 0.09 mmol) was added to the reaction mixture followed by decaborane (3.3 mg, 0.03 mmol) and the mixture was stirred for 16 hours at room temperature. The solution was concentrated under reduced pressure and the residue partitioned between ethyl acetate (2×15 mL) and saturated sodium bicarbonate (10 mL), washed with brine (10 mL), dried over sodium sulfate, filtered and concentrated under reduced pressure. The residue was dissolved in methanol (1.0 mL) and potassium hydroxide (0.149 mL, 0.298 mmol) was added. The reaction mixture was heated at 65° C. for 4 hours. It was cooled to room temperature and concentrated. Water (1 mL) followed by trifluoroacetic acid (0.3 mL) was added to the residue followed by acetonitrile (2 mL). The solution was purified by HPLC reverse phase (C-18) eluting with acetonitrile/water+0.1% TFA, to give the title compound (30 mg) as a colorless solid after lypholization (acetonitrile/water).

$^1$H NMR (CD$_3$OD): δ 8.03 (d, J=8.5 Hz, 2H), 7.74 (d, J=8.9 Hz, 1H), 7.68 (d, J=8.5 Hz, 2H), 7.0 (s, 1H), 6.92-6.90 (m, 1H), 4.75 (s, 2H), 4.00 (s, 2H), 3.87 (s, 3H), 3.84 (s, 1H), 3.78-3.70 (m, 2H), 3.58-3.50 (m, 2H), 2.40-2.30 (m, 2H), 2.32-2.20 (m, 2H).

LCMS (m/e): 437.01 (M+1)$^+$.

Example 6-3

4-{8-[(6-Methoxy-1-propyl-1H-indazol-3-yl)methyl]-2-oxo-1-oxa-3,8-diazaspiro[4.5]dec-3-yl}benzoic acid, TFA salt

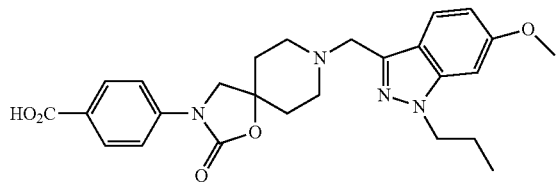 [SMILES: CCCn1nc(CN2CCC3(CC2)CN(c2ccc(C(=O)O)cc2)C(=O)O3)c2ccc(OC)cc21]

Step 1. Synthesis of 6-methoxy-1-propyl-1H-indazole-3-carbaldehyde

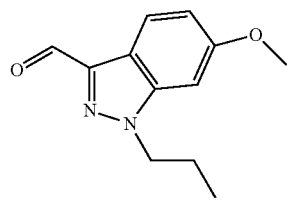 [SMILES: CCCn1nc(C=O)c2ccc(OC)cc21]

A solution of 2 M HCl in dioxane (0.47 mL, 0.94 mmol) was added to a stirred, room temperature mixture of tert-butyl 3-formyl-6-methoxy-1H-indazole-1-carboxylate (50 mg, 0.18 mmol) in dioxane (1 mL) and the mixture was stirred at room temperature for 8 hours. It was concentrated and dried under vacuum. To the residue in DMF (1.0 mL), DBU (0.08 mL, 0.54 mmol) was added and the reaction mixture was stirred for 30 minutes. Then 1-iodopropane (0.09 mL, 0.90 mmol) was added and the solution was stirred for 16 hours at room temperature. The solvent was removed in vacuo and the residue was partitioned between ethyl acetate (20 mL) and saturated sodium bicarbonate (5 mL), washed with brine, dried over sodium sulfate, filtered and concentrated under reduced pressure to give the title compound (25 mg, 63% crude yield).

LCMS (m/e): 219.13 (M+1).

Step 2. Synthesis of 4-{8-[(6-methoxy-1-propyl-1H-indazol-3-yl)methyl]-2-oxo-1-oxa-3,8-diazaspiro[4.5]dec-3-yl}benzoic acid, TFA salt

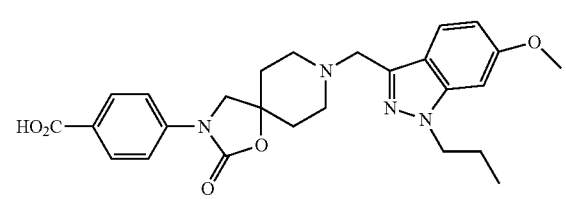 [SMILES: CCCn1nc(CN2CCC3(CC2)CN(c2ccc(C(=O)O)cc2)C(=O)O3)c2ccc(OC)cc21]

Triethylamine (9.29 mg, 0.02 mmol) was added to a stirred room temperature mixture of methyl 4-(2-oxo-1-oxa-3,8-diazaspiro[4.5]dec-3-yl)benzoate hydrochloride (30 mg, 0.09 mmol) in methanol (3.0 mL) and the mixture was stirred at room temperature for 5 minutes. 6-Methoxy-1-propyl-1H-indazole-3-carbaldehyde (20 mg, 0.09 mmol) was added to the reaction mixture followed by decaborane (3.3 mg, 0.03 mmol) and the mixture was stirred for 16 hours at room temperature. The solution was concentrated under reduced pressure and the residue partitioned between ethyl acetate (2×15 mL) and saturated sodium bicarbonate (10 mL), washed with brine (10 mL), dried over sodium sulfate, filtered and concentrated under reduced pressure. The residue was dissolved in methanol (1.0 mL) and potassium hydroxide (0.149 mL, 2N, 0.298 mmol) was added. The reaction mixture was heated at 65° C. for 4 hours. It was cooled to room temperature and concentrated. Water (1 mL) followed by trifluoroacetic acid (0.3 mL) was added to the residue followed by acetonitrile (2 mL). The solution was purified by HPLC reverse phase (C-18) eluting with acetonitrile/water+0.1% TFA to give the title compound which was isolated as a TFA salt (35 mg) as a colorless solid after lypholization (acetonitrile/water).

$^1$H NMR (CDCl$_3$): δ 7.97 d, J=8.7 Hz, 2H), 7.63 (d, J=9.0 Hz, 1H), 7.49 (d, J=8.7 Hz, 2H), 6.85 (d, J=8.9 Hz, 1H), 6.71 (s, 1H), 4.50 (s, 2H), 4.30-4.25 (m, 2H), 3.82 (s, 2H), 3.72 (s, 3H), 3.52-3.50 (m, 2H), 3.30 (s, 2H), 3.40-3.20 (m, 2H), 2.60-2.50 (m, 2H), 2.20 (d, J=9.0 Hz, 1H), 1.9-1.70 (m, 2H), 0.98 (t, J=7.5 Hz, 3H).

LCMS (m/e): 479.04 (M+1)$^+$.

Example 6-4

4-{8-[(1-Butyl-5-fluoro-1H-indazol-3-yl)methyl]-2-oxo-1-oxa-3,8-diazaspiro[4.5]dec-3-yl}benzoic acid, TFA salt

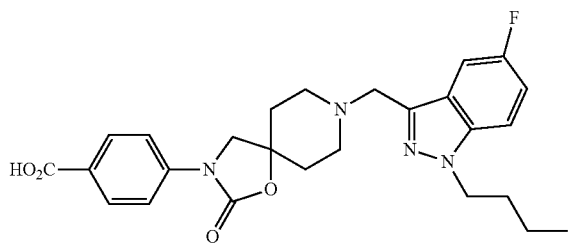 [SMILES: CCCCn1nc(CN2CCC3(CC2)CN(c2ccc(C(=O)O)cc2)C(=O)O3)c2cc(F)ccc21]

The title compound was prepared and purified using essentially the same experimental procedures in Example 6-3 and was isolated as a TFA salt.

LCMS (m/e): 481 (M+1).

Example 6-5

4-(8-{[5-Fluoro-1-(propan-2-yl)-1H-indazol-3-yl]methyl}-2-oxo-1-oxa-3,8-diazaspiro[4.5]dec-3-yl)benzoic acid, TFA salt

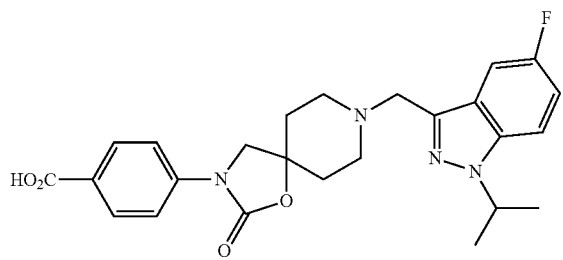 [SMILES: CC(C)n1nc(CN2CCC3(CC2)CN(c2ccc(C(=O)O)cc2)C(=O)O3)c2cc(F)ccc21]

The title compound was prepared and purified using essentially the same experimental procedures in Example 6-3 and was isolated as a TFA salt.

LCMS (m/e): 467 (M+1).

Example 6-6

4-(8-{[6-Methoxy-1-(propan-2-yl)-1H-indazol-3-yl]methyl}-2-oxo-1-oxa-3,8-diazaspiro[4.5]dec-3-yl)benzoic acid, TFA salt

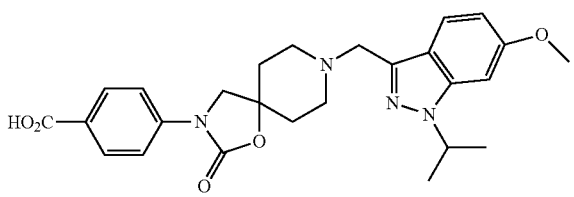

Step 1. Synthesis of 6-methoxy-1-(propan-2-yl)-1H-indole-3-carbaldehyde

Cesium carbonate (577 mg, 1.77 mmol) was added to a stirred room temperature solution of 6-methoxy-1H-indole-3-carbaldehyde (104 mg, 0.590 mmol) in DMF (1.0 mL) and the mixture was stirred at room temperature for 15 minutes when 2-iodopropane (0.118 mg, 1.181 mmol) was added. The solution was stirred at 80° C. for 2 hours. The solvent was removed under reduced pressure and the residue was partitioned between ethyl acetate (2×20 mL) and saturated sodium bicarbonate (5 mL), washed with brine (10 mL), dried over sodium sulfate, filtered and concentrated to give the title intermediate (120 mg).

LCMS (m/e): 219.13 (M+1).

Step 2. Synthesis of 4-(8-{[6-methoxy-1-(propan-2-yl)-1H-indazol-3-yl]methyl}-2-oxo-1-oxa-3,8-diazaspiro[4.5]dec-3-yl)benzoic acid, TFA salt

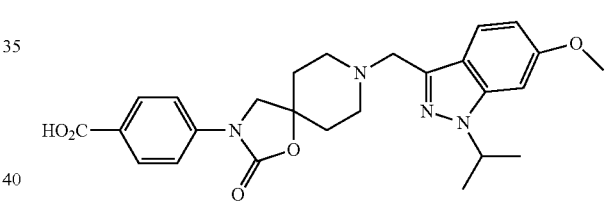

Triethylamine (9.29 mg, 0.02 mmol) was added to a stirred room temperature mixture of methyl 4-(2-oxo-1-oxa-3,8-diazaspiro[4.5]dec-3-yl)benzoate hydrochloride (30 mg, 0.09 mmol) in methanol (3.0 mL) and the mixture was stirred at room temperature for 5 minutes. 6-Methoxy-1-(propan-2-yl)-1H-indole-3-carbaldehyde (20 mg, 0.09 mmol) was added to the reaction mixture followed by decaborane (3.3 mg, 0.03 mmol) and the mixture was stirred for 16 hours at room temperature. The solution was concentrated under reduced pressure and the residue partitioned between ethyl acetate (2×15 mL) and saturated sodium bicarbonate (10 mL), washed with brine (10 mL), dried over sodium sulfate, filtered and concentrated. The residue was dissolved in methanol (1.0 mL) and potassium hydroxide (0.149 mL, 2N, 0.298 mmol) was added. The reaction mixture was heated at 65° C. for 4 hours. It was cooled to room temperature and concentrated. Water (1 mL) followed by trifluoroacetic acid (0.3 mL) was added to the residue followed by acetonitrile (2 mL). The solution was purified by HPLC reverse phase (C-18) eluting with acetonitrile/water+0.1% TFA to give the title compound (25 mg) as a colorless solid after lypholization (acetonitrile/water).

$^1$H NMR (CDCl$_3$): δ 8.05 (d, J=8.7 Hz, 2H), 7.73 (d, J=8.9 Hz, 1H), 7.69 (d, J=8.7 Hz, 2H), 7.07 (s, 1H), 6.92 (d, J=8.9 Hz, 1H), 4.99-4.97 (m, 1H), 4.74 (s, 2H), 4.02 (s, 2H), 3.91 (s,

3H), 3.75-3.68 (m, 2H), 3.64-3.59 (m, 2H), 2.40-2.35 (m, 2H), 2.32-2.20 (m, 2H), 1.59 (d, J=6.9 Hz, 6H).
LCMS (m/e): 479.12 (M+1).

Example 6-7

4-{8-[(6-Cyano-1-propyl-1H-indazol-3-yl)methyl]-2-oxo-1-oxa-3,8-diazaspiro[4.5]dec-3-yl}benzoic acid, TFA salt

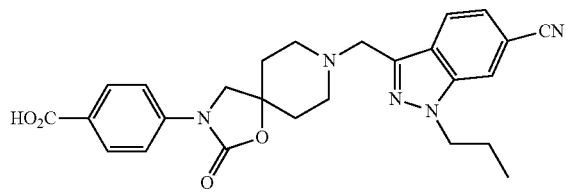 [SMILES: CCCn1nc(CN2CCC3(CC2)CN(c2ccc(C(=O)O)cc2)C(=O)O3)c2ccc(C#N)cc21]

The title compound was prepared and purified using essentially the same experimental procedures in Example 6-6 and was isolated as a TFA salt.
LCMS (m/e): 474 (M+1).

Example 6-8

4-(8-{[6-Carbamoyl-1-(propan-2-yl)-1H-indazol-3-yl]methyl}-2-oxo-1-oxa-3,8-diazaspiro[4.5]dec-3-yl)benzoic acid, TFA salt

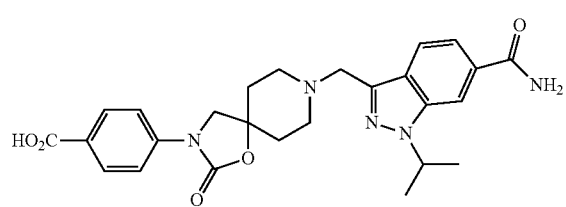 [SMILES: CC(C)n1nc(CN2CCC3(CC2)CN(c2ccc(C(=O)O)cc2)C(=O)O3)c2ccc(C(N)=O)cc21]

The title compound was prepared and purified using essentially the same experimental procedures in Example 6-6 and was isolated as a TFA salt.
LCMS (m/e): 493 (M+1).

Example 6-9

4-(8-{[6-Cyano-1-(propan-2-yl)-1H-indazol-3-yl]methyl}-2-oxo-1-oxa-3,8-diazaspiro[4.5]dec-3-yl)benzoic acid, TFA salt

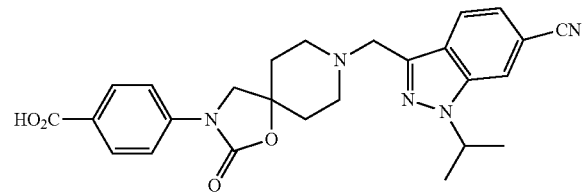 [SMILES: CC(C)n1nc(CN2CCC3(CC2)CN(c2ccc(C(=O)O)cc2)C(=O)O3)c2ccc(C#N)cc21]

The title compound was prepared and purified using essentially the same experimental procedures in Example 6-6 and was isolated as a TFA salt.
LCMS (m/e): 474 (M+1).

Example 6-10

4-(8-{[1-(2,2-Dimethylpropyl)-5-fluoro-1H-indazol-3-yl]methyl}-2-oxo-1-oxa-3,8-diazaspiro[4.5]dec-3-yl)benzoic acid, TFA salt

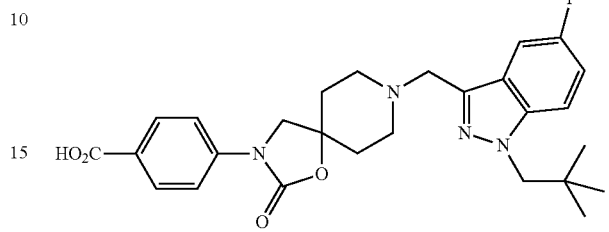

The title compound was prepared and purified using essentially the same experimental procedures in Example 6-6 and was isolated as a TFA salt.
LCMS (m/e): 495 (M+1).

Example 6-11

4-(8-{[1-(2,2-Dimethylpropyl)-6-methoxy-1H-indazol-3-yl]methyl}-2-oxo-1-oxa-3,8-diazaspiro[4.5]dec-3-yl)benzoic acid, TFA salt

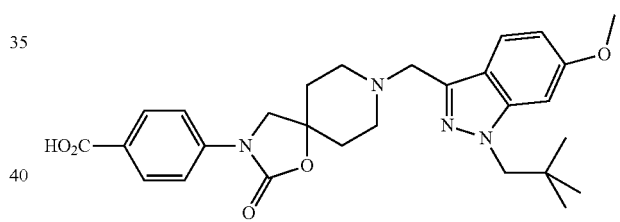

The title compound was prepared and purified using essentially the same experimental procedures in Example 6-6 and was isolated as a TFA salt.
LCMS (m/e): 507 (M+1).

Example 6-12

4-{8-[(1-Cyclopropyl-6-methoxy-1H-indazol-3-yl)methyl]-2-oxo-1-oxa-3,8-diazaspiro[4.5]dec-3-yl}benzoic acid, TFA salt

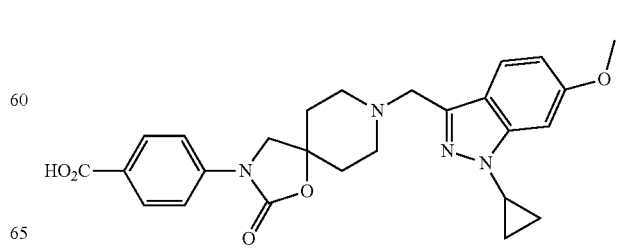

Step 1. Synthesis of 1-cyclopropyl-6-methoxy-1H-indole-3-carbaldehyde

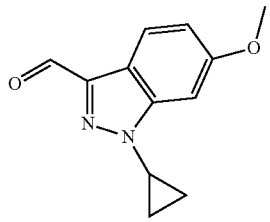 [SMILES: COc1ccc2c(C=O)nn(C3CC3)c2c1]

Dihydroxo-bis[N,N,N',N'-tetramethylenediamine)copper (II) chloride (26 mg, 0.057 mmol) was added to a stirred room temperature mixture of 6-methoxy-1H-indole-3-carbaldehyde (100 mg, 0.568 mmol) and cyclopropylboronic acid (98 mg, 1.13 mmol) in dichloromethane (3 mL). Molecular sieves (4 A°, 100 mg) were added and the mixture was stirred under oxygen at room temperature for 48 hours. The reaction mixture was filtered over a pad of silica gel, washed with dichloromethane, partitioned between dichloromethane (10 mL) and 10% ammonium hydroxide (2×10 mL). The organic layer was washed with water (10 mL) and brine (10 mL). The organic layer was dried over sodium sulfate, filtered and concentrated under reduced pressure. The residue was purified by flash chromatography (Biotage 25 M), eluting with EtOAc/hexanes to give the title compound (50 mg) as a oil.
LCMS (m/e): 217.05 (M+1)$^+$.

Step 2. Synthesis of 4-{8-[(1-cyclopropyl-6-methoxy-1H-indazol-3-yl)methyl]-2-oxo-1-oxa-3,8-diazaspiro[4.5]dec-3-yl}benzoic acid, TFA salt

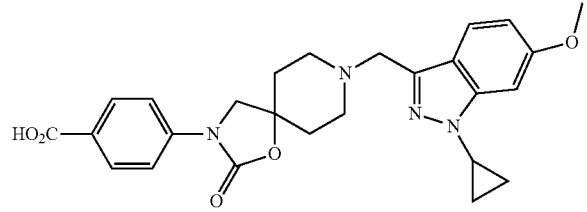 [SMILES: COc1ccc2c(CN3CCC4(CC3)CN(c3ccc(C(=O)O)cc3)C(=O)O4)nn(C3CC3)c2c1]

To a solution of 1-cyclopropyl-6-methoxy-1H-indole-3-carbaldehyde (20 mg, 0.096 mmol) and 4-(2-oxo-1-oxa-3,8-diazaspiro[4.5]dec-3-yl)benzoic acid hydrochloride (30 mg, 0.096 mmol) in DMSO (3.0 mL) was added acetic acid (0.016 mL, 0.288 mmol) and the mixture was stirred at room temperature for 15 minutes. Then sodium triacetoxyborohydride (81 mg, 0.384 mmol) was added and the solution was stirred at 65° C. for 2 hours. The reaction mixture was cooled to room temperature and water (1.0 mL) was added. After 5 minutes, TFA (0.3 mL) was added to the reaction mixture to give a clear solution. The solution was purified by HPLC reverse phase (C-18), eluting with acetonitrile/water+0.1% TFA, to give the title compound as a colorless solid after lypholization (acetonitrile/water).
$^1$H NMR (CD$_3$OD): δ 8.05 (d, J=8.7 Hz, 2H), 7.74 (d, J=9.0 Hz, 1H), 7.69 (d, J=8.7 Hz, 2H), 7.12 (s, 1H), 6.95 (d, 1H, J=9.0 Hz), 4.70 (s, 2H), 4.03 (s, 2H), 3.93 (s, 3H), 3.63-3.61 (m, 2H), 3.39-3.7 (m, 2H), 2.36-2.33 (m, 2H), 2.19-2.16 (2H), 1.22-1.20 (m, 4H).
LCMS (m/e): 474.04 (M+1).

Example 6-13

4-{8-[(6-Methoxy-1-phenyl-1H-indazol-3-yl)methyl]-2-oxo-1-oxa-3,8-diazaspiro[4.5]dec-3-yl}benzoic acid, TFA salt

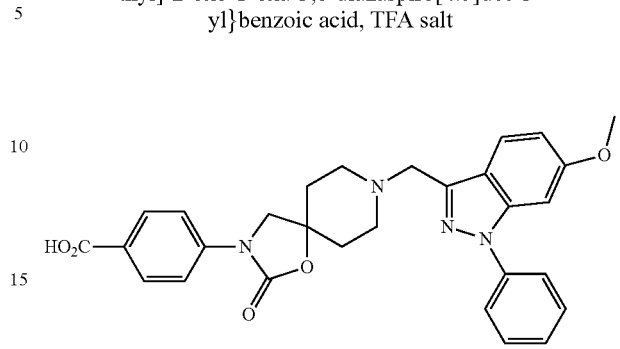

The title compound was prepared and purified using essentially the same experimental procedures in Example 6-12 and was isolated as a TFA salt.
LCMS (m/e): 513 (M+1).

Example 6-14

4-(8-{[5-(Benzyloxy)-1-(propan-2-yl)-1H-indazol-3-yl]methyl}-2-oxo-1-oxa-3,8-diazaspiro[4.5]dec-3-yl)benzoic acid, TFA salt

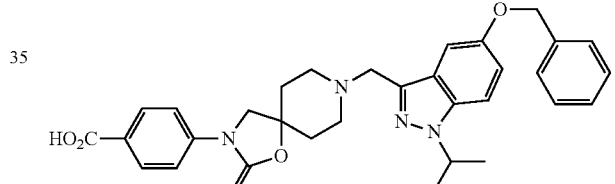

The title compound was prepared and purified using essentially the same experimental procedures in Example 6-6 and was isolated as a TFA salt.
LCMS (m/e): 555 (M+1).

Example 6-15

4-(8-{[1-(3,3-Dimethyl-2-oxobutyl)-6-methoxy-1H-indazol-3-yl]methyl}-2-oxo-1-oxa-3,8-diazaspiro[4.5]dec-3-yl)benzoic acid, TFA salt

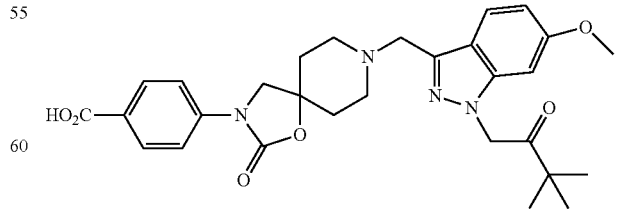

The title compound was prepared and purified using essentially the same experimental procedures in Example 6-6 and was isolated as a TFA salt.
LCMS (m/e): 535 (M+1).

Example 6-16

4-(8-{[6-Methoxy-1-(propan-2-yl)-1H-indol-3-yl]methyl}-2-oxo-1-oxa-3,8-diazaspiro[4.5]dec-3-yl)benzoic acid, TFA salt

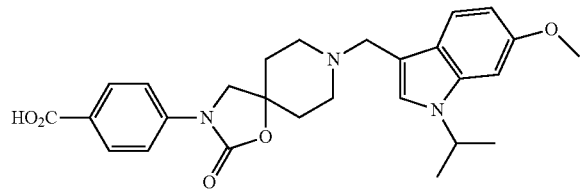

Step 1. Synthesis of 6-methoxy-1-(propan-2-yl)-1H-indole-3-carbaldehyde

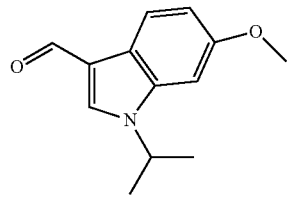 [SMILES: COc1ccc2c(C=O)cn(C(C)C)c2c1]

Cesium carbonate (558 mg, 1.71 mmol) was added to a stirred room temperature of 6-methoxy-1H-indole-3-carbaldehyde (100 mg, 0.57 mmol) in DMF (1.0 mL) and the mixture was stirred at room temperature for 15 minutes. Then 2-iodopropane (0.114 mL, 1.14 mmol) was added and the solution was stirred for 80° C. for 2 hours. The solution was concentrated under reduced pressure and the residue was partitioned between ethyl acetate (2×15 mL) and saturated sodium bicarbonate (5 mL), washed with brine (10 mL), dried over sodium sulfate, filtered and concentrated under reduced pressure to give the crude title intermediate (108 mg).

LCMS (m/e): 218.13 (M+1).

Step 2. Synthesis of 4-(8-{[6-methoxy-1-(propan-2-yl)-1H-indol-3-yl]methyl}-2-oxo-1-oxa-3,8-diazaspiro[4.5]dec-3-yl)benzoic acid, TFA salt

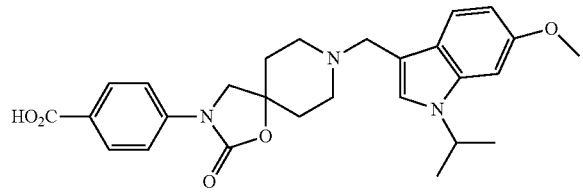 [SMILES: COc1ccc2c(CN3CCC4(CC3)CN(c3ccc(C(=O)O)cc3)C(=O)O4)cn(C(C)C)c2c1]

To a solution of 6-methoxy-1-(propan-2-yl)-1H-indole-3-carbaldehyde (35 mg, 0.16 mmol) and 4-(2-oxo-1-oxa-3,8-diazaspiro[4.5]dec-3-yl)benzoic acid hydrochloride (50 mg, 0.16 mmol) in DMSO (3.0 mL) was added acetic acid (0.03 mL, 0.48 mmol) and the mixture was stirred at room temperature for 15 minutes. Then sodium triacetoxyborohydride (136 mg, 0.64 mmol) was added and the solution was stirred at 65° C. for 2 hours. The reaction mixture was cooled to room temperature and water (1.0 mL) was added. After 5 minutes, TFA (0.3 mL) was added to the reaction mixture to give a clear solution. The solution was purified by HPLC reverse phase (C-18), eluting with acetonitrile/water+0.1% TFA, to give the title compound as a colorless solid after lypholization (acetonitrile/water).

$^1$H NMR (CD$_3$OD): δ 8.03 (d, J=8.7 Hz, 2H), 7.68 (d, J=8.7 Hz, 2H), 7.62 (d, J=8.7 Hz, 1H), 7.55 (s, 1H), 7.03 (s, 1H), 6.87 (d, J=81 Hz, 1H), 4.75 (m, 1H), 4.6 (s, 2H), 4.03 (s, 2H), 3.87 (s, 3H), 3.63-3.61 (m, 2H), 3.39-3.7 (m, 2H), 2.36-2.33 (m, 2H), 2.19-2.16 (2H), 1.55 (d, J=6.7 Hz, 6H).

LCMS (m/e): 478.18 (M+1).

Example 6-17

4-{8-[(1-tert-Butyl-5-chloro-6-fluoro-1H-indazol-3-yl)methyl]-2-oxo-1-oxa-3,8-diazaspiro[4.5]dec-3-yl}benzoic acid, TFA salt

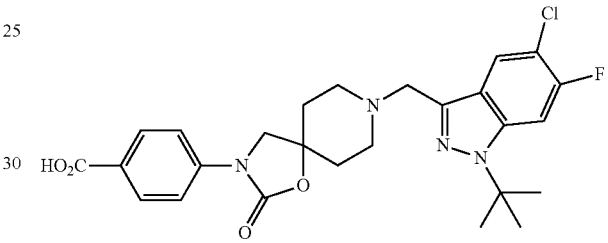

Step 1. Synthesis of 1-tert-butyl-5-chloro-6-fluoro-3-methyl-1H-indazole

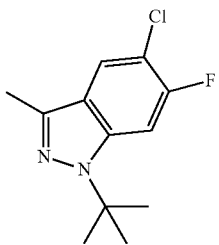 [SMILES: Cc1nn(C(C)(C)C)c2cc(F)c(Cl)cc12]

DBU (4.75 mL, 31.5 mmol) was added to a stirred room temperature mixture of t-butyl hydrazine hydrochloride (3.92 g, 31.5 mmol) and the mixture was stirred at room temperature for 15 minutes. Then 1-(4-chloro-2,5-difluorophenyl)ethanone (1.0 g, 5.25 mmol), potassium carbonate (1.08 g, 7.87 mmol) and cupric oxide (8.35 mg, 0.105 mmol) were added and the solution was heated at 110° C. for 16 hours. The solution was cooled to room temperature, partitioned between ethyl acetate (2×20 mL) and saturated sodium bicarbonate (10 mL). The organic layer was dried over sodium sulfate, filtered and concentrated under reduced pressure. The residue was purified by column chromatography on silica gel (Biotage 25 M) eluting with EtOAc/hexanes to give the title compound (852 mg) as a yellow solid.

Step 2. Synthesis of 3-(bromomethyl)-1-tert-butyl-5-chloro-6-fluoro-1H-indazole

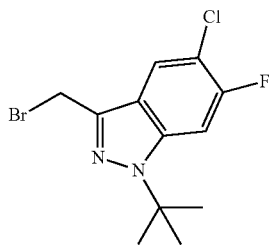 [SMILES: CC(C)(C)n1nc(CBr)c2cc(Cl)c(F)cc21]

To 1-tert-butyl-5-chloro-6-fluoro-3-methyl-1H-indazole (153 mg, 0.636 mmol) in dichloroethane (3.0 mL) were added AIBN (20.88 mg, 0.127 mmol) and NBS (124 mg, 0.699 mmol) and the reaction mixture was refluxed under a sunlamp for 3 hours. The reaction was cooled to room temperature and after filtering through a pad of celite, the solution was concentrated under reduced pressure. The residue was partitioned between ethyl acetate (2×15 mL) and water (10 mL), washed with saturated sodium bicarbonate (15 mL), brine (10 mL) and dried over sodium sulfate. The solution was filtered and concentrated under reduced pressure to give a mixture of the title compound and 1-tert-butyl-5-chloro-3-(dibromomethyl)-6-fluoro-1H-indazole (168 mg).

Step 3. Synthesis of 4-{8-[(1-tert-butyl-5-chloro-6-fluoro-1H-indazol-3-yl)methyl]-2-oxo-1-oxa-3,8-diazaspiro[4.5]dec-3-yl}benzoic acid, TFA salt

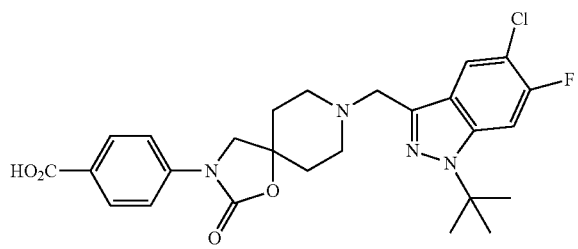 [SMILES: CC(C)(C)n1nc(CN2CCC3(CC2)CN(c2ccc(C(=O)O)cc2)C(=O)O3)c2cc(Cl)c(F)cc21]

To the above crude mixture of 3-(bromomethyl)-1-tert-butyl-5-chloro-6-fluoro-1H-indazole and 1-tert-butyl-5-chloro-3-(dibromomethyl)-6-fluoro-1H-indazole (52 mg, 0.162 mmol),) and methyl 4-(2-oxo-1-oxa-3,8-diazaspiro[4.5]dec-3-yl)benzoate hydrochloride (53 mg, 0.162 mmol) in THF (3M mL) was added triethylamine (0.045 mL, 0.324 mmol) and the reaction mixture was heated at 80° C. for 6 hours. It was cooled to room temperature and partitioned between ethyl acetate (2×15 mL) and saturated sodium bicarbonate (10 mL), washed with brine (10 mL), dried over sodium sulfate, filtered and concentrated under reduced pressure. The residue was dissolved in methanol (1.0 mL) and potassium hydroxide (0.243 mL, 2N, 0.487 mmol) was added. The reaction mixture was heated at 65° C. for 2 hours. It was cooled to room temperature and concentrated. Water (1 mL) followed by trifluoroacetic acid (0.3 mL) was added to the residue followed by acetonitrile (2 mL). The solution was purified by HPLC reverse phase (C-18), eluting with acetonitrile/water+0.1% TF, to give the title compound (65 mg) as a colorless solid after lypholization (acetonitrile/water).

$^1$H NMR (CD$_3$OD): δ 8.11 (d, J=8.8 Hz, 1H), 8.03 (d, J=8.8 Hz, 2H), 7.81 (d, J=8.8 Hz, 1H), 7.69 (d, J=8.8 Hz, 2H), 4.78 (s, 2H), 4.02 (s, 2H), 3.78-3.75 (m, 2H), 3.62-3.43 (m, 2H), 2.40-2.38 (m, 2H), 2.34-2.30 (m, 2H), 1.79 (s, 9H).
LCMS (m/e): 515.12 (M+1).

Example 6-18

4-(8-{[4-(Benzyloxy)-1-(propan-2-yl)-1H-indol-3-yl]methyl}-2-oxo-1-oxa-3,8-diazaspiro[4.5]dec-3-yl)benzoic acid, TFA salt

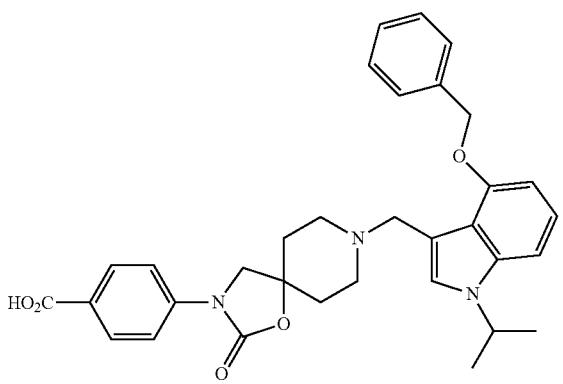 [SMILES: CC(C)n1cc(CN2CCC3(CC2)CN(c2ccc(C(=O)O)cc2)C(=O)O3)c2c(OCc3ccccc3)cccc21]

The title compound was prepared and purified using essentially the same experimental procedures in Example 6-17 and was isolated as a TFA salt.
LCMS (m/e): 554 (M+1).

Example 6-19

4-{8-[(6-Methoxy-1-methyl-1H-indol-3-yl)methyl]-2-oxo-1-oxa-3,8-diazaspiro[4.5]dec-3-yl}benzoic acid, TFA salt

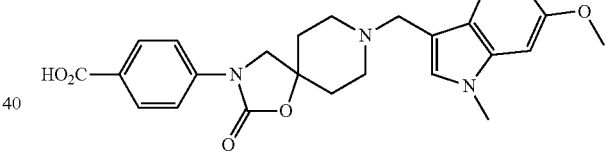

The title compound was prepared and purified using essentially the same experimental procedures in Example 6-17 and was isolated as a TFA salt.
LCMS (m/e): 450 (M+1).

Example 6-20

4-{8-[(6-Methoxy-1-propyl-1H-indol-3-yl)methyl]-2-oxo-1-oxa-3,8-diazaspiro[4.5]dec-3-yl}benzoic acid, TFA salt

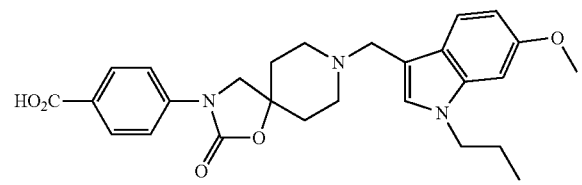 [SMILES: CCCn1cc(CN2CCC3(CC2)CN(c2ccc(C(=O)O)cc2)C(=O)O3)c2ccc(OC)cc21]

The title compound was prepared and purified using essentially the same experimental procedures in Example 6-17 and was isolated as a TFA salt.
LCMS (m/e): 478 (M+1).

Example 6-21

4-{8-[(6-Methoxy-1-butyl-1H-indol-3-yl)methyl]-2-oxo-1-oxa-3,8-diazaspiro[4.5]dec-3-yl}benzoic acid, TFA salt

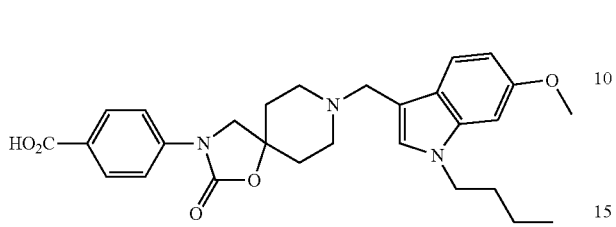

The title compound was prepared and purified using essentially the same experimental procedures in Example 6-17 and was isolated as a TFA salt.

LCMS (m/e): 492 (M+1).

Example 6-22

4-{8-[(6-Methoxy-1H-indol-3-yl)methyl]-2-oxo-1-oxa-3,8-diazaspiro[4.5]dec-3-yl}benzoic acid, TFA salt

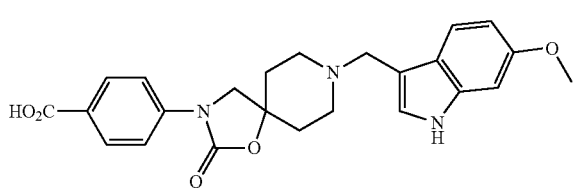 [SMILES: COc1ccc2c(CN3CCC4(CC3)CN(c3ccc(C(=O)O)cc3)C(=O)O4)c[nH]c2c1]

The title compound was prepared and purified using essentially the same experimental procedures in Example 6-17 and was isolated as a TFA salt.

LCMS (m/e): 436 (M+1).

Example 6-23

4-{8-[(6-Methoxy-1-phenyl-1H-indol-3-yl)methyl]-2-oxo-1-oxa-3,8-diazaspiro[4.5]dec-3-yl}benzoic acid, TFA salt

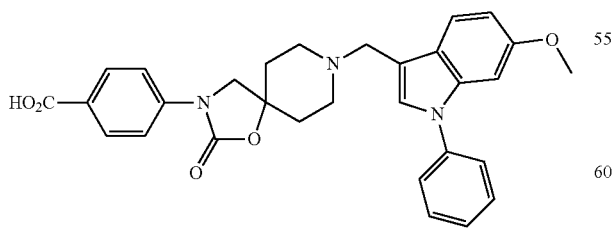

The title compound was prepared and purified using essentially the same experimental procedures in Example 6-12 and was isolated as a TFA salt.

LCMS (m/e): 512 (M+1).

Example 6-24

4-(2-Oxo-8-{[5,6,7-trifluoro-1-(propan-2-yl)-1H-indol-3-yl]methyl}-1-oxa-3,8-diazaspiro[4.5]dec-3-yl)benzoic acid, TFA salt

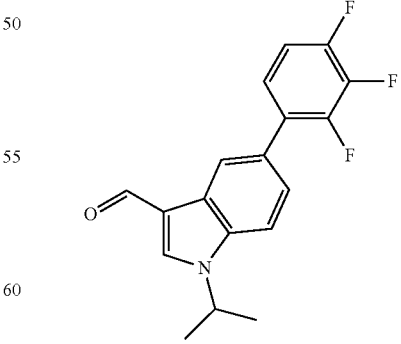

Step 1. Synthesis of 5-bromo-1-(propan-2-yl)-1H-indole-3-carbaldehyde

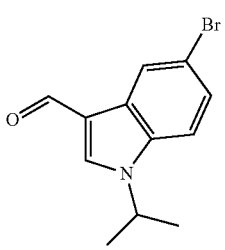

Cesium carbonate (545 mg, 1.67 mmol) was added to a stirred room temperature of 5-bromo-1H-indole-3-carbaldehyde (125 mg, 0.56 mmol) in DMF (1.0 mL) and the mixture was stirred at room temperature for 15 minutes. Then 2-iodopropane (0.112 mL, 1.116 mmol) was added and the solution was stirred at 80° C. for 2 hours. The solvent was removed under reduced pressure and the residue was partitioned between ethyl acetate (2×20 mL) and saturated sodium bicarbonate (5 mL), washed with brine (10 mL), dried over sodium sulfate, filtered and concentrated under reduced pressure to give the title compound (148 mg).

LCMS (m/e): 268.07 (M+2).

Step 2. Synthesis of 1-(propan-2-yl)-5-(2,3,4-trifluorophenyl)-1H-indole-3-carbaldehyde Sodium carbonate (0.188 mL, 2M, 0.376 mmol) was added to a stirred room temperature solution of 5-bromo-1-(propan-2-yl)-1H-indole-3-carbaldehyde (50 mg, 0.188 mmol), 2,3,4-trifluorophenylboronic acid (66 mg, 0.376 mmol) and PdCl₂(dppf) (13.7 mg, 0.019 mmol) in DMF (1.0 mL) and the reaction mixture was stirred at 80° C. for 12 hours. The reaction mixture was cooled to room temperature, partitioned between ethyl acetate (2×15 mL) and water (10 mL), washed with saturated sodium bicarbonate (10 mL), brine (10 mL), dried over sodium sulfate, filtered and concentrated under reduced pressure to give the title compound (50 mg).

LCMS (m/e): 318.14 (M+1).

Step 3. Synthesis of 4-(2-oxo-8-{[5,6,7-trifluoro-1-(propan-2-yl)-1H-indol-3-yl]methyl}-1-oxa-3,8-diazaspiro[4.5]dec-3-yl)benzoic acid, TFA salt

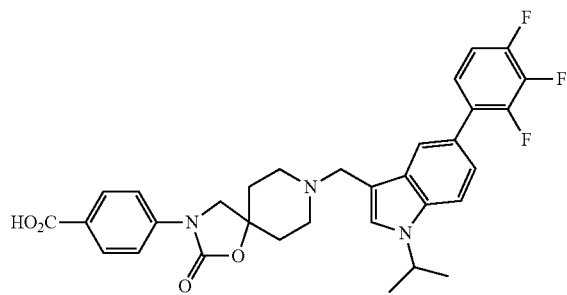 [SMILES: CC(C)n1cc(CN2CCC3(CC2)CN(c2ccc(C(=O)O)cc2)C(=O)O3)c2cc(-c3ccc(F)c(F)c3F)ccc21]

To a solution of 1-(propan-2-yl)-5-(3,4,5-trifluorophenyl)-1H-indole-3-carbaldehyde (60 mg, 0.19 mmol) and 4-(2-oxo-1-oxa-3,8-diazaspiro[4.5]dec-3-yl)benzoic acid hydrochloride (59 mg, 0.19 mmol) in DMSO (3.0 mL) was added acetic acid (0.03 mL, 0.56 mmol) and the mixture was stirred at room temperature for 15 minutes. Then sodium triacetoxyborohydride (160 mg, 0.75 mmol) was added and the solution was stirred at 65° C. for 2 hours. The reaction mixture was cooled to room temperature, and water (1.0 mL) was added. After 5 minutes, TFA (0.3 mL) was added to the reaction mixture to give a clear solution. The solution was purified by HPLC reverse phase (C-18), eluting with acetonitrile/water+0.1% TFA, to give the title compound (60 mg) as a colorless solid after lypholization (acetonitrile/water).

$^1$H NMR (CD$_3$OD): δ 8.03 (d, J=8.7 Hz, 2H), 7.95 (s, 1H), 7.77 (s, 1H), 7.67 (t, J=8.7 Hz, 2H), 7.45 (d, J=8.7 Hz, 1H), 7.40-7.32 (m, 1H), 7.24-7.16 (m, 1H), 4.62 (s, 2H), 3.95 (s, 2H), 3.70-3.62 (m, 2H), 3.48-3.39 (m, 2H), 2.38-2.32 (m, 2H), 2.22-2.15 (m, 2H), 1.60 (d, J=6.7 Hz, 6H).

LCMS (m/e): 578.15 (M+1).

Example 6-25

4-(8-{[5-Bromo-1-(propan-2-yl)-1H-indol-3-yl]methyl}-2-oxo-1-oxa-3,8-diazaspiro[4.5]dec-3-yl)benzoic acid, TFA salt

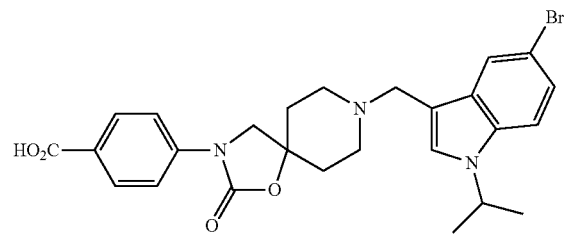 [SMILES: CC(C)n1cc(CN2CCC3(CC2)CN(c2ccc(C(=O)O)cc2)C(=O)O3)c2cc(Br)ccc21]

The title compound was prepared and purified using essentially the same experimental procedures in Example 6-17 and was isolated as a TFA salt.

LCMS (m/e): 526 (M+1).

Example 6-26

4-(8-{[5-Methoxy-1-(propan-2-yl)-1H-indol-3-yl]methyl}-2-oxo-1-oxa-3,8-diazaspiro[4.5]dec-3-yl)benzoic acid, TFA salt

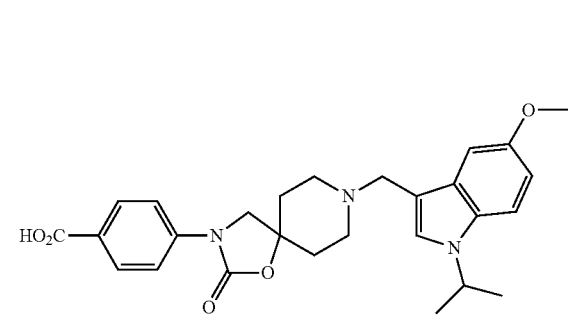 [SMILES: COc1ccc2c(c1)c(CN1CCC3(CC1)CN(c1ccc(C(=O)O)cc1)C(=O)O3)cn2C(C)C]

The title compound was prepared and purified using essentially the same experimental procedures in Example 6-17 and was isolated as a TFA salt.

LCMS (m/e): 478 (M+1).

Example 6-27

4-(8-{[5-(3-Chloro-4-fluorophenyl)-2-phenyl-1,3-oxazol-4-yl]methyl}-2-oxo-1-oxa-3,8-diazaspiro[4.5]dec-3-yl)benzoic acid, TFA salt

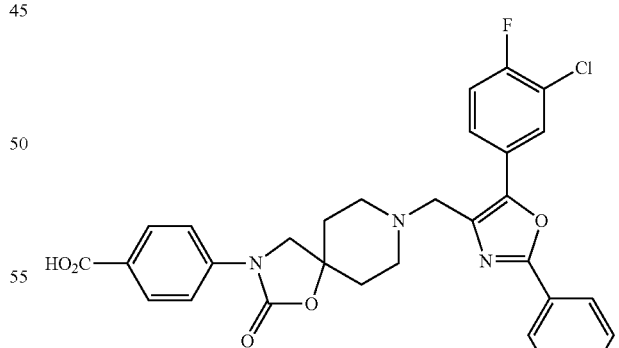

The title compound was prepared and purified using essentially the same experimental procedures in Example 6-1 and was isolated as a TFA salt.

LCMS (m/e): 562 (M+1).

Example 6-28

4-(8-{[2-Cyclohexyl-4-(4-methoxyphenyl)-1,3-thiazol-5-yl]methyl}-2-oxo-1-oxa-3,8-diazaspiro[4.5]dec-3-yl)benzoic acid, TFA salt

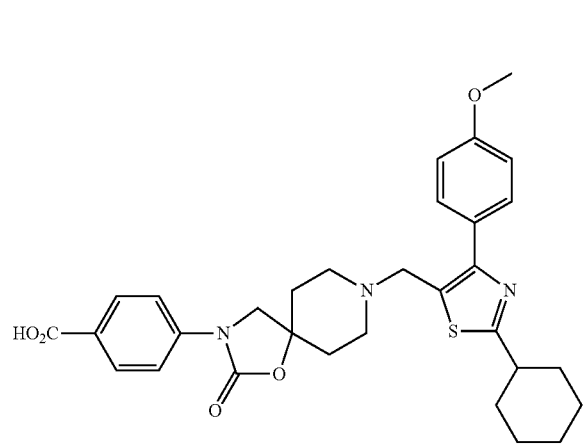 [SMILES: COc1ccc(-c2nc(C3CCCCC3)sc2CN2CCC3(CC2)CN(c2ccc(C(=O)O)cc2)C(=O)O3)cc1]

The title compound was prepared and purified using essentially the same experimental procedures in Example 6-1 and was isolated as a TFA salt.

LCMS (m/e): 562 (M+1).

Example 6-29

4-(8-{[2-tert-Butyl-4-(4-methoxyphenyl)-1,3-thiazol-5-yl]methyl}-2-oxo-1-oxa-3,8-diazaspiro[4.5]dec-3-yl)benzoic acid, TFA salt

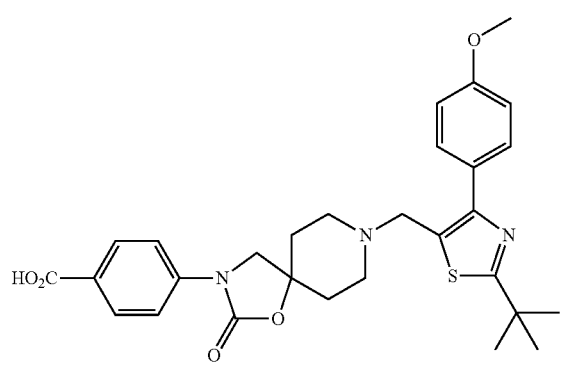 [SMILES: COc1ccc(-c2nc(C(C)(C)C)sc2CN2CCC3(CC2)CN(c2ccc(C(=O)O)cc2)C(=O)O3)cc1]

The title compound was prepared and purified using essentially the same experimental procedures in Example 6-1 and was isolated as a TFA salt.

LCMS (m/e): 536 (M+1).

Example 6-30

4-(2-Oxo-8-{[2-phenyl-5-(2,4,5-trifluorophenyl)-1,3-oxazol-4-yl]methyl}-1-oxa-3,8-diazaspiro[4.5]dec-3-yl)benzoic acid, TFA salt

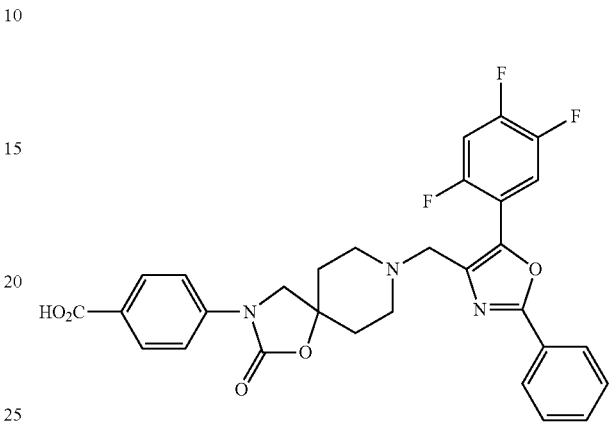

The title compound was prepared and purified using essentially the same experimental procedures in Example 6-1 and was isolated as a TFA salt.

LCMS (m/e): 564 (M+1).

Example 6-31

4-(8-{[5-(3-Chloro-4-fluorophenyl)-2-cyclopropyl-1,3-oxazol-4-yl]methyl}-2-oxo-1-oxa-3,8-diazaspiro[4.5]dec-3-yl)benzoic acid, TFA salt

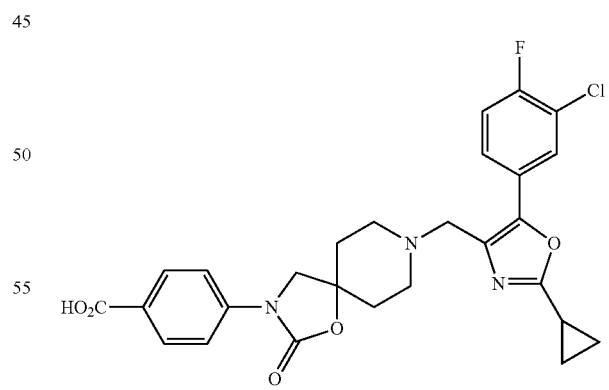

The title compound was prepared and purified using essentially the same experimental procedures in Example 6-1 and was isolated as a TFA salt.

LCMS (m/e): 526 (M+1).

Example 6-32

4-{8-[(2,4-Diphenyl-1,3-thiazol-5-yl)methyl]-2-oxo-1-oxa-3,8-diazaspiro[4.5]dec-3-yl}benzoic acid, TFA salt

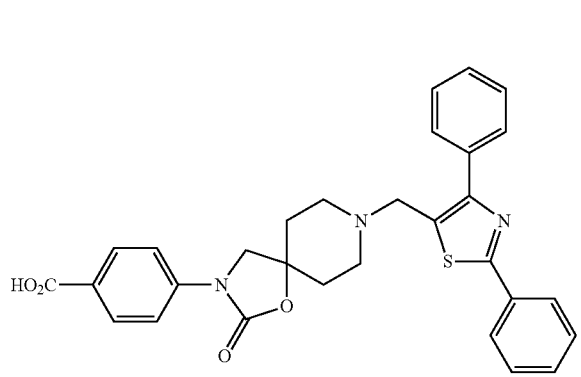 [SMILES: O=C(O)c1ccc(N2CC3(CCN(Cc4sc(-c5ccccc5)nc4-c4ccccc4)CC3)OC2=O)cc1]

The title compound was prepared and purified using essentially the same experimental procedures in Example 6-1 and was isolated as a TFA salt.

LCMS (m/e): 526 (M+1).

Example 6-33

4-{8-[(2-Methyl-4-phenyl-1,3-thiazol-5-yl)methyl]-2-oxo-1-oxa-3,8-diazaspiro[4.5]dec-3-yl}benzoic acid, TFA salt

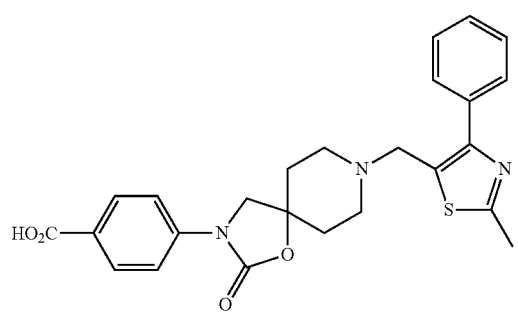 [SMILES: Cc1nc(-c2ccccc2)c(CN2CCC3(CC2)CN(c2ccc(C(=O)O)cc2)C(=O)O3)s1]

The title compound was prepared and purified using essentially the same experimental procedures in Example 6-1 and was isolated as a TFA salt.

LCMS (m/e): 464 (M+1).

Example 6-34

4-{8-[(2,5-Diphenyl-1,3-oxazol-4-yl)methyl]-2-oxo-1-oxa-3,8-diazaspiro[4.5]dec-3-yl}benzoic acid, TFA salt

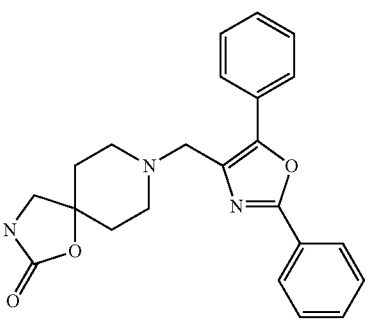

The title compound was prepared and purified using essentially the same experimental procedures in Example 6-1 and was isolated as a TFA salt.

LCMS (m/e): 510 (M+1).

Example 6-35

4-(8-{[2-tert-Butyl-4-(2,4,5-trifluorophenyl)-1,3-thiazol-5-yl]methyl}-2-oxo-1-oxa-3,8-diazaspiro[4.5]dec-3-yl)benzoic acid, TFA salt

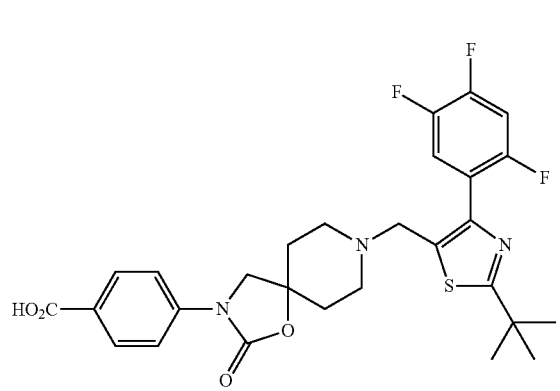 [SMILES: CC(C)(C)c1nc(-c2cc(F)c(F)cc2F)c(CN2CCC3(CC2)CN(c2ccc(C(=O)O)cc2)C(=O)O3)s1]

The title compound was prepared and purified using essentially the same experimental procedures in Example 6-1 and was isolated as a TFA salt.

LCMS (m/e): 560 (M+1).

Example 6-36

4-(2-Oxo-8-{[3-(2,4,5-trifluorophenyl)imidazo[1,2-a]pyridin-2-yl]methyl}-1-oxa-3,8-diazaspiro[4.5]dec-3-yl)benzoic acid, TFA salt

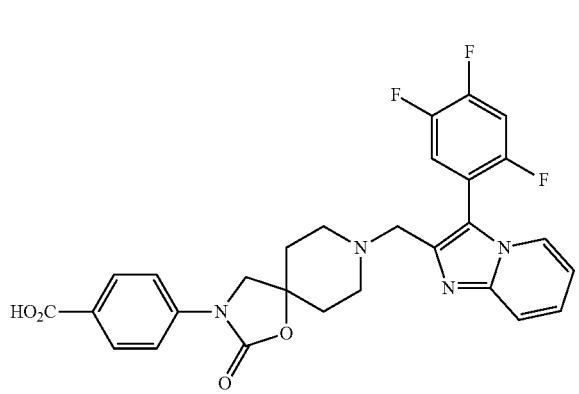 [SMILES: O=C(O)c1ccc(N2CC3(CCN(Cc4nc5ccccn5c4-c4cc(F)c(F)cc4F)CC3)OC2=O)cc1]

The title compound was prepared and purified using essentially the same experimental procedures in Example 6-1 and was isolated as a TFA salt.

LCMS (m/e): 537 (M+1).

Example 6-37

4-{2-Oxo-8-[(2-phenylimidazo[1,2-a]pyridin-3-yl)methyl]-1-oxa-3,8-diazaspiro[4.5]dec-3-yl}benzoic acid, TFA salt

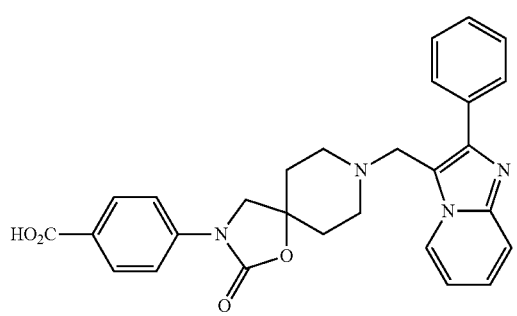 [SMILES: O=C(O)c1ccc(N2CC3(CCN(Cc4c(-c5ccccc5)nc5ccccn45)CC3)OC2=O)cc1]

The title compound was prepared and purified using essentially the same experimental procedures in Example 6-1 and was isolated as a TFA salt.

LCMS (m/e): 483 (M+1).

Example 6-38

4-{8-[(2-Methylimidazo[1,2-a]pyridin-3-yl)methyl]-2-oxo-1-oxa-3,8-diazaspiro[4.5]dec-3-yl}benzoic acid, TFA salt

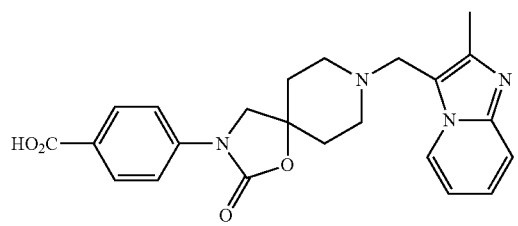

The title compound was prepared and purified using essentially the same experimental procedures in Example 6-1 and was isolated as a TFA salt.

LCMS (m/e): 421 (M+1).

Example 6-39

4-(8-{[8-Methyl-3-(2,4,5-trifluorophenyl)imidazo[1,2-a]pyridin-2-yl]methyl}-2-oxo-1-oxa-3,8-diazaspiro[4.5]dec-3-yl)benzoic acid, TFA salt

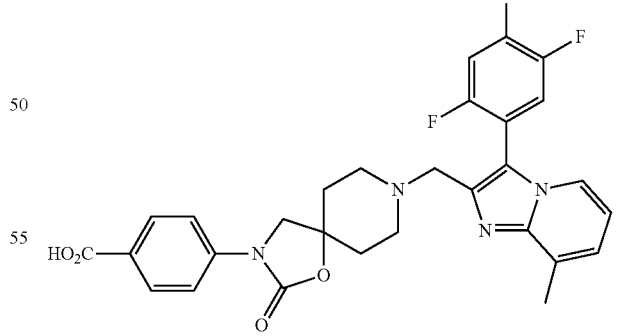

The title compound was prepared and purified using essentially the same experimental procedures in Example 6-1 and was isolated as a TFA salt.

LCMS (m/e): 551 (M+1).

Example 7-1

4-[8-(3-Bromo-4-chlorobenzyl)-2-oxo-1-oxa-3,8-diazaspiro[4.5]dec-3-yl]benzoic acid, formic acid salt

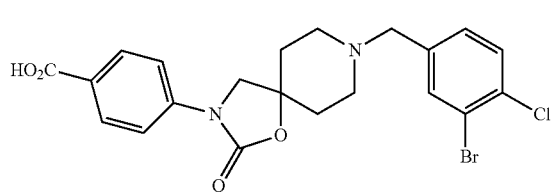 [SMILES: O=C(O)c1ccc(N2CC3(CCN(Cc4ccc(Cl)c(Br)c4)CC3)OC2=O)cc1]

To 4-(2-oxo-1-oxa-3,8-diazaspiro[4.5]dec-3-yl)benzoic acid hydrochloride salt (20 mg, 0.064 mmol; Example 5-1, Step 4), MP-cyanoborohydride (83 mg, 0.192 mmol), 3-bromo-4-chlorobenzaldehyde (15.5 mg, 0.071 mmol) and AcOH (5.49 µL, 0.096 mmol) was added DMF (1.5 mL). The mixture was shaken overnight at room temperature. The reaction mixture was filtered, the resin was washed with DMF and the solvent was evaporated. The residue was purified by reverse phase (C-18) HPLC eluting with acetonitrile/water+0.1% formic acid. The solvent was evaporated to provide the title compound as a white solid (19 mg).

LCMS (m/e): 479 (m+1).

Example 7-2

4-[8-(4-Chloro-3-ethylbenzyl)-2-oxo-1-oxa-3,8-diazaspiro[4.5]dec-3-yl]benzoic acid

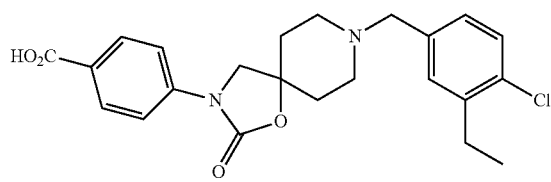 [SMILES: CCc1cc(CN2CCC3(CC2)CN(c2ccc(C(=O)O)cc2)C(=O)O3)ccc1Cl]

The title compound was prepared from 4-(2-oxo-1-oxa-3,8-diazaspiro[4.5]dec-3-yl)benzoic acid hydrochloride salt (20 mg, 0.064 mmol; Example 5-1, Step 4) and 4-chloro-3-ethylbenzaldehyde (11.86 mg, 0.070 mmol), following essentially the same procedure described in Example 7-1. The residue was purified by reverse phase (C-18) HPLC eluting with acetonitrile/water+0.1% NH$_3$. The solvent was evaporated to provide the title compound as a white solid (12 mg).

LCMS (m/e): 429 (m+1).

Example 7-3

4-{8-[4-Chloro-3-(trifluoromethoxy)benzyl]-2-oxo-1-oxa-3,8-diazaspiro[4.5]dec-3-yl}benzoic acid, formic acid salt

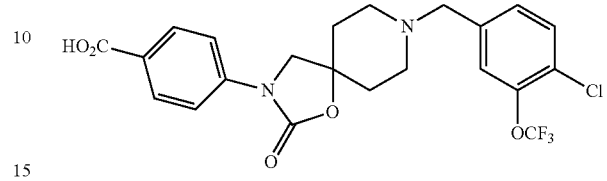

The title compound was prepared from 4-(2-oxo-1-oxa-3,8-diazaspiro[4.5]dec-3-yl)benzoic acid hydrochloride salt (20 mg, 0.064 mmol; Example 5-1, Step 4) and 4-chloro-3-trifluoromethoxybenzaldehyde (15.81 mg, 0.071 mmol), following essentially the same procedure described in Example 7-1. The title compound was obtained as a white solid (14.7 mg).

LCMS (m/e): 485 (m+1).

Example 7-4

4-{8-[4-Chloro-3-(trifluoromethyl)benzyl]-2-oxo-1-oxa-3,8-diazaspiro[4.5]dec-3-yl}benzoic acid

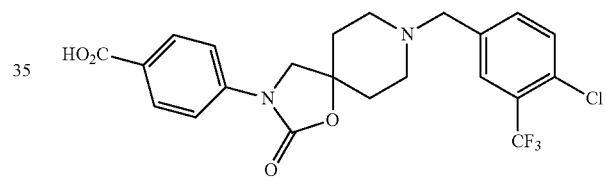

The title compound was prepared from 4-(2-oxo-1-oxa-3,8-diazaspiro[4.5]dec-3-yl)benzoic acid hydrochloride salt (20 mg, 0.064 mmol; Example 5-1, Step 4) and 4-chloro-3-trifluoromethylbenzaldehyde (14.68 mg, 0.071 mmol), following essentially the same procedure described in Example 7-1. The title compound was obtained as a white solid (17.4 mg).

LCMS (m/e): 469

Example 7-5

4-[8-(3,4-Dichlorobenzyl)-2-oxo-1-oxa-3,8-diazaspiro[4.5]dec-3-yl]benzoic acid, formic acid salt

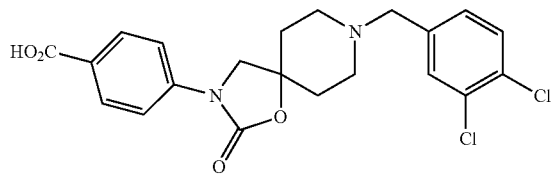 [SMILES: O=C(O)c1ccc(N2CC3(CCN(Cc4ccc(Cl)c(Cl)c4)CC3)OC2=O)cc1]

The title compound was prepared from 4-(2-oxo-1-oxa-3,8-diazaspiro[4.5]dec-3-yl)benzoic acid hydrochloride salt (20 mg, 0.064 mmol; Example 5-1, Step 4) and 3,4-dichlorobenzaldehyde (12.32 mg, 0.071 mmol), following essentially the same procedure described in Example 7-1. The title compound was obtained as a white solid (18.4 mg).
LCMS (m/e): 435

Example 7-6

4-{8-[3-cyclopropyl-4-(trifluoromethoxy)benzyl]-2-oxo-1-oxa-3,8-diazaspiro[4.5]dec-3-yl}benzoic acid, TFA salt

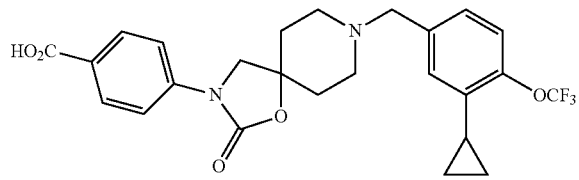 [SMILES: O=C(O)c1ccc(N2CC3(CCN(Cc4ccc(OC(F)(F)F)c(C5CC5)c4)CC3)OC2=O)cc1]

Step 1. Synthesis of methyl 4-{8-[3-bromo-4-(trifluoromethoxy)benzyl]-2-oxo-1-oxa-3,8-diazaspiro[4.5]dec-3-yl}benzoate

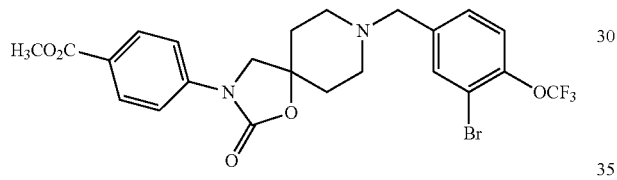

To methyl 4-(2-oxo-1-oxa-3,8-diazaspiro[4.5]dec-3-yl)benzoate hydrochloride salt (300 mg, 0.918 mmol; Example 1, Step 2), MP-cyanoborohydride (1192 mg, 2.75 mmol), 3-bromo-4-trifluoromethoxybenzaldehyde (272 mg, 1.01 mmol) and AcOH (79 µl, 1.38 mmol) was added 5 mL of DMF. The reaction mixture was filtered, the resin was washed with DMF and the solvent was evaporated. The residue was dissolved in saturated aqueous NaHCO₃ and extracted with DCM. The combined organic layers were evaporated to yield the title compound as a light yellow solid (330 mg) that was used without any further purification.
LCMS (m/e): 543

Step 2. Synthesis of 4-{8-[3-cyclopropyl-4-(trifluoromethoxy)benzyl]-2-oxo-1-oxa-3,8-diazaspiro[4.5]dec-3-yl}benzoic acid, TFA salt

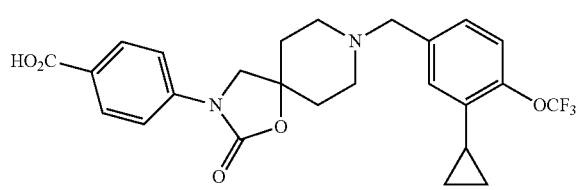 [SMILES: O=C(O)c1ccc(N2CC3(CCN(Cc4ccc(OC(F)(F)F)c(C5CC5)c4)CC3)OC2=O)cc1]

To methyl 4-{8-[3-bromo-4-(trifluoromethoxy)benzyl]-2-oxo-1-oxa-3,8-diazaspiro[4.5]dec-3-yl}benzoate (50 mg, 0.092 mmol), potassium phosphate tribasic (64.5 mg, 0.304 mmol), potassium cyclopropyltrifluoroborate (17.7 mg, 0.120 mmol) and palladium tetrakis (5.32 mg, 4.60 µmol) was added toluene (409 µL) and water (205 µL). The reaction mixture was heated to 100° C. overnight. The reaction mixture was diluted with water, extracted with DCM and evaporated in vacuo. The residue was then dissolved in water (300 uL) and THF (900 uL) and LiOH (4.41 mg, 0.184 mmol) was added. The reaction mixture stirred at 70° C. for 3 hours. The mixture was evaporated in vacuo and the residue was purified by reverse phase (C-18) HPLC eluting with acetonitrile/water+0.1% TFA. The solvent was evaporated to provide the title compound as a white solid (8 mg).
LCMS (m/e): 491

Example 7-7

4-[8-(4-Chloro-3-cyclopropylbenzyl)-2-oxo-1-oxa-3,8-diazaspiro[4.5]dec-3-yl]benzoic acid, TFA salt

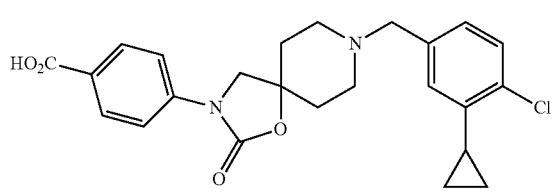 [SMILES: O=C(O)c1ccc(N2CC3(CCN(Cc4ccc(Cl)c(C5CC5)c4)CC3)OC2=O)cc1]

Step 1. Synthesis of methyl 4-[8-(3-bromo-4-chlorobenzyl)-2-oxo-1-oxa-3,8-diazaspiro[4.5]dec-3-yl]benzoate

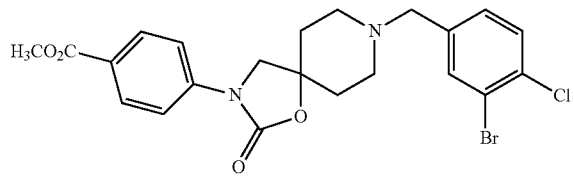 [SMILES: COC(=O)c1ccc(N2CC3(CCN(Cc4ccc(Cl)c(Br)c4)CC3)OC2=O)cc1]

The title compound was prepared from methyl 4-(2-oxo-1-oxa-3,8-diazaspiro[4.5]dec-3-yl)benzoate hydrochloride salt (60 mg, 0.185 mmol; Example 1, Step 2) and 3-bromo-4-chlorobenzaldehyde (48.6 mg, 0.222 mmol) following essentially the same procedure described in Step 1 of Example 7-6. The title compound was obtained as a yellow oil (91 mg) that was used without any further purification.
LCMS (m/e): 493.

Step 2. Synthesis of 4-[8-(4-chloro-3-cyclopropylbenzyl)-2-oxo-1-oxa-3,8-diazaspiro[4.5]dec-3-yl]benzoic acid, TFA salt

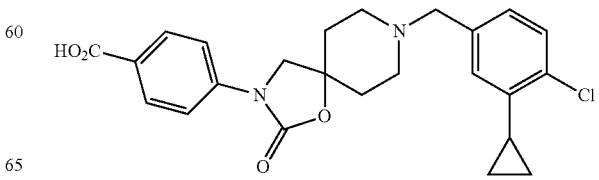

The title compound was prepared from methyl 4-[8-(3-bromo-4-chlorobenzyl)-2-oxo-1-oxa-3,8-diazaspiro[4.5]dec-3-yl]benzoate (50 mg, 0.102 mmol) following essentially the same procedure described in Step 2 of Example 7-6. The title compound was obtained as a white solid (21 mg).

$^1$H-NMR (CD$_3$OD, 400 MHz): δ 8.00 (d, J=8.8 Hz, 2H), 7.65 (d, J=8.8 Hz, 2H), 7.45 (d, J=8.0 Hz, 1H), 7.26 (dd, J=2.0, 8.0 Hz, 1H), 7.15 (d, J=2.0 Hz, 1H), 4.26 (s, 2H), 3.28-3.26 (m, 6H), 2.28-2.15 (m, 5H), 1.07-1.02 (m, 2H), 0.75-0.71 (m, 2H).

LCMS (m/e): 441.

Example 7-8

4-{8-[3-Cyclobutyl-4-(trifluoromethoxy)benzyl]-2-oxo-1-oxa-3,8-diazaspiro[4.5]dec-3-yl}benzoic acid, TFA salt

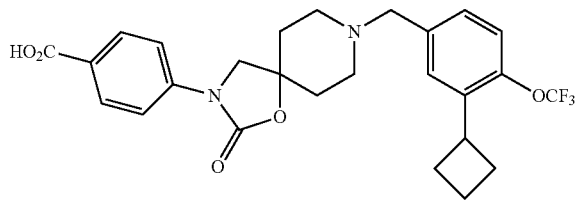 [SMILES: O=C(O)c1ccc(N2CC3(CCN(Cc4ccc(OC(F)(F)F)c(C5CCC5)c4)CC3)OC2=O)cc1]

To methyl 4-{8-[3-bromo-4-(trifluoromethoxy)benzyl]-2-oxo-1-oxa-3,8-diazaspiro[4.5]dec-3-yl}benzoate (60 mg, 0.111 mmol; Example 7-6, Step 1), Cs$_2$CO$_3$ (108 mg, 0.332 mmol), Pd(OAc)$_2$ (0.498 mg, 2.22 mot), potassium cyclobutyltrifluoroborate (21.6 mg, 0.133 mmol) and di(1-adamantyl)-n-butylphosphine (1.19 mg, 3.32 µmol) was added toluene (504 uL) and water (50.4 uL). The reaction mixture was heated to 100° C. overnight. The reaction mixture was diluted with water, extracted with DCM and evaporated in vacuo. The residue was then dissolved in water (300 uL) and THF (900 uL) and LiOH (9.46 mg, 0.395 mmol) was added. The reaction mixture stirred at 70° C. for 3 hours. The mixture was evaporated in vacuo and the residue was purified by reverse phase (C-18) HPLC eluting with acetonitrile/water+0.1% TFA. The solvent was evaporated to provide the title compound as a white solid (12 mg).

LCMS (m/e): 505.

Example 7-9

4-[8-(3,4-Dichloro-5-cyclopropylbenzyl)-2-oxo-1-oxa-3,8-diazaspiro[4.5]dec-3-yl]benzoic acid, TFA salt

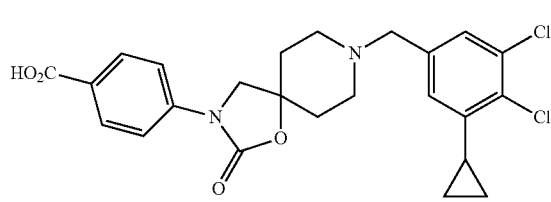 [SMILES: O=C(O)c1ccc(N2CC3(CCN(Cc4cc(Cl)c(Cl)c(C5CC5)c4)CC3)OC2=O)cc1]

Step 1. Synthesis of methyl 4-[8-(3-bromo-4,5-dichlorobenzyl)-2-oxo-1-oxa-3,8-diazaspiro[4.5]dec-3-yl]benzoate

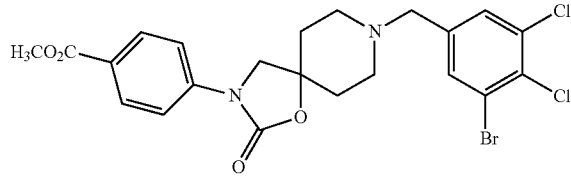 [SMILES: COC(=O)c1ccc(N2CC3(CCN(Cc4cc(Cl)c(Cl)c(Br)c4)CC3)OC2=O)cc1]

To methyl 4-(2-oxo-1-oxa-3,8-diazaspiro[4.5]dec-3-yl)benzoate hydrochloride salt (50 mg, 0.153 mmol; Example 1, Step 2) and 1-bromo-5-(bromomethyl)-2,3-dichlorobenzene (53.7 mg, 0.168 mmol; from Patent US2007/070805) was added DMF (1.5 mL) and DIPEA (107 µL, 0.612 mmol). The mixture was heated to 55° C. for 2 hours. The mixture was evaporated and the residue was dissolved in saturated aqueous NaHCO$_3$ and then extracted with DCM. The organic layer was evaporated to provide the title compound as a yellow oil (76 mg) that was used without further purification.

LCMS (m/e): 527.

Step 2. Synthesis of 4-[8-(3,4-dichloro-5-cyclopropylbenzyl)-2-oxo-1-oxa-3,8-diazaspiro[4.5]dec-3-yl]benzoic acid, TFA salt

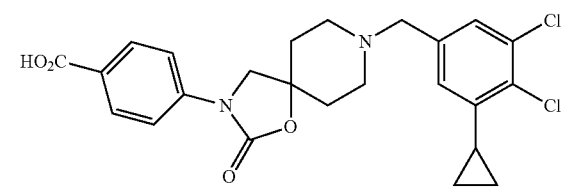 [SMILES: O=C(O)c1ccc(N2CC3(CCN(Cc4cc(Cl)c(Cl)c(C5CC5)c4)CC3)OC2=O)cc1]

The title compound was prepared from methyl 4-[8-(3-bromo-4,5-dichlorobenzyl)-2-oxo-1-oxa-3,8-diazaspiro[4.5]dec-3-yl]benzoate (60 mg, 0.114 mmol) following essentially the same procedure described in Step 2 of Example 7-6. The title compound was obtained as a white solid (21 mg).

LCMS (m/e): 475.

Example 7-10

4-[8-(4-Chloro-3,5-dicyclopropylbenzyl)-2-oxo-1-oxa-3,8-diazaspiro[4.5]dec-3-yl]benzoic acid, TFA salt

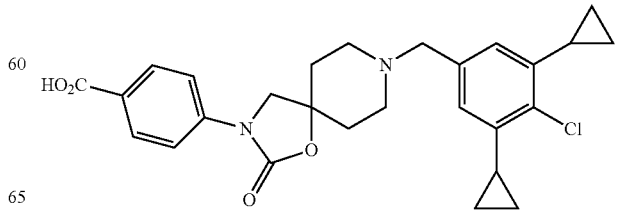

Step 1. Synthesis of 1,3-dibromo-5-(bromomethyl)-2-chlorobenzene

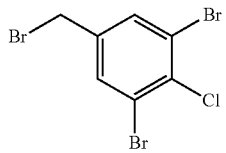

To 1,3-dibromo-2-chloro-5-methylbenzene (1000 mg, 3.52 mmol) was added NBS (688 mg, 3.87 mmol) and AIBN (57.7 mg, 0.352 mmol). The mixture was stirred at room temperature for 30 minutes and then heated to 80° C. overnight. The solution was evaporated and the residue was purified by silica gel chromatography (0-5% EtOAc/heaxnes) to provide the title compound (740 mg) as a clear oil.

Step 2. Synthesis of methyl 4-[8-(3,5-dibromo-4-chlorobenzyl)-2-oxo-1-oxa-3,8-diazaspiro[4.5]dec-3-yl]benzoate

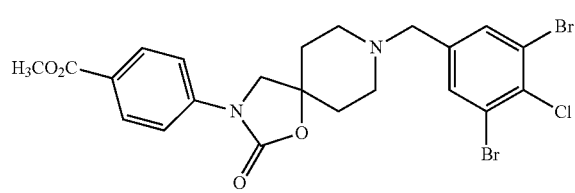

The title compound was prepared from methyl 4-(2-oxo-1-oxa-3,8-diazaspiro[4.5]dec-3-yl)benzoate hydrochloride salt (100 mg, 0.306 mmol; Example 1, Step 2) and 1,3-dibromo-5-(bromomethyl)-2-chlorobenzene (122 mg, 0.337 mmol) following essentially the same procedure described in Step 1 of Example 7-9. The title compound was obtained as a white solid (175 mg) and was used without further purification.

LCMS (m/e): 571.

Step 3. Synthesis of 4-[8-(4-chloro-3,5-dicyclopropylbenzyl)-2-oxo-1-oxa-3,8-diazaspiro[4.5]dec-3-yl]benzoic acid, TFA salt

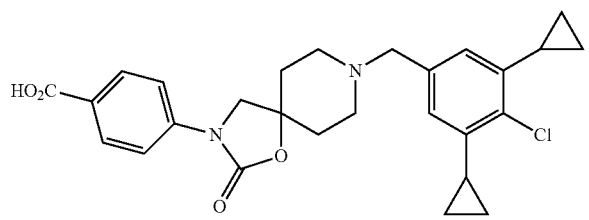 [SMILES: O=C(O)c1ccc(N2CC3(CCN(Cc4cc(C5CC5)c(Cl)c(C5CC5)c4)CC3)OC2=O)cc1]

To methyl 4-(8-(3,5-dibromo-4-chlorobenzyl)-2-oxo-1-oxa-3,8-diazaspiro[4.5]dec-3-yl)benzoate (100 mg, 0.175 mmol), Cs₂CO₃ (341 mg, 1.05 mmol), Pd(OAc)₂ (1.57 mg, 6.98 μmol), potassium cyclopropyltrifluoroborate (62 mg, 0.419 mmol) and di(1-adamantyl)-n-butylphosphine (3.76 mg, 10.48 μmol) were added toluene (1437 uL) and water (144 uL). The reaction mixture was heated to 100° C. overnight. The reaction mixture was diluted with water, extracted with DCM and evaporated in vacuo. The residue was then dissolved in water (300 uL) and THF (900 uL) and LiOH (9.46 mg, 0.395 mmol) was added. The reaction mixture was stirred at 70° C. for 3 hours. The mixture was evaporated in vacuo and the residue was purified by reverse phase (C-18) HPLC eluting with acetonitrile/water+0.1% TFA. The solvent was evaporated to provide the title compound as a white solid (34 mg).

LCMS (m/e): 481.

Example 7-11

4-{8-[3,5-Dicyclopropyl-4-(trifluoromethoxy)benzyl]-2-oxo-1-oxa-3,8-diazaspiro[4.5]dec-3-yl}benzoic acid, TFA salt

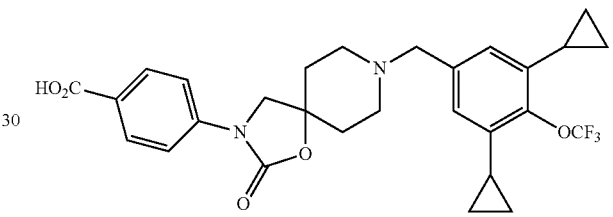

Step 1. Synthesis of methyl 3,5-dibromo-4-{[(phenylsulfanyl)carbonothioyl]oxy}benzoate

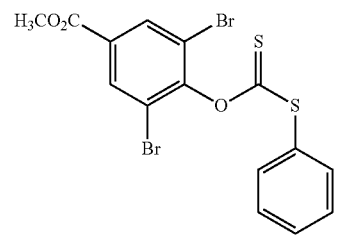 [SMILES: COC(=O)c1cc(Br)c(OC(=S)Sc2ccccc2)c(Br)c1]

Methyl 3,5-dibromo-4-hydroxybenzoate (1000 mg, 3.23 mmol) was dissolved in THF (16 mL) and N-methylmorpholine (0.709 mL, 6.45 mmol) was added. The mixture was cooled to 0° C. and phenyl chlorodithioformate (0.549 mL, 3.87 mmol) was added. The mixture was warmed to room temperature and stirred overnight. The mixture was diluted with EtOAc and washed with water. The organic layer was dried over Na₂SO₄, filtered and concentrated. The residue was purified by silica gel chromatography (0-15% EtOAc/hexanes) to yield the title compound as a clear oil (1491 mg).

LCMS (m/e): 461.

Step 2. Synthesis of methyl 3,5-dibromo-4-(trifluoromethoxy)benzoate

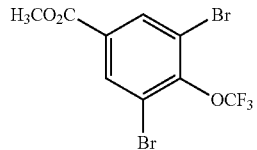 [SMILES: COC(=O)c1cc(Br)c(OC(F)(F)F)c(Br)c1]

Methyl 3,5-dibromo-4-{[(phenylsulfanyl)carbonothioyl]oxy}benzoate (1491 mg, 3.23 mmol) was placed in a polypropylene round bottom and DCM (16 mL) was added. The mixture was cooled to −78° C. and then HF-pyridine (1303 µl, 49 mmol) was added slowly. 1,3-Dibromo-5,5-dimethylhydantoin (750 mg, 2.62 mmol) was added portion-wise. The mixture was slowly warmed to room temperature over 2 hours and then the mixture was stirred for another 1 hour at room temperature. The mixture was cooled to 0° C. and carefully quenched with 10% NaOH (150 mL). The mixture was extracted with DCM and the combined organic extracts were washed with brine, dried over $Na_2SO_4$, filtered and concentrated. The residue was purified by silica gel chromatography (0-20% EtOAc/hexanes) to yield the title compound as a clear oil (1007 mg).

LCMS (m/e): 377.

Step 3. Synthesis of methyl 3,5-dicyclopropyl-4-(trifluoromethoxy)benzoate

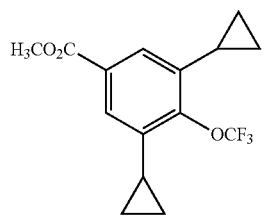 [SMILES: COC(=O)c1cc(C2CC2)c(OC(F)(F)F)c(C2CC2)c1]

To methyl 3,5-dibromo-4-(trifluoromethoxy)benzoate (500 mg, 1.32 mmol), $Cs_2CO_3$ (2586 mg, 7.94 mmol), $Pd(OAc)_2$ (11.9 mg, 0.053 mmol), potassium cyclopropyltrifluoroborate (470 mg, 3.18 mmol) and di(1-adamantyl)-n-butylphosphine (28.5 mg, 0.079 mmol) was added toluene (12 mL) and water (1.2 mL). The reaction mixture was heated to 100° C. overnight. The reaction mixture was cooled to room temperature, diluted with water, extracted with DCM and evaporated in vacuo. The residue was purified by silica gel chromatography (0-20% EtOAc/hexanes) to yield the title compound (259 mg).

LCMS (m/e): 301.

Step 4. Synthesis of [3,5-dicyclopropyl-4-(trifluoromethoxy)phenyl]methanol

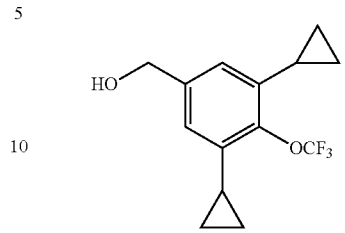

Methyl 3,5-dicyclopropyl-4-(trifluoromethoxy)benzoate (259 mg, 0.863 mmol) was dissolved in DCM (8.6 mL) and the mixture was cooled to 0° C. DIBAL in toluene (1.73 mL, 1.73 mmol) was added and the reaction mixture was allowed to warm to room temperature and stirred for 2 hours. The reaction mixture was quenched with the addition of 3N HCl and water. The mixture was stirred vigorously for 30 minutes and extracted with DCM. The combined organic extracts were washed with brine, dried over $Na_2SO_4$, filtered and concentrated. The residue was purified by silica gel chromatography (0-30% EtOAc/hexanes) to yield the title compound as a clear oil (190 mg).

Step 5. Synthesis of 3,5-dicyclopropyl-4-(trifluoromethoxy)benzaldehyde

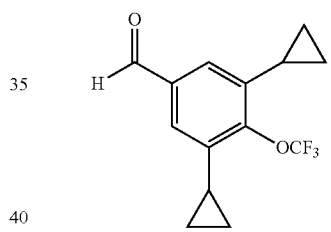

[3,5-Dicyclopropyl-4-(trifluoromethoxy)phenyl]methanol (190 mg, 0.698 mmol) was dissolved in DCM (6 mL) and Dess-Martin periodinane (444 mg, 1.05 mmol) was added. The mixture was stirred for 1 hour at room temperature. The mixture was evaporated in vacuo and the residue was purified by silica gel chromatography (0-10% EtOAc/hexanes) to yield the title compound as a clear oil (174 mg).

LCMS (m/e): 271.

Step 6. Synthesis of 4-{8-[3,5-dicyclopropyl-4-(trifluoromethoxy)benzyl]-2-oxo-1-oxa-3,8-diazaspiro[4.5]dec-3-yl}benzoic acid, TFA salt

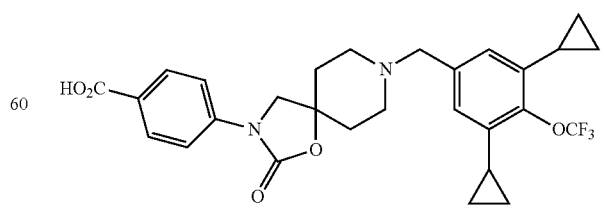

The title compound was prepared from 4-(2-oxo-1-oxa-3,8-diazaspiro[4.5]dec-3-yl)benzoic acid hydrochloride salt (20 mg, 0.064 mmol; Example 5-1, Step 4) and 3,5-dicyclopropyl-4-(trifluoromethoxy)benzaldehyde (20.7 mg, 0.077 mmol), following essentially the same procedure described in Example 7-1. The residue was purified by reverse phase (C-18) HPLC eluting with acetonitrile/water+0.1% TFA. The solvent was evaporated to provide the title compound as a white solid (16 mg).

LCMS (m/e): 531

Example 7-12

4-[8-(2,4-Dichloro-5-cyclopropylbenzyl)-2-oxo-1-oxa-3,8-diazaspiro[4.5]dec-3-yl]benzoic acid, TFA salt

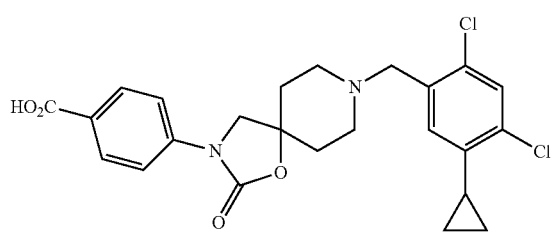 [SMILES: O=C(O)c1ccc(N2CC3(CCN(Cc4cc(C5CC5)c(Cl)cc4Cl)CC3)OC2=O)cc1]

Step 1. Synthesis of 1-bromo-5-(bromomethyl)-2,4-dichlorobenzene

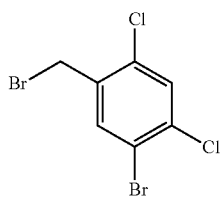 [SMILES: Clc1cc(Cl)c(CBr)cc1Br]

The title compound was prepared from 1-bromo-2,4-dichloro-5-methylbenzene (1200 mg, 5 mmol) following essentially the same procedure described for Step 1 of Example 7-10.

The title compound was obtained as a clear oil (1232 mg).

Step 2. Synthesis of methyl 4-[8-(5-bromo-2,4-dichlorobenzyl)-2-oxo-1-oxa-3,8-diazaspiro[4.5]dec-3-yl]benzoate

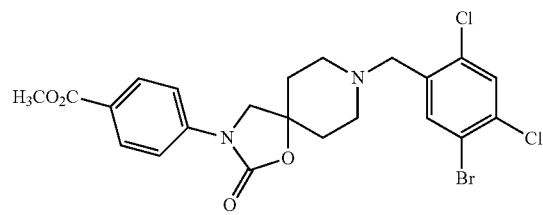 [SMILES: COC(=O)c1ccc(N2CC3(CCN(Cc4cc(Br)c(Cl)cc4Cl)CC3)OC2=O)cc1]

The title compound was prepared methyl 4-(2-oxo-1-oxa-3,8-diazaspiro[4.5]dec-3-yl)benzoate hydrochloride salt (80 mg, 0.245 mmol; Example 1, Step 2) and 1-bromo-5-(bromomethyl)-2,4-dichlorobenzene (86 mg, 0.269 mmol) following essentially the same procedure described in Step 1 of Example 7-9. The title compound was obtained as an off-white solid (129 mg) and was used without further purification.

LCMS (m/e): 527.

Step 3. Synthesis of 4-[8-(2,4-dichloro-5-cyclopropylbenzyl)-2-oxo-1-oxa-3,8-diazaspiro[4.5]dec-3-yl] benzoic acid, TFA salt

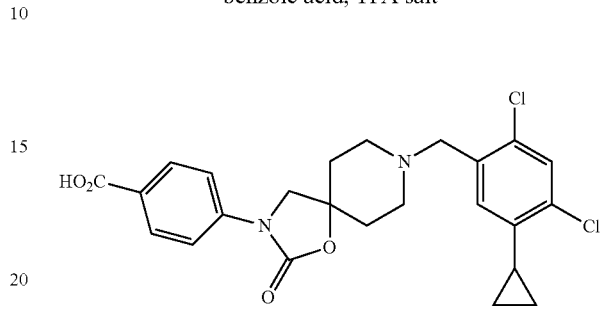

The title compound was prepared from methyl 4-[8-(5-bromo-2,4-dichlorobenzyl)-2-oxo-1-oxa-3,8-diazaspiro [4.5]dec-3-yl]benzoate (65 mg, 0.123 mmol) following essentially the same procedure described in Step 2 of Example 7-6. The title compound was obtained as a white solid (17 mg).

LCMS (m/e): 475.

Example 7-13

4-{8-[3-Chloro-5-cyclopropyl-4-(trifluoromethoxy) benzyl]-2-oxo-1-oxa-3,8-diazaspiro[4.5]dec-3-yl}benzoic acid, TFA salt

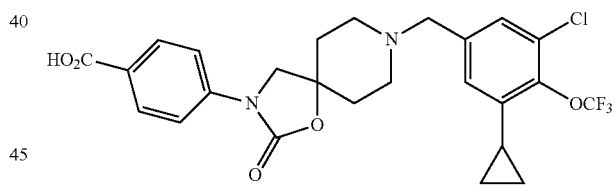

Step 1. Synthesis of O-(2,6-dichloro-4-methylphenyl) S-phenyl carbonodithioate

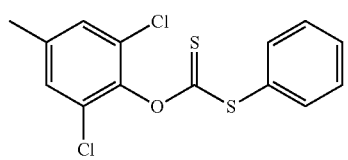 [SMILES: Cc1cc(Cl)c(OC(=S)Sc2ccccc2)c(Cl)c1]

The title compound was prepared from 2,6-dichloro-4-methylphenol (1000 mg, 5.64 mmol) following essentially the same procedure described in Step 1 of Example 7-11. The title compound was obtained as a clear oil (1860 mg).

LCMS (m/e): 329.

Step 2. Synthesis of 1,3-dichloro-5-methyl-2-(trifluoromethoxy)benzene

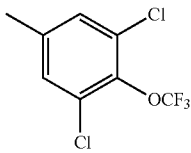

The title compound was prepared from O-(2,6-dichloro-4-methylphenyl) S-phenyl carbonodithioate (1860 mg, 5.65 mmol) following essentially the same procedure described in Step 2 of Example 7-11. The residue was purified by silica gel chromatography (0-5% EtOAc/hexanes) to yield the title compound as a clear oil (1240 mg).

Step 3. Synthesis of 1,3-dichloro-5-(dibromomethyl)-2-(trifluoromethoxy)benzene

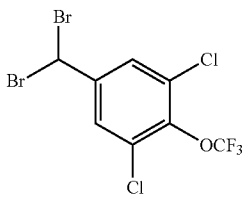 [SMILES: FC(F)(F)Oc1c(Cl)cc(C(Br)Br)cc1Cl]

To 1,3-dichloro-5-methyl-2-(trifluoromethoxy)benzene (697 mg, 2.84 mmol) was added NBS (304 mg, 1.707 mmol) and AIBN (23.36 mg, 0.142 mmol). The mixture was stirred at room temperature for 30 minutes and then heated to 80° C. overnight. The solution was evaporated and the residue was purified by silica gel chromatography (0-5% EtOAc/heaxnes) to provide the title compound as a clear oil (646 mg).

Step 4. Synthesis of methyl 4-{8-[3,5-dichloro-4-(trifluoromethoxy)benzyl]-2-oxo-1-oxa-3,8-diazaspiro[4.5]dec-3-yl}benzoate

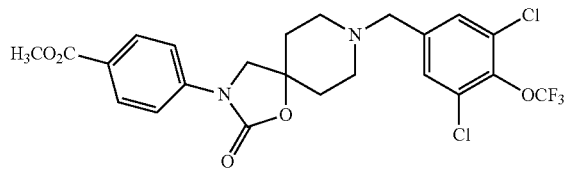 [SMILES: COC(=O)c1ccc(N2CC3(CCN(Cc4cc(Cl)c(OC(F)(F)F)c(Cl)c4)CC3)OC2=O)cc1]

To methyl 4-(2-oxo-1-oxa-3,8-diazaspiro[4.5]dec-3-yl)benzoate hydrochloride salt (80 mg, 0.245 mmol; Example 1, Step 2) and 1,3-dichloro-5-(dibromomethyl)-2-(trifluoromethoxy)benzene (108 mg, 0.269 mmol) were added DMF (1.5 mL) and DIPEA (171 μL, 0.979 mmol). The mixture was heated to 55° C. for 2 hours. The mixture was evaporated and the residue was dissolved in saturated aqueous NaHCO₃ and then extracted with DCM. The organic layer was evaporated to provide the crude intermediate as a yellow oil that was used without further purification. The residue was dissolved in MOH (1 mL) and zinc powder (64 mg, 0.979 mmol) was added. The mixture was heated to 35° C. for 10 minutes. The reaction mixture was filtered and evaporated in vacuo. The residue was dissolved in saturated aqueous NaHCO₃ and then extracted with DCM. The organic layer was evaporated and the residue was used without further purification.

LCMS (m/e): 533.

Step 5. Synthesis of 4-{8-[3-chloro-5-cyclopropyl-4-(trifluoromethoxy)benzyl]-2-oxo-1-oxa-3,8-diazaspiro[4.5]dec-3-yl}benzoic acid, TFA salt

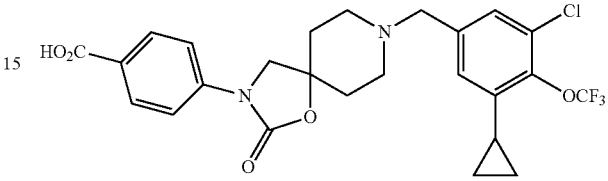

To methyl 4-{8-[3,5-dichloro-4-(trifluoromethoxy)benzyl]-2-oxo-1-oxa-3,8-diazaspiro[4.5]dec-3-yl}benzoate (65 mg, 0.122 mmol), K₂CO₃ (152 mg, 1.10 mmol), Pd(OAc)₂ (2.46 mg, 10.97 μmol), potassium cyclopropyltrifluoroborate (64.9 mg, 0.439 mmol) and 2-dicyclohexylphosphino-2',4',6'-trisisopropylbiphenyl (10.46 mg, 0.022 mmol) was added toluene (2216 uL) and water (222 uL). The reaction mixture was heated to 100° C. overnight. The reaction mixture was diluted with water, extracted with DCM and the organic layer was evaporated in vacuo. The residue was then dissolved in water (300 uL) and THF (900 uL) and LiOH (7.3 mg, 0.305 mmol) was added. The reaction mixture was stirred at 70° C. for 3 hours. The mixture was evaporated in vacuo and the residue was purified by reverse phase (C-18) HPLC eluting with acetonitrile/water+0.1% TFA. The solvent was evaporated to provide the title compound as a white solid (36 mg).

LCMS (m/e): 525.

Example 7-14

4-[2-Oxo-8-(2,4,5-tri cyclopropylbenzyl)-1-oxa-3,8-diazaspiro[4.5]dec-3-yl]benzoic acid, TFA salt

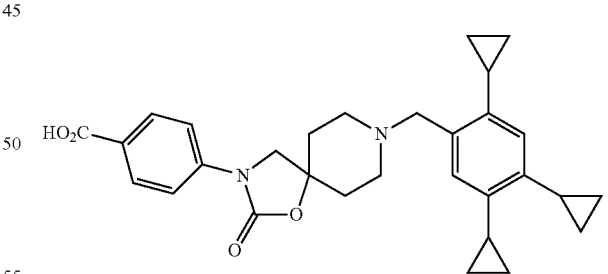

To methyl 4-[8-(5-bromo-2,4-dichlorobenzyl)-2-oxo-1-oxa-3,8-diazaspiro[4.5]dec-3-yl]benzoate (65 mg, 0.123 mmol, Example 7-12, Step 2), Cs₂CO₃ (481 mg, 1.48 mmol), Pd(OAc)₂ (2.21 mg, 9.84 μmol), potassium cyclopropyltrifluoroborate (87 mg, 0.591 mmol) and di(1-adamantyl)-n-butylphosphine (5.29 mg, 0.015 mmol) was added toluene (2237 uL) and water (224 uL). The reaction mixture was heated to 100° C. overnight. The reaction mixture was diluted with water, extracted with DCM and evaporated in vacuo. The residue was then dissolved in water (300 uL) and THF (900 uL) and LiOH (7.37 mg, 0.308 mmol) was added. The reaction mixture stirred at 70° C. for 3 hours. The mixture was evaporated in vacuo and the residue was purified by reverse phase (C-18) HPLC eluting with acetonitrile/water+0.1% TFA. The solvent was evaporated to provide the title compound as a white solid (35 mg).

LCMS (m/e): 487

Example 7-15

4-[8-(2-Chloro-5-cyclopropylbenzyl)-2-oxo-1-oxa-3,8-diazaspiro[4.5]dec-3-yl]benzoic acid

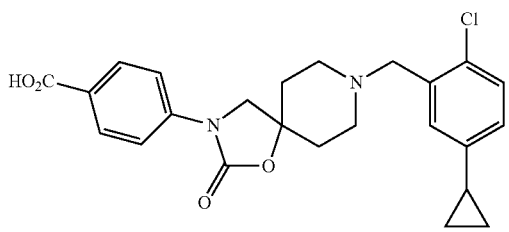 [SMILES: O=C(O)c1ccc(N2CC3(CCN(Cc4cc(C5CC5)ccc4Cl)CC3)OC2=O)cc1]

Step 1. Synthesis of methyl 4-[8-(5-bromo-2-chlorobenzyl)-2-oxo-1-oxa-3,8-diazaspiro[4.5]dec-3-yl]benzoate

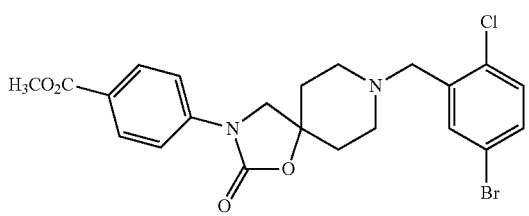 [SMILES: COC(=O)c1ccc(N2CC3(CCN(Cc4cc(Br)ccc4Cl)CC3)OC2=O)cc1]

The title compound was prepared from methyl 4-(2-oxo-1-oxa-3,8-diazaspiro[4.5]dec-3-yl)benzoate hydrochloride salt (50 mg, 0.153 mmol; Example 1, Step 2) and 3-bromo-5-chlorobenzaldehyde (43.7 mg, 0.199 mmol) following essentially the same procedure described in Step 1 of Example 7-6. The title compound was obtained as a yellow oil (76 mg) that was used without any further purification.

LCMS (m/e): 493.

Step 2. Synthesis of 4-[8-(2-chloro-5-cyclopropylbenzyl)-2-oxo-1-oxa-3,8-diazaspiro[4.5]dec-3-yl]benzoic acid

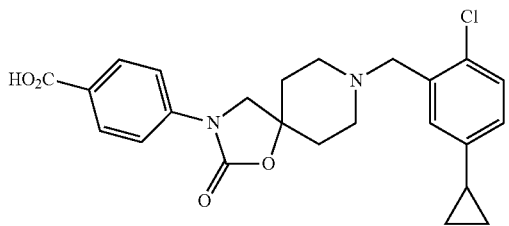 [SMILES: O=C(O)c1ccc(N2CC3(CCN(Cc4cc(C5CC5)ccc4Cl)CC3)OC2=O)cc1]

The title compound was prepared from methyl 4-[8-(5-bromo-2-chlorobenzyl)-2-oxo-1-oxa-3,8-diazaspiro[4.5] dec-3-yl]benzoate (76 mg, 0.154 mmol) following essentially the same procedure described in Step 2 of Example 7-6. The residue was purified by reverse phase (C-18) HPLC eluting with acetonitrile/water+0.1% NH$_3$. The title compound was obtained as a white solid (8.1 mg).

LCMS (m/e): 441.

Example 7-16

4-[8-(3-Chloro-5-cyclopropylbenzyl)-2-oxo-1-oxa-3,8-diazaspiro[4.5]dec-3-yl]benzoic acid

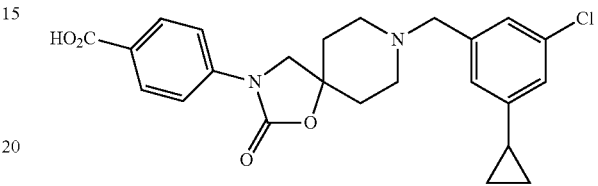

Step 1. Synthesis of methyl 4-[8-(3-bromo-5-chlorobenzyl)-2-oxo-1-oxa-3,8-diazaspiro[4.5]dec-3-yl]benzoate

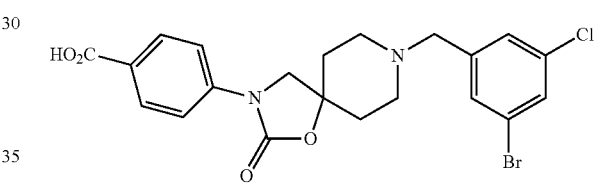

The title compound was prepared from methyl 4-(2-oxo-1-oxa-3,8-diazaspiro[4.5]dec-3-yl)benzoate hydrochloride salt (50 mg, 0.153 mmol; Example 1, Step 2) and 3-bromo-5-chlorobenzaldehyde (43.7 mg, 0.199 mmol) following essentially the same procedure described in Step 1 of Example 7-6. The title compound was obtained as a yellow oil (76 mg) that was used without any further purification.

LCMS (m/e): 493.

Step 2. Synthesis of 4-[8-(3-chloro-5-cyclopropylbenzyl)-2-oxo-1-oxa-3,8-diazaspiro[4.5]dec-3-yl]benzoic acid

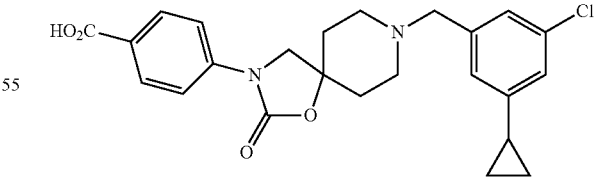

The title compound was prepared from methyl 4-[8-(3-bromo-5-chlorobenzyl)-2-oxo-1-oxa-3,8-diazaspiro[4.5] dec-3-yl]benzoate (76 mg, 0.154 mmol) following essentially the same procedure described in Step 2 of Example 7-6. The residue was purified by reverse phase (C-18) HPLC eluting with acetonitrile/water+0.1% NH$_3$. The title compound was obtained as a white solid (13.4 mg).

LCMS (m/e): 441.

Example 7-17

4-[2-Oxo-8-(3,4,5-tricyclopropylbenzyl)-1-oxa-3,8-diazaspiro[4.5]dec-3-yl]benzoic acid, TFA salt

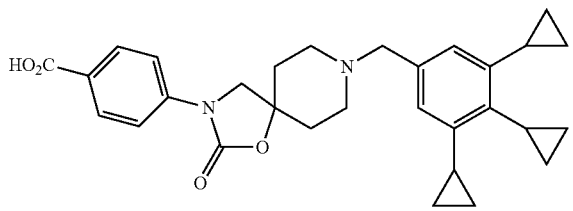 [SMILES: O=C(O)c1ccc(N2CC3(CCN(Cc4cc(C5CC5)c(C5CC5)c(C5CC5)c4)CC3)OC2=O)cc1]

The title compound was prepared from methyl 4-[8-(3,5-dibromo-4-chlorobenzyl)-2-oxo-1-oxa-3,8-diazaspiro[4.5]dec-3-yl]benzoate (30 mg, 0.052 mmol; Example 7-10, Step 2) following essentially the same procedure described in Example 7-14. The title compound was obtained as a white solid (11 mg).

LCMS (m/e): 487.

Example 7-18

4-{8-[3-Cyclopropyl-4-(trifluoromethyl)benzyl]-2-oxo-1-oxa-3,8-diazaspiro[4.5]dec-3-yl}benzoic acid, TFA salt

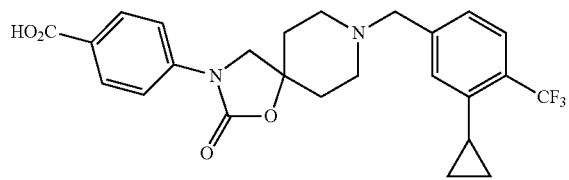 [SMILES: O=C(O)c1ccc(N2CC3(CCN(Cc4ccc(C(F)(F)F)c(C5CC5)c4)CC3)OC2=O)cc1]

Step 1. Synthesis of 2-bromo-4-(bromomethyl)-1-(trifluoromethyl)benzene

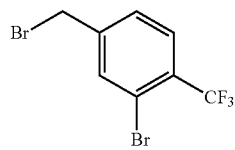 [SMILES: FC(F)(F)c1ccc(CBr)cc1Br]

The title compound was prepared from 2-bromo-4-methyl-1-(trifluoromethyl)benzene (963 mg, 3.83 mmol) following essentially the same procedure described for Step 1 of Example 7-10. The title compound was obtained as a clear oil (1043 mg).

Step 2. Synthesis of methyl 4-{8-[3-bromo-4-(trifluoromethyl)benzyl]-2-oxo-1-oxa-3,8-diazaspiro[4.5]dec-3-yl}benzoate

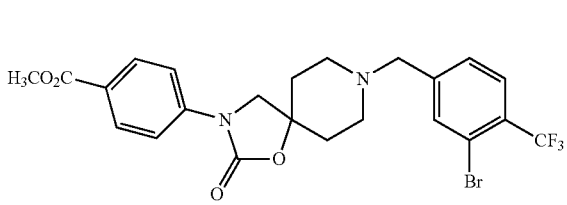 [SMILES: COC(=O)c1ccc(N2CC3(CCN(Cc4ccc(C(F)(F)F)c(Br)c4)CC3)OC2=O)cc1]

The title compound was prepared from methyl 4-(2-oxo-1-oxa-3,8-diazaspiro[4.5]dec-3-yl)benzoate hydrochloride salt (50 mg, 0.153 mmol; Example 1, Step 2) and 2-bromo-4-(bromomethyl)-1-(trifluoromethyl)benzene (53.5 mg, 0.168 mmol) following essentially the same procedure described in Step 1 of Example 7-9. The title compound was obtained as a yellow oil (91 mg) that was used without any further purification.

LCMS (m/e): 527.

Step 3. Synthesis of 4-{8-[3-cyclopropyl-4-(trifluoromethyl)benzyl]-2-oxo-1-oxa-3,8-diazaspiro[4.5]dec-3-yl}benzoic acid, TFA salt

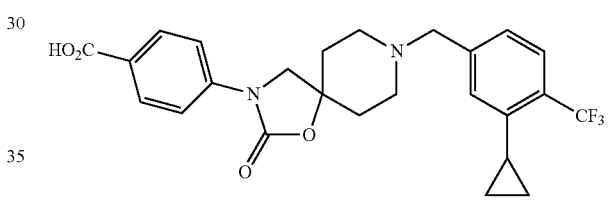

To methyl 4-{8-[3-bromo-4-(trifluoromethyl)benzyl]-2-oxo-1-oxa-3,8-diazaspiro[4.5]dec-3-yl}benzoate (75 mg, 0.142 mmol), cyclopropylboronic acid pinacol ester (59.7 mg, 0.356 mmol), 1,1'-bis(diphenylphosphino)ferrocene-palladium(II)dichloride dichloromethane complex (34.8 mg, 0.043 mmol) and LiOH (13.6 mg, 0.569 mmol) in a microwave vial was added 1,4-dioxane (356 μL) and water (119 μL). The mixture was irradiated at 120° C. for 30 minutes in the microwave. The mixture was evaporated in vacuo and the residue was purified by reverse phase (C-18) HPLC eluting with acetonitrile/water+0.1% TFA. The solvent was evaporated to provide the title compound as a white solid (15 mg).

LCMS (m/e): 475.

Example 7-19

4-{8-[4-Cyclopropyl-3-(trifluoromethoxy)benzyl]-2-oxo-1-oxa-3,8-diazaspiro[4.5]dec-3-yl}benzoic acid, TFA salt

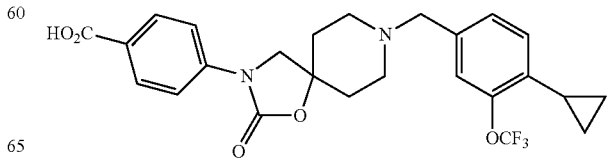

Step 1. Synthesis of methyl 4-{8-[4-chloro-3-(trifluoromethoxy)benzyl]-2-oxo-1-oxa-3,8-diazaspiro[4.5]dec-3-yl}benzoate

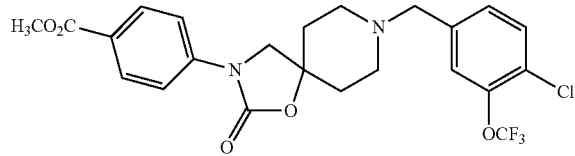 [SMILES: COC(=O)c1ccc(N2CC3(CCN(Cc4ccc(Cl)c(OC(F)(F)F)c4)CC3)OC2=O)cc1]

The title compound was prepared from methyl 4-(2-oxo-1-oxa-3,8-diazaspiro[4.5]dec-3-yl)benzoate hydrochloride salt (50 mg, 0.153 mmol; Example 1, Step 2) and 4-chloro-3-trifluoromethoxybenzaldehyde (43.7 mg, 0.199 mmol) following essentially the same procedure described in Step 1 of Example 7-6. The title compound was obtained as a yellow oil (76 mg) that was used without any further purification.

LCMS (m/e): 499.

Step 2. Synthesis of 4-{8-[4-cyclopropyl-3-(trifluoromethoxy)benzyl]-2-oxo-1-oxa-3,8-diazaspiro[4.5]dec-3-yl}benzoic acid, TFA salt

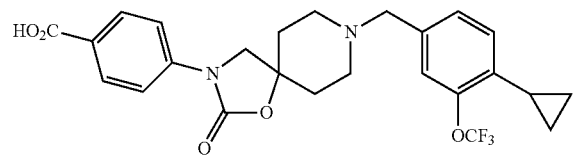 [SMILES: O=C(O)c1ccc(N2CC3(CCN(Cc4ccc(C5CC5)c(OC(F)(F)F)c4)CC3)OC2=O)cc1]

To methyl 4-{8-[4-chloro-3-(trifluoromethoxy)benzyl]-2-oxo-1-oxa-3,8-diazaspiro[4.5]dec-3-yl}benzoate (76 mg, 0.152 mmol), Cs$_2$CO$_3$ (149 mg, 0.457 mmol), Pd(OAc)$_2$ (0.684 mg, 3.05 µmol), potassium cyclobutyltrifluoroborate (27.1 mg, 0.183 mmol) and di(1-adamantyl)-n-butylphosphine (1.64 mg, 4.57 µmol) was added toluene (692 uL) and water (69.2 uL). The reaction mixture was heated to 100° C. overnight. The reaction mixture was diluted with water, extracted with DCM and evaporated in vacuo. The residue was then dissolved in water (300 uL) and THF (900 uL) and LiOH (9.46 mg, 0.395 mmol) was added. The reaction mixture stirred at 70° C. for 3 hours. The mixture was evaporated in vacuo and the residue was purified by reverse phase (C-18) HPLC eluting with acetonitrile/water+0.1% TFA. The solvent was evaporated to provide the title compound as a white solid (13 mg).

LCMS (m/e): 491.

Example 7-20

4-{8-[4-Cyclopropyl-3-(trifluoromethyl)benzyl]-2-oxo-1-oxa-3,8-diazaspiro[4.5]dec-3-yl}benzoic acid, TFA salt

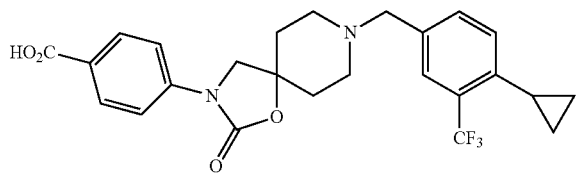 [SMILES: O=C(O)c1ccc(N2CC3(CCN(Cc4ccc(C5CC5)c(C(F)(F)F)c4)CC3)OC2=O)cc1]

Step 1. Synthesis of methyl 4-{8-[4-chloro-3-(trifluoromethyl)benzyl]-2-oxo-1-oxa-3,8-diazaspiro[4.5]dec-3-yl}benzoate

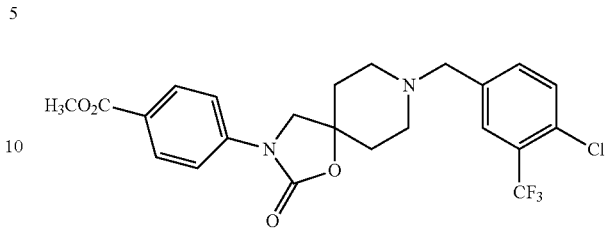

The title compound was prepared from methyl 4-(2-oxo-1-oxa-3,8-diazaspiro[4.5]dec-3-yl)benzoate hydrochloride salt (50 mg, 0.153 mmol; Example 1, Step 2) and 4-chloro-3-trifluoromethylbenzaldehyde (38.3 mg, 0.184 mmol) following essentially the same procedure described in Step 1 of Example 7-6. The title compound was obtained as a yellow solid (73 mg) that was used without any further purification.

LCMS (m/e): 483.

Step 2. Synthesis of 4-{8-[4-cyclopropyl-3-(trifluoromethyl)benzyl]-2-oxo-1-oxa-3,8-diazaspiro[4.5]dec-3-yl}benzoic acid, TFA salt

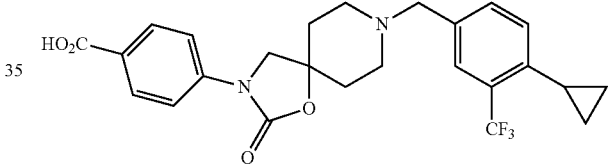

The title compound was prepared from methyl 4-{8-[4-chloro-3-(trifluoromethyl)benzyl]-2-oxo-1-oxa-3,8-diazaspiro[4.5]dec-3-yl}benzoate (74 mg, 0.153 mmol) following essentially the same procedure described in Step 2 of Example 7-19. The title compound was obtained as a white solid (26 mg).

LCMS (m/e): 475.

Example 8-1

4-{8-[(2,6-Dichloro-4'-fluorobiphen-4-yl)methyl]-2-oxo-1-oxa-3,8-diazaspiro[4.5]dec-3-yl}benzoic acid, TFA salt

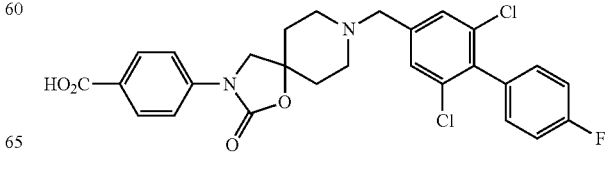

Step 1. Synthesis of (2,6-dichloro-4'-fluorobiphenyl)-4-carboxylic acid

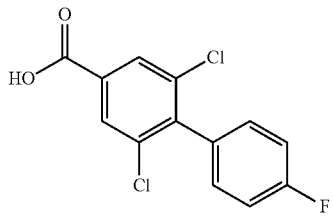 [SMILES: O=C(O)c1cc(Cl)c(-c2ccc(F)cc2)c(Cl)c1]

3,5-Dichloro-4-iodobenzoic acid (400 mg, 1.26 mmol) and 4-fluorophenylboronic acid (220 mg, 1.58 mmol) in a 20 mL microwave reaction vial were taken up in dioxane (10 mL) and 2M K$_2$CO$_3$ solution (3.2 mL, 6.4 mmol) and the vial was flushed with nitrogen. (Ph$_3$P)$_4$Pd(0) (84 mg, 0.076 mmol) was added and the vial was again flushed with nitrogen and sealed. The reaction was heated at 115° C. for 30 minutes. The reaction was diluted with water and 2M HCl and extracted twice with ethyl acetate. The organic layers were each washed with brine, dried over sodium sulfate, combined and concentrated. The residue was purified on silica gel (Combi Flash (CF) 12 gm column, 100% DCM, then 5% ethyl acetate/DCM, then a gradient of 5-20% ethyl acetate/DCM containing 1% HOAc) to give a single main band by TLC (280 mg) containing a mixture of title intermediate and 3,5-dichlorobenzoic acid bi-product by LC-MS. The mixture was used directly in Step 2.

Step 2. Synthesis of (2,6-dichloro-4'-fluorobiphenyl-4-yl)methanol

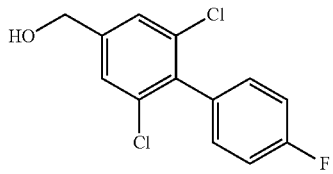 [SMILES: OCc1cc(Cl)c(-c2ccc(F)cc2)c(Cl)c1]

To a solution of 2,6-dichloro-4'-fluorobiphenyl-4-carboxylic acid (350 mg, 1.155 mmol) in THF (5 mL) was added 2M borane-methyl sulfide complex in THF (0.35 mL, 0.70 mmol) at room temperature. After 20 hours, the reaction was quenched with 2M HCl and water and was extracted twice with ethyl acetate. The organic layers were washed with brine containing some aqueous sodium bicarbonate, dried over sodium sulfate, combined and concentrated. The residue was purified on silica gel (COMBI FLASH 12 gm column, 100% DCM, then a gradient of 2-10% ethyl acetate/DCM) to give a single main band by TLC (65 mg) containing a 1:1 mixture of title intermediate and 3,5-dichlorobenzyl alcohol from the Step 1 bi-product impurity. The mixture was used directly in Step 3.

$^1$H-NMR of clean title intermediate (CDCl$_3$, 400 MHz): δ 7.395 (s, 2H), 7.21 (m, 2H), 7.12 (m, 2H), 4.692 (s, 2H), 2.0 (br s, 1H).

Step 3. Synthesis of 2,6-dichloro-4'-fluorobiphenyl-4-carboxaldehyde

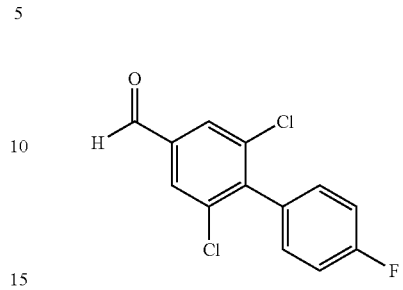

A solution of oxalyl chloride (41.3 uL, 0.47 mmol) in DCM (3 mL) under nitrogen was cooled in a dry ice/acetone bath and DMSO (84 uL, 1.18 mmol) was added slowly. After 15 minutes, the mixture of alcohols from Step 2 (65 mg) in DCM (2 mL) was added. After an additional hour at −78° C., DIPEA (0.412 mL, 2.4 mmol) in DCM (0.5 mL) was added and the reaction was warmed to room temperature for 1 hour. The reaction was diluted with water and 18% citric acid and was extracted twice with DCM. The organic layers were washed with brine containing sodium bicarbonate, dried over sodium sulfate and concentrated. The residue was purified on silica gel (COMBI FLASH 12 gm column, 100% hexanes, then a gradient of 10-20% DCM/hexanes to remove the 2,6-dichlorobenzaldehyde impurity, then 20-40% DCM/hexanes) to give the title intermediate (30 mg).

LCMS (m/e): 269 (M+1).

Step 4. Synthesis of methyl 4-{8-[(2,6-dichloro-4'-fluorobiphen-4-yl)methyl]-2-oxo-1-oxa-3,8-diazaspiro[4.5]dec-3-yl}benzoate

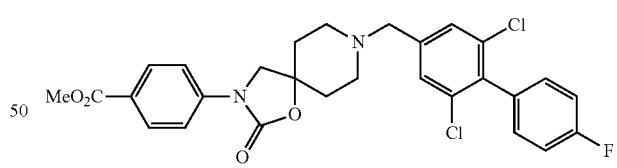

To a solution of methyl 4-(2-oxo-1-oxa-3,8-diazaspiro[4.5]dec-3-yl)benzoate (27 mg, 0.084 mmol) (from Example 1-1, Step 2) and 2,6-dichloro-4'-fluorobiphenyl-4-carboxaldehyde (15 mg, 0.056 mmol) (from Step 3) in DCE (2 mL) and methanol (2 mL) in a 20 mL scintillation vial was added acetic acid (10 uL, 0.168 mmol) and MP-cyanoborohydride resin (56 mg, 0.140 mmol, 2.49 mmol/g). The mixture was shaken at room temperature for 18 hours and was then filtered to remove the resin. The volatiles were removed in vacuo and the residue was used directly in Step 5

Step 5. Synthesis of 4-{8-[(2,6-dichloro-4'-fluorobiphen-4-yl)methyl]-2-oxo-1-oxa-3,8-diazaspiro[4.5]dec-3-yl}benzoic acid, TFA salt

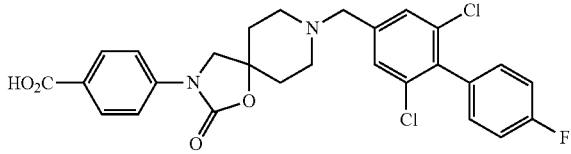 [SMILES: O=C(O)c1ccc(N2CC3(CCN(Cc4cc(Cl)c(-c5ccc(F)cc5)c(Cl)c4)CC3)OC2=O)cc1]

The crude product from Step 4, methyl 4-{8-[(4'-fluoro-2,6-dichlorobiphen-4-yl)methyl]-2-oxo-1-oxa-3,8-diazaspiro[4.5]dec-3-yl}benzoate (0.056 mmol), was taken up in methanol (3 mL) and aqueous sodium hydroxide (2N, 0.250 mL, 500 mmole) was added. The reaction was stirred at room temperature for 24 hours and was then concentrated in vacuo. The residue was taken up in acetonitrile/water/methanol and acidified with TFA and the products were isolated by reverse phase (C-18) HPLC chromatography (10-75% acetonitrile/water gradient with 0.1% TFA) to afford the title compound (20 mg) as a solid TFA salt after evaporation and trituration with ether.

LCMS (m/e): 527/529 (M+1).

Example 8-2

4-{8-[(2,6-Dichloro-2',4'-difluorobiphen-4-yl)methyl]-2-oxo-1-oxa-3,8-diazaspiro[4.5]dec-3-yl}benzoic acid, hydrochloride salt

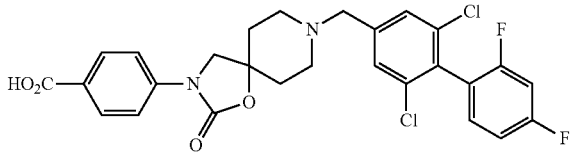 [SMILES: O=C(O)c1ccc(N2CC3(CCN(Cc4cc(Cl)c(-c5ccc(F)cc5F)c(Cl)c4)CC3)OC2=O)cc1]

Step 1: Synthesis of 3,5-dichloro-4-iodobenzyl alcohol

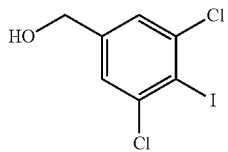 [SMILES: OCc1cc(Cl)c(I)c(Cl)c1]

Using essentially the same procedure as for Example 8-1, Step 2, 3,5-dichloro-4-iodobenzoic acid (1900 mg, 6.0 mmol) was reduced to the title intermediate (1050 mg) using 2M borane-methyl sulfide complex in THF (4.0 mL, 8.0 mmol).

$^1$H-NMR (CDCl$_3$, 400 MHz): δ 7.342 (s, 2H), 4.62 (d, J=5.9 Hz, 2H), 1.78 (t, J=5.9 Hz, 1H).

Step 2: Synthesis of (2,6-dichloro-2',4'-difluorobiphenyl-4-yl)methanol

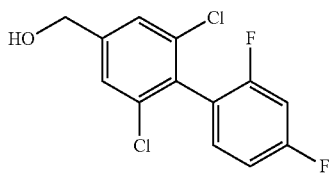 [SMILES: OCc1cc(Cl)c(-c2ccc(F)cc2F)c(Cl)c1]

Using essentially the same coupling procedure as for Example 8-1, Step 1, but heating 2,4-difluorophenylboronic acid (456 mg, 2.89 mmol) and 3,5-dichloro-4-iodobenzyl alcohol (350 mg, 1.155 mmol) in a microwave at 115° C. for 120 minutes, afforded the title intermediate (242 mg) without formation of any appreciable 3,5-dichlorobenzyl alcohol.

$^1$H-NMR (CDCl$_3$, 400 MHz): δ 7.37 (s, 2H), 7.22 (m, 1H), 6.9-7.05 (m, 2H), 4.70 (s, 2H), 1.9 (br s, 1H).

Step 3: Synthesis of 2,6-dichloro-2',4'-difluorobiphenyl-4-carboxaldehyde

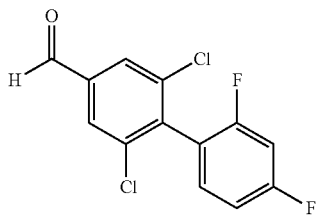 [SMILES: O=Cc1cc(Cl)c(-c2ccc(F)cc2F)c(Cl)c1]

Using essentially the same Swern procedure as for Example 8-1, Step 3, (2,6-dichloro-2',4'-difluorobiphenyl-4-yl)methanol (450 mg, 1.557 mmol) was oxidized to the title intermediate (440 mg).

$^1$H-NMR (CDCl$_3$, 400 MHz): δ. 9.963 (s, 1H), 7.899 (s, 2H), 7.22 (m, 1H), 6.9-7.05 (m, 2H).

Step 4. Synthesis of 4-{8-[(2,6-dichloro-2',4'difluorobiphen-4-yl)methyl]-2-oxo-1-oxa-3,8-diazaspiro[4.5]dec-3-yl}benzoic acid, hydrochloride salt

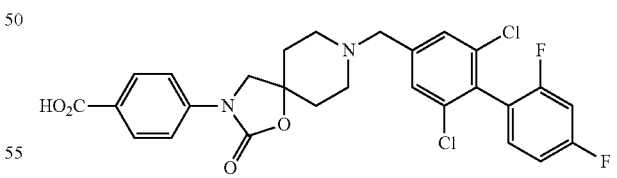

To a solution of 4-(2-oxo-1-oxa-3,8-diazaspiro[4.5]dec-3-yl)benzoic acid (27 mg, 0.087 mmol) (from Example 5-1, Step 4) and 2,6-dichloro-2',4'-difluorobiphenyl-4-carboxaldehyde (20 mg, 0.070 mmol) (from Step 3) in DMF (2 mL) in a 20 mL scintillation vial was added acetic acid (13 uL, 0.209 mmol) and MP-cyanoborohydride resin (56 mg, 0.140 mmol, 2.49 mmol/g). The mixture was shaken at room temperature for 20 hours and then was filtered to remove the resin and washed with acetonitrile/water. The mixture was acidified with TFA and used directly for reverse phase (C-18) HPLC chromatography (10-55% acetonitrile/water gradient, 0.1% TFA) to afford the desired title compound (27 mg) as a solid TFA salt. The TFA salt was converted to the title compound hydrochloride salt by taking up in DCM and addition of excess 2M hydrogen chloride in ether and evaporation (twice) followed by trituration with ether to give the HCl salt (24 mg) as a white solid.

LCMS (m/e): 547/549 (M+1).

Example 8-3

4-{8-[(2,6-Dichloro-3',4'-difluorobiphen-4-yl)methyl]-2-oxo-1-oxa-3,8-diazaspiro[4.5]dec-3-yl}benzoic acid, TFA salt

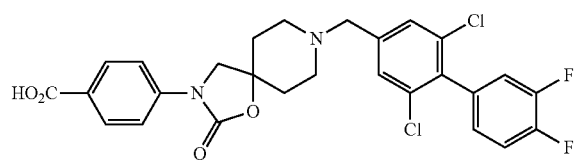 [SMILES: O=C(O)c1ccc(N2CC3(CCN(Cc4cc(Cl)c(-c5ccc(F)c(F)c5)c(Cl)c4)CC3)OC2=O)cc1]

and Example 8-4

4-{8-[(2-chloro-6-cyclopropyl-3',4'-difluorobiphen-4-yl)methyl]-2-oxo-1-oxa-3,8-diazaspiro[4.5]dec-3-yl}benzoic acid, TFA salt

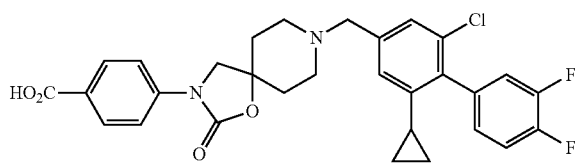 [SMILES: O=C(O)c1ccc(N2CC3(CCN(Cc4cc(Cl)c(-c5ccc(F)c(F)c5)c(C5CC5)c4)CC3)OC2=O)cc1]

Step 1. Synthesis of methyl 4-{8-[(2,6-dichloro-3',4'-difluorobiphen-4-yl)methyl]-2-oxo-1-oxa-3,8-diazaspiro[4.5]dec-3-yl}benzoate, TFA salt

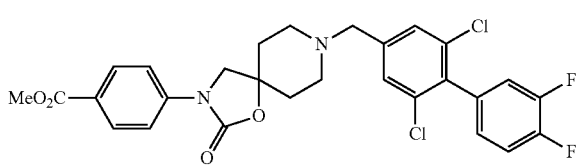 [SMILES: COC(=O)c1ccc(N2CC3(CCN(Cc4cc(Cl)c(-c5ccc(F)c(F)c5)c(Cl)c4)CC3)OC2=O)cc1]

Using essentially the same procedure as Example 8-2, Step 4, but using 2,6-dichloro-3',4'-difluorobiphenyl-4-carboxaldehyde (20 mg, 0.070 mmol) from Example 8-2, Step 3, and methyl 4-(2-oxo-1-oxa-3,8-diazaspiro[4.5]dec-3-yl)benzoate (29 mg, 0.087 mmol) (from Example 1-1, Step 2), the title intermediate was isolated by reverse phase (C-18) HPLC chromatography (10-55% acetonitrile/water gradient, 0.1% TFA) as a TFA salt (28 mg).

LCMS (m/e): 561/563 (M+1).

Step 2. Synthesis of 4-{8-[(2,6-dichloro-3',4'-difluorobiphen-4-yl)methyl]-2-oxo-1-oxa-3,8-diazaspiro[4.5]dec-3-yl}benzoic acid, TFA salt

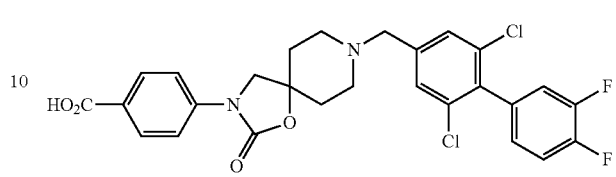

and 4-{8-[(2-chloro-6-cyclopropyl-3',4'-difluorobiphen-4-yl)methyl]-2-oxo-1-oxa-3,8-diazaspiro[4.5]dec-3-yl}benzoic acid, TFA salt

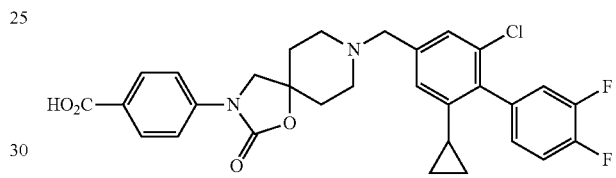

To a mixture of methyl 4-{8-[(2,6-dichloro-3',4'-difluorobiphen-4-yl)methyl]-2-oxo-1-oxa-3,8-diazaspiro[4.5]dec-3-yl}benzoate, TFA salt, from Step 1 (25 mg, 0.045 mmol), potassium cyclopropyltrifluoroborate (10 mg, 0.067 mmol) and 2M aqueous potassium carbonate (0.089 mL, 0.178 mmol) in cyclopentyl methyl ether (1 mL) under nitrogen in a 5 mL microwave reaction vial was added X-Phos (1.3 mg, 0.0027 mmol) and palladium acetate (0.30 mg, 0.0013 mmol). The vial was again purged with nitrogen, sealed and heated in an oil bath at 100° C. for 16 hours. Additional aliquots of X-Phos, palladium acetate and borate were added and heating was continued for another 8 hours. The reaction was concentrated under a stream of nitrogen and the residue was taken up in water and extracted 3 times with DCM. The DCM layers were evaporated to afford a crude 1:1 mixture of starting dichloro and mono-cyclopropyl/mono-chloro products with a small amount of dicyclopropyl product by MS.

This crude mixture was used directly for the ester hydrolysis by dissolving in THF (3 mL)/water (1 mL)/methanol (1 mL or enough to form a solution), adding excess lithium hydroxide (total 32 mg), stirring at room temperature for 20 hours and then heating at 45° C. for 3 hours. The reaction was concentrated in vacuo, acidified with TFA and the title compounds were isolated by reverse phase (C-18) HPLC chromatography (10-55% acetonitrile/water gradient, 0.1% TFA). The faster $R_f$ major component was the title dichloro product (9 mg as a TFA salt).

LCMS (m/e): 547/549 (M+1).

The slower $R_f$ second major component was the mono-cyclopropyl/mono-chloro title product (11 mg as a TFA salt).

LCMS (m/e): 553/555 (M+1).

Example 8-5

4-{8-[(2-Cyclopropyl-3',4'-difluorobiphen-4-yl)methyl]-2-oxo-1-oxa-3,8-diazaspiro[4.5]dec-3-yl}benzoic acid, TFA salt

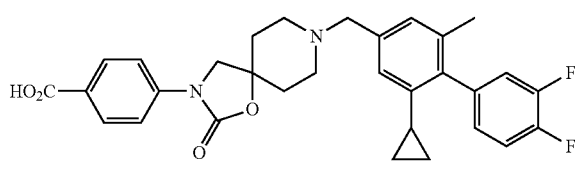 [SMILES: Cc1cc(CN2CCC3(CC2)CN(c2ccc(C(=O)O)cc2)C(=O)O3)cc(C2CC2)c1-c1ccc(F)c(F)c1]

and Example 8-6

4-{8-[(2,6-dicyclopropyl-3',4'-difluorobiphen-4-yl)methyl]-2-oxo-1-oxa-3,8-diazaspiro[4.5]dec-3-yl}benzoic acid, TFA salt

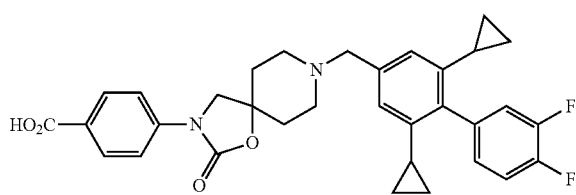 [SMILES: O=C(O)c1ccc(N2CC3(CCN(Cc4cc(C5CC5)c(-c5ccc(F)c(F)c5)c(C5CC5)c4)CC3)OC2=O)cc1]

Using essentially the same procedure as Examples 8-3 and 8-4, Step 2, but using toluene in place of cyclopentyl methyl ether and on a larger amount of methyl 4-{8-[(2,6-dichloro-3',4'-difluorobiphen-4-yl)methyl]-2-oxo-1-oxa-3,8-diazaspiro[4.5]dec-3-yl}benzoate, as the free amine (65 mg, 0.116 mmol), the reaction went further to completion and the title compounds were also isolated in addition to the major mono-chloro/mono-cyclopropyl product which was the same as Example 8-4 (27 mg).

Example 8-5: Mono-cyclopropyl (7 mg as TFA salt): LCMS (m/e): 519 (M+1).

Example 8-6: Di-cyclopropyl (7 mg as TFA salt): LCMS (m/e): 559 (M+1).

Example 8-7

4-{8-[(2-Cyclopropyl-2',4'-difluorobiphen-4-yl)methyl]-2-oxo-1-oxa-3,8-diazaspiro[4.5]dec-3-yl}benzoic acid, TFA salt

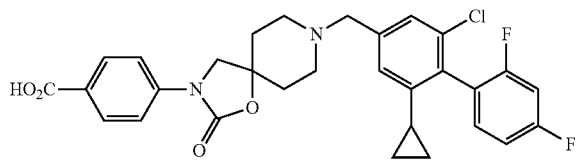

Using essentially the same procedure as Example 8-3 and 8-4, Step 2, but using methyl 4-{8-[(2,6-dichloro-2',4'-difluorobiphen-4-yl)methyl]-2-oxo-1-oxa-3,8-diazaspiro[4.5]dec-3-yl}benzoate, as the TFA salt (33 mg, 0.058 mmol), the title compound was isolated as the major product (14 mg).

LCMS (m/e): 553/555 (M+1).

Example 8-8

4-{8-[(2,6-Dicyclopropyl-2',4'-difluorobiphen-4-yl)methyl]-2-oxo-1-oxa-3,8-diazaspiro[4.5]dec-3-yl}benzoic acid, TFA salt

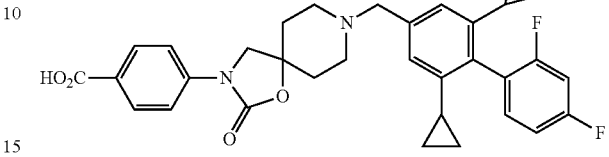

Using essentially the same procedures as Examples 8-5 and 8-6, but using methyl 4-{8-[(2,6-dichloro-2',4'-difluorobiphen-4-yl)methyl]-2-oxo-1-oxa-3,8-diazaspiro[4.5]dec-3-yl}benzoate, as the free amine (75 mg, 0.134 mmol) (prepared as in Example 8-3, Step 1, but using 2,6-dichloro-2',4'-difluorobiphenyl-4-carboxaldehyde from Step 8-1, Step 3), the reaction afforded, in addition to the major product which was the same as Example 8-7 (43 mg), the title compound (9 mg as TFA salt):

LCMS (m/e): 559 (M+1).

Example 8-9

4-{8-[(2,6-Dimethyl-4'-fluorobiphen-4-yl)methyl]-2-oxo-1-oxa-3,8-diazaspiro[4.5]dec-3-yl}benzoic acid

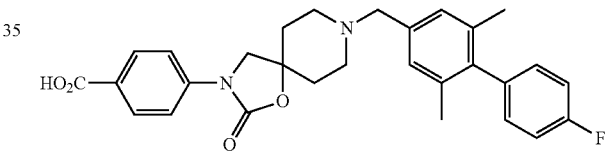

Step 1. Synthesis of 3,5-dimethyl-4-trifluoromethanesulfonyloxybenzaldehyde

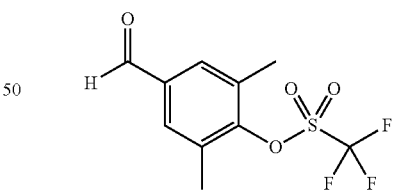

To a solution of 3,5-dimethyl-4-hydroxybenzyl alcohol (900 mg, 6.0 mmol) and N-phenyl-bis(trifluoromethanesulfonimide) (2.57 g, 7.19 mmol) under nitrogen at room temperature in anhydrous DCM (10 mL) was slowly added TEA (1.67 mL, 12 mmol). The reaction was stirred at room temperature for 20 hours and was then quenched with water and extracted three times with DCM. The organic layers were washed with brine, dried over magnesium sulfate and concentrated. The residue was purified on silica gel (COMBI FLASH 24 gm column, 100% hexanes, then a gradient of 0-35% ethyl acetate/hexanes) to give the title intermediate (1.63 g).

$^1$H-NMR (CDCl$_3$, 500 MHz): δ 10.02 (s, 1H), 7.71 (s, 2H), 2.51 (s, 6H).

LCMS (m/e): 282 (M+1).

Step 2. Synthesis of (2,6-dimethyl-4'-fluorobiphen-4-yl)carboxaldehyde

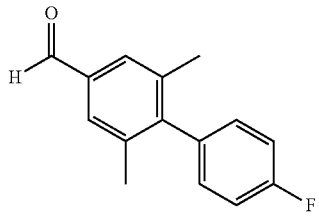 [SMILES: Cc1cc(C=O)cc(C)c1-c1ccc(F)cc1]

3,5-Dimethyl-4-trifluoromethanesulfonyloxy-benzaldehyde (100 mg, 0.35 mmol) and 4-fluorophenylboronic acid (74 mg, 0.53 mmol) in a 5 mL microwave reaction vial were taken up in dioxane (3 mL) and 1M K$_2$CO$_3$ solution (1.1 mL, 1.1 mmol) and the vial was flushed with nitrogen. Pd(Ph$_3$P)$_4$ (25 mg, 0.021 mmol) was added and the vial was again flushed with nitrogen and sealed. The reaction was heated in a microwave at 110° C. for 20 minutes. The reaction was diluted with water and the layers were separated. The organic layer was dried over sodium sulfate and concentrated. The residue could be used directly or be purified on silica gel (COMBI FLASH 12 gm column, 100% hexanes, then a gradient of 0-10% ethyl acetate/hexanes) to give the title intermediate (40 mg).

$^1$H-NMR (CDCl$_3$, 500 MHz): δ 10.02 (s, 1H), 7.74 (s, 2H), 7.12 and 7.20 (2m, 4H), 2.12 (s, 6H).

Step 3. Synthesis of methyl 4-{8-[(2,6-dimethyl-4'-fluorobiphen-4-yl)methyl]-2-oxo-1-oxa-3,8-diazaspiro[4.5]dec-3-yl}benzoate

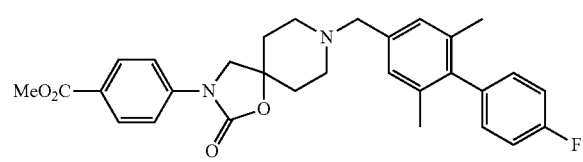 [SMILES: COC(=O)c1ccc(N2CC3(CCN(Cc4cc(C)c(-c5ccc(F)cc5)c(C)c4)CC3)OC2=O)cc1]

Using essentially the same procedures as Example 8-1, Step 4, but using methyl 4-(2-oxo-1-oxa-3,8-diazaspiro[4.5]dec-3-yl)benzoate (45 mg, 0.138 mmol) (from Example 1-1, Step 2) and 2,6-dimethyl-4'-fluorobiphenyl-4-carboxaldehyde (47 mg crude, 0.21 mmol) from Step 2, the title intermediate (5.2 mg) was obtained after mass directed reverse phase (C18) chromatography (on half of the crude reaction mixture using 0.1% ammonium hydroxide) and evaporation of the product fractions.

LCMS (m/e): 503 (M+1).

Step 4. Synthesis of 4-{8-[(2,6-dimethyl-4'-fluorobiphen-4-yl)methyl]-2-oxo-1-oxa-3,8-diazaspiro[4.5]dec-3-yl}benzoic acid

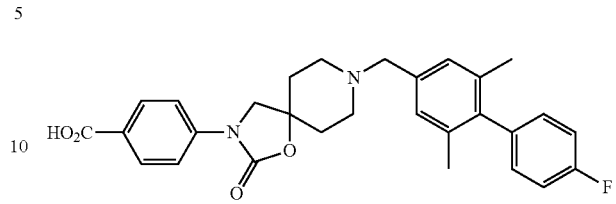

To a mixture of half of the crude methyl 4-{8-[(4'-fluoro-2,6-dimethylbiphen-4-yl)methyl]-2-oxo-1-oxa-3,8-diazaspiro[4.5]dec-3-yl}benzoate from Step 3 (~0.065 mmol) in ethanol (1 mL) was added excess aqueous potassium hydroxide and the reaction was stirred at room temperature for 24 hours. The mixture was then acidified with acetic acid and the title product (5.4 mg) was isolated by mass directed reverse phase (C18) chromatography (0.1% ammonium hydroxide) and evaporation of the product fractions.

LCMS (m/e): 489 (M+1).

$^1$H-NMR (DMSO-d$_6$, 500 MHz): δ 1.86 (m, 4H) 1.92 (s, 6H) 2.47 (m, 4H) 3.43 (s, 2H) 3.87 (s, 2H) 7.02 (s, 2H) 7.14 (dd, J=7.5, 4.5 Hz, 2H) 7.22 (dd, J=7.5, 7.5 Hz, 2H) 7.57 (d, J=7.5 Hz, 2H) 7.87 (d, J=7.5 Hz, 2H).

Example 8-10

4-{8-[(2,6-Dimethyl-2'-fluorobiphen-4-yl)methyl]-2-oxo-1-oxa-3,8-diazaspiro[4.5]dec-3-yl}benzoic acid, formic acid salt

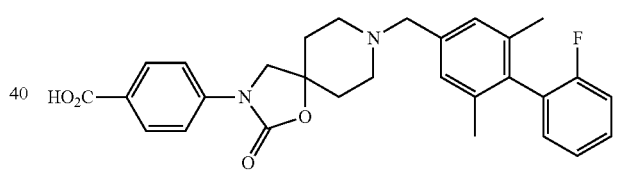

Using essentially the same procedures as Example 8-9, Steps 2-4, but using 2-fluorophenylboronic acid in Step 2, the title compound was obtained as the formic acid salt after mass directed reverse phase (C18) chromatography (0.1% formic acid) and evaporation of the product fractions.

LCMS (m/e): 489 (M+1).

Example 8-11

4-{8-[(2,6-Dimethyl-3'-fluorobiphen-4-yl)methyl]-2-oxo-1-oxa-3,8-diazaspiro[4.5]dec-3-yl}benzoic acid

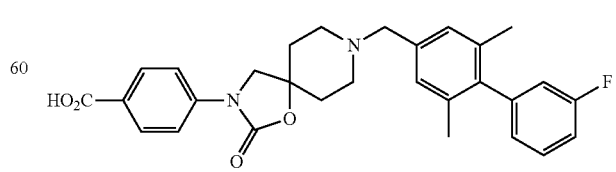

Using essentially the same procedures as Example 8-9, Steps 2-4, but using 3-fluorophenylboronic acid in Step 2, the title compound was obtained after mass directed reverse phase (C18) chromatography (0.1% ammonium hydroxide) and evaporation of the product fractions.

LCMS (m/e): 489 (M+1).

Example 8-12

4-{8-[(2,6-Dimethylbiphen-4-yl)methyl]-2-oxo-1-oxa-3,8-diazaspiro[4.5]dec-3-yl}benzoic acid

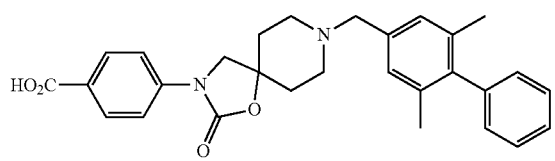

Using essentially the same procedures as Example 8-9, Steps 2-4, but using phenylboronic acid in Step 2, the title compound was obtained after mass directed reverse phase (C18) chromatography (0.1% ammonium hydroxide) and evaporation of the product fractions.

LCMS (m/e): 471 (M+1).

Example 8-13

4-{8-[(2',4'-Difluoro-2,6-dimethylbiphen-4-yl)methyl]-2-oxo-1-oxa-3,8-diazaspiro[4.5]dec-3-yl}benzoic acid

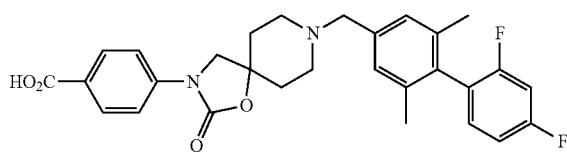

Using essentially the same procedures as Example 8-9, Steps 2-4, but using 2,4-difluorophenylboronic acid in Step 2, the title compound was obtained after mass directed reverse phase (C18) chromatography (0.1% ammonium hydroxide) and evaporation of the product fractions.

LCMS (m/e): 507 (M+1).

Example 8-14

4-{8-[(2',3'-Difluoro-2,6-dimethylbiphen-4-yl)methyl]-2-oxo-1-oxa-3,8-diazaspiro[4.5]dec-3-yl}benzoic acid

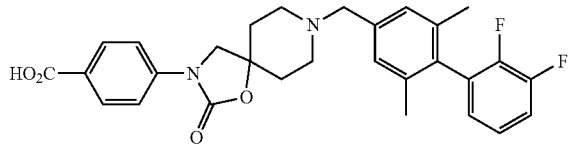 [SMILES: Cc1cc(CN2CCC3(CC2)CN(c2ccc(C(=O)O)cc2)C(=O)O3)cc(C)c1-c1cccc(F)c1F]

Using essentially the same procedures as Example 8-9, Steps 2-4, but using 2,3-difluorophenylboronic acid in Step 2, the title compound was obtained after mass directed reverse phase (C18) chromatography (0.1% ammonium hydroxide) and evaporation of the product fractions.

LCMS (m/e): 507 (M+1).

Example 8-15

4-{8-[(3',4'-Difluoro-2,6-dimethylbiphen-4-yl)methyl]-2-oxo-1-oxa-3,8-diazaspiro[4.5]dec-3-yl}benzoic acid

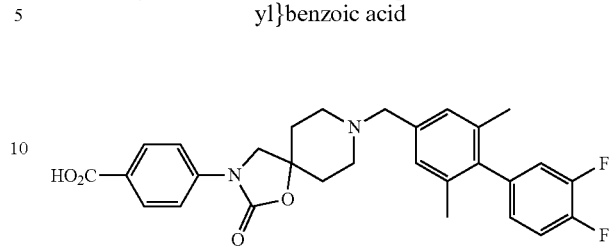

Using essentially the same procedures as Example 8-9, Steps 2-4, but using 3,4-difluorophenylboronic acid in Step 2, the title compound was obtained after mass directed reverse phase (C18) chromatography (0.1% ammonium hydroxide) and evaporation of the product fractions.

LCMS (m/e): 507 (M+1).
$^1$H-NMR (DMSO-$d_6$, 500 MHz): δ 1.86 (m, 4H) 1.93 (s, 6H) 2.46 (m, 41-1) 3.43 (s, 2H) 3.87 (s, 2H) 6.95 (br., m, 1H) 7.03 (s, 2H) 7.22 (dd, J=9.0, 6.5 Hz, 1H) 7.45 (dd, J=9.0, 7.0 Hz, 1H) 7.63 (d, J=7.5 Hz, 2H) 7.90 (d, J=7.5 Hz, 2H).

Example 8-16

4-{8-[(2',5'-Difluoro-2,6-dimethylbiphen-4-yl)methyl]-2-oxo-1-oxa-3,8-diazaspiro[4.5]dec-3-yl}benzoic acid, formic acid salt

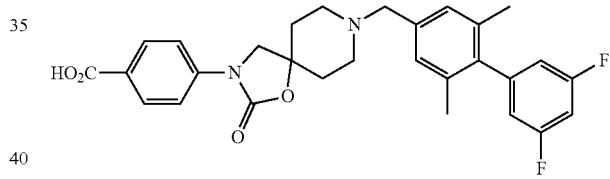

Using essentially the same procedures as Example 8-9, Steps 2-4, but using 3,4-difluorophenylboronic acid in Step 2, the title compound was obtained after mass directed reverse phase (C18) chromatography (0.1% formic acid) and evaporation of the product fractions.

LCMS (m/e): 507 (M+1).

Example 8-17

4-{8-[(4'-Fluoro-2,2',6-trimethylbiphen-4-yl)methyl]-2-oxo-1-oxa-3,8-diazaspiro[4.5]dec-3-yl}benzoic acid, formic acid salt

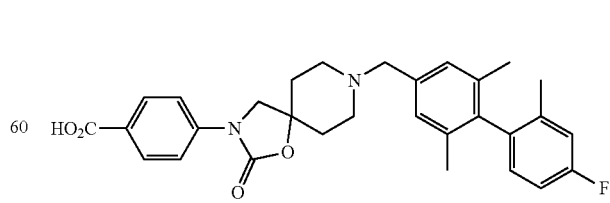

Using essentially the same procedures as Example 8-9, Steps 2-4, but using 4-difluoro-2-methylphenylboronic acid in Step 2, the title compound was obtained after mass directed reverse phase (C18) chromatography (0.1% formic acid) and evaporation of the product fractions.
LCMS (m/e): 503 (M+1).

Example 8-18

4-{8-[(2'-Fluoro-2,4',6-trimethylbiphen-4-yl)methyl]-2-oxo-1-oxa-3,8-diazaspiro[4.5]dec-3-yl}benzoic acid, formic acid salt

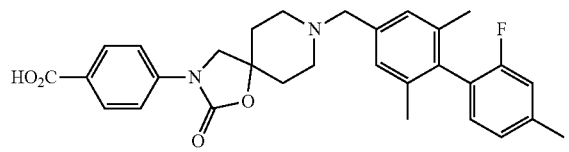 [SMILES: Cc1ccc(-c2c(C)cc(CN3CCC4(CC3)CN(c3ccc(C(=O)O)cc3)C(=O)O4)cc2C)c(F)c1]

Using essentially the same procedures as Example 8-9, Steps 2-4, but using 2-fluoro-4-methylphenylboronic acid in Step 2, the title compound was obtained after mass directed reverse phase (C18) chromatography (0.1% formic acid) and evaporation of the product fractions.
LCMS (m/e): 503 (M+1).

Example 8-19

4-{8-[(2',4'-Dichloro-2,6-dimethylbiphen-4-yl)methyl]-2-oxo-1-oxa-3,8-diazaspiro[4.5]dec-3-yl}benzoic acid, TFA salt

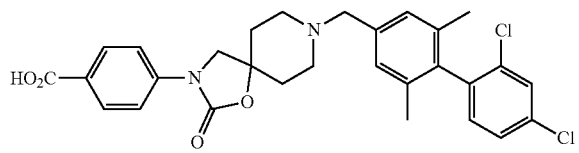 [SMILES: Cc1cc(CN2CCC3(CC2)CN(c2ccc(C(=O)O)cc2)C(=O)O3)cc(C)c1-c1ccc(Cl)cc1Cl]

Using essentially the same procedures as Example 8-9, Steps 2-4, but using 2,4-dichlorophenylboronic acid in Step 2, the title compound was obtained after mass directed reverse phase (C18) chromatography (0.1% TFA) and evaporation of the product fractions.
LCMS (m/e): 540/542 (M+1).

Example 8-20

4-{8-[(4'-Fluoro-2,3',6-trimethylbiphen-4-yl)methyl]-2-oxo-1-oxa-3,8-diazaspiro[4.5]dec-3-yl}benzoic acid

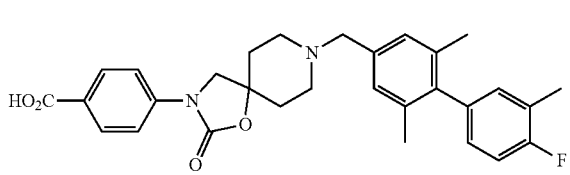 [SMILES: Cc1cc(-c2c(C)cc(CN3CCC4(CC3)CN(c3ccc(C(=O)O)cc3)C(=O)O4)cc2C)ccc1F]

Using essentially the same procedures as Example 8-9, Steps 2-4, but using 4-fluoro-3-methylphenylboronic acid in Step 2, the title compound was obtained after mass directed reverse phase (C18) chromatography (0.1% ammonium hydroxide) and evaporation of the product fractions.
LCMS (m/e): 503 (M+1).

Example 8-21

4-{8-[(4'-Chloro-2,6-dimethylbiphen-4-yl)methyl]-2-oxo-1-oxa-3,8-diazaspiro[4.5]dec-3-yl}benzoic acid

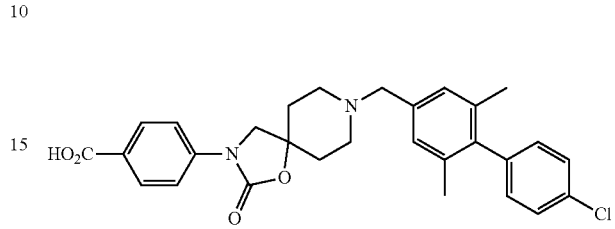

Using essentially the same procedures as Example 8-9, Steps 2-4, but using 4-chlorophenylboronic acid in Step 2, the title compound was obtained after mass directed reverse phase (C18) chromatography (0.1% ammonium hydroxide) and evaporation of the product fractions.
LCMS (m/e): 527/529 (M+1).

Example 8-22

4-{8-[(2-Methylbiphen-4-yl)methyl]-2-oxo-1-oxa-3,8-diazaspiro[4.5]dec-3-yl}benzoic acid

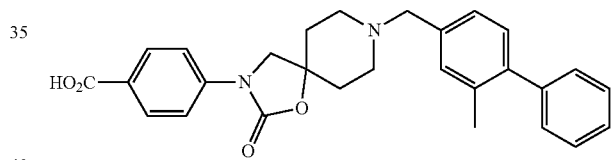

Using essentially the same procedures as Example 8-9, Steps 1-4, but using 4-hydroxy-3-methylbenzaldehyde in Step 1 and phenylboronic acid in Step 2, the title compound was obtained after mass directed reverse phase (C18) chromatography (0.1% ammonium hydroxide) and evaporation of the product fractions.
LCMS (m/e): 457 (M+1).

Example 8-23

4-{8-[(2'-Fluoro-2-methylbiphen-4-yl)methyl]-2-oxo-1-oxa-3,8-diazaspiro[4.5]dec-3-yl}benzoic acid

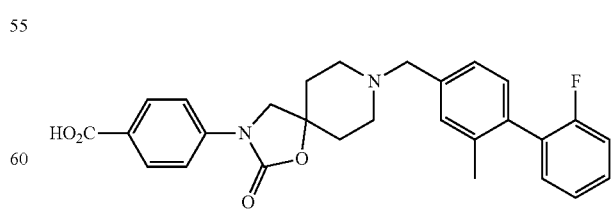

Using essentially the same procedures as Example 8-9, Steps 1-4, but using 4-hydroxy-3-methylbenzaldehyde in Step 1 and 2-fluorophenylboronic acid in Step 2, the title compound was obtained after mass directed reverse phase (C18) chromatography (0.1% ammonium hydroxide) and evaporation of the product fractions.

LCMS (m/e): 475 (M+1).

Example 8-24

4-{8-[(3'-Fluoro-2-methylbiphen-4-yl)methyl]-2-oxo-1-oxa-3,8-diazaspiro[4.5]dec-3-yl}benzoic acid, formic acid salt

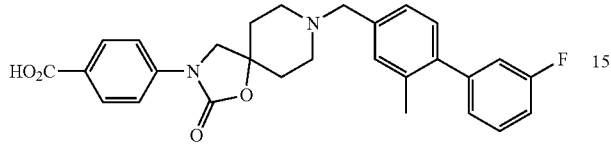

Using essentially the same procedures as Example 8-9, Steps 1-4, but using 4-hydroxy-3-methylbenzaldehyde in Step 1 and 3-fluorophenylboronic acid in Step 2, the title compound was obtained after mass directed reverse phase (C18) chromatography (0.1% formic acid) and evaporation of the product fractions.
LCMS (m/e): 475 (M+1).

Example 8-25

4-{8-[(4'-Fluoro-2-methylbiphen-4-yl)methyl]-2-oxo-1-oxa-3,8-diazaspiro[4.5]dec-3-yl}benzoic acid

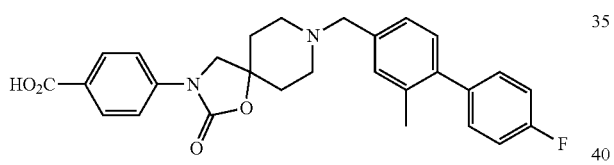

Using essentially the same procedures as Example 8-9, Steps 1-4, but using 4-hydroxy-3-methylbenzaldehyde in Step 1 and 4-fluorophenylboronic acid in Step 2, the title compound was obtained after mass directed reverse phase (C18) chromatography (0.1% ammonium hydroxide) and evaporation of the product fractions.
LCMS (m/e): 475 (M+1).

Example 8-26

4-{8-[(2',4'-Difluoro-2-methylbiphen-4-yl)methyl]-2-oxo-1-oxa-3,8-diazaspiro[4.5]dec-3-yl}benzoic acid

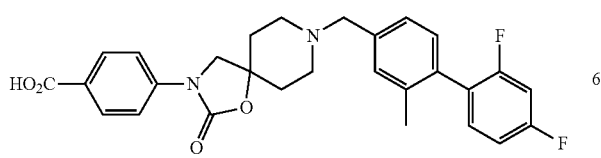

Using essentially the same procedures as Example 8-9, Steps 1-4, but using 4-hydroxy-3-methylbenzaldehyde in Step 1 and 2,4-difluorophenylboronic acid in Step 2, the title compound was obtained after mass directed reverse phase (C18) chromatography (0.1% ammonium hydroxide) and evaporation of the product fractions.
LCMS (m/e): 493 (M+1).
$^1$H-NMR (DMSO-$d_6$, 500 MHz): δ 1.87 (m, 4H) 2.07 (s, 3H) 2.46 (m, 4H) 3.49 (s, 2H) 3.88 (s, 2H) 7.11 (m, 2H) 7.18 (d, J=6.5, Hz, 1H) 7.23 (s, 1H) 7.30 (b., m, 2H) 7.62 (d, J=7.5 Hz, 2H) 7.90 (d, J=7.5 Hz, 2H).

Example 8-27

4-{8-[(2-Chloro-4'-fluorobiphen-4-yl)methyl]-2-oxo-1-oxa-3,8-diazaspiro[4.5]dec-3-yl}benzoic acid

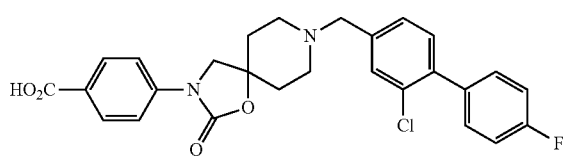 [SMILES: O=C(O)c1ccc(N2CC3(CCN(Cc4ccc(-c5ccc(F)cc5)c(Cl)c4)CC3)OC2=O)cc1]

Using essentially the same procedures as Example 8-9, Steps 1-4, but using 3-chloro-4-hydroxybenzaldehyde in Step 1 and 4-fluorophenylboronic acid in Step 2, the title compound was obtained after mass directed reverse phase (C18) chromatography (0.1% ammonium hydroxide) and evaporation of the product fractions.
LCMS (m/e): 495/497 (M+1).
$^1$H-NMR (DMSO-$d_6$, 500 MHz): δ 1.87 (m, 4H) 2.46 (m, 4H) 3.53 (s, 2H) 3.88 (s, 21-1) 7.25 (dd, J=7.5, 7.5 Hz, 2H) 7.33 (s, 2H) 7.44 (dd, J=7.5, 4.5 Hz, 2H) 7.47 (s, 1H) 7.64 (d, J=7.5 Hz, 2H) 7.91 (d, J=7.5 Hz, 2H).

Example 8-28

4-{8-[(3',4'-Difluoro-2-methylbiphen-4-yl)methyl]-2-oxo-1-oxa-3,8-diazaspiro[4.5]dec-3-yl}benzoic acid

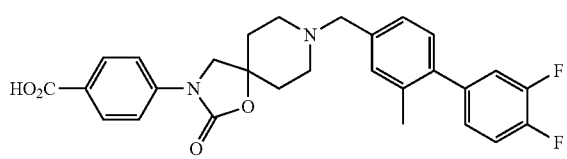 [SMILES: Cc1cc(CN2CCC3(CC2)CN(c2ccc(C(=O)O)cc2)C(=O)O3)ccc1-c1ccc(F)c(F)c1]

Using essentially the same procedures as Example 8-9, Steps 1-4, but using 4-hydroxy-3-methylbenzaldehyde in Step 1 and 3,4-difluorophenylboronic acid in Step 2, the title compound was obtained after mass directed reverse phase (C18) chromatography (0.1% ammonium hydroxide) and evaporation of the product fractions.
LCMS (m/e): 493 (M+1).

Example 8-29

4-{8-[(2-Chloro-2',4'-difluoro-6-methylbiphen-4-yl)methyl]-2-oxo-1-oxa-3,8-diazaspiro[4.5]dec-3-yl}benzoic acid

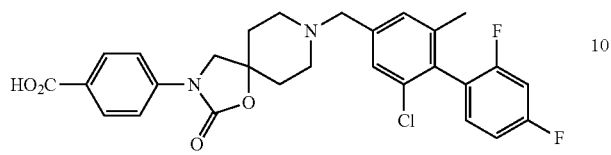

Using essentially the same procedures as Example 8-9, Steps 1-4, but using 3-chloro-4-hydroxy-5-methylbenzaldehyde in Step 1 and 2,4-difluorophenylboronic acid in Step 2, the title compound was obtained after mass directed reverse phase (C18) chromatography (0.1% ammonium hydroxide) and evaporation of the product fractions.
LCMS (m/e): 503/505 (M+1).

Example 8-30

4-{8-[(2-Chloro-3',4'-difluoro-6-methylbiphen-4-yl)methyl]-2-oxo-1-oxa-3,8-diazaspiro[4.5]dec-3-yl}benzoic acid

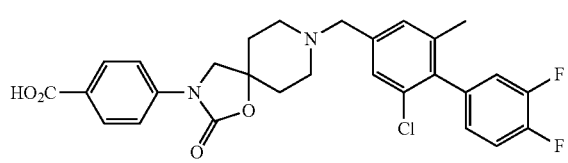 [SMILES: Cc1cc(CN2CCC3(CC2)CN(c2ccc(C(=O)O)cc2)C(=O)O3)cc(Cl)c1-c1ccc(F)c(F)c1]

Using essentially the same procedures as Example 8-9, Steps 1-4, but using 3-chloro-4-hydroxy-5-methylbenzaldehyde in Step 1 and 3,4-difluorophenylboronic acid in Step 2, the title compound was obtained after mass directed reverse phase (C18) chromatography (0.1% ammonium hydroxide) and evaporation of the product fractions.
LCMS (m/e): 503/505 (M+1).
$^1$H-NMR (DMSO-d$_6$, 500 MHz): δ 1.90 (br. m., 4H) 2.04 (s, 3H) 2.5 (br. m, 4H) 3.52 (s, 2H) 3.90 (s, 2H) 7.05 (br. m., 1H) 7.23 (s, 1H) 7.33 (s, 1H) 7.36 (br. m., 1H) 7.51 (br. m., 1H) 7.6 (d, J=9.0 Hz, 2H) 7.9 (d, J=9.0 Hz, 2H).

Example 8-31

4-{8-[(2,6-Diprop-1-ylbiphen-4-yl)methyl]-2-oxo-1-oxa-3,8-diazaspiro[4.5]dec-3-yl}benzoic acid

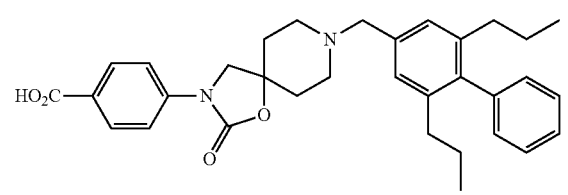 [SMILES: CCCc1cc(CN2CCC3(CC2)CN(c2ccc(C(=O)O)cc2)C(=O)O3)cc(CCC)c1-c1ccccc1]

Using essentially the same procedures as Example 8-9, Steps 1-4, but using 2,6-diprop-1-yl-4-hydroxybenzaldehyde in Step 1 and phenylboronic acid in Step 2, the title compound was obtained after mass directed reverse phase (C18) chromatography (0.1% ammonium hydroxide) and evaporation of the product fractions.
LCMS (m/e): 527 (M+1).

Example 8-32

4-{8-[(2,6-Diprop-1-yl-2'-fluorobiphen-4-yl)methyl]-2-oxo-1-oxa-3,8-diazaspiro[4.5]dec-3-yl}benzoic acid

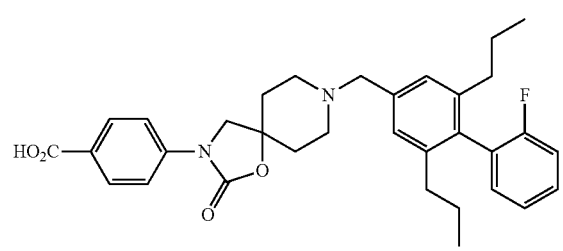 [SMILES: CCCc1cc(CN2CCC3(CC2)CN(c2ccc(C(=O)O)cc2)C(=O)O3)cc(CCC)c1-c1ccccc1F]

Using essentially the same procedures as Example 8-9, Steps 1-4, but using 2,6-diprop-1-yl-4-hydroxybenzaldehyde in Step 1 and 2-fluorophenylboronic acid in Step 2, the title compound was obtained after mass directed reverse phase (C18) chromatography (0.1% ammonium hydroxide) and evaporation of the product fractions.
LCMS (m/e): 545 (M+1).

Example 8-33

4-{8-[(2,6-Diprop-1-yl-3'-fluorobiphen-4-yl)methyl]-2-oxo-1-oxa-3,8-diazaspiro[4.5]dec-3-yl}benzoic acid

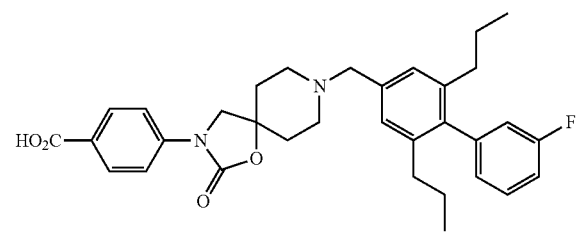 [SMILES: CCCc1cc(CN2CCC3(CC2)CN(c2ccc(C(=O)O)cc2)C(=O)O3)cc(CCC)c1-c1cccc(F)c1]

Using essentially the same procedures as Example 8-9, Steps 1-4, but using 2,6-diprop-1-yl-4-hydroxybenzaldehyde in Step 1 and 3-fluorophenylboronic acid in Step 2, the title compound was obtained after mass directed reverse phase (C18) chromatography (0.1% ammonium hydroxide) and evaporation of the product fractions.
LCMS (m/e): 545 (M+1).

Example 8-34

4-{8-[(2,6-Diprop-1-yl-4'-fluorobiphen-4-yl)methyl]-2-oxo-1-oxa-3,8-diazaspiro[4.5]dec-3-yl}benzoic acid

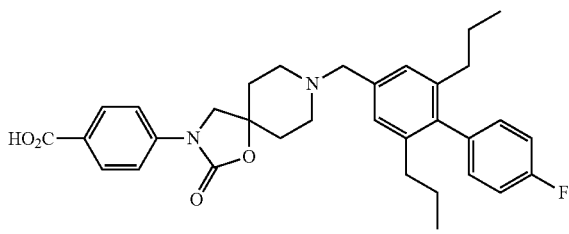 [SMILES: CCCc1cc(CN2CCC3(CC2)CN(c2ccc(C(=O)O)cc2)C(=O)O3)cc(CCC)c1-c1ccc(F)cc1]

Using essentially the same procedures as Example 8-9, Steps 1-4, but using 2,6-diprop-1-yl-4-hydroxybenzaldehyde in Step 1 and 4-fluorophenylboronic acid in Step 2, the title compound was obtained after mass directed reverse phase (C18) chromatography (0.1% ammonium hydroxide) and evaporation of the product fractions.

LCMS (m/e): 545 (M+1).

$^1$H-NMR (DMSO-$d_6$, 500 MHz): δ 0.65 (dd, J=6.0, 6.0 Hz, 6H) 1.28 (ddd, J=12.5, 12.5, 6.5 Hz, 4H) 1.86 (m, 4H) 2.16 (dd, J=6.5, 6.5 Hz, 4H) 2.46 (m, 41-1) 3.47 (s, 2H) 3.86 (s, 2H) 7.01 (s, 2H) 7.13 (dd, J=14.5, 7.0 Hz, 2H) 7.20 (dd, J=14.5, 7.0 Hz, 2H) 7.58 (d, J=7.5 Hz, 2H) 7.88 (d, J=7.5 Hz, 2H).

Example 8-35

4-{8-[(2',4'-Difluoro-2,6-diprop-1-ylbiphen-4-yl)methyl]-2-oxo-1-oxa-3,8-diazaspiro[4.5]dec-3-yl}benzoic acid

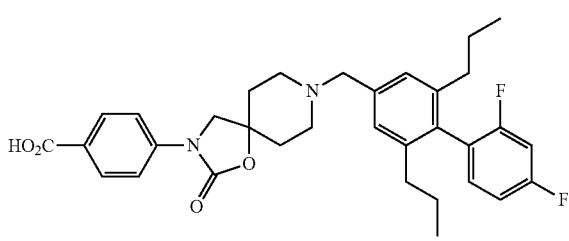 [SMILES: CCCc1cc(CN2CCC3(CC2)CN(c2ccc(C(=O)O)cc2)C(=O)O3)cc(CCC)c1-c1ccc(F)cc1F]

Using essentially the same procedures as Example 8-9, Steps 1-4, but using 2,6-diprop-1-yl-4-hydroxybenzaldehyde in Step 1 and 2,4-difluorophenylboronic acid in Step 2, the title compound was obtained after mass directed reverse phase (C18) chromatography (0.1% ammonium hydroxide) and evaporation of the product fractions.

LCMS (m/e): 563 (M+1).

Example 8-36

4-{8-[(2',5'-Difluoro-2,6-diprop-1-ylbiphen-4-yl)methyl]-2-oxo-1-oxa-3,8-diazaspiro[4.5]dec-3-yl}benzoic acid

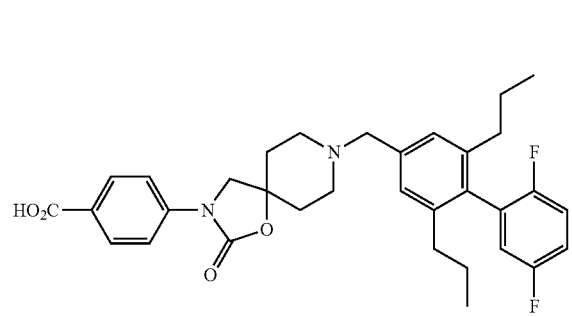 [SMILES: CCCc1cc(CN2CCC3(CC2)CN(c2ccc(C(=O)O)cc2)C(=O)O3)cc(CCC)c1-c1cc(F)ccc1F]

Using essentially the same procedures as Example 8-9, Steps 1-4, but using 2,6-diprop-1-yl-4-hydroxybenzaldehyde in Step 1 and 2,5-difluorophenylboronic acid in Step 2, the title compound was obtained after mass directed reverse phase (C18) chromatography (0.1% ammonium hydroxide) and evaporation of the product fractions.

LCMS (m/e): 563 (M+1).

Example 8-37

4-{8-[(3',4'-Difluoro-2,6-diprop-1-ylbiphen-4-yl)methyl]-2-oxo-1-oxa-3,8-diazaspiro[4.5]dec-3-yl}benzoic acid

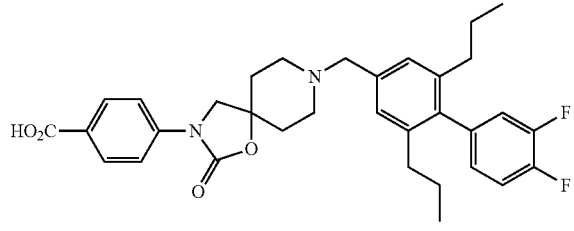 [SMILES: CCCc1cc(CN2CCC3(CC2)CN(c2ccc(C(=O)O)cc2)C(=O)O3)cc(CCC)c1-c1ccc(F)c(F)c1]

Using essentially the same procedures as Example 8-9, Steps 1-4, but using 2,6-diprop-1-yl-4-hydroxybenzaldehyde in Step 1 and 3,4-difluorophenylboronic acid in Step 2, the title compound was obtained after mass directed reverse phase (C18) chromatography (0.1% ammonium hydroxide) and evaporation of the product fractions.

LCMS (m/e): 563 (M+1).

Example 9-1

4-(8-{[1-(Propan-2-yl)-4-(2,3,4-trifluorophenyl)-1H-indol-3-yl]methyl}-2-oxo-1-oxa-3,8-diazaspiro[4.5]dec-3-yl)benzoic acid, TFA salt

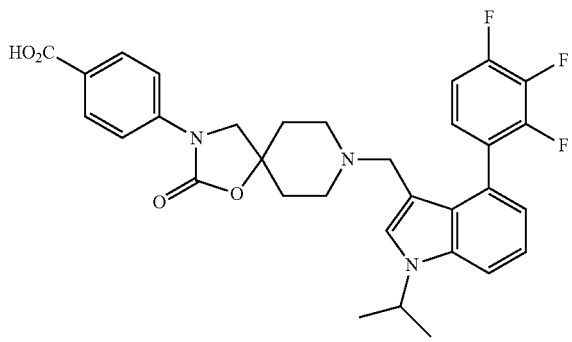 [SMILES: CC(C)n1cc(CN2CCC3(CC2)CN(c2ccc(C(=O)O)cc2)C(=O)O3)c2c(-c3ccc(F)c(F)c3F)cccc21]

Step 1. Synthesis of 4-bromo-1-(propan-2-yl)-1H-indole-3-carboxaldehyde

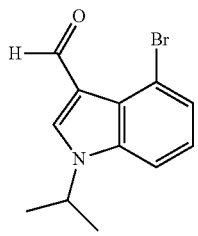

Cesium carbonate (873 mg, 12.68 mmol) was added to a solution of 4-bromo-1H-indole-3-carboxaldehyde (200 mg, 0.893 mmol) in DMF (2.0 mL) and the mixture was stirred at room temperature for 10 minutes. Then 2-iodopropane (0.179 ml, 1.785 mmol) was added and the solution was stirred for 80° C. for 2 hours. The solution was cooled to room temperature and then partitioned between ethyl acetate and water and extracted twice with ethyl acetate. The organic layers were washed twice with water and brine, dried over sodium sulfate, filtered and concentrated under reduced pressure to give the crude title intermediate (175 mg).

LCMS (m/e): 266/268 (M+1).

Step 2. Synthesis of 1-(propan-2-yl)-4-(2,3,4-trifluorophenyl)-1H-indole-3-carboxaldehyde

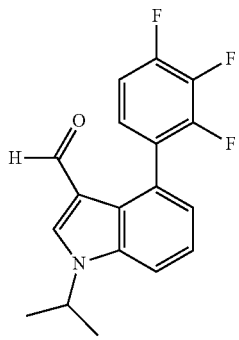 [SMILES: CC(C)n1cc(C=O)c2c(-c3ccc(F)c(F)c3F)cccc21]

To a solution of 4-bromo-1-(propan-2-yl)-1H-indole-3-carboxaldehyde (100 mg, 0.376 mmol) and 2,3,4-trifluorophenylboronic acid (79 mg, 0.451 mmol) in dioxane (2 mL) and water (0.5 mL) in a 5 mL microwave reaction vial was added potassium carbonate (156 mg, 1.13 mmol) and dichloro[1,1'-bis(di-t-butylphosphino)ferrocene]palladium (II) (25 mg, 0.038 mmol). The reaction was placed under nitrogen, sealed and heated in a microwave reactor at 140° C. for 15 minutes. The solvent was removed in vacuo and the residue was partitioned with ethyl acetate and aqueous sodium bicarbonate and extracted twice with ethyl acetate. The organic layers were washed with brine, dried over sodium sulfate, filtered and concentrated. The residue was purified on silica gel (COMBI FLASH 24 gm column, gradient of 0-100% ethyl acetate/hexanes) to give the title intermediate (82 mg).

LCMS (m/e): 318 (M+1).

Step 3. Synthesis of 4-(8-{[1-(propan-2-yl)-4-(2,3,4-trifluorophenyl)-1H-indol-3-yl]methyl}-2-oxo-1-oxa-3,8-diazaspiro[4.5]dec-3-yl)benzoic acid, TFA salt

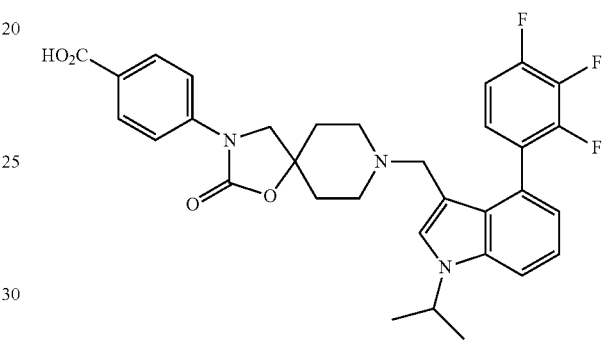

A solution of 1-(propan-2-yl)-4-(2,3,4-trifluorophenyl)-1H-indole-3-carboxaldehyde (40 mg, 0.126 mmol) and 4-(2-oxo-1-oxa-3,8-diazaspiro[4.5]dec-3-yl)benzoic acid hydrochloride (40 mg, 0.126 mmol) (from Example 5-1, Step 4) in DMF (1.5 mL) was added sodium triacetoxyborohydride (80 mg, 0.378 mmol) and the solution was stirred at 60° C. for 3 hours. The reaction mixture was cooled to room temperature and quenched with water. After 5 minutes, the mixture was acidified with TFA and purified by HPLC reverse phase (C-18), eluting with a gradient of acetonitrile/water+0.1% TFA, to give the title compound (36 mg) as a solid white TFA salt after lypholization.

LCMS (m/e): 577 (M+1), 302 (100%).

Example 9-2

4-(8-{[1-(Propan-2-yl)-4-(2-fluorophenyl)-1H-indol-3-yl]methyl}-2-oxo-1-oxa-3,8-diazaspiro[4.5]dec-3-yl)benzoic acid, TFA salt

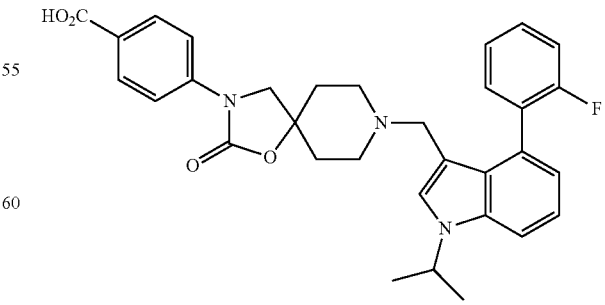

Using essentially the same procedures as Example 9-1, Steps 2-3, but using 2-fluorophenylboronic acid in Step 2 and 1-(propan-2-yl)-4-(2-fluorophenyl)-1H-indole-3-carboxaldehyde in Step 3, the title compound was obtained after reverse phase (C18) chromatography (acetonitrile/water with 0.1% TFA) and evaporation of the product fractions.

LCMS (m/e): 542 (M+1).

Example 9-3

4-(8-{[1-(Propan-2-yl)-4-(4-fluorophenyl)-1H-indol-3-yl]methyl}-2-oxo-1-oxa-3,8-diazaspiro[4.5]dec-3-yl)benzoic acid, TFA salt

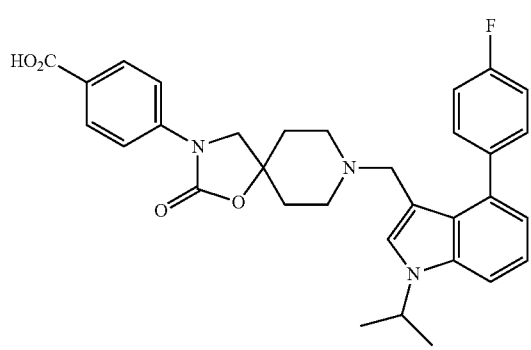 [SMILES: CC(C)n1cc(CN2CCC3(CC2)CN(c2ccc(C(=O)O)cc2)C(=O)O3)c2c(-c3ccc(F)cc3)cccc21]

Using essentially the same procedures as Example 9-1, Steps 2-3, but using 4-fluorophenylboronic acid in Step 2 and 1-(propan-2-yl)-4-(4-fluorophenyl)-1H-indole-3-carboxaldehyde in Step 3, the title compound was obtained after reverse phase (C18) chromatography (acetonitrile/water with 0.1% TFA) and evaporation of the product fractions.

LCMS (m/e): 542 (M+1).

Example 9-4

4-(8-{[1-(Propan-2-yl)-4-(2,4,5-trifluorophenyl)-1H-indol-3-yl]methyl}-2-oxo-1-oxa-3,8-diazaspiro[4.5]dec-3-yl)benzoic acid, TFA salt

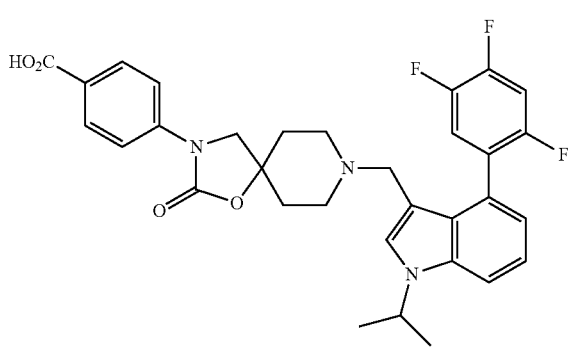 [SMILES: CC(C)n1cc(CN2CCC3(CC2)CN(c2ccc(C(=O)O)cc2)C(=O)O3)c2c(-c3cc(F)c(F)cc3F)cccc21]

Using essentially the same procedures as Example 9-1, Steps 2-3, but using 2,4,5-trifluorophenylboronic acid in Step 2 and 1-(propan-2-yl)-4-(2,4,5-trifluorophenyl)-1H-indole-3-carboxaldehyde in Step 3, the title compound was obtained after reverse phase (C18) chromatography (acetonitrile/water with 0.1% TFA) and evaporation of the product fractions.

LCMS (m/e): 577 (M+1), 302 (100%).

Example 9-5

4-(8-{[1-(Propan-2-yl)-4-(2-trifluoromethylphenyl)-1H-indol-3-yl]methyl}-2-oxo-1-oxa-3,8-diazaspiro[4.5]dec-3-yl)benzoic acid, TFA salt

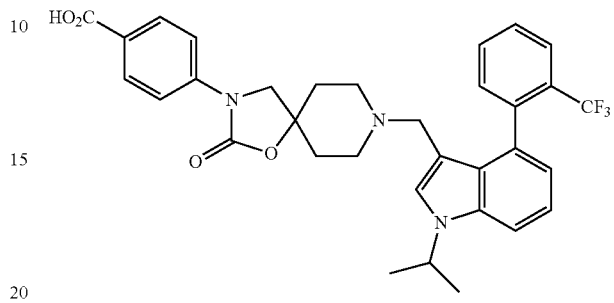

Using essentially the same procedures as Example 9-1, Steps 2-3, but using 2-trifluoromethylphenylboronic acid in Step 2 and 1-(propan-2-yl)-4-(2-trifluoromethylphenyl)-1H-indole-3-carboxaldehyde in Step 3, the title compound was obtained after reverse phase (C18) chromatography (acetonitrile/water with 0.1% TFA) and evaporation of the product fractions.

LCMS (m/e): 577 (M+1), 316 (100%).

Example 9-6

4-(8-{[1-(Propan-2-yl)-4-(6-fluoropyridin-3-yl)-1H-indol-3-yl]methyl}-2-oxo-1-oxa-3,8-diazaspiro[4.5]dec-3-yl)benzoic acid, TFA salt

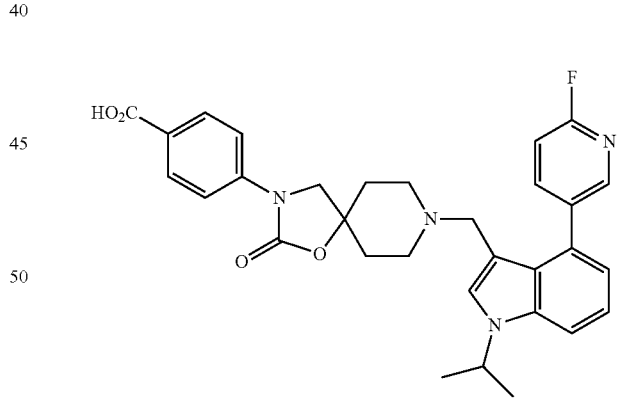

Using essentially the same procedures as Example 9-1, Steps 2-3, but using (6-fluoropyridin-3-yl)boronic acid in Step 2 and 1-(propan-2-yl)-4-(6-fluoropyridin-3-yl)-1H-indole-3-carboxaldehyde in Step 3, the title compound was obtained after reverse phase (C18) chromatography (acetonitrile/water with 0.1% TFA) and evaporation of the product fractions.

LCMS (m/e): 543 (M+1).

Example 9-7

4-(8-{[1-(Propan-2-yl)-4-(3-fluoropyridin-4-yl)-1H-indol-3-yl]methyl}-2-oxo-1-oxa-3,8-diazaspiro[4.5]dec-3-yl)benzoic acid, TFA salt

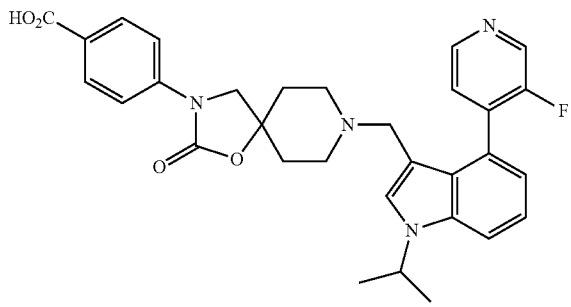 [SMILES: CC(C)n1cc(CN2CCC3(CC2)CN(c2ccc(C(=O)O)cc2)C(=O)O3)c2c(-c3ccncc3F)cccc21]

Using essentially the same procedures as Example 9-1, Steps 2-3, but using (3-fluoropyridin-4-yl)boronic acid in Step 2 and 1-(propan-2-yl)-4-(3-fluoropyridin-4-yl)-1H-indole-3-carboxaldehyde in Step 3, the title compound was obtained after reverse phase (C18) chromatography (acetonitrile/water with 0.1% TFA) and evaporation of the product fractions.

LCMS (m/e): 543 (M+1).

Example 9-8

4-(8-{[1-(Cyclopropylmethyl)-4-(2,3,4-trifluorophenyl)-1H-indol-3-yl]methyl}-2-oxo-1-oxa-3,8-diazaspiro[4.5]dec-3-yl)benzoic acid, TFA salt

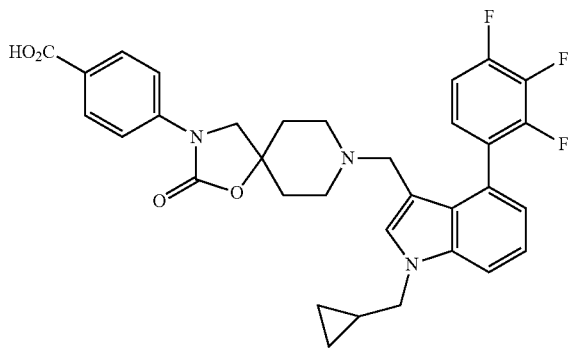 [SMILES: O=C(O)c1ccc(N2CC3(CCN(Cc4cn(CC5CC5)c5cccc(-c6ccc(F)c(F)c6F)c45)CC3)OC2=O)cc1]

Using essentially the same procedures as Example 9-1, Steps 1-3, but using iodomethylcyclopropane in Step 1, the title compound was obtained after reverse phase (C18) chromatography (acetonitrile/water with 0.1% TFA) and evaporation of the product fractions.

LCMS (m/e): 590 (M+1), 314 (100%).

Example 9-9

4-(8-{[1-(Cyclopropylmethyl)-4-(4-fluorophenyl)-1H-indol-3-yl]methyl}-2-oxo-1-oxa-3,8-diazaspiro[4.5]dec-3-yl)benzoic acid, TFA salt

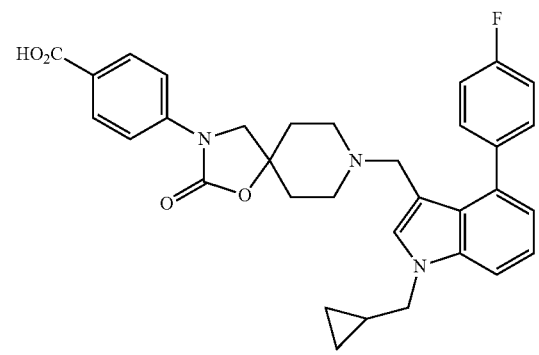 [SMILES: O=C(O)c1ccc(N2CC3(CCN(Cc4cn(CC5CC5)c5cccc(-c6ccc(F)cc6)c45)CC3)OC2=O)cc1]

Using essentially the same procedures as Example 9-1, Steps 1-3, but using iodomethylcyclopropane in Step 1, 4-fluorophenylboronic acid in Step 2, and 1-(cyclopropylmethyl)-4-(4-fluorophenyl)-1H-indole-3-carboxaldehyde in Step 3, the title compound was obtained after reverse phase (C18) chromatography (acetonitrile/water with 0.1% TFA) and evaporation of the product fractions.

LCMS (m/e): 554 (M+1)

Example 9-10

4-(8-{[1-(Propan-2-yl)-5-(4-fluorophenyl)-1H-indol-3-yl]methyl}-2-oxo-1-oxa-3,8-diazaspiro[4.5]dec-3-yl)benzoic acid, TFA salt

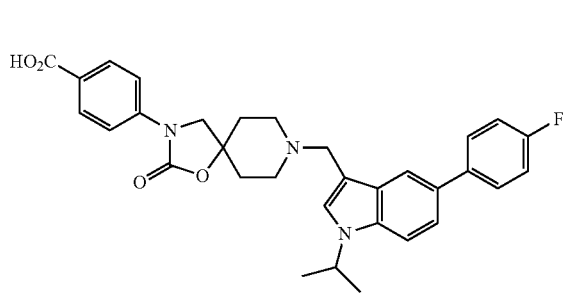 [SMILES: CC(C)n1cc(CN2CCC3(CC2)CN(c2ccc(C(=O)O)cc2)C(=O)O3)c2cc(-c3ccc(F)cc3)ccc21]

Using essentially the same procedures as Example 9-1, Steps 1-3, but using 5-bromo-1H-indole-3-carboxaldehyde in Step 1, 4-fluorophenylboronic acid in Step 2, and 1-(propan-2-yl)-5-(4-fluorophenyl)-1H-indole-3-carboxaldehyde in Step 3, the title compound was obtained after reverse phase (C18) chromatography (acetonitrile/water with 0.1% TFA) and evaporation of the product fractions.

LCMS (m/e): 542 (M+1)

Example 9-11

4-(8-{[1-(Propan-2-yl)-5-(2-fluorophenyl)-1H-indol-3-yl]methyl}-2-oxo-1-oxa-3,8-diazaspiro[4.5]dec-3-yl)benzoic acid, TFA salt

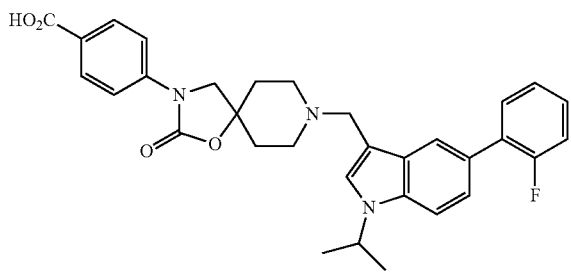 [SMILES: CC(C)n1cc(CN2CCC3(CC2)CN(c2ccc(C(=O)O)cc2)C(=O)O3)c2cc(-c3ccccc3F)ccc21]

Using essentially the same procedures as Example 9-1, Steps 1-3, but using 5-bromo-1H-indole-3-carboxaldehyde in Step 1, 2-fluorophenylboronic acid in Step 2, and 1-(propan-2-yl)-5-(2-fluorophenyl)-1H-indole-3-carboxaldehyde in Step 3, the title compound was obtained after reverse phase (C18) chromatography (acetonitrile/water with 0.1% TFA) and evaporation of the product fractions.

LCMS (m/e): 542 (M+1)

Example 9-12

4-(8-{[1-(Propan-2-yl)-5-(2,4,5-trifluorophenyl)-1H-indol-3-yl]methyl}-2-oxo-1-oxa-3,8-diazaspiro[4.5]dec-3-yl)benzoic acid, TFA salt

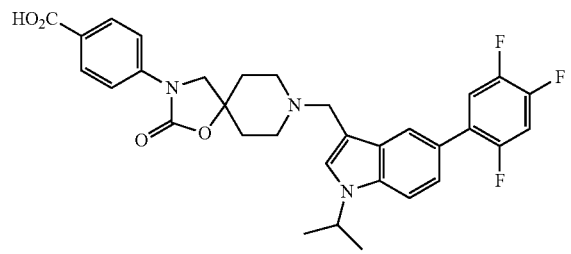 [SMILES: CC(C)n1cc(CN2CCC3(CC2)CN(c2ccc(C(=O)O)cc2)C(=O)O3)c2cc(-c3cc(F)c(F)cc3F)ccc21]

Using essentially the same procedures as Example 9-1, Steps 1-3, but using 5-bromo-1H-indole-3-carboxaldehyde in Step 1, 2,4,5-trifluorophenylboronic acid in Step 2, and 1-(propan-2-yl)-5-(2,4,5-trifluorophenyl)-1H-indole-3-carboxaldehyde in Step 3, the title compound was obtained after reverse phase (C18) chromatography (acetonitrile/water with 0.1% TFA) and evaporation of the product fractions.

LCMS (m/e): 578 (M+1), 302 (100%)

Example 9-13

4-(8-{[1-(Propan-2-yl)-5-(6-fluoropyridin-3-yl)-1H-indol-3-yl]methyl}-2-oxo-1-oxa-3,8-diazaspiro[4.5]dec-3-yl)benzoic acid, TFA salt

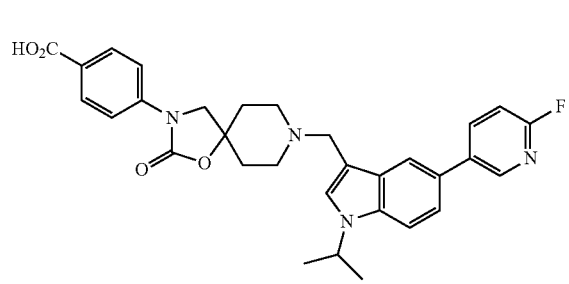 [SMILES: CC(C)n1cc(CN2CCC3(CC2)CN(c2ccc(C(=O)O)cc2)C(=O)O3)c2cc(-c3ccc(F)nc3)ccc21]

Using essentially the same procedures as Example 9-1, Steps 1-3, but using 5-bromo-1H-indole-3-carboxaldehyde in Step 1, 6-fluoropyridin-3-ylboronic acid in Step 2, and 1-(propan-2-yl)-5-(6-fluoropyridin-3-yl)-1H-indole-3-carboxaldehyde in Step 3, the title compound was obtained after reverse phase (C18) chromatography (acetonitrile/water with 0.1% TFA) and evaporation of the product fractions.

LCMS (m/e): 543 (M+1)

Example 9-14

4-(8-{[1-(Propan-2-yl)-5-(2-trifluoromethylphenyl)-1H-indol-3-yl]methyl}-2-oxo-1-oxa-3,8-diazaspiro[4.5]dec-3-yl)benzoic acid, TFA salt

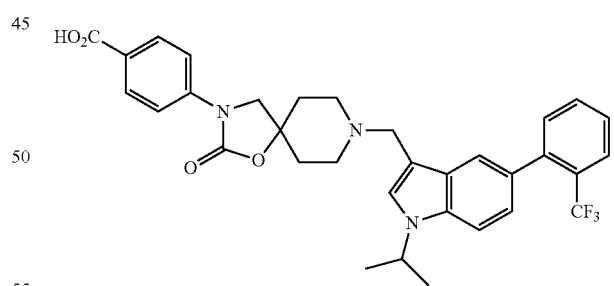

Using essentially the same procedures as Example 9-1, Steps 1-3, but using 5-bromo-1H-indole-3-carboxaldehyde in Step 1, 2-trifluorhenylboronic acid in Step 2, and 1-(propan-2-yl)-5-(2-trifluorophenyl)-1H-indole-3-carboxaldehyde in Step 3, the title compound was obtained after reverse phase (C18) chromatography (acetonitrile/water with 0.1% TFA) and evaporation of the product fractions.

LCMS (m/e): 543 (M+1)

Example 9-15

4-(8-{[1-(Methyl)-4-(4-fluorophenyl)-1H-indol-3-yl]methyl}-2-oxo-1-oxa-3,8-diazaspiro[4.5]dec-3-yl)benzoic acid, TFA salt

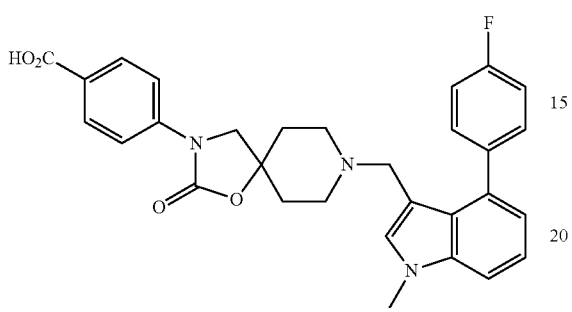

Using essentially the same procedures as Example 9-1, Steps 1-3, but using methyl iodide in Step 1, 4-fluorophenylboronic acid in Step 2 and 1-(methyl)-4-(4-fluorophenyl)-1H-indole-3-carboxaldehyde in Step 3, the title compound was obtained after reverse phase (C18) chromatography (acetonitrile/water with 0.1% TFA) and evaporation of the product fractions.

LCMS (m/e): 514 (M+1).

Example 9-15

4-(8-{[1-(Methyl)-4-(4-fluorophenyl)-1H-indol-3-yl]methyl}-2-oxo-1-oxa-3,8-diazaspiro[4.5]dec-3-yl)benzoic acid, TFA salt

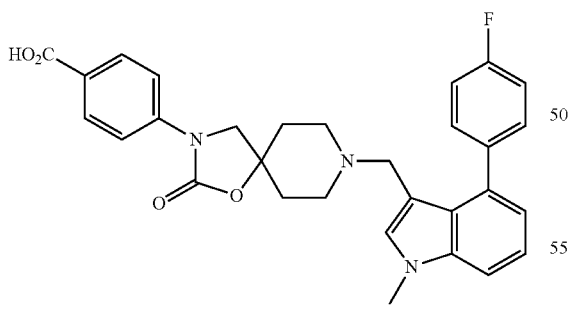

Using essentially the same procedures as Example 9-1, Steps 1-3, but using methyl iodide in Step 1, 4-fluorophenylboronic acid in Step 2 and 1-(methyl)-4-(4-fluorophenyl)-1H-indole-3-carboxaldehyde in Step 3, the title compound was obtained after reverse phase (C18) chromatography (acetonitrile/water with 0.1% TFA) and evaporation of the product fractions.

LCMS (m/e): 514 (M+1).

Example 9-16

4-(8-{[1-(Cyclopropyl)-4-(4-fluorophenyl)-1H-indol-3-yl]methyl}-2-oxo-1-oxa-3,8-diazaspiro[4.5]dec-3-yl)benzoic acid, TFA salt

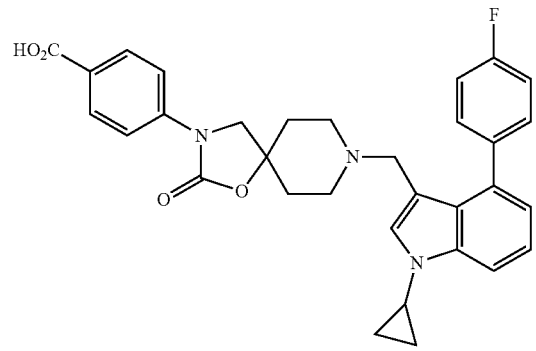 [SMILES: O=C(O)c1ccc(N2CC3(CCN(Cc4cn(C5CC5)c5cccc(-c6ccc(F)cc6)c45)CC3)OC2=O)cc1]

Step 1. Synthesis of 4-bromo-1-(cyclopropyl)-1H-indole-3-carboxaldehyde

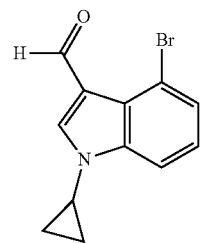 [SMILES: O=Cc1cn(C2CC2)c2cccc(Br)c12]

To a suspension of cyclopropylboronic acid (767 mg, 8.93 mmol), 5-bromo-1H-indole-3-carboxaldehyde (1000 mg, 4.46 mmol) and sodium carbonate (950 mg, 8.93 mmol) in DCE (15 mL) was added a suspension of copper(II) acetate (811 mg, 4.46 mmol) in hot DCE (5 mL). The mixture was warmed to 70° C. and stirred for 2 hours. The reaction mixture was cooled to room temperature and a saturated aqueous NH$_4$Cl solution was added followed by water. The organic layer was separated and the aqueous layer was extracted three times with DCM. The combined organic layers were washed with brine, dried, concentrated and purified on silica gel (Combi Flash 24 gm column, gradient of 0-100% ethyl acetate/hexanes) to afford the title intermediate (385 mg).

LCMS (m/e): 264/266 (M+1).

Step 2. Synthesis of 4-(8-{([1-(cyclopropyl)-4-(4-fluorophenyl)-1H-indol-3-yl]methyl}-2-oxo-1-oxa-3,8-diazaspiro[4.5]dec-3-yl)benzoic acid, TFA salt

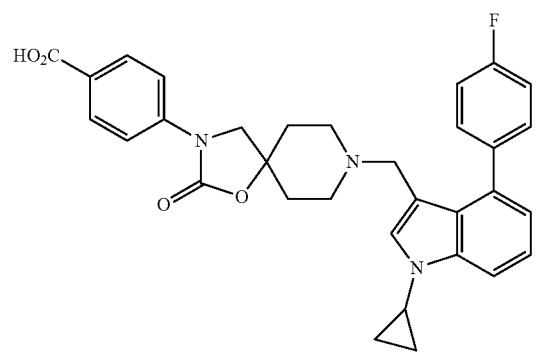 [SMILES: O=C(O)c1ccc(N2CC3(CCN(Cc4cn(C5CC5)c5cccc(-c6ccc(F)cc6)c45)CC3)OC2=O)cc1]

Using essentially the same procedures as Example 9-1, Steps 2-3, but using 4-fluorophenylboronic acid in Step 2 and 1-(cyclopropyl)-4-(4-fluorophenyl)-1H-indole-3-carboxaldehyde in Step 3, the title compound was obtained after reverse phase (C18) chromatography (acetonitrile/water with 0.1% TFA) and evaporation of the product fractions.

LCMS (m/e): 540 (M+1).

Example 9-17

4-(8-{[1-(Cyclopropyl)-4-(2,3,4-trifluorophenyl)-1H-indol-3-yl]methyl}-2-oxo-1-oxa-3,8-diazaspiro[4.5]dec-3-yl)benzoic acid, TFA salt

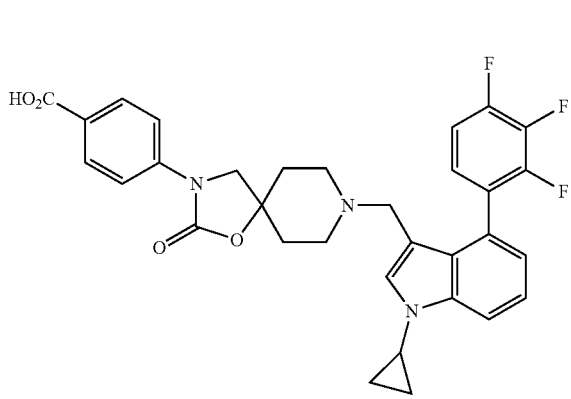 [SMILES: O=C(O)c1ccc(N2CC3(CCN(Cc4cn(C5CC5)c5cccc(-c6ccc(F)c(F)c6F)c45)CC3)OC2=O)cc1]

Using essentially the same procedures as Example 9-1, Steps 2-3, but using 4-bromo-1-(cyclopropyl)-1H-indole-3-carboxaldehyde (from Example 9-16, Step 1) in Step 2 and 1-(cyclopropyl)-4-(2,3,4-trifluorophenyl)-1H-indole-3-carboxaldehyde in Step 3, the title compound was obtained after reverse phase (C18) chromatography (acetonitrile/water with 0.1% TFA) and evaporation of the product fractions.

LCMS (m/e): 576 (M+1), 300 (100%).

Example 9-18

4-(8-{[1-(Cyclopropyl)-4-(6-fluoropyridin-3-yl)-1H-indol-3-yl]methyl}-2-oxo-1-oxa-3,8-diazaspiro[4.5]dec-3-yl)benzoic acid, TFA salt

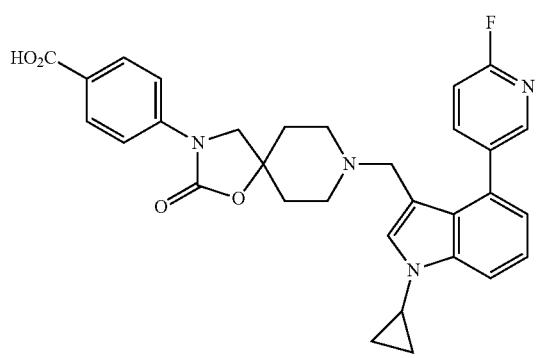 [SMILES: O=C(O)c1ccc(N2CC3(CCN(Cc4cn(C5CC5)c5cccc(-c6ccc(F)nc6)c45)CC3)OC2=O)cc1]

Using essentially the same procedures as Example 9-1, Steps 2-3, but using 4-bromo-1-(cyclopropyl)-1H-indole-3-carboxaldehyde (from Example 9-16, Step 1) and (6-fluoropyridin-3-yl)boronic acid in Step 2 and 1-(cyclopropyl)-4-(6-fluoropyridin-3-yl)-1/1-indole-3-carboxaldehyde in Step 3, the title compound was obtained after reverse phase (C18) chromatography (acetonitrile/water with 0.1% TFA) and evaporation of the product fractions.

LCMS (m/e): 541 (M+1).

Example 9-19

4-(8-{[1-(Propan-2-yl)-4-(5-fluoropyridin-2-yl)-1H-indol-3-yl]methyl}-2-oxo-1-oxa-3,8-diazaspiro[4.5]dec-3-yl)benzoic acid, TFA salt

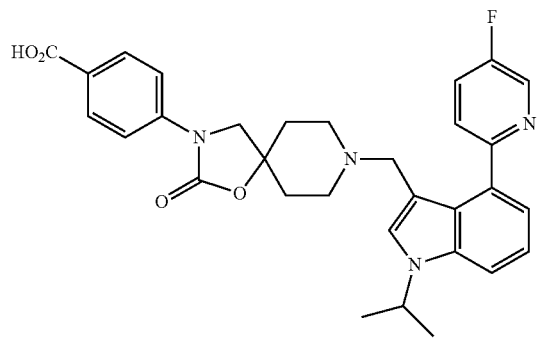 [SMILES: CC(C)n1cc(CN2CCC3(CC2)CN(c2ccc(C(=O)O)cc2)C(=O)O3)c2c(-c3ccc(F)cn3)cccc21]

Step 1. Synthesis of 1-(propan-2-yl)-4-(5-fluoropyridin-2-yl)-1H-indole-3-carboxaldehyde

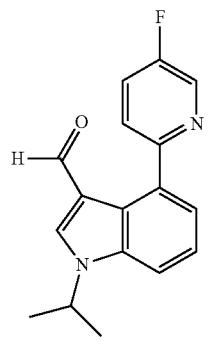 [SMILES: CC(C)n1cc(C=O)c2c(-c3ccc(F)cn3)cccc21]

An oven-dried vial was charged with 4-bromo-1-(propan-2-yl)-1H-indole-3-carboxaldehyde (50 mg, 0.188 mmol) (from Example 9-1, Step 1), pinacol 5-fluoropyridin-2-yl boronate ester (84 mg, 0.376 mmol), cesium carbonate (245 mg, 0.752 mmol), CuCl (19 mg, 0.188 mmol), Pd(OAc)$_2$ (4.2 mg, 0.019 mmol) and (diphenylphospino)ferrocene (dppf) (21 mg, 0.038 mmol). Anhydrous DMF (2 mL) was added into the vial and the mixture was stirred and purged with nitrogen for 2 minutes. The vial was sealed and heated at 100° C. for 16 hours. The reaction was allowed to cool to ambient temperature and was diluted with ethyl acetate. After washing the organic layer twice with water, the organic layer was dried over sodium sulfate, concentrated and purified by silica gel chromatography (Combi Flash 12 gm column, gradient of 0-100% ethyl acetate/hexanes) to afford the title intermediate (28 mg).

LCMS (m/e): 283 (M+1), 255 (100%).

Step 2. Synthesis of 4-(8-{[1-(propan-2-yl)-4-(5-fluoropyridin-2-yl)-1H-indol-3-yl]methyl}-2-oxo-1-oxa-3,8-diazaspiro[4.5]dec-3-yl)benzoic acid, TFA salt

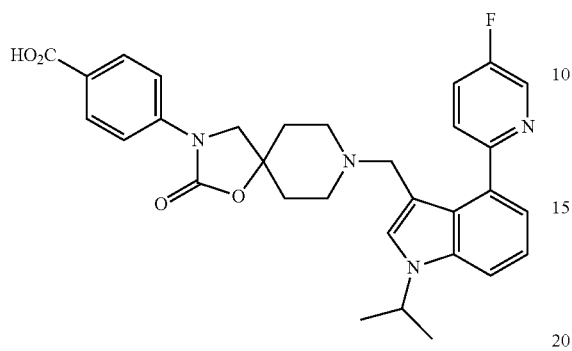

Using essentially the same procedure as Example 9-1, Step 3, but using 1-(propan-2-yl)-4-(5-fluoropyridin-2-yl)-1H-indole-3-carboxaldehyde, the title compound was obtained after reverse phase (C18) chromatography (acetonitrile/water with 0.1% TFA) and evaporation of the product fractions.

LCMS (m/e): 543 (M+1).

Example 9-20

4-(8-{[4-(4-fluorophenyl)-1H-indol-3-yl]methyl}-2-oxo-1-oxa-3,8-diazaspiro[4.5]dec-3-yl)benzoic acid, TFA salt

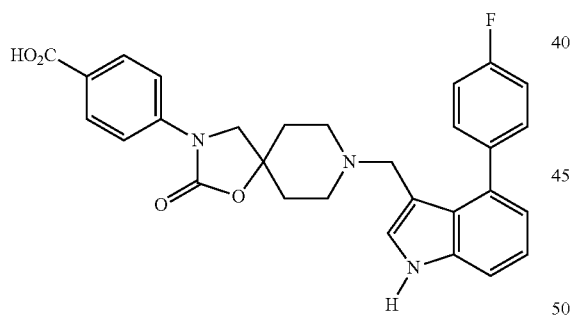

A solution of 4-(4-fluorophenyl)-1H-indole-3-carboxaldehyde (20 mg, 0.084 mmol) and 4-(2-oxo-1-oxa-3,8-diazaspiro[4.5]dec-3-yl)benzoic acid hydrochloride (26 mg, 0.084 mmol) (from Example 5-1, Step 4) in DMF (3 mL) was stirred at room temperature for 30 minutes. Acetic acid (0.024 mL, 0.418 mmol) and MP-cyanoborohydride resin (145 mg, 0.360 mmol, 2.49 mmol/g) were then added and the mixture was shaken at 55° C. for 18 hours. The reaction mixture was cooled to room temperature, quenched with water and filtered to remove the resin. The mixture was acidified with TFA and purified by HPLC reverse phase (C-18), eluting with a 5-95% gradient of acetonitrile/water with 0.1% TFA, to give the title compound (15 mg) as a solid white TFA salt after lypholization.

LCMS (m/e): 500 (M+1).

Example 9-21

4-(8-{([7-Methyl-1-(prop-2-yl)-1H-indol-3-yl]methyl}-2-oxo-1-oxa-3,8-diazaspiro[4.5]dec-3-yl)benzoic acid, TFA salt

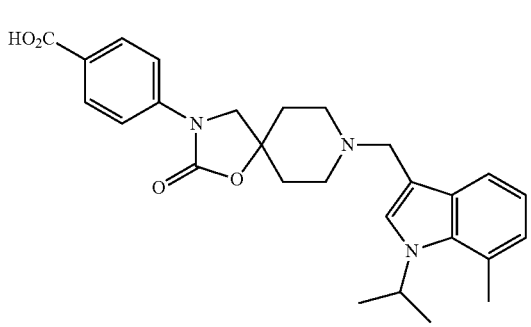 [SMILES: Cc1cccc2c(CN3CCC4(CC3)CN(c3ccc(C(=O)O)cc3)C(=O)O4)cn(C(C)C)c12]

Using essentially the same procedures as Example 9-1, Steps 1 and 3, but using 7-methyl-1H-indole-3-carboxaldehyde in Step 1, the title compound was obtained after reverse phase (C18) chromatography (acetonitrile/water with 0.1% TFA) and evaporation of the product fractions.

LCMS (m/e): 462 (M+1).

Example 9-22

4-(8-{[1-(Prop-2-yl)-4,5,6,7-tetrafluoro-1H-indol-3-yl]methyl}-2-oxo-1-oxa-3,8-diazaspiro[4.5]dec-3-yl)benzoic acid, TFA salt

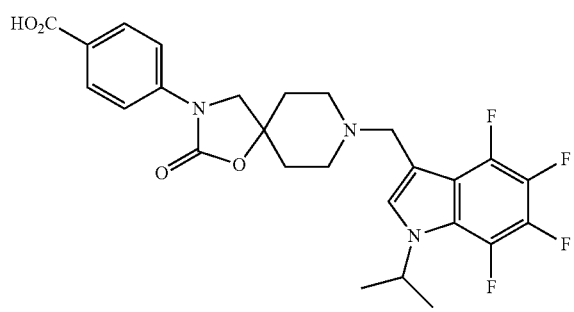 [SMILES: CC(C)n1cc(CN2CCC3(CC2)CN(c2ccc(C(=O)O)cc2)C(=O)O3)c2c(F)c(F)c(F)c(F)c21]

Using essentially the same procedures as Example 9-1, Steps 1 and 3, but using 4,5,6,7-tetrafluoro-1H-indole-3-carboxaldehyde in Step 1, the title compound was obtained after reverse phase (C18) chromatography (acetonitrile/water with 0.1% TFA) and evaporation of the product fractions.

LCMS (m/e): 520 (M+1).

Example 9-23

4-(8-{[7-Chloro-1-(prop-2-yl)-1H-indol-3-yl]methyl}-2-oxo-1-oxa-3,8-diazaspiro[4.5]dec-3-yl)benzoic acid, TFA salt

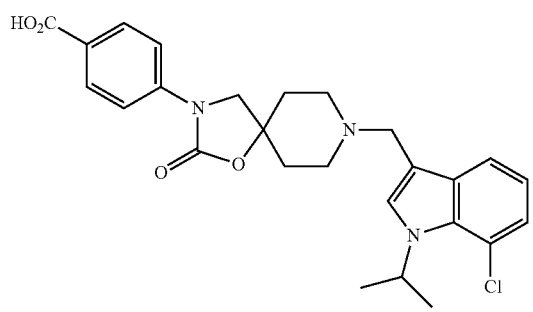 [SMILES: CC(C)n1cc(CN2CCC3(CC2)CN(c2ccc(C(=O)O)cc2)C(=O)O3)c2cccc(Cl)c21]

Using essentially the same procedures as Example 9-1, Steps 1 and 3, but using 7-chloro-1H-indole-3-carboxaldehyde in Step 1, the title compound was obtained after reverse phase (C18) chromatography (acetonitrile/water with 0.1% TFA) and evaporation of the product fractions.

LCMS (m/e): 482/484 (M+1).

Example 9-24

4-(8-{[5-Fluoro-7-methyl-1-(prop-2-yl)-1H-indol-3-yl]methyl}-2-oxo-1-oxa-3,8-diazaspiro[4.5]dec-3-yl)benzoic acid, TFA salt

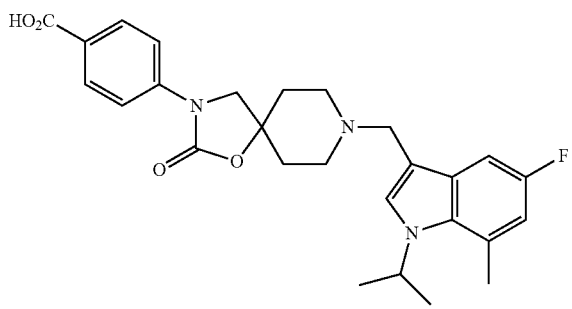 [SMILES: Cc1cc(F)cc2c(CN3CCC4(CC3)CN(c3ccc(C(=O)O)cc3)C(=O)O4)cn(C(C)C)c12]

Using essentially the same procedures as Example 9-1, Steps 1 and 3, but using 5-fluoro-7-methyl-1H-indole-3-carboxaldehyde in Step 1, the title compound was obtained after reverse phase (C18) chromatography (acetonitrile/water with 0.1% TFA) and evaporation of the product fractions.

LCMS (m/e): 480 (M+1).

Example 9-25

4-(8-{[5-Chloro-7-methyl-1-(prop-2-yl)-1H-indol-3-yl]methyl}-2-oxo-1-oxa-3,8-diazaspiro[4.5]dec-3-yl) benzoic acid, TFA salt

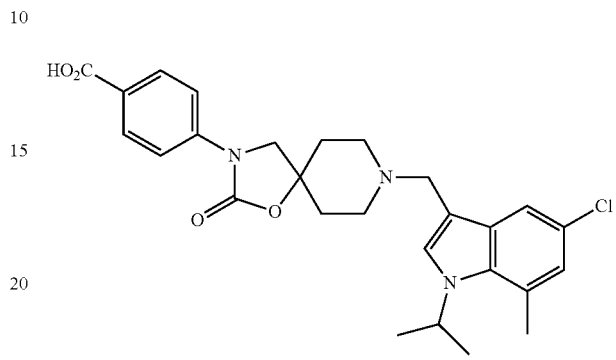

Using essentially the same procedures as Example 9-1, Steps 1 and 3, but using 5-chloro-7-methyl-1H-indole-3-carboxaldehyde in Step 1, the title compound was obtained after reverse phase (C18) chromatography (acetonitrile/water with 0.1% TFA) and evaporation of the product fractions.

LCMS (m/e): 496/498 (M+1).

Example 9-26

4-(8-{[7-Chloro-4-methyl-1-(prop-2-yl)-1H-indol-3-yl]methyl}-2-oxo-1-oxa-3,8-diazaspiro[4.5]dec-3-yl) benzoic acid, TFA salt

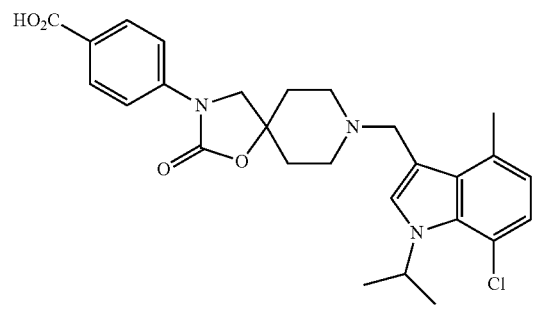 [SMILES: Cc1ccc(Cl)c2c1c(CN1CCC3(CC1)CN(c1ccc(C(=O)O)cc1)C(=O)O3)cn2C(C)C]

Using essentially the same procedures as Example 9-1, Steps 1 and 3, but using 7-chloro-4-methyl-1H-indole-3-carboxaldehyde in Step 1, the title compound was obtained after reverse phase (C18) chromatography (acetonitrile/water with 0.1% TFA) and evaporation of the product fractions.

LCMS (m/e): 496/498 (M+1).

Example 9-27

4-(8-{[4,7-Dichloro-1-(prop-2-yl)-1H-indol-3-yl]methyl}-2-oxo-1-oxa-3,8-diazaspiro[4.5]dec-3-yl)benzoic acid, TFA salt

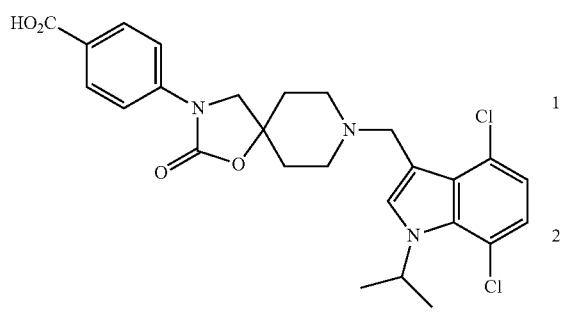

Using essentially the same procedures as Example 9-1, Steps 1 and 3, but using 4,7-dichloro-1H-indole-3-carboxaldehyde in Step 1, the title compound was obtained after reverse phase (C18) chromatography (acetonitrile/water with 0.1% TFA) and evaporation of the product fractions.

LCMS (m/e): 516/518 (M+1).

Example 9-28

4-(8-{[5,7-Dichloro-1-(prop-2-yl)-1H-indol-3-yl]methyl}-2-oxo-1-oxa-3,8-diazaspiro[4.5]dec-3-yl)benzoic acid, TFA salt

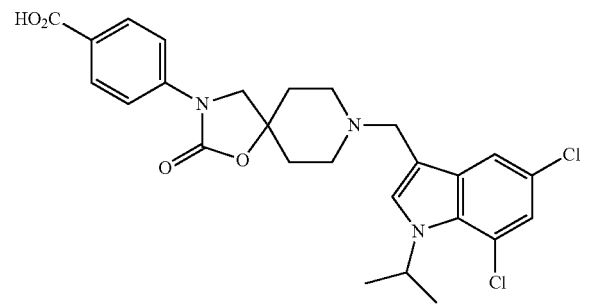 [SMILES: CC(C)n1cc(CN2CCC3(CC2)CN(c2ccc(C(=O)O)cc2)C(=O)O3)c2cc(Cl)cc(Cl)c21]

Using essentially the same procedures as Example 9-1, Steps 1 and 3, but using 5,7-dichloro-1H-indole-3-carboxaldehyde in Step 1, the title compound was obtained after reverse phase (C18) chromatography (acetonitrile/water with 0.1% TFA) and evaporation of the product fractions.

LCMS (m/e): 516/518 (M+1).

Example 9-29

4-(8-{[1-(Cyclopropyl)-7-methyl-1H-indol-3-yl]methyl}-2-oxo-1-oxa-3,8-diazaspiro[4.5]dec-3-yl)benzoic acid, TFA salt

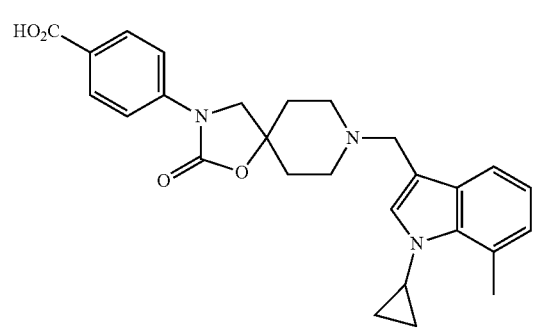 [SMILES: Cc1cccc2c(CN3CCC4(CC3)CN(c3ccc(C(=O)O)cc3)C(=O)O4)cn(C3CC3)c12]

Using essentially the same procedures as Example 9-16, Step 1, but using 7-methyl-1H-indole-3-carboxaldehyde, and Example 9-1, Step 3, the title compound was obtained after reverse phase (C18) chromatography (acetonitrile/water with 0.1% TFA) and evaporation of the product fractions.

LCMS (m/e): 460 (M+1).

Example 9-30

4-(8-{[1-(Cyclopropyl)-5-fluoro-7-methyl-1H-indol-3-yl]methyl}-2-oxo-1-oxa-3,8-diazaspiro[4.5]dec-3-yl)benzoic acid, TFA salt

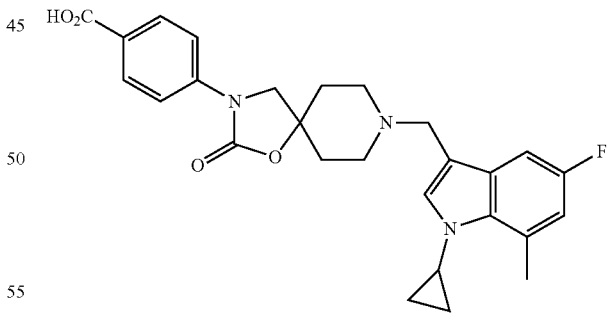

Using essentially the same procedures as Example 9-16, Step 1, but using 5-fluoro-7-methyl-1H-indole-3-carboxaldehyde, and Example 9-1, Step 3, the title compound was obtained after reverse phase (C18) chromatography (acetonitrile/water with 0.1% TFA) and evaporation of the product fractions.

LCMS (m/e): 478 (M+1).

Example 9-31

4-(8-{[7-Chloro-1-(cyclopropyl)-1H-indol-3-yl]methyl}-2-oxo-1-oxa-3,8-diazaspiro[4.5]dec-3-yl)benzoic acid, TFA salt

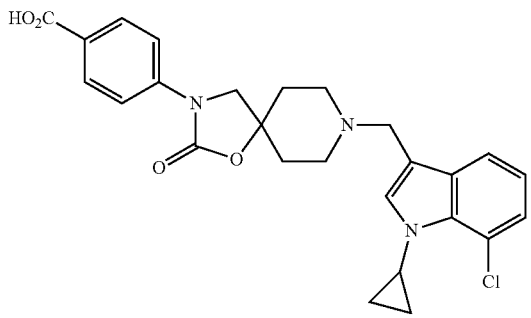 [SMILES: O=C(O)c1ccc(N2CC3(CCN(Cc4cn(C5CC5)c5c(Cl)cccc45)CC3)OC2=O)cc1]

Using essentially the same procedures as Example 9-16, Step 1, but using 7-chloro-1H-indole-3-carboxaldehyde, and Example 9-1, Step 3, the title compound was obtained after reverse phase (C18) chromatography (acetonitrile/water with 0.1% TFA) and evaporation of the product fractions.

LCMS (m/e): 482/482 (M+1).

Example 9-32

4-(8-{[5-Chloro-1-(cyclopropyl)-7-methyl-1H-indol-3-yl]methyl}-2-oxo-1-oxa-3,8-diazaspiro[4.5]dec-3-yl)benzoic acid, TFA salt

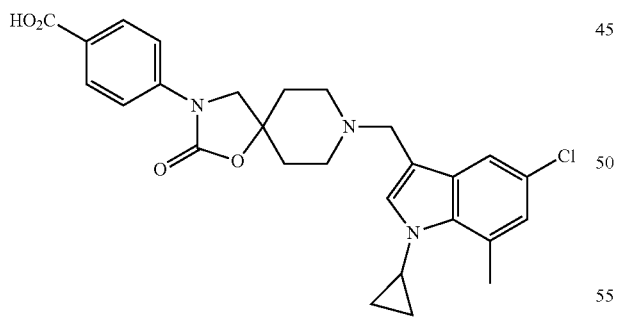

Using essentially the same procedures as Example 9-16, Step 1, but using 5-chloro-7-methyl-1H-indole-3-carboxaldehyde, and Example 9-1, Step 3, the title compound was obtained after reverse phase (C18) chromatography (acetonitrile/water with 0.1% TFA) and evaporation of the product fractions.

LCMS (m/e): 494/496 (M+1).

Example 9-33

4-(8-{([7-Chloro-1-(cyclopropyl)-4-methyl-1H-indol-3-yl]methyl}-2-oxo-1-oxa-3,8-diazaspiro[4.5]dec-3-yl)benzoic acid, TFA salt

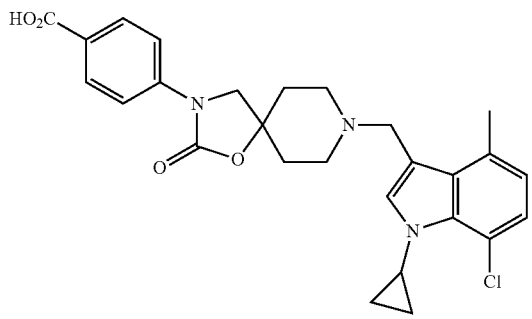 [SMILES: Cc1ccc(Cl)c2c1c(CN1CCC3(CC1)CN(c1ccc(C(=O)O)cc1)C(=O)O3)cn2C1CC1]

Using essentially the same procedures as Example 9-16, Step 1, but using 7-chloro-4-methyl-1H-indole-3-carboxaldehyde, and Example 9-1, Step 3, the title compound was obtained after reverse phase (C18) chromatography (acetonitrile/water with 0.1% TFA) and evaporation of the product fractions.

LCMS (m/e): 494/496 (M+1).

Example 9-34

4-(8-{[4-(Cyclopropyl)-1-(prop-2-yl)-1H-indol-3-yl]methyl}-2-oxo-1-oxa-3,8-diazaspiro[4.5]dec-3-yl)benzoic acid, TFA salt

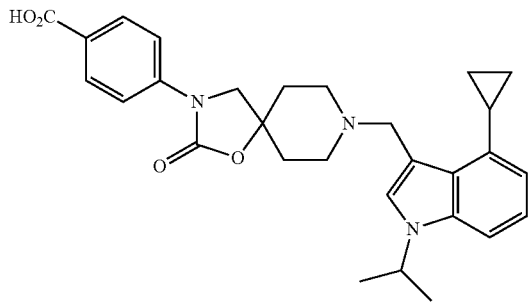 [SMILES: CC(C)n1cc(CN2CCC3(CC2)CN(c2ccc(C(=O)O)cc2)C(=O)O3)c2c(C3CC3)cccc21]

Step 1. Synthesis of 4-(cyclopropyl)-1-(prop-2-yl)-1H-indole-3-carboxaldehyde

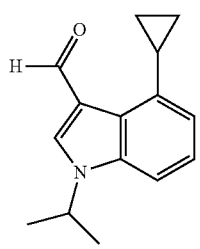 [SMILES: CC(C)n1cc(C=O)c2c(C3CC3)cccc21]

To a solution of 4-romo-1-(propan-2-yl)-1H-indole-3-carboxaldehyde (120 mg, 0.451 mmol) (from Example 9-1, Step 1) and cyclopropylboronic acid (77 mg, 0.902 mmol) in dioxane (2 mL) and water (0.5 mL) in a 5 mL microwave reaction vial was added potassium carbonate (187 mg, 1.35 mmol) and dichloro[1,1'-bis(di-t-butylphosphino)ferrocene]palladium (II) (29 mg, 0.045 mmol). The reaction was placed under nitrogen, sealed and heated in a microwave reactor at 140° C. for 25 minutes. The solvent was removed in vacuo and the residue was partitioned with ethyl acetate and aqueous sodium bicarbonate and extracted twice with ethyl acetate. The organic layers were washed with brine, dried over sodium sulfate, filtered and concentrated. The residue was purified on silica gel (COMBI FLASH 24 gm column, gradient of 0-100% ethyl acetate/hexanes) to give the title intermediate (19 mg).

LCMS (m/e): 228 (M+1).

Step 2. Synthesis of 4-(8-{[4-(cyclopropyl)-1-(prop-2-yl)-1H-indol-3-yl]methyl}-2-oxo-1-oxa-3,8-diazaspiro[4.5]dec-3-yl)benzoic acid, TFA salt

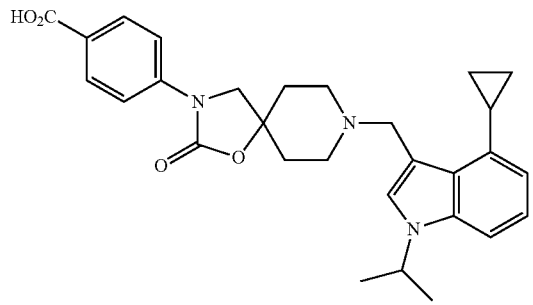 [SMILES: CC(C)n1cc(CN2CCC3(CC2)CN(c2ccc(C(=O)O)cc2)C(=O)O3)c2c(C3CC3)cccc21]

Using essentially the same procedure as Example 9-1, Step 3, but using 4-(cyclopropyl)-1-(prop-2-yl)-1H-indole-3-carboxaldehyde from Step 1, the title compound was obtained after reverse phase (C18) chromatography (acetonitrile/water with 0.1% TFA) and evaporation of the product fractions.

LCMS (m/e): 488 (M+1).

Example 9-35

4-(8-{[5-(Cyclopropyl)-1-(prop-2-yl)-1H-indol-3-yl]methyl}-2-oxo-1-oxa-3,8-diazaspiro[4.5]dec-3-yl)benzoic acid, TFA salt

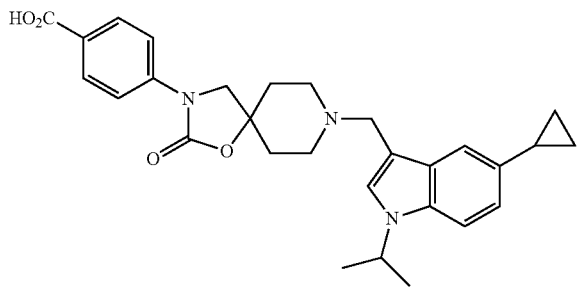 [SMILES: CC(C)n1cc(CN2CCC3(CC2)CN(c2ccc(C(=O)O)cc2)C(=O)O3)c2cc(C3CC3)ccc21]

Using essentially the same procedures as Example 9-34, Steps 1-2, but using 5-bromo-1-(prop-2-yl)-1H-indole-3-carboxaldehyde (prepared as in Example 9-1, Step 1) in Step 1, the title compound was obtained after reverse phase (C18) chromatography (acetonitrile/water with 0.1% TFA) and evaporation of the product fractions.

LCMS (m/e): 488 (M+1).

Example 9-36

4-(8-{[6-(Cyclopropyl)-1-(prop-2-yl)-1H-indol-3-yl]methyl}-2-oxo-1-oxa-3,8-diazaspiro[4.5]dec-3-yl)benzoic acid, TFA salt

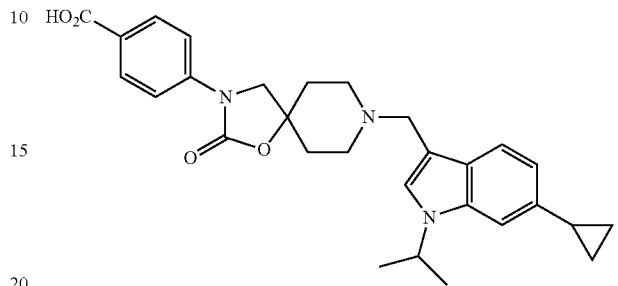

Using essentially the same procedures as Example 9-34, Steps 1-2, but using 6-bromo-1-(prop-2-yl)-1H-indole-3-carboxaldehyde (prepared as in Example 9-1, Step 1) in Step 1, the title compound was obtained after reverse phase (C18) chromatography (acetonitrile/water with 0.1% TFA) and evaporation of the product fractions.

LCMS (m/e): 488 (M+1).

Example 9-37

4-(8-{[5-(Cyclopropyl)-7-methyl-1-(prop-2-yl)-1H-indol-3-yl]methyl}-2-oxo-1-oxa-3,8-diazaspiro[4.5]dec-3-yl)benzoic acid, TFA salt

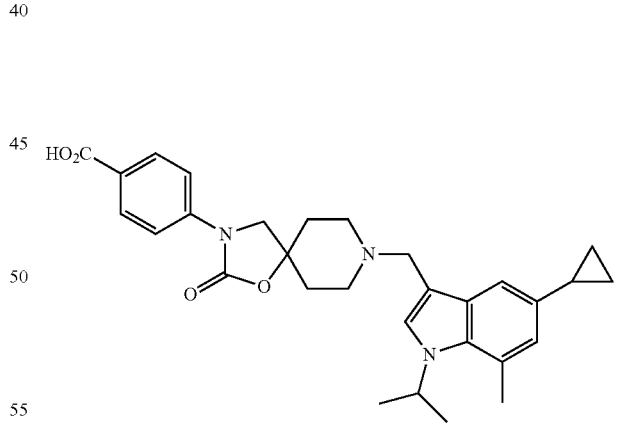

Using essentially the same procedures as Example 9-34, Steps 1-2, but using 5-bromo-7-methyl-1-(prop-2-yl)-1H-indole-3-carboxaldehyde (prepared as in Example 9-1, Step 1) in Step 1, the title compound was obtained after reverse phase (C18) chromatography (acetonitrile/water with 0.1% TFA) and evaporation of the product fractions.

LCMS (m/e): 502 (M+1).

Example 9-38

4-(8-{[1,4-(Dicyclopropyl)-1H-indol-3-yl]methyl}-2-oxo-1-oxa-3,8-diazaspiro[4.5]dec-3-yl)benzoic acid, TFA salt

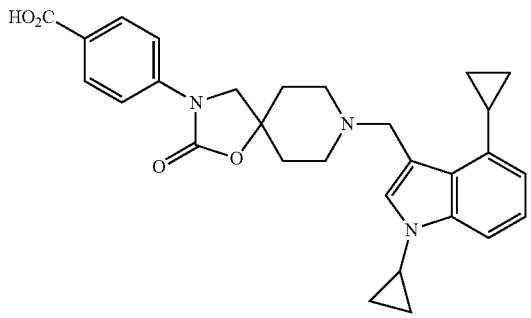 [SMILES: O=C(O)c1ccc(N2CC3(CCN(Cc4cn(C5CC5)c5cccc(C6CC6)c45)CC3)OC2=O)cc1]

Step 1. Synthesis of 1,4-(dicyclopropyl)-1H-indole-3-carboxaldehyde

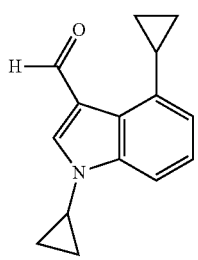 [SMILES: O=Cc1cn(C2CC2)c2cccc(C3CC3)c12]

Using essentially the same procedure as Example 9-34, Step 1, but using 4-bromo-1-(cyclopropyl)-1H-indole-3-carboxaldehyde from Example 9-16, Step 1, the title intermediate was prepared.
LCMS (m/e): 226 (M+1).

Step 2. Synthesis of 4-(8-{[1,4-(dicyclopropyl)-1H-indol-3-yl]methyl}-2-oxo-1-oxa-3,8-diazaspiro[4.5]dec-3-yl)benzoic acid, TFA salt

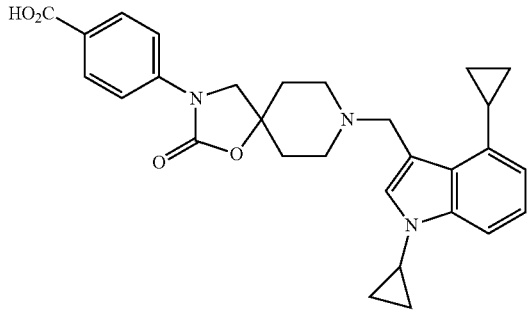 [SMILES: O=C(O)c1ccc(N2CC3(CCN(Cc4cn(C5CC5)c5cccc(C6CC6)c45)CC3)OC2=O)cc1]

Using essentially the same procedure as Example 9-1, Step 3, but using 1,4-(dicyclopropyl)-1H-indole-3-carboxaldehyde from Step 1, the title compound was obtained after reverse phase (C18) chromatography (acetonitrile/water with 0.1% TFA) and evaporation of the product fractions.
LCMS (m/e): 486 (M+1).

Example 9-39

4-(8-{[1,5-(Dicyclopropyl)-7-methyl-1H-indol-3-yl]methyl}-2-oxo-1-oxa-3,8-diazaspiro[4.5]dec-3-yl)benzoic acid, TFA salt

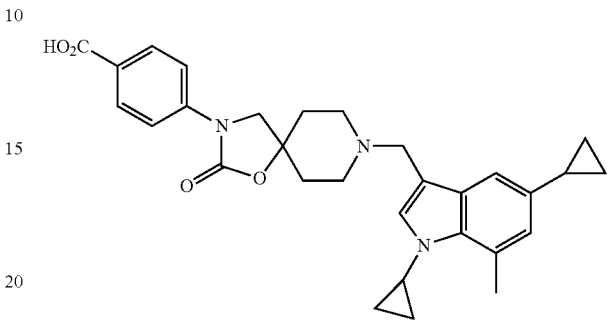

Using essentially the same procedures as Example 9-16, Step 1, Example 9-34, Step 1, and Example 9-1, Step 3, but starting with 5-bromo-7-methyl-1H-indole-3-carboxaldehyde, the title compound was obtained after reverse phase (C18) chromatography (acetonitrile/water with 0.1% TFA) and evaporation of the product fractions.
LCMS (m/e): 500 (M+1).

Example 9-40

4-(8-{[4-(4-Fluorophenyl)-1-(prop-2-yl)-1H-pyrrolo[2,3,b]pyridine-3-yl]methyl}-2-oxo-1-oxa-3,8-diazaspiro[4.5]dec-3-yl)benzoic acid, TFA salt

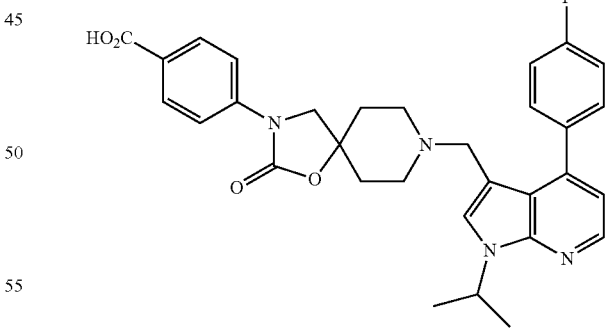

Using essentially the same procedures as Example 9-1, Steps 1-3, but starting with 4-bromo-1H-pyrrolo[2,3,b]pyridine-3-carboxaldehyde, the title compound was obtained after reverse phase (C18) chromatography (acetonitrile/water with 0.1% TFA) and evaporation of the product fractions.
LCMS (m/e): 543 (M+1).

Example 9-41

4-(8-{[1-(Prop-2-yl)-4-cyclopropyl-1H-pyrrolo[2,3,b]pyridine-3-yl]methyl}-2-oxo-1-oxa-3,8-diazaspiro[4.5]dec-3-yl)benzoic acid, TFA salt

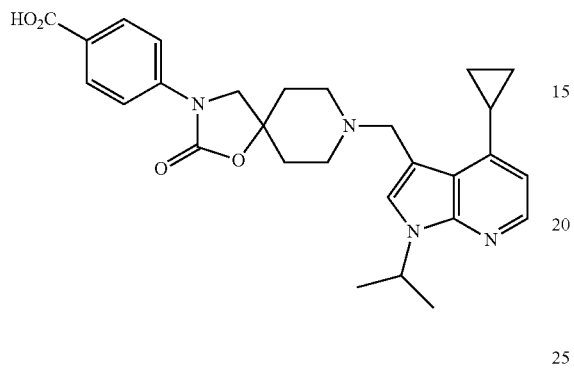

Using essentially the same procedures as Example 9-1, Step 1, and Example 9-34, Steps 1-2, but starting with 4-bromo-1H-pyrrolo[2,3,b]pyridine-3-carboxaldehyde, the title compound was obtained after reverse phase (C18) chromatography (acetonitrile/water with 0.1% TFA) and evaporation of the product fractions.

LCMS (m/e): 489 (M+1).

Example 9-42

4-(8-{[1-(Prop-2-yl)-7-chloro-1H-indol-4-yl]methyl}-2-oxo-1-oxa-3,8-diazaspiro[4.5]dec-3-yl)benzoic acid, TFA salt

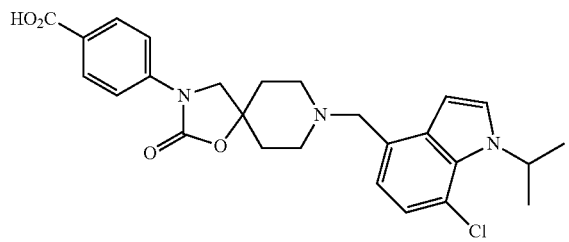 [SMILES: CC(C)n1ccc2c(CN3CCC4(CC3)CN(c3ccc(C(=O)O)cc3)C(=O)O4)ccc(Cl)c21]

Using essentially the same procedures as Example 9-1, Step 1, and Example 9-20, but starting with 7-chloro-1H-indole-4-carboxaldehyde, the title compound was obtained after reverse phase (C18) chromatography (acetonitrile/water with 0.1% TFA) and evaporation of the product fractions.

LCMS (m/e): 482 (M+1).

Example 9-43

8-{[4-(4-Fluorophenyl)-1-(prop-2-yl)-1H-indol-3-yl]methyl}-3-(4-methylphenyl)-1-oxa-3,8-diazaspiro[4.5]decan-2-one, TFA salt Step 1. Synthesis of 3-(4-methylphenyl)-1-oxa-3,8-diazaspiro[4.5]decan-2-one, hydrochloride salt

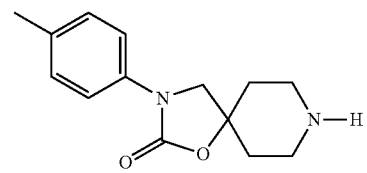 [SMILES: Cc1ccc(N2CC3(CCNCC3)OC2=O)cc1]

To a solution of t-butyl 2-oxo-1-oxa-3,8-diazaspiro[4.5]decane-8-carboxylate (100 mg, 0.390 mmol) and 4-bromo-1-iodobenzene (73 mg, 0.429 mmol) in dioxane (2 mL) were added Cu(I)I (74 mg, 0.390 mmol), N,N'-dimethylethylenediamine (34 mg, 0.390 mmol) and cesium carbonate (381 mg, 1.17 mmol). The mixture was heated at 110° C. for 20 hours, cooled and filtered through celite. The filtrate was diluted with water and extracted twice with ethyl acetate, washed with brine, dried over sodium sulfate and evaporated. The residue (120 mg) was used directly in the following reaction.

LCMS (m/e): 291 (M+1-56, 100%).

The above crude product was taken up in 4M HCl in dioxane (4 mL) and after stirring at room temperature for 2 hours afforded the title intermediate as a white solid (75 mg) after filtering and vacuum drying.

LCMS (m/e): 247 (M+1).

307

Step 2. Synthesis of 8-{[4-(4-fluorophenyl)-1-(prop-2-yl)-1H-indol-3-yl]methyl}-3-(4 methylphenyl)-1-oxa-3,8-diazaspiro[4.5]decan-2-one, TFA salt

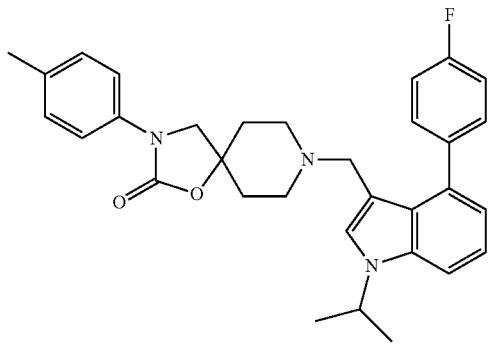 [SMILES: Cc1ccc(N2CC3(CCN(Cc4cn(C(C)C)c5cccc(-c6ccc(F)cc6)c45)CC3)OC2=O)cc1]

Using essentially the same procedure as Example 9-1, Step 3, but using 3-(4-methylphenyl)-1-oxa-3,8-diazaspiro[4.5]decan-2-one hydrochloride salt from Step 1 and 4-(4-fluorophenyl)-1-(prop-2-yl)-1H-indol-3-carboxaldehyde from Example 9-3, the title compound was obtained after reverse phase (C18) chromatography (acetonitrile/water with 0.1% TFA) and evaporation of the product fractions.

LCMS (m/e): 513 (M+1).

Example 9-44

8-{[4-(6-Fluoropyridin-3-yl)-1-(prop-2-yl)-1/1-indol-3-yl]methyl}-3-(6-methylpyridin-3-yl)-1-oxa-3,8-diazaspiro[4.5]decan-2-one, TFA salt

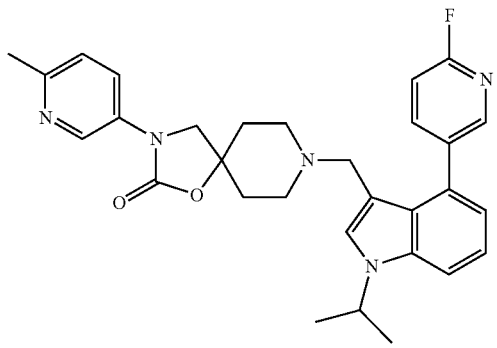 [SMILES: Cc1ccc(N2CC3(CCN(Cc4cn(C(C)C)c5cccc(-c6ccc(F)nc6)c45)CC3)OC2=O)cn1]

Using essentially the same procedures as Example 9-43, Steps 1-2, but using 2-methyl-5-bromopyridine in Step 1, the title compound was obtained after reverse phase (C18) chromatography (acetonitrile/water with 0.1% TFA) and evaporation of the product fractions.

LCMS (m/e): 514 (M+1).

308

Example 9-45

8-{[4-(6-Fluoropyridin-3-yl)-1-(prop-2-yl)-1H-indol-3-yl]methyl}-3-(6-trifluoromethylpyridin-3-yl)-1-oxa-3,8-diazaspiro[4.5]decan-2-one, TFA salt

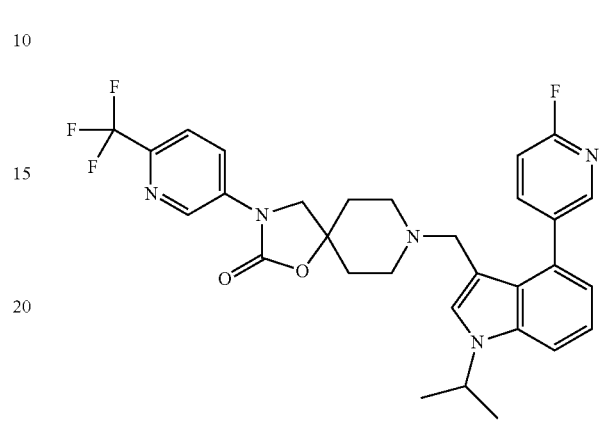

Using essentially the same procedures as Example 9-43, Steps 1-2, but using 5-bromo-2-trifluoromethylpyridine in Step 1, the title compound was obtained after reverse phase (C18) chromatography (acetonitrile/water with 0.1% TFA) and evaporation of the product fractions.

LCMS (m/e): 568 (M+1).

Example 9-46

8-{[4-(6-Fluoropyridin-3-yl)-1-(prop-2-yl)-1H-indol-3-yl]methyl}-3-(pyridin-4-yl)-1-oxa-3,8-diazaspiro[4.5]decan-2-one, TFA salt

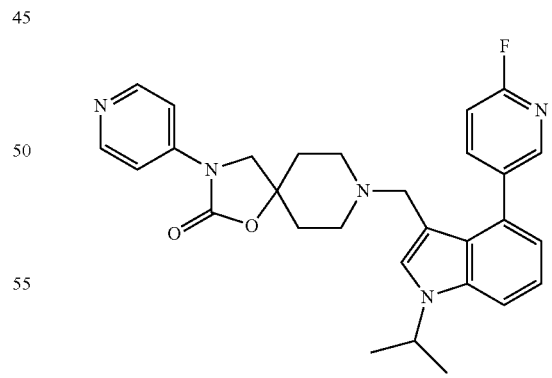

Using essentially the same procedures as Example 9-43, Steps 1-2, but using 4-bromopyridine in Step 1, the title compound was obtained after reverse phase (C18) chromatography (acetonitrile/water with 0.1% TFA) and evaporation of the product fractions.

LCMS (m/e): 500 (M+1).

Example 9-47

8-{[4-(6-Fluoropyridin-3-yl)-1-(prop-2-yl)-1H-indol-3-yl]methyl}-3-(5-fluoropyridin-2-yl)-1-oxa-3,8-diazaspiro[4.5]decan-2-one, TFA salt

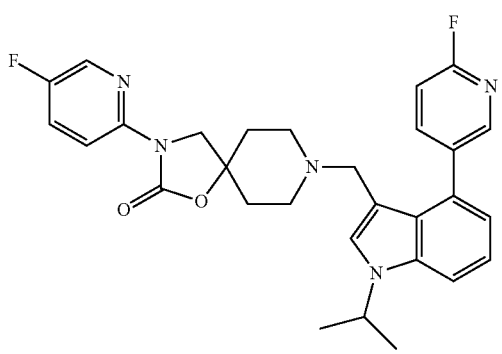 [SMILES: CC(C)n1cc(CN2CCC3(CC2)CN(c2ccc(F)cn2)C(=O)O3)c2c(-c3ccc(F)nc3)cccc21]

Using essentially the same procedures as Example 9-43, but using 2-bromo-5-fluoropyridine in Step 1, the title compound was obtained after reverse phase (C18) chromatography (acetonitrile/water with 0.1% TFA) and evaporation of the product fractions.

LCMS (m/e): 518 (M+1).

Example 9-48

8-{[4-(6-Fluoropyridin-3-yl)-1-(prop-2-yl)-1H-indol-3-yl]methyl}-3-(4-cyanophenyl)-1-oxa-3,8-diazaspiro[4.5]decan-2-one, TFA salt

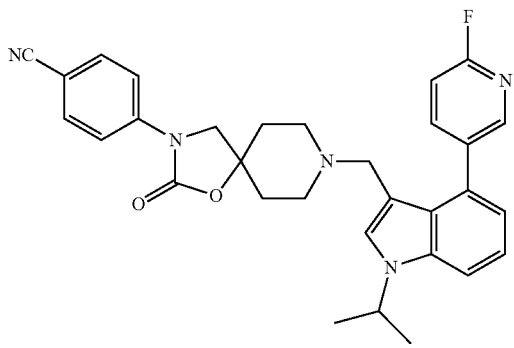 [SMILES: CC(C)n1cc(CN2CCC3(CC2)CN(c2ccc(C#N)cc2)C(=O)O3)c2c(-c3ccc(F)nc3)cccc21]

Using essentially the same procedures as Example 9-43, but using 4-bromo-1-cyanobenzene in Step 1, the title compound was obtained after reverse phase (C18) chromatography (acetonitrile/water with 0.1% TFA) and evaporation of the product fractions.

LCMS (m/e): 524 (M+1).

Example 9-49

8-{[4-(6-Fluoropyridin-3-yl)-1-(prop-2-yl)-1H-indol-3-yl]methyl}-3-(4-fluorophenyl)-1-oxa-3,8-diazaspiro[4.5]decan-2-one, TFA salt

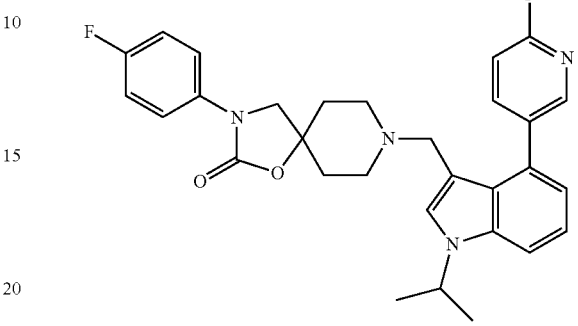

Using essentially the same procedures as Example 9-43, but using 4-bromofluorobenzene in Step 1, the title compound was obtained after reverse phase (C18) chromatography (acetonitrile/water with 0.1% TFA) and evaporation of the product fractions.

LCMS (m/e): 552 (M+1), 302 (100%).

Biological Assays

SSTR5 antagonists can be identified using SSTR5 and nucleic acid encoding for SSTR5. Suitable assays include detecting compounds competing with a SSTR5 agonist for binding to SSTR5 and determining the functional effect of compounds on a SSTR5 cellular or physiologically relevant activity. SSTR5 cellular activities include cAMP phospholipase C increase, tyrosine phosphatases increase, endothelial nitric oxide synthase (eNOS) decrease, K+ channel increase, Na+/H+ exchange decrease, and ERK decrease. (Lahlou et al., Ann. N.Y. Acad. Sci. 1014:121-131, 2004.) Functional activity can be determined using cell lines expressing SSTR5 and determining the effect of a compound on one or more SSTR5 activities (e.g., Poitout et al., J. Med. Chem. 44:29900-3000, (2001); Hocart et al., J. Med. Chem. 41:1146-1154, (1998); J. Med. Chem. 50, 6292-6295 (2007) and 3. Med. Chem. 50, 6295-6298 (2007)).

SSTR5 binding assays can be performed by labeling somatostatin and determining the ability of a compound to inhibit somatostatin binding. (Poitout et al., J. Med. Chem. 44:29900-3000, (2001); Hocart et al., J. Med. Chem. 41:1146-1154, (1998); J. Med. Chem. 50, 6292-6295 (2007) and J. Med. Chem. 50, 6295-6298 (2007)). Additional formats for measuring binding of a compound to a receptor are well-known in the art.

A physiologically relevant activity for SSTR5 inhibition is stimulating insulin secretion. Stimulation of insulin secretion can be evaluated in vitro or in vivo.

Antagonists can be characterized based on their ability to bind to SSTR5 (Ki) and effect SSTR5 activity (IC50), and to selectively bind to SSTR5 and selectively affect SSTR5 activity. Preferred antagonists strongly and selectively bind to SSTR5 and inhibit SSTR5 activity. Ki can be measured as described by Poitout et al., J. Med. Chem. 44:29900-3000, (2001) and described herein.

A selective SSTR5 antagonist binds SSTR5 at least 10 times stronger than it binds SSTR1, SSTR2, SSTR3, and SSTR4. In different embodiments concerning selective SSTR5 binding, the antagonist binds to each of SSTR1, SSTR2, SSTR3, and SSTR4 with a Ki greater than 1000 nM, or preferably greater than 2000 nM and/or binds SSTR5 at least 40 times, more preferably at least 100 times, or more preferably at least 500 times, greater than it binds to SSTR1, SSTR2, SSTR3, and SSTR4.

IC50 can be determined by measuring inhibition of somatostatin-14 or somatostatin-28 induced reduction of cAMP accumulation due to forskolin (1 µM) in CHO-K1 cells expressing SSTR5, as described by Poitout et al., J. Med. Chem. 44:29900-3000, (2001).

SSTR Binding Assays:

The receptor-ligand binding assays of all 5 subtype of SSTRs were performed with membranes isolated from Chinese hamster ovary (CHO)-K1 cells stably expressing the cloned human somatostatin receptors in 96-well format as previous reported. (Yang et al. PNAS 95:10836-10841, (1998), Birzin et al. Anal. Biochem. 307:159-166, (2002)).

The stable cell lines for SSTR1-SSTR5 were developed by stably transfecting with DNA for all five SSTRs using Lipofectamine. Neomycin-resistant clones were selected and maintained in medium containing 400 µg/mL G418 (Rohrer et al. Science 282:737-740, (1998)). Binding assays were performed using (3-125I-Tyr11)-SRIF-14 or (3-125I-Tyr11)-SRIF-28 as the radioligand (used at 0.1 nM) and The Packard Unifilter assay plate. The assay buffer consisted of 50 mM TrisHCl (pH 7.8) with 1 mM EGTA, 5 in M MgCl2, leupeptin (10 µg/mL), pepstatin (10 µg/mL), bacitracin (200 µg/mL), and aprotinin (0.5 µg/mL). CHO-K1 cell membranes, radiolabeled somatostatin, and unlabeled test compounds were resuspended or diluted in this assay buffer. Unlabeled test compounds were examined over a range of concentrations from 0.01 nM to 10,000 nM. The Ki values for compounds were determined as described by Cheng and Prusoff Biochem Pharmacol. 22:3099-3108 (1973).

The compounds of the present invention, particularly the compounds of Examples 1-1 to 4-28, 5-1 to 5-18, and 6-1 to 6-39 were tested in the SSTR5 binding assay and found to have Ki values in the range of 0.1 nM to 10 µM against SSTR5 and were found to have Ki values greater than 100 nM against SSTR1, SSTR2, SSTR3, and SSTR4 receptors. The compounds of the present invention, particularly the compounds of Examples 4-29 to 4-70, 5-19 to 5-31, and 7-1 to 9-49 were tested in the SSTR5 binding assay and found to have Ki values in the range of 0.05 nM to 100 nM against SSTR5 and were found to have Ki values greater than 100 nM against SSTR1, SSTR2, SSTR3, and SSTR4 receptors. Preferred compounds of the present invention were found to have Ki values in the range of 0.1 nM to 100 nM against SSTR5, and Ki values greater than 100 nM against SSTR1, SSTR2, SSTR3, and SSTR4 receptors. More preferred compounds of the present invention were found to have Ki values in the range of 0.1 nM to 10 nM against SSTR5, and Ki values greater than 100 nM against SSTR1, SSTR2, SSTR3, and SSTR4 receptors.

Functional Assay to Assess the Inhibition of SSTR5 Mediated Cyclic AMP Production:

The effects of compounds that bind to human and murine SSTR5 with various affinities on the functional activity of the receptor were assessed by measuring cAMP production in the presence of Forskolin (FSK) alone or FSK plus SS-28 in SSTR5 expressing CHO cells. FSK acts to induce cAMP production in these cells by activating adenylate cyclases, whereas SS-28 suppresses cAMP production in the SSTR5 stable cells by binding to SSTR5 and the subsequent inhibition of adenylate cyclases via an alpha subunit of GTP-binding protein.

To measure the agonism activity of the compounds, human or mouse SSTR5 stable CHO cells were pre-incubated with the compounds for 15 min, followed by a one-hour incubation of the cells with 5 µM FSK (in the continuous presence of the compounds). The amount of cAMP produced during the incubation was quantified with the Lance cAMP assay kit (PerkinElmer, CA) according to the manufacturer's instruction, as well as, an IC50 value was obtained by an eight-point titration.

Compounds exemplified were tested in the SSTR5 binding assay. The results are shown in the table below. Preferred compounds of the present invention were found to have IC50 values in the range of 0.1 nM to 100.

| Example | IC50 (nM) | Example | IC50 (nM) |
|---|---|---|---|
| 1-1 | 2.235 | 3-7 | 7.063 |
| 1-2 | 0.9429 | 3-8 | 1.419 |
| 1-3 | 2.811 | 3-9 | 1.207 |
| 1-4 | 4.586 | 3-10 | 8.413 |
| 1-5 | 1.533 | 3-11 | 0.9414 |
| 1-6 | 1.543 | 3-12 | 0.3227 |
| 1-7 | 2.62 | 3-13 | 3.802 |
| 1-8 | 2.164 | 3-14 | 9.153 |
| 1-9 | 2.005 | 3-15 | 2.789 |
| 1-10 | 2.863 | 3-16 | 1.184 |
| 1-11 | 6.242 | 3-17 | 2.215 |
| 1-12 | 5.324 | 3-18 | 1.153 |
| 1-13 | 4.089 | 3-19 | 0.359 |
| 1-14 | 4.702 | 3-20 | 0.129 |
| 1-15 | 1.804 | 3-21 | 0.4374 |
| 1-16 | 3.795 | 4-1 | 0.7934 |
| 1-17 | 2.136 | 4-2 | 13.2 |
| 1-18 | 2.702 | 4-3 | 0.4898 |
| 1-19 | 1.327 | 4-4 | 0.5024 |
| 1-20 | 5.325 | 4-5 | 0.5561 |
| 1-21 | 3.214 | 4-6 | 0.5465 |
| 1-22 | 4.87 | 4-7 | 0.4089 |
| 1-23 | 2.257 | 4-8 | 0.4739 |
| 1-24 | 2.01 | 4-9 | 0.439 |
| 1-25 | 0.7403 | 4-10 | 1.492 |
| 1-26 | 2.719 | 4-11 | 0.1523 |
| 1-27 | 12.92 | 4-12 | 0.1881 |
| 1-28 | 0.421 | 4-13 | 0.9834 |
| 1-29 | 0.5824 | 4-14 | 0.4067 |
| 1-30 | 1.954 | 4-15 | 218.5 |
| 1-31 | 2.088 | 4-16 | 0.2715 |
| 1-32 | 2.046 | 4-17 | 0.1645 |
| 1-33 | 1.291 | 4-18 | 0.2277 |
| 1-34 | 4.666 | 4-19 | 0.2432 |
| 1-35 | 36.18 | 4-20 | 0.6318 |
| 1-36 | 509.4 | 4-21 | 0.3973 |
| 1-37 | 1.589 | 4-22 | 0.4677 |
| 1-38 | 5.292 | 4-23 | 2.302 |
| 1-39 | 44.58 | 4-24 | 1.134 |
| 1-40 | 8.335 | 4-25 | 1.308 |
| 1-41 | 10.42 | 4-26 | 9.352 |
| 1-42 | 4.679 | 4-27 | 1.503 |
| 1-43 | 2.879 | 4-28 | 0.3946 |
| 1-44 | 14.35 | 5-1 | 2.38 |
| 1-45 | 22.99 | 5-2 | 0.7036 |
| 1-46 | 40.9 | 5-3 | 0.9803 |
| 1-47 | 79.05 | 5-4 | 65.21 |
| 2-1 | 2947 | 5-5 | 0.6501 |
| 2-2 | 4315 | 5-6 | 0.1715 |
| 2-3 | 89.33 | 5-7 | 0.2329 |
| 2-4 | 111.9 | 5-8 | 0.4239 |
| 2-5 | 190.9 | 5-9 | 11.26 |
| 2-6 | 280.7 | 5-10 | 1.536 |
| 2.7 | 1.834 | 5-11 | 14.04 |
| 2.8 | 10.37 | 5-12 | 29.43 |
| 2.9 | 14.89 | 5-13 | 0.3174 |
| 2.10 | 307 | 5-14 | 3.617 |
| 2.11 | 206.7 | 5-15 | 1.253 |
| 2.12 | 4.935 | 5-16 | 1.815 |

-continued

| Example | IC50 (nM) | Example | IC50 (nM) |
|---|---|---|---|
| 2.13 | 26.14 | 5-17 | 209.7 |
| 2.14 | 26.77 | 5-18 | 45.28 |
| 2.15 | 58.66 | 6-1 | 1172 |
| 2.16 | 5.633 | 6-2 | 1739 |
| 2.17 | 32.71 | 6-3 | 156.2 |
| 3-1 | 0.7683 | 6-4 | 98.68 |
| 3-2 | 1.464 | 6-5 | 148.8 |
| 3-3 | 228.6 | 6-6 | 68.06 |
| 3-4 | 1.402 | 6-7 | 1200 |
| 3-5 | 2.120 | 6-8 | 1200 |
| 3-6 | 9.471 | 6-9 | 121 |
| 6-10 | 136.7 | 6-26 | 1.446 |
| 6-11 | 410.4 | 6-27 | 118.9 |
| 6-12 | 216.1 | 6-28 | 1.337 |
| 6-13 | 185.1 | 6-29 | 0.7052 |
| 6-14 | 0.2602 | 6-30 | 89.92 |
| 6-15 | 1200 | 6-31 | 414.5 |
| 6-16 | 0.8512 | 6-32 | 69.06 |
| 6-17 | 61.64 | 6-33 | 152.8 |
| 6-18 | 0.2245 | 6-34 | 86.02 |
| 6-19 | 6.791 | 6-35 | 1.735 |
| 6-20 | 1.065 | 6-36 | 1200 |
| 6-21 | 11.73 | 6-37 | 13.43 |
| 6-22 | 8.642 | 6-38 | 1012 |
| 6-23 | 9.061 | 6-39 | 442.4 |
| 6-24 | 0.3418 | 6-25 | 0.5502 |

Enhancement of Glucose Dependent Insulin Secretion (GDIS) by SSTR3 Antagonists in Isolated Mouse Islet Cells:

Pancreatic islets of Langerhans were isolated from the pancreas of normal C57BL/6J mice (Jackson Laboratory, Maine) by collagenase digestion and discontinuous Ficoll gradient separation, a modification of the original method of Lacy and Kostianovsky (Lacy et al., Diabetes 16:35-39, 1967). The islets were cultured overnight in RPMI 1640 medium (11 mM glucose) before GDIS assay.

To measure GDIS, islets were first preincubated for 30 minutes in the Krebs-Ringer bicarbonate (KRB) buffer with 2 mM glucose (in petri dishes). The KRB medium contains 143.5 mM Na+, 5.8 mM K+, 2.5 mM Ca2+, 1.2 mM Mg2+, 124.1 mM Cl−, 1.2 mM PO43−, 1.2 mM SO42+, 25 mM CO32−, 2 mg/mL bovine serum albumin (pH 7.4). The islets were then transferred to a 96-well plate (one islet/well) and incubated at 37° C. for 60 minutes in 200 μl of KRB buffer with 2 or 16 mM glucose, and other agents to be tested such as octreotide and a SST3 antagonist. (Zhou et al., J. Biol. Chem. 278:51316-51323, 2003.) Insulin was measured in aliquots of the incubation buffer by ELISA with a commercial kit (ALPCO Diagnostics, Windham, N.H.).

Glucose Tolerance Test in Mice:

Male C57BL/6N mice (7-12 weeks of age) are housed 10 per cage and given access to normal diet rodent chow and water ad libitum. Mice are randomly assigned to treatment groups and fasted 4 to 6 h. Baseline blood glucose concentrations are determined by glucometer from tail nick blood. Animals are then treated orally with vehicle (0.25% methylcellulose) or test compound. Blood glucose concentration is measured at a set time point after treatment (t=0 min) and mice are then challenged with dextrose intraperitoneally—(2-3 g/kg) or orally (3-5 g/kg). One group of vehicle-treated mice is challenged with saline as a negative control. Blood glucose levels are determined from tail bleeds taken at 20, 40, 60 minutes after dextrose challenge. The blood glucose excursion profile from t=0 to t=60 min is used to integrate an area under the curve (AUC) for each treatment. Percent inhibition values for each treatment are generated from the AUC data normalized to the saline-challenged controls. A similar assay may be performed in rats. Compounds of the present invention are active after an oral dose in the range of 0.1 to 100 mg/kg.

Example of a Pharmaceutical Formulation

As a specific embodiment of an oral composition of a compound of the present invention, 50 mg of the compound of any of the Examples is formulated with sufficient finely divided lactose to provide a total amount of 580 to 590 mg to fill a size O hard gelatin capsule.

As a second specific embodiment of an oral composition of a compound of the present invention, 100 mg of the compound of any of the Examples, microcrystalline cellulose (124 mg), croscarmellose sodium (8 mg), and anhydrous unmilled dibasic calcium phosphate (124 mg) are thoroughly mixed in a blender; magnesium stearate (4 mg) and sodium stearyl fumarate (12 mg) are then added to the blender, mixed, and the mix transferred to a rotary tablet press for direct compression. The resulting tablets are unsubstituted or film-coated with Opadry® II for taste masking.

While the invention has been described and illustrated in reference to specific embodiments thereof, those skilled in the art will appreciate that various changes, modifications, and substitutions can be made therein without departing from the spirit and scope of the invention. For example, effective dosages other than the preferred doses as set forth hereinabove may be applicable as a consequence of variations in the responsiveness of the human being treated for a particular condition. Likewise, the pharmacologic response observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended therefore that the invention be limited only by the scope of the claims which follow and that such claims be interpreted as broadly as is reasonable.

What is claimed is:

1. A compound of structural formula I:

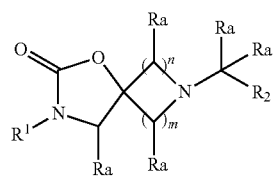

I or a pharmaceutically acceptable salt thereof, wherein each occurrence of Ra is independently selected from the group consisting of hydrogen, halogen, —$C_1$-$C_{10}$alkyl and halogen-substituted$C_1$-$C_{10}$alkyl;

$R^1$ is selected from the group consisting of hydrogen, phenyl and heterocycle, wherein the phenyl or heterocycle is substituted with at least one substituent selected from α;

$R^2$ is selected from the group consisting of aryl and heterocycle, wherein the aryl or heterocycle is substituted with 1-5 substituents independently selected from α;

α is selected from the group consisting of:
halogen,
—$C_1$-$C_{10}$alkyl,
—$C_3$-$C_{10}$cycloalkyl,
heterocycle, aryl,
—OH,
—O—C$_1$-C$_{10}$alkyl,
—O—C$_3$-C$_{10}$cycloalkyl,
—O-aryl,
—O-heterocycle,
—NRbS(O)$_2$Rc,
—NRbRc,
—CN,
—NRbC(O)Rc,
—S(O)$_2$Rb,
—S(O)$_2$NRbRc,
—C(O)NRbRc,
—C(O)NRb(C$_1$-C$_{10}$alkyl-NH—C$_1$-C$_{10}$alkyl),
—NRbC(O)ORc,
—NRbC(O)NRcRd,
—NRbC(O)NH$_2$,
—NRbS(O)$_2$Rc,
—NO$_2$,
—C(O)Rd,
—COORd, and
—OC(O)Rd,
wherein, Rb, Rc and Rd are independently selected from the group consisting of hydrogen, —C$_1$-C$_{10}$alkyl, —C$_3$-C$_{10}$cycloalkyl, aryl, and heterocycle; and wherein any —C$_3$-C$_{10}$cycloalkyl, aryl, or heterocycle is independently unsubstituted or substituted with 1-4 substituents selected from the group consisting of halogen, NH$_2$, N(CH$_2$)$_2$, —C$_3$-C$_{10}$cycloalkyl, hetrocycle, —COORd, —OH, —O—C$_1$-C$_{10}$alkyl and —C$_1$-C$_{10}$alkyl; and wherein any —C$_1$-C$_{10}$alkyl or —OC$_1$-C$_{10}$alkyl is independently unsubstituted or substituted with 1-4 substituents selected from the group consisting of halogen, —OH, —COORd, —C$_3$-C$_{10}$cycloalkyl and aryl; and wherein n and m are each independently 1.

2. A compound of claim 1 or a pharmaceutically acceptable salt thereof, wherein at each occurrence of Ra, Ra is hydrogen.

3. A compound of claim 1 or a pharmaceutically acceptable salt thereof, wherein R$^1$ is phenyl.

4. A compound of claim 1 or a pharmaceutically acceptable salt thereof, wherein R$^1$ is pyridine.

5. A compound of claim 1 or a pharmaceutically acceptable salt thereof, wherein R$^1$ is substituted with —OH, —C$_1$-C$_{10}$alkyl, —COOH, —COO—C$_1$-C$_{10}$alkyl, —O—C$_1$-C$_{10}$alkyl, —C$_3$-C$_{10}$cycloalkyl, —SO$_2$C$_1$-C$_{10}$alkyl, —CON(C$_1$-C$_{10}$alkyl)$_2$NH$_2$(C$_1$-C$_{10}$alkyl) or heterocycle, wherein the —C$_1$-C$_{10}$alkyl, —C$_3$-C$_{10}$cycloalkyl or —OC$_1$-C$_{10}$alkyl is unsubstituted or substituted with 1-4 substituents selected from the group consisting of halogen and —COOH.

6. A compound of claim 1 or a pharmaceutically acceptable salt thereof, wherein R$^2$ is imidazole, naphthalene, phenyl, pyridine, benzimidazole, indole, oxazole, thiazole, benzofuran, benzocyclopentane, benzotetrahydropyran or pyrazole.

7. A compound of claim 1 or a pharmaceutically acceptable salt thereof, wherein R$^2$ is phenyl.

8. A compound of claim 1 or a pharmaceutically acceptable salt thereof, wherein R$^2$ is pyridine.

9. A compound of claim 1 or a pharmaceutically acceptable salt thereof, wherein R$^2$ is imidazole.

10. A compound of claim 1 or a pharmaceutically acceptable salt thereof, wherein R$^2$ is substituted with two substituents independently selected from α.

11. A compound of claim 1 or a pharmaceutically acceptable salt thereof, wherein R$^2$ is substituted with three substituents independently selected from α.

12. A compound of claim 1 or a pharmaceutically acceptable salt thereof, wherein R$^2$ is substituted with 1-4 substituents selected from the group consisting of halogen, —C$_1$-C$_{10}$alkyl, —O—C$_1$-C$_{10}$alkyl, aryl, heterocycle and —C$_3$-C$_{10}$cycloalkyl wherein the aryl, —C$_1$-C$_{10}$alkyl, heterocycle, —O—C$_1$-C$_{10}$alkyl or —C$_3$-C$_{10}$cycloalkyl is unsubstituted or substituted with 1-4 substituents selected from the group consisting of halogen, —C$_1$-C$_{10}$alkyl and —O—C$_1$-C$_{10}$alkyl.

13. A compound claim 1 or a pharmaceutically acceptable salt thereof, wherein R$^2$ is substituted with 1-3 substituents selected from the group consisting of —O—C$_1$-C$_{10}$alkyl, —O-halogen-substitutedC$_1$-C$_{10}$alkyl and halogen-substituted phenyl.

14. A compound, or pharmaceutically acceptable salt, selected from the group consisting of:

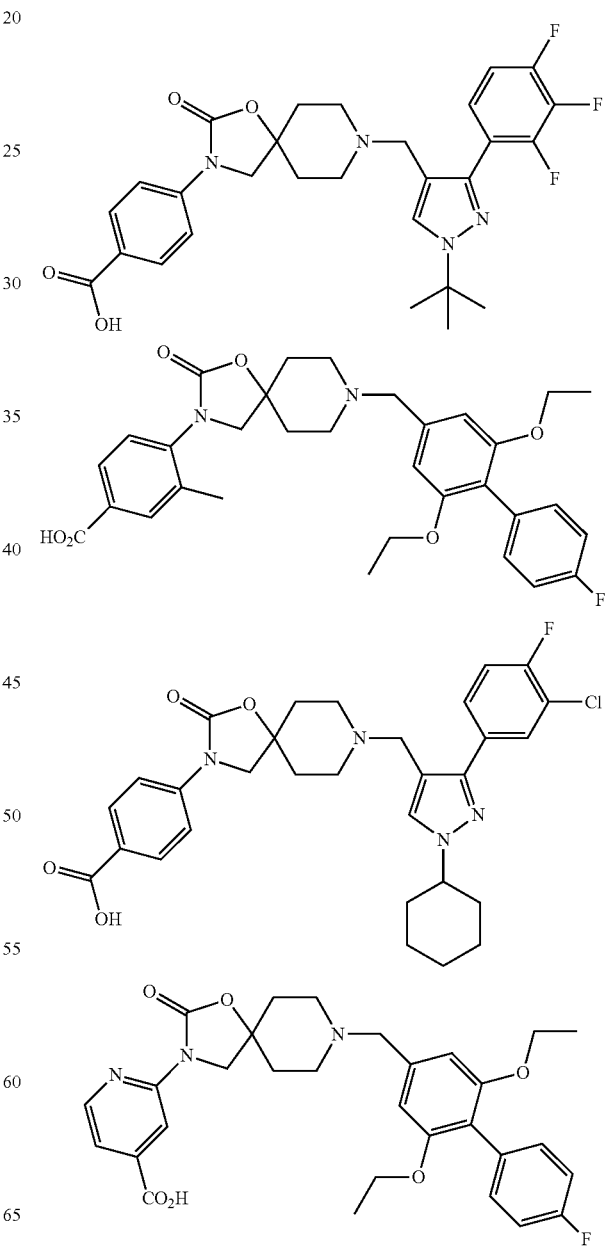

317
-continued
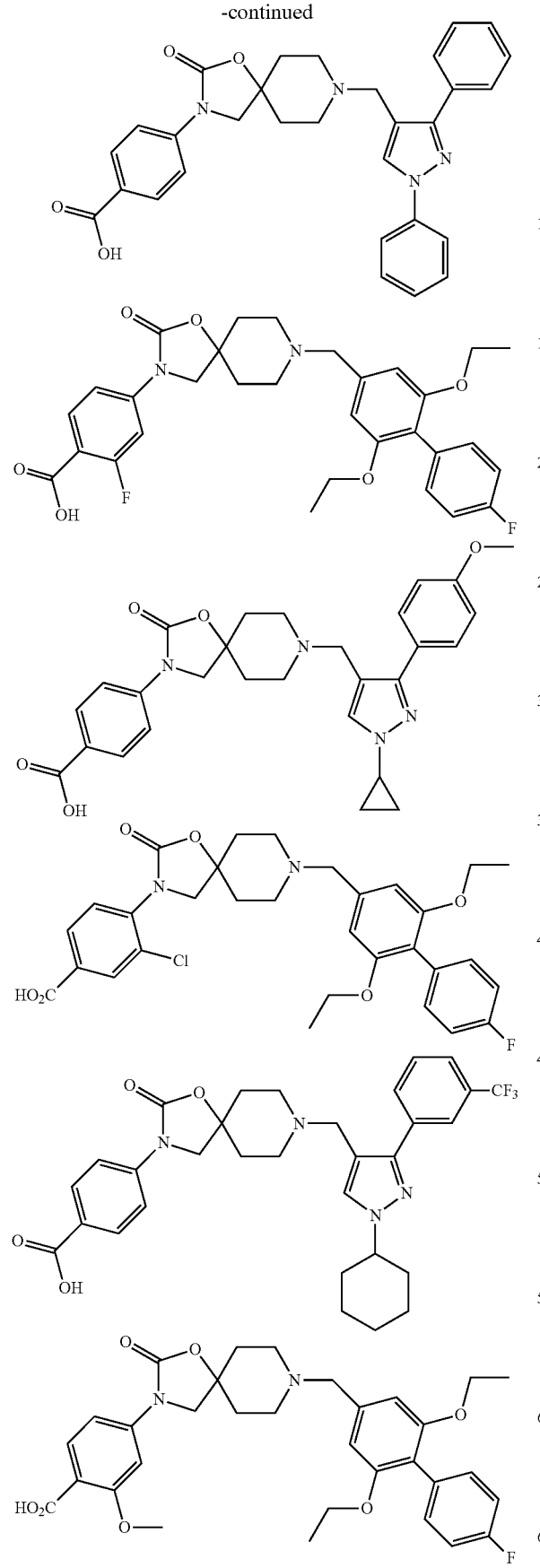
318
-continued
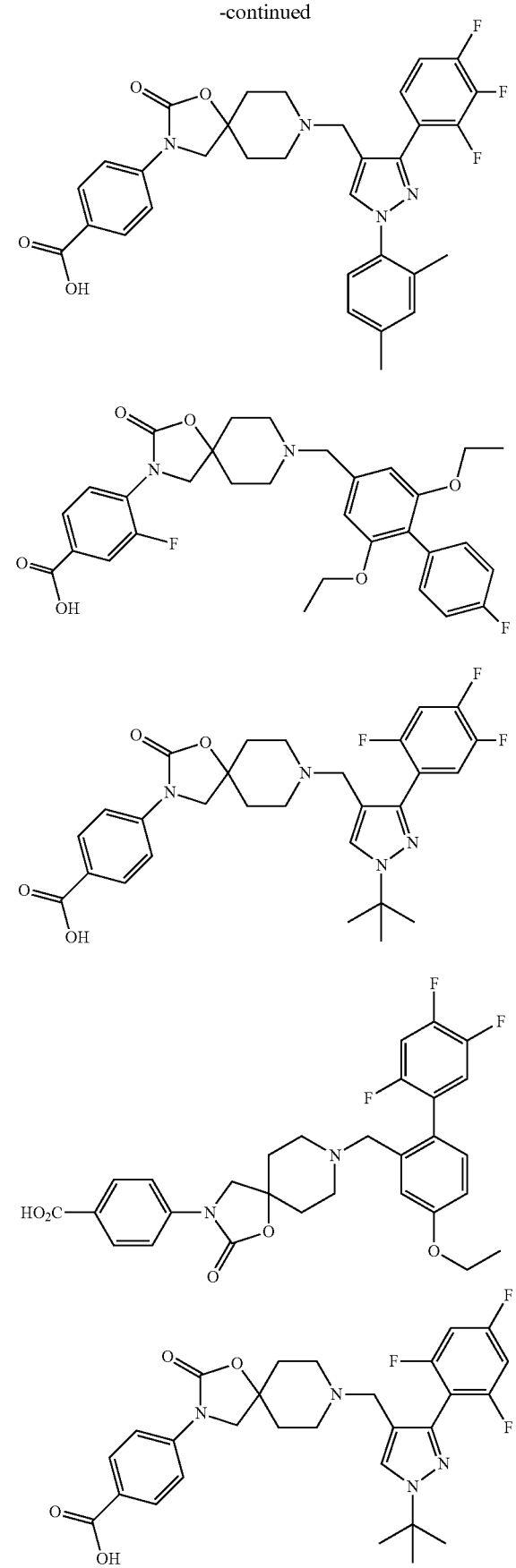

319
-continued
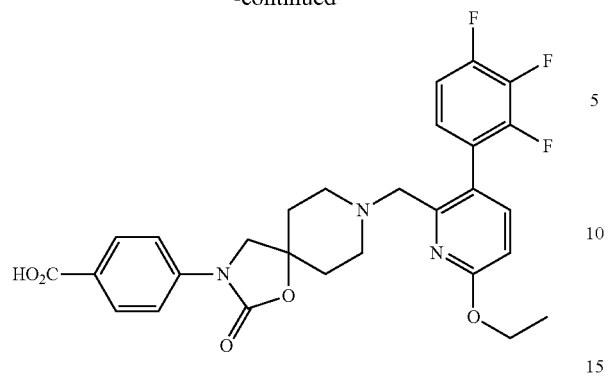
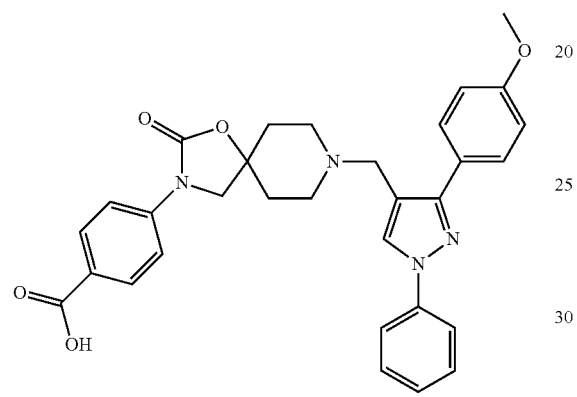
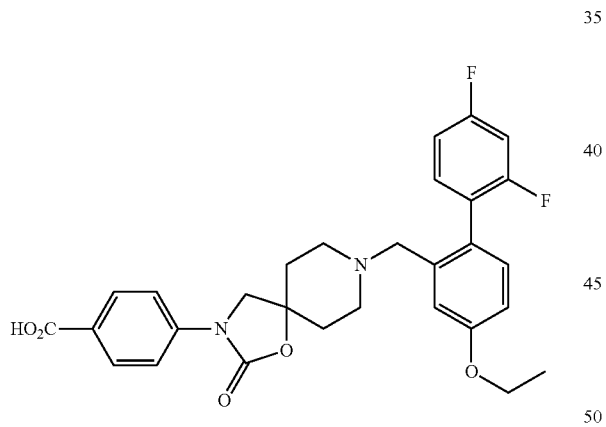
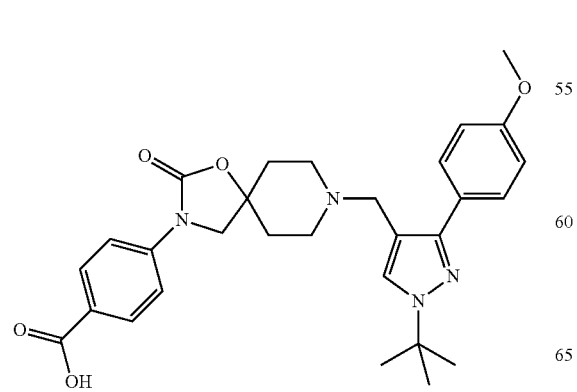
320
-continued
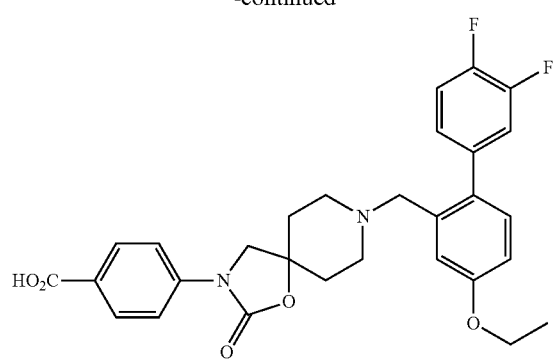

321
-continued
322
-continued
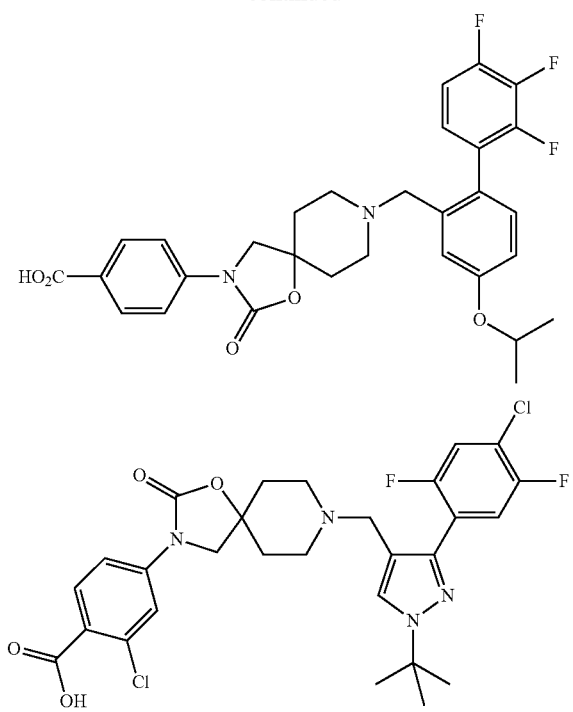
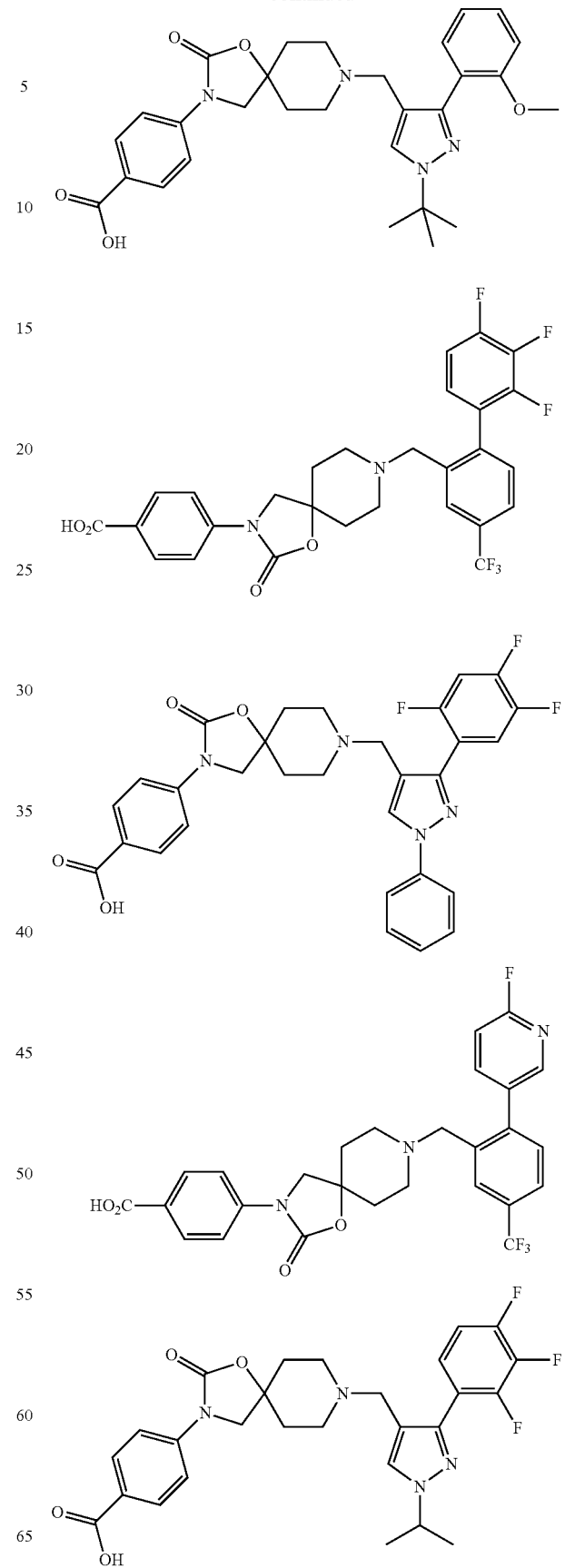

323
-continued
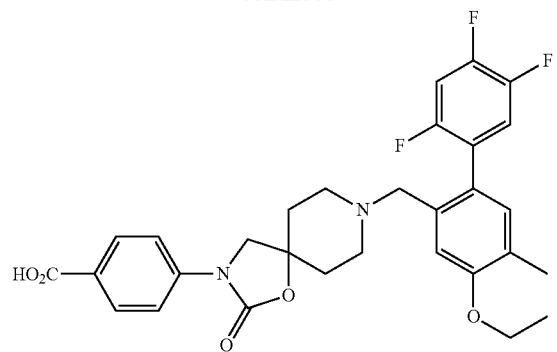
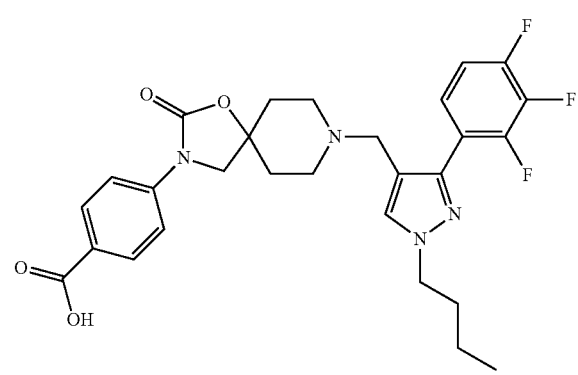
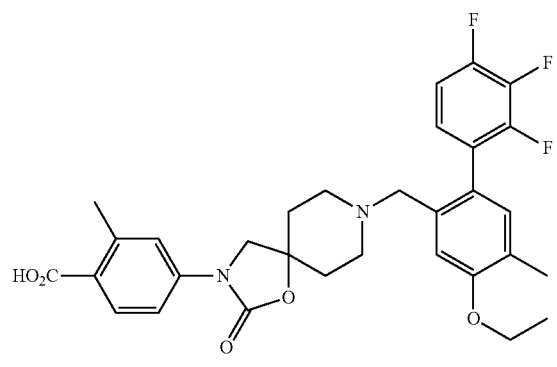
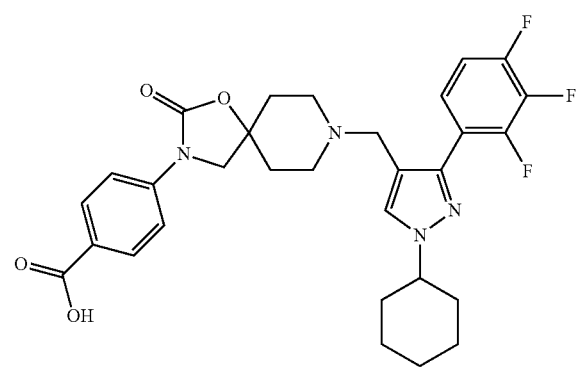
324
-continued
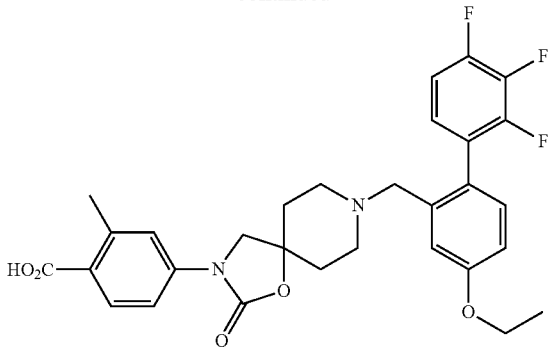
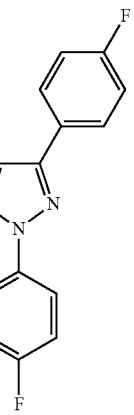
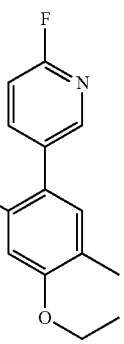
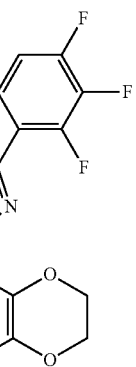

325
-continued
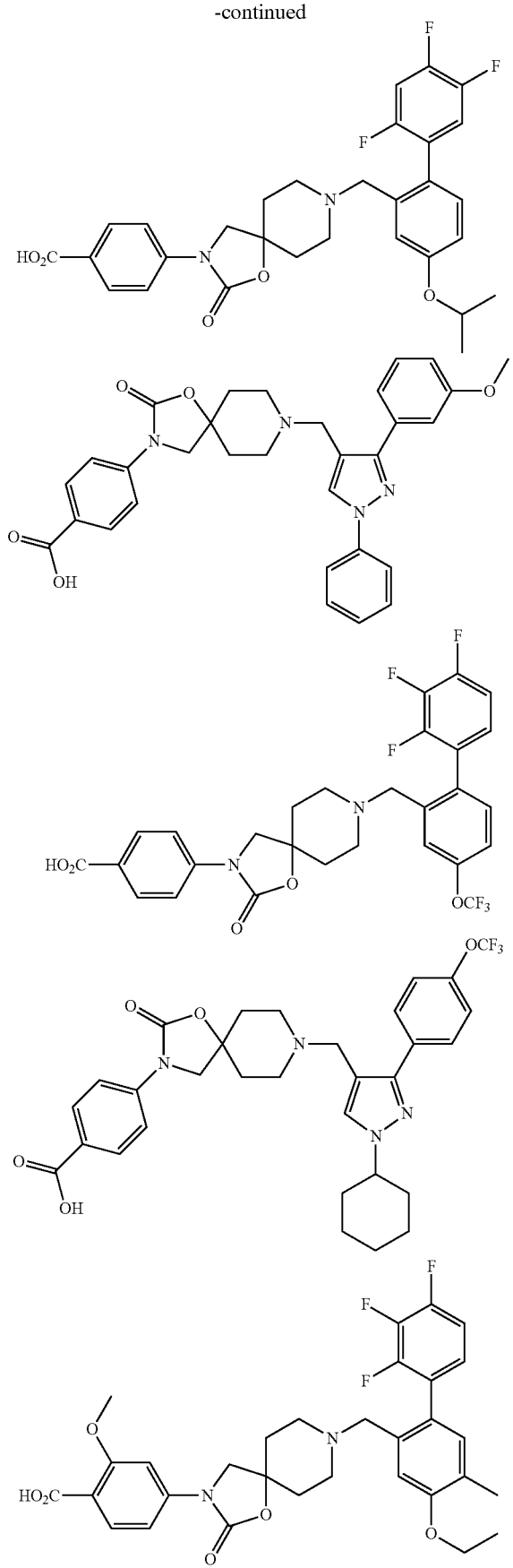
326
-continued

327
-continued
328
-continued
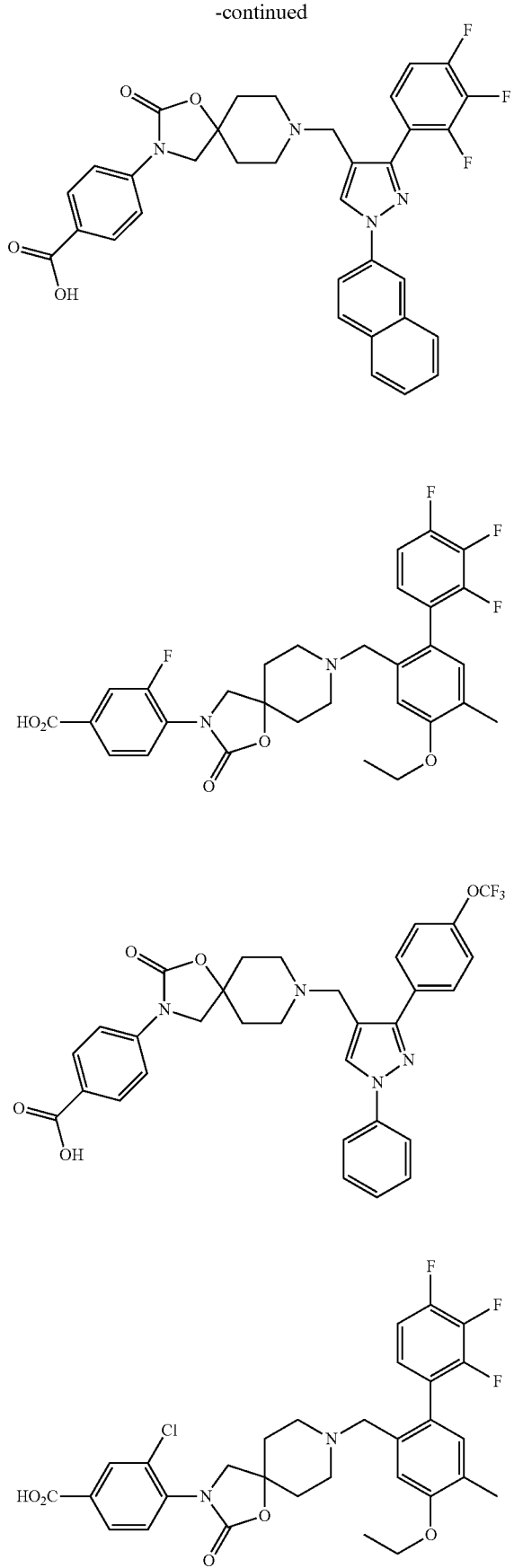
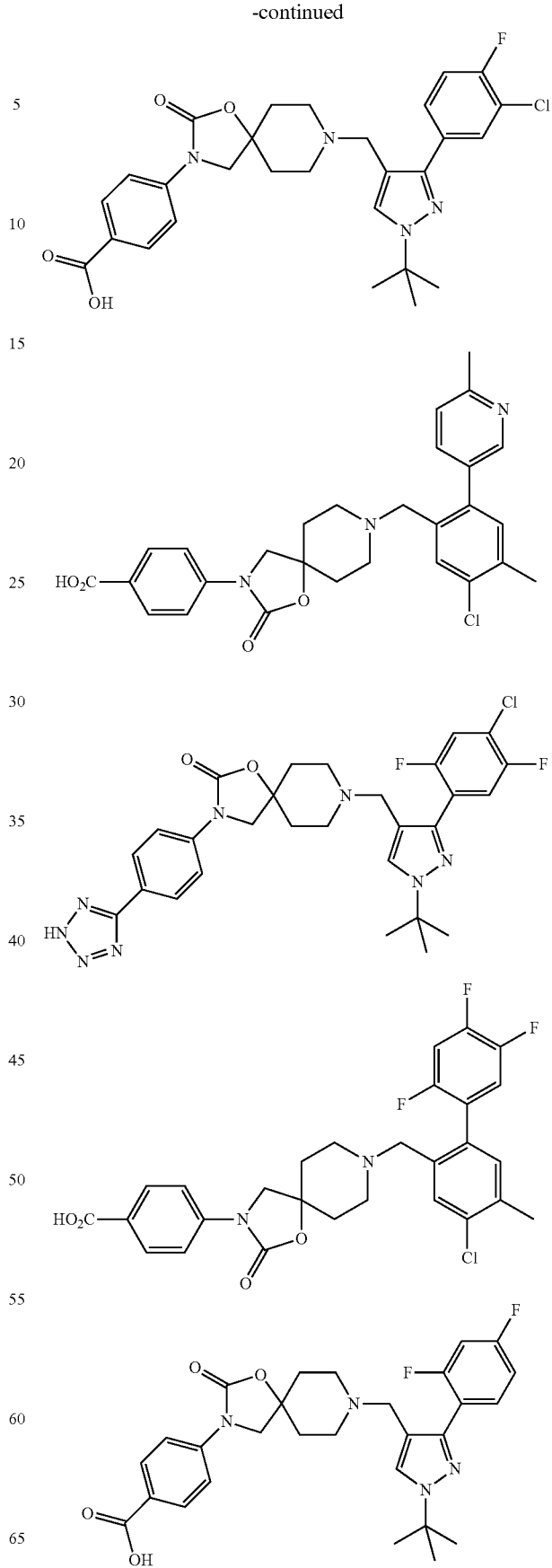

329
-continued
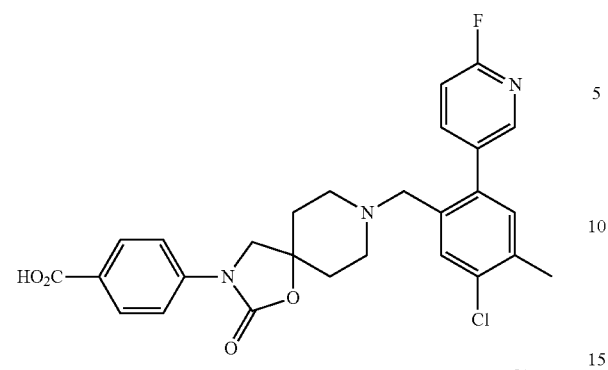
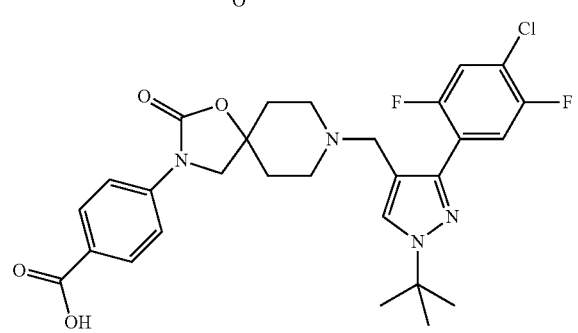
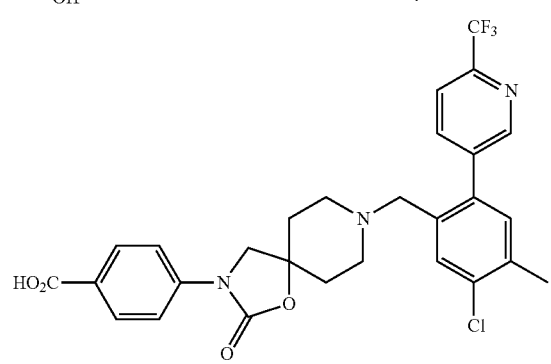
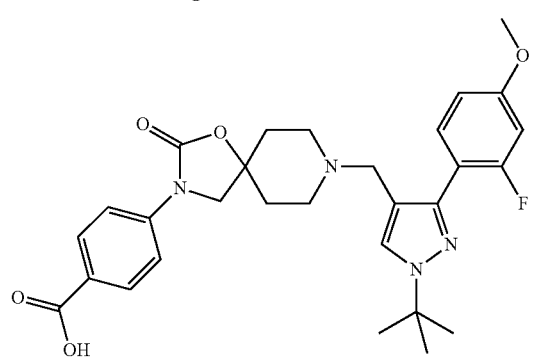
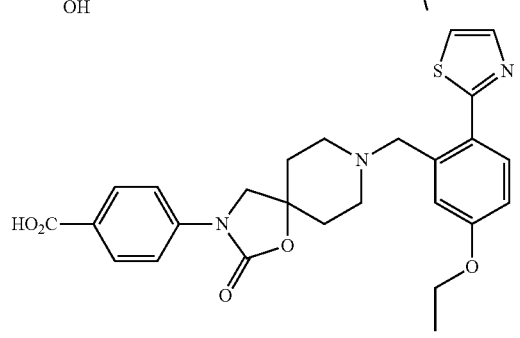
330
-continued
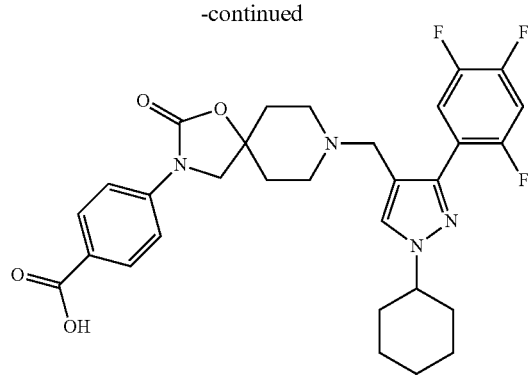
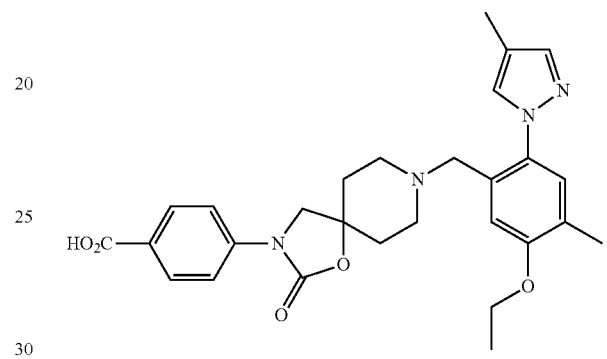
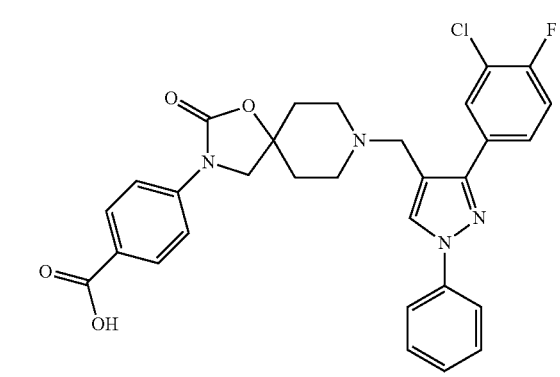
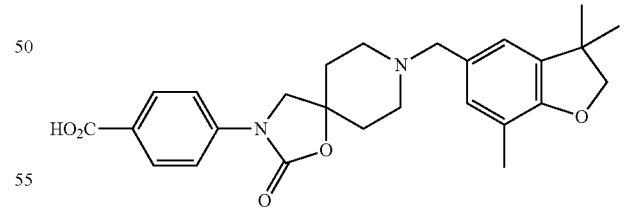
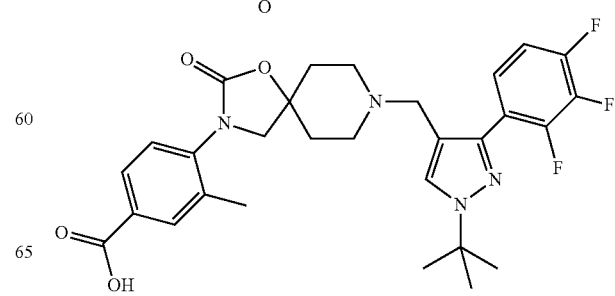

331
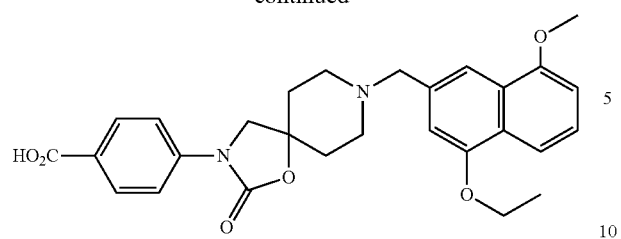
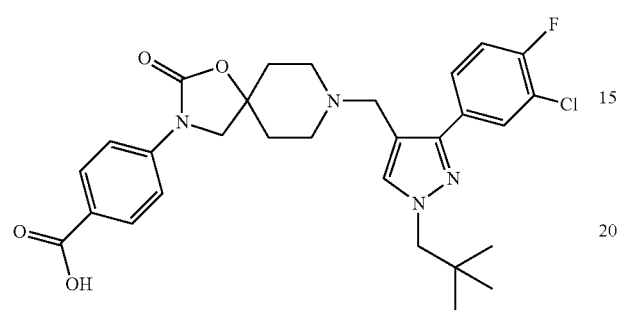
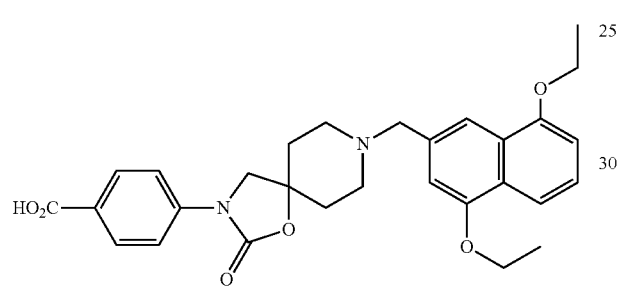
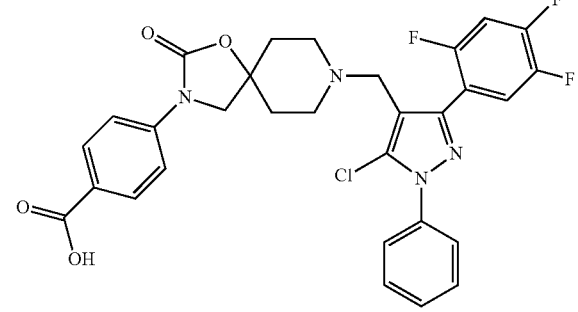
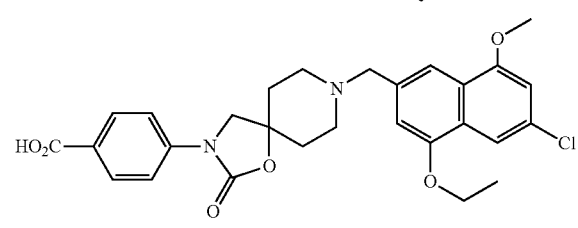
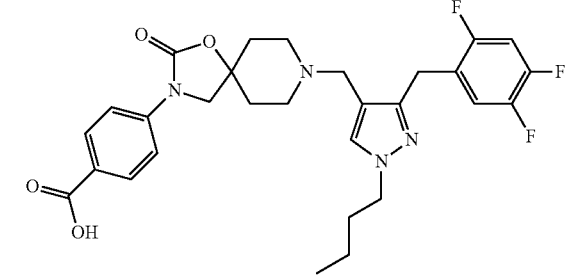
332
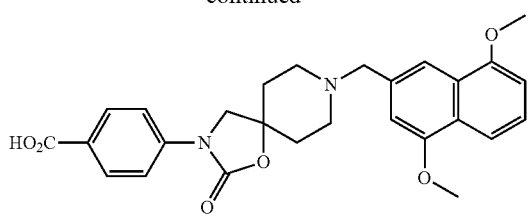
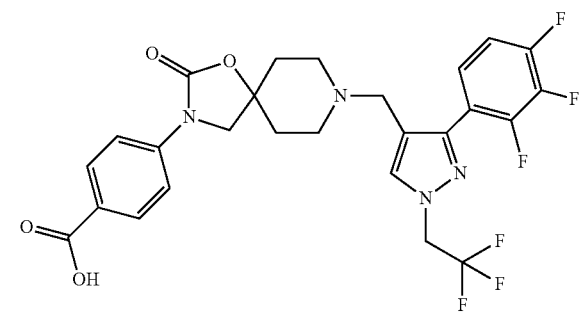
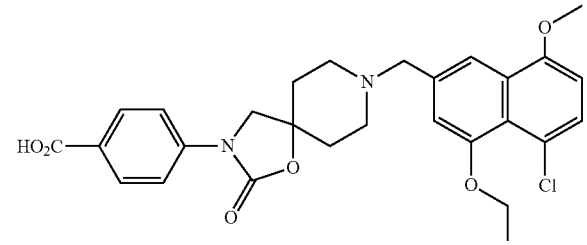
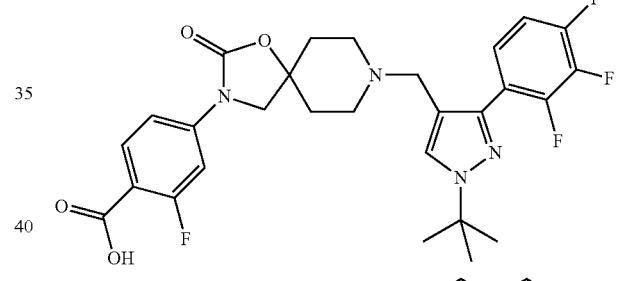
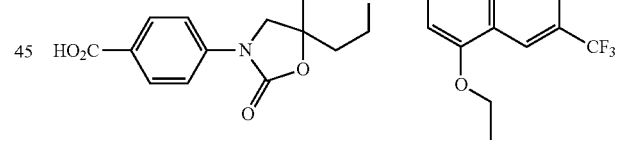
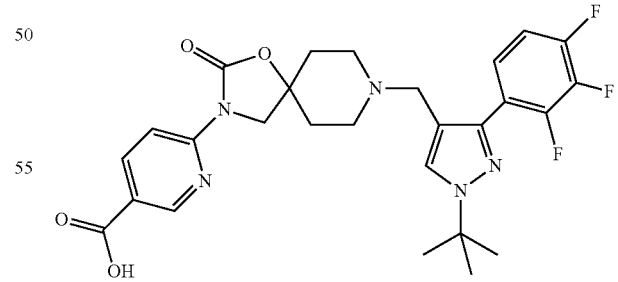
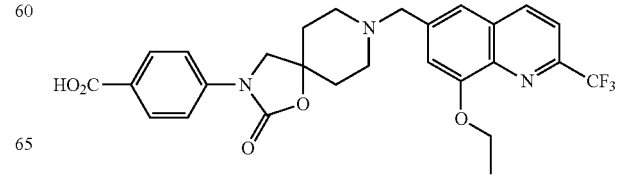

333
-continued
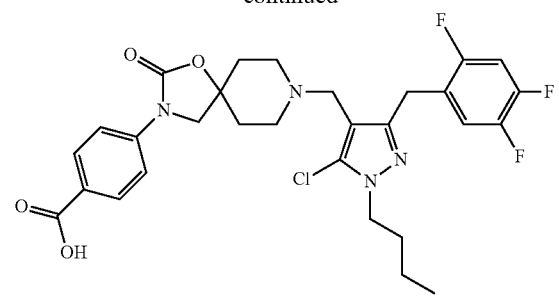
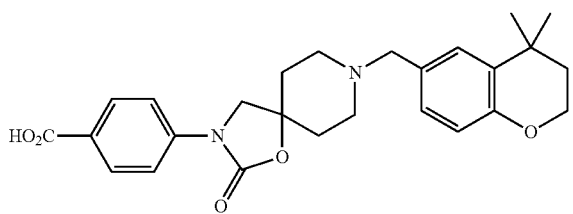
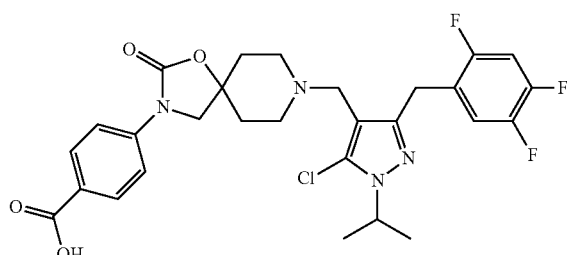
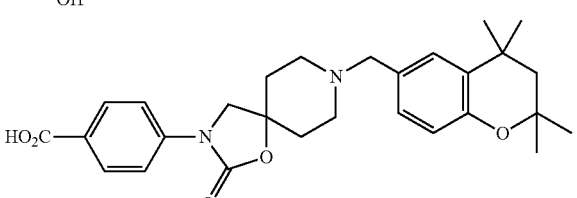
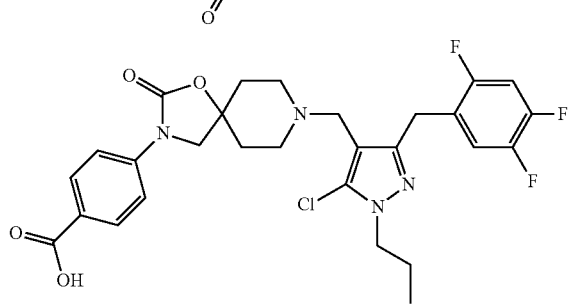
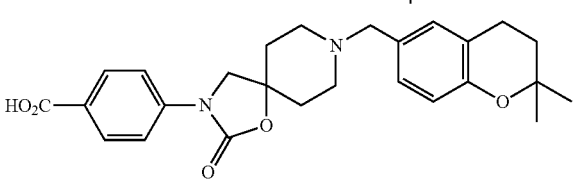
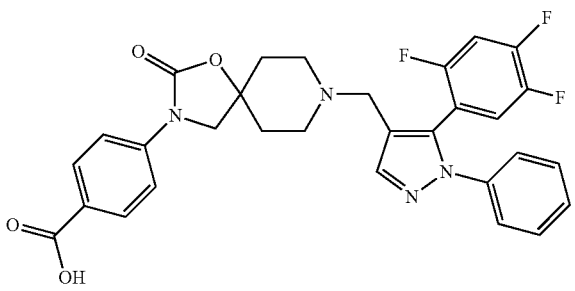
334
-continued
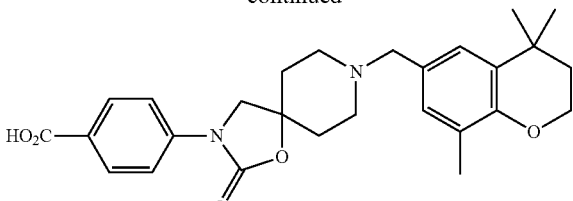
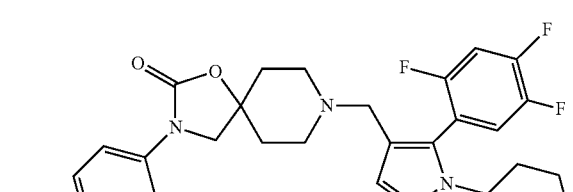
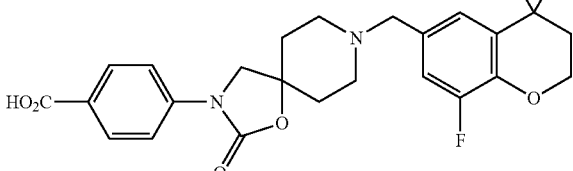
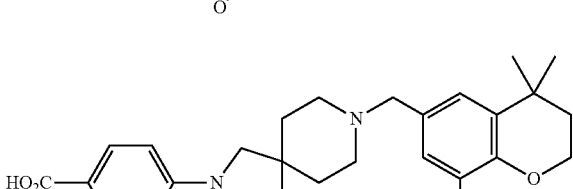
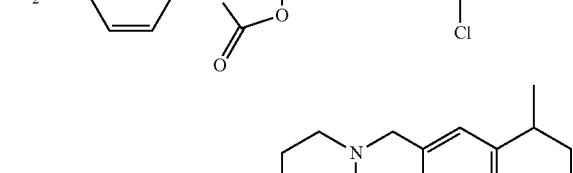
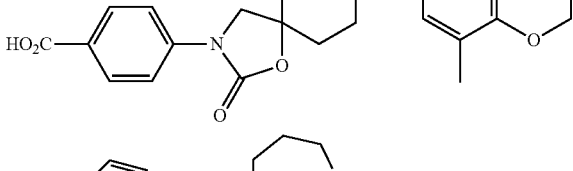
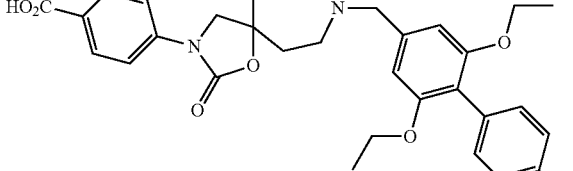
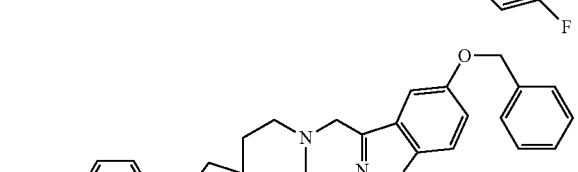
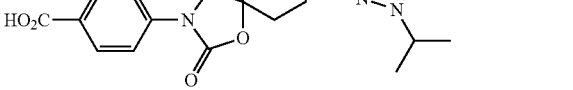

335
-continued
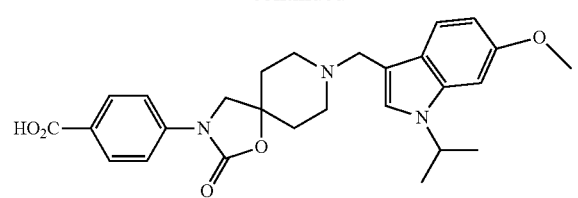
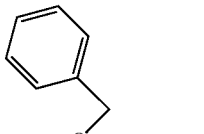
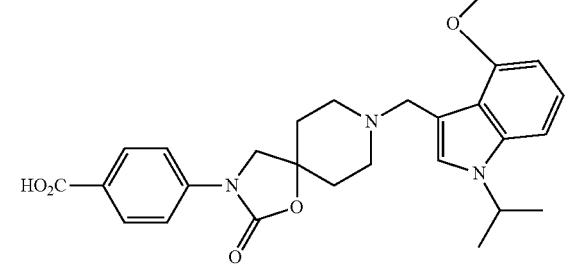
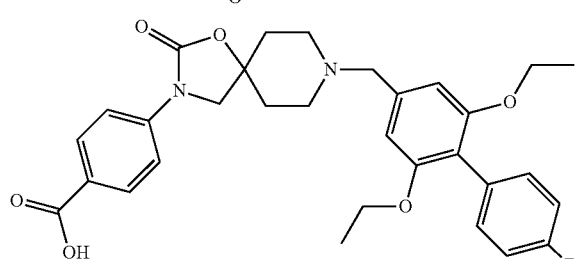
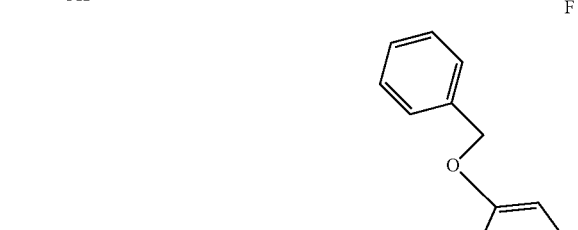
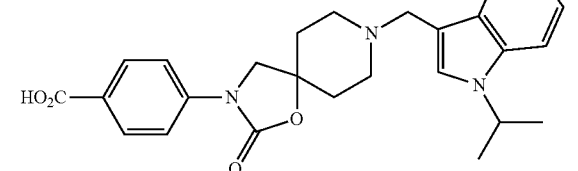
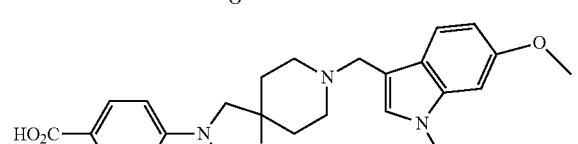
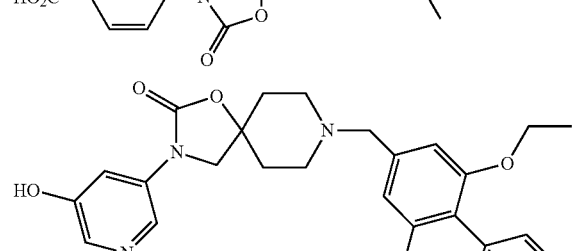
336
-continued
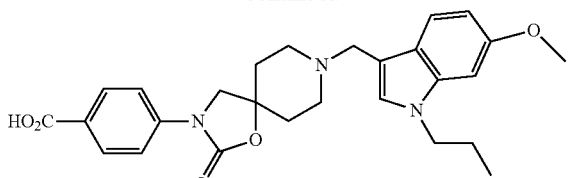
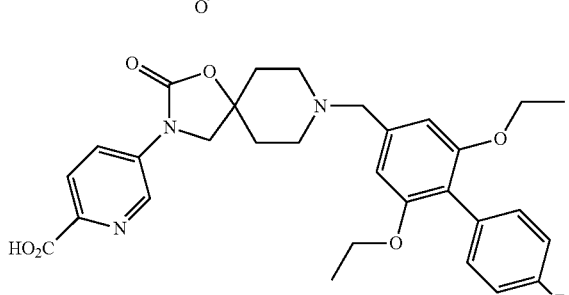
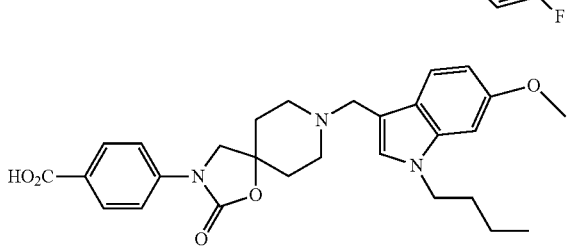
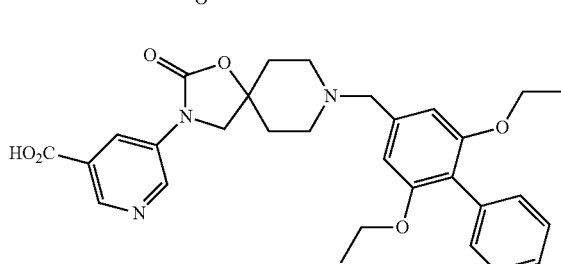
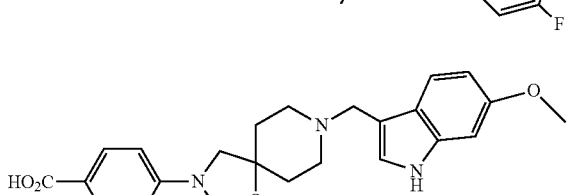
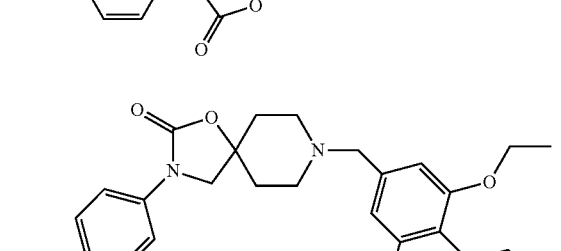
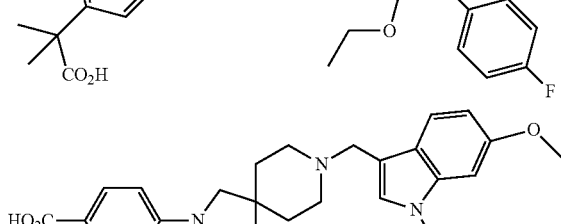
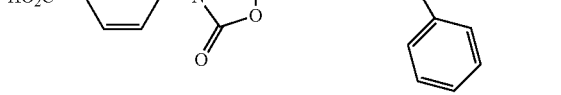

337
-continued
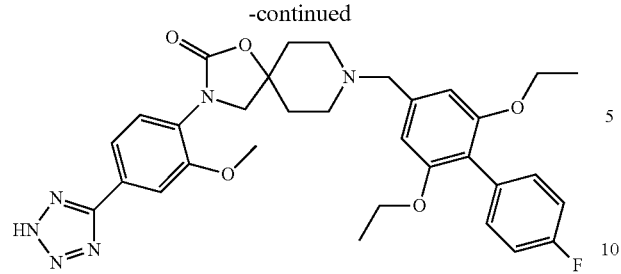
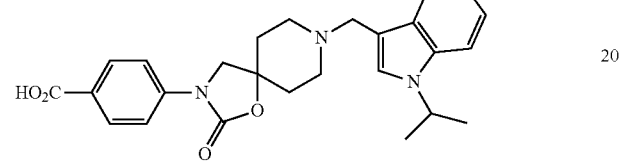
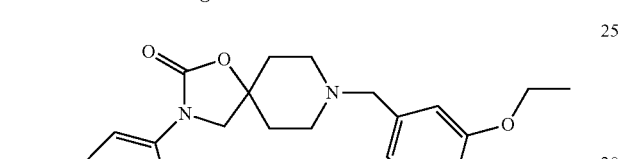
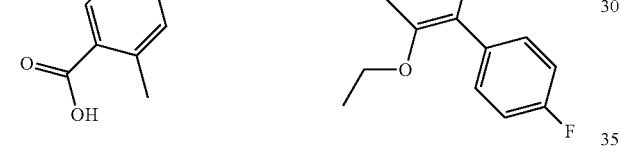
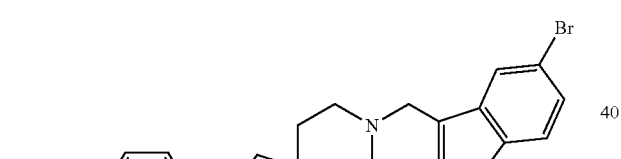
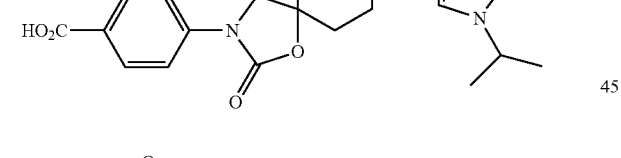
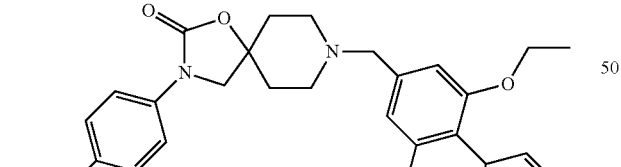
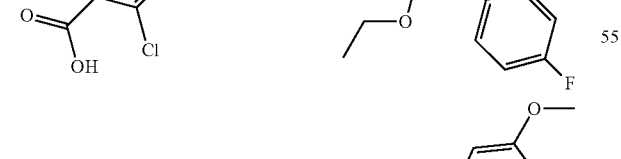
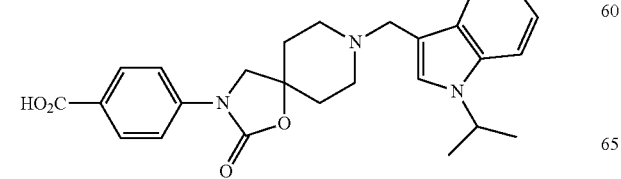
338
-continued
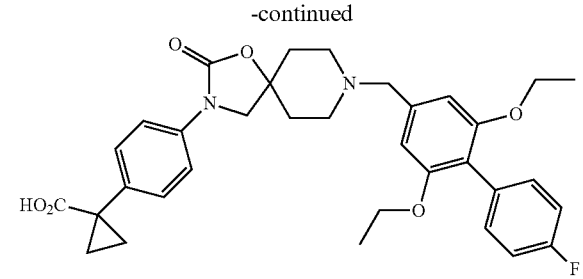
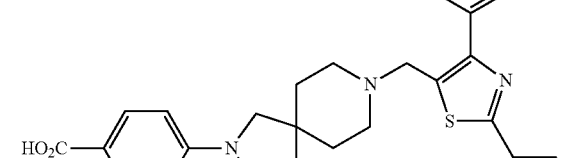
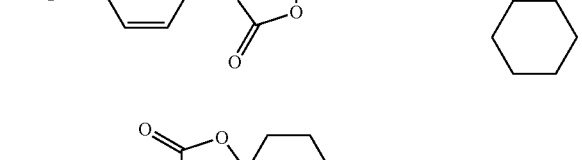
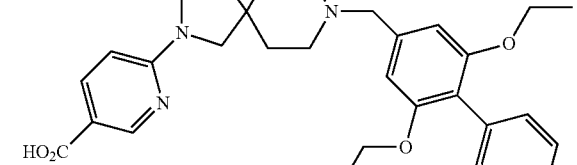
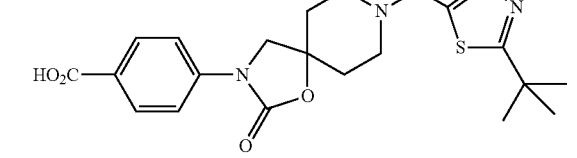
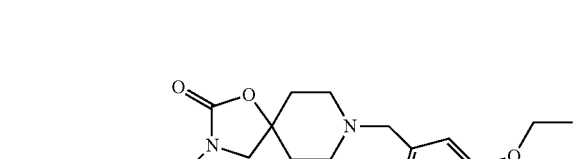

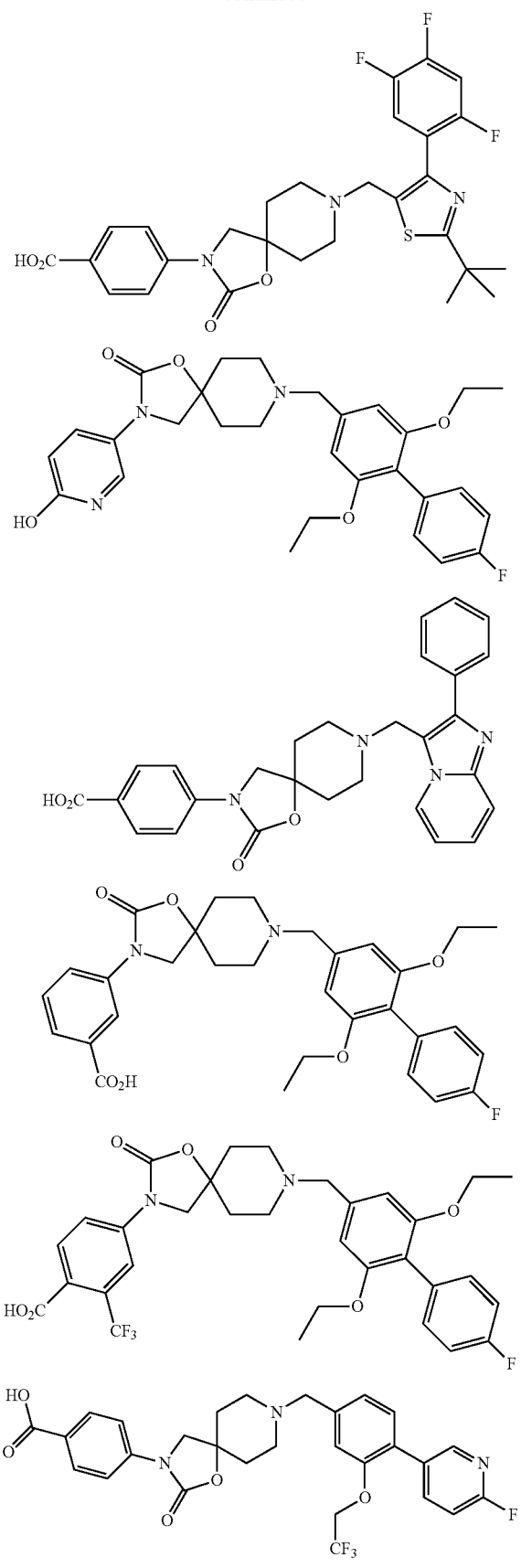
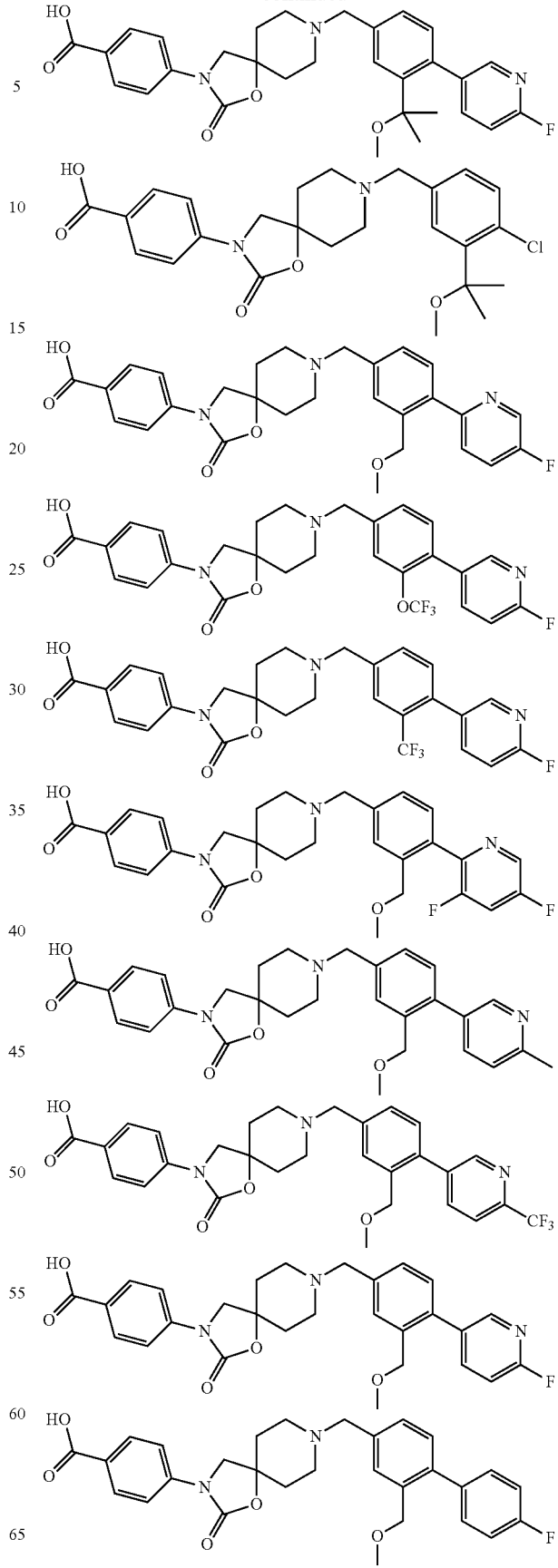

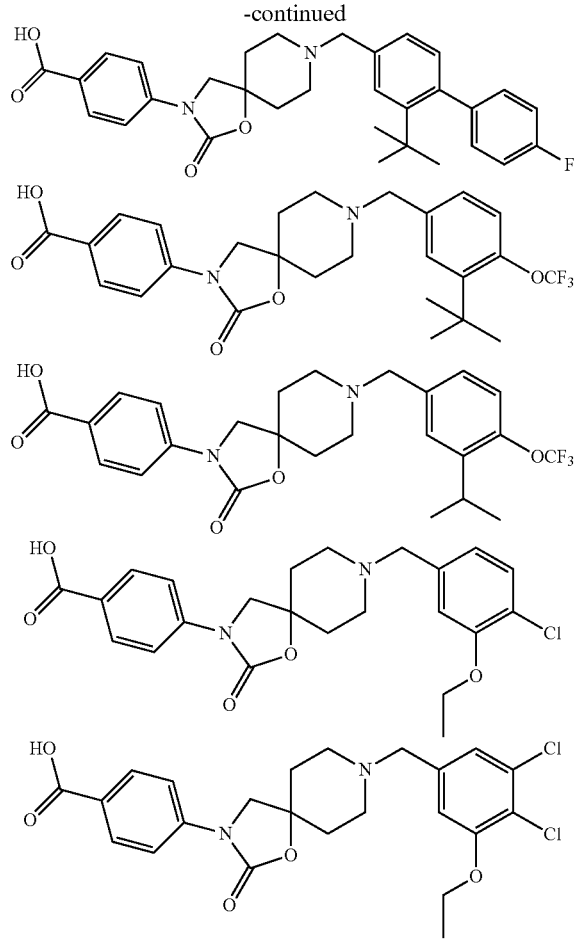
15. A method of treating a disorder, condition, or disease selected from the group consisting of Type 2 diabetes and insulin resistance, comprising administering a compound of claim 1 to a subject in need thereof.
* * * * *